(12) United States Patent
Chesworth et al.

(10) Patent No.: US 9,029,343 B2
(45) Date of Patent: May 12, 2015

(54) MODULATORS OF HISTONE METHYLTRANSFERASE, AND METHODS OF USE THEREOF

(75) Inventors: Richard Chesworth, Concord, MA (US); Kevin W. Kuntz, Woburn, MA (US); Edward J. Olhava, Newton, MA (US); Michael A. Patane, Andover, MA (US)

(73) Assignee: Epizyme, Inc., Cambridge, MA (US)

(*) Notice: Subject to any disclaimer, the term of this patent is extended or adjusted under 35 U.S.C. 154(b) by 0 days.

(21) Appl. No.: 13/991,321

(22) PCT Filed: Dec. 5, 2011

(86) PCT No.: PCT/US2011/063309
§ 371 (c)(1),
(2), (4) Date: Jul. 24, 2013

(87) PCT Pub. No.: WO2012/082436
PCT Pub. Date: Jun. 21, 2012

(65) Prior Publication Data
US 2013/0310333 A1 Nov. 21, 2013

Related U.S. Application Data

(60) Provisional application No. 61/419,591, filed on Dec. 3, 2010.

(51) Int. Cl.
*C07H 19/16* (2006.01)
*C07H 19/167* (2006.01)
*C07D 473/34* (2006.01)

(52) U.S. Cl.
CPC ............. *C07H 19/16* (2013.01); *C07D 473/34* (2013.01); *C07H 19/167* (2013.01)

(58) Field of Classification Search
CPC ............................. C07H 19/16; C07H 19/167
See application file for complete search history.

(56) References Cited

U.S. PATENT DOCUMENTS

| | | | |
|---|---|---|---|
| 6,534,651 B2 * | 3/2003 | Jagtap et al. | 544/144 |
| 8,580,762 B2 | 11/2013 | Olhava et al. | |
| 8,722,877 B2 | 5/2014 | Chesworth et al. | |
| 2004/0147464 A1 | 7/2004 | Roberts et al. | |
| 2006/0189636 A1 | 8/2006 | Critchley et al. | |
| 2010/0144655 A1 | 6/2010 | Chen et al. | |
| 2013/0310334 A1 | 11/2013 | Chesworth et al. | |
| 2013/0338173 A1 | 12/2013 | Olhava et al. | |
| 2014/0051654 A1 | 2/2014 | Olhava et al. | |

FOREIGN PATENT DOCUMENTS

| | | |
|---|---|---|
| EP | 2332953 A1 | 6/2011 |
| WO | WO-2004007512 A2 | 1/2004 |
| WO | WO-2007100304 A1 | 9/2007 |
| WO | WO-2010027005 A1 | 3/2010 |

OTHER PUBLICATIONS

Cohen et al. "Determinants of Cofactor Binding to DNA Methyltransferases: Insights From a Systematic Series of Structural Variants of S-adenosylhomocysteine." *Org. Biomol. Chem.* 3.1(2005):152-161.
Min et al. "Structure of the Catalytic Domain of Human DOT1L, a non-SET Domain Nucleosomal Histone Methyltransferase." *Cell.* 112.5(2003):711-723.

* cited by examiner

*Primary Examiner* — Traviss C McIntosh, III
(74) *Attorney, Agent, or Firm* — Cooley LLP; Heidi A. Erlacher; Lian Ouyang

(57) ABSTRACT

Disclosed are compounds, pharmaceutical compositions containing the compounds, and the uses of the compounds and compositions as modulators of histone methyltransferases, and for treating diseases influenced by modulation of histone methyltransferase activity.

24 Claims, 9 Drawing Sheets

| compound | biochemical IC$_{50}$ (µM) |
|---|---|
| 125 | ≤ 1 |
| 114 | > 1 |
| 116 | > 1 |
| 118 | < 0.1 |
| 131 | ≤ 1 |
| 94 | ≤ 1 |

| # | IC$_{50}$ (µM) |
|---|---|
| 5 | ≤ 1 |
| 9 | ≤ 1 |
| 11 | ≤ 1 |
| 14 | ≤ 1 |
| 17 | > 1 |
| 21 | > 1 |
| 25 | ≤ 1 |
| 26 | > 1 |
| 27 | > 1 |
| 28 | > 1 |
| 29 | > 1 |
| 30 | > 1 |
| 31 | ≤ 1 |
| 32 | > 1 |
| 33 | > 1 |
| 34 | > 1 |
| 38 | > 1 |
| 41 | > 1 |
| 42 | > 1 |
| 43 | > 1 |
| 44 | > 1 |
| 45 | > 1 |

| # | IC$_{50}$ (µM) |
|---|---|
| 46 | > 1 |
| 50 | > 1 |
| 53 | > 1 |
| 55 | > 1 |
| 57 | ≤ 1 |
| 62 | > 1 |
| 64 | > 1 |
| 67 | ≤ 1 |
| 68 | > 1 |
| 71 | > 1 |
| 75 | ≤ 1 |
| 78 | > 1 |
| 81 | < 0.1 |
| 82 | < 0.1 |
| 86 | > 1 |
| 88 | ≤ 1 |
| 92 | > 1 |
| 94 | ≤ 1 |
| 96 | > 1 |
| 98 | > 1 |
| 105 | ≤ 1 |
| 108 | ≤ 1 |

| # | IC$_{50}$ (µM) |
|---|---|
| 111 | ≤ 1 |
| 114 | > 1 |
| 116 | > 1 |
| 118 | < 0.1 |
| 121 | > 1 |
| 125 | ≤ 1 |
| 129 | > 1 |
| 131 | ≤ 1 |
| 134 | > 1 |
| 135 | > 1 |
| 139 | ≤ 1 |
| 143 | ≤ 1 |
| 145 | > 1 |
| 149 | < 0.1 |
| 152 | ≤ 1 |
| 154 | > 1 |
| 159 | < 0.1 |
| 163 | ≤ 1 |
| 165 | < 0.1 |
| 167 | ≤ 1 |
| 168 | > 1 |
| # | IC$_{50}$ (µM) |

| # | IC$_{50}$ (µM) |
|---|---|
| 169 | < 0.1 |
| 173 | ≤ 1 |
| 179 | < 0.1 |
| 183 | ≤ 1 |
| 185 | ≤ 1 |
| 190 | > 1 |
| 193 | ≤ 1 |
| 195 | < 0.1 |
| 199 | ≤ 1 |
| 201 | < 0.1 |
| 206 | < 0.1 |
| 209 | ≤ 1 |
| 213 | ≤ 1 |
| 223 | < 0.1 |

Figure 7A

| # | EZH2 IC$_{50}$ (μM) | PRMT5 IC$_{50}$ (μM) | CARM1 IC$_{50}$ (μM) | EHMT2 IC$_{50}$ (μM) |
|---|---|---|---|---|
| 21 | > 100 | > 1 | - | - |
|    | > 1 | ≤ 1 | > 1 | > 1 |
| 26 | > 1 | > 1 | - | - |
| 27 | > 50 | > 1 | - | - |
| 28 | > 100 | > 1 | - | - |
| 29 | > 50 | > 50 | - | - |
| 30 | > 100 | > 1 | - | - |
| 25 | > 1 | > 1 | - | - |
| 31 | > 1 | > 1 | - | - |
| 32 | > 100 | > 1 | - | - |
| 33 | > 100 | > 1 | - | - |
| 34 | > 50 | > 1 | - | - |
| 38 | > 100 | ≤ 1 | > 1 | - |
| 41 | > 100 | ≤ 1 | - | - |
| 42 | > 100 | ≤ 1 | > 1 | - |
| 43 | > 100 | ≤ 1 | > 1 | > 50 |
| 44 | > 100 | ≤ 1 | - | - |
| 50 | > 50 | ≤ 1 | > 1 | - |
| 45 | > 100 | ≤ 1 | > 50 | - |
| 53 | > 1 | ≤ 1 | > 1 | - |
| 55 | > 50 | > 1 | - | - |
| 57 | > 100 | > 1 | > 1 | > 50 |
|    | > 50 | > 1 | - | - |
| 64 | > 100 | ≤ 1 | - | > 1 |
| 62 | > 100 | ≤ 1 | - | - |
| 67 | > 50 | > 1 | - | - |
| 46 | > 100 | ≤ 1 | > 1 | - |
| 68 | > 50 | ≤ 1 | - | - |
|    | > 100 | ≤ 1 | - | - |
|    | > 50 | ≤ 1 | - | - |
|    | > 100 | ≤ 1 | - | - |
| 71 | > 1 | ≤ 1 | - | - |
| 75 | > 1 | ≤ 1 | > 1 | > 1 |
| 78 | > 1 | ≤ 1 | > 1 | ≤ 1 |
| 81 | > 50 | ≤ 1 | - | > 1 |
|    | > 50 | ≤ 1 | - | > 1 |
|    | > 50 | ≤ 1 | > 1 | > 1 |
| 82 | > 50 | ≤ 1 | - | - |

Figure 7B

| # | EZH2 IC$_{50}$ (µM) | PRMT5 IC$_{50}$ (µM) | CARM1 IC$_{50}$ (µM) | EHMT2 IC$_{50}$ (µM) |
|---|---|---|---|---|
| 86 | > 50 | > 1 | - | - |
| 88 | > 50 | - | - | - |
| 92 | > 50 | > 1 | > 1 | - |
| 94 | > 50 | > 1 | - | - |
| 96 | > 50 | > 1 | - | - |
| 98 | > 50 | - | - | - |
| 105 | > 50 | ≤ 1 | > 1 | - |
| 108 | > 50 | ≤ 1 | - | - |
| 111 | > 50 | ≤ 1 | - | - |
| 168 | > 50 | > 1 | - | - |
| 17 | > 50 | > 1 | - | - |
| 14 | > 50 | ≤ 1 | - | - |
| 11 | > 50 | > 1 | - | - |
| 9 | > 50 | > 1 | - | - |
| 5 | > 50 | > 1 | - | - |
| 125 | > 50 | > 1 | - | - |
| 114 | > 50 | > 1 | - | - |
| 116 | > 50 | > 1 | - | - |
| 118 | > 50 | - | - | - |
| 118 | > 50 | - | - | > 50 |
| 118 | > 1 | - | - | - |
| 118 | > 50 | ≤ 1 | - | - |
| 121 | > 50 | ≤ 1 | - | - |
| 129 | > 50 | > 1 | - | - |
| 131 | > 50 | > 1 | - | - |
| 134 | > 50 | > 1 | - | - |
| 139 | > 50 | > 50 | - | - |
| 143 | > 50 | > 1 | - | - |
| 145 | > 50 | > 1 | - | - |
| 149 | > 50 | > 1 | - | - |
| 135 | > 50 | > 1 | - | - |
| 154 | > 50 | - | - | - |

Figure 8

| # | IC$_{50}$ (μM) |
|---|---|
| 224 | > 100 |
| 225 | > 100 |
| 226 | > 100 |
| 227 | > 1 |
| 228 | > 1 |
| 229 | > 1 |
| 230 | > 1 |
| 231 | > 1 |
| 232 | > 1 |
| 233 | > 1 |
| 234 | > 100 |
| 235 | > 100 |
| 236 | > 100 |
| 237 | > 100 |
| 238 | > 100 |
| 239 | > 100 |
| 240 | > 100 |
| 241 | > 100 |
| 242 | > 100 |
| 243 | > 100 |
| 244 | > 100 |
| 245 | > 100 |

| | |
|---|---|
| 246 | > 100 |
| 247 | > 100 |
| 248 | > 100 |
| 249 | > 100 |
| 250 | ≤ 1 |
| 251 | ≤ 1 |
| 252 | ≤ 1 |
| 254 | ≤ 1 |

MODULATORS OF HISTONE METHYLTRANSFERASE, AND METHODS OF USE THEREOF

CROSS-REFERENCE TO RELATED APPLICATIONS

This application is a national stage application, filed under 35 U.S.C. §371, of International Application No. PCT/US2011/063309, filed Dec. 5, 2011, which claims priority to, and the benefit of, U.S. provisional application No. 61/419,591, filed Dec. 3, 2010, the contents of each of which are incorporated herein by reference in their entireties.

BACKGROUND OF THE INVENTION

In eukaryotic cells DNA is packaged with histones to form chromatin. Approximately 150 base pairs of DNA are wrapped twice around an octamer of histones (two each of histones 2A, 2B, 3 and 4) to form a nucleosome, the basic unit of chromatin. Changes in the ordered structure of chromatin can lead to alterations in transcription of associated genes. This process is highly controlled because changes in gene expression patterns can profoundly affect fundamental cellular processes such as differentiation, proliferation and apoptosis. Control of changes in chromatin structure (and hence of transcription) is mediated by covalent modifications to histones, most notably of their N-terminal tails. These modifications are often referred to as epigenetic because they can lead to heritable changes in gene expression, but do not affect the sequence of the DNA itself. Covalent modifications (for example, methylation, acetylation, phosphorylation and ubiquitination) of the side chains of amino acids are enzymatically mediated.

The selective addition of methyl groups to specific amino acid sites on histones is controlled by the action of a unique family of enzymes known as histone methyltransferases (HMTs). The level of expression of a particular gene is influenced by the presence or absence of a methyl group at a relevant histone site. The specific effect of a methyl group at a particular histone site persists until the methyl group is removed by a histone demethylase, or until the modified histone is replaced through nucleosome turnover. In a like manner, other enzyme classes can decorate DNA and histones with other chemical species and still other enzymes can remove these species to provide temporal control of gene expression.

The orchestrated collection of biochemical systems behind transcriptional regulation must be tightly controlled in order for cell growth and differentiation to proceed optimally. Disease states result when these controls are disrupted by aberrant expression and/or activity of the enzymes responsible for DNA and histone modification. In human cancers, for example, there is a growing body of evidence to suggest that dysregulated epigenetic enzyme activity contributes to the uncontrolled cell proliferation associated with cancer as well as other cancer-relevant phenotypes such as enhanced cell migration and invasion.

Rearrangements of the mixed lineage leukemia (MLL) gene on chromosome 11q23 are associated with aggressive leukemias with a poor prognosis. MLL translocations result in aberrant recruitment of DOT1L, a histone methyltransferase that methylates lysine 79 of histone H3 (H3K79), to chromatin leading to ectopic H3K79 methylation and increased expression of genes involved in leukemogenesis. These rearrangements, which are found in over 70% of infant leukemias and approximately 10% of adult acute myeloid leukemias (AML), result in the expression of fusion proteins in which the C-terminal sequences of MLL, including a SET-domain that methylates lysine 4 of histone H3 (H3K4), are replaced with sequences derived from a variety of fusion partners, including AF4, AF9, and ENL. The majority of these fusion partners are components of transcriptional elongation complexes that, directly or indirectly, recruit DOT1L to genomic loci bound by the MLL-fusion protein. This results in elevated H3K79 methylation and increased mRNA expression of MLL-fusion target genes, such as HOXA9 and MEIS1 that are central to the pathogenesis of leukemia.

Mistargeted DOT1L enzymatic activity has therefore been proposed as a driver of disease in MLL patients, however in the absence of specific DOT1L methyltransferase inhibitors; this hypothesis has not been directly addressed in model systems.

Beyond cancer, there is growing evidence for a role of epigenetic enzymes in a number of other human diseases, including metabolic diseases (such as diabetes), inflammatory diseases (such as Crohn's disease), neurodegenerative diseases (such as Alzheimer's disease) and cardiovascular diseases. Therefore, selectively modulating the aberrant action of epigenetic enzymes holds great promise for the treatment of a range of diseases.

SUMMARY OF THE INVENTION

One aspect of the present invention relates to compounds that selectively modulate the activity of the histone methyltransferase DOT1L. For example, one aspect of the invention relates to a compound of formula I:

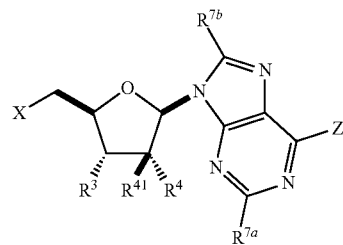

or a pharmaceutically acceptable salt, hydrate, enantiomer or stereoisomer thereof, wherein independently for each occurrence, X is

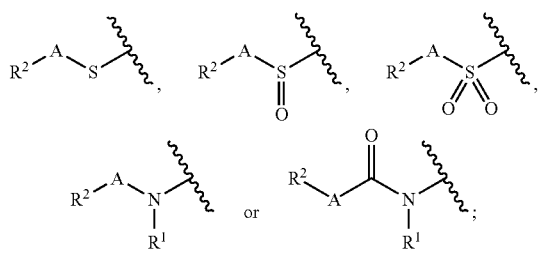

$R^1$ is hydrogen, alkyl, cycloalkyl, alkylcycloalkyl, alkylaryl, haloalkyl, formyl, heterocyclyl, heterocyclylalkyl,

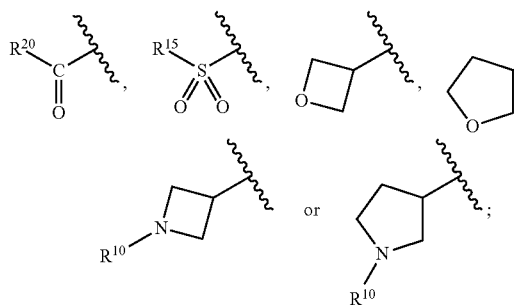

or (C$_2$-C$_4$)alkyl substituted with

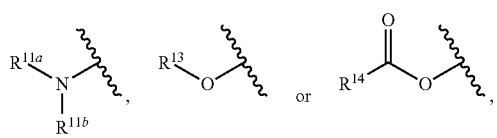

except that when X is

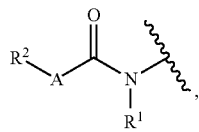

R$^1$ is not

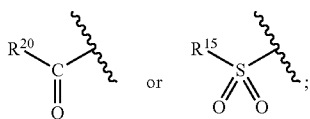

R$^{10}$ is hydrogen or alkyl;
R$^{11a}$ is hydrogen, alkyl, or alkyl-cycloalkyl;
R$^{11b}$ is hydrogen or alkyl; or taken together with R$^{11a}$ and the nitrogen to which it is attached forms a 4- to 8-membered heterocyclyl comprising 0 or 1 additional heteroatoms;
R$^{13}$ is hydrogen, alkyl, aryl, heteroaryl, aralkyl, heteroaralkyl or silyl;
R$^{14}$ is hydrogen, alkyl, aryl, heteroaryl, aralkyl or heteroaralkyl;
R$^{15}$ is alkyl, cycloalkyl or cycloalkylalkyl;
R$^{20}$ is hydrogen, alkyl, cycloalkyl or cycloalkylalkyl;
A is

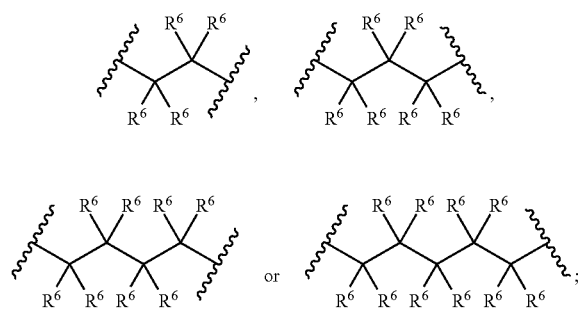

R$^2$ is

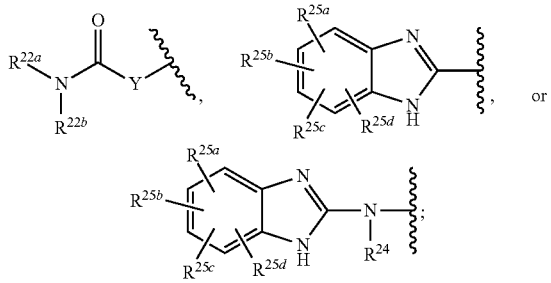

Y is —NH—, —N(alkyl)-, —O—, or —CR$^6{}_2$—;
R$^{22a}$ is aryl, heteroaryl, aralkyl, heteroaralkyl, fused bicyclyl, biaryl, aryloxyaryl, heteroaryloxyaryl, aryloxyheteroaryl or heteroaryloxyheteroaryl;
R$^{22b}$ is hydrogen or alkyl;
R$^{24}$ is hydrogen or alkyl;
R$^{25a}$, R$^{25b}$, R$^{25c}$, R$^{25d}$ are independently -M$_2$-T$_2$, in which M$_2$ is a bond, SO$_2$, SO, S, CO, CO$_2$, O, O—C$_1$-C$_4$ alkyl linker, C$_1$-C$_4$ alkyl linker, NH, or N(R$_t$), R$_t$ being C$_1$-C$_6$ alkyl, and T$_2$ is H, halo, or R$_{S4}$, R$_{S4}$ being C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 8-membered heterocycloalkyl, or 5 to 10-membered heteroaryl, and each of O—C$_1$-C$_4$ alkyl linker, C$_1$-C$_4$ alkyl linker, R$_t$, and R$_{S4}$ being optionally substituted with one or more substituents selected from the group consisting of halo, hydroxyl, carboxyl, cyano, C$_1$-C$_6$ alkyl, C$_2$-C$_6$ alkenyl, C$_2$-C$_6$ alkynyl, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;
R$^3$ is hydrogen, halogen, hydroxy, alkyloxy, aralkyloxy, alkylcarbonyloxy or silyloxy;
R$^4$ is hydrogen, halogen, hydroxy, alkyloxy, aralkyloxy, alkylcarbonyloxy or silyloxy;
R$^{41}$ is hydrogen, alkyl or alkynyl;
Z is hydrogen or $$\begin{matrix} & R^{5a} \\ \xi{-}N{\diagdown} & \\ & R^{5b}; \end{matrix}$$

R$^{5a}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkoxy, aryloxy, aralkyloxy, nitro, amino, amido, aryl and heteroaryl;
R$^{5b}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkoxy, aryloxy, aralkyloxy, nitro, amino, amido, aryl and heteroaryl; or taken together with R$^{5a}$ and the nitrogen to which it is attached forms a 4- to 8-membered heterocyclyl comprising 0 or 1 additional heteroatoms;

$R^6$ is hydrogen, alkyl or halo; or two geminal $R^6$ taken together are ethylene, propylene or butylene;

$R^{7a}$ is hydrogen, lower alkyl, lower haloalkyl, cyano, halo, lower alkoxy, or C3-C5 cycloalkyl, optionally substituted with 1, 2 or 3 substituents independently selected from the group consisting of cyano, lower alkoxy and halo; and $R^{7b}$ is hydrogen, lower alkyl, lower haloalkyl, cyano, halo, lower alkoxy, or C3-C5 cycloalkyl, optionally substituted with 1, 2 or 3 substituents independently selected from the group consisting of cyano, lower alkoxy and halo.

Another aspect of the invention relates to a pharmaceutical composition comprising a compound of the invention (e.g., a compound of formula I, or a pharmaceutically acceptable salt, hydrate, enantiomer or stereoisomer thereof), and one or more pharmaceutically acceptable carriers. A pharmaceutical composition of the invention may also comprise a second therapeutic agent. Such pharmaceutical compositions of the invention can be administered in accordance with a method of the invention (for example, as part of a therapeutic regimen for treatment or prevention of conditions and disorders related to cancer and/or neurodegenerative disorders). In one embodiment, the invention relates to a packaged pharmaceutical comprising a therapeutically effective amount of the compound or composition. In one embodiment, the invention relates to a packaged pharmaceutical comprising a prophylactically effective amount of the compound or composition.

Another aspect of the invention relates to a method of treating or preventing a disorder in which DOT1-mediated protein methylation plays a part, comprising administering to a subject in need thereof a therapeutically effective amount of a compound of the present invention. Such methods can be used to ameliorate any condition which is caused by or potentiated by the activity of DOT1.

Another aspect of the invention relates to a method of inhibiting or reducing the level of DOT1L activity in a cell comprising the step of contacting a cell with or providing to a subject a compound of the present invention.

Another aspect of the invention relates to a method of inhibiting or reducing the level of histone H3 lysine residue 79 (H3K79) methylation in a cell, comprising the step of contacting a cell with or providing to a subject a compound of the present invention. Such methods can be used to ameliorate any condition which is caused by or potentiated by the activity of DOT1 through H3K79 methylation.

Another aspect of the invention relates to a method of treating or preventing specific disorders in which DOT1 methylation plays a part, for example, in cancer or a neurological disorder. Such methods comprise the step of administering to a subject in need thereof a therapeutically effective amount of a compound or pharmaceutical composition of the invention.

BRIEF DESCRIPTION OF THE FIGURES

FIG. 6 depicts a table of selected compounds of the invention and their $IC_{50}$ values against DOT1L.

FIGS. 7A and 7B depict tables of selected compounds of the invention and their $IC_{50}$ values against EZH2, PRMT5, CARM1 and EHMT2. In addition to those shown, compounds 152, 159, 163, 167, 169, 173, 179, 183, 185, 190, 195, 199, 201, 206, 209, 213, and 223 all have EZH2 $IC_{50}$ values of greater than 50 μM.

FIG. 8 depicts a table of selected compounds of the invention and their $IC_{50}$ values against DOT1L.

DETAILED DESCRIPTION OF THE INVENTION

Underlying Molecular Biology

Figure 1:
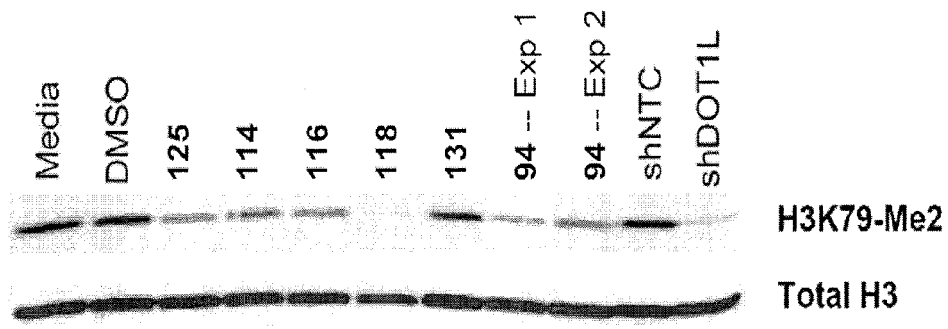
FIG. 1 depicts results demonstrating that 118 and related compounds inhibit H3K79 methylation in THP-1 cells. THP-1 cells were incubated in the presence 50 μM of the indicated compounds for seven days. Untreated (media) and vehicle (DMSO)-treated cells were included as controls. Following treatment, cells were harvested, and histones were extracted, fractionated by SDS-PAGE on a 4-20% gel, transferred to nitrocellulose membranes, and probed with antibodies to histone H3 and histone H3 dimethylated at lysine 79 (H3K79me2). Histones extracted from THP-1 cells expressing control (shNTC) and DOT1L targeting (shDOT1L) shRNAs were included as controls.

Chromatin structure is important in gene regulation and epigenetic inheritance. Post-translational modifications of histones are involved in the establishment and maintenance of higher-order chromatin structure; for example, the tails of certain core histones are modified by acetylation, methylation, phosphorylation, ribosylation and ubiquitination.

One aspect of the present invention relates to compounds that selectively modulate the activity of the histone methyltransferase DOT1L, an enzyme known to methylate lysine 79 of histone H3 ("H3K79") in vivo (Feng et al. (2002) *Curr. Biol.* 12:1052-1058). Similar to other HMTases, DOT1L contains a S-adenosylmethionine (SAM) binding site and uses SAM as a methyl donor. However, unlike other reported HMTases, the DOT1 polypeptides do not contain a SET domain.

DOT1L nucleic acid and polypeptides have previously been described (see, e.g., U.S. Patent Application Publication No. 2005-0048634 A1 (incorporated by reference); Feng et al. (2002) *Curr. Biol.* 12:1052-1058; and Okada et al. (2005) *Cell* 121:167-78). The yeast homolog of DOT1 was originally identified as a Disruptor of Telomeric silencing (the protein and nucleic acid sequences of yeast DOT1 can be found at GenBank Accession No. NP010728, incorporated herein by reference in its entirety). The human DOT1 homolog has been cloned, isolated, and designated as hDOT1L (human DOT1-like protein). The sequences of the human nucleic acid and protein have been deposited under GenBank Accession No. AF509504, which is hereby incorporated by reference in its entirety. Only the approximately 360 N-terminal amino acids of hDOT1L share significant sequence similarity with the yeast DOT1. In addition, DOT1 homologs from *C. elegans* (GenBank Accession Nos. NP510056 and CAA90610), *Drosophila* (GenBank Accession Nos. CG10272 and AAF54122), mouse (GenBank Accession No. XP125730), *Anopheles gambiae* (GenBank Accession No. EAA03558), and *Neurospora crassa* (GenBank Accession No. EAA33634) are available in public databases (the disclosures of which are incorporated by reference herein in their entireties). The SAM binding domain among these homologs is conserved (approximately 30-100% amino acid sequence identity and 50-100% amino acid similarity). Various aspects of the present invention can be practiced with any DOT1L polypeptide or nucleic acid.

The 2.5 angstrom resolution structure of a fragment of the hDOT1L protein containing the catalytic domain (amino acids 1-416) has been solved, and the atomic coordinates for amino acids 1-416 of hDOT1L have been determined and deposited in the RCSB database under ID code 1NW3 and described in the scientific literature (Min et al. (2003) *Cell* 112:711-723), the disclosures of both of which are incorporated herein by reference in their entireties.

It has recently been demonstrated that hDOT1L plays an important role in MLL-AF10-mediated leukemogenesis (Okada et al. (2005) *Cell* 121:167-78). It was also shown that mistargeting of hDOT1L to the Hoxa9 gene by MLL-AF10 results in H3K79 methylation and Hoxa9 upregulation which contributes to leukemic transformation (Okada et al. (2005) *Cell* 121:167-78). It was further demonstrated that the hDOT1L and MLL-AF10 interaction involves the OM-LZ (octapeptide motif-leucine zipper) region of AF10, required for MLL-AF10-mediated leukemic transformation (DiMartino et al. (2002) *Blood* 99:3780-5). It has also been shown that CALM-AF10 fusion appears to be both necessary and sufficient to mediate leukemogenesis in vitro and in vivo; that hDOT1L and its H3K79 methyltransferase activity are implicated in CALM-AF10-mediated leukemic transformation; and that the Hoxa5 gene is involved in CALM-AF10-mediated transformation (U.S. Patent Application Publication No. 2009-0061443 A1, which is hereby incorporated by reference in its entirety). Aberrant recruitment of DOT1L leading to deregulated gene expression may be a common feature of many other oncogenic MLL-fusion proteins. For example, the MLL fusion partners ENL, AF4, and AF9 are normally found in nuclear complexes with DOT1L (Bitoun et al. (2007) *Hum. Mol. Genet.* 16:92-106, Mueller et al. (2007) *Blood* 110:4445-54, Zhang et al. (2006) *J. Biol. Chem.* 281:18059-68), and altered H3K79 methylation profiles are a feature of murine and human MLL-AF4 leukemias (Krivstov et al. (2008) *Cancer Cell* 14:355-368).

Compounds

One aspect of the invention relates to a compound of formula I:

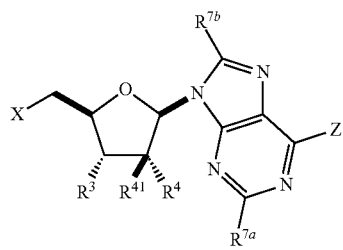

or a pharmaceutically acceptable salt, hydrate, enantiomer or stereoisomer thereof, wherein independently for each occurrence, X is

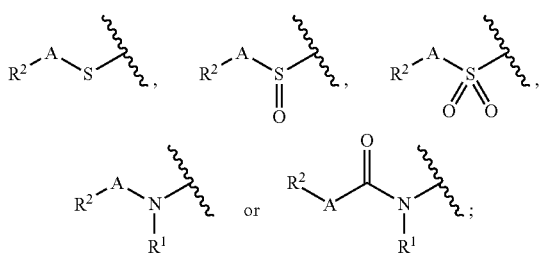

$R^1$ is hydrogen, alkyl, cycloalkyl, alkylcycloalkyl, alkylaryl, haloalkyl, formyl, heterocyclyl, heterocyclylalkyl,

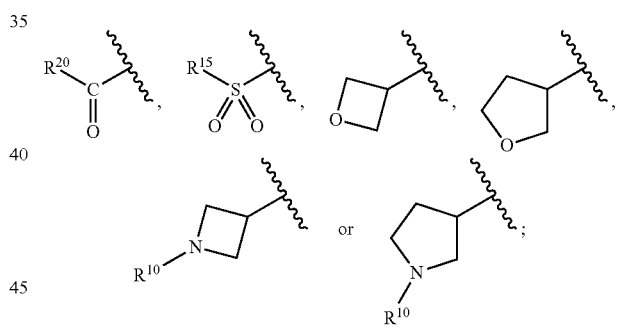

or $(C_2\text{-}C_4)$alkyl substituted with

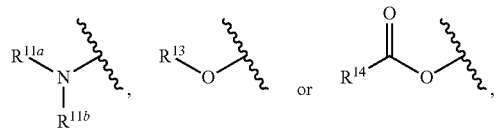

except that when X is

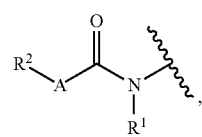

$R^1$ is not

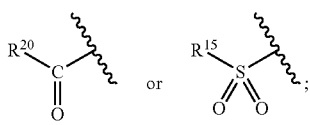

$R^{10}$ is hydrogen or alkyl;
$R^{11a}$ is hydrogen, alkyl, or alkyl-cycloalkyl;
$R^{11b}$ is hydrogen or alkyl; or taken together with $R^{11a}$ and the nitrogen to which it is attached forms a 4- to 8-membered heterocyclyl comprising 0 or 1 additional heteroatoms;
$R^{13}$ is hydrogen, alkyl, aryl, heteroaryl, aralkyl, heteroaralkyl or silyl;
$R^{14}$ is hydrogen, alkyl, aryl, heteroaryl, aralkyl or heteroaralkyl;
$R^{15}$ is alkyl, cycloalkyl or cycloalkylalkyl;
$R^{20}$ is hydrogen, alkyl, cycloalkyl or cycloalkylalkyl;
A is

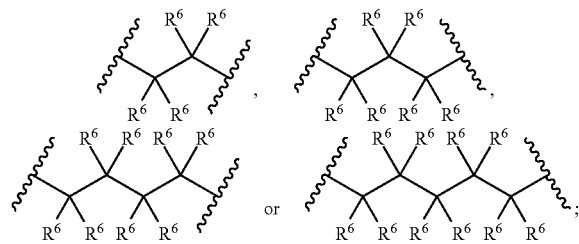

$R^2$ is

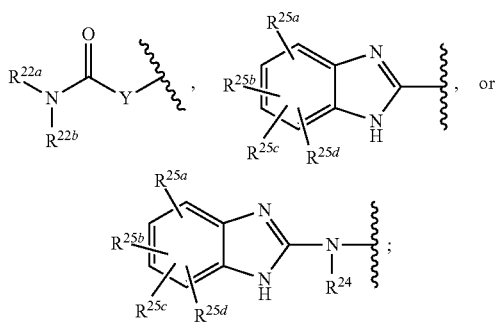

Y is —NH—, —N(alkyl)-, —O—, or —$CR^6_2$—;
$R^{22a}$ is aryl, heteroaryl, aralkyl, heteroaralkyl, fused bicyclyl, biaryl, aryloxyaryl, heteroaryloxyaryl, aryloxyheteroaryl or heteroaryloxyheteroaryl;
$R^{22b}$ is hydrogen or alkyl;
$R^{24}$ is hydrogen or alkyl;
$R^{25a}$, $R^{25b}$, $R^{25c}$, $R^{25d}$ are independently -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R^3$ is hydrogen, halogen, hydroxy, alkyloxy, aralkyloxy, alkylcarbonyloxy or silyloxy;

$R^4$ is hydrogen, halogen, hydroxy, alkyloxy, aralkyloxy, alkylcarbonyloxy or silyloxy;

$R^{41}$ is hydrogen, alkyl or alkynyl;

Z is hydrogen or

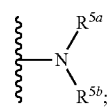

$R^{5a}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl;

$R^{5b}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl; or taken together with $R^{5a}$ and the nitrogen to which it is attached forms a 4- to 8-membered heterocyclyl comprising 0 or 1 additional heteroatoms;

$R^6$ is hydrogen, alkyl or halo; or two geminal $R^6$ taken together are ethylene, propylene or butylene; and $R^{7a}$ is hydrogen, lower alkyl, lower haloalkyl, cyano, halo, lower alkoxy, or $C_3$-$C_5$ cycloalkyl, optionally substituted with 1, 2 or 3 substituents independently selected from the group consisting of cyano, lower alkoxy and halo; and $R^{7b}$ is hydrogen, lower alkyl, lower haloalkyl, cyano, halo, lower alkoxy, or $C_3$-$C_5$ cycloalkyl, optionally substituted with 1, 2 or 3 substituents independently selected from the group consisting of cyano, lower alkoxy and halo.

In certain embodiments, the invention relates to any one of the aforementioned compounds, wherein X is

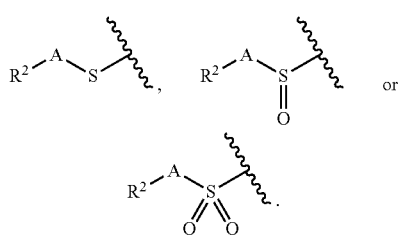

In certain embodiments, the invention relates to any one of the aforementioned compounds, wherein X is

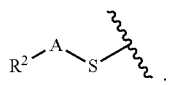

In certain embodiments, the invention relates to any one of the aforementioned compounds, wherein X is

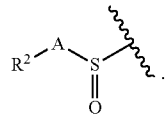

In certain embodiments, the invention relates to any one of the aforementioned compounds, wherein X is

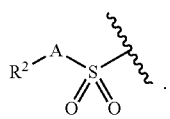

In certain embodiments, the invention relates to any one of the aforementioned compounds, wherein X is

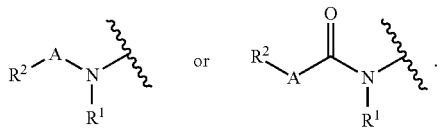

In certain embodiments, the invention relates to any one of the aforementioned compounds, wherein X is

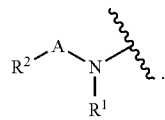

In certain embodiments, the invention relates to any one of the aforementioned compounds, wherein X is

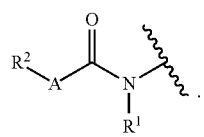

In certain embodiments, the invention relates to any one of the aforementioned compounds, wherein $R^2$ is

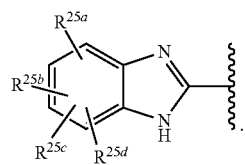

In certain embodiments, the invention relates to any one of the aforementioned compounds, wherein $R^2$ is

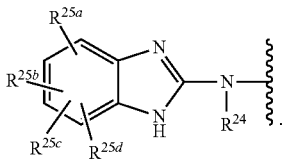

In certain embodiments, the invention relates to any one of the aforementioned compounds, wherein $R^{24}$ is hydrogen or alkyl.

In certain embodiments, the invention relates to any one of the aforementioned compounds, wherein $R^{24}$ is hydrogen.

In certain embodiments, the invention relates to any one of the aforementioned compounds, wherein $R^{25a}$ is hydrogen, alkyl, —O-alkyl, halogen, trifluoroalkyl, —O-trifluoromethyl, or —SO$_2$-trifluoromethyl.

In certain embodiments, the invention relates to any one of the aforementioned compounds, wherein $R^{25b}$ is hydrogen, alkyl, halogen, or trifluoroalkyl.

In certain embodiments, the invention relates to any one of the aforementioned compounds, wherein $R^{25c}$ is hydrogen, alkyl, or halogen.

In certain embodiments, the invention relates to any one of the aforementioned compounds, wherein $R^{25c}$ is hydrogen or halogen.

In certain embodiments, the invention relates to any one of the aforementioned compounds, wherein $R^2$ is

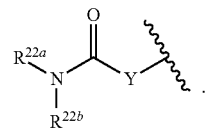

In certain embodiments, the invention relates to any one of the aforementioned compounds, wherein Y is —NH— or —N(alkyl)-.

In certain embodiments, the invention relates to any one of the aforementioned compounds, wherein Y is —NH—.

In certain embodiments, the invention relates to any one of the aforementioned compounds, wherein Y is —N(CH$_3$)—.

In certain embodiments, the invention relates to any one of the aforementioned compounds, wherein Y is —O—.

In certain embodiments, the invention relates to any one of the aforementioned compounds, wherein Y is —CH$_2$—.

In certain embodiments, the invention relates to any one of the aforementioned compounds, wherein $R^{22a}$ is aryl or aralkyl.

In certain embodiments, the invention relates to any one of the aforementioned compounds, wherein $R^{22a}$ is substituted phenyl or substituted benzyl.

In certain embodiments, the invention relates to any one of the aforementioned compounds, wherein $R^{22a}$ is

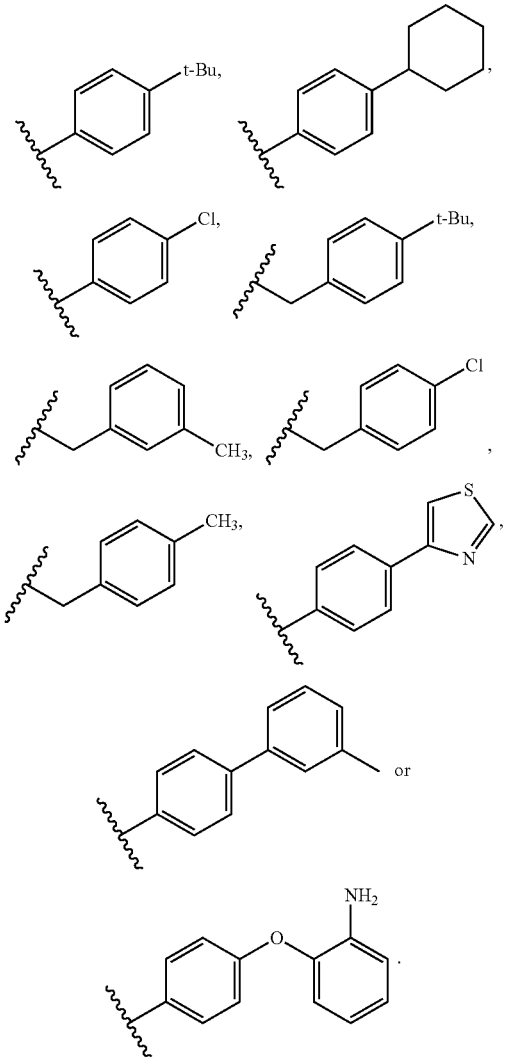

In certain embodiments, the invention relates to any one of the aforementioned compounds, wherein $R^{22a}$ is

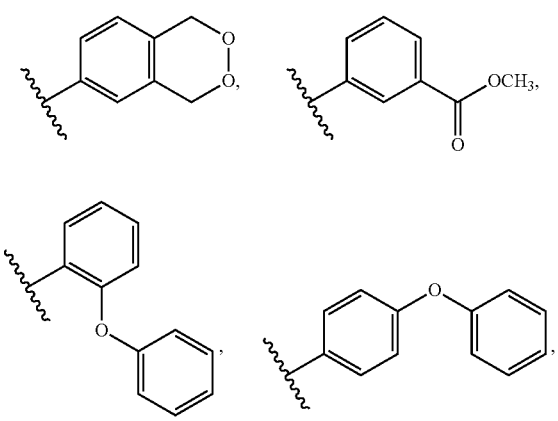

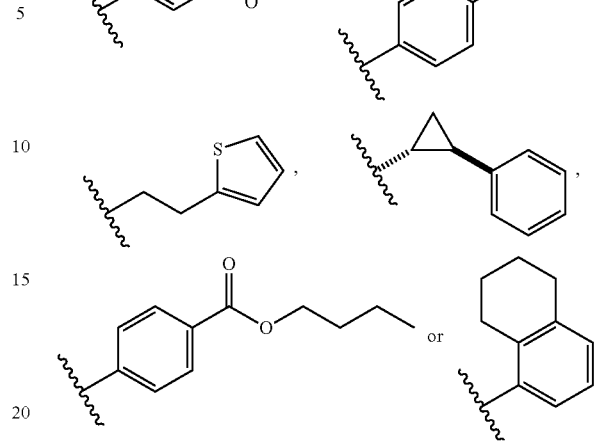

In certain embodiments, the invention relates to any one of the aforementioned compounds, wherein $R^{22b}$ is hydrogen.

In certain embodiments, the invention relates to any one of the aforementioned compounds, wherein $R^{22b}$ is methyl.

In certain embodiments, the invention relates to any one of the aforementioned compounds, wherein $R^1$ is hydrogen.

In certain embodiments, the invention relates to any one of the aforementioned compounds, wherein $R^1$ is alkyl.

In certain embodiments, the invention relates to any one of the aforementioned compounds, wherein $R^1$ is —CH$_3$, —CH$_2$CH$_3$, —CH$_2$CH(CH$_3$)$_2$ or —CH$_2$CH$_2$CH(CH$_3$)$_2$.

In certain embodiments, the invention relates to any one of the aforementioned compounds, wherein $R^1$ is

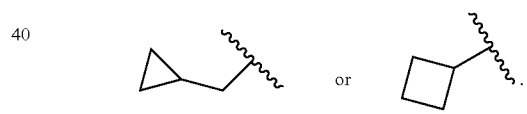

In certain embodiments, the invention relates to any one of the aforementioned compounds, wherein $R^1$ is —CH$_2$CF$_3$.

In certain embodiments, the invention relates to any one of the aforementioned compounds, wherein $R^1$ is —CH$_2$Ph.

In certain embodiments, the invention relates to any one of the aforementioned compounds, wherein $R^1$ is —C(=O)H.

In certain embodiments, the invention relates to any one of the aforementioned compounds, wherein $R^1$ is —C(=O)CH$_3$.

In certain embodiments, the invention relates to any one of the aforementioned compounds, wherein $R^1$ is heterocyclyl or heterocyclylalkyl.

In certain embodiments, the invention relates to any one of the aforementioned compounds, wherein $R^1$ is

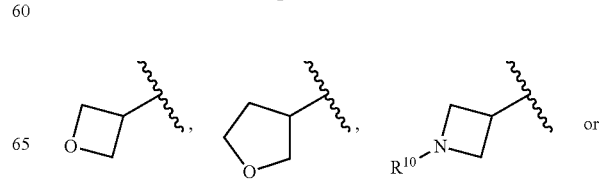

-continued

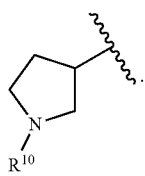

In certain embodiments, the invention relates to any one of the aforementioned compounds, wherein $R^1$ is

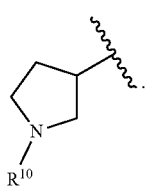

In certain embodiments, the invention relates to any one of the aforementioned compounds, wherein $R^1$ is

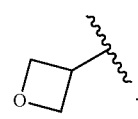

In certain embodiments, the invention relates to any one of the aforementioned compounds, wherein $R^1$ is

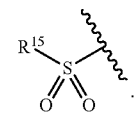

In certain embodiments, the invention relates to any one of the aforementioned compounds, wherein $R^{15}$ is alkyl.

In certain embodiments, the invention relates to any one of the aforementioned compounds, wherein $R^{15}$ is methyl.

In certain embodiments, the invention relates to any one of the aforementioned compounds, wherein $R^{15}$ is cycloalkyl.

In certain embodiments, the invention relates to any one of the aforementioned compounds, wherein $R^{15}$ is cycloalkylalkyl.

In certain embodiments, the invention relates to any one of the aforementioned compounds, wherein $R^1$ is $(C_2-C_4)$alkyl substituted with

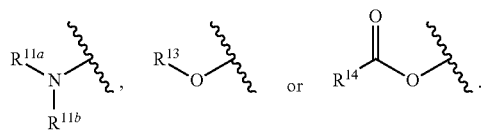

In certain embodiments, the invention relates to any one of the aforementioned compounds, wherein $R^1$ is

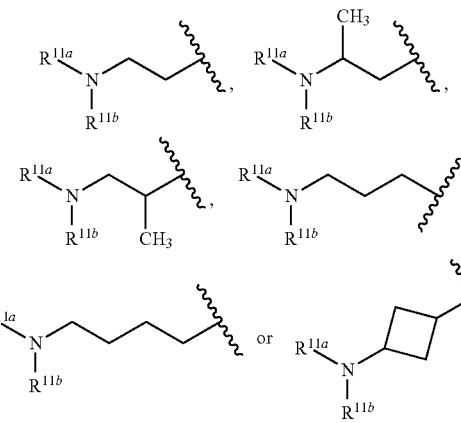

In certain embodiments, the invention relates to any one of the aforementioned compounds, wherein $R^{11a}$ is hydrogen, alkyl, or alkyl-cycloalkyl.

In certain embodiments, the invention relates to any one of the aforementioned compounds, wherein $R^{11a}$ is hydrogen, methyl, or i-propyl.

In certain embodiments, the invention relates to any one of the aforementioned compounds, wherein $R^{22a}$ is heteroaryl.

In certain embodiments, the invention relates to any one of the aforementioned compounds, wherein $R^{22a}$ is substituted phenyloxyphenyl, substituted 4-(phenyl)phenyl or optionally substituted 4-(heteroaryl)phenyl.

In certain embodiments, the invention relates to any one of the aforementioned compounds, wherein $R^{22a}$ is

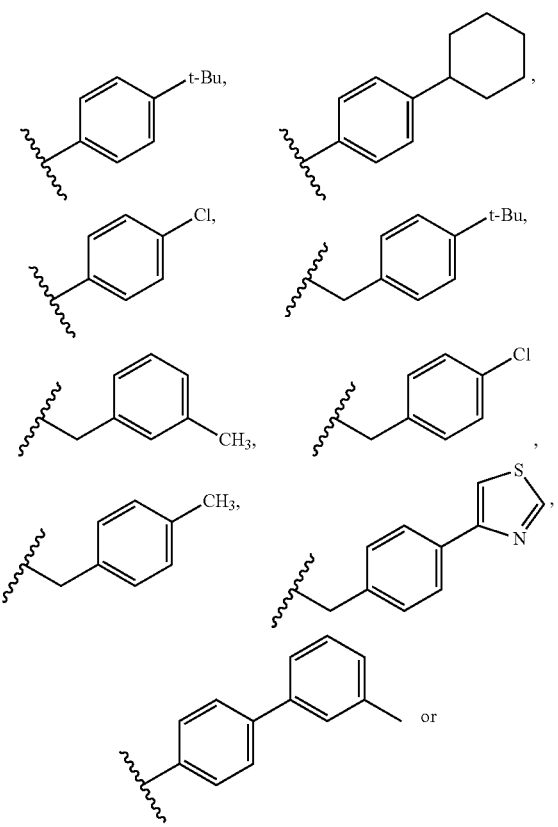

-continued

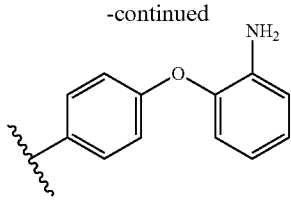

In certain embodiments, the invention relates to any one of the aforementioned compounds, wherein $R^{22a}$ is

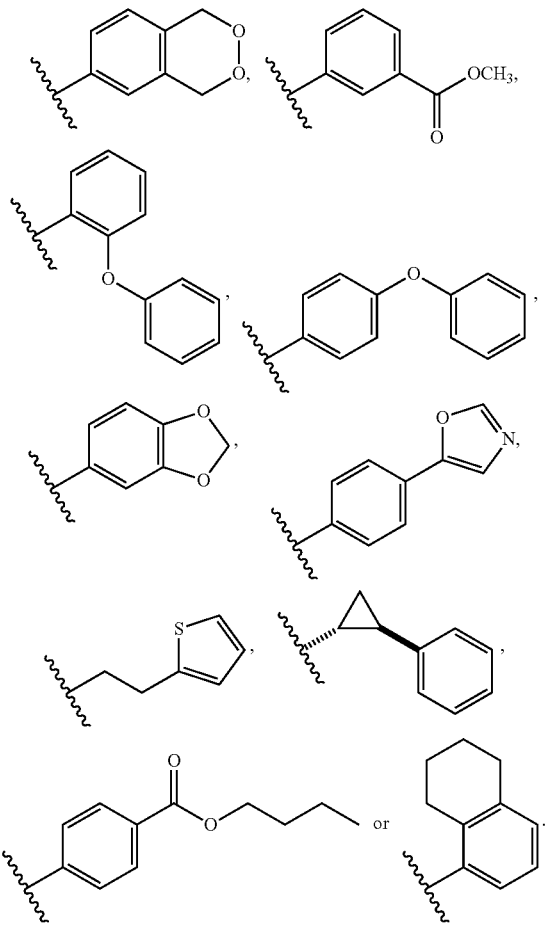

In certain embodiments, the invention relates to any one of the aforementioned compounds, wherein $R^{11a}$ is hydrogen.

In certain embodiments, the invention relates to any one of the aforementioned compounds, wherein $R^{11b}$ is hydrogen.

In certain embodiments, the invention relates to any one of the aforementioned compounds, wherein $R^{11b}$ is methyl.

In certain embodiments, the invention relates to any one of the aforementioned compounds, wherein $R^1$ is

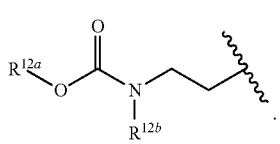

In certain embodiments, the invention relates to any one of the aforementioned compounds, wherein $R^1$ is

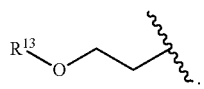

In certain embodiments, the invention relates to any one of the aforementioned compounds, wherein $R^{13}$ is hydrogen.

In certain embodiments, the invention relates to any one of the aforementioned compounds, wherein $R^1$ is

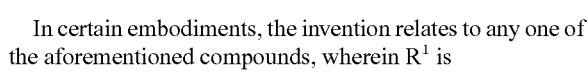

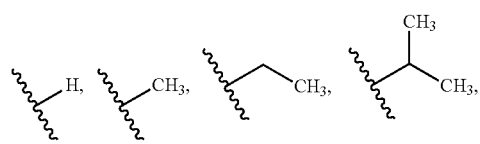

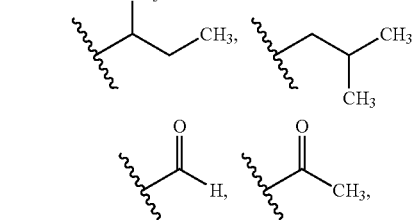

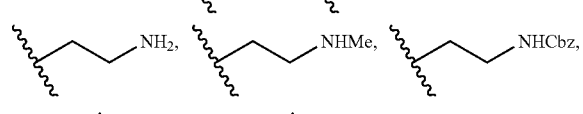

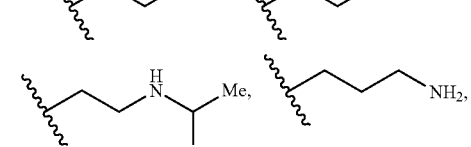

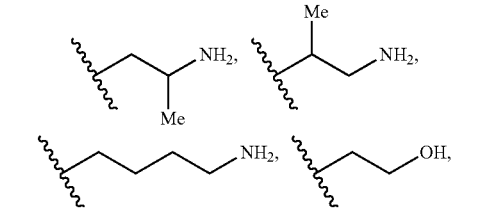

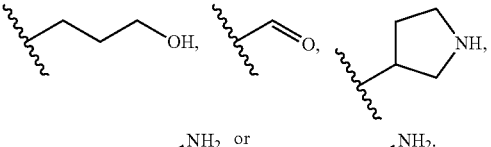

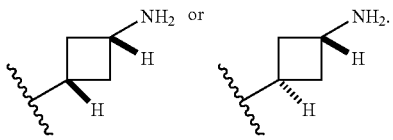

In certain embodiments, the invention relates to any one of the aforementioned compounds, wherein A is

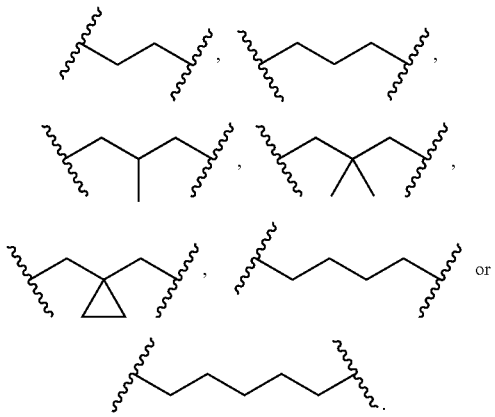
or

In certain embodiments, the invention relates to any one of the aforementioned compounds, wherein A is

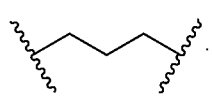

In certain embodiments, the invention relates to any one of the aforementioned compounds, wherein A is

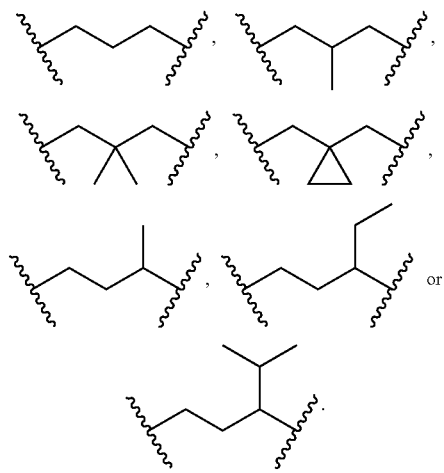
or

In certain embodiments, the invention relates to any one of the aforementioned compounds, wherein A is

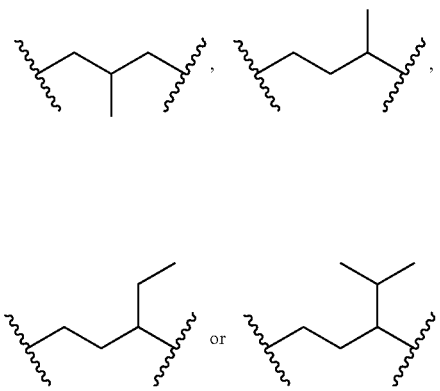
or

In certain embodiments, the invention relates to any one of the aforementioned compounds, wherein A is

In certain embodiments, the invention relates to any one of the aforementioned compounds, wherein A is

In certain embodiments, the invention relates to any one of the aforementioned compounds, wherein A is

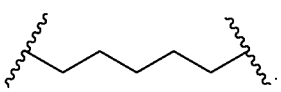 [SMILES: *CCCCC*]

In certain embodiments, the invention relates to any one of the aforementioned compounds, wherein A is

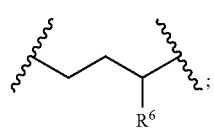

and $R^6$ is alkyl.

In certain embodiments, the invention relates to any one of the aforementioned compounds, wherein A is

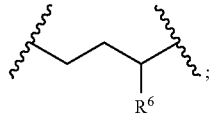

and $R^6$ is methyl, ethyl or isopropyl.

In certain embodiments, the invention relates to any one of the aforementioned compounds, wherein $R^3$ is hydroxyl.

In certain embodiments, the invention relates to any one of the aforementioned compounds, wherein $R^3$ is hydrogen.

In certain embodiments, the invention relates to any one of the aforementioned compounds, wherein $R^4$ is hydroxyl.

In certain embodiments, the invention relates to any one of the aforementioned compounds, wherein $R^4$ is hydrogen.

In certain embodiments, the invention relates to any one of the aforementioned compounds, wherein $R^{41}$ is hydrogen.

In certain embodiments, the invention relates to any one of the aforementioned compounds, wherein $R^{41}$ is methyl.

In certain embodiments, the invention relates to any one of the aforementioned compounds, wherein $R^3$ is hydroxyl; and $R^4$ is hydroxyl.

In certain embodiments, the invention relates to any one of the aforementioned compounds, wherein $R^3$ is hydroxyl; $R^4$ is hydroxyl; and $R^{41}$ is hydrogen.

In certain embodiments, the invention relates to any one of the aforementioned compounds, wherein $R^3$ is hydroxyl; $R^4$ is hydroxyl; and $R^{41}$ is methyl.

In certain embodiments, the invention relates to any one of the aforementioned compounds, wherein $R^3$ is hydrogen; and $R^4$ is hydroxyl.

In certain embodiments, the invention relates to any one of the aforementioned compounds, wherein $R^3$ is hydrogen; $R^4$ is hydroxyl; and $R^{41}$ is hydrogen.

In certain embodiments, the invention relates to any one of the aforementioned compounds, wherein $R^3$ is hydrogen; $R^4$ is hydroxyl; and $R^{41}$ is methyl.

In certain embodiments, the invention relates to any one of the aforementioned compounds, wherein $R^3$ is hydroxyl; and $R^4$ is hydrogen.

In certain embodiments, the invention relates to any one of the aforementioned compounds, wherein $R^3$ is hydroxyl; $R^4$ is hydrogen; and $R^{41}$ is hydrogen.

In certain embodiments, the invention relates to any one of the aforementioned compounds, wherein $R^3$ is hydroxyl; $R^4$ is hydrogen; and $R^{41}$ is methyl.

In certain embodiments, the invention relates to any one of the aforementioned compounds, wherein Z is hydrogen or

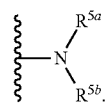

In certain embodiments, the invention relates to any one of the aforementioned compounds, wherein Z is hydrogen.

In certain embodiments, the invention relates to any one of the aforementioned compounds, wherein Z is

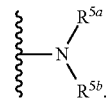

In certain embodiments, the invention relates to any one of the aforementioned compounds, wherein $R^{5a}$ is hydrogen, alkyl, carbocyclyl, heterocyclyl, aryl, heteroaryl, carbocyclylalkyl, heterocyclylalkyl, aralkyl, or heteroaralkyl.

In certain embodiments, the invention relates to any one of the aforementioned compounds, wherein $R^{5a}$ is hydrogen, aralkyloxyalkyl, alkyl, aryl, aralkyl, aminoalkyl or hydroalkyl.

In certain embodiments, the invention relates to any one of the aforementioned compounds, wherein $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_3$, —CH$_2$Ph, —CH$_2$CH$_2$NH$_2$, —CH$_2$(cyclohexyl) or —CH$_2$CH$_2$OH.

In certain embodiments, the invention relates to any one of the aforementioned compounds, wherein $R^{5b}$ is hydrogen, alkyl, carbocyclyl, heterocyclyl, aryl, heteroaryl, carbocyclylalkyl, heterocyclylalkyl, aralkyl, or heteroaralkyl.

In certain embodiments, the invention relates to any one of the aforementioned compounds, wherein $R^{5b}$ is hydrogen, aralkyloxyalkyl, alkyl, aryl, aralkyl, aminoalkyl or hydroalkyl.

In certain embodiments, the invention relates to any one of the aforementioned compounds, wherein $R^{5b}$ is hydrogen.

In certain embodiments, the invention relates to any one of the aforementioned compounds, wherein $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_3$, —CH$_2$Ph, —CH$_2$CH$_2$NH$_2$, —CH$_2$(cyclohexyl) or —CH$_2$CH$_2$OH; and $R^{5b}$ is —H.

In certain embodiments, the invention relates to any one of the aforementioned compounds, wherein $R^{7a}$ is hydrogen or lower alkyl.

In certain embodiments, the invention relates to any one of the aforementioned compounds, wherein $R^{7a}$ is hydrogen.

In certain embodiments, the invention relates to any one of the aforementioned compounds, wherein $R^{7b}$ is hydrogen or lower alkyl.

In certain embodiments, the invention relates to any one of the aforementioned compounds, wherein $R^{7b}$ is hydrogen.

One aspect of the invention relates to a compound, or a pharmaceutically acceptable salt, hydrate, enantiomer or stereoisomer thereof, selected from the group consisting of

23
24
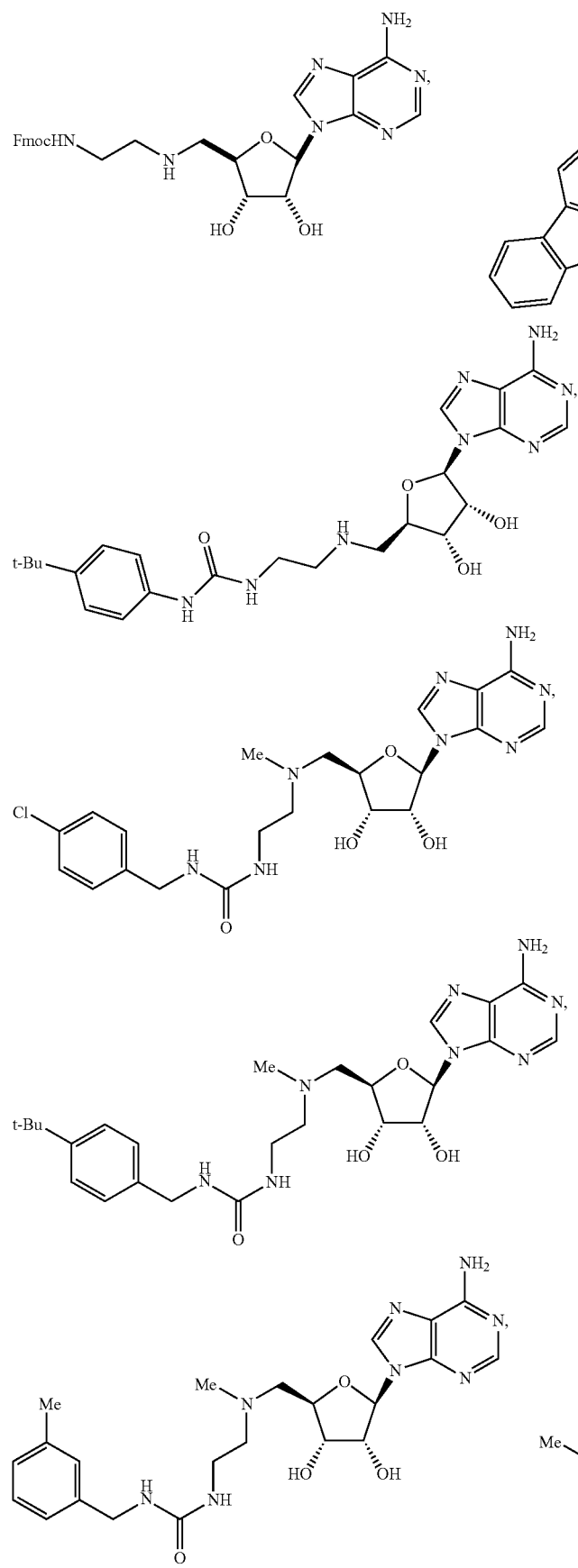
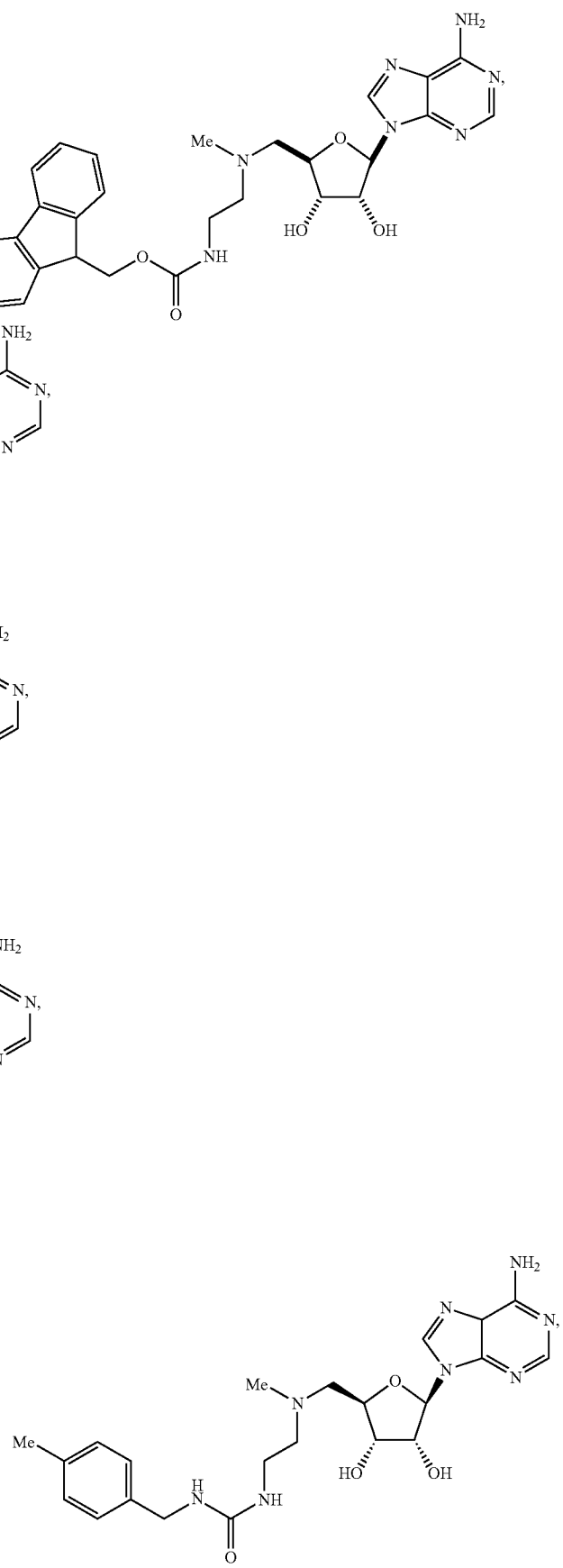

-continued
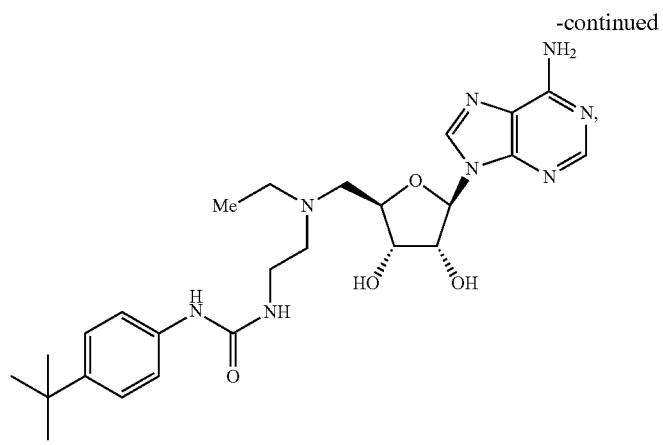
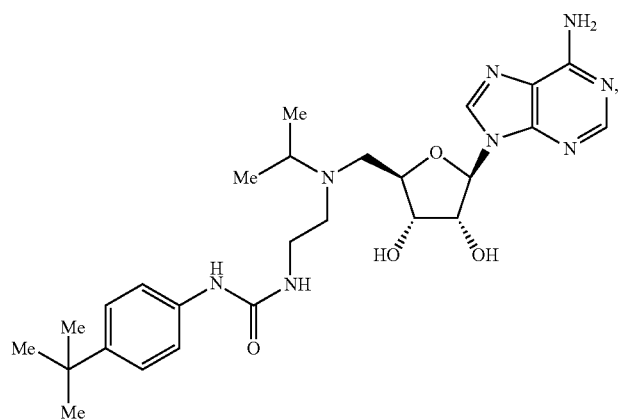
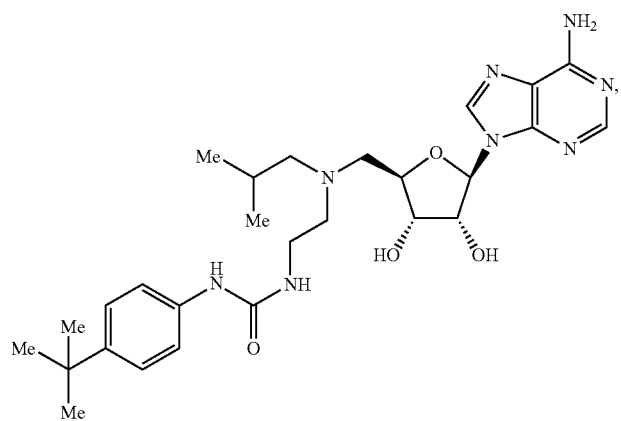
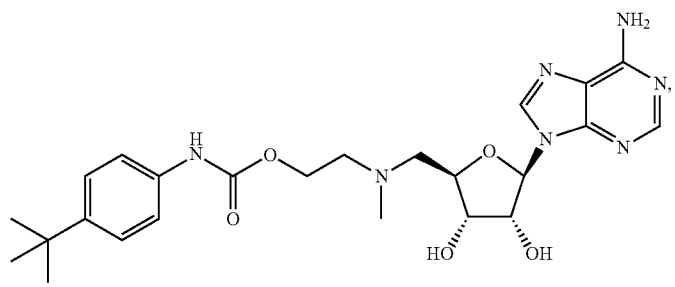

-continued
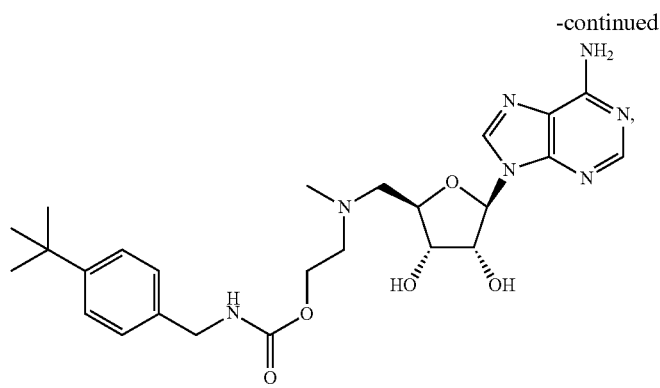
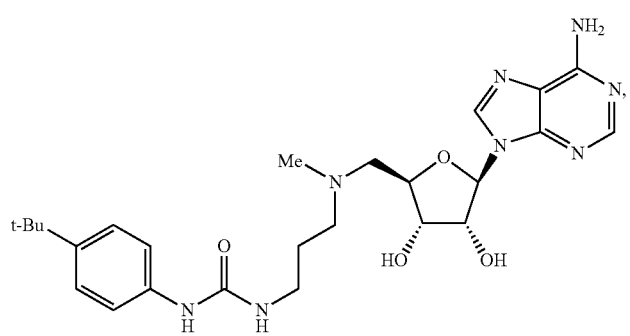
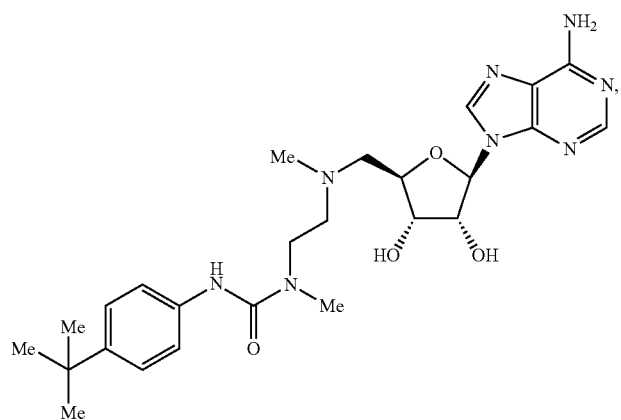
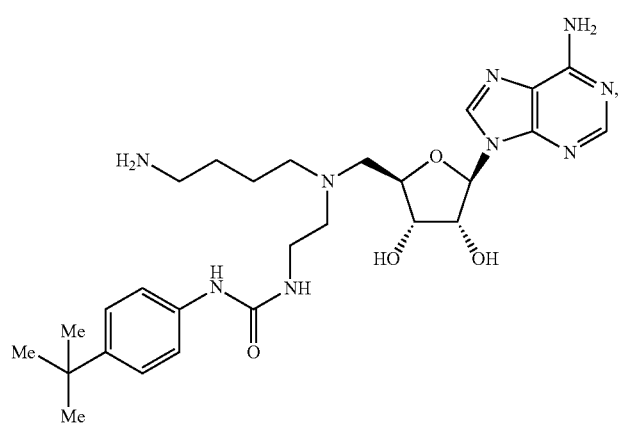

-continued
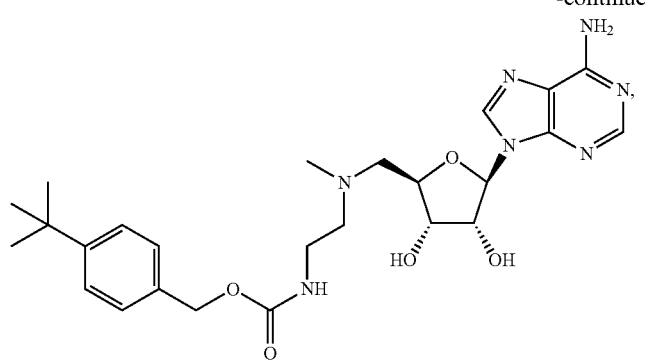
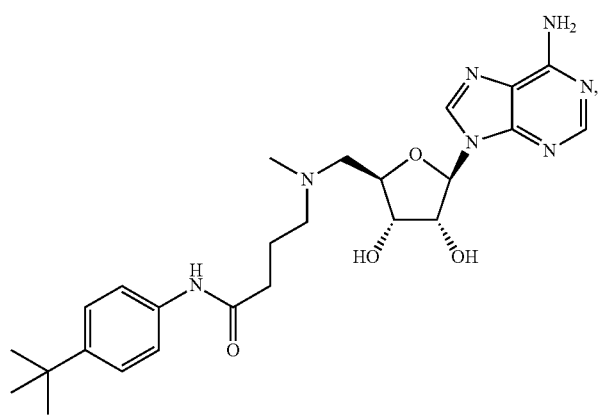
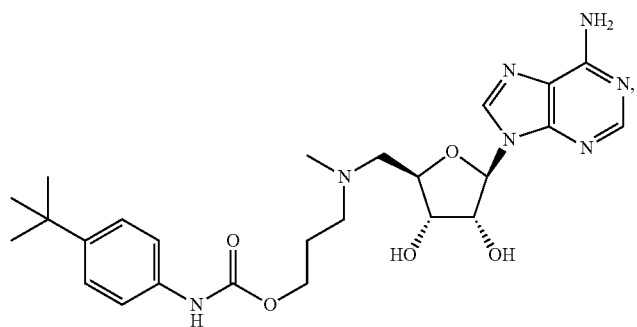
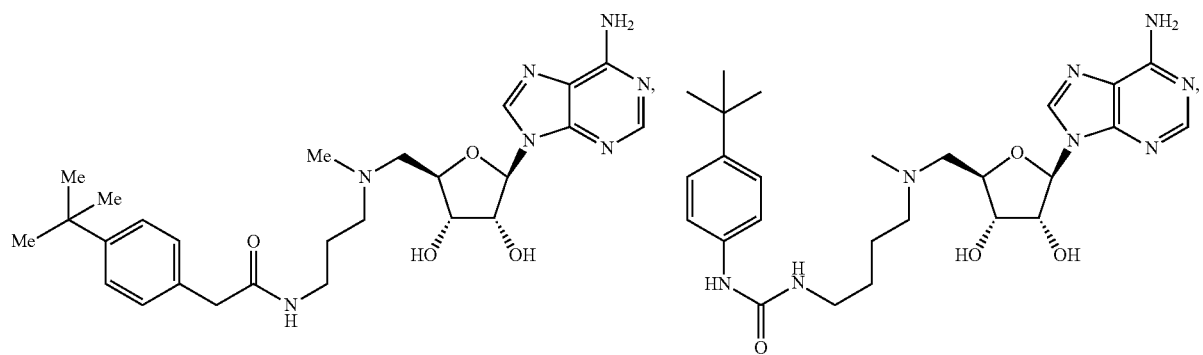

-continued
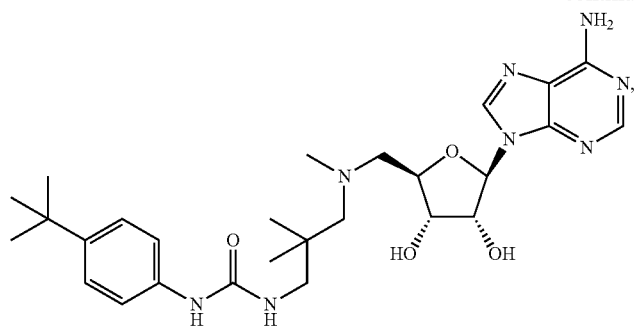
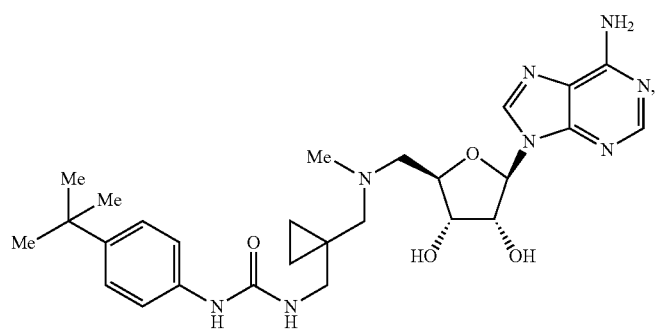
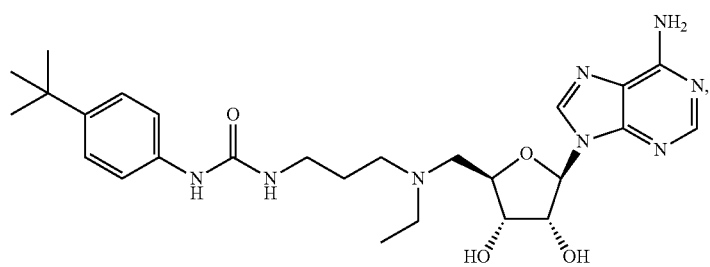
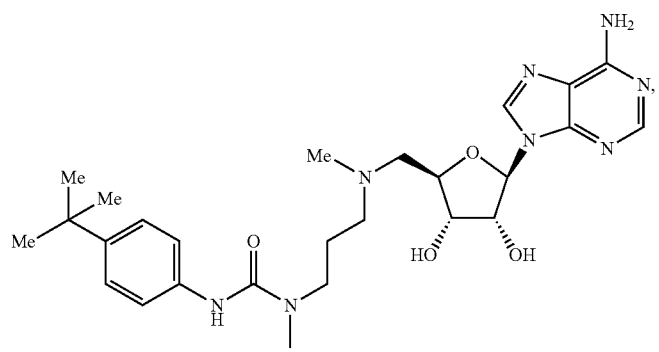
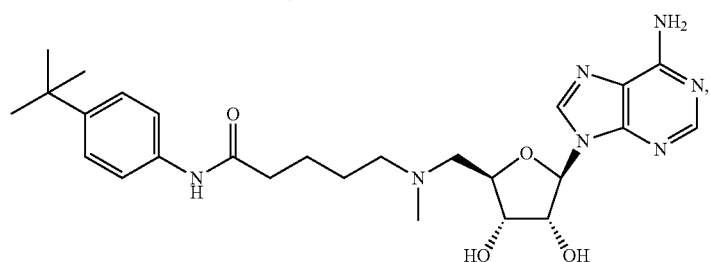

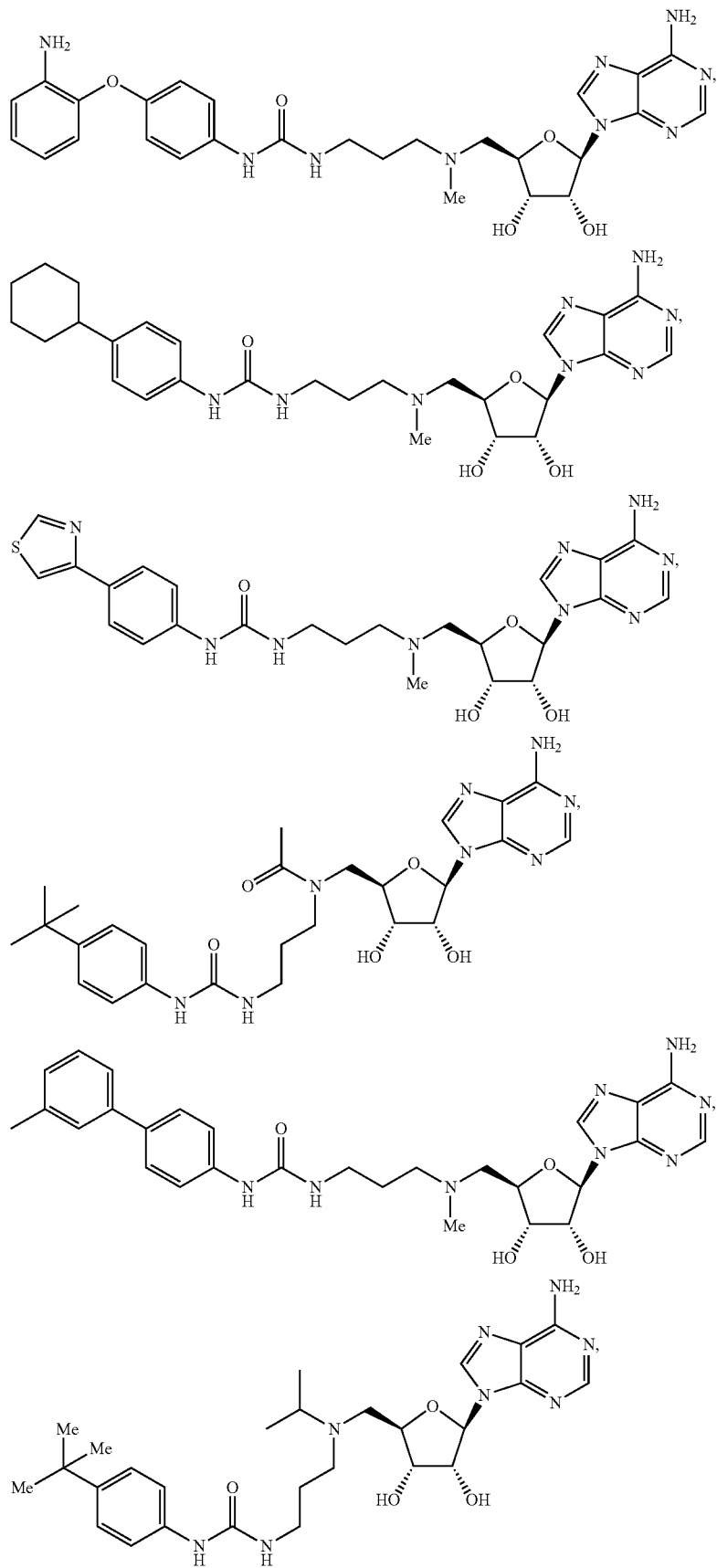

-continued
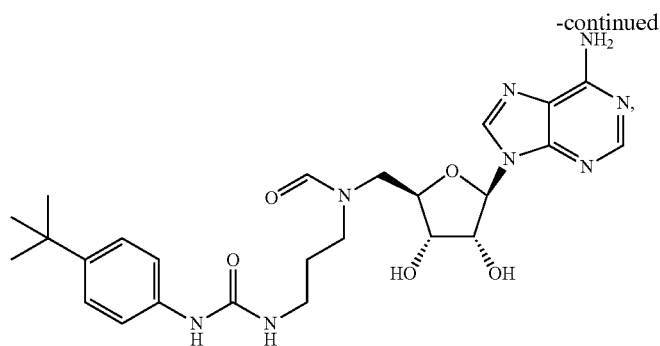
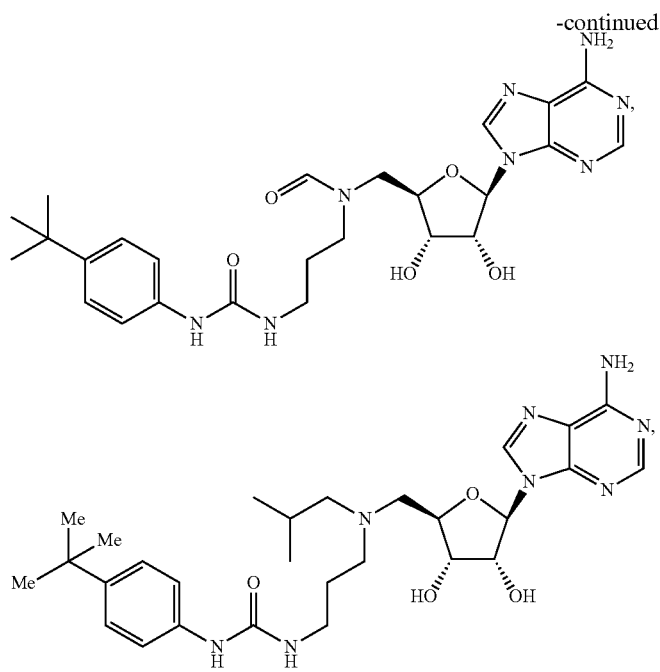
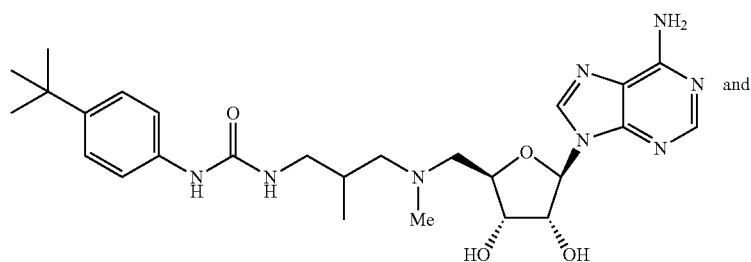
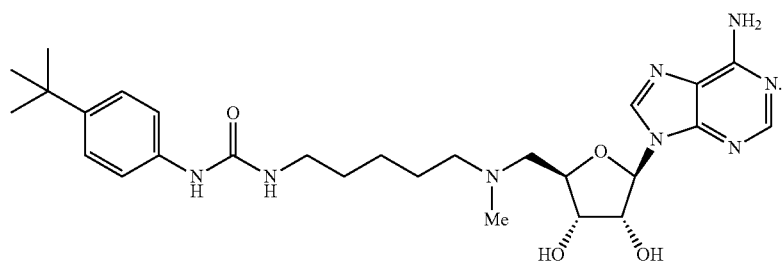
One aspect of the invention relates to a compound, or a pharmaceutically acceptable salt, hydrate, enantiomer or stereoisomer thereof, selected from the group consisting of
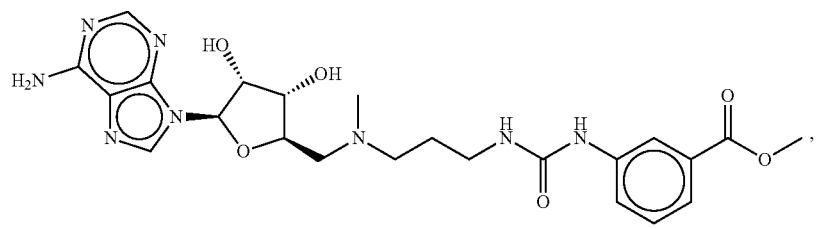

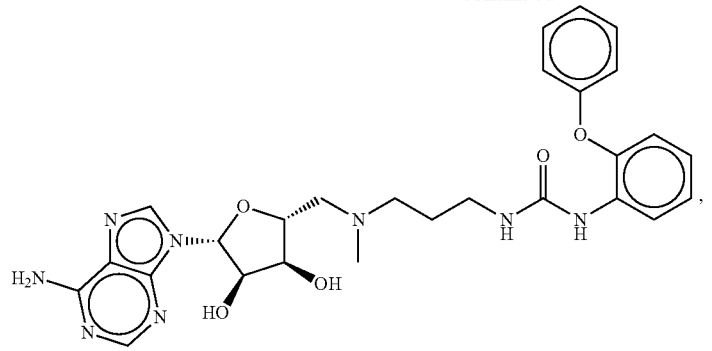
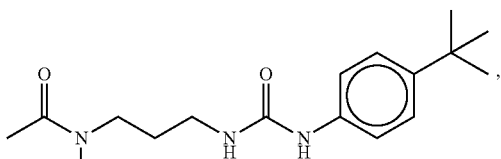
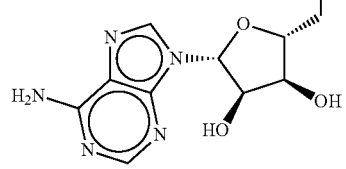
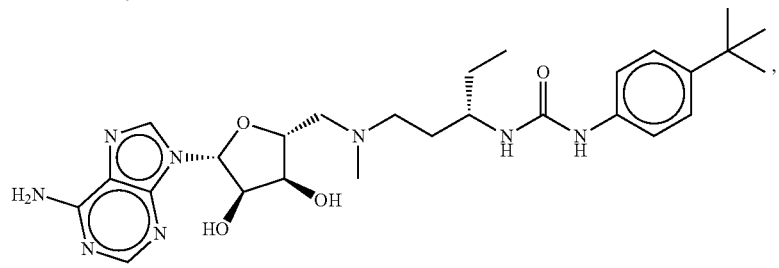
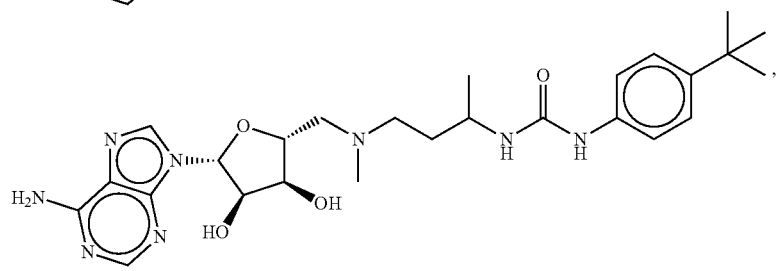
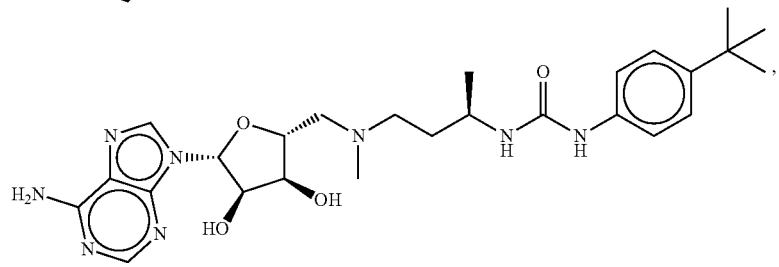
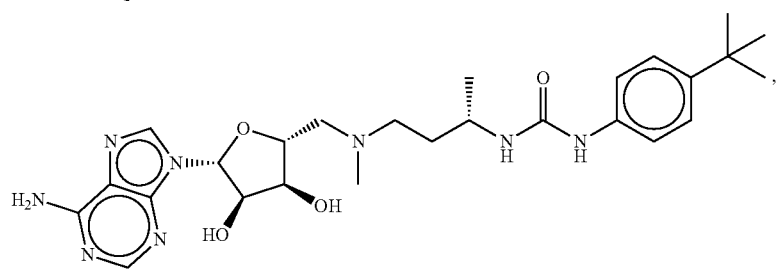

-continued
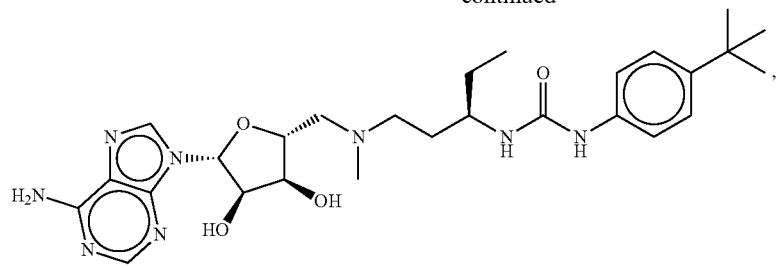
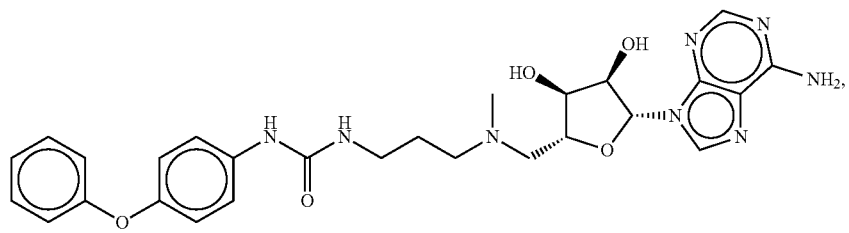
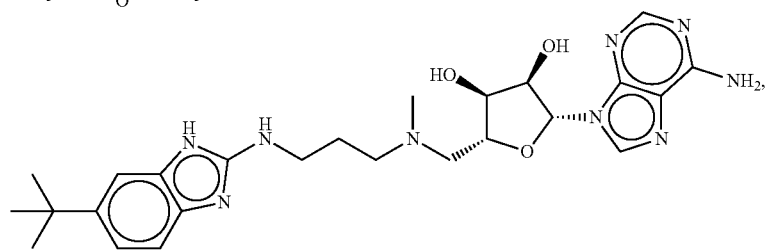
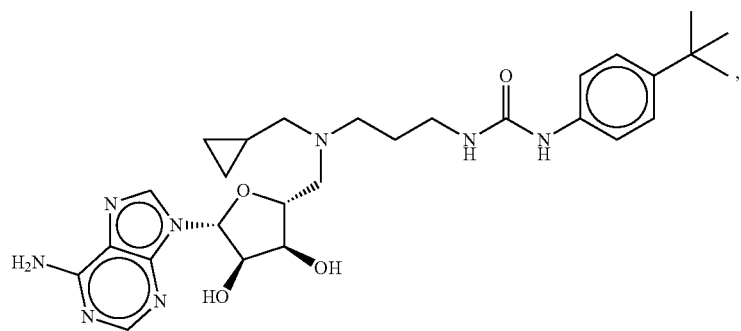
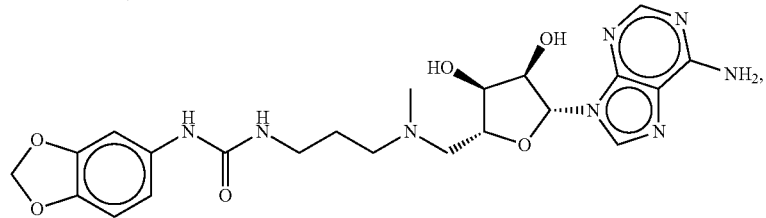
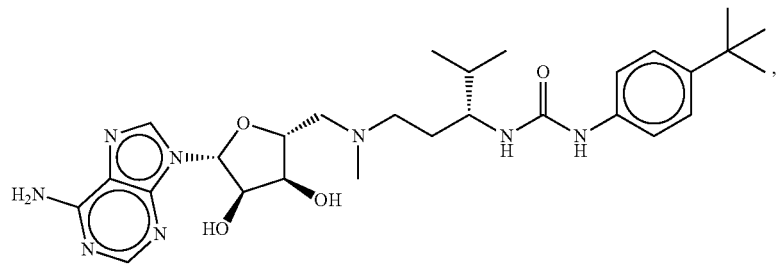

-continued
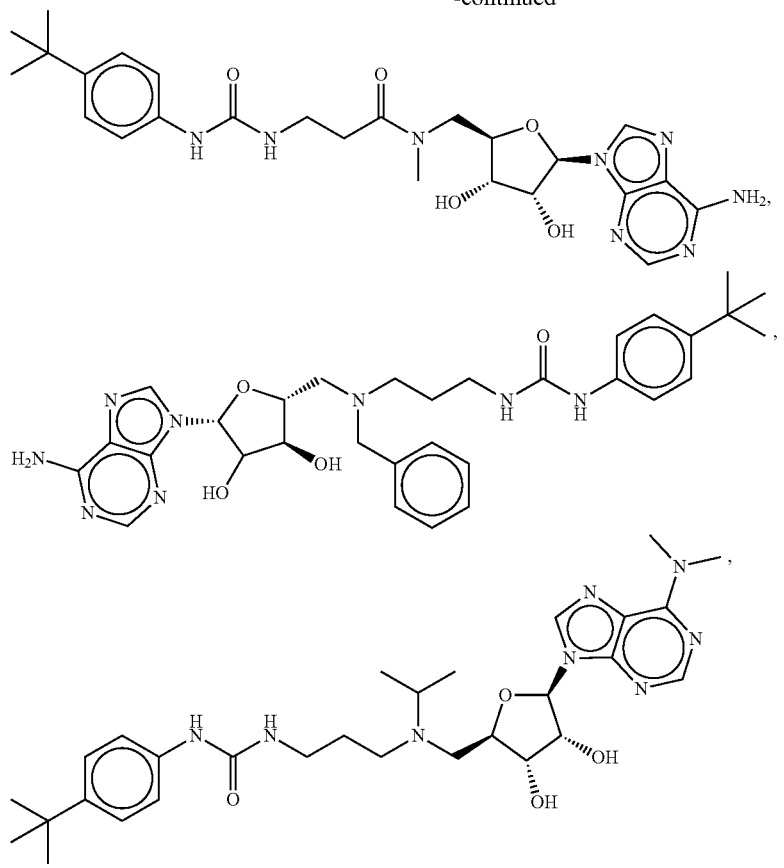
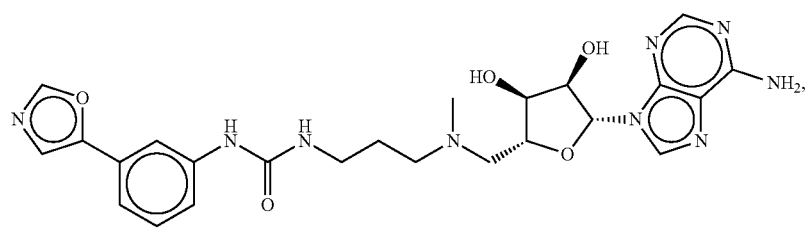
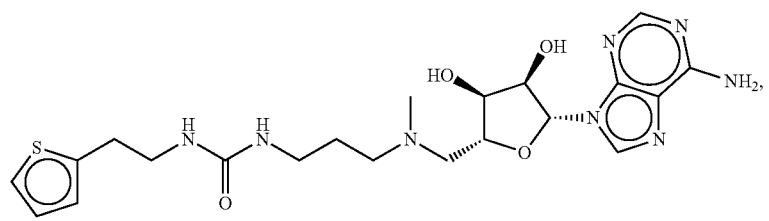
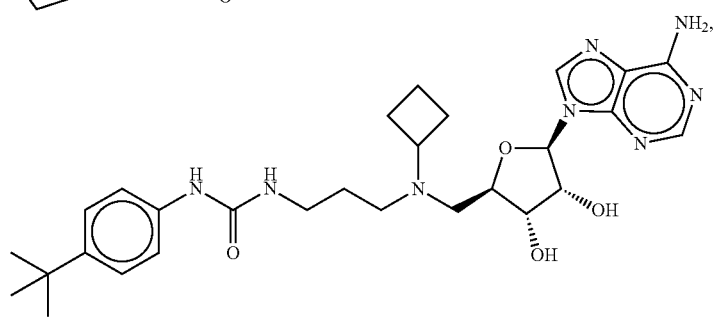

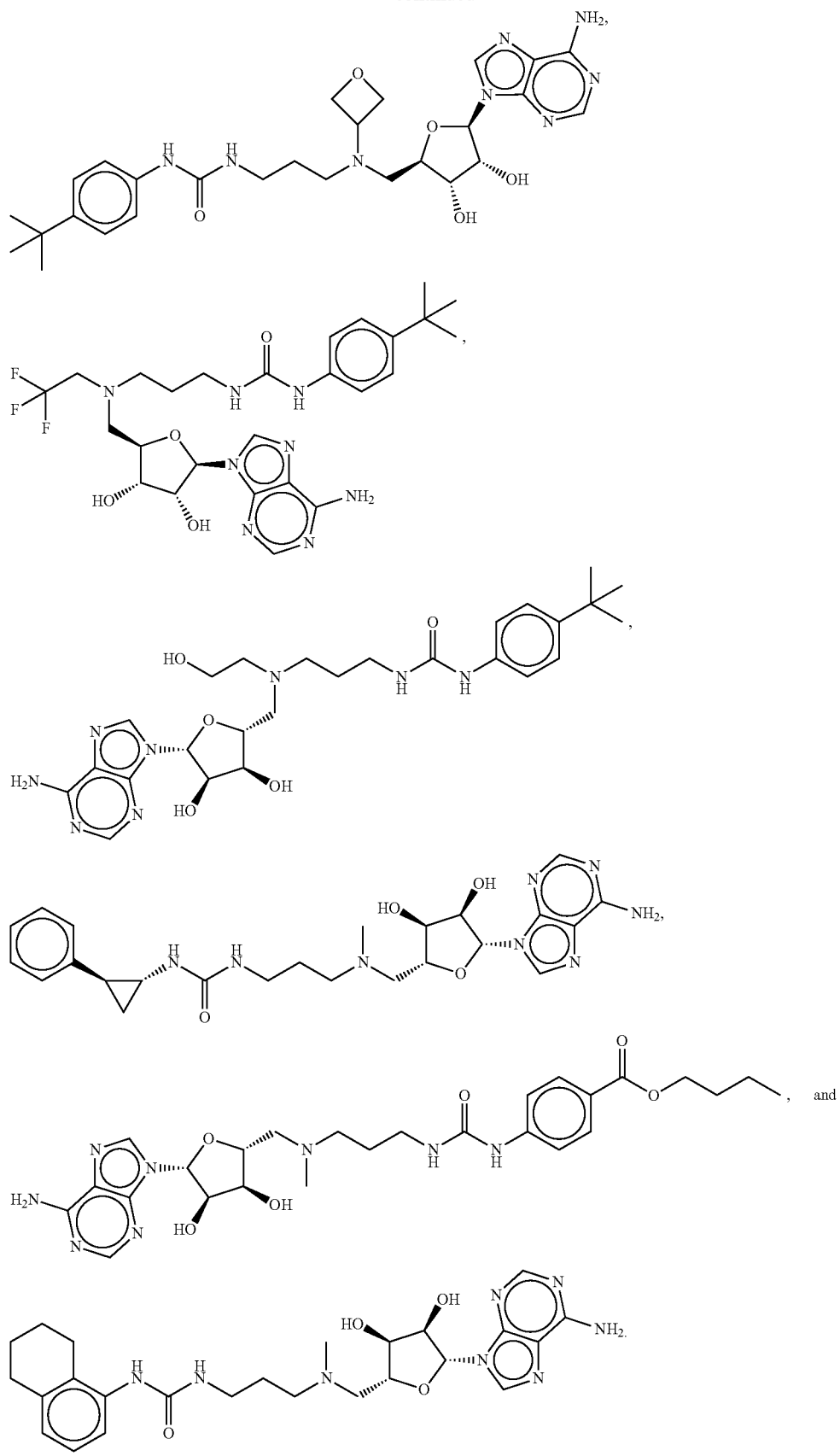

One aspect of the invention relates to a compound, or a pharmaceutically acceptable salt, hydrate, enantiomer or stereoisomer thereof, selected from the group consisting of

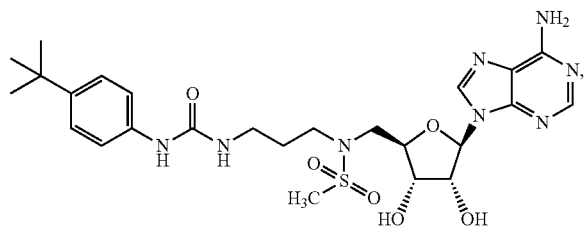

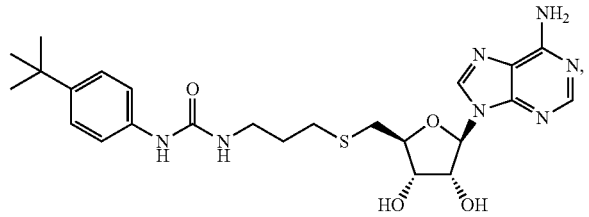

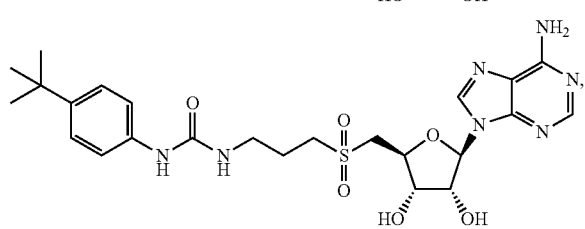

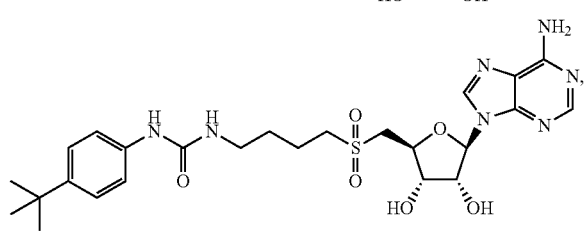

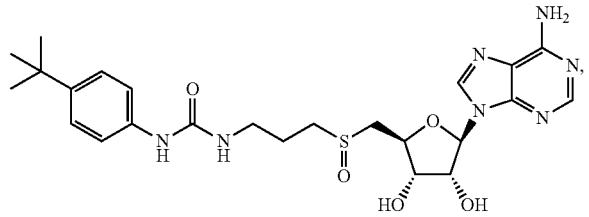

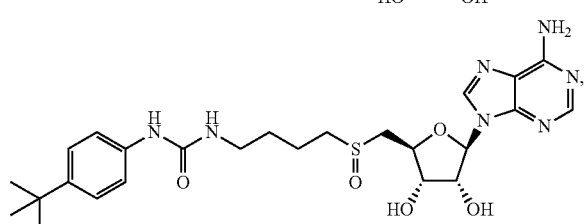

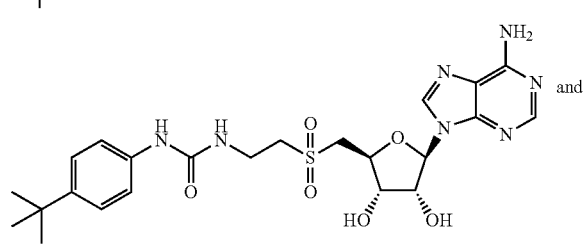

and

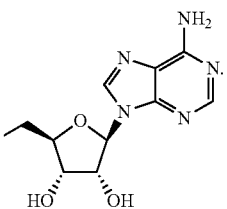

In certain embodiments, the invention relates to any one of the aforementioned compounds, wherein the compound inhibits DOT1L with an $IC_{50}$ of less than about 10 µM. In certain embodiments, the invention relates to any one of the aforementioned compounds, wherein the compound inhibits DOT1L with an $IC_{50}$ of less than about 5 µM. In certain embodiments, the invention relates to any one of the aforementioned compounds, wherein the compound inhibits DOT1L with an $IC_{50}$ of less than about 1 µM. In certain embodiments, the invention relates to any one of the aforementioned compounds, wherein the compound inhibits DOT1L with an $IC_{50}$ of less than about 750 nM. In certain embodiments, the invention relates to any one of the aforementioned compounds, wherein the compound inhibits DOT1L with an $IC_{50}$ of less than about 500 nM. In certain embodiments, the invention relates to any one of the aforementioned compounds, wherein the compound inhibits DOT1L with an $IC_{50}$ of less than about 250 nM. In certain embodiments, the invention relates to any one of the aforementioned compounds, wherein the compound inhibits DOT1L with an $IC_{50}$ of less than about 100 nM.

In certain embodiments, the invention relates to any one of the aforementioned compounds, wherein the compound is a selective inhibitor of DOT1L.

In certain embodiments, the invention relates to any one of the aforementioned compounds, wherein the compound inhibits both DOT1L and EZH2; the compound has a DOT1L $IC_{50}$ of between about 0.001 µM and about 10 µM; and the ratio of the EZH2 $IC_{50}$ to the DOT1L $IC_{50}$ is between about 10 and about 50. In certain embodiments, the invention relates to any one of the aforementioned compounds, wherein the compound inhibits both DOT1L and EZH2; the compound has a DOT1L $IC_{50}$ of between about 0.001 µM and about 10 µM; and the ratio of the EZH2 $IC_{50}$ to the DOT1L $IC_{50}$ is between about 50 and about 100. In certain embodiments, the invention relates to any one of the aforementioned compounds, wherein the compound inhibits both DOT1L and EZH2; the compound has a DOT $IC_{50}$ of between about 0.001 µM and about 10 µM; and the ratio of the EZH2 $IC_{50}$ to the DOT1L $IC_{50}$ is between about 100 and about 1,000.

In certain embodiments, the invention relates to any one of the aforementioned compounds, wherein the compound inhibits both DOT1L and EHMT2; the compound has a DOT1L $IC_{50}$ of between about 0.001 µM and about 10 µM; and the ratio of the EHMT2 $IC_{50}$ to the DOT1L $IC_{50}$ is between about 10 and about 50. In certain embodiments, the invention relates to any one of the aforementioned compounds, wherein the compound inhibits both DOT1L and EHMT2; the compound has a DOT1L $IC_{50}$ of between about 0.001 µM and about 10 µM; and the ratio of the EHMT2 $IC_{50}$ to the DOT1L $IC_{50}$ is between about 50 and about 100. In certain embodiments, the invention relates to any one of the aforementioned compounds, wherein the compound inhibits both DOT1L and EHMT2; the compound has a DOT1L $IC_{50}$ of between about 0.001 µM and about 10 µM; and the ratio of the EHMT2 $IC_{50}$ to the DOT1L $IC_{50}$ is between about 100 and about 1,000.

In certain embodiments, the invention relates to any one of the aforementioned compounds, wherein the compound inhibits both DOT1L and CARM1; the compound has a DOT $IC_{50}$ of between about 0.001 µM and about 10 µM; and the ratio of the CARM1 $IC_{50}$ to the DOT1L $IC_{50}$ is between about 10 and about 50. In certain embodiments, the invention relates to any one of the aforementioned compounds, wherein the compound inhibits both DOT1L and CARM1; the compound has a DOT1L $IC_{50}$ of between about 0.001 µM and about 10 µM; and the ratio of the CARM1 $IC_{50}$ to the DOT1L $IC_{50}$ is between about 50 and about 100. In certain embodiments, the invention relates to any one of the aforementioned compounds, wherein the compound inhibits both DOT1L and CARM1; the compound has a DOT1L $IC_{50}$ of between about 0.001 µM and about 10 µM; and the ratio of the CARM1 $IC_{50}$ to the DOT1L $IC_{50}$ is between about 100 and about 1,000.

In certain embodiments, the invention relates to any one of the aforementioned compounds, wherein the compound inhibits both DOT1L and PRMT5; the compound has a DOT1L $IC_{50}$ of between about 0.001 µM and about 10 µM; and the ratio of the PRMT5 $IC_{50}$ to the DOT1L $IC_{50}$ is between about 10 and about 50. In certain embodiments, the invention relates to any one of the aforementioned compounds, wherein the compound inhibits both DOT1L and PRMT5; the compound has a DOT1L $IC_{50}$ of between about 0.001 µM and about 10 µM; and the ratio of the PRMT5 $IC_{50}$ to the DOT1L $IC_{50}$ is between about 50 and about 100. In certain embodiments, the invention relates to any one of the aforementioned compounds, wherein the compound inhibits both DOT1L and PRMT5; the compound has a DOT1L $IC_{50}$ of between about 0.001 µM and about 10 µM; and the ratio of the PRMT5 $IC_{50}$ to the DOT1L $IC_{50}$ is between about 100 and about 1,000.

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a subject. Pharmaceutically compatible salts may be formed with many acids, including but not limited to hydrochloric, sulfuric, acetic, lactic, tartaric, malic, and succinic acids. Salts tend to be more soluble in water or other protic solvents than their corresponding free base forms. The present invention includes such salts.

Pharmaceutically acceptable acid addition salts include those formed with mineral acids such as hydrochloric acid and hydrobromic acid, and also those formed with organic acids such as maleic acid. For example, acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di alkyl-N-(hydroxy alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Certain compounds of the invention and their salts may exist in more than one crystalline form (i.e., polymorph); the present invention includes each of the crystal forms and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures thereof. The enantiomers may be resolved by methods known to those skilled in the art; for example, enantiomers may be resolved by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example, via enzymatic esterification; or gas-liquid or liquid chromatography in a chiral environment, for example, on a chiral support; suitable include chiral supports (e.g., silica with a bound chiral ligand) or in the presence of a chiral solvent. Where the desired enantiomer is converted into another chemical entity by one of the separation procedures described above, a further step may be used to liberate the desired purified enantiomer. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art (for example, chromatography or crystallization) and the individual enantiomers may be separated as described above. The present invention includes the various diastereoisomers of compounds of the invention, and mixtures thereof. Compounds of the invention may exist in different tautomeric forms or as different geometric isomers, and the present invention includes each tautomer and/or geometric isomer of compounds of the invention, and mixtures thereof. Compounds of the invention may exist in zwitterionic form. The present invention includes each zwitterionic form of compounds of the invention, and mixtures thereof.

As used herein the term "prodrug" refers to an agent which is converted into the parent drug in vivo by some physiological chemical process (e.g., a prodrug on being brought to the physiological pH is converted to the desired drug form). Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present invention wherein it is administered as an ester (the "prodrug") to facilitate transmittal across a cell membrane where water solubility is not beneficial, but then it is metabolically hydrolyzed to the carboxylic acid once inside the cell where water solubility is beneficial. Prodrugs have many useful properties. For example, a prodrug may be more water soluble than the ultimate drug, thereby facilitating intravenous administration of the drug. A prodrug may also have a higher level of oral bioavailability than the ultimate drug. After administration, the prodrug is enzymatically or chemically cleaved to deliver the ultimate drug in the blood or tissue.

Exemplary prodrugs release an amine of a compound of the invention wherein the free hydrogen of an amine or alcohol is replaced by $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyl-oxymethyl, N—$(C_1-C_6)$alkoxycarbonylamino-methyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O$(C_1-C_6)$alkyl)$_2$ or glycosyl (the radical resulting from detachment of the hydroxyl of the hemiacetal of a carbohydrate).

Other exemplary prodrugs upon cleavage release a corresponding free acid, and such hydrolyzable ester-forming residues of the compounds of the invention include but are not limited to carboxylic acid substituents (e.g., —(CH$_2$)C(O)OH or a moiety that contains a carboxylic acid) wherein the free hydrogen is replaced by $(C_1-C_4)$alkyl, $(C_2-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$alkyl.

"Tautomer" is one of two or more structural isomers that exist in equilibrium and which readily convert from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs include: ketone-enol, amide-nitrile, lactam-lactim, amide-imidic acid tautomerism in heterocyclic rings (e.g., in nucleobases such as guanine, thymine and cytosine), amine-enamine and enamine-enamine.

Benzimidazoles also exhibit tautomerism: when the benzimidazole contains one or more substituents in the 4-, 5-, 6- or 7-positions, the possibility of different isomers arises. For example, 2,5-dimethyl-1H-benzo[d]imidazole can exist in equilibrium with its isomer 2,6-dimethyl-1H-benzo[d]imidazole via tautomerization.

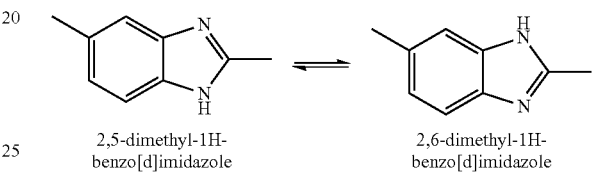

2,5-dimethyl-1H-benzo[d]imidazole     2,6-dimethyl-1H-benzo[d]imidazole

It is to be understood that the compounds of the present invention may be depicted as different tautomers. It should also be understood that when compounds have tautomeric forms, all tautomeric forms are intended to be included in the scope of the present invention, and the specific naming convention used for a particular compound does not exclude any tautomer form.

By protecting a reactive functional group, reactions involving other unprotected reactive functional groups can be performed without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (C(=O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(=O)R) or a urethane (—NRC(=O)OR), for example, as: a methyl amide (—NHC(=O)CH$_3$); a benzyloxy amide (—NHC(=O)OCH$_2$C$_6$H$_5$NHCbz); as a t-butoxy amide (—NHC=(=O)OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(=O)CH$_3$).

For example, a benzimidazole group may be protected with a SEM or benzyl protecting group.

Pharmaceutical Compositions

One or more compounds of the invention can be administered to a human patient by themselves or in pharmaceutical compositions where they are mixed with suitable carriers or excipient(s) at doses to treat or ameliorate a disease or condition as described herein. Mixtures of these compounds can also be administered to the patient as a simple mixture or in suitable formulated pharmaceutical compositions. For example, one aspect of the invention relates to pharmaceutical composition comprising a therapeutically effective dose of a compound of formula I, or a pharmaceutically acceptable salt, hydrate, enantiomer or stereoisomer thereof; and a pharmaceutically acceptable diluent or carrier; wherein the compound of formula I is represented by

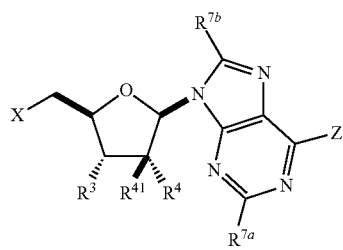

I wherein independently for each occurrence,
X is

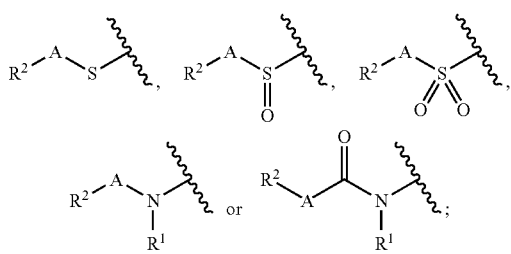

R$^1$ is hydrogen, alkyl, cycloalkyl, alkylcycloalkyl, alkylaryl, haloalkyl, formyl, heterocyclyl, heterocyclylalkyl,

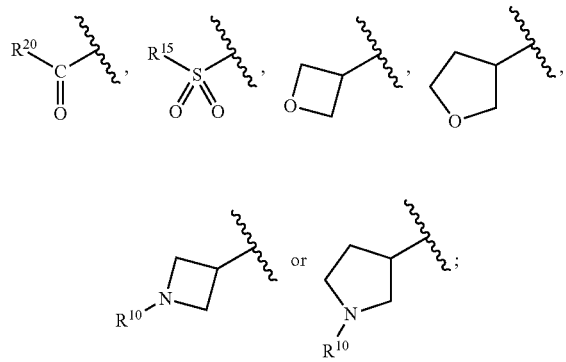

or (C$_2$-C$_4$)alkyl substituted with

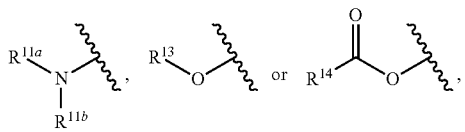

except that when X is

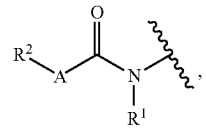

R$^1$ is not

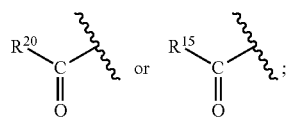

R$^{10}$ is hydrogen or alkyl;
R$^{11a}$ is hydrogen, alkyl, or alkyl-cycloalkyl;
R$^{11b}$ is hydrogen or alkyl; or taken together with R$^{11a}$ and the nitrogen to which it is attached forms a 4- to 8-membered heterocyclyl comprising 0 or 1 additional heteroatoms;
R$^{13}$ is hydrogen, alkyl, aryl, heteroaryl, aralkyl, heteroaralkyl or silyl;
R$^{14}$ is hydrogen, alkyl, aryl, heteroaryl, aralkyl or heteroaralkyl;
R$^{15}$ is alkyl, cycloalkyl or cycloalkylalkyl;
R$^{20}$ is hydrogen, alkyl, cycloalkyl or cycloalkylalkyl;
A is

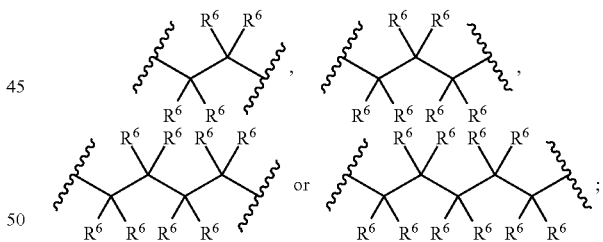

R$^2$ is

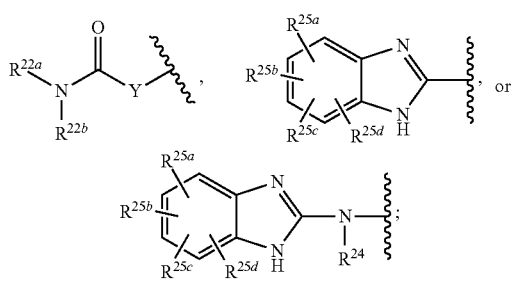

Y is —NH—, —N(alkyl)-, —O—, or —CR$^6_2$—;

R$^{22a}$ is aryl, heteroaryl, aralkyl, heteroaralkyl, fused bicyclyl, biaryl, aryloxyaryl, heteroaryloxyaryl, aryloxyheteroaryl or heteroaryloxyheteroaryl;

R$^{22b}$ is hydrogen or alkyl;

R$^{24}$ is hydrogen or alkyl;

R$^{25a}$, R$^{25b}$, R$^{25c}$, R$^{25d}$ are independently -M$_2$-T$_2$, in which M$_2$ is a bond, SO$_2$, SO, S, CO, CO$_2$, O, O—C$_1$-C$_4$ alkyl linker, C$_1$-C$_4$ alkyl linker, NH, or N(R$_t$), R$_t$ being C$_1$-C$_6$ alkyl, and T$_2$ is H, halo, or R$_{S4}$, R$_{S4}$ being C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 8-membered heterocycloalkyl, or 5 to 10-membered heteroaryl, and each of O—C$_1$-C$_4$ alkyl linker, C$_1$-C$_4$ alkyl linker, R$_t$, and R$_{S4}$ being optionally substituted with one or more substituents selected from the group consisting of halo, hydroxyl, carboxyl, cyano, C$_1$-C$_6$ alkyl, C$_2$-C$_6$ alkenyl, C$_2$-C$_6$ alkynyl, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

R$^3$ is hydrogen, halogen, hydroxy, alkyloxy, aralkyloxy, alkylcarbonyloxy or silyloxy;

R$^4$ is hydrogen, halogen, hydroxy, alkyloxy, aralkyloxy, alkylcarbonyloxy or silyloxy;

R$^{41}$ is hydrogen, alkyl or alkynyl;

Z is hydrogen or

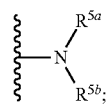

R$^{5a}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl;

R$^{5b}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl; or taken together with R$^{5a}$ and the nitrogen to which it is attached forms a 4- to 8-membered heterocyclyl comprising 0 or 1 additional heteroatoms;

R$^6$ is hydrogen, alkyl or halo; or two geminal R$^6$ taken together are ethylene, propylene or butylene;

R$^{7a}$ is hydrogen, lower alkyl, lower haloalkyl, cyano, halo, lower alkoxy, or C$_3$-C$_5$ cycloalkyl, optionally substituted with 1, 2 or 3 substituents independently selected from the group consisting of cyano, lower alkoxy and halo; and R$^{7b}$ is hydrogen, lower alkyl, lower haloalkyl, cyano, halo, lower alkoxy, or C$_3$-C$_5$ cycloalkyl, optionally substituted with 1, 2 or 3 substituents independently selected from the group consisting of cyano, lower alkoxy and halo.

Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer a compound in a local rather than a systemic manner, for example, via injection of the compound directly into an edematous site, often in a depot or sustained release formulation.

Furthermore, one may administer a compound in a targeted drug delivery system, for example, in a liposome coated with endothelial-cell-specific antibody.

The pharmaceutical compositions of the present invention may be manufactured, e.g., by conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants are used in the formulation appropriate to the barrier to be permeated. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for reconstitution before use with a suitable vehicle, e.g., sterile pyrogen-free water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives (for example, as a sparingly soluble salt).

Alternatively, other delivery systems for hydrophobic pharmaceutical compounds may be employed. Liposomes and emulsions are examples of delivery vehicles or carriers for hydrophobic drugs. Certain organic solvents such as dimethysulfoxide also may be employed. Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions may also comprise suitable solid or gel phase carriers or excipients. Examples of such carriers or excipients include but are not limited to calcium carbonate, calcium phosphate, various sugars, starches, cellulose derivatives, gelatin, and polymers, such as polyethylene glycols.

Methods of Treatment

Provided herein are methods of treating or preventing conditions and diseases the course of which can be influenced by modulating the methylation status of histones or other proteins, wherein said methylation status is mediated at least in part by the activity of DOT1. Modulation of the methylation status of histones can in turn influence the level of expression of target genes activated by methylation, and/or target genes suppressed by methylation. For example, one aspect of the invention relates to a method comprising administering to a subject in need thereof a therapeutically effective amount of a compound of formula I, or a pharmaceutically acceptable salt, hydrate, enantiomer or stereoisomer thereof; wherein the compound of formula I is represented by

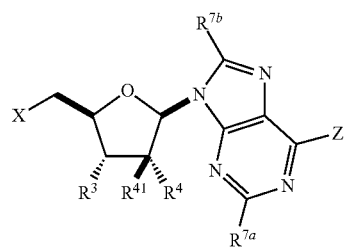

I wherein independently for each occurrence,

X is

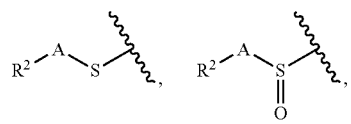

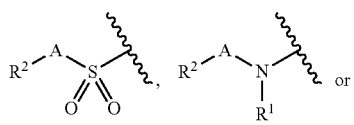

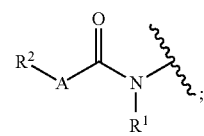

$R^1$ is hydrogen, alkyl, cycloalkyl, alkylcycloalkyl, alkylaryl, haloalkyl, formyl, heterocyclyl, heterocyclylalkyl,

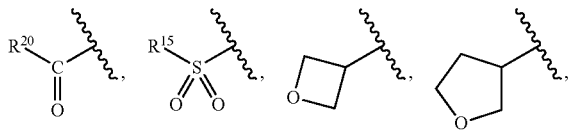

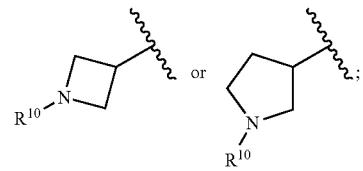

or $(C_2-C_4)$alkyl substituted with

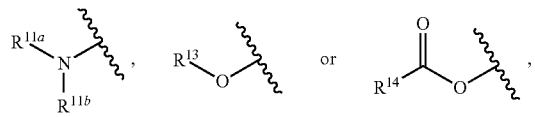

except that when X is

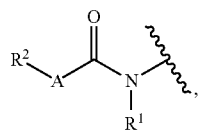

$R^1$ is not

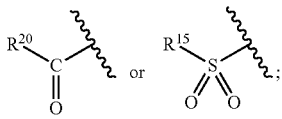

$R^{10}$ is hydrogen or alkyl;

$R^{11a}$ is hydrogen, alkyl, or alkyl-cycloalkyl;

$R^{11b}$ is hydrogen or alkyl; or taken together with $R^{11a}$ and the nitrogen to which it is attached forms a 4- to 8-membered heterocyclyl comprising 0 or 1 additional heteroatoms;

$R^{13}$ is hydrogen, alkyl, aryl, heteroaryl, aralkyl, heteroaralkyl or silyl;

$R^{14}$ is hydrogen, alkyl, aryl, heteroaryl, aralkyl or heteroaralkyl;

$R^{15}$ is alkyl, cycloalkyl or cycloalkylalkyl;

$R^{20}$ is hydrogen, alkyl, cycloalkyl or cycloalkylalkyl;

A is

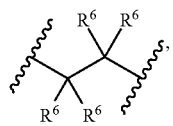 , 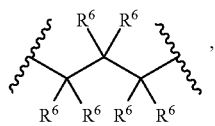 ,

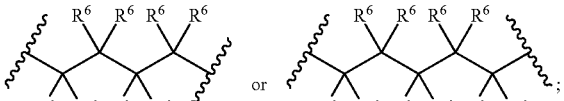

$R^2$ is

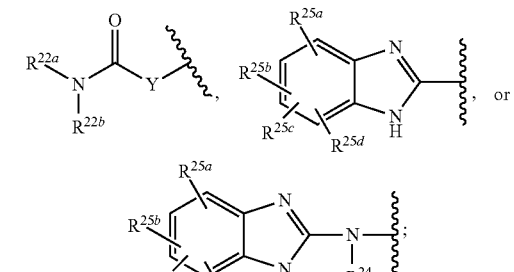

Y is —NH—, —N(alkyl)-, —O—, or —$CR^6_2$—;

$R^{22a}$ is aryl, heteroaryl, aralkyl, heteroaralkyl, fused bicyclyl, biaryl, aryloxyaryl, heteroaryloxyaryl, aryloxyheteroaryl or heteroaryloxyheteroaryl;

$R^{22b}$ is hydrogen or alkyl;

$R^{24}$ is hydrogen or alkyl;

$R^{25a}$, $R^{25b}$, $R^{25c}$, $R^{25d}$ are independently -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R^3$ is hydrogen, halogen, hydroxy, alkyloxy, aralkyloxy, alkylcarbonyloxy or silyloxy;

$R^4$ is hydrogen, halogen, hydroxy, alkyloxy, aralkyloxy, alkylcarbonyloxy or silyloxy;

$R^{41}$ is hydrogen, alkyl or alkynyl;

Z is hydrogen or

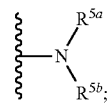

$R^{5a}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl;

$R^{5b}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkyl-carbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl; or taken together with $R^{5a}$ and the nitrogen to which it is attached forms a 4- to 8-membered heterocyclyl comprising 0 or 1 additional heteroatoms;

$R^6$ is hydrogen, alkyl or halo; or two geminal $R^6$ taken together are ethylene, propylene or butylene;

$R^{7a}$ is hydrogen, lower alkyl, lower haloalkyl, cyano, halo, lower alkoxy, or $C_3$-$C_5$ cycloalkyl, optionally substituted with 1, 2 or 3 substituents independently selected from the group consisting of cyano, lower alkoxy and halo; and $R^{7b}$ is hydrogen, lower alkyl, lower haloalkyl, cyano, halo, lower alkoxy, or $C_3$-$C_5$ cycloalkyl, optionally substituted with 1, 2 or 3 substituents independently selected from the group consisting of cyano, lower alkoxy and halo.

In certain embodiments, the invention related to any one of the aforementioned methods, wherein Z is hydrogen.

In certain embodiments, the invention related to any one of the aforementioned methods, wherein Z is

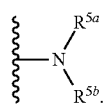

In certain embodiments, the invention relates to any one of the aforementioned methods, wherein X is

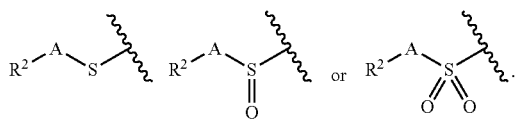

In certain embodiments, the invention relates to any one of the aforementioned methods, wherein X is

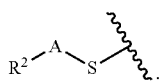

In certain embodiments, the invention relates to any one of the aforementioned methods, wherein X is

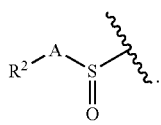

In certain embodiments, the invention relates to any one of the aforementioned methods, wherein X is

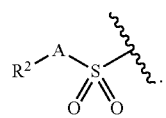

In certain embodiments, the invention relates to any one of the aforementioned methods, wherein X is

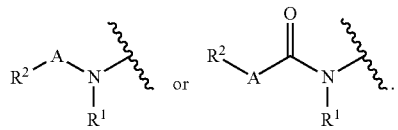

In certain embodiments, the invention relates to any one of the aforementioned methods, wherein X is

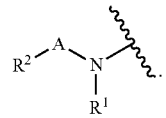

In certain embodiments, the invention relates to any one of the aforementioned methods, wherein X is

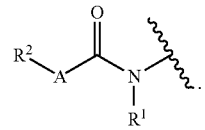

In certain embodiments, the invention relates to any one of the aforementioned methods, wherein $R^2$ is aryloxycarbonyl, heteroaryloxycarbonyl, aralkylcarbonyl, heteroaralkylcarbonyl or 9-fluorenylmethyloxycarbonyl.

In certain embodiments, the invention relates to any one of the aforementioned methods, wherein $R^2$ is

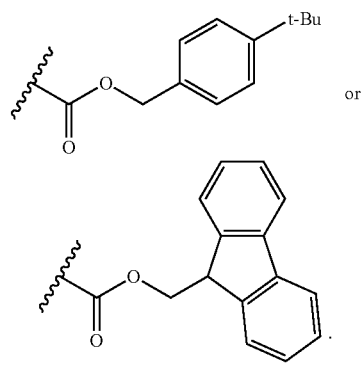

In certain embodiments, the invention relates to any one of the aforementioned methods, wherein $R^2$ is

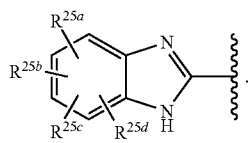

In certain embodiments, the invention relates to any one of the aforementioned methods, wherein $R^2$ is

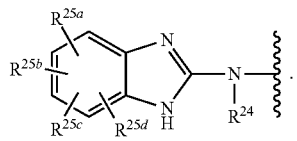

In certain embodiments, the invention relates to any one of the aforementioned methods, wherein $R^{24}$ is hydrogen or alkyl.

In certain embodiments, the invention relates to any one of the aforementioned methods, wherein $R^{24}$ is hydrogen.

In certain embodiments, the invention relates to any one of the aforementioned methods, wherein $R^{25a}$ is hydrogen, alkyl, —O-alkyl, halogen, trifluoroalkyl, —O-trifluoromethyl, or —SO$_2$-trifluoromethyl.

In certain embodiments, the invention relates to any one of the aforementioned methods, wherein $R^{25b}$ is hydrogen, alkyl, halogen, or trifluoroalkyl.

In certain embodiments, the invention relates to any one of the aforementioned methods, wherein $R^{25c}$ is hydrogen, alkyl, or halogen.

In certain embodiments, the invention relates to any one of the aforementioned methods, wherein $R^{25c}$ is hydrogen or halogen.

In certain embodiments, the invention relates to any one of the aforementioned methods, wherein $R^2$ is

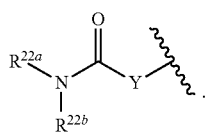

In certain embodiments, the invention relates to any one of the aforementioned methods, wherein Y is —NH— or —N(alkyl)-.

In certain embodiments, the invention relates to any one of the aforementioned methods, wherein Y is —NH—.

In certain embodiments, the invention relates to any one of the aforementioned methods, wherein Y is —N(CH$_3$)—.

In certain embodiments, the invention relates to any one of the aforementioned methods, wherein Y is —O—.

In certain embodiments, the invention relates to any one of the aforementioned methods, wherein Y is —CH$_2$—.

In certain embodiments, the invention relates to any one of the aforementioned methods, wherein $R^{22a}$ is aryl or aralkyl.

In certain embodiments, the invention relates to any one of the aforementioned methods, wherein $R^{22a}$ is substituted phenyl or substituted benzyl.

In certain embodiments, the invention relates to any one of the aforementioned methods, wherein $R^{22a}$ is

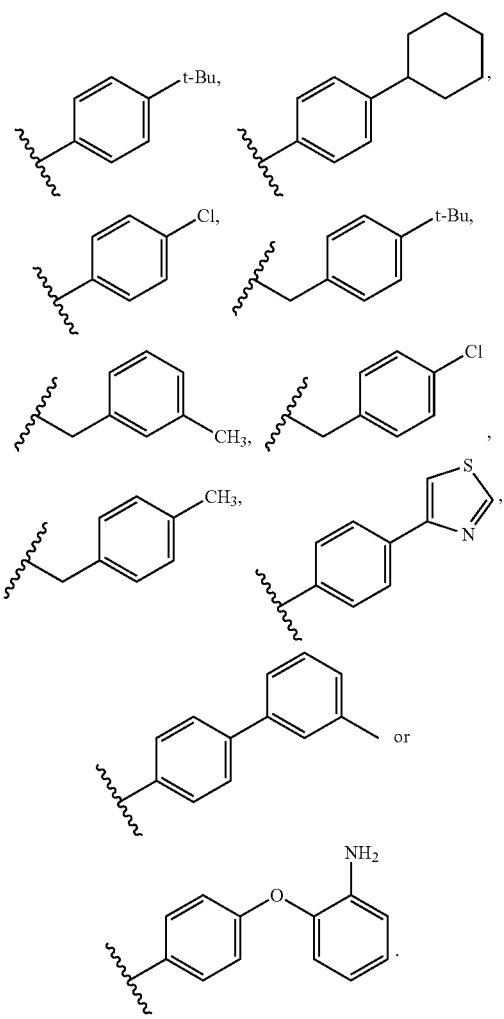

In certain embodiments, the invention relates to any one of the aforementioned methods, wherein $R^{22a}$ is

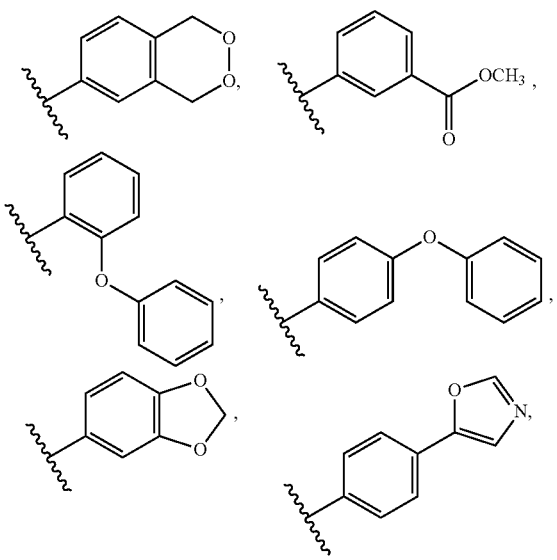

-continued

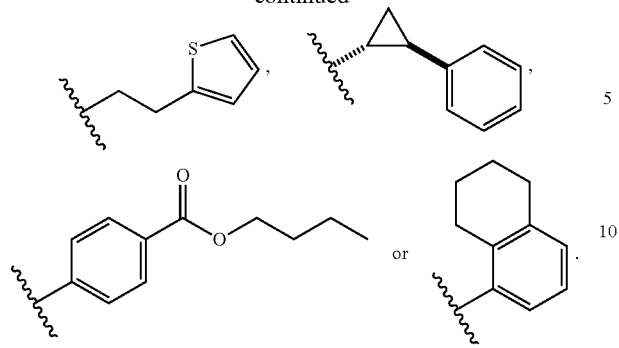

In certain embodiments, the invention relates to any one of the aforementioned methods, wherein $R^{22b}$ is hydrogen.

In certain embodiments, the invention relates to any one of the aforementioned methods, wherein $R^{22b}$ is methyl.

In certain embodiments, the invention relates to any one of the aforementioned methods, wherein $R^{23}$ is hydrogen.

In certain embodiments, the invention relates to any one of the aforementioned methods, wherein $R^1$ is hydrogen.

In certain embodiments, the invention relates to any one of the aforementioned methods, wherein $R^1$ is alkyl.

In certain embodiments, the invention relates to any one of the aforementioned methods, wherein $R^1$ is —CH$_3$, —CH$_2$CH$_3$, —CH$_2$CH(CH$_3$)$_2$ or —CH$_2$CH$_2$CH(CH$_3$)$_2$.

In certain embodiments, the invention relates to any one of the aforementioned methods, wherein $R^1$ is

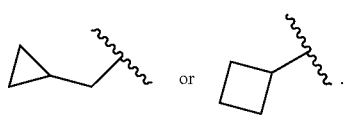 [SMILES: *CC1CC1 ; *C1CCC1]

In certain embodiments, the invention relates to any one of the aforementioned methods, wherein $R^1$ is —CH$_2$CF$_3$.

In certain embodiments, the invention relates to any one of the aforementioned methods, wherein $R^1$ is —CH$_2$Ph.

In certain embodiments, the invention relates to any one of the aforementioned methods, wherein $R^1$ is —C(=O)H.

In certain embodiments, the invention relates to any one of the aforementioned methods, wherein $R^1$ is —C(=O)CH$_3$.

In certain embodiments, the invention relates to any one of the aforementioned compounds, wherein $R^1$ is heterocyclyl or heterocyclylalkyl.

In certain embodiments, the invention relates to any one of the aforementioned compounds, wherein $R^1$ is

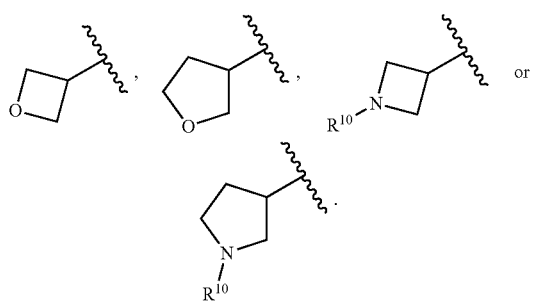

In certain embodiments, the invention relates to any one of the aforementioned methods, wherein $R^1$ is

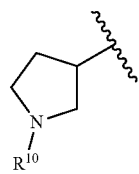

In certain embodiments, the invention relates to any one of the aforementioned compounds, wherein $R^1$ is

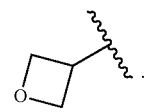

In certain embodiments, the invention relates to any one of the aforementioned methods, wherein $R^1$ is

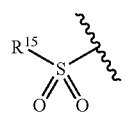

In certain embodiments, the invention relates to any one of the aforementioned methods, wherein $R^{15}$ is alkyl.

In certain embodiments, the invention relates to any one of the aforementioned methods, wherein $R^{15}$ is methyl.

In certain embodiments, the invention relates to any one of the aforementioned methods, wherein $R^{15}$ is cycloalkyl.

In certain embodiments, the invention relates to any one of the aforementioned methods, wherein $R^{15}$ is cycloalkylalkyl.

In certain embodiments, the invention relates to any one of the aforementioned methods, wherein $R^1$ is (C$_2$-C$_4$)alkyl substituted with

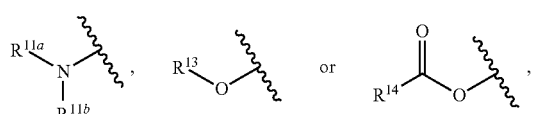

In certain embodiments, the invention relates to any one of the aforementioned methods, wherein $R^1$ is

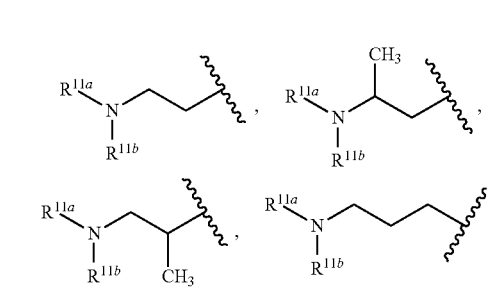

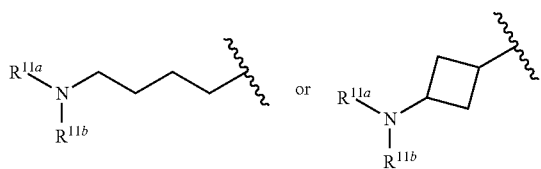

In certain embodiments, the invention relates to any one of the aforementioned methods, wherein $R^{11a}$ is hydrogen, alkyl, or alkyl-cycloalkyl.

In certain embodiments, the invention relates to any one of the aforementioned methods, wherein $R^{11a}$ is hydrogen, methyl, or i-propyl.

In certain embodiments, the invention relates to any one of the aforementioned methods, wherein $R^{22a}$ is substituted phenyloxyphenyl, substituted 4-(phenyl)phenyl or optionally substituted 4-(heteroaryl)phenyl.

In certain embodiments, the invention relates to any one of the aforementioned methods, wherein $R^{22a}$ is

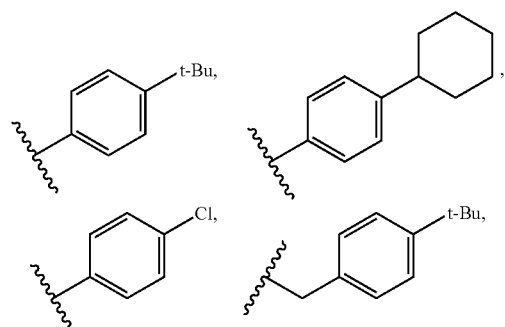

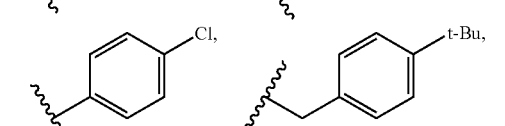

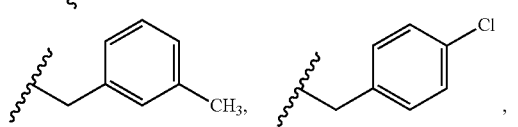


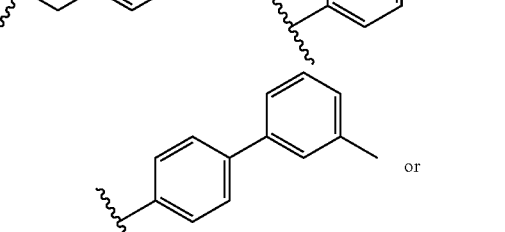

In certain embodiments, the invention relates to any one of the aforementioned compounds, wherein $R^{22a}$ is

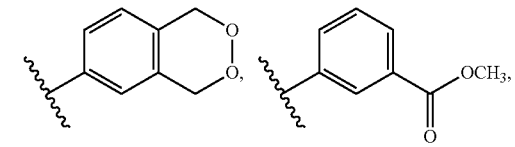

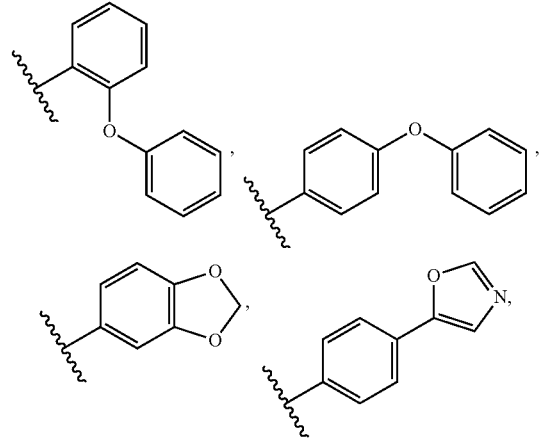

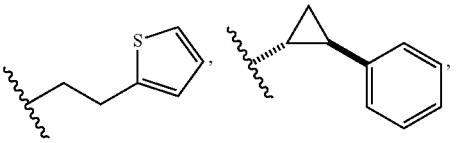

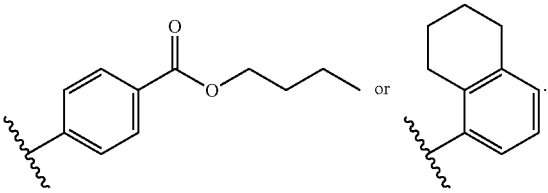

In certain embodiments, the invention relates to any one of the aforementioned methods, wherein $R^{11a}$ is hydrogen.

In certain embodiments, the invention relates to any one of the aforementioned methods, wherein $R^1$ is hydrogen.

In certain embodiments, the invention relates to any one of the aforementioned methods, wherein $R^{11b}$ is methyl.

In certain embodiments, the invention relates to any one of the aforementioned methods, wherein $R^1$ is

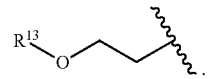

In certain embodiments, the invention relates to any one of the aforementioned methods, wherein $R^{13}$ is hydrogen.

In certain embodiments, the invention relates to any one of the aforementioned methods, wherein $R^1$ is

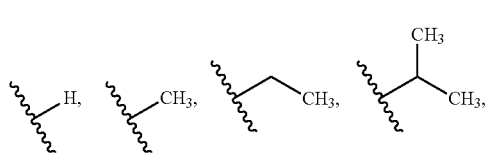

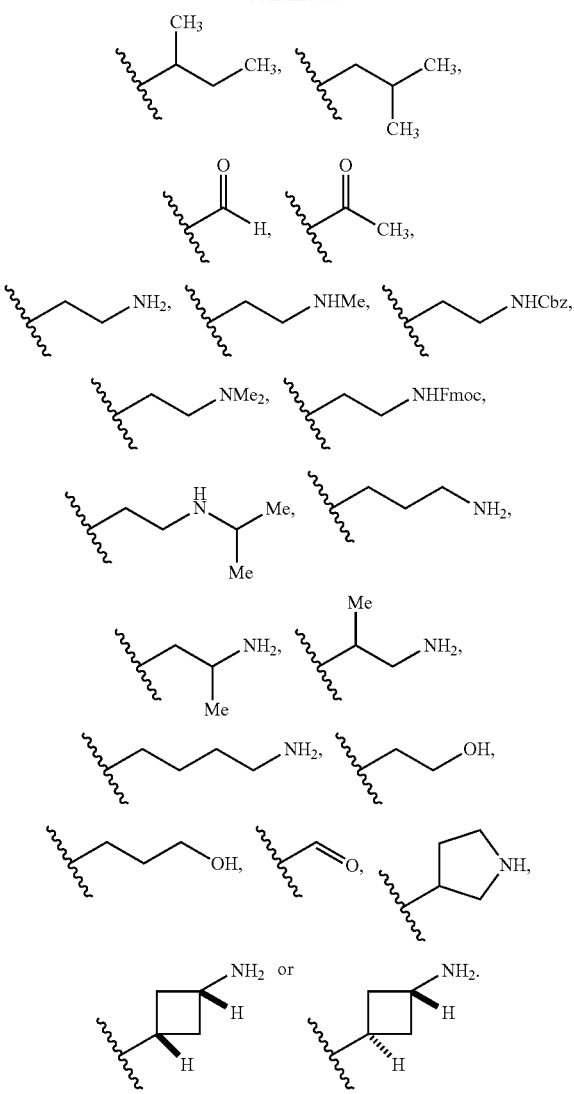

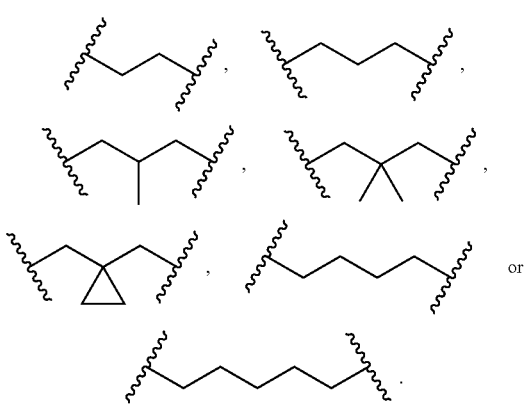

In certain embodiments, the invention relates to any one of the aforementioned methods, wherein A is

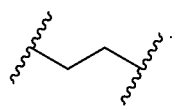 [SMILES: *CC*]

In certain embodiments, the invention relates to any one of the aforementioned methods, wherein A is

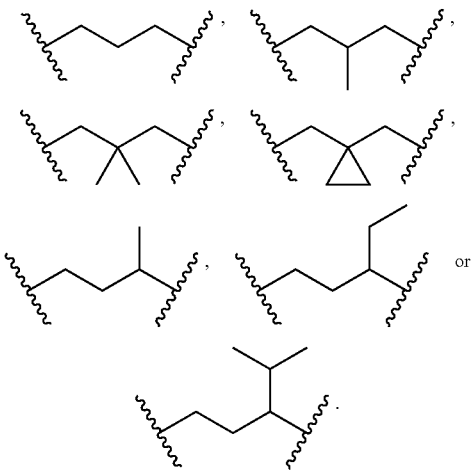

In certain embodiments, the invention relates to any one of the aforementioned methods, wherein A is

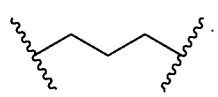 [SMILES: *CCC*]

In certain embodiments, the invention relates to any one of the aforementioned methods, wherein A is

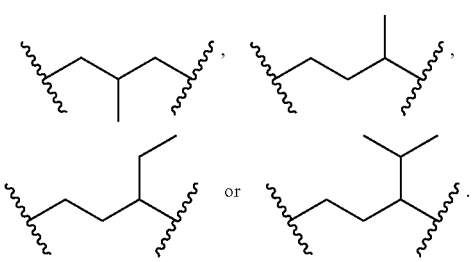

In certain embodiments, the invention relates to any one of the aforementioned methods, wherein A is

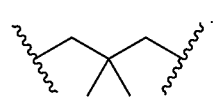

In certain embodiments, the invention relates to any one of the aforementioned methods, wherein A is

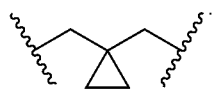

In certain embodiments, the invention relates to any one of the aforementioned methods, wherein A is

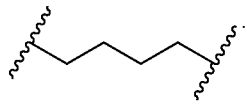 [SMILES: "." ; *CCCC*]

In certain embodiments, the invention relates to any one of the aforementioned methods, wherein A

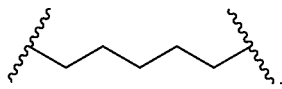 [SMILES: *CCCCC* ; "."]

In certain embodiments, the invention relates to any one of the aforementioned methods, wherein A is

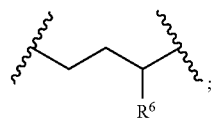

and $R^6$ is alkyl.

In certain embodiments, the invention relates to any one of the aforementioned methods, wherein A is

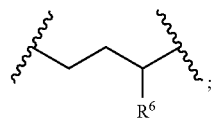

and $R^6$ is methyl, ethyl or isopropyl.

In certain embodiments, the invention relates to any one of the aforementioned methods, wherein $R^3$ is hydroxyl.

In certain embodiments, the invention relates to any one of the aforementioned methods, wherein $R^3$ is hydrogen.

In certain embodiments, the invention relates to any one of the aforementioned methods, wherein $R^4$ is hydroxyl.

In certain embodiments, the invention relates to any one of the aforementioned methods, wherein $R^4$ is hydrogen.

In certain embodiments, the invention relates to any one of the aforementioned methods, wherein $R^{41}$ is hydrogen.

In certain embodiments, the invention relates to any one of the aforementioned methods, wherein $R^{41}$ is methyl.

In certain embodiments, the invention relates to any one of the aforementioned methods, wherein $R^3$ is hydroxyl; and $R^4$ is hydroxyl.

In certain embodiments, the invention relates to any one of the aforementioned methods, wherein $R^3$ is hydroxyl; $R^4$ is hydroxyl; and $R^{41}$ is hydrogen.

In certain embodiments, the invention relates to any one of the aforementioned methods, wherein $R^3$ is hydroxyl; $R^4$ is hydroxyl; and $R^{41}$ is methyl.

In certain embodiments, the invention relates to any one of the aforementioned methods, wherein $R^3$ is hydrogen; and $R^4$ is hydroxyl.

In certain embodiments, the invention relates to any one of the aforementioned methods, wherein $R^3$ is hydrogen; $R^4$ is hydroxyl; and $R^{41}$ is hydrogen.

In certain embodiments, the invention relates to any one of the aforementioned methods, wherein $R^3$ is hydrogen; $R^4$ is hydroxyl; and $R^{41}$ is methyl.

In certain embodiments, the invention relates to any one of the aforementioned methods, wherein $R^3$ is hydroxyl; and $R^4$ is hydrogen.

In certain embodiments, the invention relates to any one of the aforementioned methods, wherein Z is hydrogen of

In certain embodiments, the invention relates to any one of the aforementioned methods, wherein Z is hydrogen.

In certain embodiments, the invention relates to any one of the aforementioned methods, wherein Z is

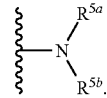

In certain embodiments, the invention relates to any one of the aforementioned methods, wherein $R^{5a}$ is hydrogen, alkyl, carbocyclyl, heterocyclyl, aryl, heteroaryl, carbocyclylalkyl, heterocyclylalkyl, aralkyl, or heteroaralkyl.

In certain embodiments, the invention relates to any one of the aforementioned methods, wherein $R^{5a}$ is hydrogen, aralkyloxyalkyl, alkyl, aryl, aralkyl, aminoalkyl or hydroalkyl.

In certain embodiments, the invention relates to any one of the aforementioned methods, wherein $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_3$, —CH$_2$Ph, —CH$_2$CH$_2$NH$_2$, —CH$_2$ (cyclohexyl) or —CH$_2$CH$_2$OH.

In certain embodiments, the invention relates to any one of the aforementioned methods, wherein $R^{5b}$ is hydrogen, alkyl, carbocyclyl, heterocyclyl, aryl, heteroaryl, carbocyclylalkyl, heterocyclylalkyl, aralkyl, or heteroaralkyl.

In certain embodiments, the invention relates to any one of the aforementioned methods, wherein $R^{5b}$ is hydrogen, aralkyloxyalkyl, alkyl, aryl, aralkyl, aminoalkyl or hydroalkyl.

In certain embodiments, the invention relates to any one of the aforementioned methods, wherein $R^{5b}$ is hydrogen.

In certain embodiments, the invention relates to any one of the aforementioned methods, wherein $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_3$, —CH$_2$Ph, —CH$_2$CH$_2$NH$_2$, —CH$_2$ (cyclohexyl) or —CH$_2$CH$_2$OH; and $R^{5b}$ is —H.

In certain embodiments, the invention relates to any one of the aforementioned methods, wherein $R^{7a}$ is hydrogen or lower alkyl.

In certain embodiments, the invention relates to any one of the aforementioned methods, wherein $R^{7a}$ is hydrogen.

In certain embodiments, the invention relates to any one of the aforementioned methods, wherein $R^{7b}$ is hydrogen or lower alkyl.

In certain embodiments, the invention relates to any one of the aforementioned methods, wherein $R^{7b}$ is hydrogen.

In certain embodiments, the invention relates to any one of the aforementioned methods, wherein the compound, or a pharmaceutically acceptable salt, hydrate, enantiomer or stereoisomer thereof, is selected from the group consisting of

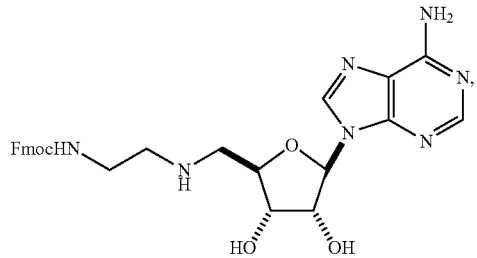

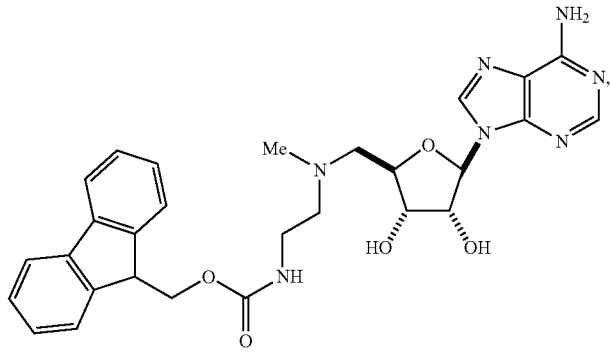

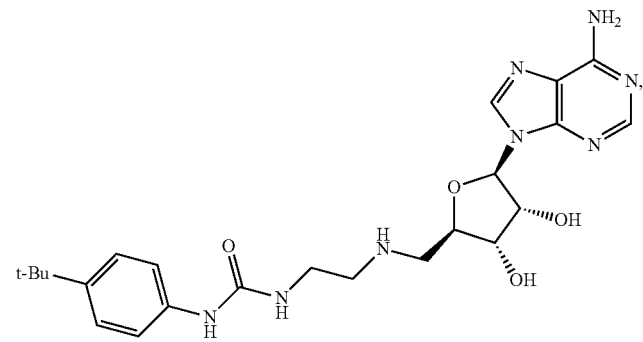

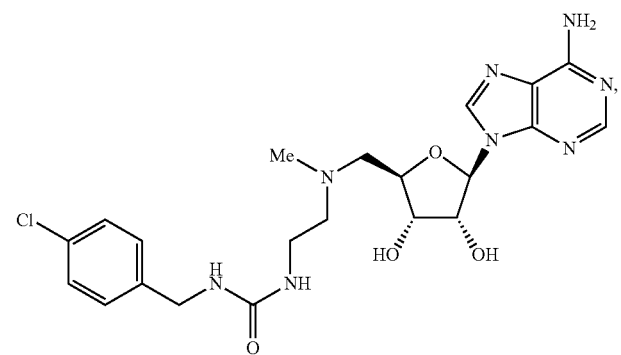

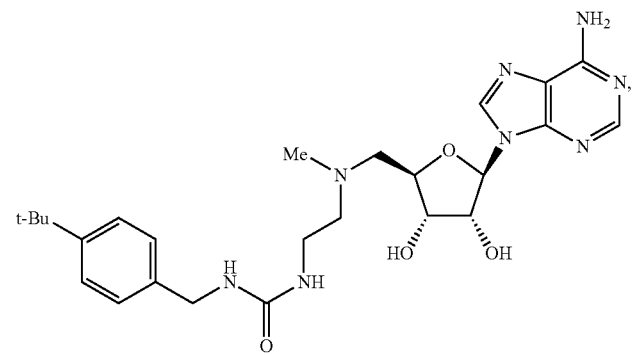

-continued
73
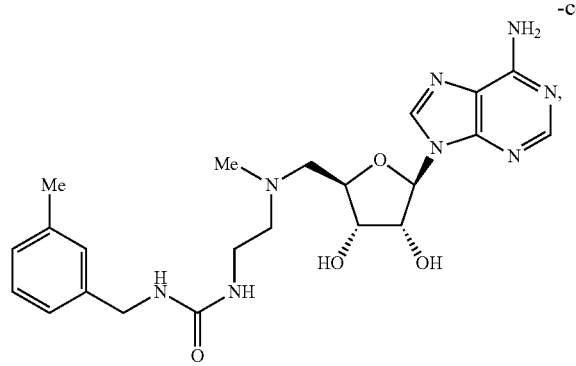
74
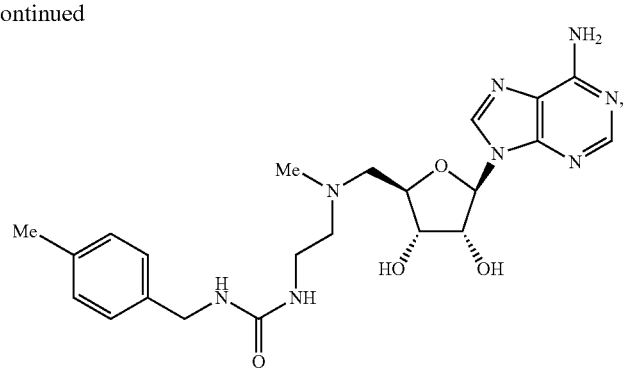
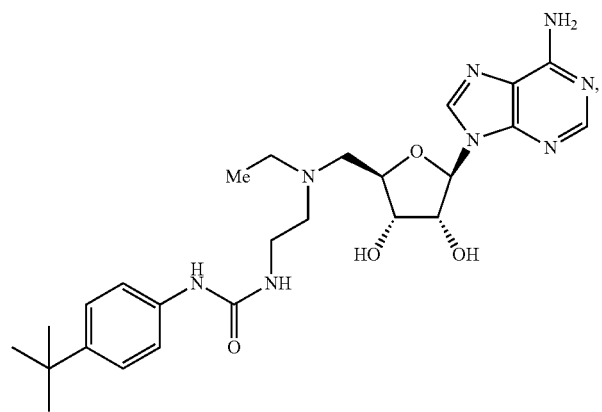
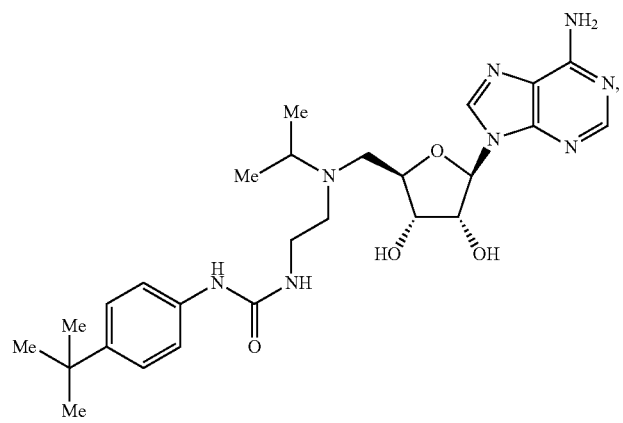
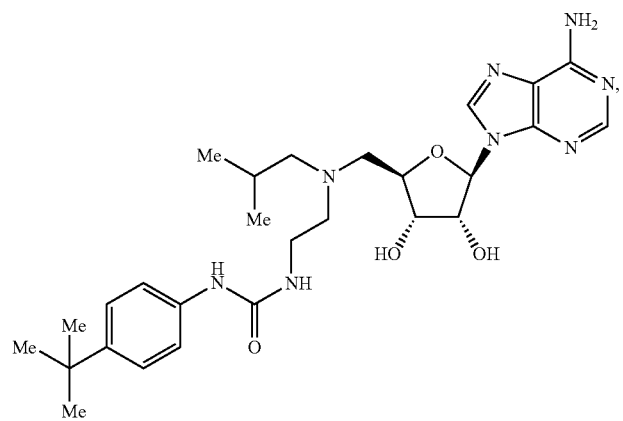

-continued
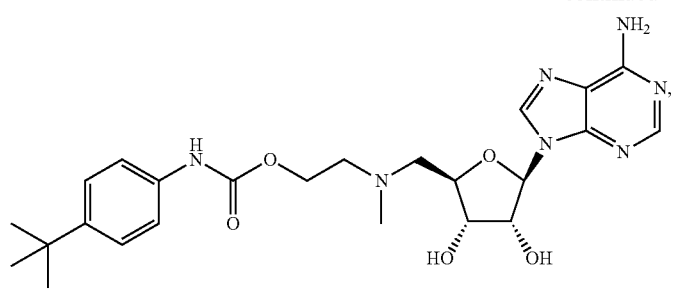
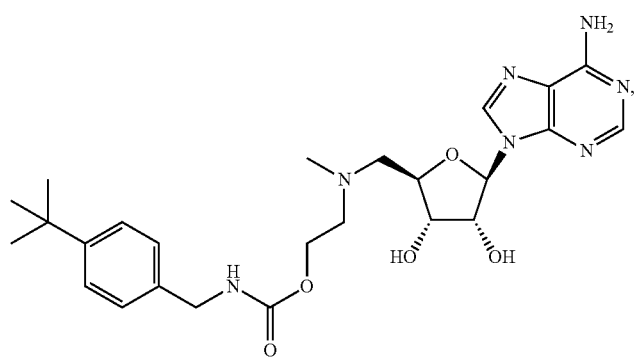
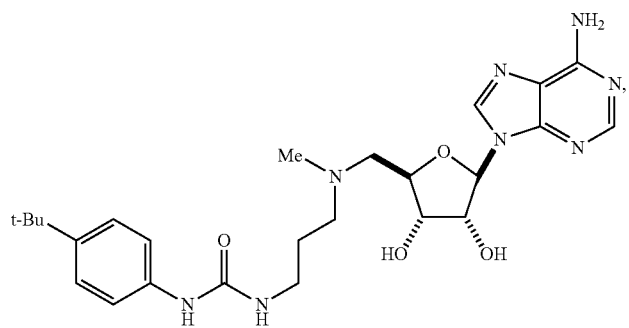
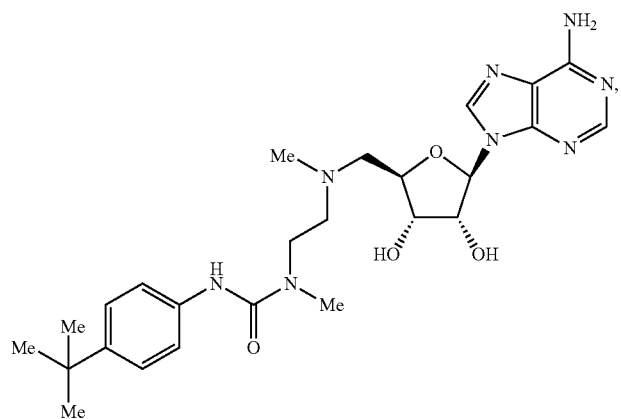

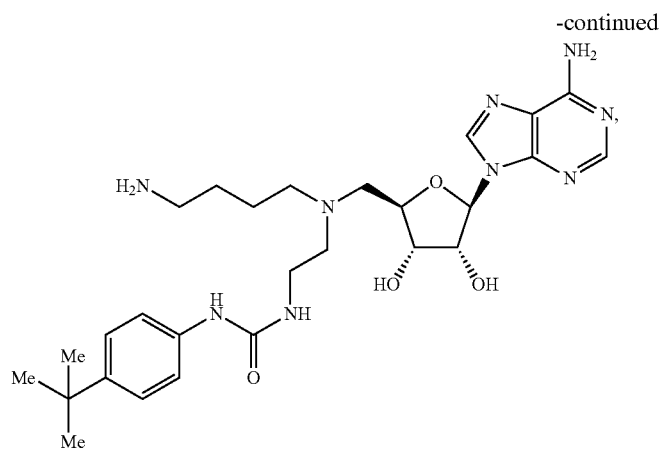
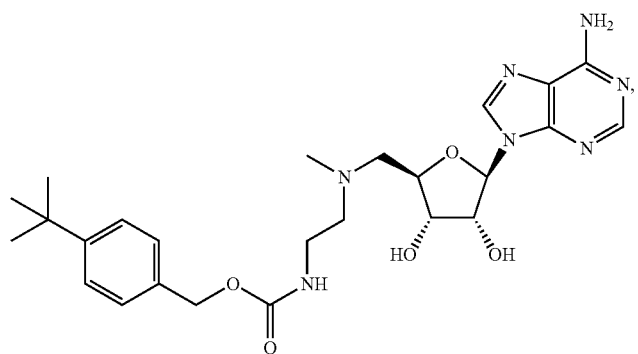
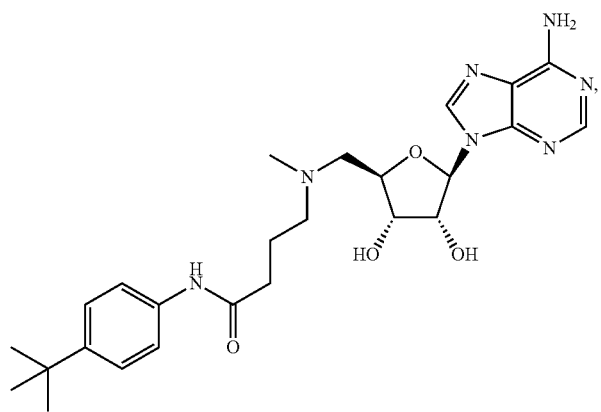
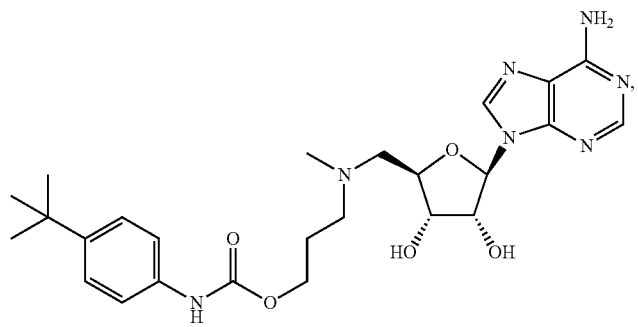

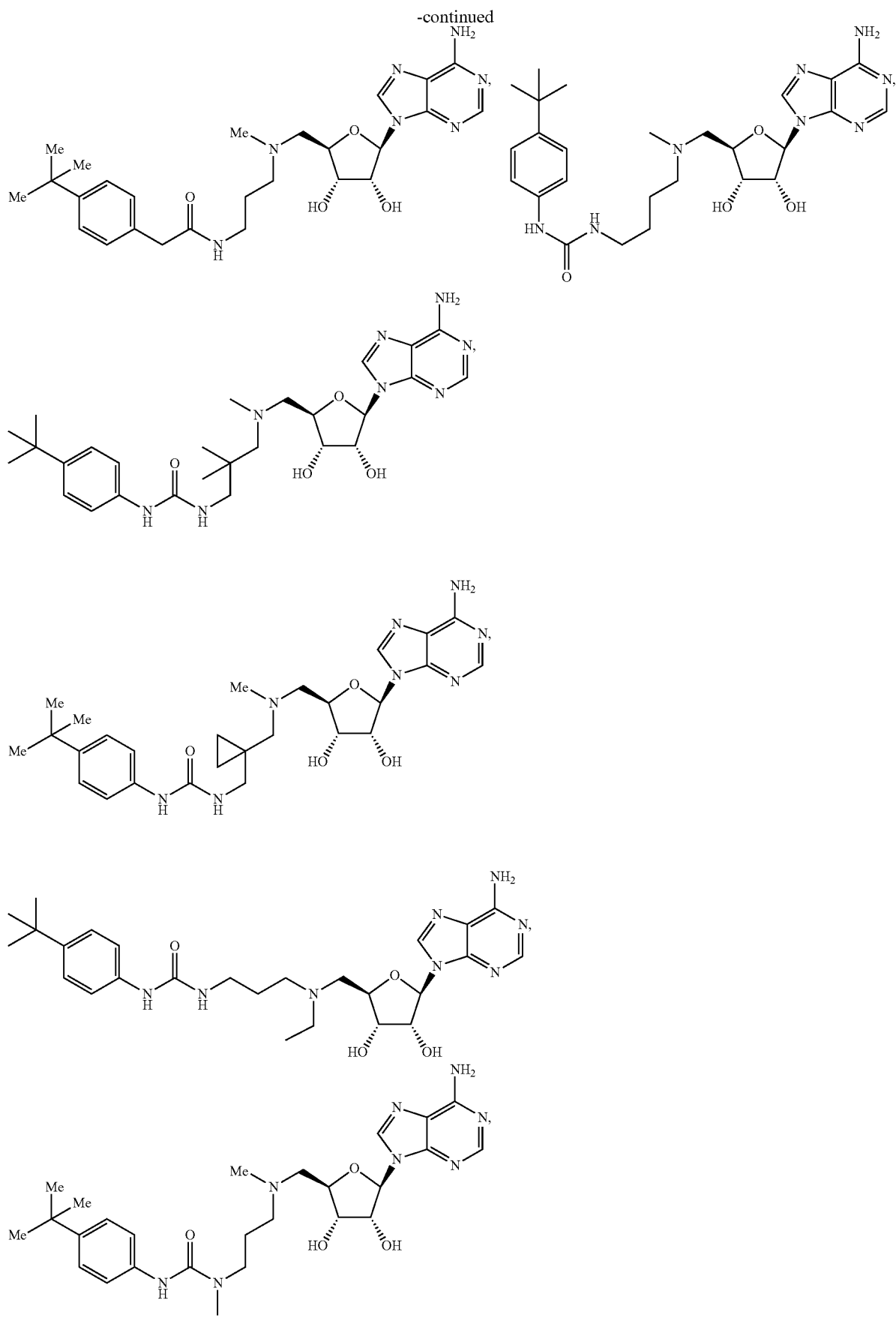

-continued
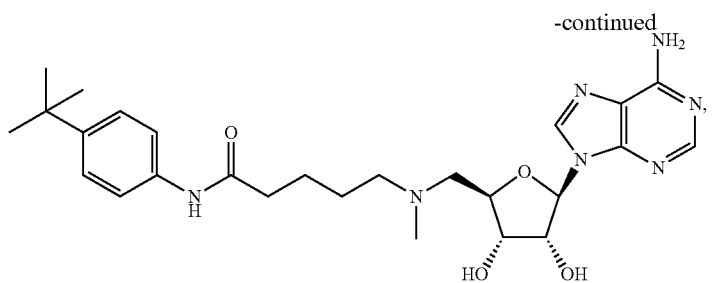
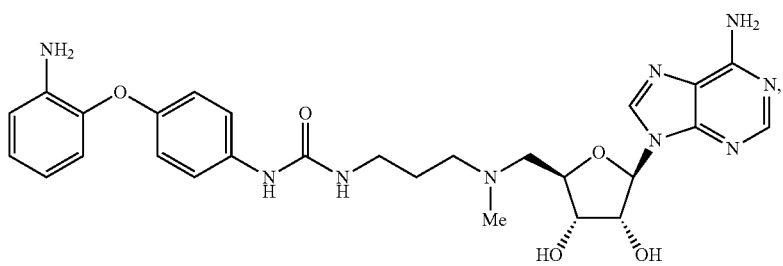
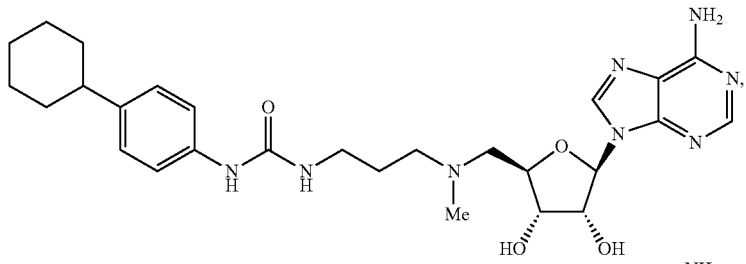
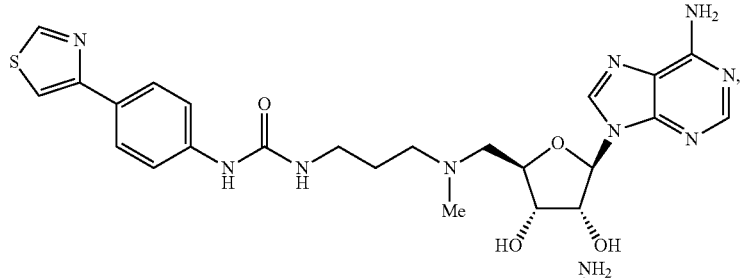
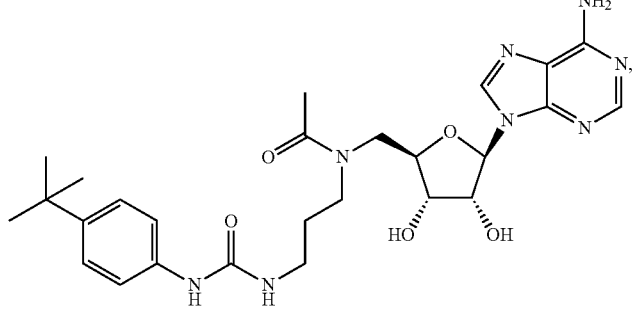
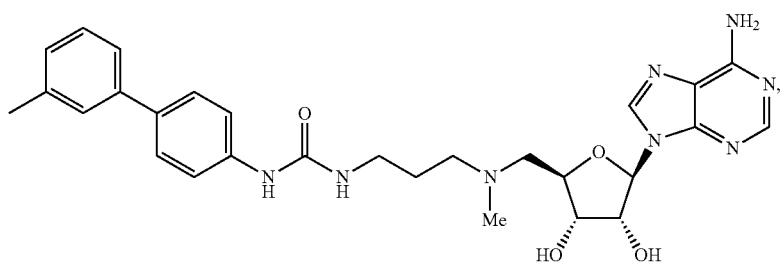

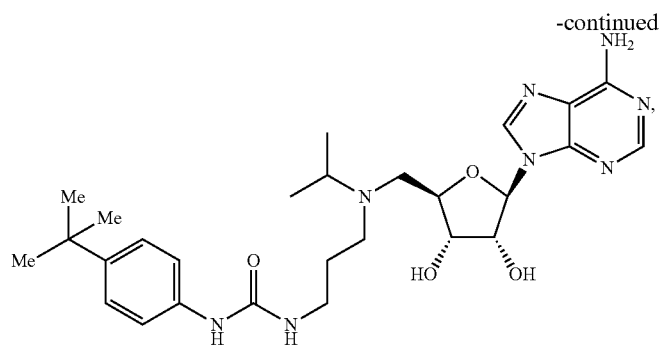
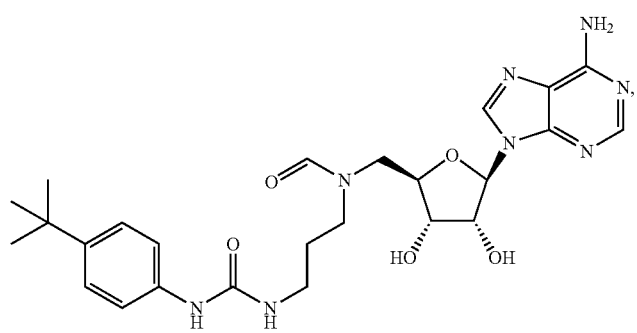
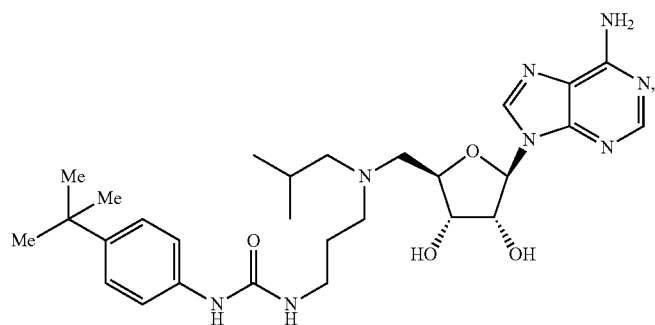
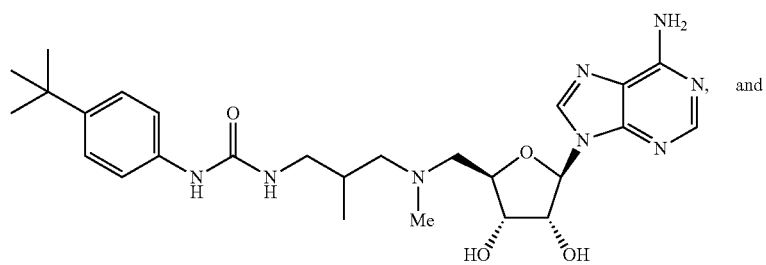
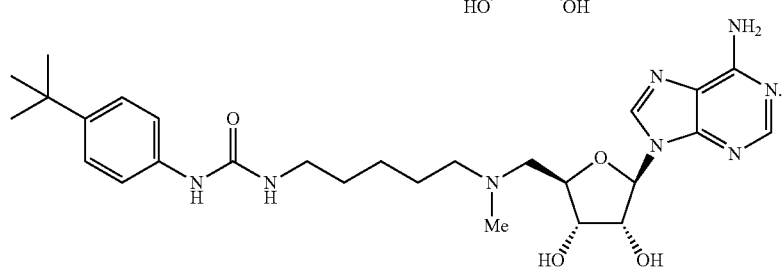
In certain embodiments, the invention relates to any one of the aforementioned methods, wherein the compound, or a pharmaceutically acceptable salt, hydrate, enantiomer or stereoisomer thereof, is selected from the group consisting of

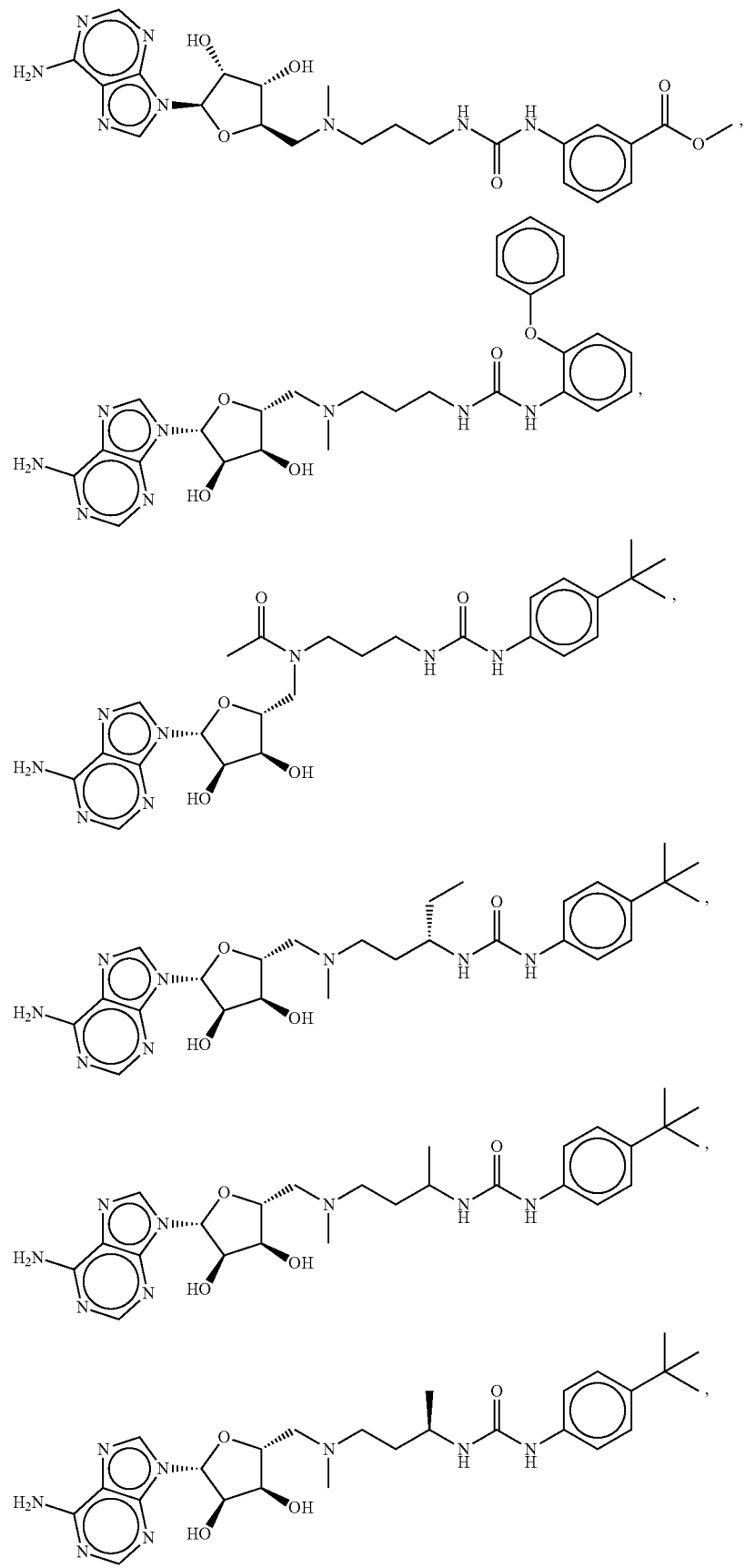

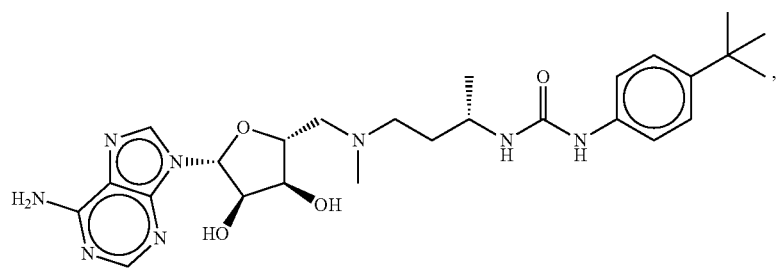
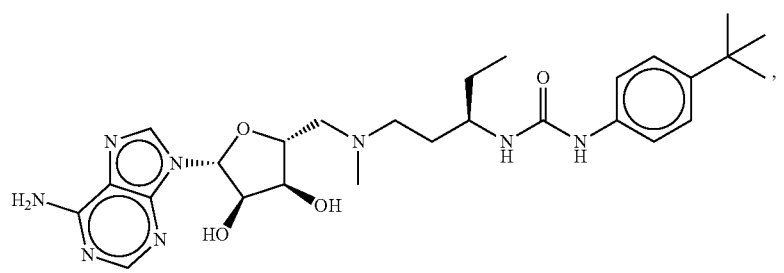
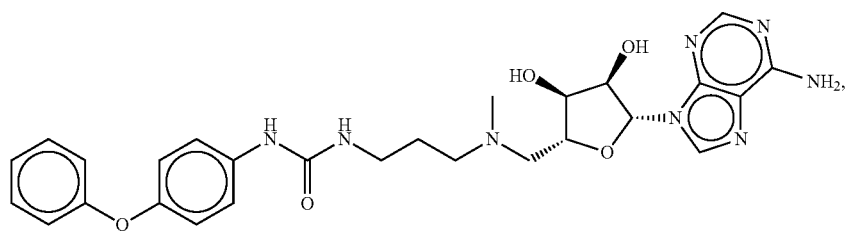
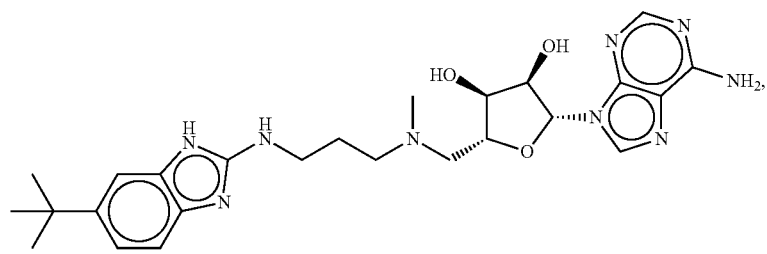
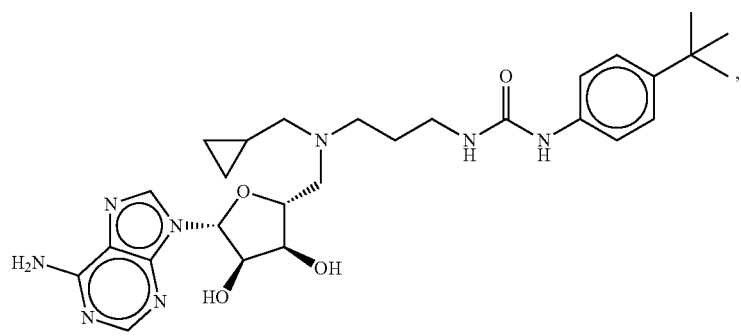
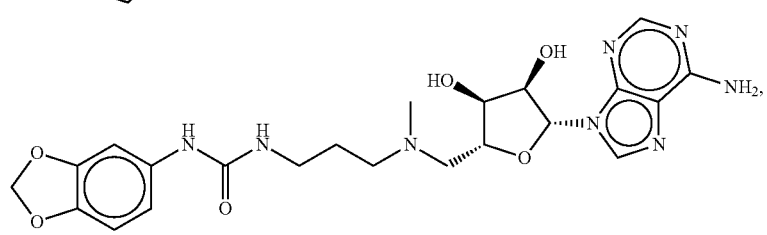

-continued
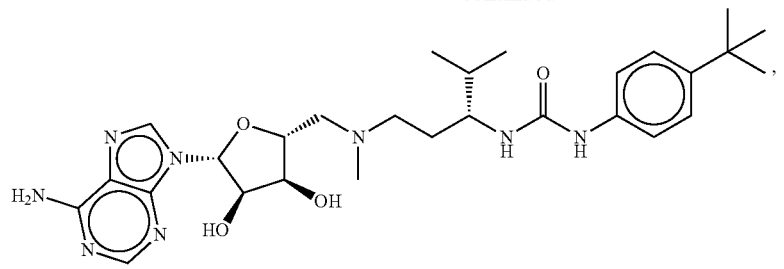
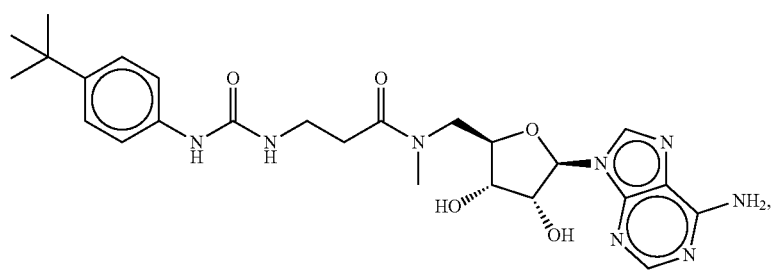
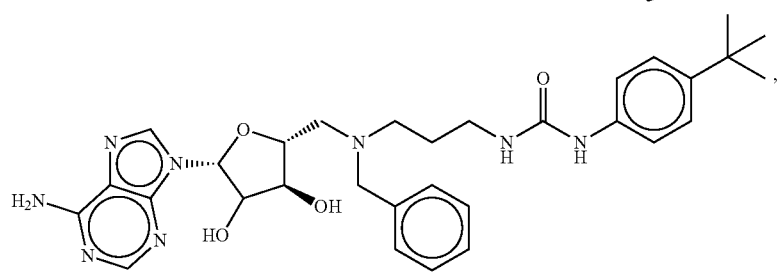
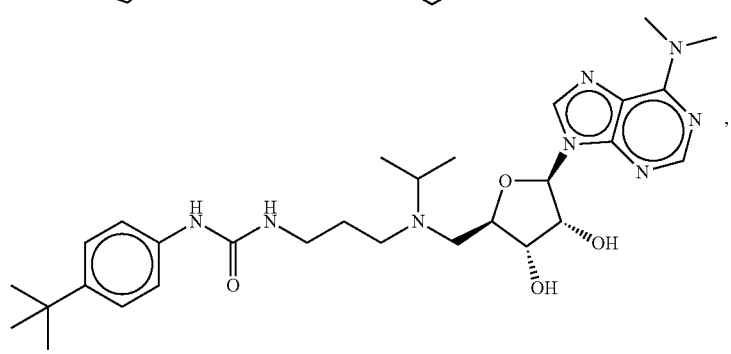
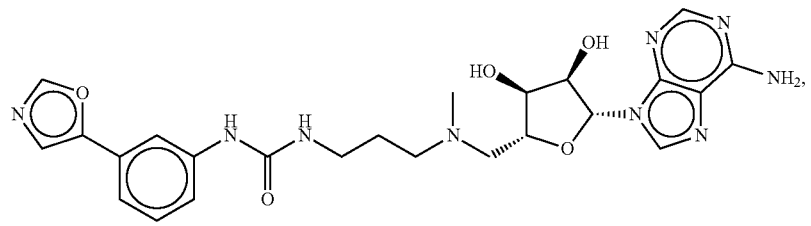
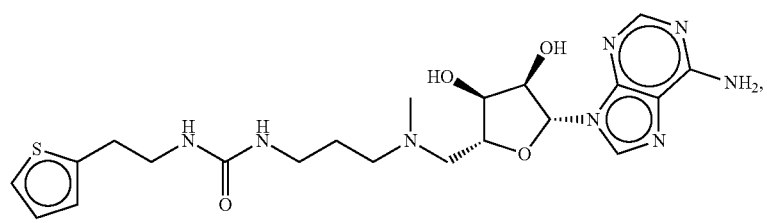

-continued
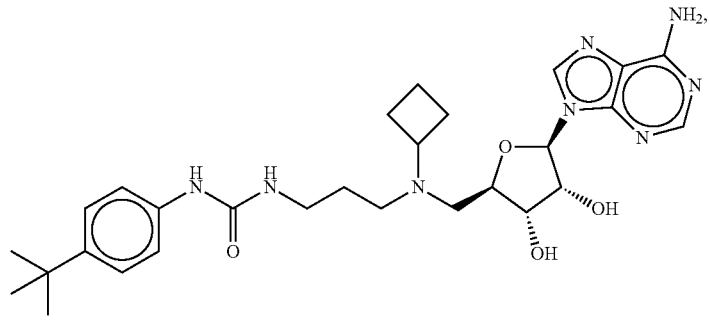
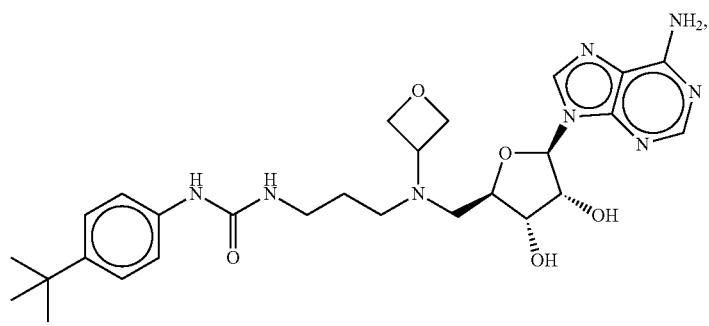
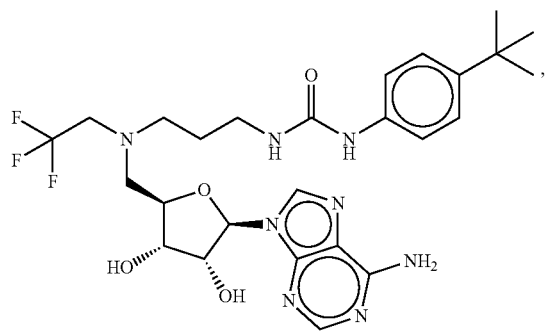
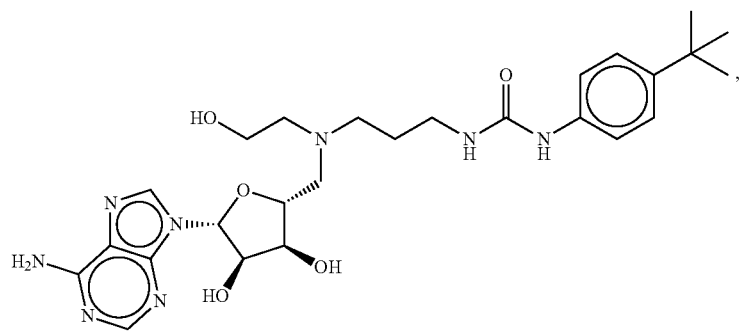
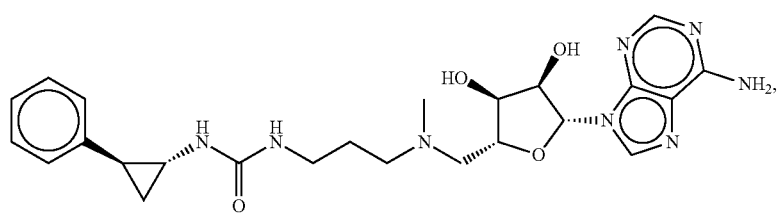

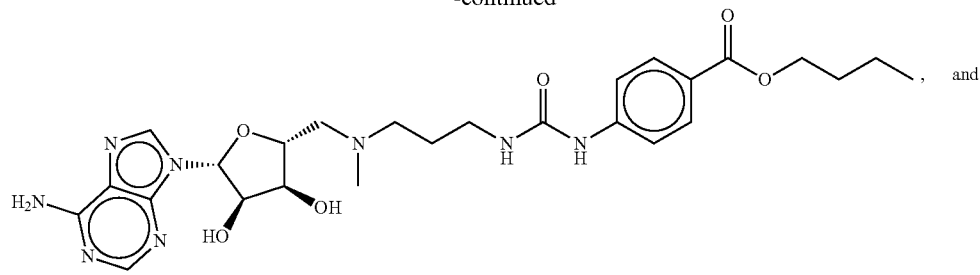

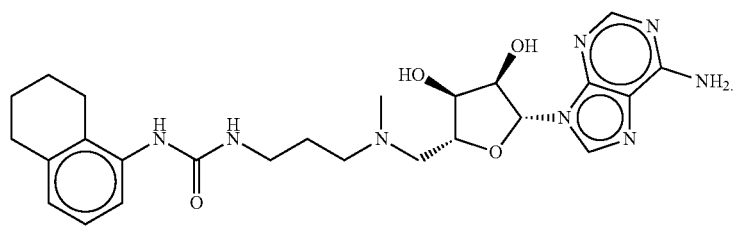

In certain embodiments, the invention relates to any one of the aforementioned methods, wherein the compound, or a pharmaceutically acceptable salt, hydrate, enantiomer or stereoisomer thereof, is selected from the group consisting of

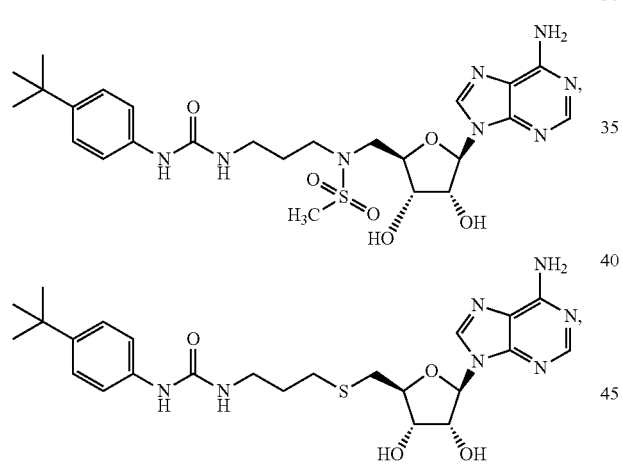

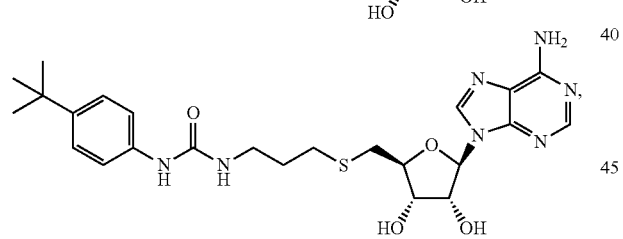

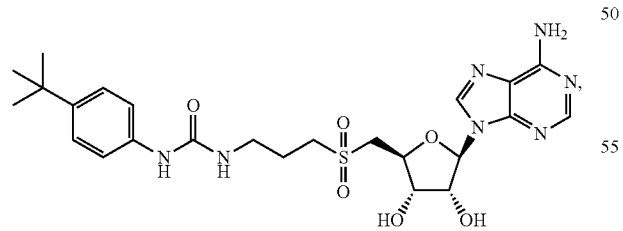

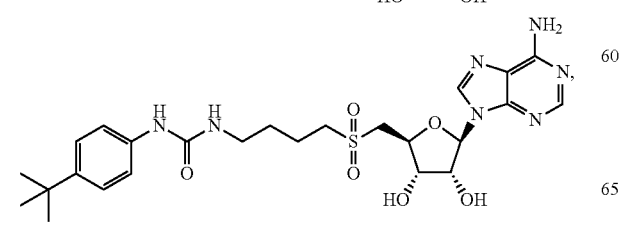

-continued

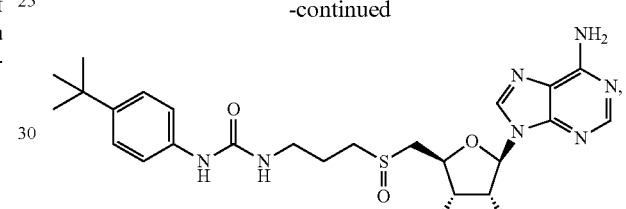

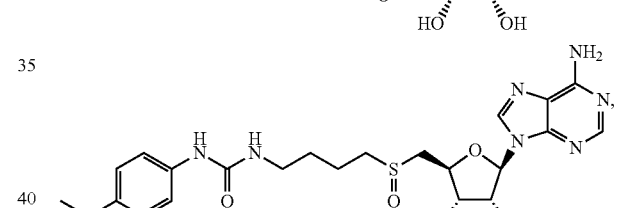

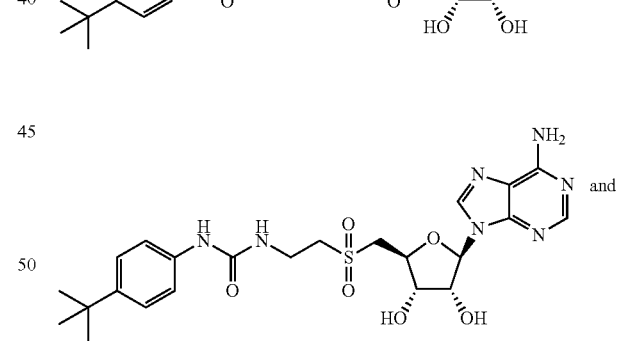

In certain embodiments, the invention relates to any one of the aforementioned methods, wherein the compound, or a pharmaceutically acceptable salt, hydrate, enantiomer or stereoisomer thereof, is selected from the group consisting of

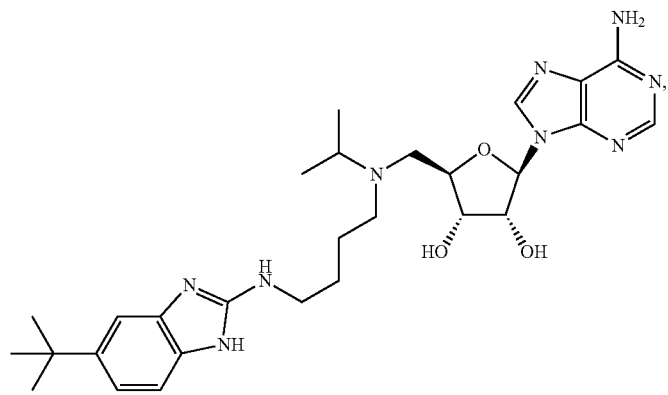
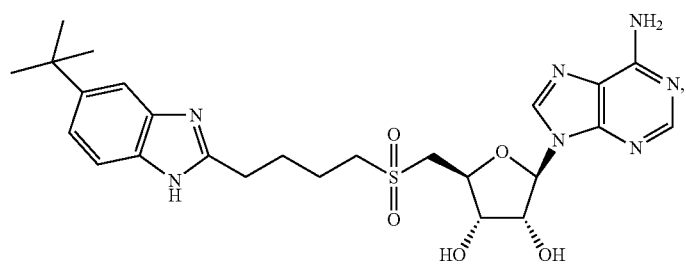
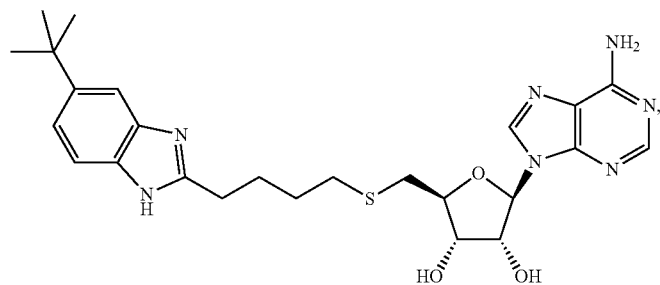
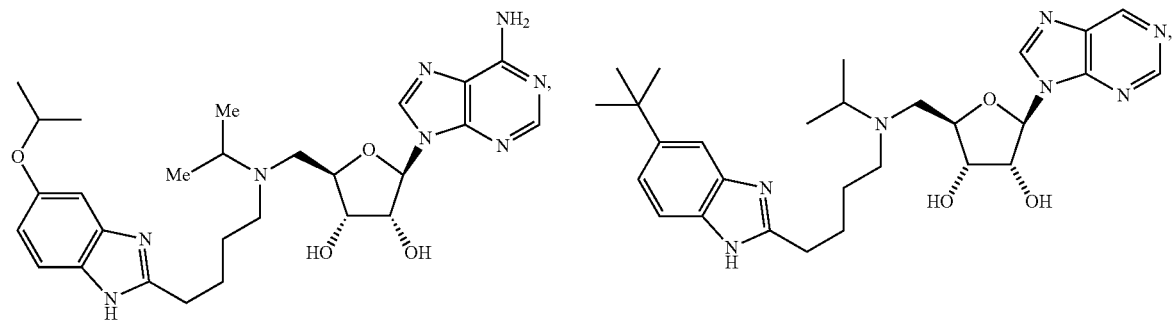
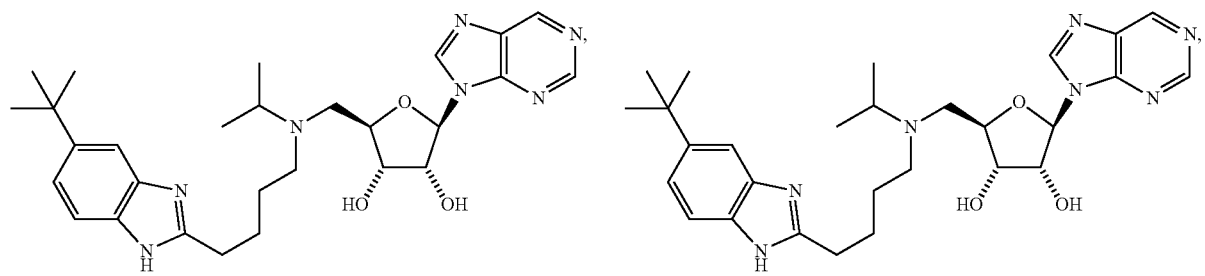

-continued
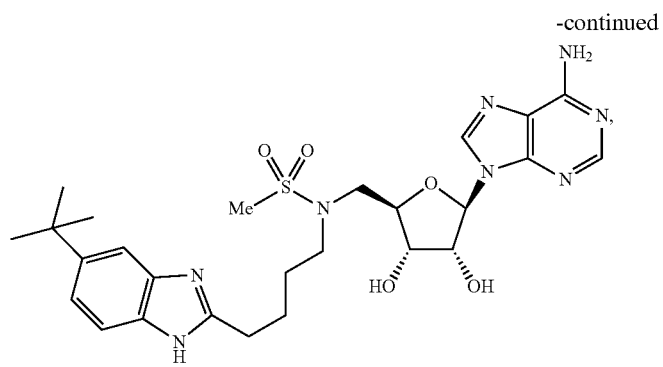
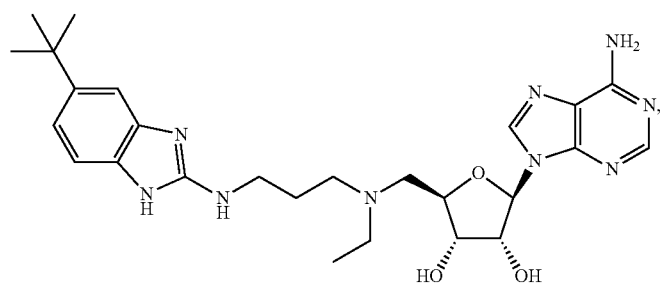
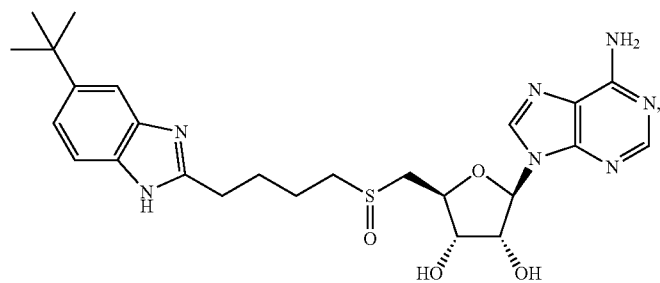
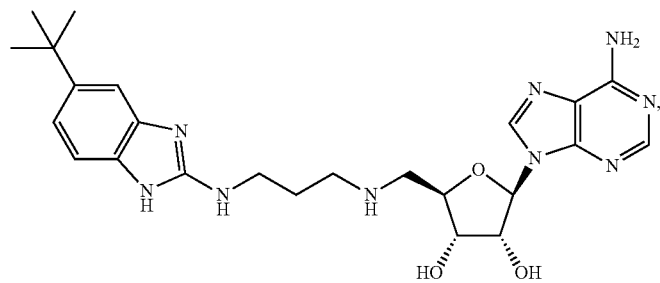
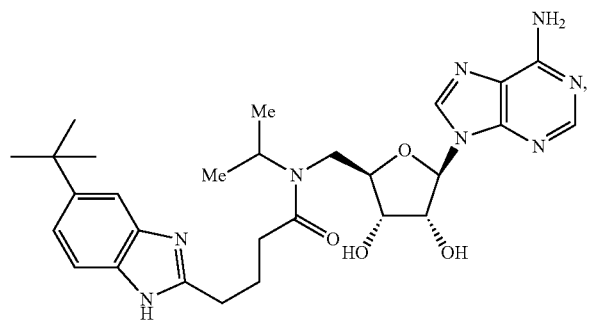

-continued
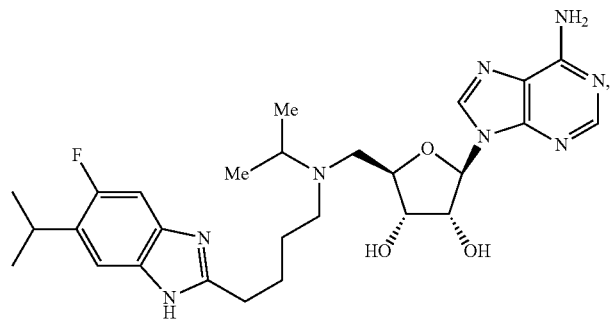
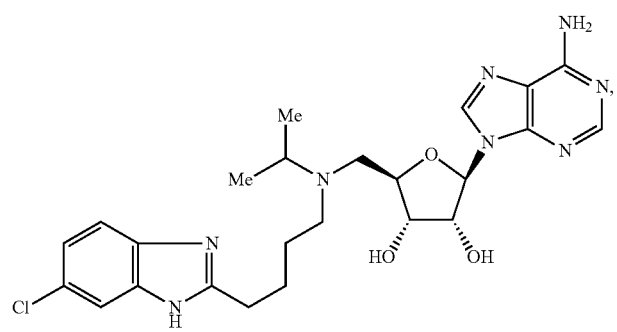
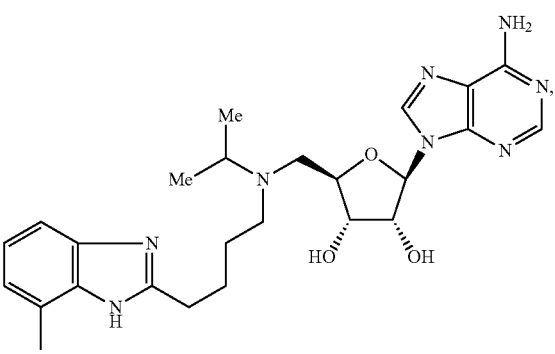
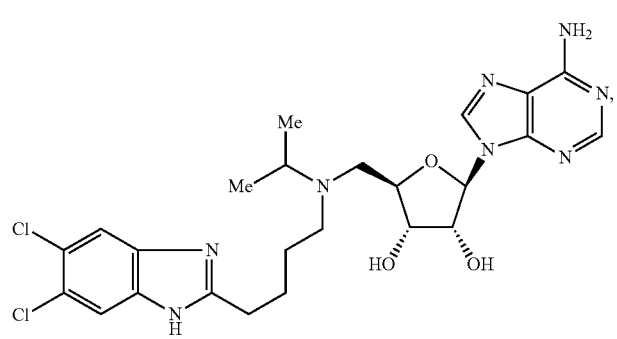
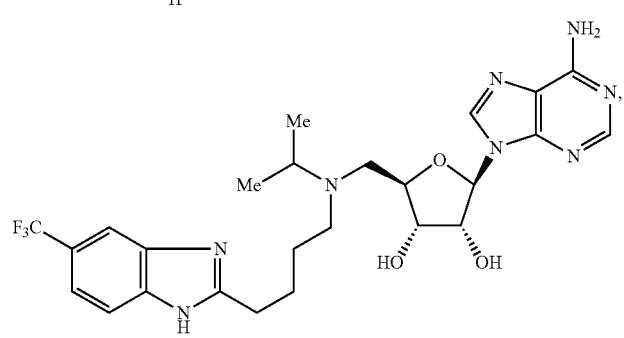
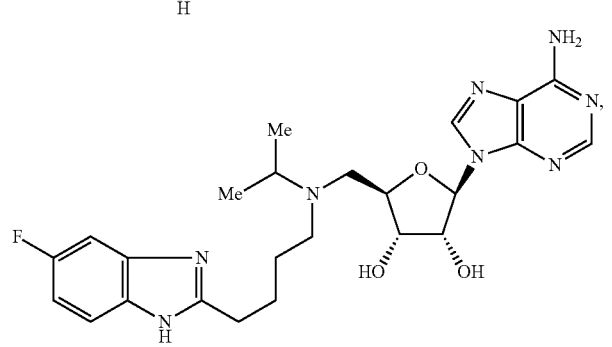

-continued
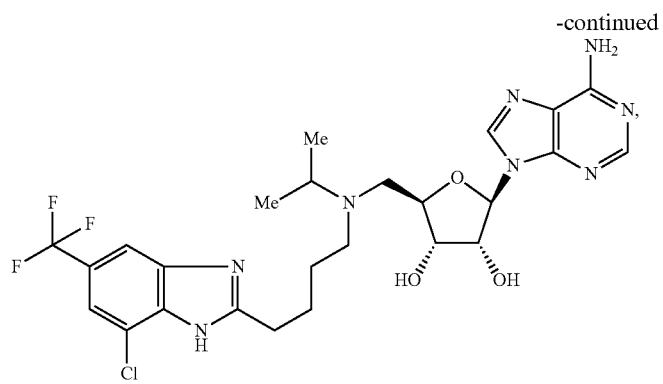
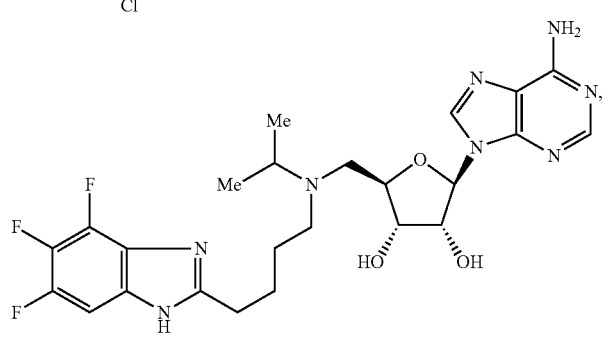
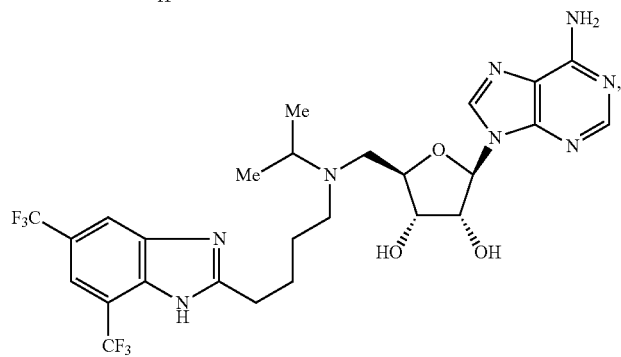
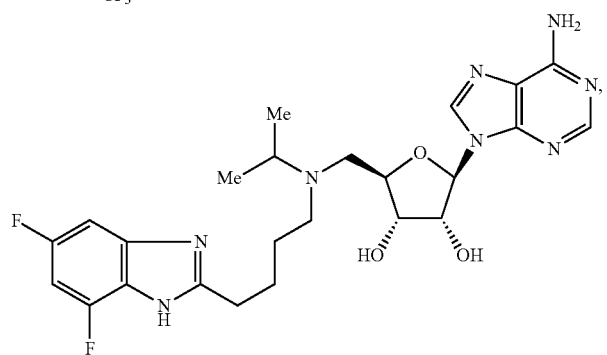
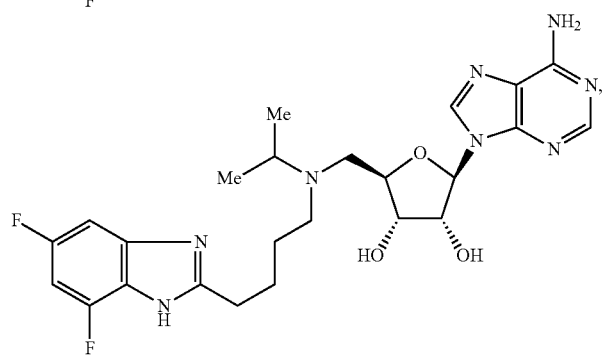

-continued
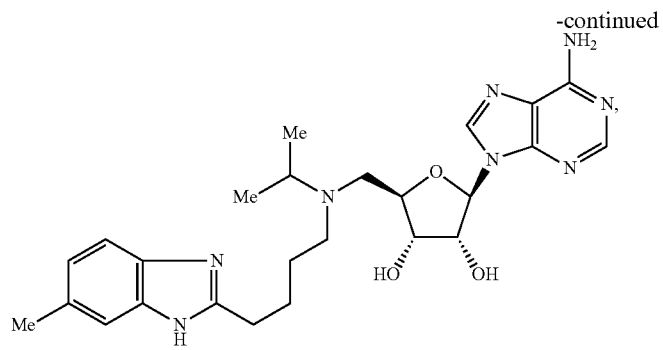
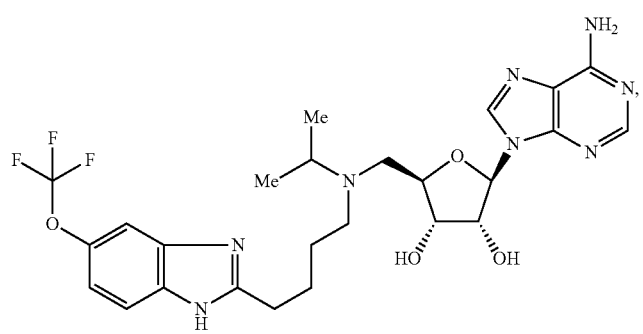
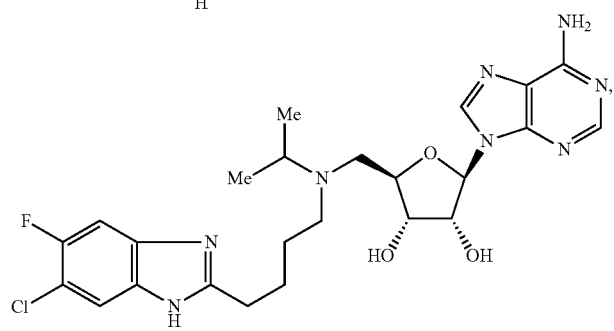
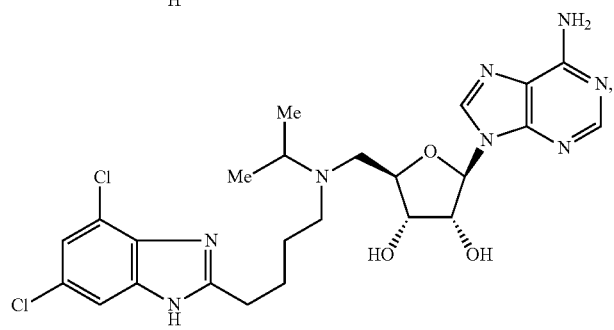
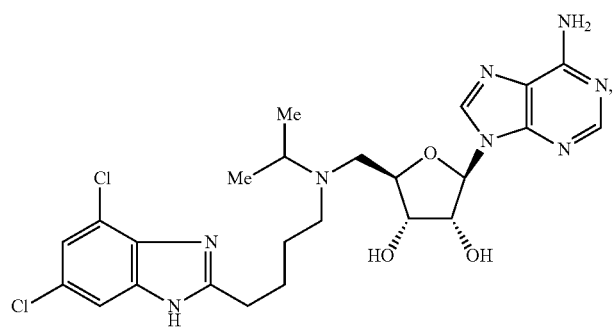

105 106
-continued
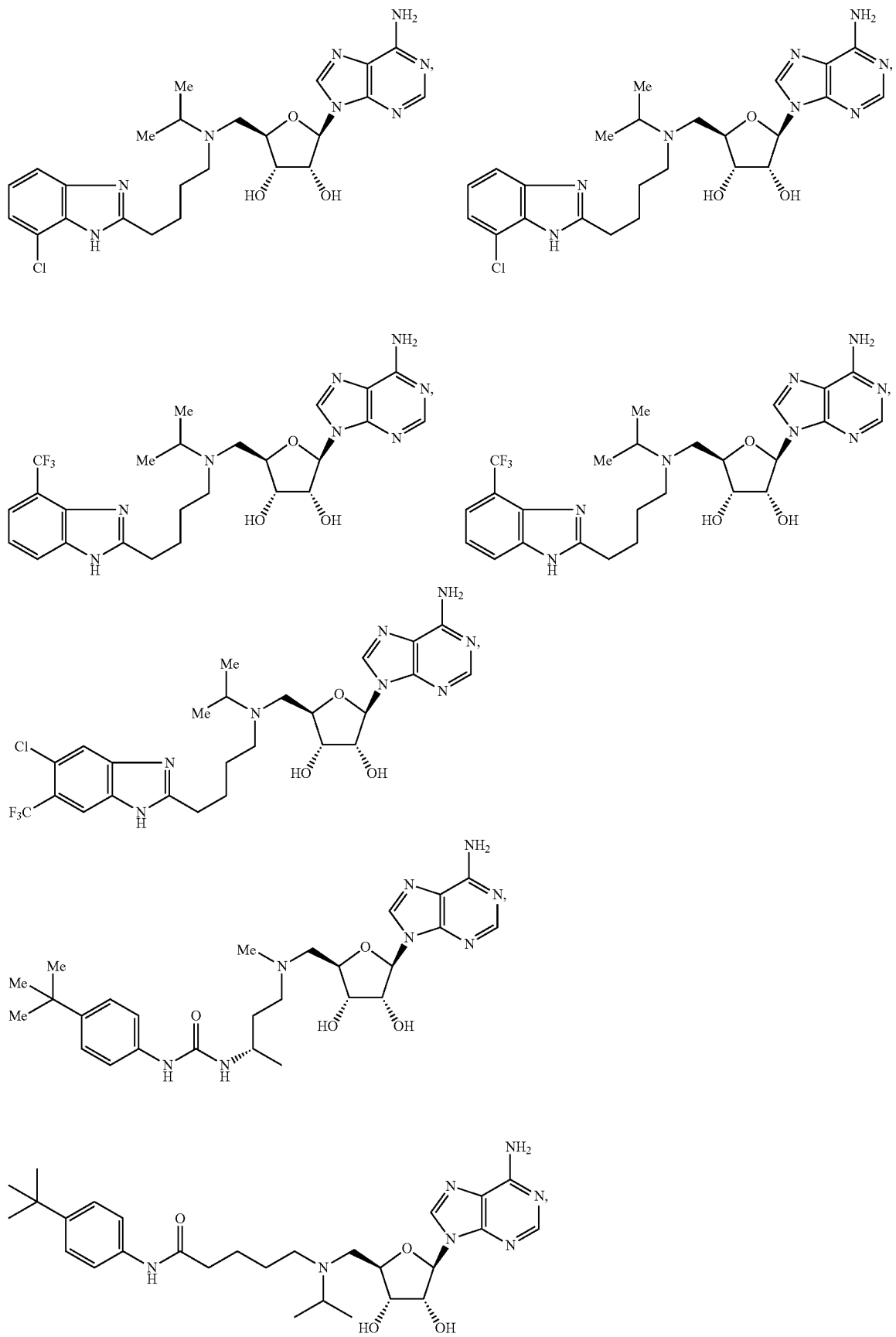

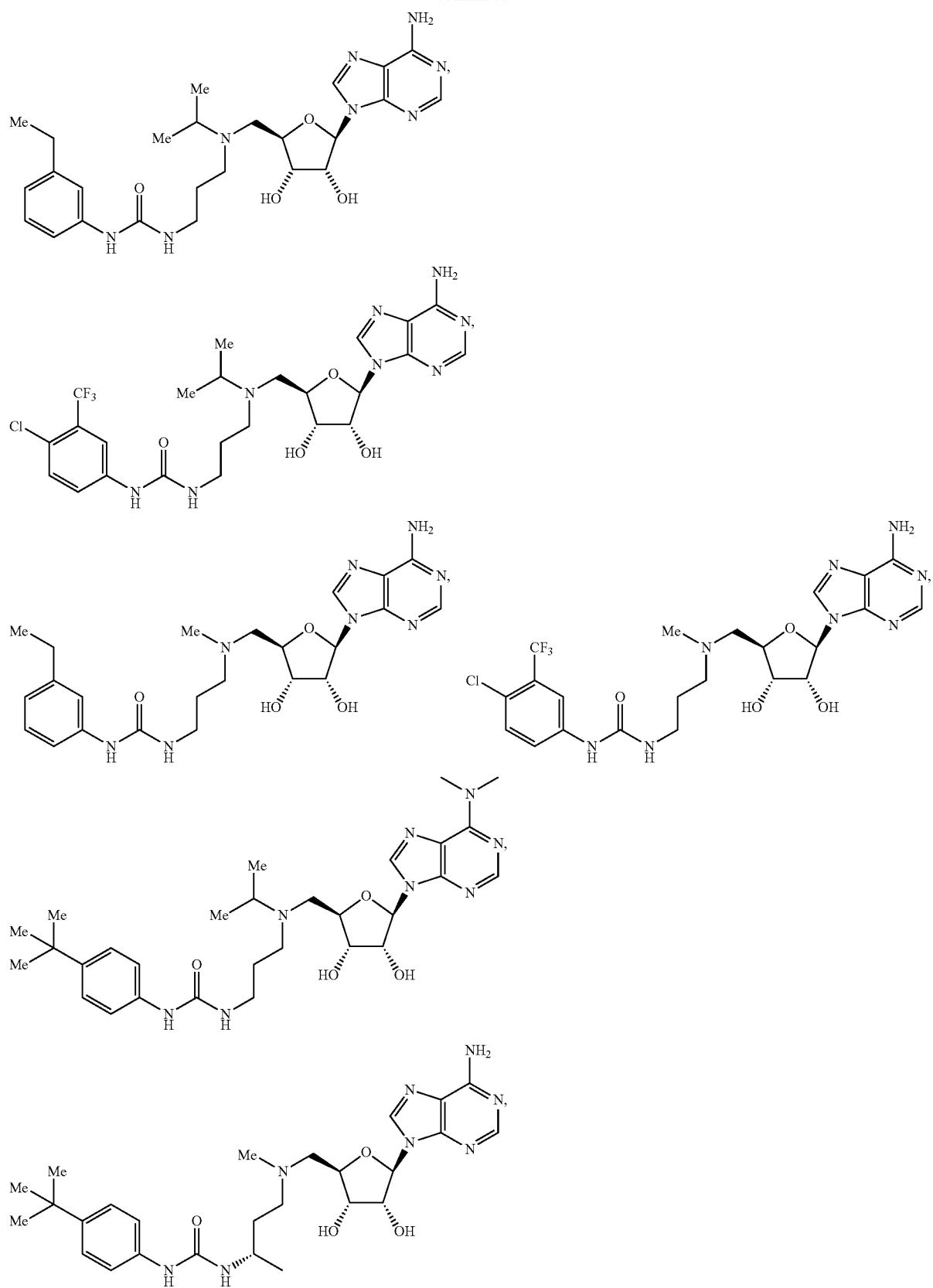

-continued
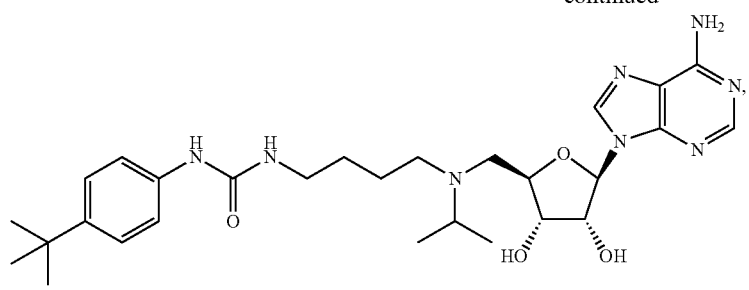
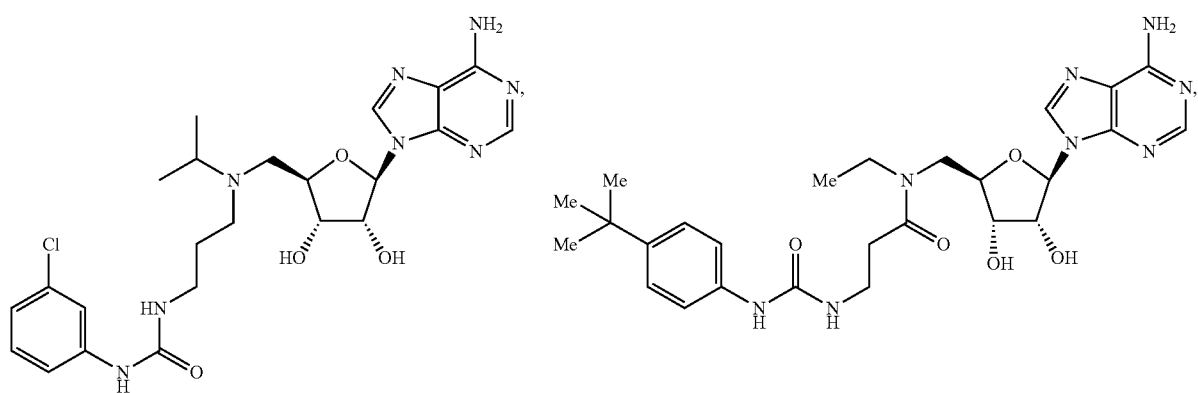
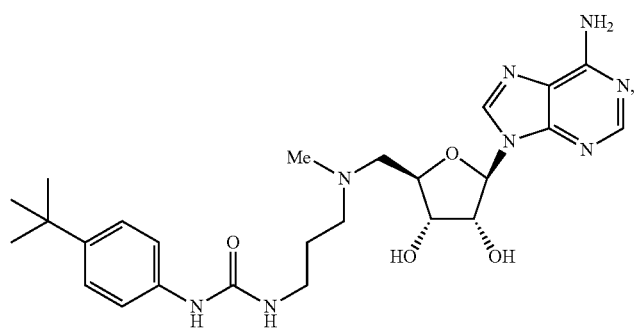
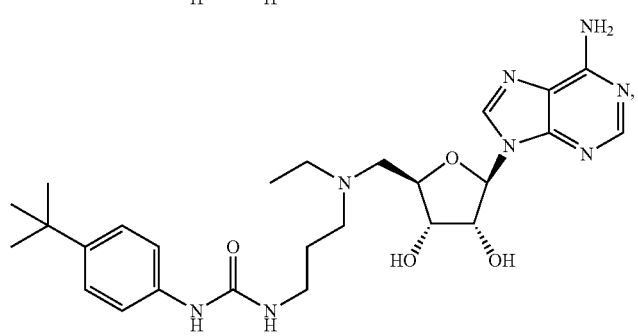
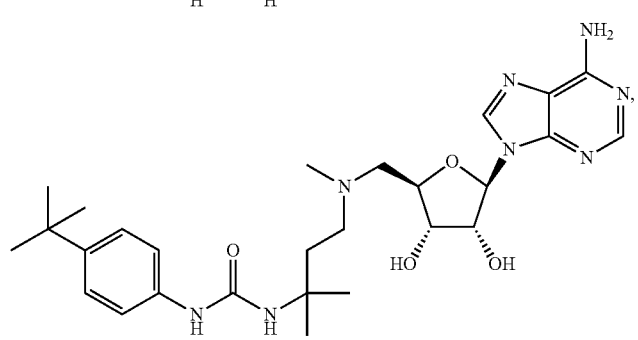

-continued
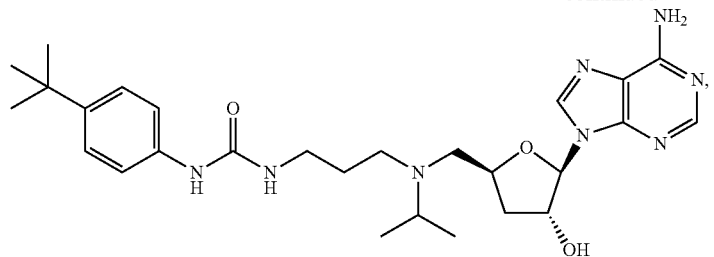 [SMILES: CC(C)N(CCCNC(=O)Nc1ccc(C(C)(C)C)cc1)C[C@@H]1C[C@@H](O)[C@H](n2cnc3c(N)ncnc32)O1]
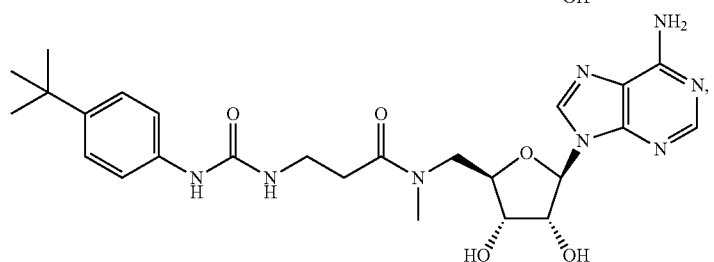
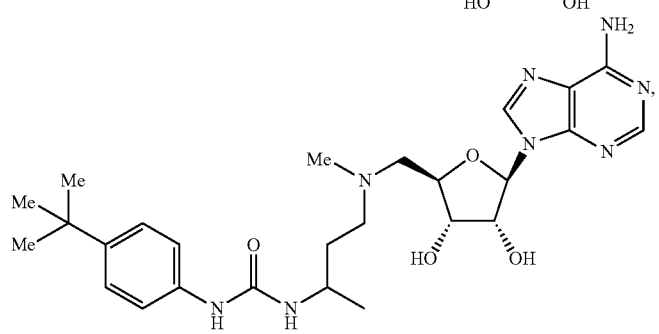
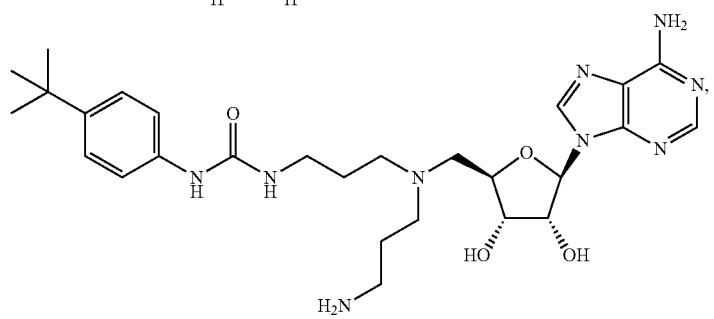
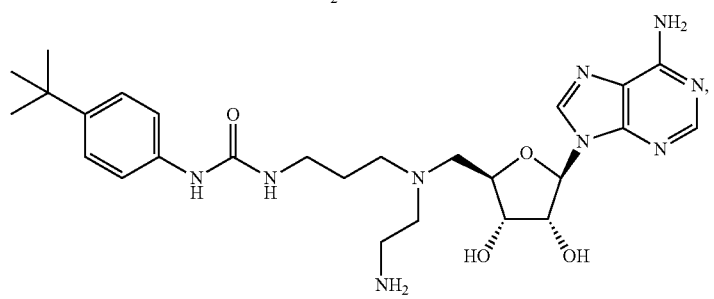
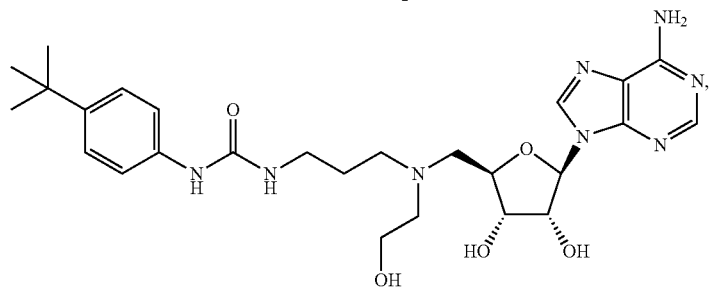

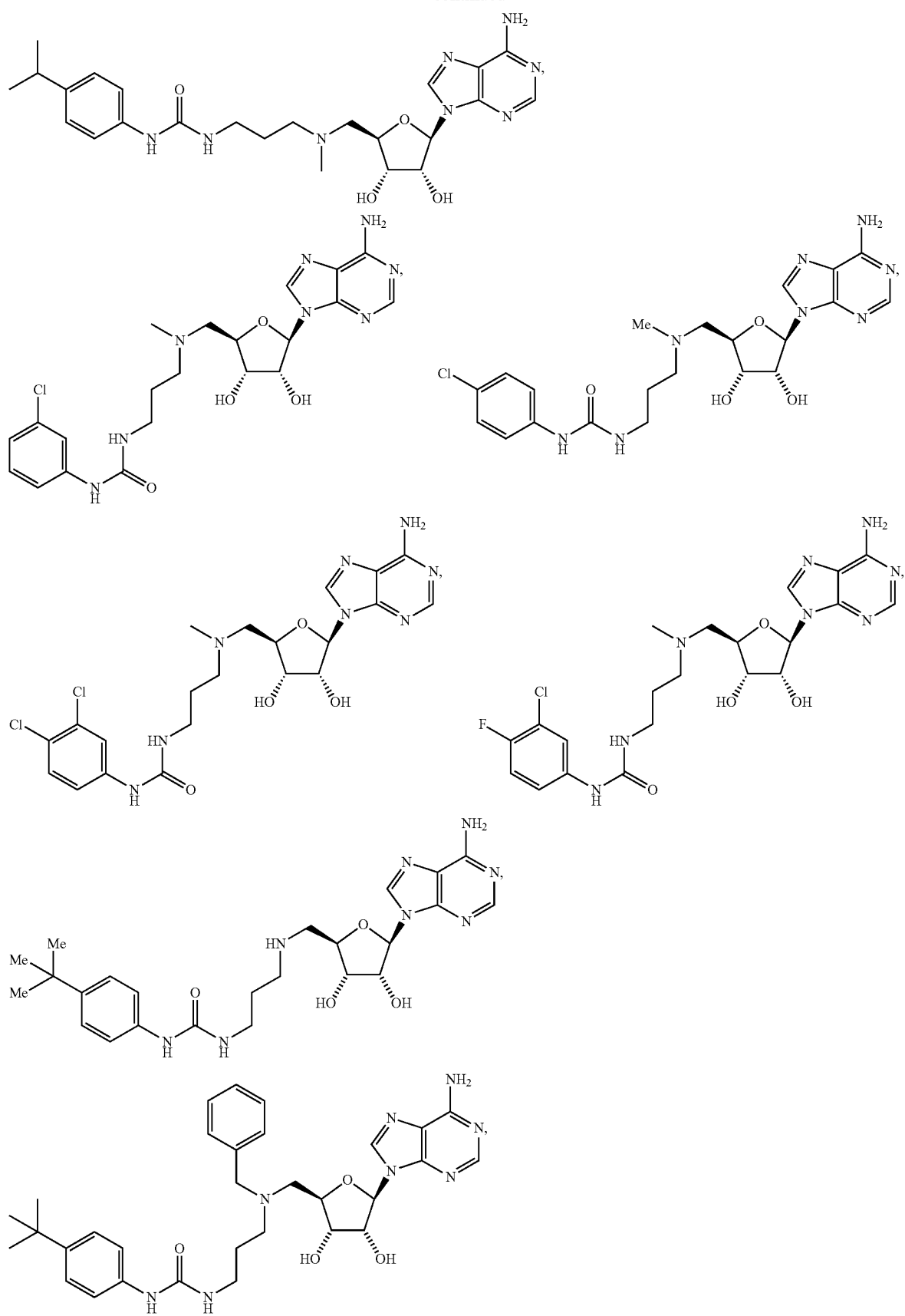

-continued
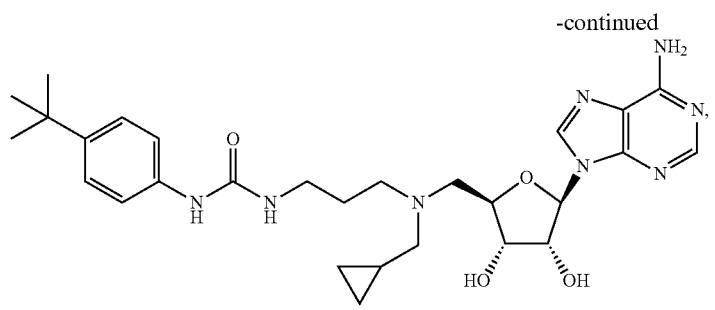
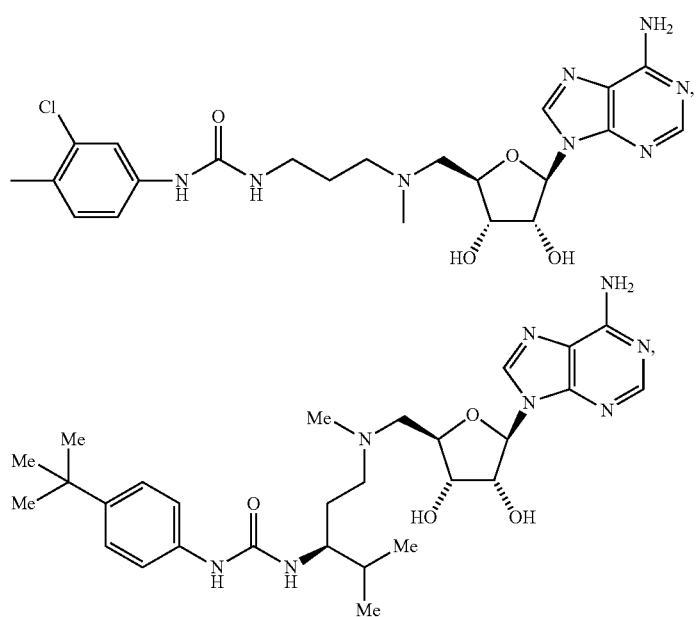
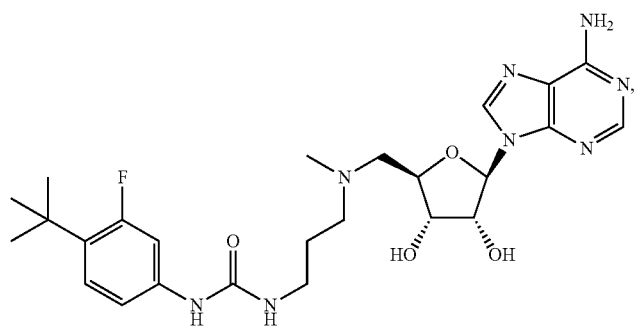
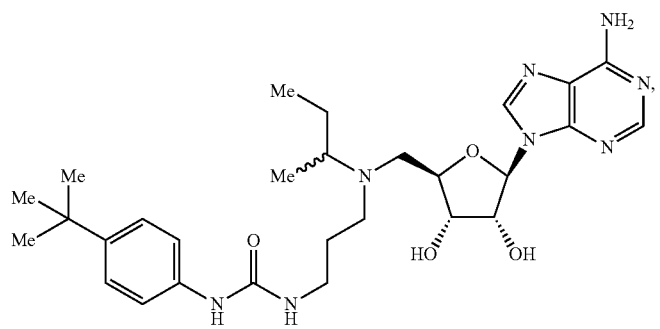

-continued

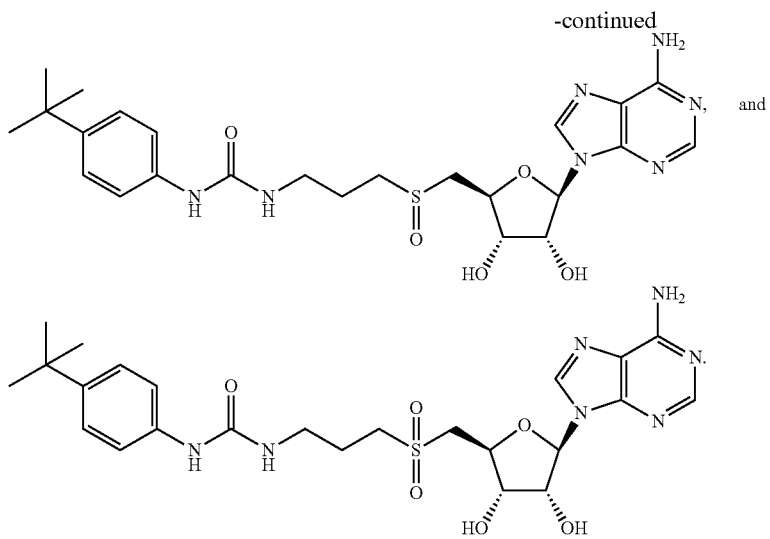

Diseases such as cancers and neurological disease can be treated by administration of modulators of protein (e.g., histone) methylation, e.g., modulators of histone methyltransferase, or histone demethylase enzyme activity. Histone methylation has been reported to be involved in aberrant expression of certain genes in cancers, and in silencing of neuronal genes in non-neuronal cells. Modulators described herein can be used to treat these diseases, i.e., to restore normal methylation states of histones or other proteins to affected cells.

Based at least on the fact that increased histone methylation has been found to be associated with certain cancers, a method for treating cancer in a subject comprises administering to the subject in need thereof a therapeutically effective amount of a compound that decreases methylation or restores methylation to roughly its level in counterpart normal cells. It is important to note that disease-specific increase in methylation can occur at chromatin in key genomic loci in the absence of a global increase in cellular levels of histone or protein methylation. For example, it is possible for aberrant hypermethylation at key disease-relevant genes to occur against a backdrop of global histone or protein hypomethylation, Modulators of methylation can be used for modulating cell proliferation, generally. For example, in some cases excessive proliferation may be reduced with agents that decrease methylation, whereas insufficient proliferation may be stimulated with agents that increase methylation. Accordingly, diseases that may be treated include hyperproliferative diseases, such as benign cell growth and malignant cell growth.

Exemplary cancers that may be treated include leukemias, e.g., acute lymphoid leukemia and myeloid leukemia, and carcinomas, such as colorectal carcinoma and hepatocarcinoma. Other cancers include Acute Lymphoblastic Leukemia; Acute Lymphoblastic Leukemia; Acute Myeloid Leukemia; Acute Myeloid Leukemia; Adrenocortical Carcinoma Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma, see Skin Cancer (non-Melanoma); Bile Duct Cancer, Extrahepatic; Bladder Cancer; Bladder Cancer; Bone Cancer, osteosarcoma/Malignant Fibrous Histiocytoma; Brain Stem Glioma; Brain Tumor; Brain Tumor, Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Brain Tumor; Breast Cancer; Breast Cancer and Pregnancy; Breast Cancer; Breast Cancer, Male; Bronchial Adenomas/Carcinoids; Burkitt's Lymphoma; Carcinoid Tumor; Carcinoid Tumor, Gastrointestinal; Carcinoma of Unknown Primary; Central Nervous System Lymphoma, Primary; Cerebellar Astrocytoma; Cerebral Astrocytoma/Malignant Glioma; Cervical Cancer; Childhood Cancers; Chronic Lymphocytic Leukemia; Chronic Myelogenous Leukemia; Chronic Myeloproliferative Disorders; Colon Cancer; Colorectal Cancer; Cutaneous T-Cell Lymphoma, see Mycosis Fungoides and Sezary Syndrome; Endometrial Cancer; Ependymoma; Esophageal Cancer; Esophageal Cancer; Ewing's Family of Tumors; Extracranial Germ Cell Tumor; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer; Gastrointestinal Carcinoid Tumor; Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma; Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Laryngeal Cancer; Leukemia, Acute Lymphoblastic; Leukemia, Acute Lymphoblastic; Leukemia, Acute Myeloid; Leukemia, Acute Myeloid; Leukemia, Chronic Lymphocytic; Leukemia; Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt's; Lymphoma, Cutaneous T-Cell, see Mycosis Fungoides and Sezary Syndrome; Lymphoma, Hodgkin's; Lymphoma, Hodgkin's; Lymphoma, Hodgkin's During Pregnancy; Lymphoma, Non- Hodgkin's; Lymphoma, Non-Hodgkin's; Lymphoma, Non-Hodgkin's During Pregnancy; Lymphoma, Primary Central Nervous System; Macroglobulinemia, Waldenstrom's; Malignant Fibrous Histiocytoma of Bone/Osteosarcoma; Medulloblastoma; Melanoma; Melanoma, Intraocular (Eye); Merkel Cell Carcinoma; Mesothelioma, Adult Malignant; Mesothelioma; Metastatic Squamous Neck Cancer with Occult Primary; Multiple Endocrine Neoplasia Syndrome; Multiple Myeloma/Plasma Cell Neoplasm' Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer; Neuroblastoma; Non-Hodgkin's Lymphoma; Non-Hodgkin's Lymphoma; Non-Hodgkin's Lymphoma During Pregnancy; Non-Small Cell Lung Cancer; Oral Cancer; Oral Cavity Cancer, Lip and; Oropharyngeal Cancer; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer; Pancreatic Cancer, Islet Cell; Paranasal Sinus and Nasal Cavity Cancer; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Prostate Cancer; Rectal Cancer; Renal Cell (Kidney) Cancer; Renal Cell (Kidney) Cancer; Renal Pelvis and Ureter, Transitional Cell Cancer; Retinoblastoma; Rhabdomyosarcoma; Salivary Gland Cancer; Salivary Gland Cancer; Sarcoma, Ewing's Family of Tumors; Sarcoma, Kaposi's; Sarcoma, Soft Tissue; Sarcoma, Soft Tissue; Sarcoma, Uterine; Sezary Syndrome; Skin Cancer (non-Melanoma); Skin Cancer; Skin Cancer (Melanoma); Skin Carcinoma, Merkel Cell; Small Cell Lung Cancer; Small Intestine Cancer; Soft Tissue Sarcoma; Soft Tissue Sarcoma; Squamous Cell Carcinoma, see Skin Cancer (non-Melanoma); Squamous Neck Cancer with Occult Primary, Metastatic; Stomach (Gastric) Cancer; Stomach (Gastric) Cancer; Supratentorial Primitive Neuroectodermal Tumors; T-Cell Lymphoma, Cutaneous, see Mycosis Fungoides and Sezary Syndrome; Testicular Cancer; Thymoma; Thymoma and Thymic Carcinoma; Thyroid Cancer; Thyroid Cancer; Transitional Cell Cancer of the Renal Pelvis and Ureter; Trophoblastic Tumor, Gestational; Unknown Primary Site, Carcinoma of; Unknown Primary Site, Cancer of; Unusual Cancers of Childhood; Ureter and Renal Pelvis, Transitional Cell Cancer; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; Wilms' Tumor; and Women's Cancers.

Neurologic diseases that may be treated include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's disease, amyotrophic lateral sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease), Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12).

Any other disease in which epigenetic methylation, which is mediated by DOT1, plays a role may be treatable or preventable using compounds and methods described herein.

Combination Therapy

In one aspect of the invention, a compound of the invention, or a pharmaceutically acceptable salt thereof, can be used in combination with another therapeutic agent to treat diseases such cancer and/or neurological disorders. For example, the additional agent can be a therapeutic agent that is art-recognized as being useful to treat the disease or condition being treated by the compound of the present invention. The additional agent also can be an agent that imparts a beneficial attribute to the therapeutic composition (e.g., an agent that affects the viscosity of the composition).

The combination therapy contemplated by the invention includes, for example, administration of a compound of the invention, or a pharmaceutically acceptable salt thereof, and additional agent(s) in a single pharmaceutical formulation as well as administration of a compound of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

The agents set forth below are for illustrative purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

For example, one aspect of the invention relates to the use of a compound of the invention (e.g., those of formula I) in combination with another anticancer agent, e.g., a compound that effects histone modifications, such as an HDAC inhibitor, for the treatment of cancer and/or a neurological disorder. In certain embodiments, the other anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®) biologics (such as Alpha Interferon, *Bacillus* Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Tykerb®, Velcade® and Zevalin™) corticosteroids, (such as dexamethasone sodium phosphate, DeltaSone® and Delta-Cortef®), hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®) and radiopharmaceuticals (such as Iodotope®, Metastron®, Phosphocol® and Samarium SM-153).

Dosage

As used herein, a "therapeutically effective amount" or "therapeutically effective dose" is an amount of a compound of the invention or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount may be determined by methods known to those of skill in the art.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from these cell culture assays and animal studies can be used in formulating a range of dosage for use in humans. Dosage may also be guided by monitoring compound effects on pharmacodynamic markers of enzyme inhibition (e.g., histone methylation or target gene expression) in diseased or surrogate tissue. Cell culture or animal experiments can be used to determine the relationship between doses required for changes in pharmacodynamic markers and doses required for therapeutic efficacy can be determined in cell culture or animal experiments or early stage clinical trials. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. In the treatment of crises, the administration of an acute bolus or an infusion approaching the MTD may be required to obtain a rapid response.

Dosage amount and interval may be adjusted individually to provide plasma levels of the active moiety which are sufficient to maintain the methyltransferase modulating effects, or minimal effective concentration (MEC) for the required period of time to achieve therapeutic efficacy. The MEC will vary for each compound but can be estimated from in vitro data and animal experiments. Dosages necessary to achieve the MEC will depend on individual characteristics and route of administration. However, HPLC assays or bioassays can be used to determine plasma concentrations.

Dosage intervals can also be determined using the MEC value. In certain embodiments, compounds should be administered using a regimen which maintains plasma levels above the MEC for 10-90% of the time, preferably between 30-90% and most preferably between 50-90% until the desired amelioration of symptoms is achieved. In other embodiments, different MEC plasma levels will be maintained for differing amounts of time. In cases of local administration or selective uptake, the effective local concentration of the drug may not be related to plasma concentration.

One of skill in the art can select from a variety of administration regimens and the amount of composition administered will, of course, be dependent on the subject being treated, on the subject's weight, the severity of the affliction, the manner of administration and the judgment of the prescribing physician.

Kits

The compounds and compositions of the invention (e.g., compounds and compositions of formula I) may, if desired, be presented in a kit (e.g., a pack or dispenser device) which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Instructions for use may also be provided.

Assessment of Activity of Compounds

DOT1L polypeptides and nucleic acids can be used to screen for compounds that bind to and/or modulate (e.g., increase or decrease) one or more biological activities of DOT1L, including but not limited to H3K79 HMTase activity, SAM binding activity, histone and/or nucleosome binding activity, AF10 binding activity, AF10-MLL or other MLL fusion protein binding activity, and/or any other biological activity of interest. A DOT1L polypeptide can be a functional fragment of a full-length DOT1L polypeptide or functional equivalent thereof, and may comprise any DOT1 domain of interest, including but not limited to the catalytic domain, the SAM binding domain and/or the positively charged domain, the AF10 interaction domain and/or a nuclear export signal.

Methods of assessing DOT1L binding to histones, nucleosomes, nucleic acids or polypeptides can be carried out using standard techniques that will be apparent to those skilled in the art (see the Exemplification for exemplary methods). Such methods include yeast and mammalian two-hybrid assays and co-immunoprecipitation techniques.

For example, a compound that modulates DOT1L H3K79 HMTase activity can be verified by: contacting a DOT1L polypeptide with a histone or peptide substrate comprising H3 in the presence of a test compound; detecting the level of H3K79 methylation of the histone or peptide substrate under conditions sufficient to provide H3K79 methylation, wherein an elevation or reduction in H3K79 methylation in the presence of the test compound as compared with the level of histone H3K79 methylation in the absence of the test compound indicates that the test compound modulates DOT1L H3K79 HMTase activity.

The screening methods of the invention can be carried out in a cell-based or cell-free system. As a further alternative, the assay can be performed in a whole animal (including transgenic non-human animals). Further, with respect to cell-based systems, the DOT1L polypeptide (or any other polypeptide used in the assay) can be added directly to the cell or can be produced from a nucleic acid in the cell. The nucleic acid can be endogenous to the cell or can be foreign (e.g., a genetically modified cell).

Any compound of interest can be screened according to the present invention. Suitable test compounds include small organic compounds. Small organic compounds include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, terpenes, porphyrins, toxins, catalysts, as well as combinations thereof.

DEFINITIONS

For convenience, certain terms employed in the specification, examples, and appended claims are collected here. All definitions, as defined and used herein, supersede dictionary definitions, definitions in documents incorporated by reference, and/or ordinary meanings of the defined terms.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "hydrate" refers to a pharmaceutically acceptable foam of a specified compound, with one or more water molecules, that retains the biological effectiveness of such compound.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e., six carbons or less). For example "lower alkyl" refers to an alkyl group containing 1-6 carbons, and "lower alkenyl" refers to an alkenyl group containing 2-6 carbons.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing $4n+2$ electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic hydrocarbon radical containing from 1 to 20 carbon atoms. In one embodiment the term "alkyl" refers to an aliphatic hydrocarbon radical containing from 1 to 15 carbon atoms. In one embodiment the term "alkyl" refers to an aliphatic hydrocarbon radical containing from 1 to 10 carbon atoms. In one embodiment the term "alkyl" refers to an aliphatic hydrocarbon radical containing from 1 to 6 carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 2-methylcyclopentyl, 1-(1-ethylcyclopropyl)ethyl and 1-cyclohexylethyl.

The term "cycloalkyl" refers to a cyclic hydrocarbon radical containing from 3 to 15 carbon atoms. In one embodiment the term "cycloalkyl" refers to a cyclic hydrocarbon radical containing from 3 to 10 carbon atoms. In one embodiment the term "cycloalkyl" refers to a cyclic hydrocarbon radical containing from 3 to 7 carbon atoms. Representative examples of cycloalkyl include, but are not limited to, cyclopropyl and cyclobutyl.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene," is art-recognized, and as used herein pertains to a diradical obtained by removing two hydrogen atoms of an alkyl group, as defined above.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein refers to a radical of a non-aromatic, ring system, including, but not limited to, monocyclic, bicyclic and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substiuents bound to the heterocyclyl group through an alkylene moiety (e.g., methylene).

The term "aryl," as used herein means a phenyl, naphthyl, phenanthrenyl, or anthracenyl group. The aryl groups of the present invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substiuents bound to the heterocyclyl group through an alkylene moiety (e.g., methylene).

The term "arylene" is art-recognized, and as used herein pertains to a diradical obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "biaryl," as used herein means an aryl-substituted aryl, an aryl-substituted heteroaryl, a heteroaryl-substituted aryl or a heteroaryl-substituted heteroaryl, wherein aryl and heteroaryl are as defined herein. Representative examples include 4-(phenyl)phenyl and 4-(4-methoxyphenyl)pyridinyl.

The term "fused bicyclyl" as used herein means the radical of a bicyclic ring system wherein the two rings are ortho-fused, and each ring, contains a total of four, five, six or seven atoms (i.e. carbons and heteroatoms) including the two fusion atoms, and each ring can be completely saturated, can contain one or more units of unsaturation, or can be completely unsaturated (e.g., in some case, aromatic). For the avoidance of doubt, the degree of unsaturation in the fused bicyclyl does not result in an aryl or heteroaryl moiety.

The term "heteroaryl" as used herein include radicals of aromatic ring systems, including, but not limited to, monocyclic, bicyclic and tricyclic rings, which have 3 to 12 atoms including at least one heteroatom, such as nitrogen, oxygen, or sulfur. For purposes of exemplification, which should not be construed as limiting the scope of this invention: aminobenzimidazole, benzimidazole, azaindolyl, benzo[b]thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g., methylene).

The term "heteroarylene," is art-recognized, and as used herein pertains to a diradical obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl) ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein some or all of the hydrogens are replaced with fluorines.

The term "haloalkylene," as used herein pertains to diradical obtained by removing two hydrogen atoms of a haloalkyl group, as defined above.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkyenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethyl-phenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through a sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluoroalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxy" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy" are likewise defined.

The term "amino" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.

The term "nitro" as used herein means a —NO$_2$ group.

The term "azido" as used herein means a —N$_3$ group.

The term "phosphinyl" or "phosphino" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH$_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes H$_3$Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

The term "treating" as used herein, encompasses the administration and/or application of one or more compounds described herein, to a subject, for the purpose of providing prevention of or management of, and/or remedy for a condition. "Treatment" for the purposes of this disclosure, may, but does not have to, provide a cure; rather, "treatment" may be in the form of management of the condition. When the compounds described herein are used to treat unwanted proliferating cells, including cancers, "treatment" includes partial or total destruction of the undesirable proliferating cells with minimal destructive effects on normal cells. A desired mechanism of treatment of unwanted rapidly proliferating cells, including cancer cells, at the cellular level is apoptosis.

The term "preventing" as used herein includes either preventing or slowing the onset of a clinically evident disease progression altogether or preventing or slowing the onset of a preclinically evident stage of a disease in individuals at risk. This includes prophylactic treatment of those at risk of developing a disease.

The term "subject" for purposes of treatment includes any human or animal subject who has been diagnosed with, has symptoms of, or is at risk of developing a disorder. For methods of prevention the subject is any human or animal subject. To illustrate, for purposes of prevention, a subject may be a human subject who is at risk of or is genetically predisposed to obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds described herein are also useful for veterinary treatment of mammals, including companion animals and farm animals, such as, but not limited to dogs, cats, horses, cows, sheep, and pigs.

Except as otherwise indicated, standard methods can be used for the production of recombinant and synthetic polypeptides, fusion proteins, antibodies or antigen-binding fragments thereof, manipulation of nucleic acid sequences, production of transformed cells, and the like. Such techniques are known to those skilled in the art. See, e.g., Sambrook et al., *Molecular Cloning: A Laboratory Manual* 2nd Ed. (Cold Spring Harbor, N.Y., 1989); F. M. Ausubel et al., *Current Protocols in Molecular Biology* (Green Publishing Associates, Inc. and John Wiley & Sons, Inc., New York).

The term "DOT1L polypeptide" encompasses functional fragments of the full-length polypeptides and functional equivalents of either of the foregoing that have substantially similar or substantially identical amino acid sequences (at least about 75%, 80%, 85%, 90%, 95% 98% or more amino acid sequence similarity or identity), where the functional fragment or functional equivalent retains one or more of the functional properties of the native polypeptide.

By "functional" it is meant that the polypeptide (or nucleic acid) has the same or substantially similar activity with respect to one or more of the biological properties of the native polypeptide (or nucleic acid), e.g., at least about 50%, 75%, 85%, 90%, 95% or 98% or more of the activity of the native polypeptide (or nucleic acid).

The term "modulate" (and grammatical equivalents) refers to an increase or decrease in activity. In particular embodiments, the term "increase" or "enhance" (and grammatical equivalents) means an elevation by at least about 25%, 50%, 75%, 2-fold, 3-fold, 5-fold, 10-fold, 15-fold, 20-fold or more. In particular embodiments, the terms "decrease" or "reduce" (and grammatical equivalents) means a diminishment by at least about 25%, 40%, 50%, 60%, 75%, 80%, 85%, 90%, 95%, 98% or more. In some embodiments, the indicated activity, substance or other parameter is not detectable. Specifically provided are inhibitors of DOT1L.

The term "pharmacodynamic marker" refers to a molecular marker of drug response that can be measured in patients receiving the drug. The marker should be a direct measure of modulation of the drug target and be able to show quantitative changes in response to dose. A potential pharmacodynamic marker for a DOT1L inhibitor could be levels of histone H3K79 methylation in disease or surrogate tissue.

EXEMPLIFICATION

The invention now being generally described, it will be more readily understood by reference to the following examples, which are included merely for purposes of illustration of certain aspects and embodiments of the present invention, and are not intended to limit the invention.

Abbreviations

| Abbreviation | Definition |
|---|---|
| AA | ammonium acetate |
| Ac | acetyl |
| ACN | acetonitrile |
| AcOH | acetic acid |
| atm | atmosphere |
| Bn | benzyl |
| BOC | tert-butoxy carbonyl |
| BOP | (benzotriazol-1-yloxy)tris(dimethylamino)phosphonium hexafluorophosphate |
| Cbz | benzyloxy carbonyl |
| COMU | (1-Cyano-2-ethoxy-2-oxoethylidenaminooxy)dimethylamino-morpholino-carbenium hexafluorophosphate |
| d | days |

-continued

| Abbreviation | Definition |
|---|---|
| DBU | 1,8-diazabicyclo[5.4.0]undec-7-ene |
| DCE | 1,2 dichloroethane |
| DCM | dichloromethane |
| DEAD | Diethyl azodicarboxylate |
| DIAD | Diisopropyl azodicarboxylate |
| DiBAL-H | di-isobutyl aluminum hydride |
| DIPEA | N,N-diisopropylethylamine (Hunig's base) |
| DMAP | N,N-dimethyl-4-aminopyridine |
| DMB | 2,4 dimethoxy benzyl |
| DMF | dimethylformamide |
| DMSO | Dimethyl sulfoxide |
| DPPA | Diphenylphophonic azide |
| EA or EtOAc | Ethyl acetate |
| EDC or EDCI | N-(3-Dimethylaminopropyl)-N'-ethylcarbodiimide |
| ELS | Evaporative Light Scattering |
| ESI− | Electrospray negative mode |
| ESI+ | Electrospray positive mode |
| $Et_2O$ | diethyl ether |
| $Et_3N$ or TEA | triethylamine |
| EtOH | ethanol |
| FA | formic acid |
| FC | Flash chromatography |
| h | hours |
| $H_2O$ | water |
| HATU | O-(7-Azabenzotriazol-1-yl)-N,N,N',N'-tetramethyluronium hexafluorophosphate |
| HCl | hydrochloric acid |
| HOAT | 1-Hydroxy-7-azabenzotriazole |
| HOBt | 1-Hydroxybenzotriazole |
| HO-Su | N-Hydroxysuccinimide |
| HPLC | High performance liquid chromatography |
| KHMDs | Potassium hexamethyldisilazide |
| LC/MS or LC-MS | liquid chromatography mass spectrum |
| LDA | Lithium diisopropylamide |
| LG | leaving group |
| LiHMDs | Lithium hexamethyldisilazide |
| M | Molar |
| m/z | mass/charge ratio |
| m-CPBA | meta-chloroperbenzoic acid |
| MeCN | Acetonitrile |
| MeOD | $d_4$-methanol |
| MeOH | methanol |
| $MgSO_4$ | magnesium sulfate |
| min | minutes |
| MS | Mass Spectrometry |
| Ms | Mesyl |
| MS | mass spectrum |
| MsCl | Mesyl chloride |
| MsO | Mesylate |
| MWI | microwave irradiation |
| $Na_2CO_3$ | sodium carbonate |
| $NaHCO_3$ | sodium bicarbonate |
| NaHMDs | Sodium hexamethyldisilazide |
| NaOH | sodium hydroxide |
| NIS | N-iodosuccinimide |
| NMR | Nuclear Magnetic Resonance |
| o/n or O/N | overnight |
| PE | Petroleum Ether |
| PG | protecting group |
| PMB | para methoxybenzyl |
| PPAA | 1-Propanephosphonic acid cyclic anhydride |
| ppm | parts per million |
| prep HPLC | preparative High performance liquid chromatography |
| prep TLC | preparative thin layer chromatography |
| p-TsOH | para-toluenesulfonic acid |
| rt or RT | room temperature |
| SEM | 2-(Trimethylsilyl)ethoxymethyl |
| SEMCl | -(Trimethylsilyl)ethoxymethyl chloride |
| SFC | Super critical chromatography |
| SGC | silica gel chromatogrpahy |
| STAB | Sodium triacetoxy borohydride |
| TBAF | tetra-n-butylammonium fluoride |
| TFA | trifluoroacetic acid |
| TfO | triflate |
| THF | tetrahydrofuran |
| THP | tetrahydropyran |
| TLC | thin layer chromatography |
| Ts | tosyl |
| TsOH | tosic acid |
| UV | ultraviolet |

General Methods

Cell Culture.

Human Leukemia cell lines THP-1, RS4; 11, and MV4-11 were obtained from ATCC, MOLM-13 cells were obtained from DSMZ. All lines were grown in RPMI 1640 containing 10% FBS and maintained using the vendors recommended cell densities and environmental conditions. Media was supplemented with non essential amino acids and L-Glutamine. THP-1 cells were also supplemented with 0.05 mM 13-Mercaptoethanol.

Methylation Analysis.

Cells were seeded at $5\times10^5$ cells/mL in a 12 well plate at a final volume of 2 mLs. Cells were dosed with compounds to the appropriate concentration from a 50 mM DMSO stock solution. Compound and media were refreshed every two days over the course of seven day incubation by counting cells using trypan blue exclusion (Vicell), pelleting at 200 g for 5 minutes and resuspending in fresh media containing compound at a final cell concentration of $5\times10^5$ cells/mL. Following compound incubation, histones were extracted from $1\times10^6$ cells using a commercial histone extraction kit (Active Motif). Purified histones were quantitated using the BCA protein assay (Pierce) with a BSA standard curve. 400 ng of isolated histones were fractionated by SDS-PAGE on a 4-20% gel and transferred to nitrocellulose membranes. Membranes were incubated with various primary and secondary antibodies and imaged on the Licor imaging system (Odyssey). The H3K79-Me2 rabbit polyclonal was purchased from Abcam. Other rabbit polyclonal antibodies including H3K4-Me3, H3K9-Me3, H3K27-Me2, and H3K27-Me3 were purchased from Cell Signaling Technologies (CST). A mouse monoclonal total H3 antibody was used as a loading control (CST). Fluorescently labeled secondary antibodies were purchased from Odyssey.

Cell Growth and Viability Analysis.

Cells were harvested from exponentially growing cell cultures and seeded at $3\times10^4$ cells per well. Samples were maintained in a 96 well black walled clear bottom plate (Corning). A final concentration of 50 uM compound in 0.2% DMSO was added to the appropriate wells on Day 0. Treatment of MV4-11 and MOLM-13 lasted 14 days, while THP-1 cells were treated for 18 days. Compound and media were replaced every two days during incubation by transferring samples to a V-bottom plate (Corning), spinning at 200 g for 5 minutes in a room temperature rotor, resuspending in fresh media containing compound and transferring back to the assay plate. Cells were counted periodically using the Guava Viacount assay and read on the EasyCyte Plus instrument (Millipore). Assay plates were split when necessary to within recommended cell densities. Final cell counts were adjusted to take cell splits into account and reported as total viable cells/well HOXA9 (qPCR).

Cells were treated with compound for 7 days similar to methylation assay. Cells were pelleted at 200 g in a room temperature rotor and total RNA isolated using the Qiagen RNeasy kit. RNA concentration and quality was determined by using the Nanovue (GE Healthcare). Total RNA was reverse transcribed using a high capacity cDNA reverse transcription kit (Applied Biosystems). A predesigned labeled primer set for HOXA9 was purchased from Applied Biosystems. qPCR reactions contained 50 ng cDNA, 1× labeled primer and 1× Taqman universal PCR master mix (Applied Biosystems). Samples were run on a 7900 HT Fast Real Time PCR machine (Applied Biosystems) with PCR conditions of 2 min 50° C., 10 min 95° C., 40 cycles at 15 sec 95° C. and 1 min 60° C. HOXA9 cycle numbers were normalized to the house keeping gene B2 microglobulin (B2M predesigned control from Applied Biosystems). Percent of DMSO control was calculated with the equation, percent control=$(2^{-\Delta\Delta CT})$ *100 where the ΔΔCT is the difference between normalized HOXA9 sample and control (ACT sample−ACT control=ΔΔCT).

Determination of $IC_{50}$.

Compound was serially diluted 3 fold in DMSO for 10 points and 1 µl was plated in a 384 well microtiter plate. Positive control (100% inhibition standard) was 2.5 uM final concentration of S-adenosyl-L-homocysteine and negative control (0% inhibition standard) contained 1 µl of DMSO. Compound was then incubated for 30 minutes with 40 µl per well of DOT1L(1-416) (0.25 nM final concentration in assay buffer: 20 mM TRIS, pH 8.0, 10 mM NaCl, 0.002% Tween20, 0.005% Bovine Skin Gelatin, 100 mM KCl, and 0.5 mM DTT). 10 µl per well of substrate mix (same assay buffer with 200 nM 5-[methyl-$^3$H]-adenosyl-L methionine, 600 nM of unlabeled S-[methyl-$^3$H]-adenosyl-L methionine, and 20 nM oligonucleosome) was added to initiate the reaction. Reaction was incubated for 120 minutes at room temperature and quenched with 10 µl per well of 100 µM S-methyl-adenosyl-L methionine. For detection, substrate from 50 µl of reaction was immobilized on a 384 well Streptavidin coated Flashplate (Perkin Elmer) (also coated with 0.2% polyethyleneimine) and read on a Top Count scintillation counter (Perkin Elmer).

General Synthetic Schemes.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

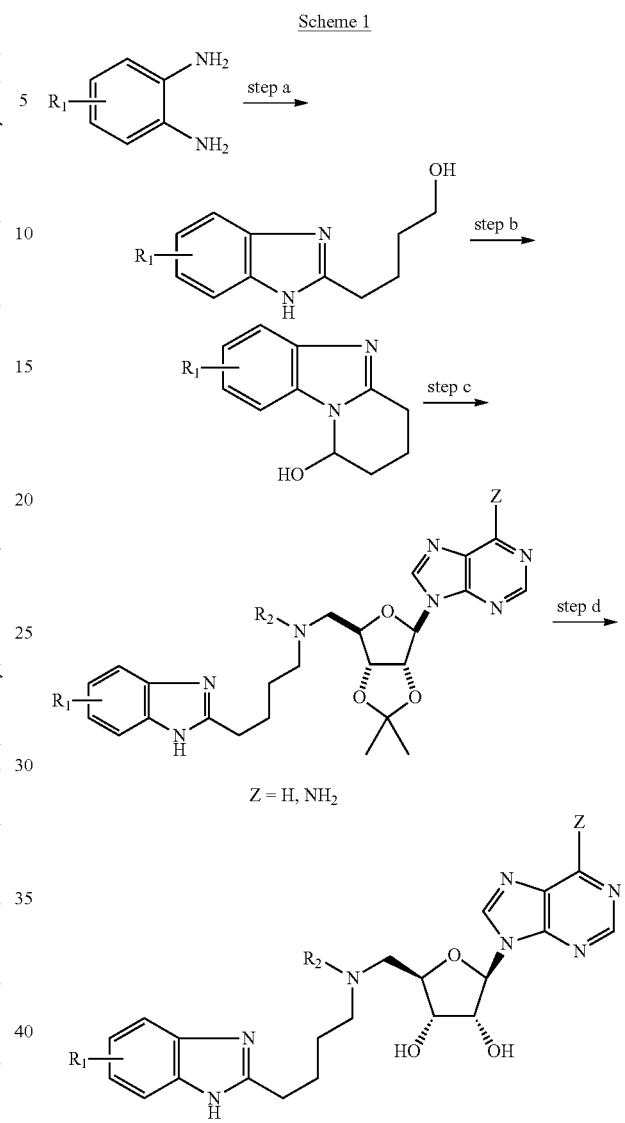

Scheme 1 shows the synthesis of modified aminopurine analogs following a general route that utilizes well-established chemistry. Condensation of and tetrahydropyran-2-one with an appropriately substituted diaminobenzene derivative would provide the benzimidazole (step a). Oxidation with a suitable reagent like IBX in ethyl acetate would give the modified benzimidazole (step b). Reductive amination with the amine using sodium acetoxyborohydride in dichloroethane would give coupled product (step c). Removal of the acetonide protecting group under acidic conditions using HCl in MeOH would give the desired diol (step d).

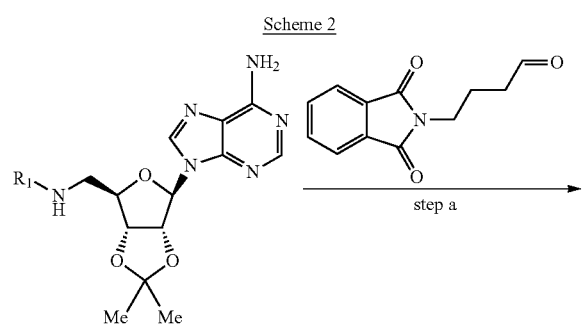

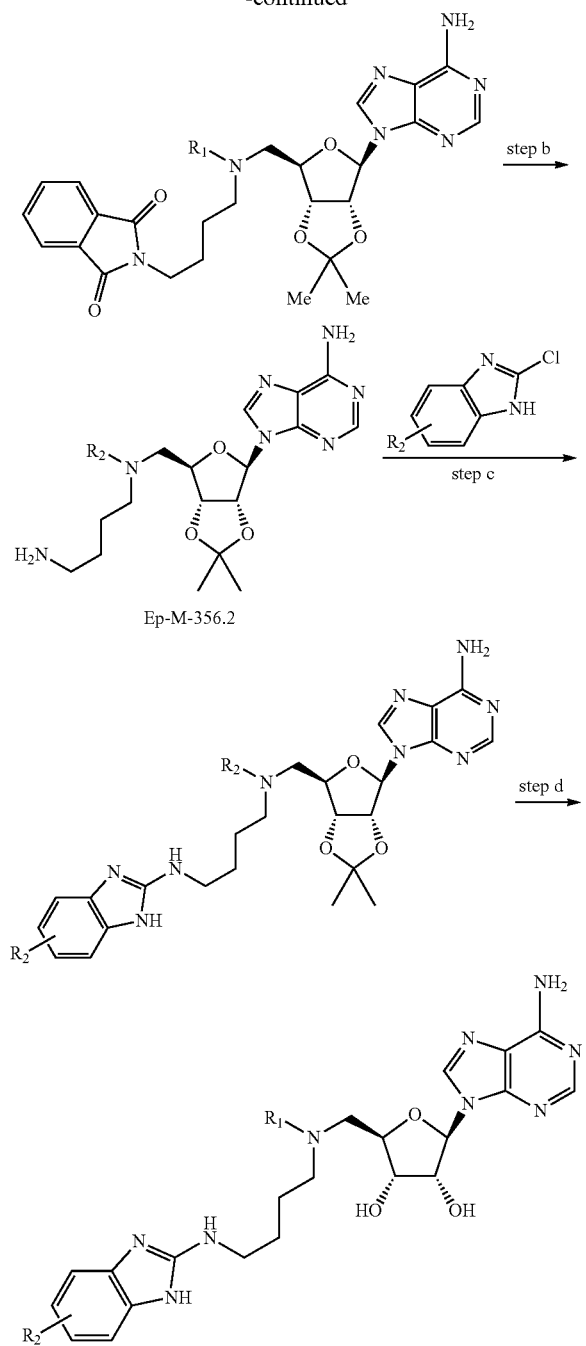

Ep-M-356.2

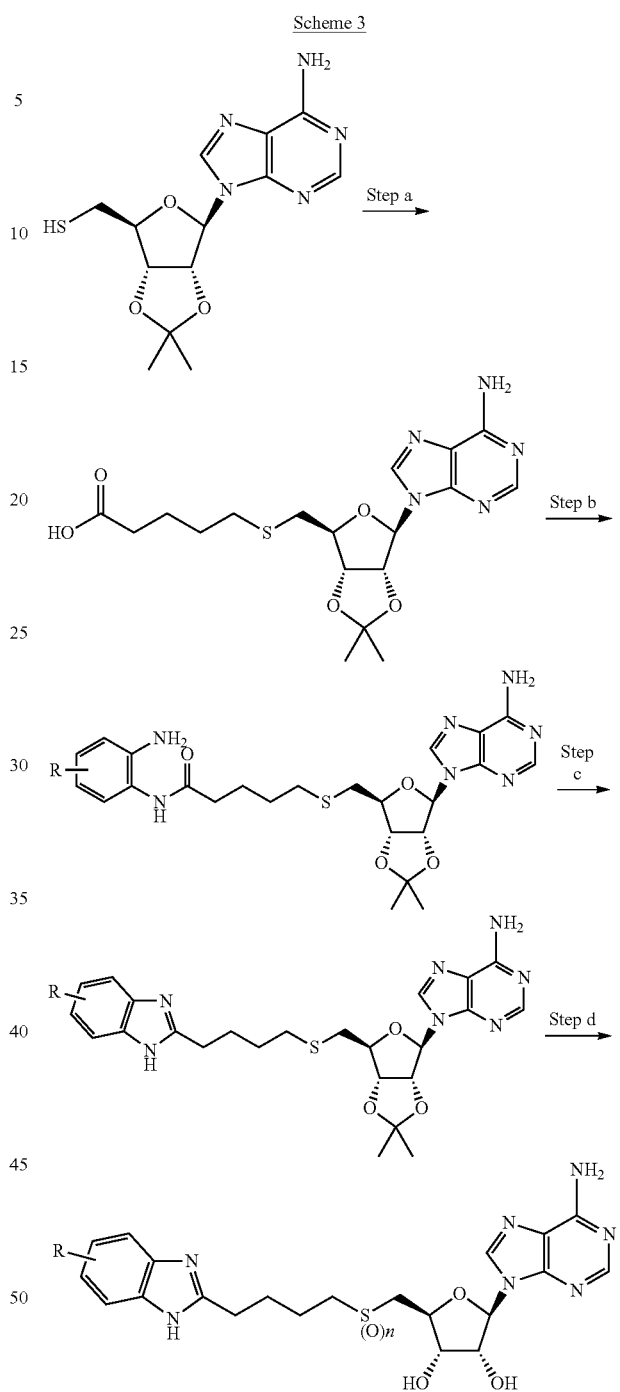

Scheme 3

Scheme 2 details a synthesis of related aminopurine analogs containing an aminobenzimidazole moiety. Condensation of an amine with 4-(1,3-dioxoisoindolin-2-yl)butanal using sodium acetoxyborohydride in dichloroethane would give the protected amine (step a). Removal of the amine protecting group would be accomplished by treating this intermediate with hydrazine in refluxing ethanol and would give the free amine (step b). Condensation of the amine with an appropriately substituted 2-chlorobenzamidazole at elevated temperature in tert-butanol would give the desired aminobenzimidazole (step c). Removal of the acetonide protecting group under acidic conditions using HCl in MeOH would give the desired diol (step d).

Scheme 3 details a synthesis of related aminopurine analogs containing an amino-benzimidazole moiety with a sulfur containing linker. The starting thiol would be modified with an appropriate halo ester using a mild base like $K_2CO_3$ in a polar solvent like acetone to give the thioester that would be then saponified with a strong base like LiOH in a polar solvent like MeOH to give the desired acid (Step a). The acid would be coupled with an appropriate diamine using standard amide coupling conditions to give the desired amino amide (Step b). The amino amide would be cyclized to the benzimidazole using a mild acid like acetic acid as a reagent and solvent to give the benzimidazole (Step c). The oxidation state of the sulfur atom would be adjusted (n=0-2) with a variety of selective oxidation reagents like m-CPBA followed by removal of the acetonide protecting group by treatment with a strong acid like HCl in a polar solvent like MeOH to give the final product (Step d).

Scheme 4

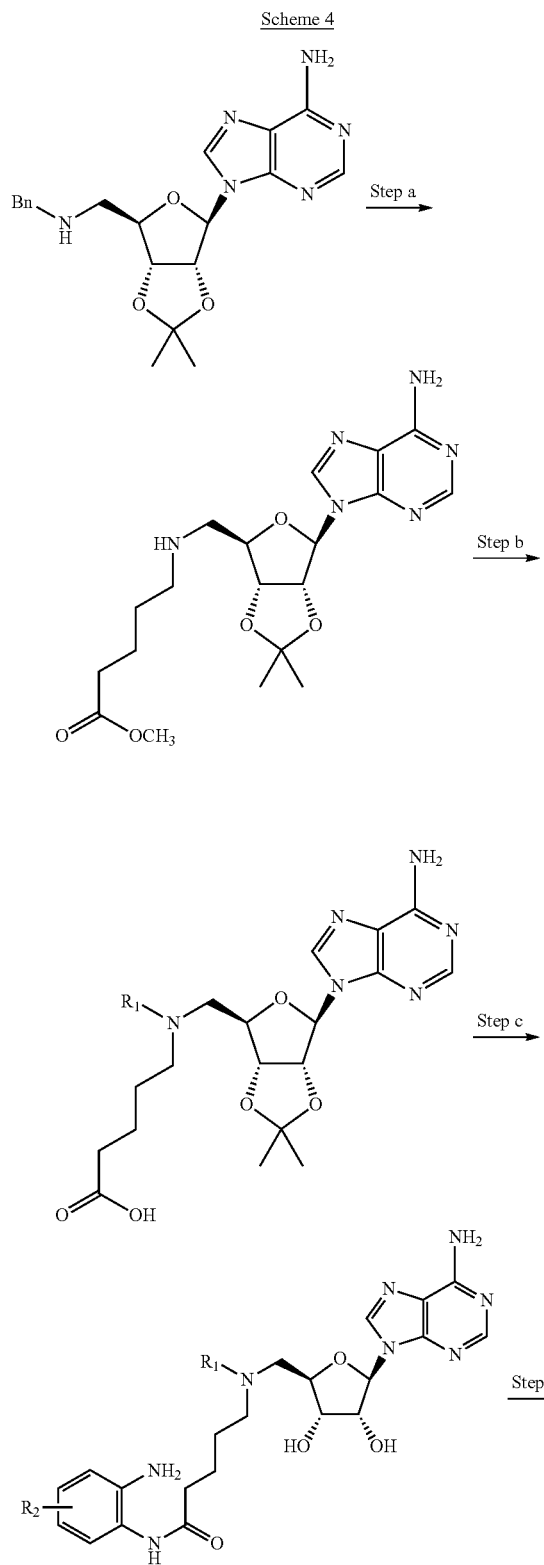

-continued

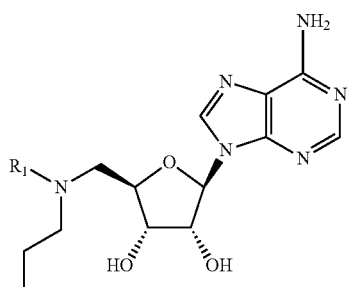

Scheme 4 details a synthesis of related aminopurine analogs containing an aminobenzimidazole moiety with a substituted amine containing linker. The benzyl protected amine would be alkylated with an appropriate halo ester in the presence of a mild base like $K_2CO_3$ in a polar solvent like acetone to give the desired ester that would be subjected to catalytic hydrogenation using hydrogen gas and an appropriate catalyst like palladium on carbon in a polar solvent like EtOH to give the free amine (Step a). A variety of substituents ($R_1$) would be introduced using either reductive amination conditions or alkylation conditions to give the $R_1$ substituted amine. The ester would be then hydrolyzed with a strong base like LiOH in a polar solvent like MeOH to give the acid (Step b). The acid would be coupled with an appropriate diamine using standard amide coupling conditions to give the desired amino amide (Step c). The amino amide would be cyclized to the benzimidazole using a mild acid like acetic acid as a reagent and solvent to give the benzimidazole and the acetonide protecting group would be removed using a strong acid like HCl in a polar solvent like MeOH to give the final product (Step d).

Scheme 5

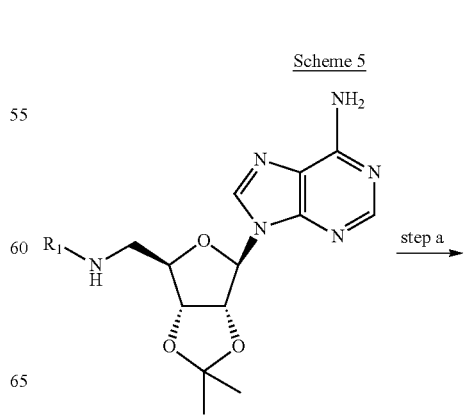

141
-continued

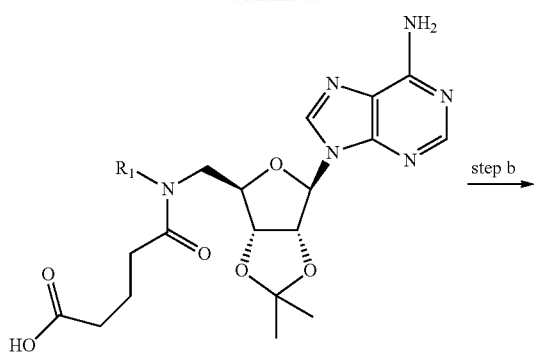

142
-continued

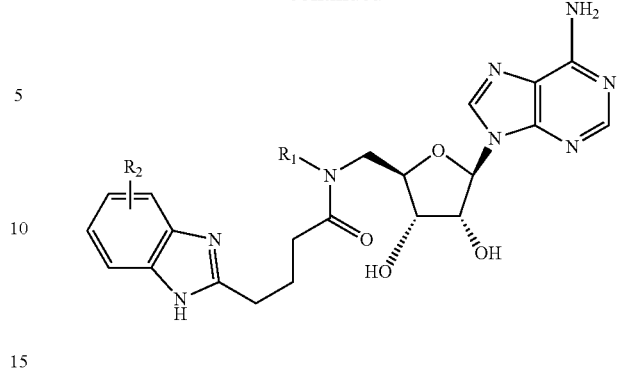

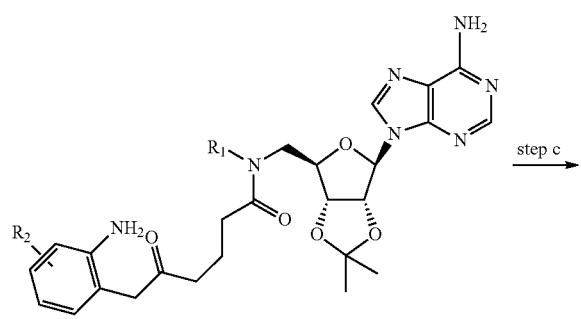

Scheme 5 details a synthesis of related aminopurine analogs containing an aminobenzimidazole moiety with a substituted amide containing linker. Starting with the amine that was previously described in Scheme 2 and treating with an appropriately substituted acid ester under standard amide coupling conditions would give the amide ester that would be hydrolyzed using a strong base like LiOH in a polar solvent like MeOH to give the acid (step a). The acid would be coupled with an appropriate diamine using standard amide coupling conditions to give the desired amino amide (step b). The amino amide would be cyclized to the benzimidazole using a mild acid like acetic acid as a reagent and solvent to give the benzimidazole and the acetonide protecting group would be removed using a strong acid like HCl in a polar solvent like MeOH to give the final product (step c).

Scheme 6

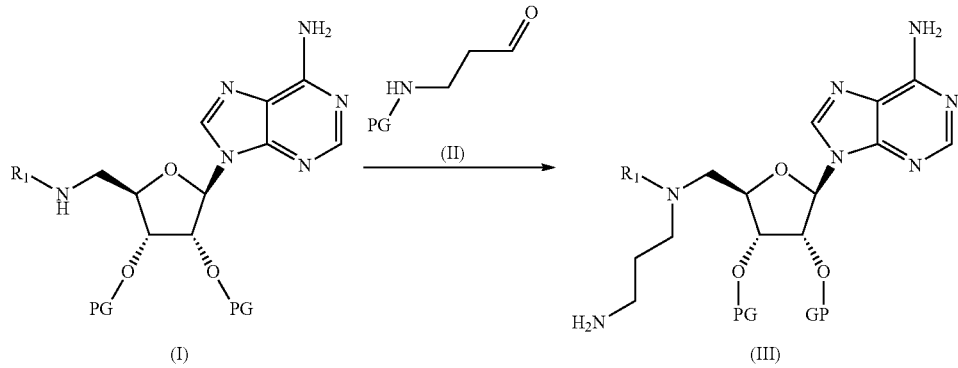

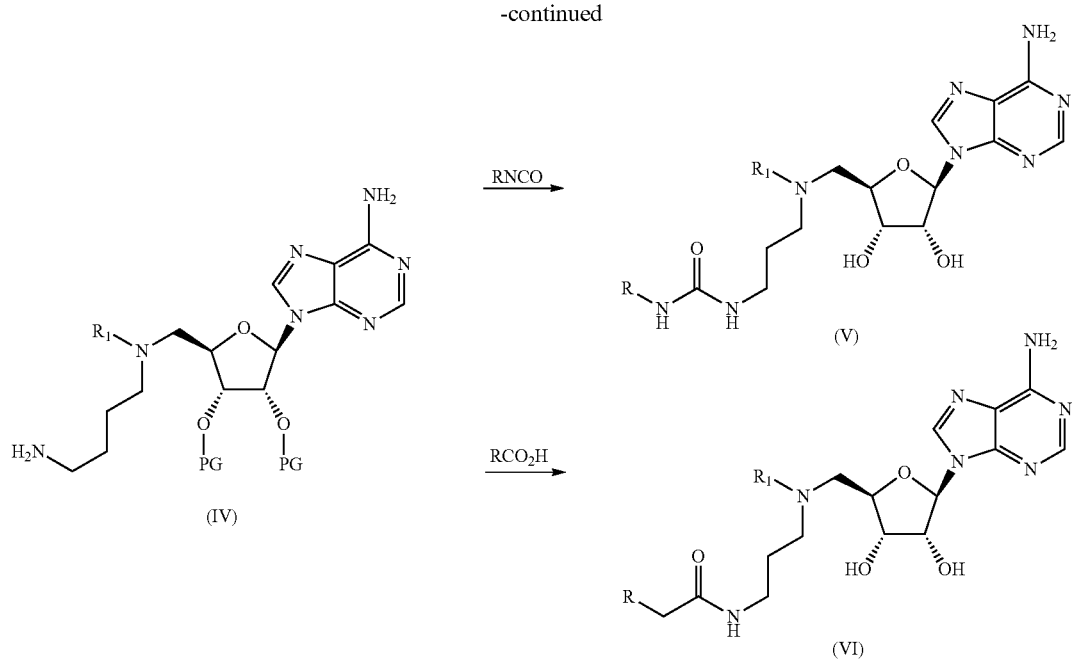

The ureas (V) and amides (VI) may be synthesized as depicted in Scheme 6. The diamine may undergo reductive amination with the aldehyde (II). The reductive amination can be performed with a suitable reducing agent such as NaCN(BH$_3$) or Na(OAc)$_3$BH in the presence of an acid if required such as HCl or AcOH or a Lewis acid/dehydrating agent such as Ti(OiPr)$_4$ or MgSO$_4$. The urea (V) is then formed by treatment of the primary amine (IV) with the appropriate isocyanate, R—C=N=O in the presence of a base such as Et$_3$N or K$_2$CO$_3$ in an inert solvent such as CH$_2$Cl$_2$. The amides (VI) are formed by treating the amine (IV) with the appropriate acids in the presence of a suitable coupling agent (e.g., HATU, PPAA, COMU, EDC), in the presence of a base (e.g., Et$_3$N, Hunig's base, K$_2$CO$_3$). Additional reagents, such as HOAT, HOBt or HO-Su, may be added if necessary.

Preparation of Compound 5

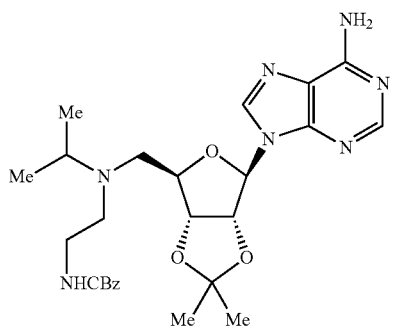

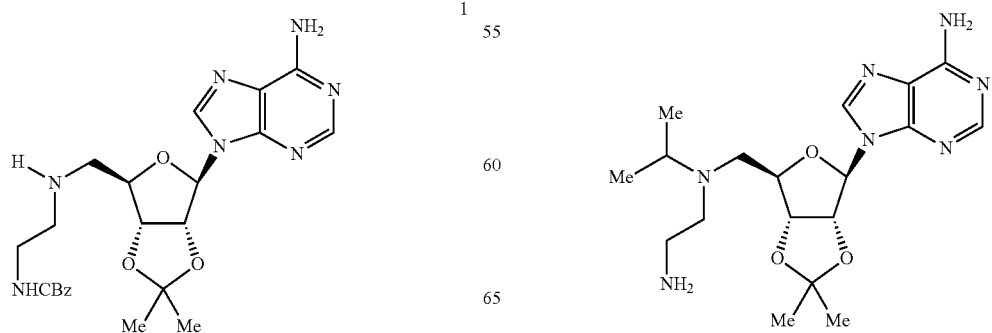

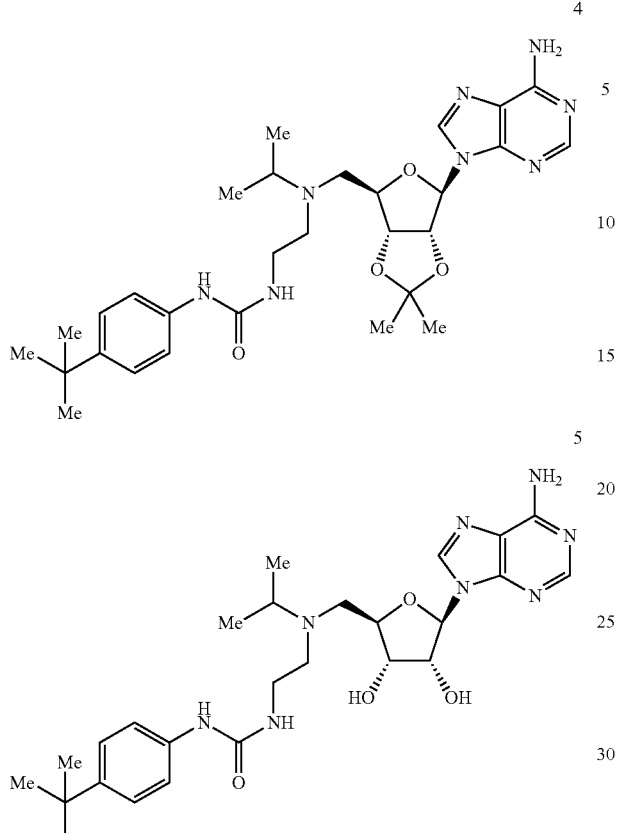

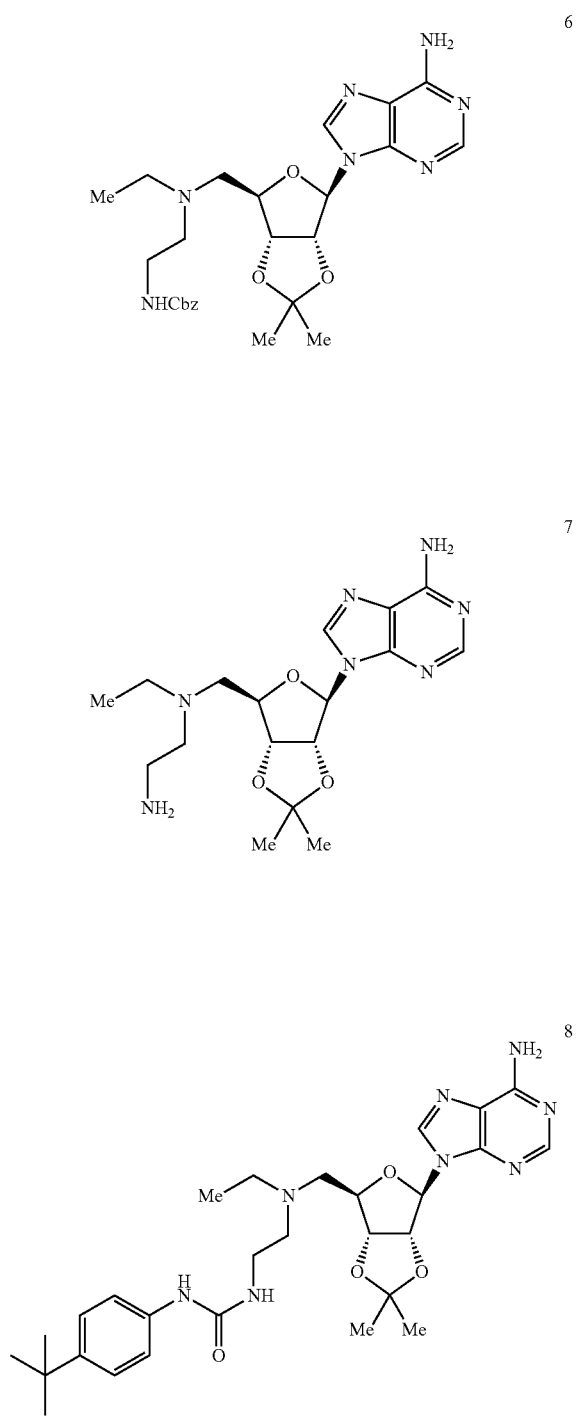

Step 1.

To a solution of 1 (300 mg, 0.62 mmol) and acetone (108 mg, 1.86 mmol) in DCE (20 mL) was added NaB(OAc)$_3$H (526 mg, 2.48 mmol). The mixture was stirred at room temperature overnight. To the reaction was added acetone (500 mg) and NaB(OAc)$_3$H (526 mg) and the mixture was stirred at room temperature overnight. NaHCO$_3$ was added to quench the reaction and DCM (10 mL) and water (5 mL) was added. The mixture was extracted with DCM (15 mL×4). The combined organic phase was concentrated. The crude product was purified by prep-TLC (DCM:MeOH=20:1) to afford 2 (200 mg, yield: 60%) as a white solid. LC/MS (m/z): 526.7 [M+1]$^+$.

Step 2.

A mixture of 2 (180 mg, 0.342 mmol) and 10% Pd/C (36 mg, 0.0342 mmol) in 10 mL of MeOH was stirred at room temperature under 1 atm H$_2$ overnight. The mixture was filtered and the filtrate was concentrated to give 3 as a pale solid (133 mg, yield 99%). LC/MS (m/z): 392.7 [M+1]$^+$.

Step 3.

To a stirred solution of 3 (125 mg, 0.319 mmol) in 1 mL of DMF was added 1-(tert-butyl)-4-isocyanatobenzene (68 mg, 0.383 mmol) and DIPEA (0.16 mL, 0.957 mmol). Then the mixture was stirred at room temperature overnight. The mixture was diluted with EtOAc (10 mL×3). The organic layer was concentrated and the residue was purified by prep-TLC (CH$_3$OH:CH$_2$Cl$_2$=1:15) to afford 4 (62 mg, yield: 34%) as white solid. LC/MS (m/z): 567.7 [M+1]$^+$.

Step 4.

To a mixture of TFA (0.9 mL) and water (0.1 mL) was added 4 (33 mg, 0.0663 mmol). The solution was stirred at room temperature for 1.5 h and evaporated to dryness. The residue was co-evaporated with methanol twice, then dissolved in MeOH (10 mL). The solution was neutralized by basic resin (200 mg) with stirring for 1 h, filtered, and the filtrate was concentrated to obtain 5 (31 mg, yield 100%) as white solid. $^1$H NMR (400 MHz, MeOD): δ 8.20 (s, 1H), 8.17 (s, 1H), 7.24-7.14 (m, 4H), 5.96 (d, 1H, J=4.8 Hz), 4.79-4.77 (m, 1H), 4.38-4.26 (m, 2H), 3.21-3.11 (m, 2H), 3.42-3.37 (m, 1H), 2.95-2.92 (m, 2H), 1.34 (s, 9H), 1.29-1.16 (m, 6H) ppm. LC/MS (m/z): 527.7 [M+1]$^+$.

Preparation of Compound 9

-continued

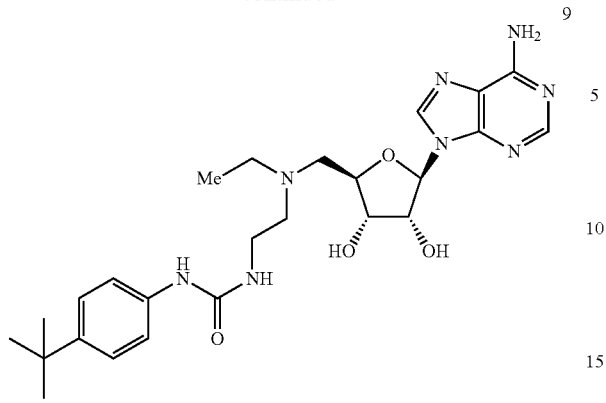

9

Step 1.

To a solution of 1 (300 mg, 0.62 mmol) and CH₃CHO (aq, 40%, 752 mg) in DCE (20 mL) was added NaBH₃CN (195 mg, 3.10 mmol). The mixture was stirred at room temperature overnight. DCM (10 mL) and water (5 mL) was added. The mixture was extracted with DCM. The combined organic phase was washed with brine (20 mL), dried over Na₂SO₄ and concentrated. The crude product was purified by prep-TLC (DCM:MeOH=20:1) to afford 6 (149 mg, yield: 36%) as a white solid. LC/MS (m/z): 512.7 [M+1]⁺.

Step 2.

A mixture of 6 (140 mg, 0.274 mmol) and 10% Pd/C (29 mg, 0.0274 mmol) in 10 mL of MeOH was stirred at room temperature under 1 atm H₂ for 2 days. The mixture was filtered and the filtrate was concentrated to give 7 as a solid (84 mg, yield 82%). LC/MS (m/z): 378.7 [M+1]⁺.

Step 3.

To a stirred solution of 7 (80 mg, 0.212 mmol) in 1 mL of DMF was added 1-(tert-butyl)-4-isocyanatobenzene (45 mg, 0.254 mmol) and DIPEA (0.1 mL, 0.636 mmol). Then the mixture was stirred at room temperature overnight. The mixture was diluted with EA (10 mL×3). The organic layer was concentrated and the residue was purified by prep-TLC (CH₃OH:CH₂Cl₂=1:12) to afford 8 (40 mg, yield: 34%) as white solid. LC/MS (m/z): 553.7 [M+1]⁺.

Step 4.

To a mixture of TFA (0.9 mL) and water (0.1 mL) was added 8 (35 mg, 0.0663 mmol). The solution was stirred at room temperature for 1.5 h and evaporated to dryness. The residue was co-evaporated with methanol twice, then dissolved in MeOH (10 mL). The solution was neutralized by basic resin (250 mg) with stirring for 1 h, filtered, and the filtrate was concentrated to obtain 9 (32 mg, yield 97%) as white solid. ¹H NMR (400 MHz, MeOD): δ 8.22 (s, 1H), 8.21 (s, 1H), 7.25-7.14 (m, 4H) 5.99 (d, 1H, J=4.4 Hz), 4.76 (d, 1H, J=4.8 Hz), 4.33 (m, 2H), 3.38 (m, 2H), 3.33-3.31 (m, 2H), 2.97 (m, 4H), 1.30 (s, 9H), 1.15-1.20 (m, 3H) ppm. LC/MS (m/z): 513.7 [M+1]⁺.

Preparation of Compound 38

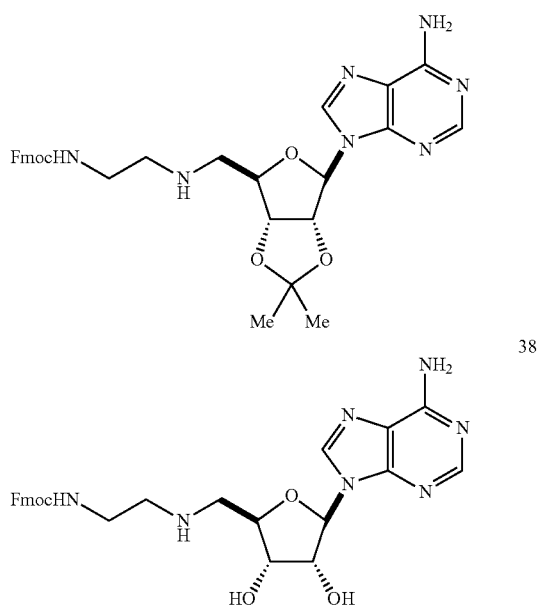

Step 1.

To a solution of 9-((3aR,4R,6R,6aR)-6-(aminomethyl)-2,2-dimethyltetrahydrofuro[3,4-d][1,3]dioxol-4-yl)-9H-purin-6-amine (Townsend, A. P. et al. *Org. Let.* 2009, 11, 2976-2979) (3.05 g, 9.96 mmol) in DCE (250 mL) was added (9H-fluoren-9-yl)methyl (2-oxoethyl)carbamate (2.8 g, 9.96 mmol) and NaB(OAc)₃H (2.96 g, 13.95 mmol), the mixture stirred for 4 h at room temperature K₂CO₃ solution was added to pH at 8-9. DCM was added, the organic layer was dried with Na2SO4, concentrated and purified by SGC (DCM:MeOH=30:1) to give 37 (2.9 g, yield: 50.9%).

Step 2.

A solution of 37 (40 mg, 0.07 mmol) in TFA (90%, 0.6 mL) was stirred at r.t. for 30 min and concentrated. Basic resin (600 mg) and MeOH (10 mL) were added and the mixture stirred for another 30 min at room temperature The mixture was concentrated and purified by preparative plate TLC (DCM:MeOH=5:1) to give 38 (20 mg, yield: 54%). LC/MS (m/z): 532.1 [M+1]⁺.

Preparation of Compound 64

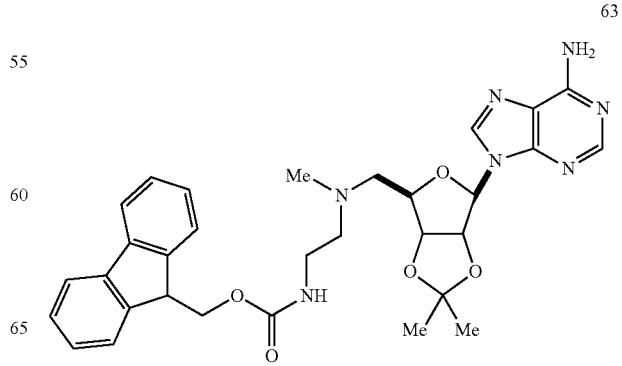

-continued

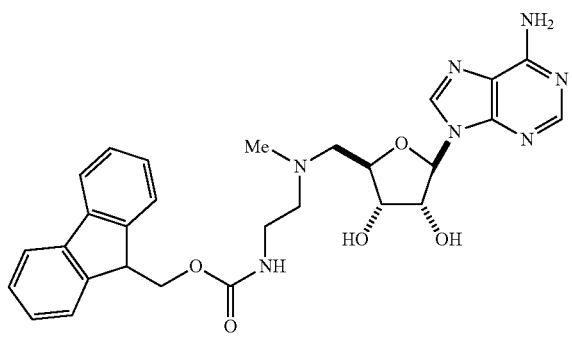
64

Step 1.

To a solution of 9-((3aR,4R,6R,6aR)-2,2-dimethyl-6-((methylamino)methyl)tetrahydrofuro[3,4-d][1,3]dioxol-4-yl)-9H-purin-6-amine (250 mg, 0.78 mmol) 120 mg and (9H-fluoren-9-yl)methyl 2-oxoethylcarbamate (0.12 g, 0.38 mmol) in DCE (20 mL) was added NaB(OAc)₃H (0.138 g, 0.64 mmol). The mixture was stirred at 25° C. for 2 h. Saturated aqueous NaHCO₃ (30 ml) was added to quench the reaction. The mixture was extracted with DCM (100 mL×3). The combined organic phase was washed with brine (20 mL), dried over Na₂SO₄ and concentrated. The crude was purified by prep-TLC (DCM:MeOH=15:1) to afford 63 (100 mg, yield: 55%, purity=100%) as white power. LC/MS (m/z): 586.3 [M+1]⁺.

Step 2.

To a mixture of TFA (2.7 mL) and water (0.3 mL) was added 63 (170 mg, 0.22 mmol). The solution was stirred at 25° C. for 1 h and evaporated to dryness. The residue was co-evaporated with methanol twice, then dissolved in MeOH (10 mL). The solution was neutralized by basic resin (1.3 g) with stirring for 30 min. The filtrate was concentrated to obtain the crude, the 64 was purified by prep-TLC (40 mg, yield: 50%, purity>96%) as white power. LC/MS (m/z): 546.3 [M+1]⁺.

Preparation of Compound 81

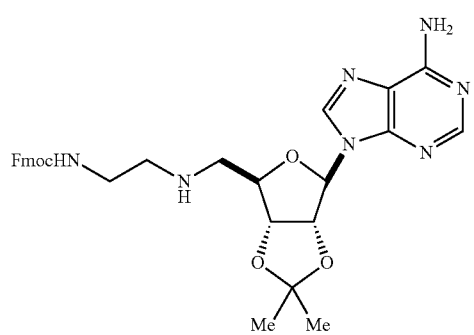
37

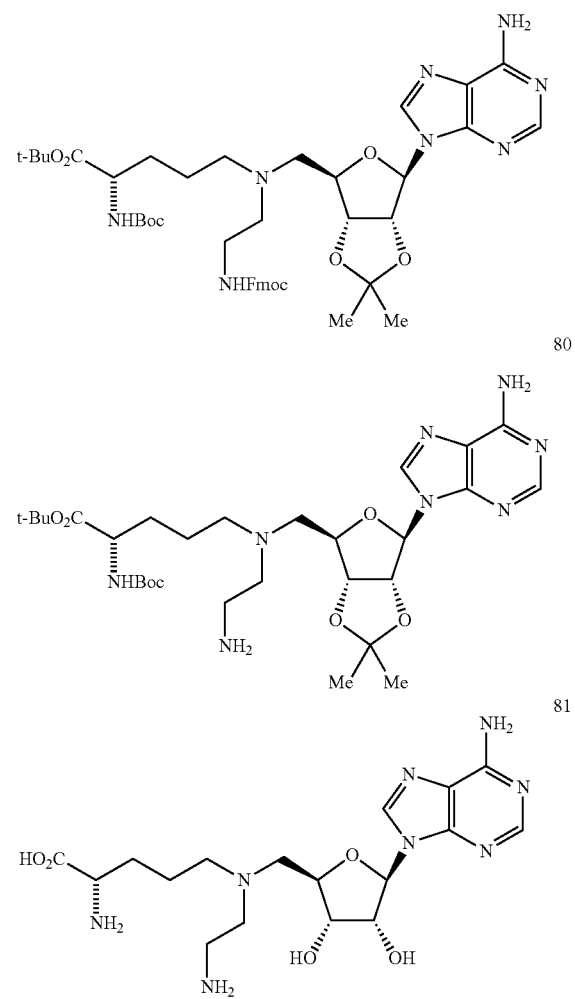

Step 1.

To a solution of 37 (570 mg, 1.0 mmol) and (S)-tert-butyl 2-((tert-butoxycarbonyl)amino)-5-oxopentanoate (1.0 g) in DCE (5 mL) was added NaB(OAc)₃H (424 mg, 2.0 mmol). The mixture was stirred at 20° C. for 2 h. Saturated aqueous NaHCO₃ (10 mL) was added to quench the reaction. The mixture was extracted with DCM (50 mL×3). The combined organic phase was washed with brine (20 mL), dried over Na₂SO₄ and concentrated. The crude was purified by SGC (DCM:MeOH=15:1) to afford 79 (550 mg, yield: 65%, purity>97%) as a yellowish solid.

Step 2.

Compound 79 (700 mg, 0.83 mmol) was added to a premixed solution of diethylamine (2 mL) and DCM (2 mL) and the solution was stirred for 2 h (25° C.). The mixture was concentrated and purified by SGC (DCM:MeOH=10:1). Compound 80 (350 mg, yield: 68%) was obtained as a yellow solid.

Step 3.

To a mixture of HCl/EA (2.0 mL) was added 80 (45 mg, 0.07 mmol). The solution was allowed to stand at 25° C. for 4 h and evaporated. The residue was washed with DCM to afford 81 (22 mg, yield: 71%) as a yellow powder. LC/MS (m/z): 425.2 [M+1]⁺.

Preparation of Compound 86

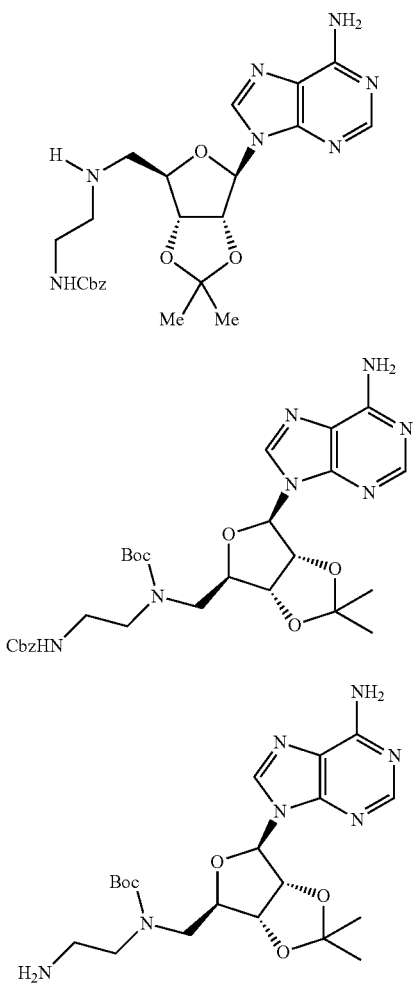

Step 1.

To a stirred solution of 1 (9.38 g, 19.4 mmol) and triethylamine (4.1 mL, 29.1 mmol) in DCM (180 mL) was added a solution of (Boc)$_2$O (8.0 g, 36.7 mmol) in DCM (20 mL) at 0° C. The reaction mixture was warmed to room temperature and stirred for 2 h. The reaction was quenched with water. The organic layer was washed with brine and dried over Na$_2$SO$_4$, then filtered and concentrated. The crude product was purified by flash chromatography on silica gel eluting with DCM/MeOH (40/1 to 20/1, v/v) to give 9.4 g of 83 as a white solid.

Step 2.

Compound 83 (9.4 g, 16.1 mmol) was dissolved in methanol (150 mL) at rt. To the mixture was added 10% Pd/C (0.94 g). The reaction was degassed three times and put under hydrogen atmosphere. The reaction was stirred overnight. The suspension was filtered and washed with methanol (20 mL×3). The filtrate was concentrated under reduced pressure to give 6.4 g of 84 as a white solid. $^1$H NMR (500 MHz, CD$_3$OD) δ 8.3 (s, 1H), 8.2 (s, 1H), 6.1 (s, 1H), 5.2-5.4 (m, 1H), 4.9 (t, J=5.5 Hz, 1H), 4.2-4.4 (m, 1H), 3.2-3.7 (m, 4H), 2.9 (s, 2H), 1.5 (s, 3H), 1.4 (s, 9H), 1.2 (s, 3H).

Step 3.

To a stirred solution of 84 (70 mg, 0.156 mmol) and triethylamine (17 mg, 0.17 mmol) in DCM (2 mL) was dropwise added a solution of 1-(tert-butyl)-4-isocyanatobenzene (26 mg, 0.16 mmol) at −20° C. The reaction mixture was stirred for 30 min and then quenched with methanol (0.1 mL). The reaction mixture was concentrated under reduced pressure. The residue was purified by prep-TLC eluting with CH$_2$Cl$_2$/MeOH (20/1, v/v) to give 85.

Step 4.

Compound 85 (73.6 mg, 0.12 mmol) was dissolved in HCl.MeOH (6 mL, 2 M). The reaction mixture was stirred at room temperature for 3 h. The solvent was evaporated under reduced pressure. The residue was purified by reverse-phase chromatography using water (0.3% TFA)/methanol as eluent to give 86. LC/MS (m/z): 485.3 [M+1]$^+$.

Preparation of Compound 92

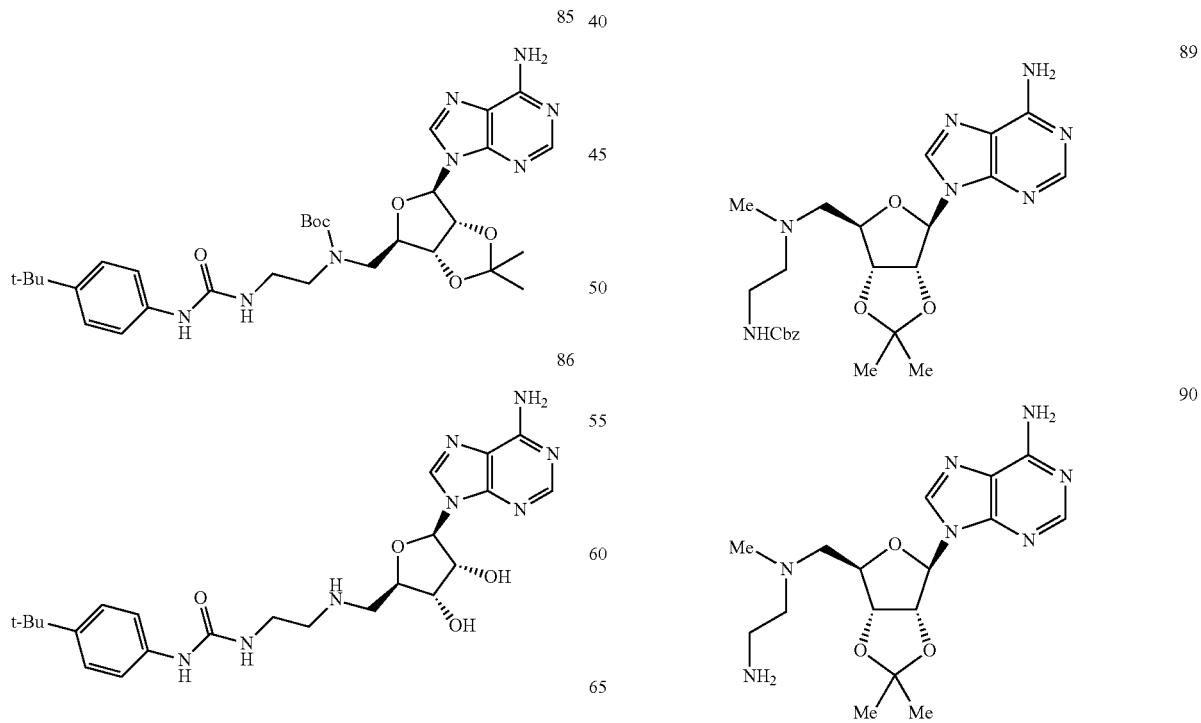

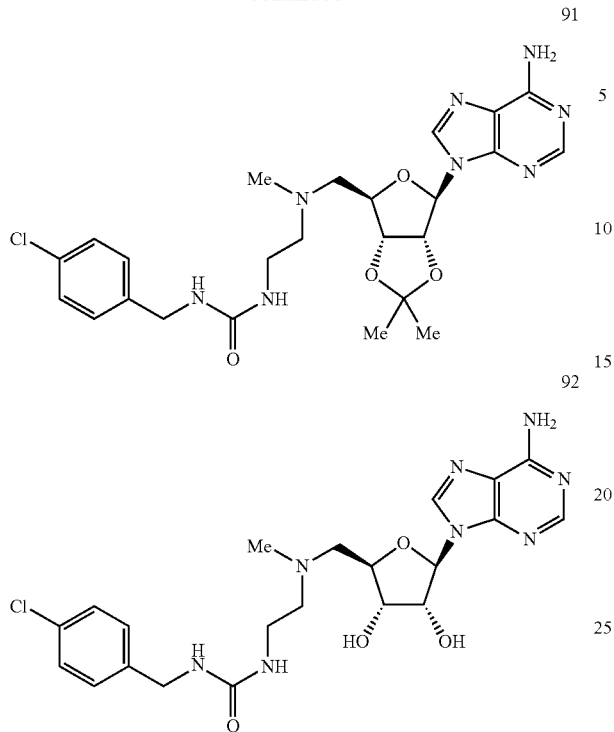

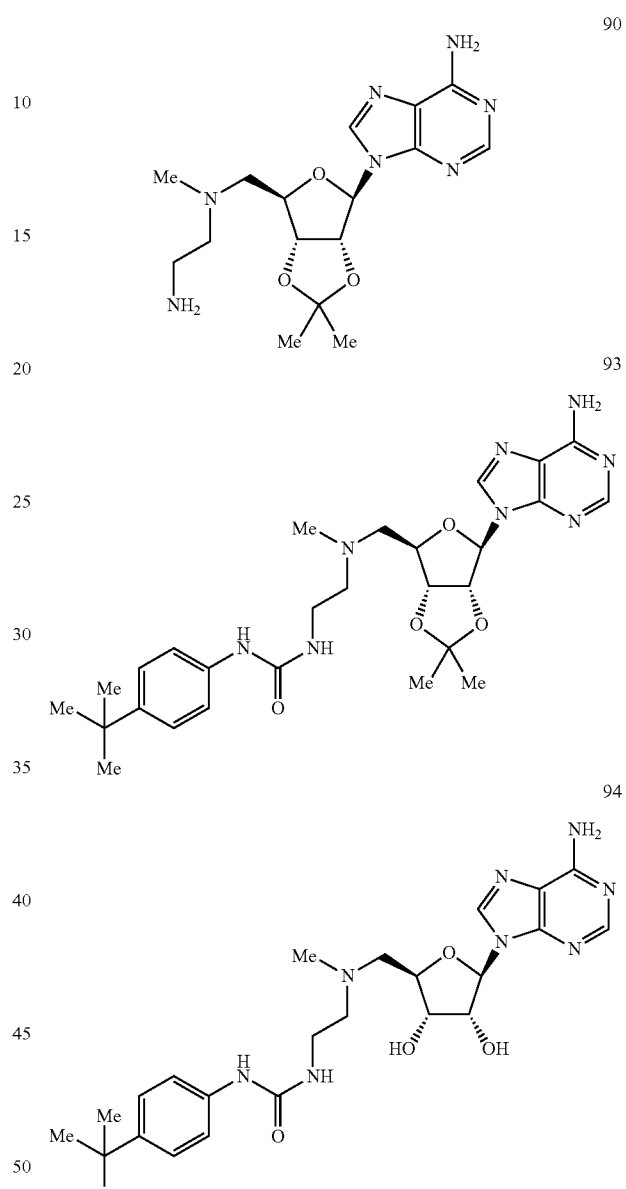

Step 1.

To a solution of 9-((3aR,4R,6R,6aR)-2,2-dimethyl-6-((methylamino)methyl)-tetrahydrofuro[3,4-d][1,3]dioxol-4-yl)-9H-purin-6-amine (8 g, 25 mmol) and benzyl (2-oxoethyl)carbamate (4.85 g, 25.1 mmol) in DCE (100 mL) was added NaB(OAc)$_3$H (10.6 g, 50 mmol) in one portion. Then the resulting reaction mixture was stirred at room temperature overnight. Saturated aqueous NaHCO$_3$ (150 mL) was added to quench the reaction. The aqueous layer was extracted with DCM (150 mL×3). The organic layers were dried over anhydrous Na$_2$SO$_4$ and concentrated. The crude was purified by SGC (DCM:MeOH=60:1 to 30:1) to afford 89 (4.1 g, yield: 34%) as a white solid. LC-MS (m/z): 498.1 [M+1]$^+$.

Step 2.

Compound 89 (4.1 g, 8.25 mmol) was dissolved in MeOH (60 mL). 10% Pd/C (875 mg) was added and the resultant mixture was stirred at 1 atm H$_2$ at room temperature overnight. The mixture was then filtered and rinsed with MeOH (50 mL×3). The filtrate was evaporated in vacuo to afford the 90 (2.4 g, yield: 80%) as a white solid. LC-MS (m/z): 364.2 [M+1]$^+$.

Step 3.

To a solution of 90 (90 mg, 0.248 mmol) in 1 mL of DMF was added 1-chloro-4-(isocyanatomethyl)benzene (52 mg, 0.297 mmol) and DIPEA (96 mg, 0.744 mmol) and the mixture was stirred at room temperature overnight. The mixture was diluted with EtOAc (10 mL×2). The organic phase was concentrated and the residue was purified by prep-TLC (CH$_3$OH:CH$_2$Cl$_2$=1:15) to afford 91 (55 mg, yield: 42%) as white solid. MS (ESI): m/z 532.7 [M+1]$^+$.

Step 4.

To a mixture of TFA (0.9 mL) and water (0.1 mL) was added 91 (45 mg, 0.0847 mmol). The solution was stirred at 25° C. for 1.5 h and evaporated to dryness. The residue was co-evaporated with methanol twice, then dissolved in MeOH (10 mL). The solution was neutralized by basic resin (400 mg) with stirring for 1 h. After filtered, the filtrate was concentrated to obtain 92 (40 mg, yield 100%) as pale solid. LC/MS (m/z): 491.7 [M+1]+.

Preparation of Compound 94

Step 1.

To a solution of 90 (90 mg, 0.248 mmol) in 1 mL of DMF was added 1-(tert-butyl)-4-isocyanatobenzene (52 mg, 0.297 mmol) and DIPEA (0.1 mL, 0.744 mmol) and the mixture was stirred at room temperature overnight. The mixture was diluted with EtOAc (10 mL×2). The organic layer was concentrated and the residue was purified by prep-TLC (CH$_3$OH:CH$_2$Cl$_2$=1:15) to afford 93 (60 mg, yield: 45%) as white solid. LC/MS (m/z): 539.7 [M+1]$^+$.

Step 2.

To a mixture of TFA (0.9 mL) and water (0.1 mL) was added 93 (53 mg, 0.0984 mmol). The solution was stirred at room temperature for 1.5 h and evaporated to dryness. The residue was co-evaporated with methanol twice, then dissolved in MeOH (10 mL). The solution was neutralized by basic resin (500 mg) with stirring for 1 h. After filtered, the filtrate was concentrated to obtain 94 (50 mg, yield 100%) as white solid. $^1$H NMR (500 MHz, MeOD): δ 8.21 (d, 2H, J=5.0 Hz), 7.23 (d, 2H, J=8.5 Hz), 7.13 (d, 2H, J=8.5 Hz), 5.98 (d, 1H, J=4.5 Hz), 4.74 (t, 1H, J=5.0 Hz), 4.26-4.31 (m, 2H), 3.36 (d, 2H, J=3.5 Hz), 2.83-3.16 (m, 2H), 2.82 (d, 2H, J=4.5 Hz), 2.55 (s, 3H), 1.27 (s, 9H) ppm. LC/MS (m/z): 499.7 [M+1]$^+$.

Preparation of Compound 96 room temperature for 1.5 h and evaporated to dryness. The residue was co-evaporated with methanol twice, then dissolved in MeOH (10 mL). The solution was neutralized by basic resin (400 mg) with stirring for 1 h. After filtered, the filtrate was concentrated to obtain 96 (34 mg, yield 92%) as pale solid. $^1$H NMR (500 MHz, MeOD): δ 8.23 (s, 1H), 8.21 (s, 1H) 7.14-7.11 (m, 1H), 7.02-6.97 (m, 3H), 5.98 (d, 1H, J=5.0 Hz), 4.76 (t, 1H, J=5.0 Hz), 4.29-4.25 (m, 2H), 4.11 (s, 2H), 3.31-3.28 (m, 2H), 3.12-3.00 (m, 2H), 2.79-2.77 (m, 2H), 2.51 (s, 3H), 2.27 (s, 3H) ppm. LC/MS (m/z): 471.7 [M+1]$^+$.

Preparation of Compound 98

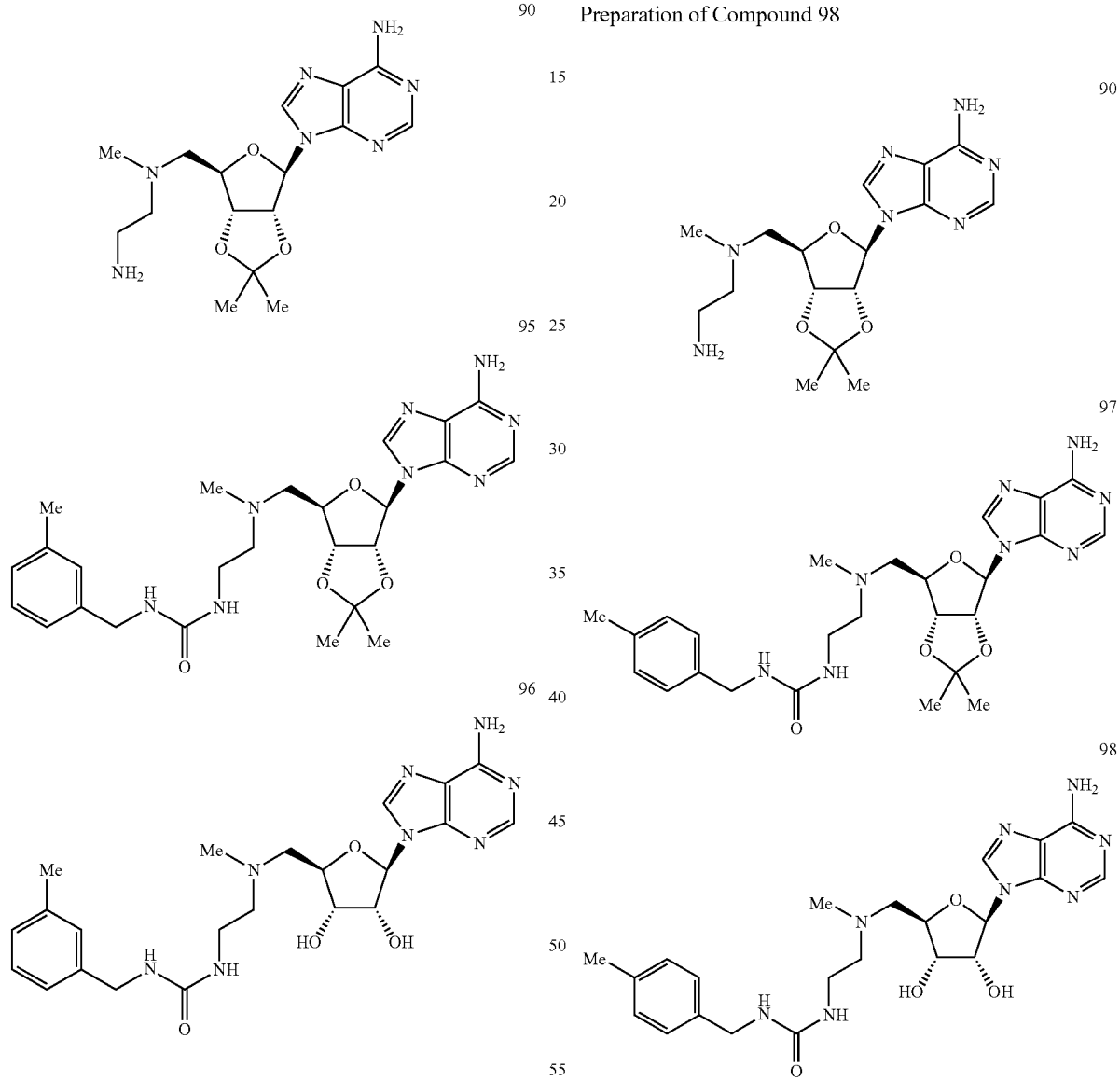

Step 1.

To a stirred solution of 90 (100 mg, 0.275 mmol) and TEA (0.42 mL, 0.30 mmol) in 4 mL of DCM was added 1-(isocyanatomethyl)-3-methylbenzene (42 mg, 0.282 mmol) at −20° C. Then the mixture was stirred at this temperature for 30 min and quench with methanol. The reaction mixture was concentrated under reduced pressure. The residue was purified by prep-TLC (CH$_3$OH:CH$_2$Cl$_2$=1:12) to afford 95 (45 mg, yield: 32%) as white solid. LC/MS (m/z): 511.7 [M+1]$^+$.

Step 2.

To a mixture of TFA (0.9 mL) and water (0.1 mL) was added 95 (40 mg, 0.078 mmol). The solution was stirred at Step 1.

To a mixture of p-tolylmethanamine (134 mg, 1.10 mmol) in 10 mL of DCM was added DIPEA (0.44 mL, 2.64 mmol) and the resultant mixture was cooled to 0° C. 4-nitrophenyl carbonochloridate (224 mg, 1.10 mmol) was slowly added. The ice-bath was removed and the mixture was stirred at room temperature for 0.5 h. 90 (200 mg, 0.55 mmol) was slowly added and the mixture was stirred at room temperature overnight. The mixture was washed with water (15 mL), dried over Na$_2$SO4, evaporated, and purified by prep-TLC (CH₃OH:CH₂Cl₂=1:12) to afford 97 (70 mg, yield: 25%) as pale solid. LC/MS (m/z): 511.7 [M+1]⁺.

Step 2.

To a mixture of TFA (0.9 mL) and water (0.1 mL) was added 97 (60 mg, 0.118 mmol). The solution was stirred at room temperature for 1 h and evaporated to dryness. The residue was co-evaporated with methanol twice, then dissolved in MeOH (10 mL). The solution was neutralized by basic resin (550 mg) with stirring for 1 h. After filtered, the filtrate was concentrated to obtain 98 (40 mg, yield 73%) as pale solid. ¹H NMR (500 MHz, MeOD): δ 8.20 (d, 2H, J=19.5 Hz), 7.06 (d, 2H, J=8.0 Hz), 7.04 (d, 2H, J=8.0 Hz), 5.95 (d, 1H, J=5.0 Hz), 4.70 (s, 1H), 4.21 (d, 2H, J=2.5 Hz), 4.11 (s, 2H), 3.29-3.32 (m, 2H), 3.24-3.28 (m, 2H), 2.68 (s, 2H), 2.42 (s, 3H), 2.24 (s, 3H) ppm. LC/MS (m/z): 471.7 [M+1]⁺.

Preparation of Compound 114

Step 1.

To a suspension of 9-((3aR,4R,6R,6aR)-2,2-dimethyl-6-((methylamino)methyl)-tetrahydrofuro[3,4-d][1,3]dioxol-4-yl)-9H-purin-6-amine (1 g, 3.12 mmol) and anhydrous K₂CO₃ (863 mg, 6.24 mmol) in acetonitrile (12 mL) was added 2-iodoethanol (591 mg, 3.4 mmol) slowly. The mixture was stirred at 80° C. overnight. After dilution with water (6 mL), the organic solvent was removed in vacuo. The residue was extracted with CH₂Cl₂ (10 mL×3). The combined organic phase was dried over anhydrous Na₂SO₄ and concentrated. The crude product was purified by SGC (DCM: MeOH=50:1-15:1) to afford 112 (382 mg, yield: 34%) as a light yellow solid. ESI-MS (m/z): 365.2 [M+1]⁺.

Step 2.

To a solution of 112 (130 mg, 0.36 mmol) in DCM (1.5 mL) was added 1-(tert-butyl)-4-isocyanatobenzene (69 mg, 0.39 mmol). The mixture was stirred at room temperature overnight. Water (0.5 mL) was added and the mixture was extracted with DCM (5 mL×3). The combined organic layers were washed with brine (10 mL), dried over Na₂SO₄, filtered and concentrated. The crude was purified by prep TLC (DCM:MeOH=20:1) to obtain 113 (60 mg, yield: 31%) as a white solid. ESI-MS (m/z): 540.3 [M+1]⁺.

Step 3.

To a mixture of TFA (0.5 mL) and water (0.05 mL) was added 113 (35 mg, 0.065 mmol). The solution was allowed to stand at room temperature for 1 h and evaporated to dryness. The residue was co-evaporated with methanol twice. Then, the residue was dissolved in MeOH (5 mL). The solution was neutralized by basic resin (150 mg) with stirring for 1 h. After filtered, the filtrate was concentrated to dryness to afford 114 (32 mg, yield: 99%) as a white solid. NMR (400 MHz, MeOD): δ 8.29 (s, 1H), 8.22 (s, 1H), 7.29 (s, 4H), 6.00 (d, J=5.0 Hz, 1H), 4.70 (d, J=5.5 Hz, 1H), 4.31-4.29 (m, 4H), 3.05 (d, J=5.0 Hz, 2H), 2.95 (d, J=5.0, 2H), 2.52 (s, 3H), 1.34-1.29 (m, 9H) ppm; ESI-MS (m/z): 500.3 [M+1]⁺.

Preparation of Compound 116

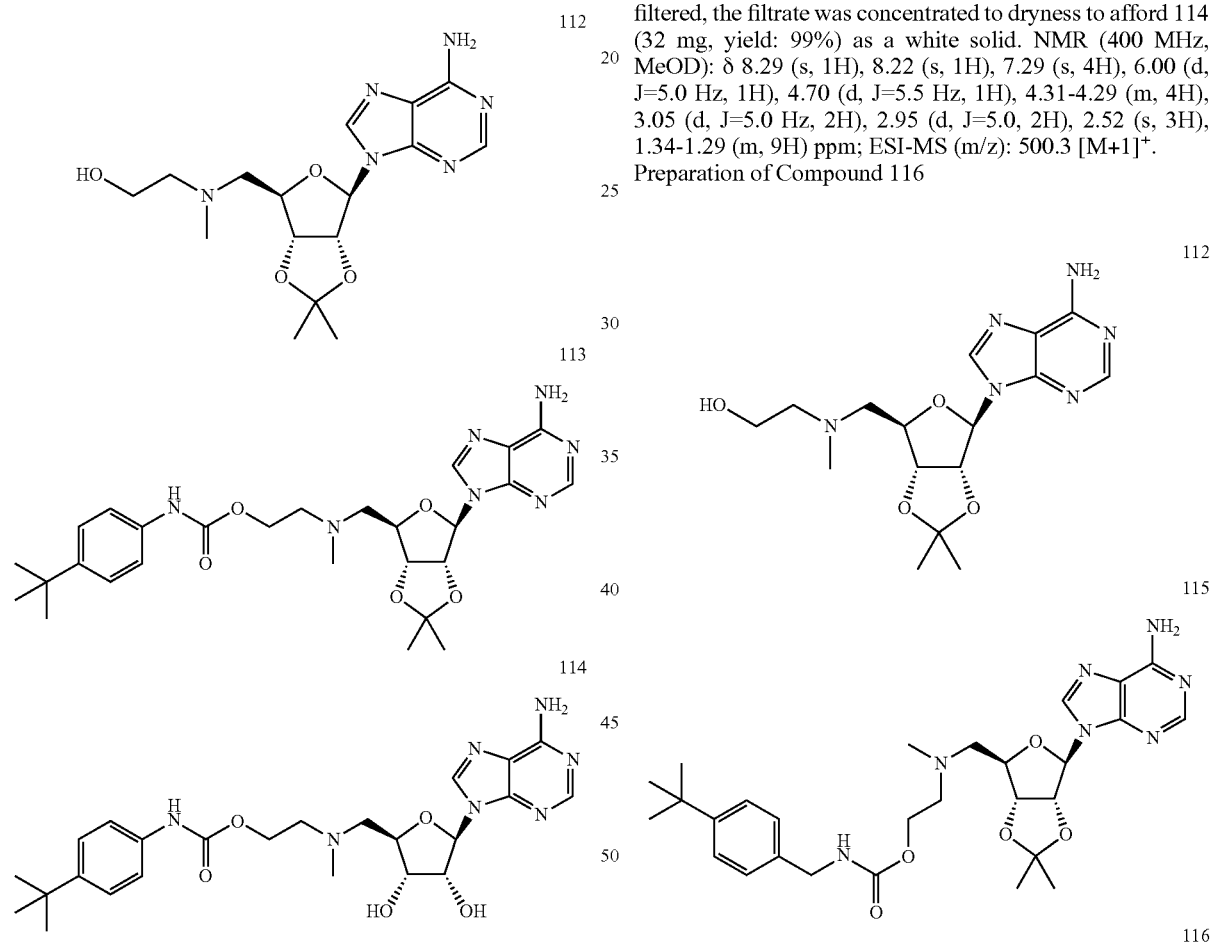

Step 1.

To a solution of 112 (150 mg, 0.412 mmol) in DCM (5 mL) was added DIPEA (106 mg, 0.824 mmol), and then the resulting mixture was cooled to 0° C. 4-Nitrophenyl carbonochloridate (83 mg, 0.412 mmol) added slowly. The ice-water bath was removed and the reaction mixture was stirred at room temperature for 0.5 h. (4-tert-butylphenyl) methanamine (54 mg, 0.33 mmol) was added slowly and the resulting reaction mixture was stirred at room temperature overnight. Solvent was removed in vacuo and the crude residue was purified by prep-TLC (DCM:MeOH=10:1) to afford 115 (85 mg, yield: 37%) as a white solid. ESI-MS (m/z): 554.3 [M+1]$^+$.

Step 2.

To a mixture of TFA (0.9 mL) and water (0.1 mL) was added 115 (45 mg, 0.08 mmol). The solution was allowed to stand at room temperature for 1 h and evaporated to dryness. The residue was co-evaporated with methanol twice. Then the residue was dissolved in MeOH (8 mL). The solution was neutralized by basic resin (185 mg) with stirring at room temperature for 1 h. After filtered, the filtrate was concentrated to dryness to afford 116 (40 mg, yield: 96%) as a white solid. NMR (500 MHz, MeOD): δ 8.31 (s, 1H), 8.22 (s, 1H), 7.32 (d, J=7.5 Hz, 2H), 7.18 (d, J=7.5 Hz, 2H), 6.00 (d, J=3.0 Hz, 1H), 4.69 (m, 1H), 4.29-4.21 (m, 6H), 3.10-3.03 (m, 2H), 2.94 (m, 2H), 2.52 (s, 3H), 2.06-1.97 (m, 4H), 1.37 (s, 9H) ppm; ESI-MS (m/z): 514.2 [M+1]$^+$.

Preparation of Compound 118

Step 1.

To a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (McCloskey, D. E.; et al *J. Med. Chem.* 2009, 52, 1388-1407) (130 mg, 0.34 mmol) in DMF (1 mL) was added 1-(tert-butyl)-4-isocyanatobenzene (60 mg, 0.34 mmol) dropwise with stirring. The mixture was stirred at room temperature for 2 h, then MeOH (2 mL) was added to quench the reaction. The mixture was concentrated under vacuum to afford 117 (210 mg) as a white solid. The material was purified by prep-TLC (DCM: MeOH=10:1, v/v) twice to afford the target (60 mg, yield: 32%) as a white solid. LC/MS (m/z): 553.3 [M+1]$^+$.

Step 2.

To a mixture of TFA (0.9 mL) and water (0.1 mL) was added 117 (50 mg, 0.090 mmol). The solution was stirred at room temperature for 1 h and evaporated to dryness. The residue was co-evaporated with methanol (5 mL) twice, then dissolved in MeOH (10 mL). The solution was neutralized by basic resin (200 mg) with stirring for 30 min. The reaction was filtered and the filtrate was concentrated to afford 118 (45 mg, yield: 97%) as a yellowish solid. $^1$H NMR (500 MHz, MeOD) δ 8.25 (s, 1H), 8.20 (s, 1H), 7.23 (dd, J=8.5, 19.5 Hz, 4H), 5.99 (d, J=4.0 Hz, 1H), 4.73-4.71 (m, 1H), 4.27-4.25 (m, 2H), 3.23-3.19 (m, 2H), 2.88-2.84 (m, 2H), 2.59 (t, J=7.0 Hz, 2H), 2.35 (s, 3H), 1.72 (t, J=7.0 Hz, 2H), 1.29 (s, 9H) ppm; LC/MS (m/z): 513.3 [M+1]$^+$.

Preparation of Compound 125

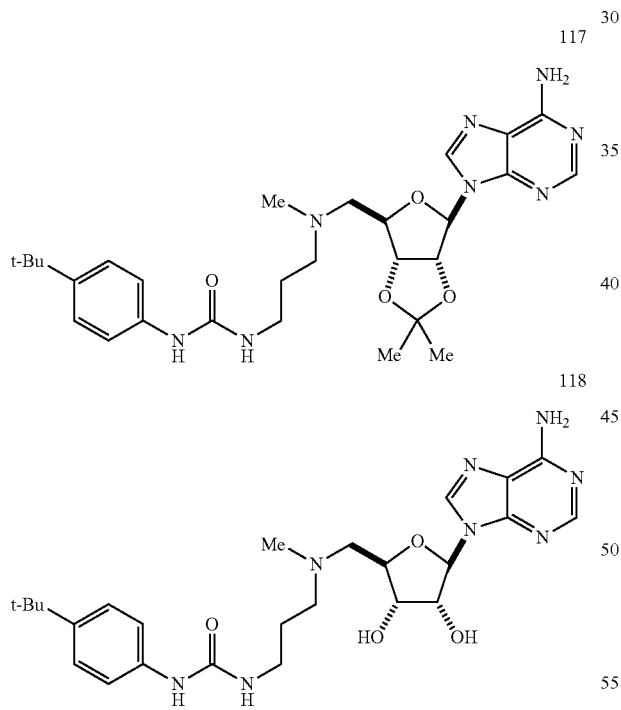

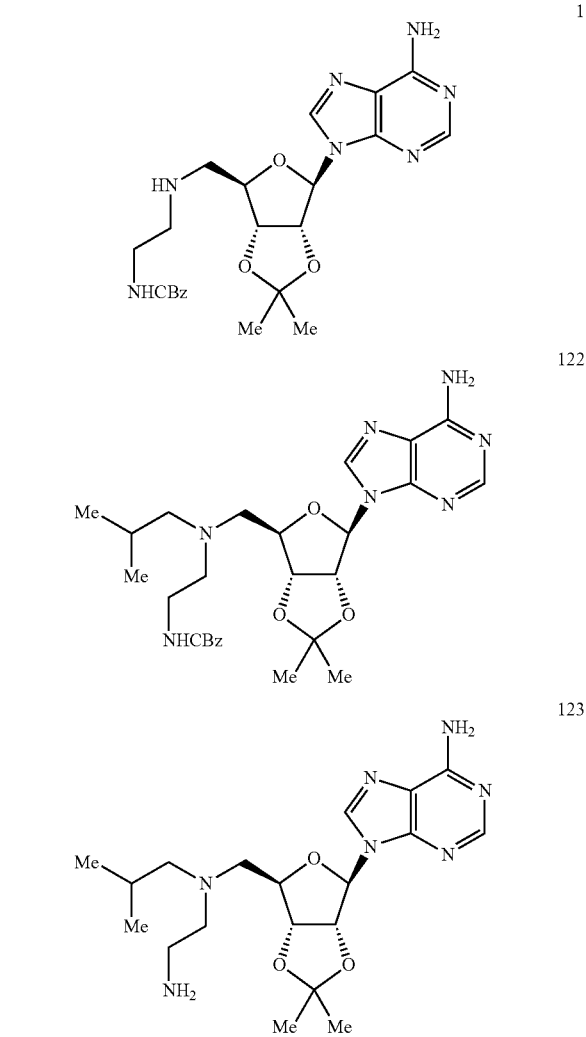

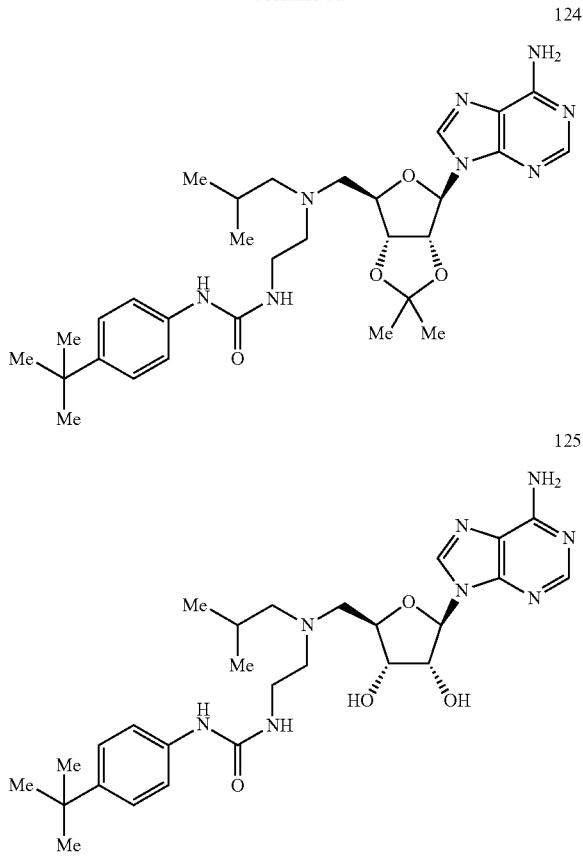

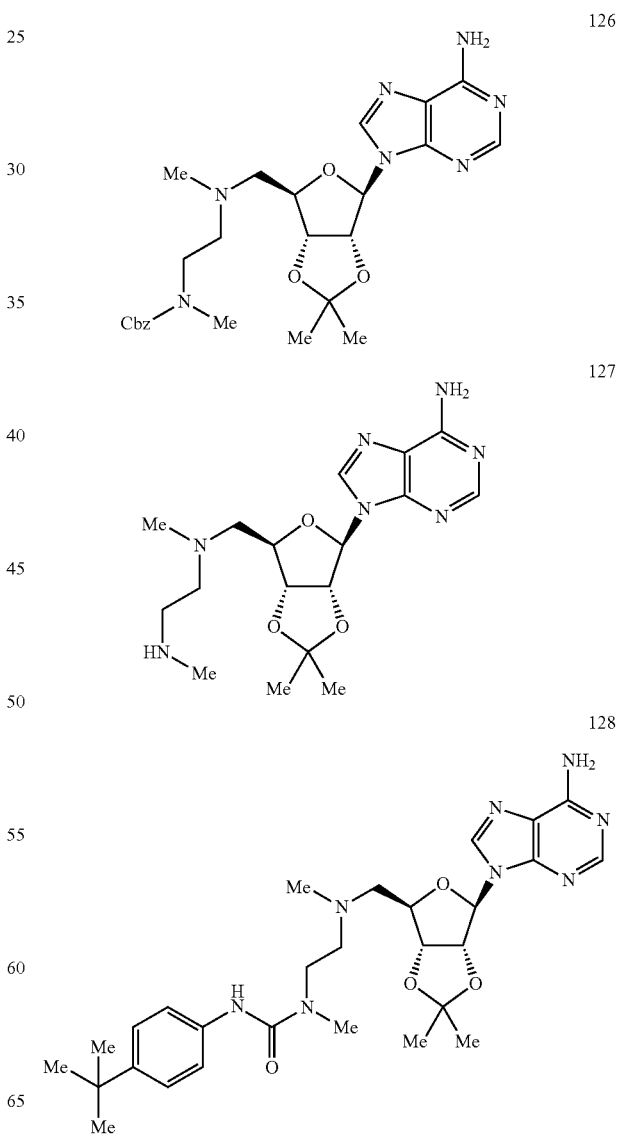

Step 1.

To a solution of 9-((3aR,4R,6R,6aR)-6-(aminomethyl)-2,2-dimethyltetrahydrofuro[3,4-d][1,3]dioxol-4-yl)-9H-purin-6-amine (Townsend, A. P. et al *Org. Let.* 2009, 11, 2976-2979) (306 mg, 1 mmol) and benzyl (2-oxoethyl)carbamate (290 mg, 1.5 mmol) in MeOH (4 mL, dry) was added two drops of HOAc and 4A MS (10 mg), then the reaction mixture was stirred at room temperature overnight. NaBH$_4$ (60 mg, 1.6 mmol) was added slowly, then stirred for another 1 h, quenched with NaHCO$_3$ (sat, aqueous, 5 mL), the mixture was extracted with DCM (10 mL×3), dried over Na$_2$SO$_4$ and concentrated. The crude was purified by prep-TLC eluting with DCM:MeOH (10:1) to afford the desired product 1 as a white solid (135 mg, 28%). LC/MS (m/z): 483.9 [M+1]$^+$.

Step 2.

To a solution of 1 (300 mg, 0.62 mmol) and isobutyraldehyde (112 mg, 1.55 mmol) in DCE (20 mL) was added NaB(OAc)$_3$H (526 mg, 2.48 mmol). The mixture was stirred at room temperature overnight. NaHCO$_3$ was added to quench the reaction and DCM (10 mL) and water (5 mL) was added. The mixture was extracted with DCM (15 mL x4). The combined organic phase was concentrated. The crude product was purified by prep-TLC (DCM:MeOH=20:1) to afford 122 (235 mg, yield: 70%) as a white solid. LC/MS (m/z): 540.7 [M+1]$^+$.

Step 3.

A mixture of 122 (150 mg, 0.278 mmol) and Pd/C (30 mg, 0.028 mmol) in 10 mL of MeOH was stirred at room temperature under 1 atm H$_2$ overnight. The mixture was filtered and the filtrate was concentrated to give 123 as a pale solid (109 mg, yield 96%). LC/MS (m/z): 406.7 [M+1]$^+$.

Step 4.

To a stirred solution of 123 (105 mg, 0.259 mmol) in 1 mL of DMF was added 1-(tert-butyl)-4-isocyanatobenzene (59 mg, 0.311 mmol) and DIPEA (0.15 mL, 0.777 mmol). Then the mixture was stirred at room temperature overnight. The mixture was extracted with EtOAc (10 mL×3). The organic layer was concentrated and the residue was purified by prep-TLC(CH$_3$OH:CH$_2$Cl$_2$=1:12) to afford 124 (49 mg, yield: 33%) as white solid. LC/MS (m/z): 581.7 [M+1]$^+$.

Step 5.

To a mixture of TFA (0.9 mL) and water (0.1 mL) was added 124 (44 mg, 0.0757 mmol). The solution was stirred at room temperature for 1.5 h and evaporated to dryness. The residue was co-evaporated with methanol twice, then dissolved in MeOH (10 mL). The solution was neutralized by basic resin (360 mg) with stirring for 1 h. The mixture was filtered and the filtrate was concentrated to obtain 125 (41 mg, yield 100%) as white solid. LC/MS (m/z): 541.7 [M+1]$^+$.

Preparation of Compound 129

163

-continued

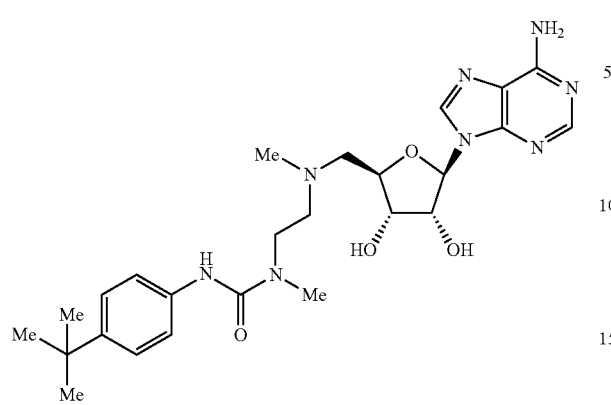

129

Step 1.

A solution of 9-((3aR,4R,6R,6aR)-2,2-dimethyl-6-((methylamino)methyl)-tetrahydrofuro[3,4-d][1,3]dioxol-4-yl)-9H-purin-6-amine (1.5 g, 4.7 mmol) and benzyl methyl(2-oxoethyl)carbamate (Martin, S. F. et al *J. Org. Chem.* 1987, 52, 1962-1972) (1.06 g, 4.7 mmol) in DCE (20 mL) was added NaSH(OAc)$_3$ (1.46 g, 7.2 mmol), The mixture was stirred at room temperature overnight, Then saturated aqueous NaHCO$_3$ (20 mL) was added to the reaction mixture. The mixture was extracted with DCM (30 mL×2). The combined organic layers were washed with brine and dried over Na$_2$SO$_4$ and concentrated. The residue was purified by SGC (DCM:MeOH=80:1 to 40:1) to afford 126 (1.5 g, yield: 58%) as white solid. ESI-MS (m/z): 512.7 [M+1]$^+$.

Step 2.

A mixture of 126 (1.0 g, 1.96 mmol) and Pd(OH)$_2$ (400 mg) in EtOH (25 mL) was stirred at room temperature under H$_2$ overnight. The mixture was filtered and the filtrate was concentrated to give 127 (600 mg, yield: 81%) as white powder. ESI-MS (m/z): 378.7 [M+1]$^+$.

Step 3.

A solution of 127 (200 mg, 0.53 mmol) and 1-(tert-butyl)-4-isocyanatobenzene (111 mg, 0.64 mmol) and DIPEA (205 mg, 1.59 mmol) in dry DCM (5 mL) was stirred at room temperature overnight, Then MeOH (5 mL) was added and the mixture was concentrated to dryness. The residue was purified by prep-TLC (DCM:MeOH=10:1) to afford 128 (160 mg, yield: 54%) as white solid. LC-MS (m/z): 553.7 [M+1]$^+$.

Step 4.

A solution of 128 (60 mg, 0.109 mmol) in 90% TFA (1.5 mL) was stirred at room temperature for 2 h, then concentrated to dryness. The residue was dissolved in MeOH (5 mL) and basic resin (1.2 g) was added and stirred at room temperature for 1 h, then filtered and the filtrate was concentrated to give 129 (90% y) as a white solid. $^1$H NMR (500 MHz, MeOD) δ 8.19 (s, 1H), 8.09 (s, 1H), 7.08-7.02 (m, 4H), 5.89-5.88 (m, 1H), 5.49 (s, 1H), 4.73-4.71 (m, 1H), 4.23-4.22 (m, 2H), 3.44-3.43 (m, 2H), 3.10-3.03 (m, 1H), 2.93 (s, 3H), 2.84-2.81 (m, 1H), 2.74-2.71 (m, 2H), 2.43 (s, 3H), 1.24 (s, 9H) ppm; ESI-MS (m/z): 513.7 [M+1]$^+$.

164

Preparation of Compound 131

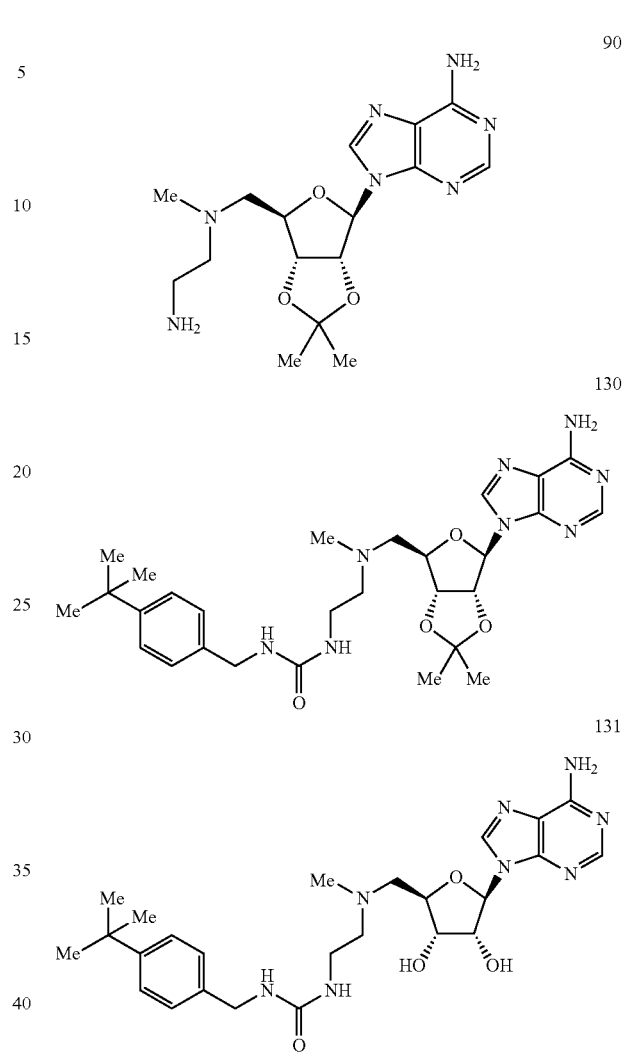

Step 1.

To a mixture of (4-tert-butylphenyl)methanamine (180 mg, 1.10 mmol) in DCM was added DIPEA (0.44 mL, 2.64 mmol) and the resultant mixture was cooled to 0° C. 4-Nitrophenyl carbonochloridate (222 mg, 1.10 mmol) was slowly added. The ice-bath was removed and the mixture was stirred at room temperature for 0.5 h. 90 (200 mg, 0.55 mmol) was slowly added and the mixture was stirred at room temperature overnight. The mixture was washed with water (15 mL), and organic phase was dried over Na$_2$SO$_4$ and concentrated. The residue was purified by prep-TLC(CH$_3$OH:CH$_2$Cl$_2$=1:10) to afford the 130 (85 mg, yield: 28%) as pale solid. ESI-MS: m/z 553.7 [M+1]$^+$.

Step 2.

To a mixture of TFA (0.9 mL) and water (0.1 mL) was added 130 (64 mg, 0.116 mmol). The solution was stirred at 25° C. for 1 h and evaporated to dryness. The residue was co-evaporated with methanol twice, then dissolved in MeOH (10 mL). The solution was neutralized by basic resin (500 mg) with stirring for 1 h. After filtered, the filtrate was concentrated to obtain 131 (49 mg, yield 83%) as pale solid. ESI-MS: m/z 513.7 [M+1]$^+$.

Preparation of Compound 143

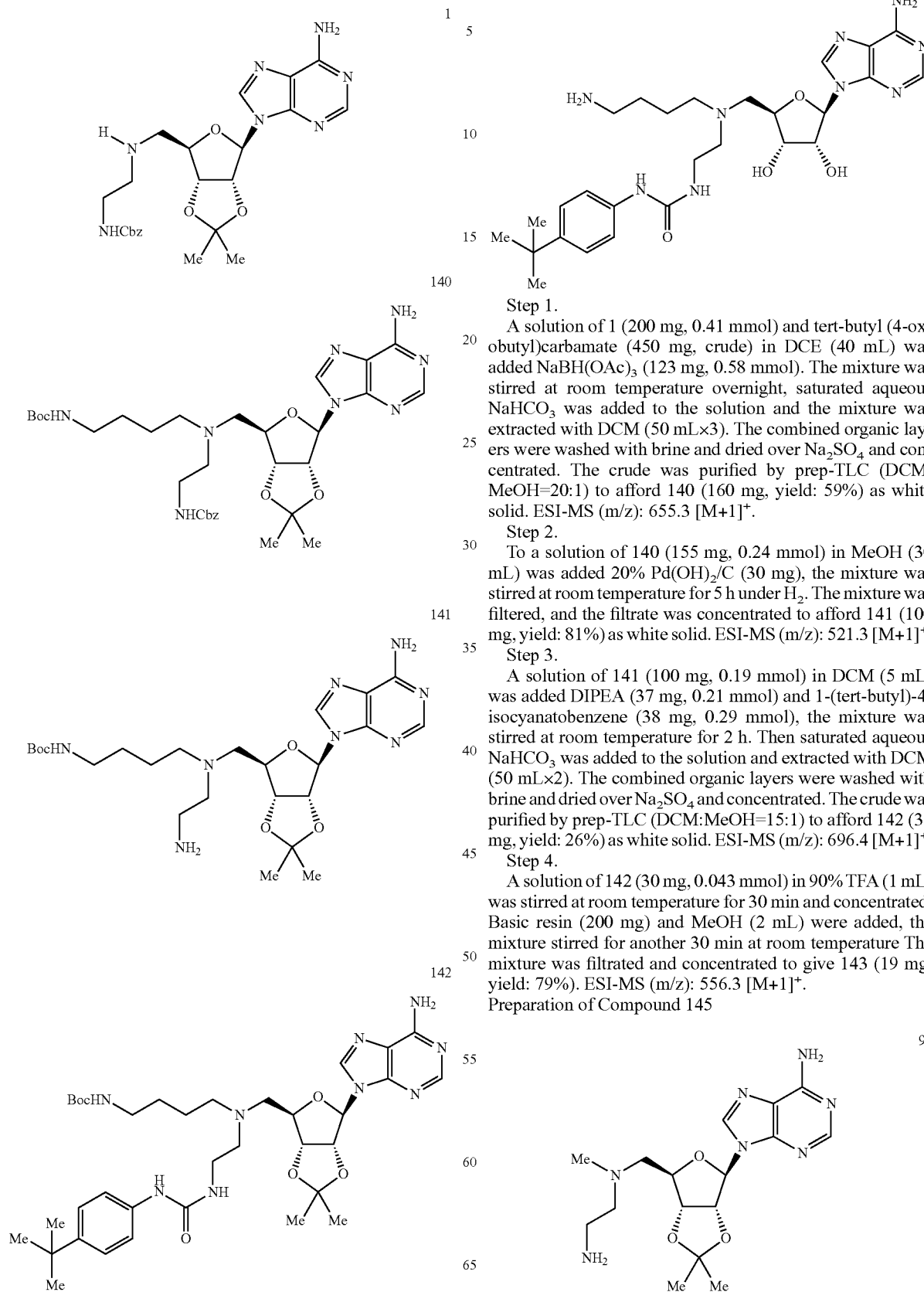

Step 1.

A solution of 1 (200 mg, 0.41 mmol) and tert-butyl (4-oxobutyl)carbamate (450 mg, crude) in DCE (40 mL) was added NaBH(OAc)$_3$ (123 mg, 0.58 mmol). The mixture was stirred at room temperature overnight, saturated aqueous NaHCO$_3$ was added to the solution and the mixture was extracted with DCM (50 mL×3). The combined organic layers were washed with brine and dried over Na$_2$SO$_4$ and concentrated. The crude was purified by prep-TLC (DCM: MeOH=20:1) to afford 140 (160 mg, yield: 59%) as white solid. ESI-MS (m/z): 655.3 [M+1]$^+$.

Step 2.

To a solution of 140 (155 mg, 0.24 mmol) in MeOH (30 mL) was added 20% Pd(OH)$_2$/C (30 mg), the mixture was stirred at room temperature for 5 h under H$_2$. The mixture was filtered, and the filtrate was concentrated to afford 141 (100 mg, yield: 81%) as white solid. ESI-MS (m/z): 521.3 [M+1]$^+$.

Step 3.

A solution of 141 (100 mg, 0.19 mmol) in DCM (5 mL) was added DIPEA (37 mg, 0.21 mmol) and 1-(tert-butyl)-4-isocyanatobenzene (38 mg, 0.29 mmol), the mixture was stirred at room temperature for 2 h. Then saturated aqueous NaHCO$_3$ was added to the solution and extracted with DCM (50 mL×2). The combined organic layers were washed with brine and dried over Na$_2$SO$_4$ and concentrated. The crude was purified by prep-TLC (DCM:MeOH=15:1) to afford 142 (35 mg, yield: 26%) as white solid. ESI-MS (m/z): 696.4 [M+1]$^+$.

Step 4.

A solution of 142 (30 mg, 0.043 mmol) in 90% TFA (1 mL) was stirred at room temperature for 30 min and concentrated. Basic resin (200 mg) and MeOH (2 mL) were added, the mixture stirred for another 30 min at room temperature The mixture was filtrated and concentrated to give 143 (19 mg, yield: 79%). ESI-MS (m/z): 556.3 [M+1]$^+$.

Preparation of Compound 145

167

-continued

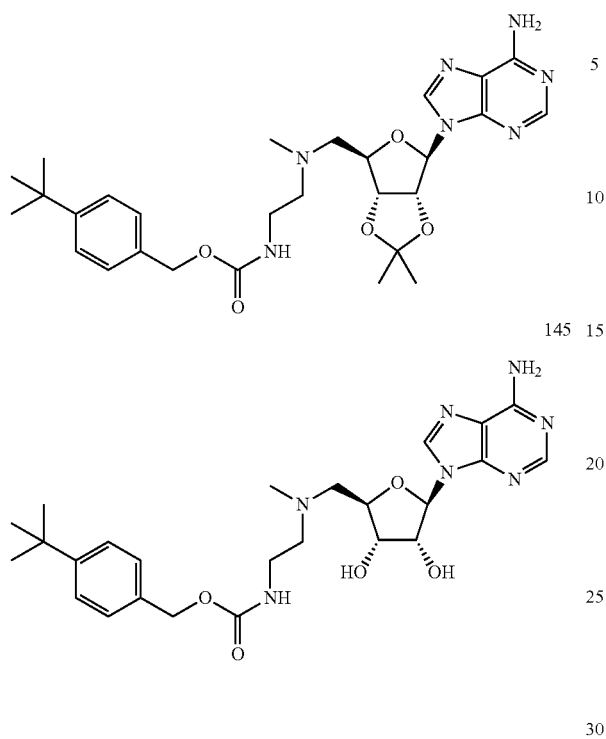

Step 1.

To a solution of (4-tert-butylphenyl) methanol (226 mg, 1.38 mmol) and DIPEA (356 mg, 2.76 mmol) in DCM (4 mL) was added a solution of 4-nitrophenyl carbonochloridate (278 mg, 1.38 mmol), in DCM (1 mL) slowly at 0° C. The solution was stirred at 0° C. for 1 h. Then, a solution of 90 (200 mg, 0.55 mmol) in DCM (2 mL) was added, and the reaction mixture was further stirred at room temperature overnight. Water (2 mL) was added and the mixture was extracted with DCM (10 mL×3). The combined organic layers were dried over anhydrous $Na_2SO_4$ and concentrated to obtain the crude. The crude was purified by prep TLC (DCM:MeOH=15:1). Then, the product was purified by prep TLC (DCM:MeOH=10:1). Then, the product was further purified by prep TLC (100% EtOAc) to afford 144 (62 mg, yield: 20%) as a solid. ESI-MS (m/z): 554.3 $[M_++1]^+$.

Step 2.

To 144 (55 mg, 0.099 mmol) was added a solution of TFA (0.5 mL) and water (0.05 mL). The solution was allowed to stand at room temperature for 1 h and evaporated to dryness. The residue was co-evaporated with methanol twice. Then, the residue was dissolved in MeOH (5 mL). The solution was neutralized by basic resin (225 mg) with stirring for 1 h. After filtered, the filtrate was concentrated to dryness to afford the crude product (54 mg). Then, the crude was purified by prep TLC (DCM:MeOH=8:1 to 5:1) to afford 145 (8 mg, yield: 16%) as a white solid. $^1$H NMR (500 MHz, MeOD): δ 8.28 (s, 1H), 8.22 (s, 1H), 7.36 (d, J=6.5 Hz, 2H), 7.24 (d, J=7.0 Hz, 2H), 6.00 (s, 1H), 5.04-4.97 (m, 2H), 4.70 (s, 1H), 4.25 (s, 1H), 4.20 (s, 1H), 3.25 (s, 2H), 2.83 (s, 2H), 2.60 (s, 2H), 2.33 (s, 3H), 1.31 (s, 9H) ppm; LC/MS (m/z): 514.2 [M+1]$^+$.

168

Preparation of Compound 149

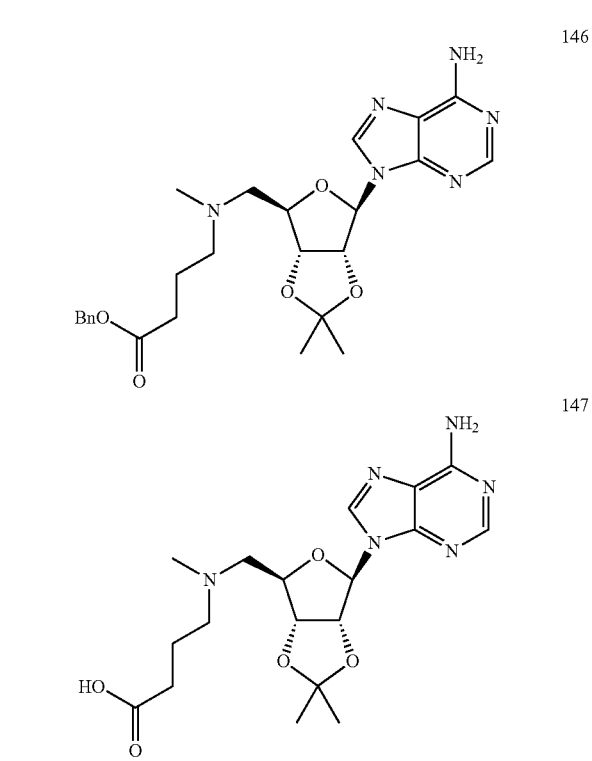

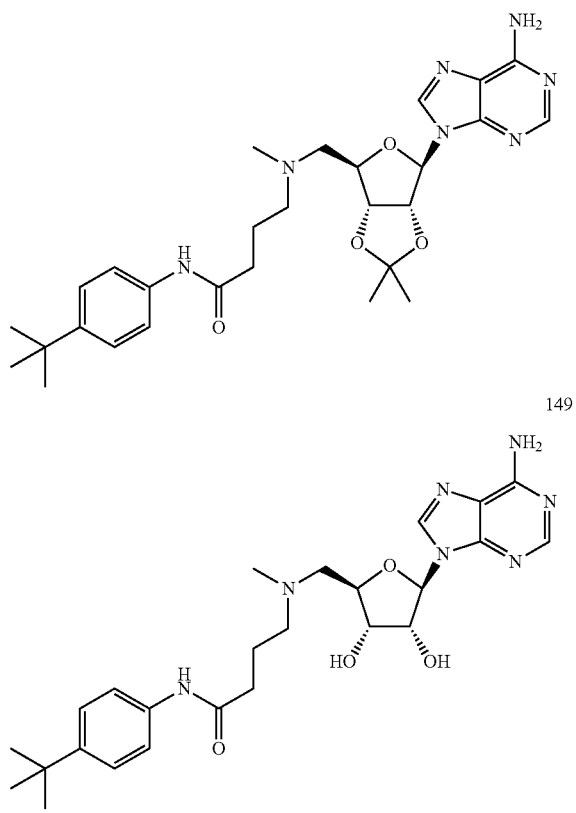

Step 1.

A solution of 9-((3aR,4R,6R,6aR)-2,2-dimethyl-6-((methylamino)methyl)-tetrahydrofuro[3,4-d][1,3]dioxol-4-yl)-

9H-purin-6-amine (800 mg, 2.5 mmol) and benzyl 4-oxobutanoate (Krafft, M. E. et al *J. Org. Chem.* 2003, 68, 6039-6042) (480 mg, 2.5 mmol) in DCE (30 mL) was added NaBH(OAc)₃ (742 mg, 3.5 mmol). The mixture was stirred at room temperature for overnight, then saturated aqueous NaHCO₃ solution was added. The mixture was extracted with DCM (20 mL×3). The combined organic layers were washed with brine (20 mL×2) and dried over Na₂SO₄ and concentrated. The crude was purified by SGC (PE:EtOAc=1:5) to afford the 146 (800 mg, yield: 65%) as white solid. ESI-MS (m/z): 497.0 [M+1]⁺.

Step 2.

A mixture of 146 (400 mg, 0.81 mmol) and 10% Pd/C (100 mg) in EtOH (40 mL) was stirred at room temperature under H₂ overnight. The mixture was filtered and the filtrate was concentrated to give crude solid, which was further washed with EtOH to give 147 (307 mg, yield 94%). ESI-MS (m/z): 407.0 [M+1]⁺, Step 3.

Compound 147 (307 mg, 0.76 mmol), BOP reagent (369 mg, 0.84 mmol) and 1-tert-butyl-4-aminobenzene (170 mg, 1.14 mmol) were dissolved in the mixture of DMF (2 mL) and Et₃N (154 mg, 1.52 mmol). The reaction mixture was stirred at room temperature overnight. The mixture was extracted with DCM (10 mL×3). The combined organic layers were washed with brine (10 mL×2) and dried over Na₂SO₄ and concentrated. The crude was purified by silica gel chromatography (PE:EtOAc=1:5) to give 148 as a straw yellow solid (200 mg, Yield: 49%). ESI-MS (m/z): 538.0 [M+1]⁺.

Step 4.

A solution of 148 (80 mg, 0.12 mmol) in 90% TFA (2 mL) was stirred at room temperature for 1 hour. The residue was co-evaporated with methanol (5 mL×2) to give the TFA salt (80 mg). The TFA salt was dissolved in 20 mL MeOH, and basic resin (134 mg) was added. The resulting mixture was stirred at room temperature for 1 h, filtered and the filtrate was concentrated to give 149 (35 mg. yield 35%). ¹H NMR (500 MHz, MeOD): δ 8.26 (s, 1H), 8.23 (s, 1H), 7.35 (m, 4H), 5.98 (d, J=4.5 Hz, 1H), 4.74 (s, 1H), 4.27 (d, J=3.5 Hz, 2H), 2.93 (m, 2H), 2.65 (s, 2H), 2.41 (m, 5H), 1.90 (m, 2H), 1.31 (s, 9H) ppm; ESI-MS (m/z): 498.0 [M+1]⁺.

Preparation of Compound 152

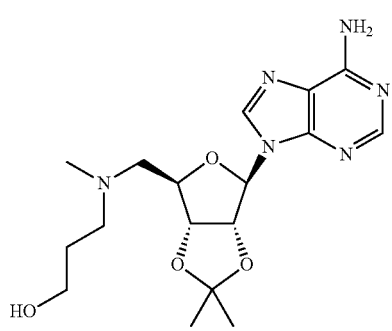

150

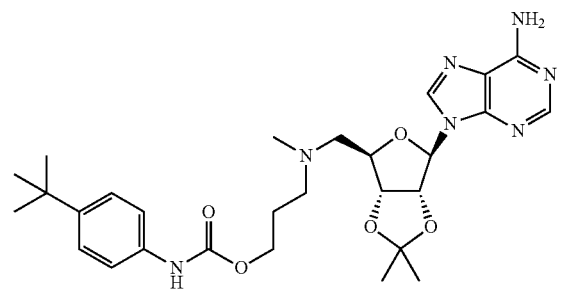

151

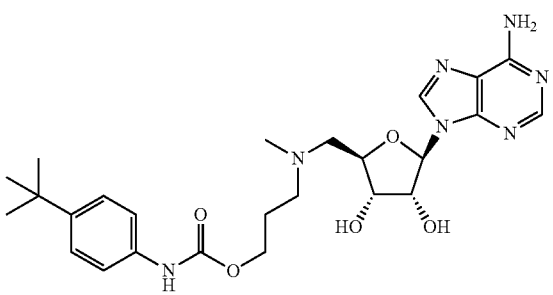

152

Step 1.

To a suspension of 9-((3aR,4R,6R,6aR)-2,2-dimethyl-6-((methylamino)methyl)-tetrahydrofuro[3,4-d][1,3]dioxol-4-yl)-9H-purin-6-amine (700 mg, purity 80%, 1.75 mmol) and anhydrous K₂CO₃ (484 mg, 3.50 mmol) in acetonitrile (12 mL) was added 3-bromopropan-1-ol (340 mg, 2.45 mmol). The mixture was stirred at 80° C. for 6 h. After dilution with water (5 mL), the organic solvent was removed in vacuo. The residue was extracted with CH₂Cl₂ (20 mL×3). The combined organic phase was dried over anhydrous Na₂SO₄ and concentrated. The crude product was purified by SGC (DCM:MeOH=50:1-10:1) to afford 150 (340 mg, yield: 51%) as a white solid. ESI-MS (m/z): 379.2 [M+1]⁺.

Step 2.

To a solution of 150 (100 mg, 0.264 mmol) in DCM (1 mL) was added 4-tert-butylphenyl isocyanate (51 mg, 0.291 mmol). The mixture was stirred at room temperature overnight, and then concentrated. The residue was purified by prep-TLC (DCM:MeOH=15:1) to afford 151 (38 mg, yield: 26%) as a white solid. ESI-MS (m/z): 554.3 [M+1]⁺.

Step 3.

To 151 (40 mg, 0.072 mmol) was added a solution of TFA (0.5 mL) and water (0.05 mL). The solution was allowed to stand at room temperature for 1 h and evaporated to dryness. The residue was co-evaporated with methanol twice. Then, the residue was dissolved in MeOH (7 mL), and neutralized by basic resin (162 mg) with stirring for 1 h. The mixture was filtered and the filtrate was concentrated to afford 152 (35 mg, yield: 88%) as a white solid. ¹H NMR (500 MHz, MeOD): δ 8.12 (s, 2H), 7.20-7.17 (m, 4H), 5.90 (d, J=5.0 Hz, 1H), 4.67 (t, J=5.0 Hz, 1H), 4.25-4.21 (m, 2H), 4.07-4.04 (m, 2H), 3.21-3.18 (m, 1H), 3.08-3.05 (m, 1H), 2.85 (t, J=7.5 Hz, 2H), 2.52 (s, 3H), 1.90-1.85 (m, 2H), 1.20 (s, 9H) ppm; ESI-MS (m/z): 514.2 [M+1]⁺.

Preparation of Compound 154

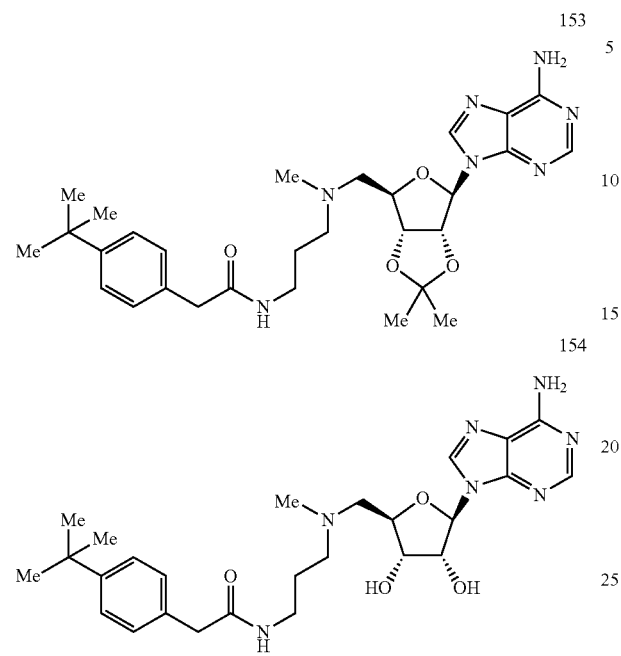

Step 1.

To a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (PCT Int. Appl (2009), WO 200918541; hereby incorporated by reference in its entirety) (377 mg, 1 mmol) and 2-(4-(tert-butyl)phenyl) acetic acid (192 mg, 1 mmol) in DMF (4 mL) was added TBTU (480 mg, 1.5 mmol). The mixture was stirred at room temperature for 4 h. Water (50 mL) was added to quench the reaction. The mixture was extracted with DCM (20 mL×5). The combined organic phase was washed with water (30 mL) and brine (10 mL), dried and concentrated to the crude (480 mg). The crude was purified by SGC (DCM:MeOH=30:1) to obtain 153 (330 mg, Yield: 60%). ESI-MS (m/z): 552.3 [M+1]$^+$.

Step 2.

A solution of 153 (100 mg, 0.18 mmol) in TFA (0.90 mL) and 0.10 mL of water was stirred for 1.5 hours at rt. The reaction was concentrated to dryness, dissolved in MeOH (5 mL) and added resin (240 mg), stirred at room temperature for 1 h, then filtered. The resin was washed with MeOH (2 mL×3) and the filtrate was concentrated to obtain 154 (90 mg, Yield 95%) as pale brown solid. $^1$H NMR (500 MHz, MEOD): δ 8.22 (s, 1H), 8.21 (s, 1H), 7.32 (d, J=8.5 Hz, 2H), 7.17 (d, J=8.0 Hz, 2H), 6.02 (d, J=5.0 Hz, 1H), 4.87-4.84 (m, 1H), 4.44-4.41 (m, 1H), 4.39-4.37 (m, 1H), 3.75-3.71 (m, 1H), 3.43-3.41 (m, 3H), 3.21-3.18 (m, 2H), 3.12-3.09 (m, 2H), 2.81 (s, 3H), 1.88-1.84 (m, 2H), 1.27 (s, 9H) ppm; LC/MS (m/z): 512.3 [M+1]$^+$.

Preparation of Compound 159

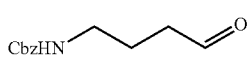

155

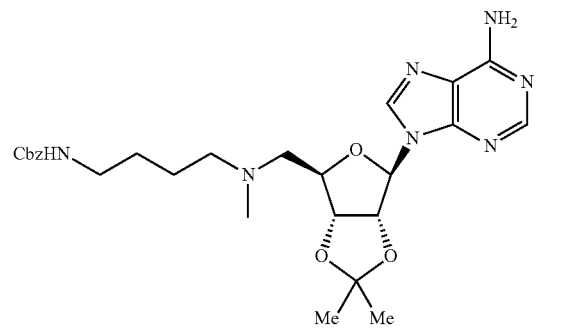

156

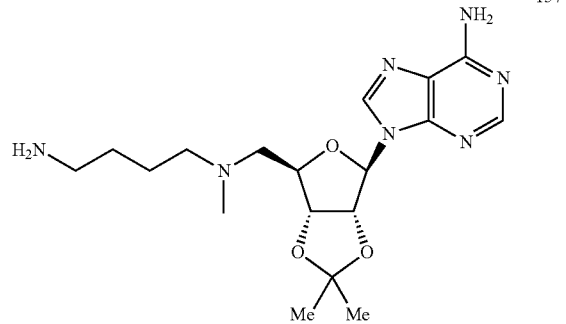

157

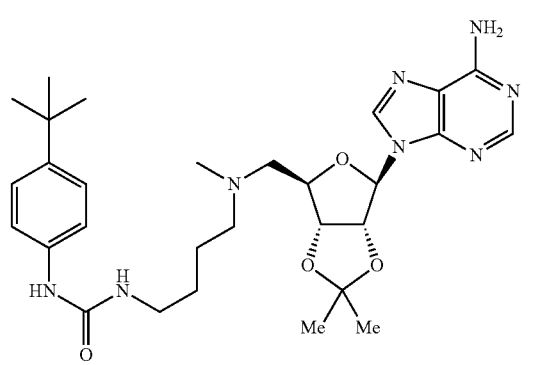

158

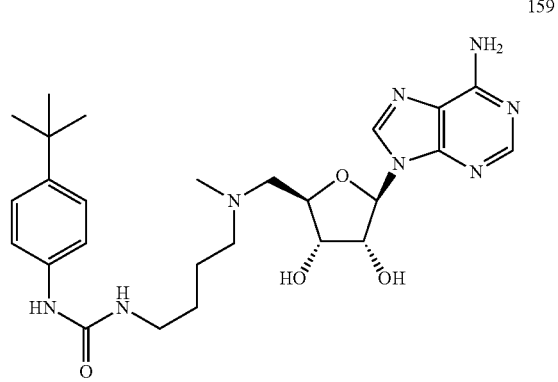

159

Step 1.

To a solution of benzyl (4-hydroxybutyl)carbamate (800 mg, 3.59 mmol) in EtOAc (50 ml) was added IBX (3.0 g, 10.76 mmol). The mixture was heated to reflux for 2 h. After cooling, the mixture was filtered, and the filtrate was concentrated to give 156 (750 mg), which was used for next reaction without further purification.

Step 2.

To a solution of 9-((3aR,4R,6R,6aR)-2,2-dimethyl-6-((methylamino)methyl)tetrahydrofuro[3,4-d][1,3]dioxol-4-yl)-9H-purin-6-amine (250 mg, 0.78 mmol) and 156 (750 mg, crude) in DCE (50 mL) was added NaBH(OAc)₃ (234 mg, 1.09 mmol). The mixture was stirred at room temperature overnight, then saturated aqueous NaHCO₃ was added to the solution and extracted with DCM (50 mL×3). The combined organic layers were washed with brine and dried over Na₂SO₄ and concentrated. The crude was purified by prep-TLC (DCM:MeOH=20:1) to afford 156 (180 mg, yield: 44%) as white solid. ESI-MS (m/z): 526.2 [M+1]⁺.

Step 3.

To a solution of 156 (175 mg, 0.33 mmol) in MeOH (25 mL) was added 20% Pd(OH)₂ (20 mg), the mixture was stirred at room temperature overnight under H₂. The mixture was filtered, and the filtrate was concentrated to afford 157 (120 mg, yield: 92%) as white solid. ESI-MS (m/z): 392.2 [M+1]⁺.

Step 4.

To a solution of 157 (120 mg, 0.31 mmol) in DCM (10 mL) was added DIPEA (59 mg, 0.46 mmol) and 1-(tert-butyl)-4-isocyanatobenzene (65 mg, 0.37 mmol), the mixture was stirred at room temperature overnight. Then water was added to the solution and extracted with DCM (50 mL×2). The combined organic layers were washed with brine and dried over Na₂SO₄ and concentrated. The crude was purified by prep-TLC (DCM:MeOH=8:1) to afford 158 (35 mg, yield: 63%) as white solid. ESI-MS (m/z): 567.3 [M+1]⁺.

Step 5.

A solution of 158 (70 mg, 0.124 mmol) in 90% TFA (1 mL) was stirred at room temperature for 30 min and concentrated. Basic resin (300 mg) and MeOH (5 mL) were added, the mixture stirred for another 30 min at rt. The mixture was filtrated and concentrated, purified by prep-TLC (DCM:MeOH=3:1) to give 160 (30 mg, yield: 46%). ¹H NMR (500 MHz, MeOD): δ8.24 (s, 1H), 8.21 (s, 1H), 7.27-7.21 (m, 4H), 5.99 (d, J=4.5 Hz, 1H), 4.75 (t, J=8.0 Hz, 1H), 4.28 (m, 2H), 3.19-3.06 (m, 4H), 2.75 (s, 2H), 2.51 (s, 3H), 1.62-1.51 (m, 4H), 1.27 (s, 9H) ppm; ESI-MS (m/z): 527.3 [M+1]⁺.

Preparation of Compound 163

160A

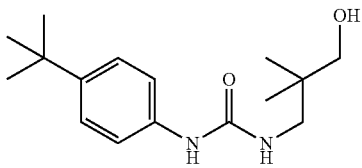

160B

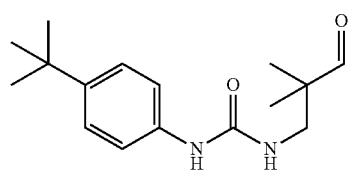

161

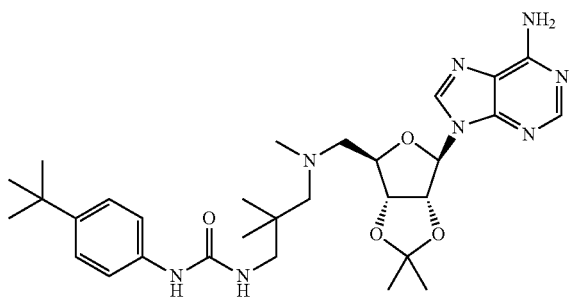

162

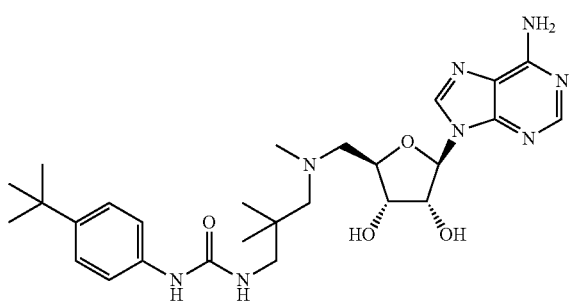

163

Step 1.

To a solution of 1-tert-butyl-4-isocyanatobenzene (350 mg, 2 mmol) in DCM (3 mL) was added 160A (206 mg, 2 mmol) slowly at 0° C. The resulting mixture was stirred at 0° C. for 1 h, then at room temperature for 1 h. DCM (20 mL) and petroleum ether (40 mL) was added. The resultant suspension was stirred at room temperature for 10 min, and then filtered. The solid was washed with petroleum ether (20 mL) to afford 160B (510 mg, yield: 91%) as white solid. ESI-MS (m/z): 279.3 [M+1]⁺.

Step 2.

To a solution of 160B (278 mg, 1 mmol) in EtOAc (5 mL) was added IBX (840 mg, 3 mmol). The mixture was refluxed for 2 h and filtered. The filtrate was concentrated to give 161 (280 mg, yield: 100%, crude) as brown solid. The crude was directly used in the next step without further purification.

Step 3.

To a solution of 9-((3aR,4R,6R,6aR)-2,2-dimethyl-6-((methylamino)methyl)tetrahydrofuro[3,4-d][1,3]dioxol-4-yl)-9H-purin-6-amine (320 mg, 1 mmol) and 161 (280 mg, crude from previous step) in DCE (4 mL) was added NaBH(OAc)₃ (424 mg, 1 mmol). The mixture was stirred at room temperature overnight. Saturated aqueous Na₂CO₃ (5 mL) was added to quench the reaction. The mixture was extracted with DCM (20 mL×4). The combined organic phase was washed with water (10 mL), brine (10 mL), and concentrated. The residue was purified by prep-TLC (DCM:MeOH=12:1) to afford the product as crude. Then, the crude was further purified by prep-TLC (DCM:MeOH=12:1) to afford pure 162 (50 mg, yield: 8.6% for two steps) as a white solid. ESI-MS (m/z): 581.3 [M+1]⁺.

Step 4.

To 162 (43 mg, 0.074 mmol) was added a solution of TFA (0.95 mL) and water (0.05 mL). The mixture was allowed to stand at room temperature for 3.5 h and evaporated to dryness. The residue was co-evaporated with methanol twice. Then, the residue was dissolved in MeOH (5 mL). The solution was neutralized by basic resin (170 mg) with stirring for 1 h. After filtered, the filtrate was concentrated to dryness to afford 163 (35 mg, yield: 88%) as a white solid. ESI-MS (m/z): 541.3 [M+1]⁺.

Preparation of Compound 167

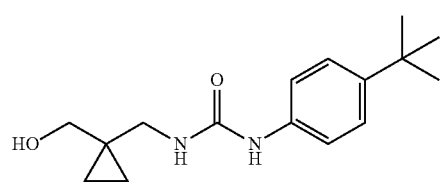
164

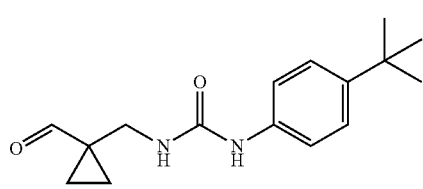
165

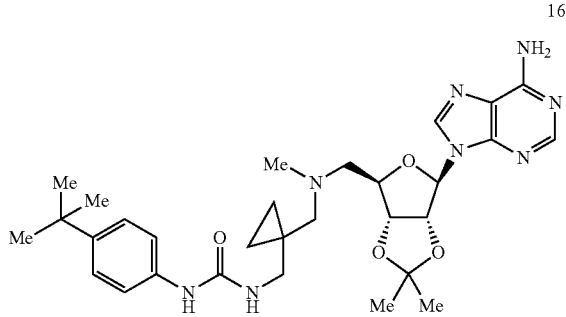
166

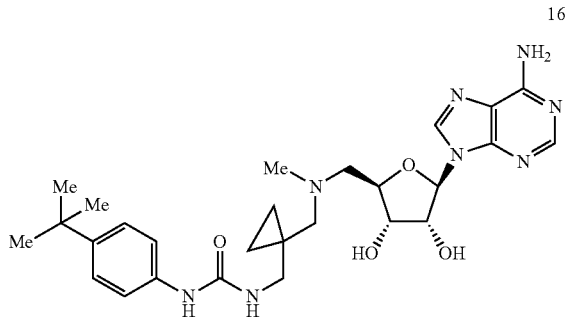
167

Step 1.

A solution of (1-(aminomethyl)cyclopropyl)methanol (65 mg, 0.64 mmol) and 1-tert-butyl-4-isocyanatobenzene (111 mg, 0.64 mmol) and DIPEA (250 mg, 1.92 mmol) in dry DCM (5 mL) was stirred at room temperature overnight, then MeOH (5 mL) was added and concentrated to give crude product, which was purified by prep-TLC (DCM:MeOH=20:1) to afford pure 164 (750 mg, yield 43%) as white solid. ESI-MS (m/z): 277.7 [M+1]⁺.

Step 2.

A mixture of 164 (75 mg, 0.27 mmol) and IBX (228 mg, 0.81 mmol) in EtOAc (10 mL) was refluxed for 2 h. After the solid was filtered and washed with EtOAc (10 mL×2), the combined organic layers were concentrated to afford 165 (70 mg, yield: 94%) as yellowish powder. ESI-MS (m/z): 275.7 [M+1]⁺.

Step 3.

A solution of 9-((3aR,4R,6R,6aR)-2,2-dimethyl-6-((methylamino)methyl)tetrahydrofuro-[3,4-d][1,3]dioxol-4-yl)-9H-purin-6-amine (80 mg, 0.25 mmol) and 165 (70 mg, 0.25 mmol) in DCE (5 mL) was added NaB(OAc)₃H (80 mg, 0.37 mmol), The mixture was stirred at room temperature overnight, Then saturated aqueous NaHCO₃ (5 mL) was added to the solution. The mixture was extracted with DCM (20 mL×2). The combined organic layers were washed with brine and dried over Na₂SO₄ and concentrated. The crude was purified by prep-TLC (DCM:MeOH=10:1) to afford the pure 166 (70 mg, yield: 50%) as white solid. ESI-MS (m/z): 579.7 [M+1]⁺.

Step 4.

A solution of 166 (67 mg, 0.12 mmol) in 90% TFA (2 mL) was stirred at room temperature for 1 h, then concentrated to remove TFA. The residue was dissolved in MeOH (5 mL) and basic resin (520 mg) was added and stirred at room temperature for 0.5 h. After filtration, the filtrate was concentrated to give 167 (41 mg, yield: 63%) as a white solid. ESI-MS (m/z): 539.7 [M+1]⁺.

Preparation of Compound 169

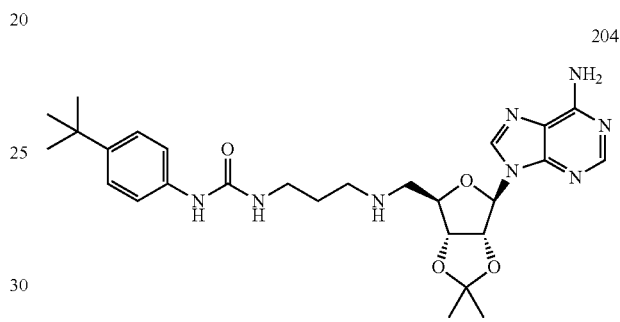
204

168

169

Step 1.

A mixture of 204 (150 mg, 0.27 mmol) and acetaldehyde (2 mL, 40% aqueous solution) in THF (6 mL) was stirred at room temperature for 0.5 h, then NaBH(OAc)₃ (120 mg, 0.55 mmol) was added. The reaction was stirred at room temperature overnight, then quenched with saturated aqueous NaHCO₃ solution (1 mL). The resulting mixture was extracted with DCM (10 mL×3), washed with brine (10 mL). The organic phase was dried over Na₂SO₄ and concentrated. The residue was purified by SGC (DCM:MeOH/40:1) to obtain 168 (95 mg, Yield 68%). ESI-MS (m/z): 567.3 [M+1]⁺.

Step 2.

A solution of 168 (90 mg, 0.16 mmol) in TFA (90%, 1 mL) was stirred at room temperature for 1.5 hours, then concentrated to dryness. The residue was dissolved in MeOH (5 mL) and basic resin (150 mg) was added. The resulting mixture was stirred at room temperature for 1 h. The resin was removed by filtration, and the filtrate was concentrated to obtain the crude product. The crude material was purified by prep-TLC to obtain 169 (75 mg, Yield: 85%) as pale white solid. $^1$H NMR (500 MHz, MeOD): δ 8.25 (s, 1H), 8.21 (s, 1H), 7.26-7.22 (m, 4H), 6.01 (d, J=4.0 Hz, 1H), 4.76-4.74 (m, 1H), 4.37-4.35 (m, 1H), 4.33-4.30 (m, 1H), 3.24-3.17 (m, 4H), 2.91-2.86 (m, 4H), 1.80-1.77 (m, 2H), 1.29 (s, 9H), 1.15 (t, J=7.0 Hz, 3H) ppm; ESI-MS (m/z): 527.3 [M+1]$^+$.

Preparation of Compound 173

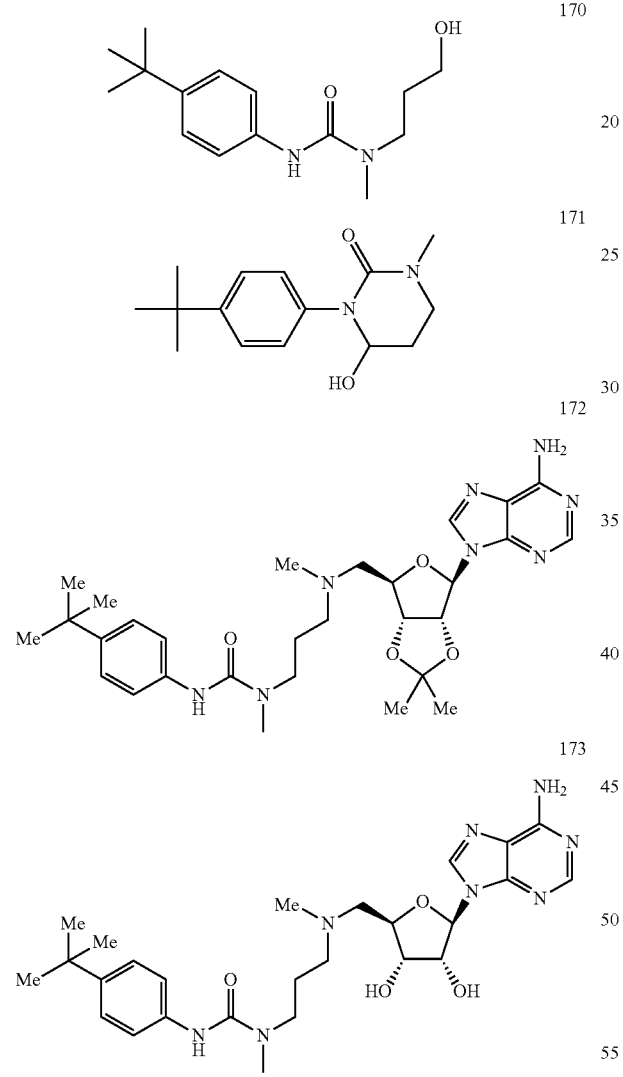

Step 1.

To a mixture of 1-(tert-butyl)-4-isocyanatobenzene (200 mg, 1.14 mmol) in 10 mL of DCM was added 3-(methylamino)propan-1-ol (104 mg, 1.20 mmol) and the resultant mixture was stirred at room temperature overnight. Then HCl (5%, 15 mL) was added and the mixture was extracted with DCM (15 mL x3). The organic phase was evaporated to afford 170 (294 mg, yield: 98%) as white solid. ESI-MS (m/z): 265.7 [M+1]$^+$.

Step 2.

A mixture of 170 (745 mg, 2.82 mmol) and IBX (2.37 g, 8.45 mmol) in 50 mL of EtOAc was refluxed for 2 h. The mixture was filtered and filtrate was concentrated to give 171 as pale solid (750 mg, yield: 100%). ESI-MS (m/z): 263.7 [M+1]$^+$.

Step 3.

To a stirred solution of 9-((3aR,4R,6R,6aR)-2,2-dimethyl-6-((methylamino)methyl)tetrahydrofuro[3,4-d][1,3]dioxol-4-yl)-9H-purin-6-amine (200 mg, 0.624 mmol) and 171 (750 mg, 2.85 mmol) in 20 mL of DCE was added NaBH(OAc)$_3$ (600 mg, 2.83 mmol). Then the mixture was stirred at room temperature overnight. NaHCO$_3$ (aq) (8 mL) was added to quench the reaction and the mixture was extracted with DCM (15 mL×4). The organic phase was dried over Na$_2$SO$_4$ and filtered. The filtrate was concentrated and the residue was purified by prep-TLC (CH$_3$OH:DCM=1:8) to afford the 172 (191 mg, yield: 54%) as pale solid. ESI-MS (m/z): 567.7 [M+1]$^+$.

Step 4.

To a mixture of TFA (0.9 mL) and water (0.1 mL) was added 172 (49 mg, 0.08 mmol). The solution was stirred at room temperature for 1 h and evaporated to dryness. The residue was co-evaporated with methanol twice, then dissolved in MeOH (10 mL). The solution was neutralized by basic resin (400 mg) with stirring for 1 h. After filtered, the filtrate was concentrated to obtain 173 (40 mg, yield 87%) as pale solid. $^1$H NMR (500 MHz, MeOD): δ 8.19 (s, 1H), 8.13 (s, 1H), 7.23-7.21 (m, 2H), 7.20-7.17 (m, 2H), 5.93 (d, J=4.5 Hz, 1H), 4.78 (t, J=5.5 Hz, 1H), 4.32-4.29 (m, 2H), 3.44-3.41 (m, 1H), 3.20-3.15 (m, 2H), 2.89-2.84 (m, 4H), 2.69-2.62 (m, 2H), 2.47 (s, 3H), 1.86-1.82 (m, 2H), 1.27 (s, 9H) ppm. ESI-MS (m/z): 527.7 [M+1]$^+$.

Preparation of Compound 179

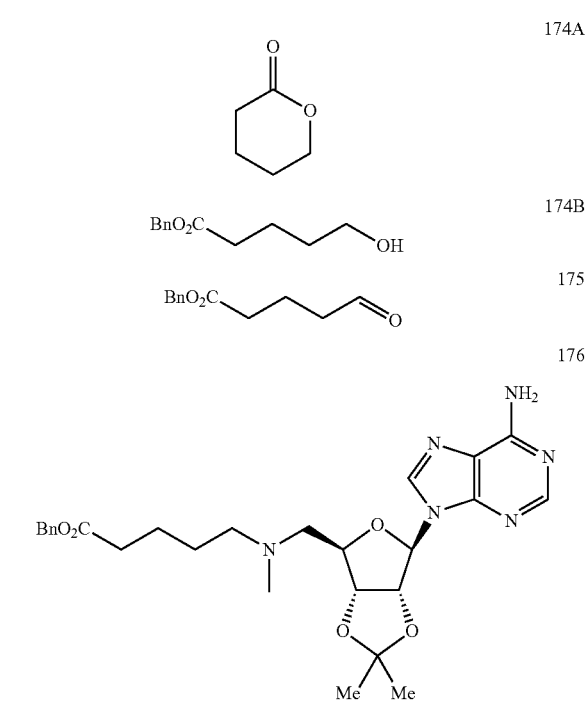

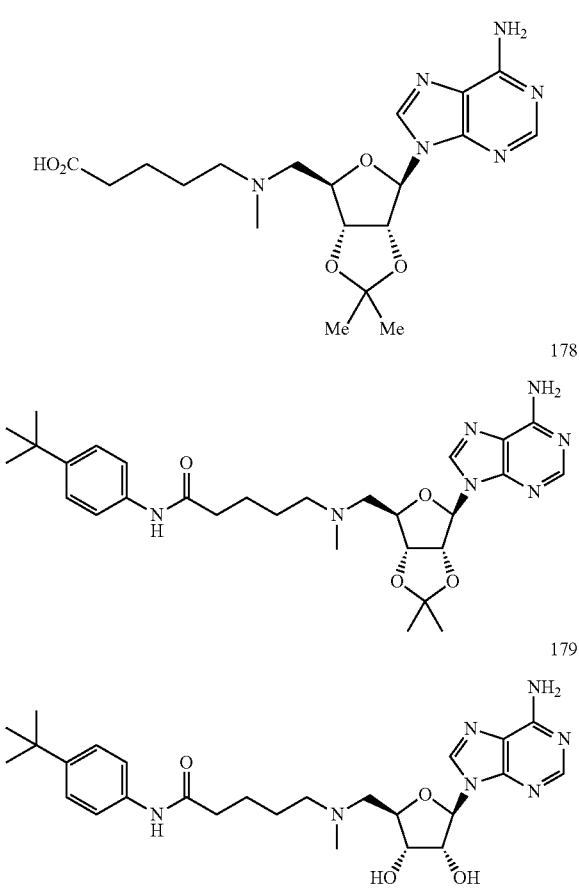

Step 1.

A mixture of 174A (3.0 g, 30 mmol) and 1.0 M tetrabutylammonium hydroxide (7.77 g, 30 mmol) in methanol (30 mL) was heated to reflux for 2 h. The solvent was removed in vacuo to afford an oil. The oil was dissolved in 25 mL of DMF, and then benzyl bromide (5.1 g, 30 mmol) was added slowly. After having been stirred at room temperature for 2 h, water (150 mL) was added into the mixture. The mixture was extracted with EtOAc (150 mL×2). The combined organic layers were dried over Na$_2$SO$_4$ and concentrated. The crude was purified by SGC (PE:EtOAc=20:1→15:1→10:1→5:1) to afford 174B (3.2 g, yield: 50%) as colorless oil. LC-MS (m/z): 209.7 [M+1]$^+$.

Step 2.

A mixture of 174B (500 mg, 2.4 mmol) and IBX (2.02 g, 7.2 mmol) in EtOAc (20 mL) was refluxed for 2 h. After the solid was filtered and washed with EtOAc (10 mL×2), the combined organic layers were concentrated to afford 175 (400 mg, yield: 80%) as colorless oil, which was used for next step without purification. LC-MS (m/z): 207.7 [M+1]$^+$.

Step 3.

To a solution of 9-((3aR,4R,6R,6aR)-2,2-dimethyl-6-((methylamino)methyl)-tetrahydrofuro[3,4-d][1,3]dioxol-4-yl)-9H-purin-6-amine (400 mg, 1.25 mmol) and 175 (400 mg, 1.94 mmol) in DCE (15 mL) was added NaB(OAc)$_3$H (427 g, 1.94 mmol), the mixture was stirred at room temperature overnight, Then saturated aqueous NaHCO$_3$ (20 mL) was added to the solution. The mixture was extracted with DCM (30 mL×3). The combined organic layers were washed with brine and dried over Na$_2$SO$_4$ and concentrated. The crude was purified by SGC (DCM:MeOH=80:1→50:1) to afford pure 176 (350 mg, yield: 55%) as a white solid. LC-MS (m/z): 511.7 [M+1]+.

Step 4.

A mixture of 176 (340 mg, 0.67 mmol) and 10% Pd/C (71 mg) in MeOH (10 mL) was stirred under H$_2$ at room temperature overnight. The mixture was filtered and the filtrate was concentrated to give 177 (270 mg, yield 96%) as a white powder. LC-MS (m/z): 421.7 [M+1]$^+$.

Step 5.

To a stirred solution of 177 (260 mg, 0.64 mmol) and BOP (427 mg, 0.96 mmol) and TEA (130 mg, 1.28 mmol) in dry DMF (2 mL) was added 4-tert-butylbenzenamine (144 mg, 0.96 mmol) and the reaction mixture was stirred at room temperature overnight. Water (20 mL) was added and the resultant mixture was extracted with DCM (50 mL×3). The combined organic layers were dried over Na$_2$SO$_4$ and concentrated to give crude product. The crude was purified by prep TLC (DCM:MeOH=6:1) to afford pure 178 (160 mg, yield: 47%) as a white solid. LC-MS (m/z): 552.7 [M+1]$^+$.

Step 6.

A solution of 178 (80 mg, 0.15 mmol) in 90% TFA (2 mL) was stirred at room temperature for 1 h. Then it was concentrated. The residue was dissolved in MeOH (5 mL) and basic resin (480 mg) was added. After stirring at room temperature for 0.5 h, the mixture was filtered and the filtrate was concentrated to give crude product. The crude was purified by prep-TLC (DCM:MeOH=3:2) to afford 179 (30 mg, yield: 42%) as a white solid. $^1$H NMR (500 MHz, MeOD): δ 8.26 (s, 1H), 8.22 (s, 1H), 7.44-7.42 (m, 2H), 7.33-7.32 (m, 2H), 6.00 (d, J=3.0 Hz, 1H), 4.75 (t, J=4.5 Hz, 1H), 4.30-4.28 (m, 2H), 3.11-3.01 (m, 2H), 2.73 (t, J=7.5 Hz, 2H), 2.49 (s, 3H), 2.37 (t, J=7.5 Hz, 2H), 1.70-1.63 (m, 4H), 1.30 (s, 9H), ppm; LC-MS (m/z): 512.7 [M+1]$^+$.

Preparation of Compound 183

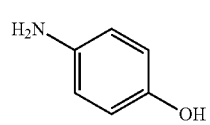

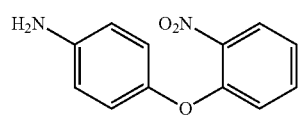

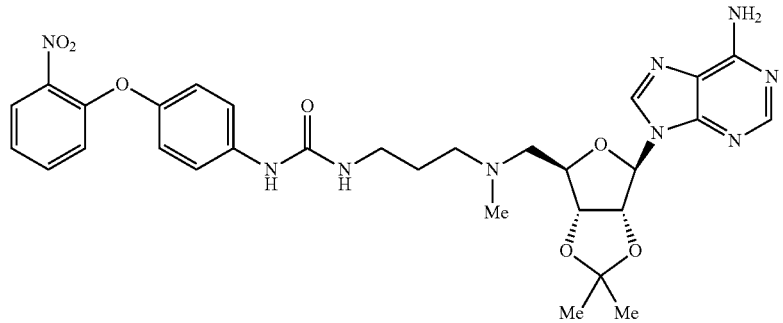

181

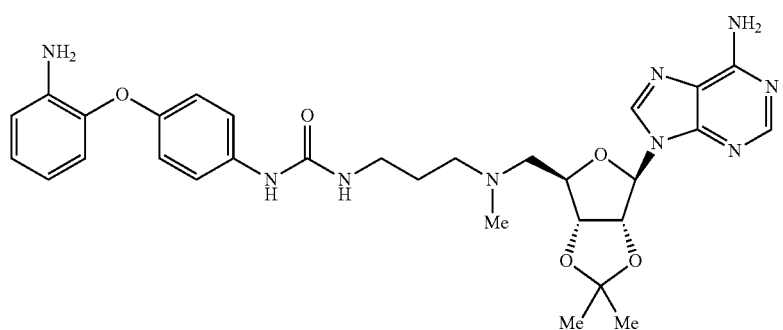

182

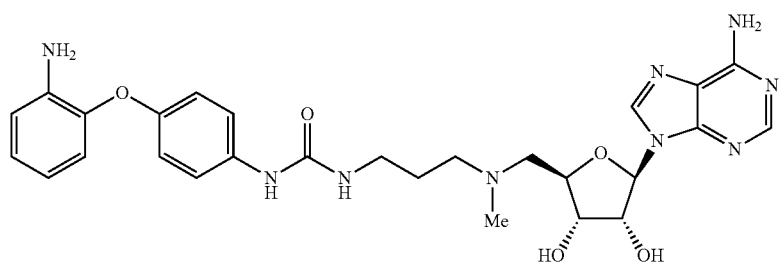

183

Step 1.

To a suspension of M-286-0 (872 mg, 8 mmol) and anhydrous $K_2CO_3$ (6.62 g, 48 mmol) in DMF (20 mL) was added M-286-1 (1.13 g, 8 mmol). The mixture was refluxed for 6 h. After dilution with water (80 mL), the mixture was extracted with EtOAc (80 mL×3). The combined organic phase was washed with brine (50 mL), dried over anhydrous $Na_2SO_4$ and concentrated. The crude was purified by SGC (PE:EtOAc=10:1 to 5:1) to afford 180 (1.56 g, yield: 83%) as a yellow solid. LC-MS (m/z): 231.1 $[M+1]^+$.

Step 2.

A solution of 180 (460 mg, 2 mmol) and DIPEA (516 mg, 4 mmol) in DCM (3 mL) was added to a solution of triphosgene (267 mg, 0.9 mmol) in DCM (2 mL) dropwise at 0° C. The reaction mixture was stirred at room temperature for 1.5 h, then the solution was used for preparing 181 directly.

At 0° C. to a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (230 mg, 0.7 mmol) and DIPEA (250 mg, 2 mmol) in DCM (10 mL) was added the prepared isocyanate solution dropwise. The resulting reaction mixture was stirred at room temperature overnight. Water (10 mL) was added to quench the reaction. The mixture was extracted with DCM (15 mL×3), dried over anhydrous $Na_2SO_4$ and concentrated. The crude was purified by prep-TLC (DCM:MeOH=8:1) to afford 181 (101 mg, yield: 27%) as a yellow solid. LC-MS (m/z): 634.2 $[M+1]^+$.

Step 3.

181 (65 mg, 0.103 mmol) was dissolved in EtOH (15 mL). 10% Pd/C (15 mg) was added and the resultant mixture was stirred at 1 atm $H_2$ overnight. The mixture was then filtered and rinsed with EtOH (5 mL×3). The filtrate was evaporated in vacuo to afford 182 (60 mg, yield: 97%) as a yellow powder, which was used for next step without further purification. LC-MS (m/z): 604.3 $[M+1]^+$.

Step 4.

To a mixture of TFA (0.9 mL) and water (0.1 mL) was added 182 (55 mg, 0.091 mmol). The solution was allowed to stand at room temperature for 1 h and evaporated to dryness. The residue was co-evaporated with methanol twice. Then the residue was dissolved in MeOH (5 mL) and neutralized by basic resin (400 mg) with stirring at room temperature for 1 h. After filtration, the filtrate was concentrated. The residue was purified by prep-TLC (DCM:MeOH:25% $NH_3.H_2O$=180:30:3) to afford 183 (28 mg, yield: 55%) as a white solid. NMR (500 MHz, MeOD): δ 8.23 (s, 1H), 8.20 (s, 1H), 7.24 (dd, J=2.5, 7.0 Hz, 2H), 6.92-6.84 (m, 4H), 6.74 (dd, J=1.0, 7.5 Hz, 1H), 6.66 (dd, J=1.5, 7.5 Hz, 1H), 5.99 (d, J=5.0 Hz, 1H), 4.74 (m, 1H), 4.29-4.28 (m, 2H), 3.23-2.96 (m, 4H), 2.74 (m, 2H), 2.48 (s, 3H), 1.77 (t, J=7.0 Hz, 2H) ppm; LC-MS (m/z): 564.1 $[M+1]^+$.

Preparation of Compound 185

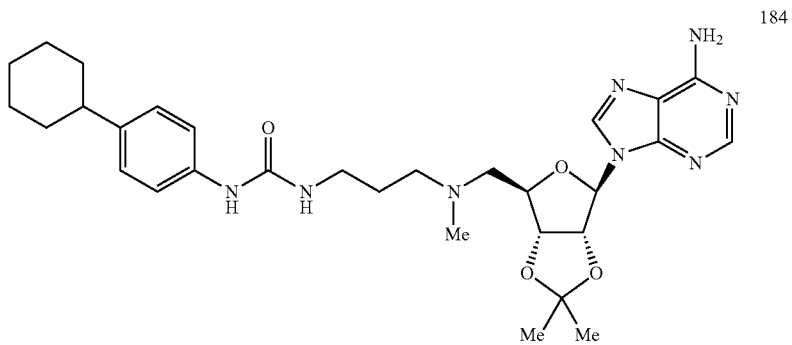

184

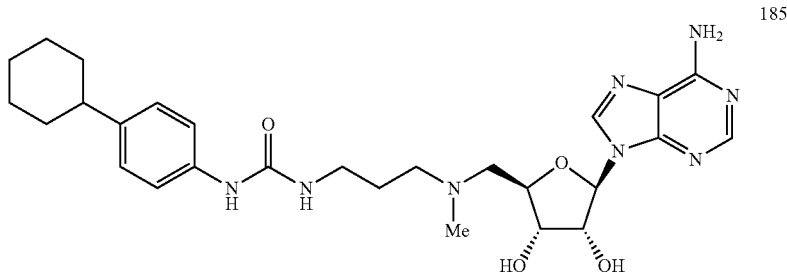

185

Step 1.

To a solution of triphosgene (62.8 mg, 0.21 mmol) in 10 mL of dry DCM at 0° C. was stirred, a solution of 4-cyclohexylbenzenamine (91 mg, 0.52 mmol) and TEA (105.0 mg, 1.0 mmol) was added dropwise. The reaction mixture was stirred for 5 min at 0° C. and the resulting solution of isocyanate was added slowly to a solution $N^1$-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (100 mg, 0.26 mmol) at room temperature and was stirred for 2 h. The reaction was quenched with H2O, extracted with DCM (10 mL×3), washed with brine (10 mL), dried and concentrated to the crude. The crude was purified by SGC (DCM:MeOH=10:1) to obtain 184 (100 mg, Yield: 65.4%) LC-MS (m/z): 579.3 [M+1]$^+$.

Step 2.

A solution of 184 (80 mg, 0.138 mmol) in TFA (0.90 mL) and 0.10 mL of water was stirred for 1.5 hours at room temperature. The reaction was concentrated to dryness, dissolved in MeOH (5 mL) and added resin (130 mg), stirred at room temperature for 1 h. Then filtered, washed with MeOH (2 mL*3) and concentrated to obtain a crude product. The crude product was purified by prep-TLC to obtain 185 (40 mg, Yield 54%) as pale white solid. LC-MS (m/z): 579.3[M+1]$^+$ppm; LC-MS (m/z): 539.3 [M+1]$^+$.

Preparation of Compound 190

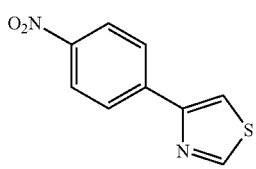

186

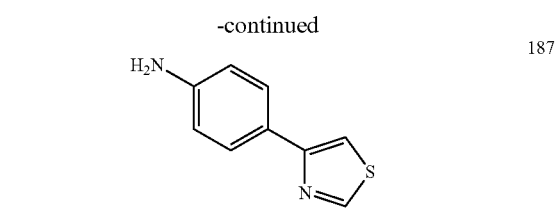

187

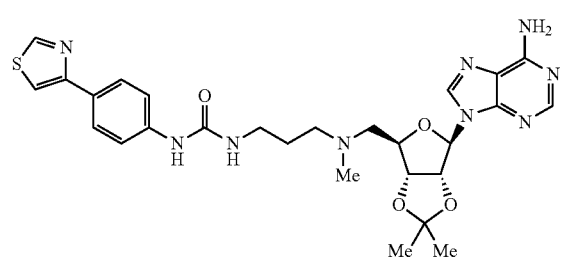

189

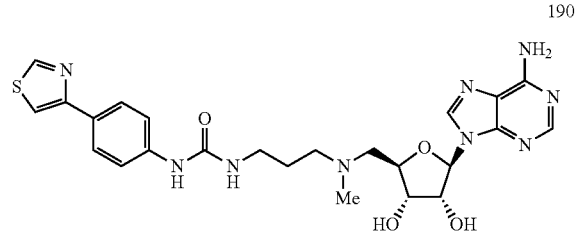

190

Step 1.

A mixture of phosphorus pentasulfide (4.4 g, 20 mmol), dioxane (75 ml), and N,N-dimethylformamide (30 mL) was heated at gentle reflux for one hour under nitrogen atmosphere. The resulting solution was cooled, decanted, and added to 2-bromo-1-(4-nitrophenyl)ethanone (3.90 g, 16 mmol) and the resulting solution was heated at reflux for one hour. Cooled to room temperature, added water (300 mL), neutralized to basic with magnesium carbonate (5 g). After one hour collected by filtration, washed with water (3 times) to give 186 as a brown solid (2.3 g, Yield: 70%). LC-MS (m/z): 207.0 [M+1]⁺.

Step 2.

To a solution of 186 (2 g, 9.7 mmol), Fe (2.7 g, 48.5 mmol), NH₄Cl (52 mg, 9.7 mmol) in EtOH (50 mL) was stirred for 2 h at reflux, cooled, filtered, and concentrated to obtain 187 as pale white solid which was used in the next step without further purification (1.58 g, Yield: 93%). LC-MS (m/z): 177.1 [M+1]⁺.

Step 3.

To a solution of triphosgene (62.8 mg, 0.21 mmol) in 10 mL of dry DCM at 0 deg was stirred, a solution of 187 (91 mg, 0.52 mmol) and TEA (105.0 mg, 1.0 mmol) was added dropwise. The reaction mixture was stirred for 5 min at 0° C., TLC indicated that the starting material used up and the product isocyanate was formed. The solution of isocyanate was added slowly to a solution N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (100 mg, 0.26 mmol) at room temperature and was stirred for 2 h. The reaction was quenched with water, extracted with DCM (10 mL×3), washed with brine (10 mL), dried and concentrated. The crude material was purified by SGC (DCM:MeOH/10:1) to obtain 189 (90 mg, Yield: 60%) LC-MS (m/z): 580.3 [M+1]⁺.

Step 4.

A solution of 189 (60 mg, 0.104 mmol) in TFA (0.90 mL) and 0.10 mL of water was stirred for 1.5 hours at room temperature. The reaction was concentrated to dryness, dissolved in MeOH (5 mL), basic resin was added (130 mg) and the mixture was stirred at room temperature for 1 h. The mixture was filtered and the filtrate was washed with MeOH (2 mL×3) and concentrated to obtain the crude. The crude was purified by prep-TLC to obtain 190 (30 mg, Yield 53.7%) as pale white solid. LC-MS (m/z): 540.2 [M+1]⁺.

Preparation of Compound 195

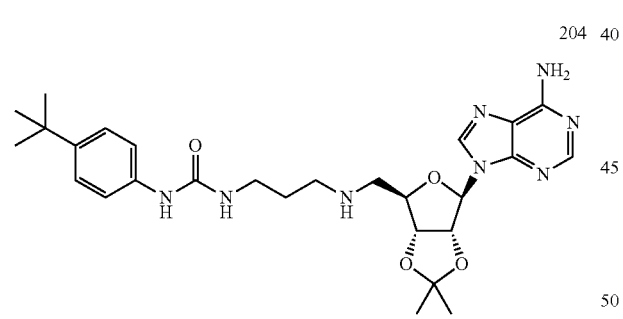

204

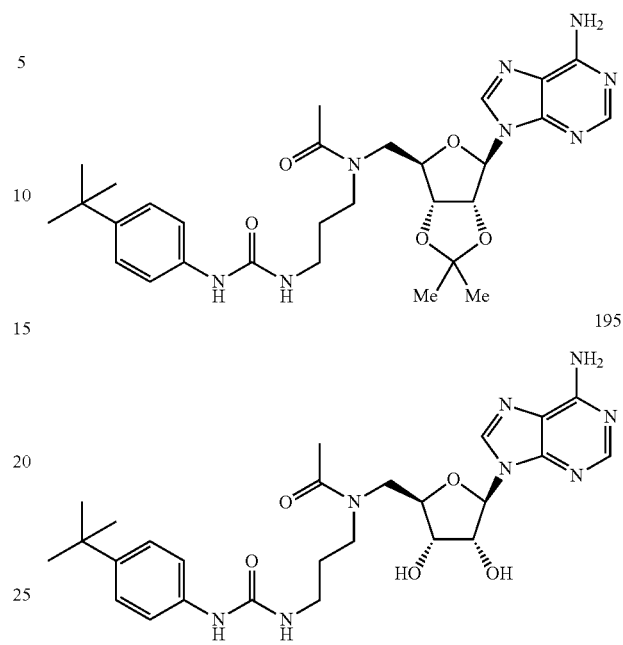

194

195

Step 1.

To a solution of DIPEA (74 mg, 0.57 mmol), CH₃COOH (53 mg, 0.95 mmol) and EDCI (53 mg, 0.28 mmol) in DCM (3 mL) was added 204 (100 mg, 0.19 mmol). The mixture was stirred at room temperature overnight. Brine (10 mL) was added and the mixture was extracted with DCM (15 mL×3). The combined organic phase was dried over Na₂SO₄ and concentrated. The crude was purified by SGC (DCM:MeOH=12:1) to afford the 194 (130 mg) as a white solid. ESI-MS (m/z): 581.3 [M+1]⁺.

Step 2.

A solution of 194 (50 mg, 0.086 mmol) in 90% TFA (1 mL) was stirred at room temperature for 1 h and evaporated to dryness. The residue was co-evaporated with methanol. The mixture was dissolved in 10 mL MeOH, and K₂CO₃ (60 mg, 0.43 mmol) was added. Then water was added dropwise until all K₂CO₃ was dissolved. The reaction mixture was stirred at room temperature for 1.5 h, then concentrated to remove MeOH and water. The residue was purified by prep-TLC (DCM:MeOH=5:1) give 195 (16 mg, yield: 34%). ESI-MS (m/z): 541.3 [M+1]⁺.

Preparation of Compound 199

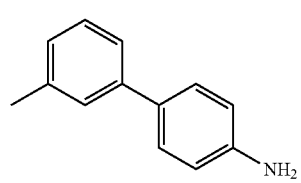

196

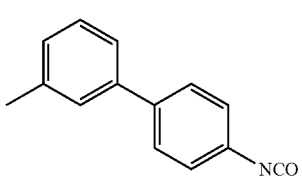

197

-continued

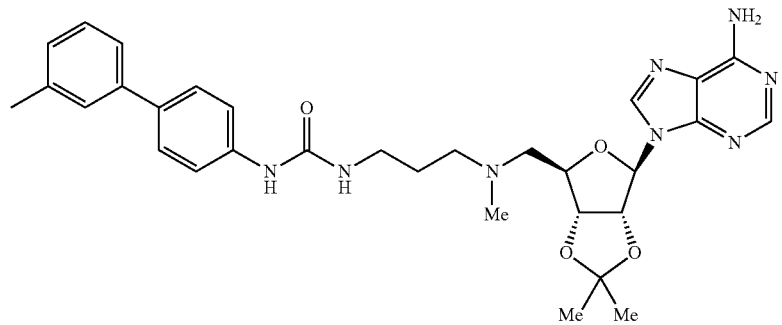

198

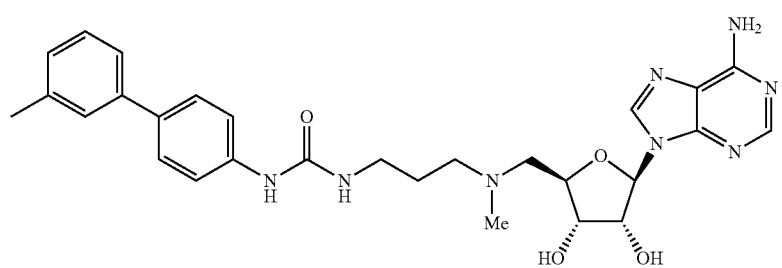

199

Step 1.

To a solution of 4-bromoaniline (1.50 g, 8.72 mmol) in 1,4-dioxane (50 mL) m-tolylboronic acid (1.42 g, 10.46 mmol), Pd(dppf)$_2$Cl$_2$ (100 mg) and K$_2$CO$_3$ (1.80 g, 13.08 mmol) were added. The mixture was heated to 90° C. for 4 h. After cooling, the mixture was filtered. Then saturated aqueous NaHCO$_3$ (20 mL) was added to the filtrate and the resultant solution was extracted with EtOAc (100 mL×3). The combined organic layers were dried over Na$_2$SO$_4$, concentrated and purified by SGC (DCM:PE=1:3) to give 196 (300 mg, yield: 19%). LC-MS (m/z): 184.1 [M+1]$^+$.

Step 2.

To a solution of triphosgene (291 mg, 0.98 mmol) in DCM (5 mL), a mixture of 196 (300 mg, 1.639 mmol) and Et$_3$N (116 mg, 1.64 mmol) in DCM (5 mL) was added slowly at 0° C. The mixture was stirred at room temperature for 1 h and used to next step directly.

Step 3.

To a solution of the crude 197 (750 mg crude) in DCM (10 mL) was added N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (160 mg, 0.42 mmol) and DIPEA (60 mg, 0.42 mmol). The mixture was stirred at room temperature overnight, Then water (20 mL) was added to the solution and the mixture was extracted with DCM (50 mL×3). The combined organic layers were dried over Na$_2$SO$_4$ and concentrated. The crude was purified by prep-TLC (DCM:MeOH=15:1) to afford 198 (100 mg, yield: 40%) as a white solid. LC-MS (m/z): 587.3 [M+1]$^+$.

Step 4.

A solution of 198 (70 mg, 0.12 mmol) in 90% TFA (1 mL) was stirred at room temperature for 30 min and concentrated. Basic resin (300 mg) and MeOH (5 mL) were added. The mixture was stirred at room temperature for another 30 min. The mixture was filtrated, concentrated, and purified by pre-TLC (DCM:MeOH:25% NH$_3$.H$_2$O=10:1:0.1) to give 199 (28 mg, yield: 43%). LC-MS (m/z): 547.3 [M+1]$^+$.

Preparation of Compound 201

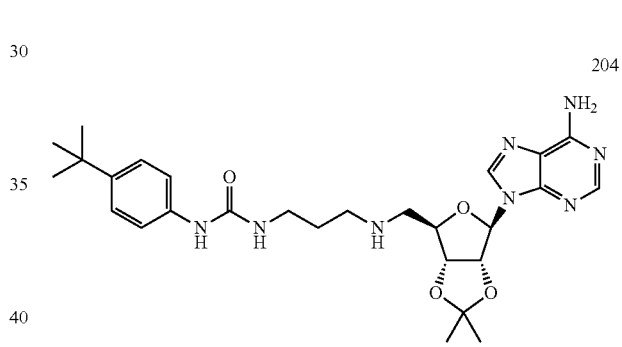

204

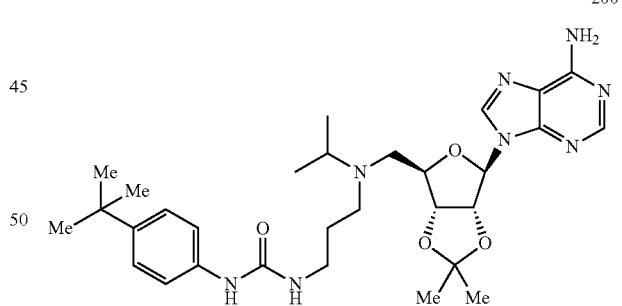

200

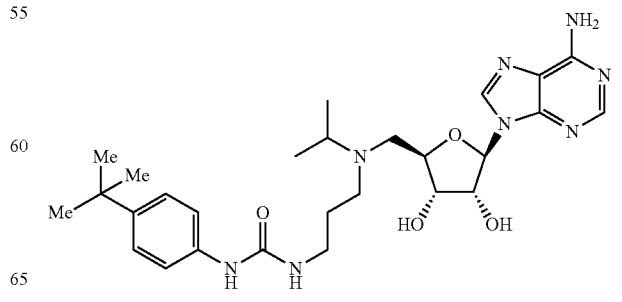

201

Step 1.

A mixture of 204 (100 mg, 0.18 mmol), propanone (4 mL), HOAc (30 mg, 0.41 mmol) and 4 Å sieves (150 mg) in THF:MeOH (4:1; 3 mL) was stirred at room temperature for 6 h. NaCNBH$_3$ (324 mg, 1.67 mmol) was added and the reaction was stirred at room temperature overnight. The reaction was quenched with sat. NaHCO$_3$ (2 mL), filtered, extracted with DCM (10 mL×3), washed with brine (10 mL), dried and concentrated. The residue was purified by SGC (DCM:MeOH=10:1) to afford 200 (75 mg, Yield 70%). ESI-MS (m/z): 581.3[M+1]$^+$.

Step 2.

A solution of 200 (100 mg, 0.172 mmol) in TFA (0.90 mL) and 0.10 mL of water was stirred at room temperature for 1.5 h. The reaction was concentrated to dryness, dissolved in MeOH (5 mL) and neutralized by basic resin (180 mg) at room temperature for 1 h. The mixture was filtered, washed with MeOH (2 mL×3) and concentrated. The residue was purified by prep-TLC to afford 201 (88 mg, Yield: 89%) as a pale white solid. $^1$H NMR (500 MHz, MeOD): δ 8.20 (s, 2H), 7.26 (d, J=8.5 Hz, 2H), 7.21 (d, J=7.5 Hz, 2H), 5.97 (d, J=4.5 Hz, 1H), 4.76-4.74 (m, 1H), 4.42 (t, J=7.5 Hz, 1H), 4.31-4.28 (m, 1H), 3.46 (br s, 1H), 3.27-3.21 (m, 4H), 2.95 (br s, 2H), 1.82-1.80 (m, 2H), 1.28 (s, 9H), 1.24 (t, J=8.5 Hz, 3H), 1.18 (t, J=86 Hz, 3H) ppm; ESI-MS (m/z): 541.3 [M+1]$^+$.

Preparation of Compound 206

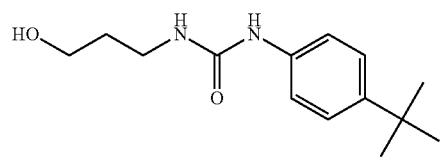

202

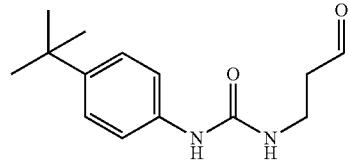

203

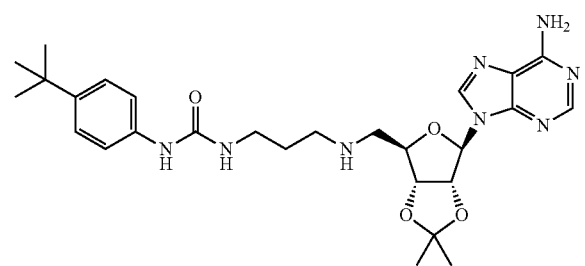

204

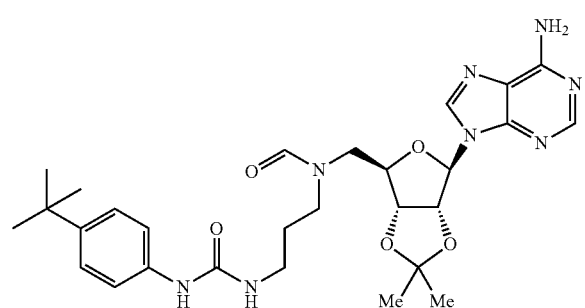

205

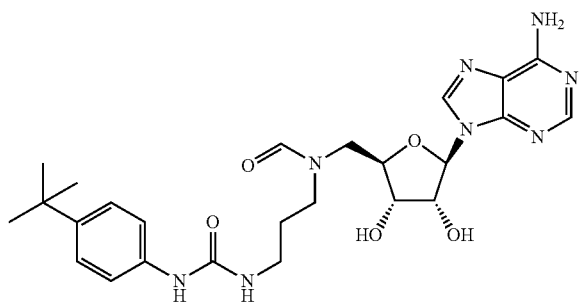

206

Step 1.

To a solution of triphosgene (3 g, 10.6 mmol) in DCM (40 mL) at 0° C. was added dropwise a solution of 4-(tert-butyl) aniline (4.5 g, 30.2 mmol) and TEA (9.15 g, 90.6 mmol) in DCM (30 mL). The resulting mixture was stirred at 0° C. for 10 min, then 3-aminopropan-1-ol (4.53 g, 60.4 mmol) was added in one portion. The mixture was stirred at 0° C. for another 30 min, then water (50 mL) was added to quench the reaction. The reaction mixture was extracted with DCM (60 mL×3). The combined organic layers were washed with brine (50 mL×2), dried over Na$_2$SO$_4$ and concentrated. The residue was purified by SGC (PE:EtOAc=1:5) to afford 202 (6.1 g, yield: 80%) as a white solid. ESI-MS (m/z): 251.0 [M+1]$^+$.

Step 2.

A mixture of 202 (600 mg, 2.4 mmol) and IBX (1.34 g, 4.8 mmol) in EtOAc (50 mL) was refluxed for 2 h. The mixture was filtered and filtrate was concentrated to afford the 203 (590 mg, crude) as yellow oil, which was used for next step directly.

Step 3.

To a solution of 9-((3aR,4R,6R,6aR)-6-(aminomethyl)-2,2-dimethyltetrahydrofuro[3,4-d][1,3]dioxol-4-yl)-9H-purin-6-amine (700 mg, 2.29 mmol) and 203 (590 mg) in DCE (50 mL) was added NaBH(OAc)$_3$ (630 mg, 2.97 mmol) slowly. The mixture was stirred at room temperature overnight, then saturated aqueous NaHCO$_3$ was added to quench the reaction. The resulting mixture was extracted with DCM (20 mL×3). The combined organic layers were washed with brine (30 mL×2), dried over Na$_2$SO$_4$ and concentrated. The residue was purified by SGC (MeOH:DCM=1:12) to afford 204 (400 mg, yield: 33%) as white solid. ESI-MS (m/z): 539.0 [M+1]$^+$.

Step 4.

To a solution of HCO$_2$H (12 mg, 0.25 mmol) and EDCI (266 mg, 1.4 mmol) in DCM (3 mL) was added 204 (150 mg, 0.28 mmol). The mixture was stirred at room temperature overnight. Brine (10 mL) was added and the mixture was extracted with DCM (15 mL×3). The combined organic phase was dried over Na$_2$SO$_4$ and concentrated. The residue was purified by SGC (DCM:MeOH=12:1) to afford 205 (30 mg, Yield: 19%) as a white solid. ESI-MS (m/z): 566.0 [M+1]$^+$.

Step 5.

A solution of 205 (55 mg, 0.086 mmol) in 90% TFA (1 mL) was stirred at room temperature for 1 h and then evaporated to dryness. The residue was co-evaporated with methanol. Then the residue was dissolved in 10 mL MeOH, K$_2$CO$_3$ (55 mg, 0.40 mmol) was added. Water was added dropwise until all K$_2$CO$_3$ dissolved. The reaction was stirred at room temperature for 1.5 h, then concentrated to remove MeOH and water. The residue was purified by prep-TLC (DCM:MeOH=5:1) give 206 (20 mg, yield 38%) ESI-MS (m/z): 527.2 [M+1]$^+$.

Preparation of Compound 209

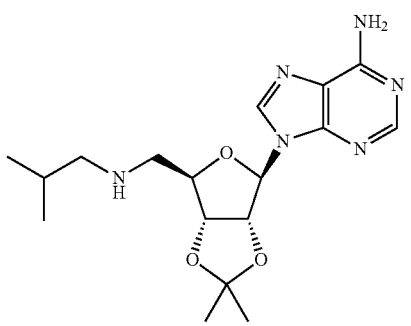

207

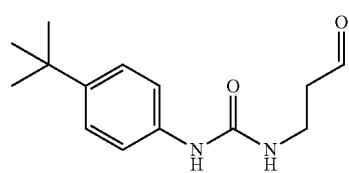

203

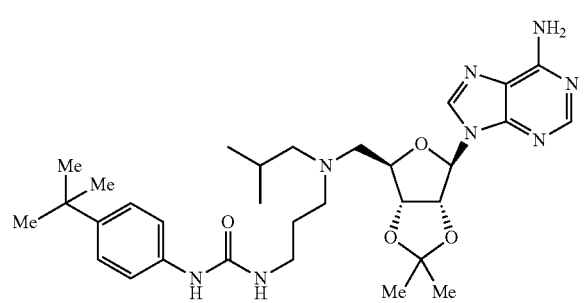

208

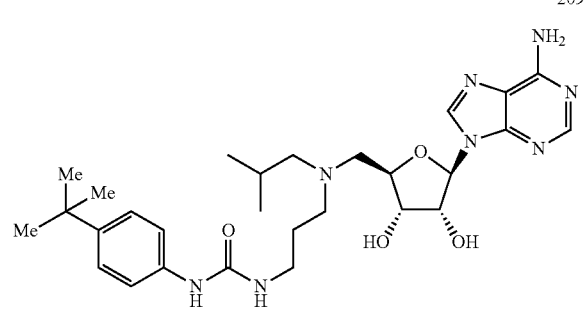

209

Step 1.

A mixture of ((3aR,4R,6R,6aR)-6-(6-amino-9H-purin-9-yl)-2,2-dimethyltetrahydrofuro[3,4-d][1,3]dioxol-4-yl)methyl 4-methylbenzenesulfonate (1.0 g) and 2-methylpropan-1-amine (15 mL) was stirred at room temperature overnight. The solvent was removed and the residue was purified by SGC (DCM:CH$_3$OH=20:1) afford 207 (230 mg, yield: 30%) as pale oil. LC-MS (ESI): m/z 263.7 [M+1]$^+$.

Step 2.

To a stirred solution of 207 (230 mg, 0.635 mmol) and 203 (357 mg, 1.44 mmol) in 30 mL of DCE was added NaBH(OAc)$_3$ (405 mg, 1.91 mmol). Then the mixture was stirred at room temperature overnight. NaHCO$_3$ (aq, 15 mL) was added to quench the reaction and the mixture was extracted with DCM (20 mL×4). The organic phase was concentrated and the residue was purified by prep-TLC(CH$_3$OH:DCM=1:14) to afford 208 [i: 2 mg (pure); ii: 180 mg (impure); yield: about 20%)] as a pale solid. LC-MS (ESI): m/z 595.7 [M+1]$^+$.

Step 3.

To a mixture of TFA (0.9 mL) and water (0.1 mL) was added 208 (180 mg, 0.303 mmol). The solution was stirred at room temperature for 1 h and evaporated to dryness. The residue was co-evaporated with methanol (2 mL) twice and dissolved in MeOH (10 mL). The solution was neutralized by basic resin (600 mg) with stirring for 1 h. After filtration, the filtrate was concentrated and the residue was purified by prep-HPLC to afford 209 (18 mg, yield 30%) as a pale solid. $^1$H NMR (500 MHz, MeOD): δ 8.24 (s, 1H), 8.17 (s, 1H), 7.25 (d, J=9.0 Hz, 2H), 7.19 (d, J=8.5 Hz, 2H), 5.97 (d, J=5.0 Hz, 1H), 4.77 (t, J=5.0 Hz, 1H), 4.19-4.27 (m, 2H), 3.17-3.24 (m, 2H), 2.72-2.77 (m, 2H), 2.53-2.59 (m, 2H), 2.22 (d, J=7.0 Hz, 2H), 1.66-1.77 (m, 3H), 1.28 (d, J=3.5 Hz, 9H), 0.90 (d, J=7.0 Hz, 3H), 0.85 (d, J=3.5 Hz, 3H) ppm. MS (ESI): m/z 555.7 [M+1]$^+$.

Preparation of Compound 213

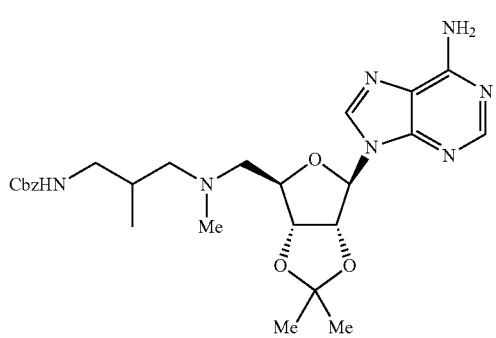

220

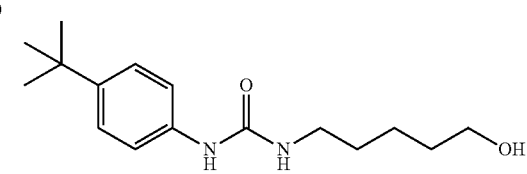

210

211

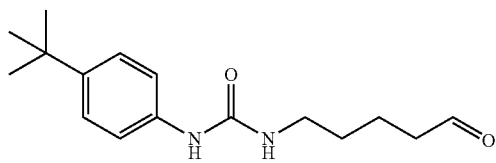

212

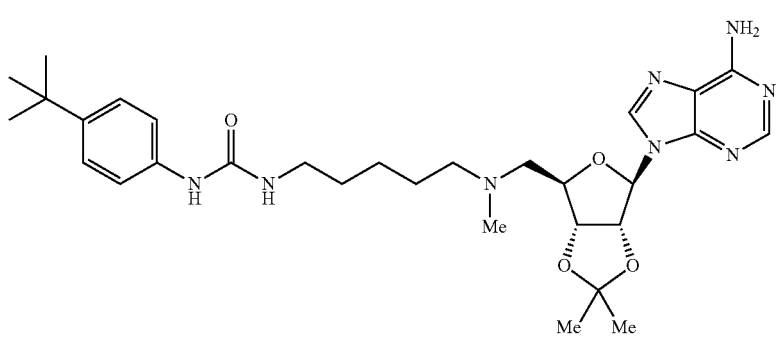

213

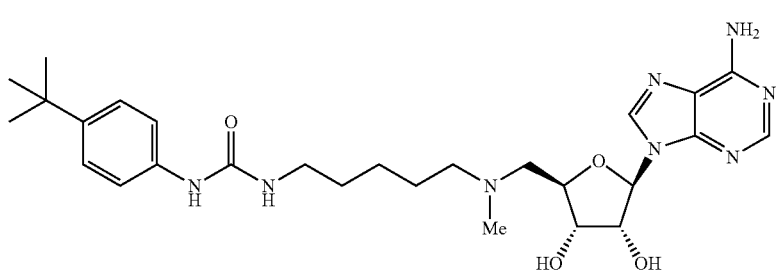

Step 1.

A solution of 220 (525 mg, 3.0 mmol) and 5-aminopentan-1-ol (309 mg, 3.0 mmol) and DIPEA (1.16 g, 9.0 mmol) in dry DCM (10 mL) was stirred at room temperature overnight, MeOH (2 mL) was added and concentrated to give crude product. The crude was purified by SGC (PE:EtOAc=5:1→1:1→pure EA) to afford 210 (700 mg, yield: 84%) as a white solid. LC-MS (m/z): 279.7 [M+1]$^+$.

Step 2.

A mixture of 210 (300 mg, 1.08 mmol) and IBX (906 mg, 3.24 mmol) in EtOAc (10 mL) was refluxed for 1 h. After the solid was filtered and washed with EtOAc (10 mL×2), the combined organic layers were concentrated to afford 211 (370 mg, crude) as yellowish oil, which was used directly for next step. LC-MS (m/z): 277.7 [M+1]$^+$.

Step 3.

To a solution of 9-((3aR,4R,6R,6aR)-2,2-dimethyl-6-((methylamino)methyl)-tetrahydrofuro[3,4-d][1,3]dioxol-4-yl)-9H-purin-6-amine (214 mg, 0.67 mmol) and 211 (370 mg, crude) in DCE (10 mL) was added NaBH(OAc)$_3$ (427 mg, 2.01 mmol). The mixture was stirred at room temperature overnight, Saturated aqueous NaHCO$_3$ (15 mL) was added to the solution. The mixture was extracted with DCM (20 mL×2). The combined organic layers were washed with brine and dried over Na$_2$SO$_4$ and concentrated. The crude was purified by prep-TLC (DCM:MeOH=9:1) to afford 212 (65 mg, yield: 17%) as a white solid. LC-MS (m/z): 581.7 [M+1]$^+$.

Step 4.

A solution of 212 (65 mg, 0.11 mmol) in 90% TFA (1.5 mL) was stirred at room temperature for 1 h, then it was concentrated. The residue was dissolved in MeOH (5 mL) followed by addition of K$_2$CO$_3$ (42 mg, 0.33 mmol). The mixture was stirred at room temperature for 1 h, filtered and concentrated to give crude product. The crude was purified by prep-TLC (DCM:MeOH=1:1.5) to afford 213 (40 mg, yield: 62%) as a white solid. LC-MS (m/z): 541.7 [M+1]$^+$.

Preparation of Compound 223

217

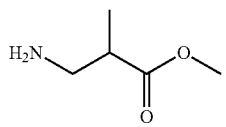

218

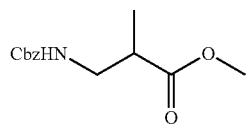

219

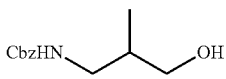

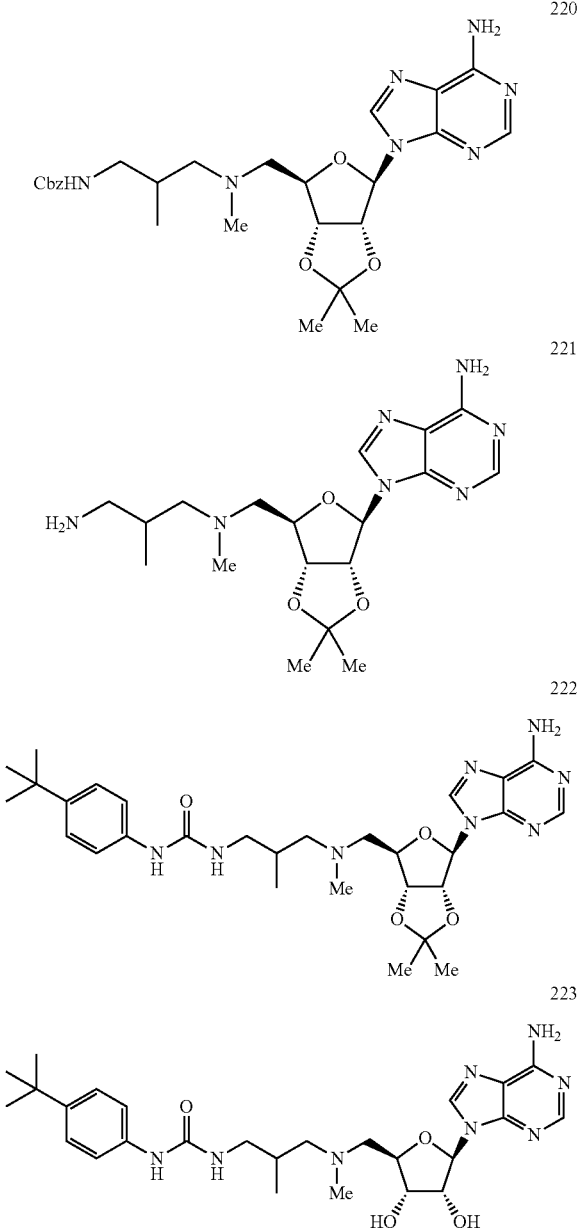

Step 1.

To a solution of 3-amino-2-methylpropanoic acid (1 g, 10 mmol) in MeOH (dry, 10 mL) at 0° C. was added SOCl$_2$ (2.36 g, 20 mmol) slowly. And then the resulting reaction mixture was stirred at room temperature overnight. Solvent was removed in vacuo to afford 217 (1.53 g, yield: 99%) as a straw yellow solid, which was used for next step without further purification.

Step 2.

To a solution of 217 (1.52 g, 10 mmol) and TEA (3.23 g, 32 mmol) in DCM (20 mL) at 0° C. was added CbzCl (2.04 g, 12 mmol) slowly. And then the resulting reaction mixture was stirred at room temperature overnight. The reaction was diluted with DCM (30 mL), then washed with water (20 mL) and brine (20 mL). The organic phase was dried over Na$_2$SO$_4$ and concentrated. The residue was purified by SGC (PE: EtOAc=8:1 to 5:1) to afford 218 (1.31 g, yield: 52%) as a colorless oil. ESI-MS (m/z): 252.2 [M+1]$^+$.

Step 3.

To a solution of 218 (1.26 g, 5 mmol) in THF (dry, 15 mL) at 0° C. was added a solution of LiBH$_4$ (88 mg, 20 mmol) in THF (dry, 5 mL) slowly. And then the resulting reaction mixture was stirred at room temperature overnight. Water (60 mL) was added to quench the reaction, then extracted with EtOAc (50 mL×3), the combined organic layer was washed with brine (30 mL), dried over Na$_2$SO$_4$ and concentrated to afford 219 (1.15 g, yield: 98%) as a colorless oil. ESI-MS (m/z): 224.1 [M+1]$^+$.

Step 4.

Compound 219 (1 g, 4.48 mmol) and IBX (3.76 g, 13.44 mmol) were dissolved in EtOAc (40 mL), and the reaction mixture was heated to reflux for 3 h. And then the mixture was filtered and the solid was rinsed with EtOAc (25 mL×3). The combined filtrate was concentrated to afford benzyl (2-methyl-3-oxopropyl)carbamate (1.02 g, crude) as a colorless oil. This was combined with 9-((3aR,4R,6R,6aR)-2,2-dimethyl-6-((methylamino)methyl)tetrahydrofuro[3,4-d][1,3]dioxol-4-yl)-9H-purin-6-amine (1.14 g, 3.46 mmol) in DCE (60 mL), and to this was added NaB(OAc)$_3$H (1.5 g, 7 mmol) in one portion. Then the resulting reaction mixture was stirred at room temperature overnight. Then saturated aqueous NaHCO$_3$ (50 mL) was added to quench the reaction. The reaction mixture was extracted with DCM (60 mL×3), dried over anhydrous Na$_2$SO$_4$ and concentrated. The residue was purified by SGC (DCM:MeOH=60:1 to 40:1) to afford 220 (1.6 g, yield: 81%) as a white solid (containing two diastereomers, ~1:1 by NMR). ESI-MS (m/z): 526.3 [M+1]$^+$.

Step 5.

Compound 220 (1.4 g, 3.05 mmol) was dissolved in MeOH (45 mL), 20% Pd(OH)$_2$/C (450 mg) was added and the resultant mixture was stirred under 1 atm H$_2$ atmosphere overnight. The mixture was then filtered and the solid rinsed with MeOH (20 mL×3). The combined filtrate was evaporated in vacuo to afford 221 (970 mg, yield: 93%) as a white solid, which was used for next step without further purification. The sample contains two diastereomers (nearly 1:1 from NMR). ESI-MS (m/z): 392.3 [M+1]$^+$.

Step 6.

To a solution of 221 (470 mg, 1.2 mmol) and TEA (162 mg, 1.6 mmol) in DCM (dry, 10 mL) at 0° C. was added a solution of 1-tert-butyl-4-isocyanatobenzene (280 mg, 1.6 mmol) in DCM (dry, 1 mL) dropwise. And then the resulting reaction mixture was stirred at room temperature overnight. Water (10 mL) was added to quench the reaction, then extracted with DCM (20 mL×3). The combined organic layer was washed with brine (10 mL), dried over Na$_2$SO$_4$, and then concentrated. The residue was purified by SGC (DCM:MeOH=60:1 to 30:1) to afford 222 (575 mg, yield: 85%) as a white solid. This sample contains two diastereomers (nearly 1:1 from NMR). NMR (500 MHz, MeOD): LC-MS (m/z): 567.3 [M+1]$^+$.

Step 7.

To a mixture of TFA (1.8 mL) and water (0.2 mL) was added 222 (100 mg, 0.177 mmol). The solution was allowed to stand at room temperature for 3 h and evaporated to dryness. The residue was co-evaporated with methanol twice. Then the residue was dissolved in MeOH (8 mL). The solution was neutralized by K$_2$CO$_3$ (146 mg, dissolved in 2 mL of H$_2$O) with stirring at room temperature for 1 h. Solvent was removed in vacuo, then the crude was purified by prep-TLC (DCM:MeOH:NH$_3$.H$_2$O=180:20:2) to afford 223 (68 mg, yield: 73%) as a white solid. This sample contains two diastereomers (~1:1 by NMR). LC-MS (m/z): 527.3 [M+1]+.

Compound 300

1-[(1S)-3-[[(2R,3S,4R,5R)-5-(6-aminopurin-9-yl)-3,4-dihydroxy-tetrahydrofuran-2-yl]methyl-methylamino]-1-methyl-propyl]-3-(4-tert-butylphenyl)urea

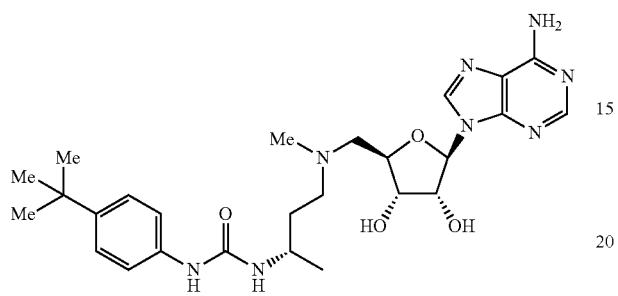

Step 1. Preparation of tert-butyl (3S)-3-[(4-tert-butylphenyl)carbamoylamino]butanoate

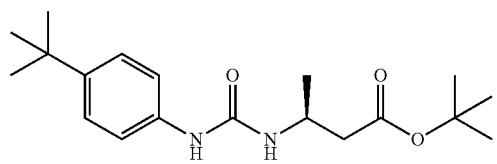 [SMILES: C[C@@H](CC(=O)OC(C)(C)C)NC(=O)Nc1ccc(C(C)(C)C)cc1]

To a stirred solution of tert-butyl (3S)-3-aminobutanoate (250 mg, 1.57 mmol) and DIPEA (405 mg, 3.14 mmol) in dry DCM (5 mL) was added 4-tert-butylbenzenamine (302 mg, 1.73 mmol) dropwise at 0° C. The reaction mixture was stirred at rt overnight, then extracted with DCM (10 mL×2), dried over Na$_2$SO$_4$ and concentrated to give crude product. The crude was purified by Prep TLC (PE:EA=3.5:1) to afford the pure tert-butyl (3S)-3-[(4-tertbutylphenyl) carbamoylamino]butanoate (430 mg, yield: 82%) as a white solid. $^1$H NMR (500 MHz, CDCl$_3$): δ7.32-7.30 (m, 2H), 7.21-7.19 (m, 2H), 4.26-4.22 (m, 2H), 2.49-2.39 (m, 2H), 1.41 (s, 9H), 1.29 (s, 9H), 1.23 (d, J=6.5 Hz, 3H) ppm; ESI-MS (m/z): 335.7 [M+1]+.

Step 2. Preparation of 1-(4-tert-butylphenyl)-3-[(1S)-3-hydroxy-1-methyl-propyl]urea

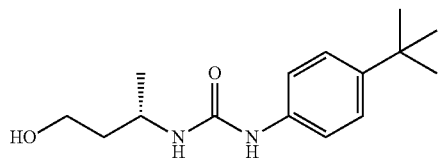 [SMILES: C[C@@H](CCO)NC(=O)Nc1ccc(C(C)(C)C)cc1]

A mixture of tert-butyl (3S)-3-[(4-tert-butylphenyl)carbamoylamino]butanoate (430 mg, 1.29 mmol) and LiBH$_4$ (124 mg, 5.15 mmol) in dry THF (5 mL) was stirred at RT overnight then extracted with EtOAc (20 mL×2), washed with brine, dried with Na$_2$SO$_4$ and concentrated to afford 1-(4-tert-butylphenyl)-3-[(1S)-3-hydroxy-1-methyl-propyl]urea (306 mg, yield 90%) without further purification. $^1$H NMR (500 MHz, CDCl$_3$): δ7.35 (t, J=8.5 Hz, 2H), 7.17 (t, J=8.5 Hz, 2H), 4.66-4.62 (m, 1H), 4.15-4.11 (m, 1H), 3.68-3.64 (m, 2H), 1.96-1.81 (m, 1H), 1.30 (s, 9H), 1.21-1.17 (m, 3H) ppm; ESI-MS (m/z): 265.7 [M+1]+.

Step 3. Preparation of 1-[(1S)-3-[[(3aR,4R,6R,6aR)-4-(6-aminopurin-9-yl)-2,2-dimethyl-3a,4,6,6a-tetrahydrofuro[3,4-d][1,3]dioxol-6-yl]methyl-methylamino]-1-methyl-propyl]-3-(4-tert-butylphenyl)urea A mixture of 1-(4-tert-butylphenyl)-3-[(1S)-3-hydroxy-1-methyl-propyl]urea (180 mg, 0.68 mmol) and IBX (572 mg, 2.04 mmol) in EA (10 mL) was refluxed for 2 h. After the solid was filtered and washed with EA (10 mL×2), the combined organic layers were concentrated to afford 1-(4-tert-butylphenyl)-3-[(1S)-1-methyl-3-oxo-propyl]urea (180 mg, crude) without further purification.

A solution of 9-[(3aR,4R,6R)-2,2-dimethyl-4-(methylaminomethyl)-3a,4,6,6a-tetrahydrofuro[3,4-d][1,3]dioxol-6-yl]purin-6-amine (140 mg, 0.44 mmol) and 1-(4-tert-butylphenyl)-3-[(1S)-1-methyl-3-oxo-propyl]urea (180 mg, crude) in DCE (5 mL) was added NaB(OAc)$_3$H (139 mg, 0.66 mmol). The mixture was stirred at rt overnight. Then saturated aqueous NaHCO$_3$ (10 mL) was added to the solution. The mixture was extracted with DCM (20 mL×2). The combined organic layers were washed with brine and dried over Na$_2$SO$_4$ and concentrated. The crude was purified by Prep TLC (DCM:MeOH=10:1) to afford the pure 1-[(1S)-3-[[(3aR,4R,6R,6aR)-4-(6-aminopurin-9-yl)-2,2-dimethyl-3a,4,6,6a-tetrahydrofuro[3,4-d][1,3]dioxol-6-yl]methyl-methyl-amino]-1-methyl-propyl]-3-(4-tert-butylphenyl)urea (25 mg, yield: 15%) as white solid. $^1$H NMR (500 MHz, MeOD): δ8.25-8.22 (m, 2H), 7.29-7.21 (m, 4H), 6.17 (d, J=2.0 Hz, 1H), 5.49-5.48 (m, 1H), 5.04-5.02 (m, 1H), 4.43-4.39 (m, 1H), 3.68-3.62 (m, 2H), 2.69-2.68 (m, 1H), 2.53-2.49 (m, 2H), 2.28 (s, 3H), 1.71 (s, 3H), 1.64-1.49 (m, 2H), 1.36 (s, 3H), 1.29 (s, 12H), 1.09 (d, J=7.0 Hz, 3H) ppm; ESI-MS (m/z): 567.7 [M+1]+.

Step 5. Preparation of 1-[(1S)-3-[[(2R,3S,4R,5R)-5-(6-aminopurin-9-yl)-3,4-dihydroxy-tetrahydrofuran-2-yl]methyl-methyl-amino]-1-methyl-propyl]-3-(4-tert-butylphenyl)urea

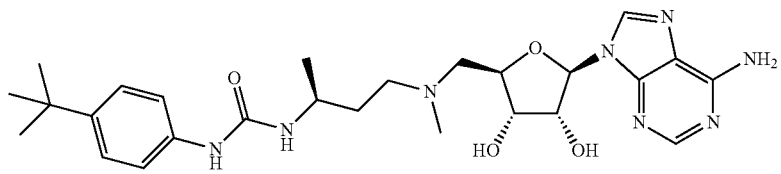 [SMILES: C[C@@H](CCN(C)C[C@H]1O[C@@H](n2cnc3c(N)ncnc32)[C@H](O)[C@@H]1O)NC(=O)Nc1ccc(C(C)(C)C)cc1]

A solution of 1-[(1S)-3-[[(3aR,4R,6R,6aR)-4-(6-aminopurin-9-yl)-2,2-dimethyl-3a,4,6,6a-tetrahydrofuro[3,4-d][1,3]dioxol-6-yl]methyl-methyl-amino]-1-methyl-propyl]-3-(4-tert-butylphenyl)urea (25 mg, 0.044 mmol) in 90% TFA (1.5 mL) was stirred at rt for 2 h, then concentrated as a solid to remove TFA, dissolved in MeOH (5 mL) and H$_2$O (1 mL), K$_2$CO$_3$ (24 mg, 0.176 mmol) was added and stirred at rt for 0.5 h then filtered and the filtrate was concentrated to give crude product. The crude was purified by Prep TLC (DCM: MeOH=5:1) to afford the 1-[(1S)-3-[[(2R,3S,4R,5R)-5-(6-aminopurin-9-yl)-3,4-dihydroxy-tetrahydrofuran-2-yl]methyl-methyl-amino]-1-methyl-propyl]-3-(4-tert-butylphenyl)urea (15 mg, yield: 65%) as a white solid. $^1$H NMR (500 MHz, MeOD): S 8.23 (s, 1H), 8.20 (s, 1H), 7.28-7.21 (m, 4H), 6.02 (d, J=4.5 Hz, 1H), 4.85 (m, 1H), 4.48-4.46 (m, 1H), 4.40-4.38 (m, 1H), 3.78-3.73 (m, 2H), 3.50-3.43 (m, 1H), 3.23-3.17 (m, 2H), 2.90 (s, 3H), 2.88 (s, 3H), 1.96-1.90 (m, 1H), 1.78-1.74 (m, 1H), 1.28 (s, 9H), 1.15 (d, J=6.5 Hz, 3H) ppm; ESI-MS (m/z): 527.7 [M+1]$^+$.

Compound 301

1-((R)-1-((((2R,3S,4R,5R)-5-(6-amino-9H-purin-9-yl)-3,4-dihydroxytetrahydrofuran-2-yl)methyl)(methyl)amino)pentan-3-yl)-3-(4-(tert-butyl)phenyl)urea

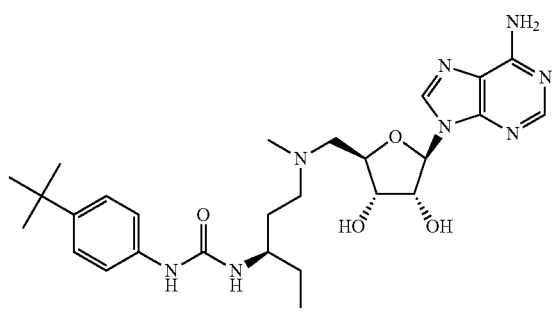 [SMILES: CC[C@H](CCN(C)C[C@H]1O[C@@H](n2cnc3c(N)ncnc32)[C@H](O)[C@@H]1O)NC(=O)Nc1ccc(C(C)(C)C)cc1]

(R)-methyl 3-aminopentanoate hydrochloride

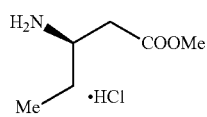

SOCl$_2$ (1 mL) was added to MeOH (10 mL) at −10° C. and the solution was stirred for 1 h, upon which (R)-3-aminopentanoic acid (200 mg, 1.70 mmol) was added in one portion and the mixture was stirred at rt for 15 h. The reaction was concentrated to obtain the title compound (280 mg, yield: 98%) as a light yellow oil. $^1$H NMR (500 MHz, DMSO) δ 8.16 (s, 3H), 3.64 (s, 3H), 2.67 (d, J=4.0 Hz, 2H), 1.62-1.59 (m, 2H), 0.90 (s, 3H) ppm.

(R)-methyl 3-(3-(4-(tert-butyl)phenyl)ureido)pentanoate

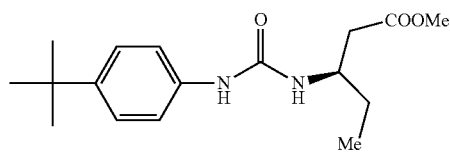 [SMILES: CC[C@H](CC(=O)OC)NC(=O)Nc1ccc(C(C)(C)C)cc1]

To a solution of (R)-methyl 3-aminopentanoate hydrochloride (280 mg, 1.67 mmol) in DCM (10 mL) was added TEA (507 mg, 5.01 mmol) at 0° C. and the solution was stirred at 0° C. for 1 h. 1-tert-Butyl-4-isocyanatobenzene (293 mg, 1.67 mmol) was added and the mixture was stirred at rt for 15 h. The solution was concentrated and purified by Prep-TLC (DCM:MeOH=30:1) to obtain the title compound (370 mg, yield: 73%) as a light yellow oil. $^1$H NMR (500 MHz, MeOD): δ 7.30-7.23 (m, 4H), 4.02-4.01 (m, 1H), 3.67 (s, 3H), 2.57-2.50 (m, 2H), 1.62-1.53 (m, 2H), 1.28 (s, 9H), 0.96 (t, J=7.5 Hz, 3H) ppm; ESI-MS (m/z): 307.3 [M+1]$^+$.

3 Preparation of M-418-3(R)

(R)-1-(4-(tert-butyl)phenyl)-3-(1-hydroxypentan-3-yl)urea

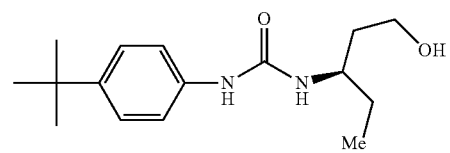 [SMILES: CC[C@H](CCO)NC(=O)Nc1ccc(C(C)(C)C)cc1]

To a solution of (R)-methyl 3-(3-(4-(tert-butyl)phenyl)ureido)pentanoate (200 mg, 0.65 mmol) in THF (dry, 7 mL) was added LiBH$_4$ (57 mg, 2.61 mmol) and the solution was stirred at 0° C. for 1 h. Then, the mixture was stirred at rt for 15 h. Water (2 mL) was added to quench the reaction and the mixture was extracted with DCM (20 mL×4). The combined organic phase was washed with brine (5 mL×1), dried over anhydrous Na$_2$SO$_4$ and concentrated to obtain the title compound (160 mg, yield: 89%) as a white solid. $^1$H NMR (500 MHz, MeOD): δ 7.30-7.23 (m, 4H), 3.77-3.74 (m, 1H), 3.66-3.62 (m, 2H), 1.79-1.76 (m, 1H), 1.62-1.55 (m, 2H), 1.50-1.45 (m, 1H), 1.29 (s, 9H), 0.96 (t, J=7.5 Hz, 3H) ppm; ESI-MS (m/z): 279.3 [M+1]$^+$.

(R)-1-(4-(tert-butyl)phenyl)-3-(1-oxopentan-3-yl) urea

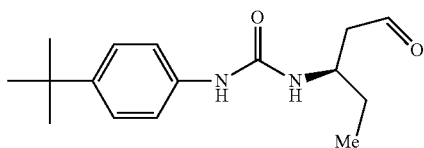 [SMILES: CC[C@H](CC=O)NC(=O)Nc1ccc(C(C)(C)C)cc1]

To a solution of (R)-1-(4-(tert-butyl)phenyl)-3-(1-hydroxypentan-3-yl)urea (160 mg, 0.57 mmol) in EtOAc (10 mL) were added IBX (402 mg, 1.44 mmol) and the mixture was refluxed for 1.5 h under an atmosphere of N$_2$. The mixture was filtered and the filtrate was concentrated to obtain the title compound (158 mg, yield: 99%) as a light yellow solid. The crude was used to the next step without further purification. ESI-MS (m/z): 277.3 [M+1]$^+$.

1-((R)-1-(((3aR,4R,6R,6aR)-6-(6-amino-9H-purin-9-yl)-2,2-dimethyltetrahydrofuro[3,4-d][1,3]dioxol-4-yl)methyl)(methyl)amino)pentan-3-yl)-3-(4-(tert-butyl)phenyl)urea

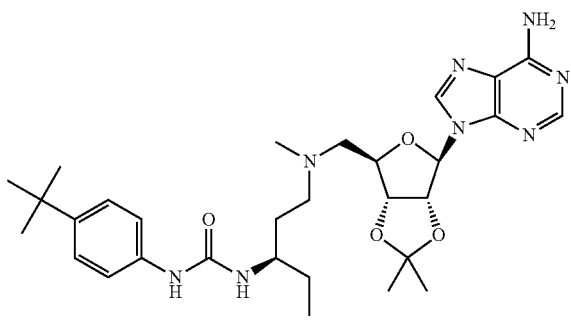 [SMILES: CC[C@H](CCN(C)C[C@H]1O[C@@H](n2cnc3c(N)ncnc32)[C@@H]2OC(C)(C)O[C@@H]21)NC(=O)Nc1ccc(C(C)(C)C)cc1]

A mixture of (R)-1-(4-(tert-butyl)phenyl)-3-(1-oxopentan-3-yl)urea (158 mg, 0.57 mmol) and 9-((3aR,4R,6R,6aR)-2,2-dimethyl-6-((methylamino)methyl)tetrahydrofuro[3,4-d][1,3]dioxol-4-yl)-9H-purin-6-amine (183 mg, 0.57 mmol) in DCE (8 mL) was stirred at rt for 0.5 h, upon which, NaBH(OAc)$_3$ (182 mg, 0.86 mmol) was added and the solution was stirred at rt for 15 h. The crude mixture was concentrated in vacuo and the residue was purified by Prep-TLC (DCM:MeOH=15:1) to obtain the title compound (80 mg, yield: 24%) as a light yellow solid. $^1$H NMR (500 MHz, MeOD): δ 8.31-8.30 (m, 2H), 7.37-7.30 (m, 4H), 6.25 (d, J=2.0 Hz, 1H), 5.55-5.53 (m, 1H), 5.10-5.07 (m, 1H), 4.51-4.48 (m, 1H), 3.67-3.63 (m, 1H), 2.99-2.96 (m, 1H), 2.89-2.85 (m, 1H), 2.64 (t, J=6.0 Hz, 2H), 2.41 (s, 3H), 1.71-1.66 (m, 1H), 1.64 (s, 3H), 1.55-1.51 (m, 1H), 1.47-1.40 (m, 2H), 1.43 (s, 3H), 1.36 (s, 9H), 0.97 (t, J=8.0 Hz, 3H) ppm; ESI-MS (m/z): 581.4 [M+1]$^+$.

R)-1-((((2R,3S,4R,5R)-5-(6-amino-9H-purin-9-yl)-3,4-dihydroxytetrahydrofuran-2-yl)methyl)(methyl) amino)pentan-3-yl)-3-(4-(tert-butyl)phenyl)urea

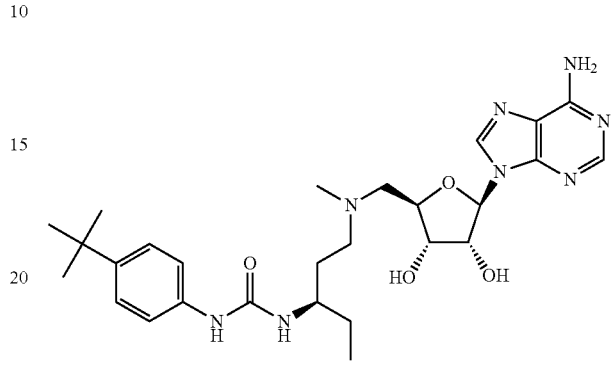

A solution of 1-((R)-1-(((3aR,4R,6R,6aR)-6-(6-amino-9H-purin-9-yl)-2,2-dimethyltetrahydrofuro[3,4-d][1,3]dioxol-4-yl)methyl)(methyl)amino)pentan-3-yl)-3-(4-(tert-butyl)phenyl)urea (80 mg, 0.14 mmol) in 2.5 M HCl/MeOH (5 mL) was stirred at 30° C. for 1.5 h and evaporated to dryness. The residue was co-evaporated with methanol twice. Then, the residue was dissolved in MeOH (5 mL). Saturated K$_2$CO$_3$ solution was added to adjust the solution to pH=8. Then, the mixture was stirred for 5 min and concentrated in vacuo. The residue was purified by Prep-TLC (DCM:MeOH=5:1) to obtain the title compound (52 mg, yield: 70%) as a light yellow solid. $^1$H NMR (500 MHz, MeOD): δ 8.14 (s, 1H), 8.11 (s, 1H), 7.19-7.12 (m, 4H), 5.89 (d, J=4.0 Hz, 1H), 4.661-4.643 (m, 1H), 4.20-4.18 (m, 2H), 3.56-3.53 (m, 1H), 3.00-2.90 (m, 2H), 2.70-2.65 (m, 2H), 2.37 (s, 3H), 1.72-1.70 (m, 1H), 1.50-1.41 (m, 2H), 1.36-1.31 (m, 1H), 1.15 (s, 9H), 0.82 (t, J=7.0 Hz, 3H) ppm; ESI-MS (m/z): 541.3 [M+1]$^+$.

Compound 302

1-(3-((((2R,3S,4R,5R)-5-(6-amino-9H-purin-9-yl)-3,4-dihydroxytetrahydrofuran-2-yl)methyl)(2,2,2-trifluoroethyl)amino)propyl)-3-(4-(tert-butyl)phenyl) urea

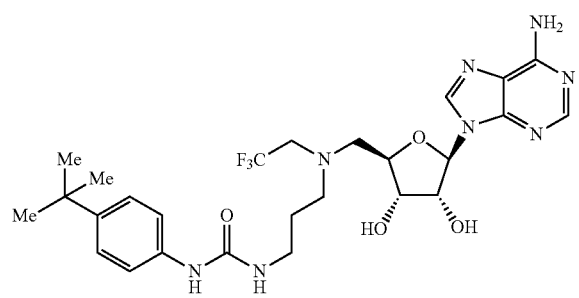 [SMILES: CC(C)(C)c1ccc(NC(=O)NCCCN(C[C@H]2O[C@@H](n3cnc4c(N)ncnc43)[C@H](O)[C@@H]2O)CC(F)(F)F)cc1]

Step 1. 9-((3aR,4R,6R,6aR)-2,2-dimethyl-6-(((2,2,2-trifluoroethyl)amino)methyl)tetrahydrofuro[3,4-d][1,3]dioxol-4-yl)-9H-purin-6-amine

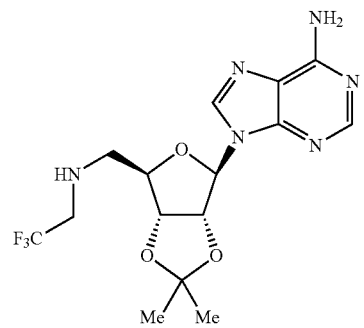 [SMILES: CC1(C)O[C@@H]2[C@H](O1)[C@@H](CNCC(F)(F)F)O[C@H]2n1cnc2c(N)ncnc21]

TEA (0.28 mL, 2.0 mmol) and 2,2,2-trifluoroethyl trifluoromethanesulfonate (465 mg, 2.0 mmol) were carefully added to a solution of 9-((3aR,4R,6R,6aR)-6-(aminomethyl)-2,2-dimethyltetrahydrofuro[3,4-d][1,3]dioxol-4-yl)-9H-purin-6-amine (306 mg, 1.0 mmol) in 8 mL of dry THF under $N_2$. The resultant mixture was stirred at rt overnight. Then the solvent was removed and 10 mL of water was added. The mixture was extracted with DCM (15 mL×3). The combined organic phases were dried over $Na_2SO_4$, filtered and concentrated to afford the title compound (332 mg, yield: 85%) as a white solid. $^1$H NMR (500 MHz, MeOD): δ8.28 (s, 1H), 8.20 (s, 1H), 6.13 (d, J=3.0 Hz, 1H), 5.45 (dd, J=3.0, 6.5 Hz, 1H), 5.02-5.04 (m, 1H), 4.30-4.33 (m, 1H), 3.17-3.22 (m, 2H), 2.91-3.01 (m, 2H), 1.61 (s, 3H), 1.38 (s, 3H) ppm. MS (ESI): m/z 389.7 [M+1]$^+$.

Step 2. 1-(3-((((3aR,4R,6R,6aR)-6-(6-amino-9H-purin-9-yl)-2,2-dimethyltetrahydrofuro[3,4-d][1,3]dioxol-4-yl)methyl)(2,2,2-trifluoroethyl)amino)propyl)-3-(4-(tert-butyl)phenyl)urea

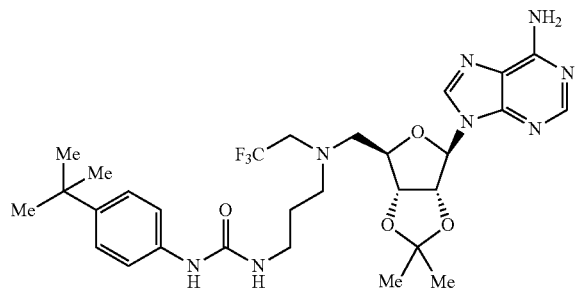 [SMILES: CC1(C)O[C@@H]2[C@H](O1)[C@@H](CN(CCCNC(=O)Nc1ccc(C(C)(C)C)cc1)CC(F)(F)F)O[C@H]2n1cnc2c(N)ncnc21]

To a stirred solution of 9-((3aR,4R,6R,6aR)-2,2-dimethyl-6-(((2,2,2-trifluoroethyl)amino)methyl)tetrahydrofuro[3,4-d][1,3]dioxol-4-yl)-9H-purin-6-amine (200 mg, 0.515 mmol) and 1-(4-(tert-butyl)phenyl)-3-(3-oxopropyl)urea (278 mg, 1.12 mmol) in 20 mL of DCE was added NaBH(OAc)$_3$ (328 mg, 1.55 mmol). Then the mixture was stirred at rt overnight. NaHCO$_3$ (aq) (20 mL) was added to quench the reaction and the mixture was extracted with DCM (15 mL×4). The organic phase was concentrated and the residue was purified by Prep-HPLC to afford the title compound (232 mg, yield: 73%) as a white solid. 1H NMR (500 MHz, MeOD): δ8.26 (s, 1H), 8.23 (s, 1H), 7.24-7.31 (m, 4H), 6.19 (d, J=2.0 Hz, 1H), 5.53-5.55 (m, 1H), 5.04-5.06 (m, 1H), 4.380-4.374 (m, 1H), 3.15-3.20 (m, 4H), 2.92-2.97 (m, 2H), 2.70 (t, J=7.0 Hz, 2H), 1.59-1.64 (m, 5H), 1.39 (s, 3H), 1.30 (s, 9H) ppm. MS (ESI): m/z 621.7 [M+1]$^+$.

Step 3. 1-(3-((((2R,3S,4R,5R)-5-(6-amino-9H-purin-9-yl)-3,4-dihydroxytetrahydrofuran-2-yl)methyl)(2,2,2-trifluoroethyl)amino)propyl)-3-(4-(tert-butyl)phenyl)urea

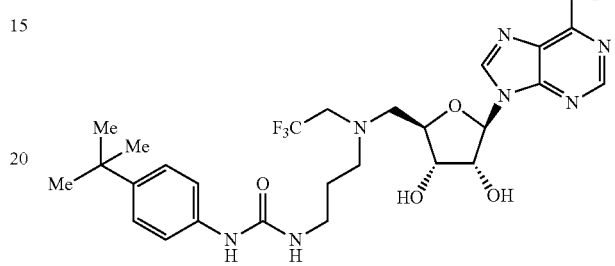

To a mixture of TFA (1.35 mL) and water (0.15 mL) was added 1-(3-((((3aR,4R,6R,6aR)-6-(6-amino-9H-purin-9-yl)-2,2-dimethyltetrahydrofuro[3,4-d][1,3]dioxol-4-yl)methyl)(2,2,2-trifluoroethyl)amino)propyl)-3-(4-(tert-butyl)phenyl)urea (200 mg, 0.515 mmol) and 1-(4-(tert-butyl)phenyl)-3-(3-oxopropyl)urea (150 mg, 0.242 mmol). The solution was stirred at rt for 1 h and evaporated to dryness. The residue was co-evaporated with methanol twice, then dissolved in MeOH (10 mL). The solution was neutralized by K$_2$CO$_3$ (100 mg, 0.725 mmol) in 1 mL of water with stirring for 1 h. Then the solvent was removed and the residue was purified by Prep-TLC (MeOH:DCM:NH$_4$OH=200 mL:25 mL:10 mL) to give the title compound (130 mg, yield 92%) as a white solid. 1H NMR (500 MHz, MeOD): δ 8.20 (s, 1H), 8.16 (s, 1H), 7.18-7.25 (m, 4H), 5.95 (d, J=4.5 Hz, 1H), 4.74-4.72 (m, 1H), 4.17-4.25 (m, 2H), 3.17-3.31 (m, 4H), 3.02-3.10 (m, 2H), 2.70-2.84 (m, 2H), 1.65-1.68 (m, 2H), 1.25 (s, 9H) ppm. MS (ESI): m/z 581.7 [M+1]$^+$.

Compound 303

1-(3-((((2R,3S,4R,5R)-5-(6-amino-9H-purin-9-yl)-3,4-dihydroxytetrahydrofuran-2-yl)methyl)(benzyl)amino)propyl)-3-(4-(tert-butyl)phenyl)urea

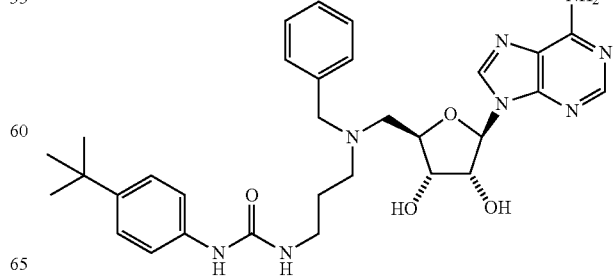

Step 1. 9-((3aR,4R,6R,6aR)-6-((benzylamino)methyl)-2,2-dimethyltetrahydrofuro[3,4-d][1,3]dioxol-4-yl)-9H-purin-6-amine

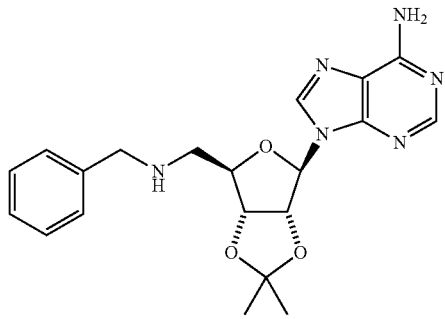

A solution of 9-((3aR,4R,6R,6aR)-6-(aminomethyl)-2,2-dimethyltetrahydrofuro[3,4-d][1,3]dioxol-4-yl)-9H-purin-6-amine (10.58 g, 34.56 mmol) and benzaldehyde (4.63 g, 43.72 mmol) in methanol (200 mL) was stirred for 0.5 h at rt. After 0.5 h NaBH(OAc)$_3$ (11.73 g, 55.3 mmol) was added. The reaction mixture was stirred for 2 h. The reaction mixture was adjusted to pH=8 with saturated aqueous potassium carbonate (120 ml). The precipitate was removed by filtration. The filtrate was evaporated to afford the crude. The crude was purified by SGC to elute with EtOAc:MeOH (0%-10%) to obtain the title compound (7.6 g, yield 56%) as pale yellowish solid. $^1$H NMR (500 MHz, MeOD): δ 8.24 (s, 1H), 8.02 (s, 1H), 7.27-7.20 (m, 5H), 6.19 (d, J=2.0 Hz, 1H), 5.48-5.46 (m, 1H), 5.08-5.06 (m, 1H), 4.43 (t, J=4.0, Hz, 1H), 3.83-3.81 (m, 2H), 3.01-2.99 (br s, 2H), 1.60 (s, 3H), 1.38 (s, 3H) ppm. LCMS (m/z): 395.8 [M+H]$^+$.

Step 2. 1-(3-((((3aR,4R,6R,6aR)-6-(6-amino-9H-purin-9-yl)-2,2-dimethyltetrahydrofuro[3,4-d][1,3]dioxol-4-yl)methyl)(benzyl)amino)propyl)-3-(4-(tert-butyl)phenyl)urea

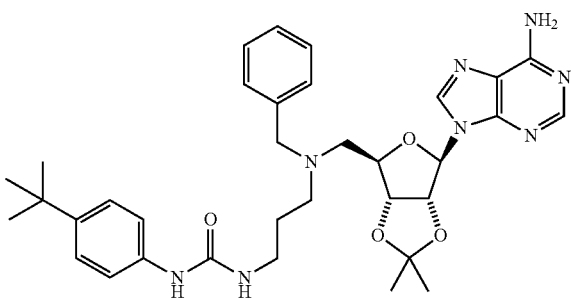

A solution of 9-((3aR,4R,6R,6aR)-6-((benzylamino)methyl)-2,2-dimethyltetrahydrofuro[3,4-d][1,3]dioxol-4-yl)-9H-purin-6-amine (150 mg, 0.38 mmol) and 1-(4-tert-butylphenyl)-3-(3-oxopropyl)urea (540 mg, crude) in DCE (8 mL) was stirred at rt for 0.5 h. Then NaBH(OAc)$_3$ (184 mg, 0.87 mmol) was added. The reaction was stirred at rt overnight. The reaction was quenched with saturated NaHCO$_3$ (2 mL) and extracted with DCM (10 mL×3), washed with brine (10 mL), dried over Na$_2$SO$_4$ and concentrated: The residue was purified by prep-TLC (DCM:MeOH=10:1) to afford the title compound (80 mg, Yield 34%). $^1$H NMR (500 MHz, MeOD): δ 8.15 (s, 1H), 8.09 (s, 1H), 7.27-7.14 (m, 9H), 6.14 (d, J=2.5 Hz, 1H), 5.40-5.38 (m, 1H), 4.95-4.93 (m, 1H), 4.38-4.32 (m, 1H), 3.61-3.46 (m, 2H), 3.16-3.13 (m, 2H), 2.70-2.50 (m, 4H), 1.76-1.58 (m, 2H), 1.54 (s, 3H), 1.34 (s, 3H), 1.28 (s, 9H); ESI-MS (m/z): 629.3[M+1]$^+$.

Step 3. 1-(3-((((2R,3S,4R,5R)-5-(6-amino-9H-purin-9-yl)-3,4-dihydroxytetrahydrofuran-2-yl)methyl)(benzyl)amino)propyl)-3-(4-(tert-butyl)phenyl)urea

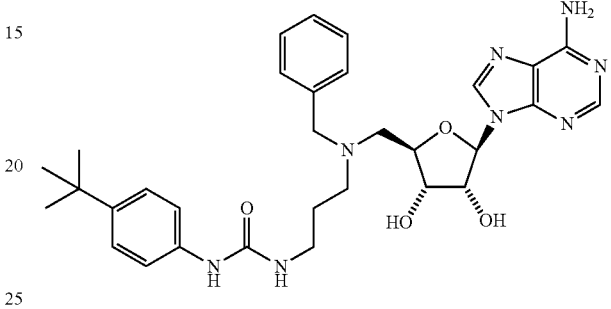

A solution of 1-(3-((((3aR,4R,6R,6aR)-6-(6-amino-9H-purin-9-yl)-2,2-dimethyltetrahydrofuro[3,4-d][1,3]dioxol-4-yl)methyl)(benzyl)amino)propyl)-3-(4-(tert-butyl)phenyl)urea (75 mg, 0.12 mmol) in TFA (0.90 mL) and 0.10 mL of water were stirred for 1 h at room temperature. The reaction was concentrated to dryness, dissolved in MeOH (5 mL) and added dropwise K$_2$CO$_3$ (60 mg) in water (0.5 mL). The reaction was stirred at rt for 0.5 h. Then the reaction was concentrated. The residue was purified by prep-TLC (DCM:MeOH:NH$_4$OH=150:15:4) (V/V) to afford the title compound (30 mg, Yield 52%) as a pale white solid. $^1$H NMR (500 MHz, MeOD): δ8.12 (s, 1H), 8.11 (s, 1H), 7.34-7.20 (m, 9H), 5.99 (d, J=4.0 Hz, 1H), 4.67 (t, J=4.5 Hz, 1H), 4.332 (s, 1H), 4.328 (s, 1H), 3.85 (br s, 2H), 3.25-3.15 (m, 2H), 3.05 (br s, 2H), 2.77 (br s, 2H), 1.79 (t, J=6.5 Hz, 2H), 1.27 (s, 9H); ESI-MS (m/z): 589.3 [M+1]$^+$.

Compound 304

1-((S)-1-((((2R,3S,4R,5R)-5-(6-amino-9H-purin-9-yl)-3,4-dihydroxytetrahydrofuran-2-yl)methyl)(methyl)amino)pentan-3-yl)-3-(4-(tert-butyl)phenyl)urea

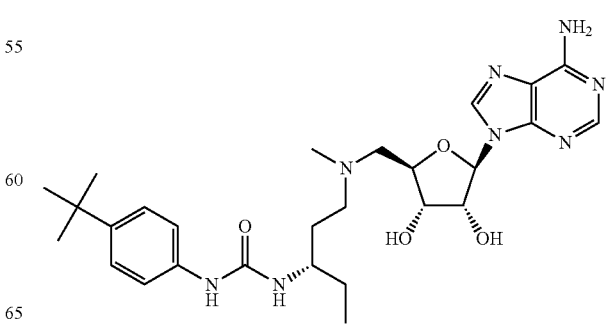

Step 1. (S)-methyl 3-aminopentanoate

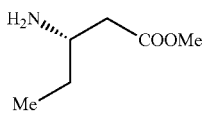

SOCl$_2$ (170 mg, 1.45 mmol) was added to MeOH (5 mL) at −10° C. and the solution was stirred for 1 h. Then, (S)-3-aminopentanoic acid (85 mg, 0.72 mmol) was added in one portion and the mixture was stirred at rt for 15 h. The reaction mixture was concentrated to obtain the title compound (120 mg, yield: 98%) as a light yellow oil. $^1$H NMR (500 MHz, MeOD) δ3.75 (s, 3H), 3.52-3.47 (m, 1H), 2.95-2-2.77 (m, 1H), 2.66-2.61 (m, 1H), 1.75-1.68 (m, 2H), 1.03 (t, J=7.5 Hz, 3H ppm.

Step 2. (S)-methyl 3-(3-(4-(tert-butyl)phenyl)ureido)pentanoate

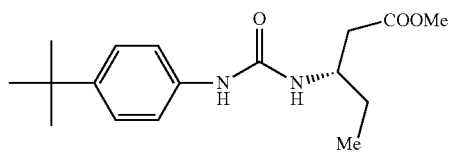 [SMILES: CC[C@@H](CC(=O)OC)NC(=O)Nc1ccc(C(C)(C)C)cc1]

To a solution of (S)-methyl 3-aminopentanoate (100 mg, 0.76 mmol) in DCM (5 mL) was added TEA (507 mg, 5.01 mmol) at 0° C., upon which, 1-tert-Butyl-4-isocyanatobenzene (134 mg, 0.76 mmol) was added and the mixture was stirred at rt for 2 h. The solution was concentrated and purified by preparative-TLC (DCM:MeOH=20:1) to obtain the title compound (150 mg, yield: 72%) as a light yellow oil. $^1$H NMR (500 MHz, MeOD): δ 7.30-7.23 (m, 4H), 4.04-4.00 (m, 1H), 3.67 (s, 3H), 2.56-2.52 (m, 2H), 1.62-1.53 (m, 2H), 1.29 (s, 9H), 0.97 (t, J=7.5 Hz, 3H) ppm; ESI-MS (m/z): 307.2 [M+1]$^+$.

Step 3. (S)-1-(4-(tert-butyl)phenyl)-3-(1-hydroxypentan-3-yl)urea

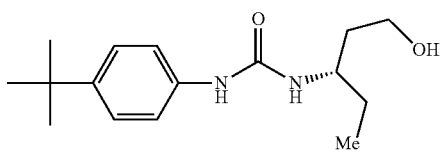 [SMILES: CC[C@@H](CCO)NC(=O)Nc1ccc(C(C)(C)C)cc1]

To a solution of (S)-methyl 3-(3-(4-(tert-butyl)phenyl)ureido)pentanoate (140 mg, 0.36 mmol) in THF (dry, 10 mL) was added LiBH$_4$ (32 mg, 1.44 mmol) and the solution was stirred at 0° C. for 1 h. Then, the mixture was stirred at rt for 15 h. Water (2 mL) was added to quench the reaction and the mixture was extracted with DCM (20 mL×4). The combined organic phases were washed with brine (5 mL), dried over anhydrous Na$_2$SO$_4$, filtered and concentrated to obtain the title compound (109 mg, yield: 89%) as a white solid. $^1$H NMR (500 MHz, MeOD): δ 7.30-7.23 (m, 4H), 3.77-3.75 (m, 1H), 3.66-3.62 (m, 2H), 1.80-1.76 (m, 1H), 1.62-1.54 (m, 2H), 1.51-1.46 (m, 1H), 1.29 (s, 9H), 0.96 (t, J=7.5 Hz, 3H) ppm; ESI-MS (m/z): 279.2 [M+1]$^+$.

Step 4. (S)-1-(4-(tert-butyl)phenyl)-3-(1-oxopentan-3-yl)urea

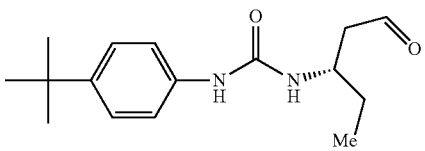 [SMILES: CC[C@@H](CC=O)NC(=O)Nc1ccc(C(C)(C)C)cc1]

To a solution (S)-1-(4-(tert-butyl)phenyl)-3-(1-hydroxypentan-3-yl)urea (109 mg, 0.36 mmol) in EA (10 mL) were added IBX (252 mg, 0.90 mmol) and the mixture was refluxed for 1.5 h under an atmosphere of N$_2$. The mixture was filtered and the filtrate was concentrated to obtain the title compound (100 mg, yield: 100%) as a light yellow solid. The crude was used to the next step without further purification. ESI-MS (m/z): 277.3 [M+1]$^+$.

Step 5. 1-((S)-1-((((3aR,4R,6R,6aR)-6-(6-amino-9H-purin-9-yl)-2,2-dimethyltetrahydrofuro[3,4-d][1,3]dioxol-4-yl)methyl)(methyl)amino)pentan-3-yl)-3-(4-(tert-butyl)phenyl)urea

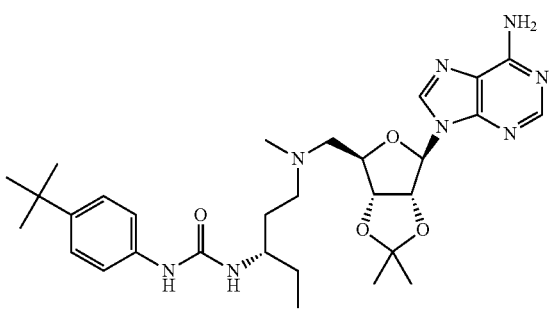 [SMILES: CC[C@@H](CCN(C)C[C@H]1O[C@@H](n2cnc3c(N)ncnc32)[C@@H]2OC(C)(C)O[C@@H]21)NC(=O)Nc1ccc(C(C)(C)C)cc1]

A mixture of (S)-1-(4-(tert-butyl)phenyl)-3-(1-oxopentan-3-yl)urea (100 mg, 0.36 mmol) and 9-((3aR,4R,6R,6aR)-2,2-dimethyl-6-((methylamino)methyl)tetrahydrofuro[3,4-d][1,3]dioxol-4-yl)-9H-purin-6-amine (104 mg, 0.33 mmol) in DCE (25 mL) was stirred at rt for 0.5 h, upon which, NaBH(OAc)$_3$ (120 mg, 0.54 mmol) was added and the solution was stirred at rt for 15 h. NaHCO$_3$ was added and the mixture was extracted with EtOAc (15 mL×3). The combined organic phases were washed with brine (5 mL×1), dried over anhydrous Na$_2$SO$_4$, filtered and concentrated. The crude was purified by preparative-TLC (first pure EA, then DCM:MeOH=15:1) to obtain the title compound (94 mg, yield: 45%) as a light yellow solid.

Step 6. 1-((S)-1-((((2R,3S,4R,5R)-5-(6-amino-9H-purin-9-yl)-3,4-dihydroxytetrahydrofuran-2-yl)methyl)(methyl)amino)pentan-3-yl)-3-(4-(tert-butyl)phenyl)urea

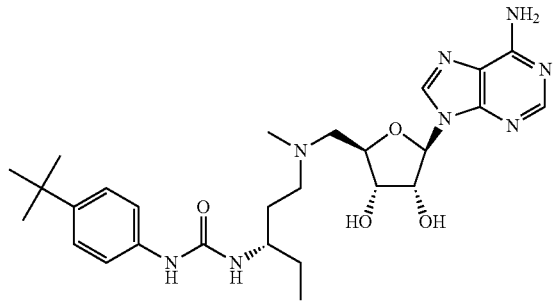 [SMILES: CC[C@@H](CCN(C)C[C@H]1O[C@@H](n2cnc3c(N)ncnc32)[C@H](O)[C@@H]1O)NC(=O)Nc1ccc(C(C)(C)C)cc1]

A solution of 1-((S)-1-((((3aR,4R,6R,6aR)-6-(6-amino-9H-purin-9-yl)-2,2-dimethyltetrahydrofuro[3,4-d][1,3]dioxol-4-yl)methyl)(methyl)amino)pentan-3-yl)-3-(4-(tert-butyl)phenyl)urea (94 mg, 0.15 mmol) in 2.5 M HCl/MeOH (5 mL) was stirred at 30° C. for 1.5 h and evaporated to dryness. The residue was co-evaporated with methanol twice. Then, the residue was dissolved in MeOH (5 mL) Saturated $K_2CO_3$ solution was added to adjust the solution to pH=8, upon which the mixture was stirred for 5 min and concentrated in vacuo. The residue was purified by preparative-TLC (DCM:MeOH=5:1) to obtain the title compound (61 mg, yield: 75%) as a light yellow solid. $^1$H NMR (500 MHz, MeOD): δ 8.19 (s, 2H), 7.26-7.20 (m, 4H), 5.95 (d, J=4.0 Hz, 1H), 4.721-4.703 (m, 1H), 4.30-4.25 (m, 2H), 3.60-3.56 (m, 1H), 2.97-2.84 (m, 2H), 2.69-2.63 (m, 2H), 2.38 (s, 3H), 1.80-1.75 (m, 1H), 1.57-1.35 (m, 3H), 1.28 (s, 9H), 0.91-0.86 (m, 3H) ppm; ESI-MS (m/z): 541.4 [M+1]$^+$.

1-((R)-1-((((2R,3S,4R,5R)-5-(6-amino-9H-purin-9-yl)-3,4-dihydroxytetrahydrofuran-2-yl)methyl)(methyl)amino)-4-methylpentan-3-yl)-3-(4-(tert-butyl)phenyl)urea

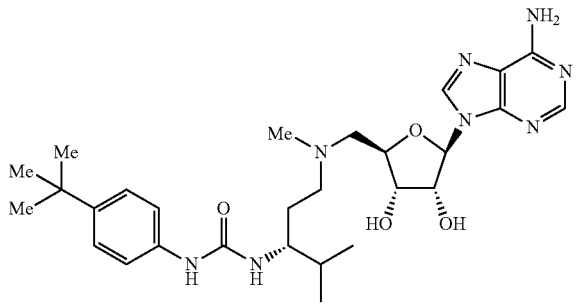 [SMILES: CC(C)[C@@H](CCN(C)C[C@H]1O[C@@H](n2cnc3c(N)ncnc32)[C@H](O)[C@@H]1O)NC(=O)Nc1ccc(C(C)(C)C)cc1]

Step 1. (R)-methyl 3-amino-4-methylpentanoate hydrochloride

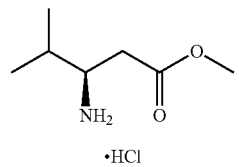

Sulfurous dichloride (1 mL, 7.63 mmol) was added to MeOH (10 mL) at −20° C. The reaction was stirred for 1 h. Then (R)-3-amino-4-methylpentanoic acid (1 g, 3.82 mmol) was added in one portion. The reaction was stirred at 25° C. overnight. The reaction was concentrated to obtain the title compound (1.1 g, Yield 80%). The crude was used directly next step without further purification.

Step 2. (R)-methyl 3-(((benzyloxy)carbonyl)amino)-4-methylpentanoate

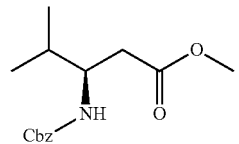 [SMILES: COC(=O)C[C@@H](NC(=O)OCc1ccccc1)C(C)C]

A solution of (R)-methyl 3-amino-4-methylpentanoate hydrochloride (1.1 g, 6.07 mmol) and Et$_3$N (1.84 g, 18.21 mmol) in THF (80 mL) was stirred for 0.5 h. Then CbzCl (1.24 g, 7.29 mmol) was added dropwise. The reaction was stirred at rt for 3 h. The reaction was quenched with sat. NaHCO$_3$, extracted with DCM (80 mL×3), washed with brine (50 mL), dried and concentrated. The residue was purified by SGC to obtain the title compound (850 mg, Yield 40%). 1H NMR (500 MHz, DMSO): δ 7.37-7.31 (m, 5H), 5.18-5.15 (m, 1H), 5.03-5.00 (m, 2H), 3.54 (s, 3H), 2.50-2.46 (m, 2H), 2.36-2.31 (m, 1H), 1.69 (t, J=6.0 Hz, 1H), 1.28 (s, 9H), 0.83-0.80 (m, 6H) ppm; ESI-MS (m/z): 280.3 [M+1]$^+$.

Step 3. (R)-benzyl (1-hydroxy-4-methylpentan-3-yl)carbamate

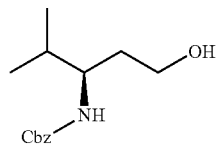 [SMILES: CC(C)[C@@H](CCO)NC(=O)OCc1ccccc1]

To a solution (R)-methyl 3-(((benzyloxy)carbonyl)amino)-4-methylpentanoate (850 mg, 3.04 mmol) in THF (30 mL) was added LiBH$_4$ (269 mg, 12.19 mmol) at rt. The reaction was stirred at rt overnight. The reaction was quenched with water (12 mL), extracted with DCM (20 mL×3), dried and concentrated to obtain the title compound (330 mg, Yield 59%). ESI-MS (m/z): 252.2 [M+1]$^+$.

Step 4. (R)-benzyl (4-methyl-1-oxopentan-3-yl)carbamate

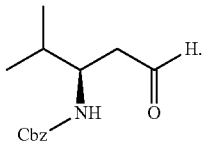

A suspension of (R)-benzyl (1-hydroxy-4-methylpentan-3-yl)carbamate (330 mg, 1.31 mmol) and IBX (1108 mg, 3.93 mmol) in EtOAc (10 mL) was refluxed or 1.5 h. The reaction was filtered and the filtrate was concentrated to obtain the title compound (220 mg, crude). The residue was directly used for next step without further purification. ESI-MS (m/z): 250.1 [M+1]$^+$.

Step 5. benzyl((R)-1-((((3aR,4R,6R,6aR)-6-(6-amino-9H-purin-9-yl)-2,2-dimethyltetrahydrofuro[3,4-d][1,3]dioxol-4-yl)methyl)(methyl)amino)-4-methylpentan-3-yl)carbamate

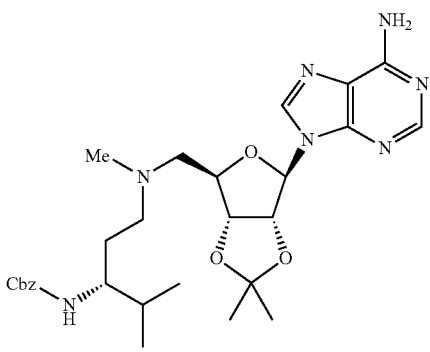 [SMILES: CC(C)[C@@H](CCN(C)C[C@H]1O[C@@H](n2cnc3c(N)ncnc32)[C@@H]2OC(C)(C)O[C@@H]21)NC(=O)OCc1ccccc1]

A solution of (R)-benzyl (4-methyl-1-oxopentan-3-yl)carbamate (220 mg, 0.88 mmol) and 9-((3aR,4R,6R,6aR)-2,2-dimethyl-6-((methylamino)methyl)tetrahydrofuro[3,4-d][1,3]dioxol-4-yl)-9H-purin-6-amine (282 mg, 0.88 mmol) in DCE (10 mL) was stirred at rt for 0.5 h, then NaBH(OAc)$_3$ (292 mg, 1.32 mmol) was added. The reaction was stirred at rt overnight. The reaction was quenched with sat. NaHCO$_3$ (5 mL), extracted with DCM (10 mL×3), the combined extracts were washed with brine (10 mL), dried, filtered and concentrated. The residue was purified by Prep-TLC (DCM:MeOH:NH$_4$OH=200:10:4) (V/V) to obtain the title compound (240 mg, Yield 47%). $^1$H NMR (500 MHz, MeOD): δ 8.23 (s, 1H), 8.21 (s, 1H), 7.34-7.26 (m, 5H), 6.16 (m, 1H), 5.467-5.446 (m, 1H), 5.08-5.04 (m, 2H), 5.01-4.97 (m, 1H), 4.38-4.32 (m, 1H), 3.56-3.55 (m, 1H), 2.73-2.64 (m, 2H), 2.42-2.39 (m, 2H), 2.24 (s, 3H), 1.62-1.60 (m, 4H), 1.39-1.38 (m, 4H), 0.83-0.79 (m, 6H) ppm; ESI-MS (m/z): 554.3[M+1]$^+$.

Step 6. (R)—N1-(((3aR,4R,6R,6aR)-6-(6-amino-9H-purin-9-yl)-2,2-dimethyltetrahydrofuro[3,4-d][1,3]dioxol-4-yl)methyl)-N1,4-dimethylpentane-1,3-diamine

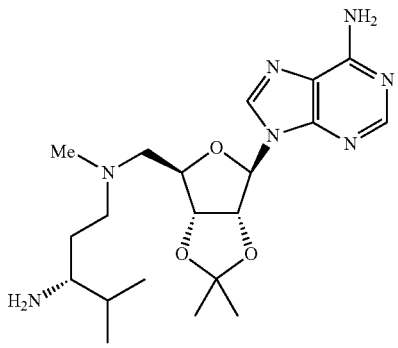 [SMILES: CC(C)[C@H](N)CCN(C)C[C@H]1O[C@@H](n2cnc3c(N)ncnc32)[C@@H]2OC(C)(C)O[C@@H]21]

A solution of benzyl((R)-1-((((3aR,4R,6R,6aR)-6-(6-amino-9H-purin-9-yl)-2,2-dimethyltetrahydrofuro[3,4-d][1,3]dioxol-4-yl)methyl)(methyl)amino)-4-methylpentan-3-yl)carbamate (240 mg, 0.43 mmol) in MeOH (10 mL) was added Pd(OH)$_2$/C (80 mg). The mixture was stirred at rt for 2 h under H$_2$, upon which the reaction was filtered and evaporated to obtain the title compound (130 mg, crude, yield 71%). The residue was directly used for next step without further purification. ESI-MS (m/z): 420.3[M+1]$^+$.

Step 7. 1-((R)-1-((((3aR,4R,6R,6aR)-6-(6-amino-9H-purin-9-yl)-2,2-dimethyltetrahydrofuro[3,4-d][1,3]dioxol-4-yl)methyl)(methyl)amino)-4-methylpentan-3-yl)-3-(4-(tert-butyl)phenyl)urea

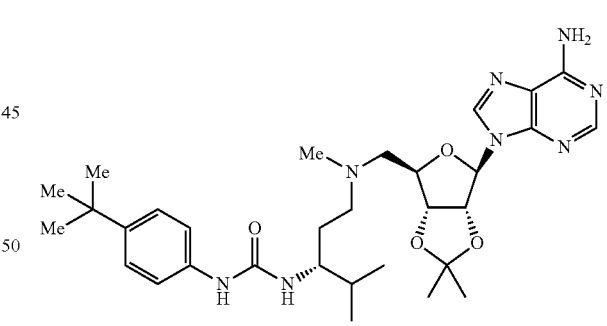

A solution of (R)—N1-(((3aR,4R,6R,6aR)-6-(6-amino-9H-purin-9-yl)-2,2-dimethyltetrahydrofuro[3,4-d][1,3]dioxol-4-yl)methyl)-N1,4-dimethylpentane-1,3-diamine (130 mg, 0.39 mmol) and Et$_3$N (118 mg, 1.17 mmol) in DCM (5 mL) was stirred for 0.5 h. Then tert-butylbenzene isocyanate (74 mg, 0.42 mmol) was added. The reaction was stirred at rt for 1 h. The reaction was concentrated to dryness. The residue was purified by Prep-TLC (PE:EA:NH4OH=210:370:5) (V/V) to obtain the title compound (150 mg, Yield 81%). $^1$H NMR (500 MHz, MeOD): δ 8.24 (s, 1H), 8.23 (s, 1H), 7.29-7.23 (m, 4H), 6.17 (d, J=2.0 Hz, 1H), 5.47-5.45 (m, 1H), 5.00-4.98 (m, 1H), 4.39-4.35 (m, 1H), 3.55-3.53 (m, 1H), 2.77 (brs, 1H), 2.69 (br s, 1H), 2.48 (br s, 2H), 2.25 (s, 3H), 1.66-1.58 (m, 2H), 1.56 (s, 3H), 1.35 (s, 9H), 1.28 (s, 9H), 0.88-0.85 (m, 6H) ppm; ESI-MS (m/z): 595.5 [M+1]$^+$.

Step 8. 1-((R)-1-((((2R,3S,4R,5R)-5-(6-amino-9H-purin-9-yl)-3,4-dihydroxytetrahydrofuran-2-yl)methyl)(methyl)amino)-4-methylpentan-3-yl)-3-(4-(tert-butyl)phenyl)urea

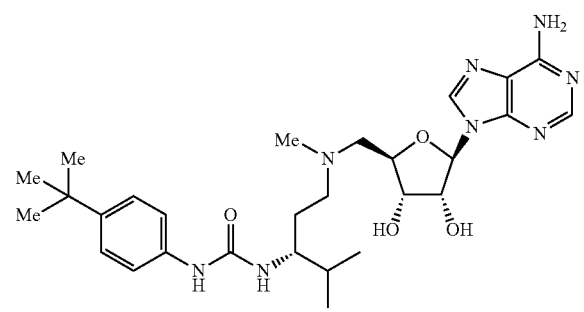 [SMILES: CC(C)[C@@H](CCN(C)C[C@H]1O[C@@H](n2cnc3c(N)ncnc32)[C@H](O)[C@@H]1O)NC(=O)Nc1ccc(C(C)(C)C)cc1]

A solution of 1-((R)-1-((((3aR,4R,6R,6aR)-6-(6-amino-9H-purin-9-yl)-2,2-dimethyltetrahydrofuro[3,4-d][1,3]dioxol-4-yl)methyl)(methyl)amino)-4-methylpentan-3-yl)-3-(4-(tert-butyl)phenyl)urea (100 mg, 0.17 mmol) in 2.5 M HCl in MeOH (5 mL) was stirred at 25° C. for 3 h. The reaction was concentrated to dryness, dissolved in MeOH (5 mL) and adjusted pH=8 with sat. K$_2$CO$_3$. The reaction was stirred at rt for 0.5 h. Then the reaction was concentrated. The residue was purified by Prep-TLC (DCM:MeOH:NH$_4$OH=300:30:8) (V/V) to obtain the title compound (50 mg, Yield 54%). $^1$H NMR (500 MHz, MeOD): δ 8.22 (s, 1H), 8.19 (s, 1H), 7.28-7.21 (m, 4H), 5.97 (d, J=5.5 Hz, 1H), 4.74-4.71 (m, 1H), 4.28-4.21 (m, 2H), 3.59-3.56 (m, 1H), 2.99-2.91 (m, 2H), 2.69 (br s, 2H), 2.47 (s, 3H), 1.82-1.68 (m, 2H), 1.53-1.47 (m, 1H), 1.27 (s, 9H), 0.90-0.86 (m, 6H) ppm; ESI-MS (m/z): 555.4 [M+1]$^+$.

Compound 306

1-(3-((((2R,3S,4R,5R)-5-(6-amino-9H-purin-9-yl)-3,4-dihydroxytetrahydrofuran-2-yl)methyl)(cyclobutyl)amino)propyl)-3-(4-(tert-butyl)phenyl)urea

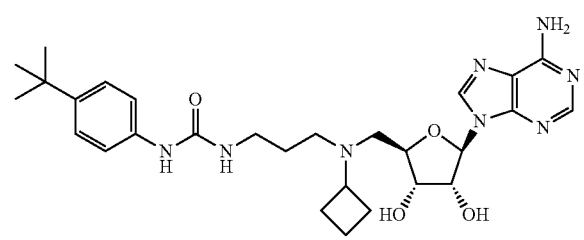 [SMILES: CC(C)(C)c1ccc(NC(=O)NCCCN(C[C@H]2O[C@@H](n3cnc4c(N)ncnc43)[C@H](O)[C@@H]2O)C2CCC2)cc1]

Step 1

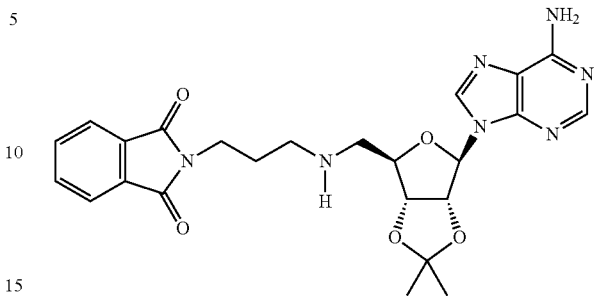

A solution of 9-((3aR,4R,6R,6aR)-6-(aminomethyl)-2,2-dimethyltetrahydrofuro[3,4-d][1,3]dioxol-4-yl)-9H-purin-6-amine (400 mg, 1.3 mmol) and 3-(1,3-dioxoisoindolin-2-yl)propanal (293 mg, crude 1.44 mmol) in DCE (8 mL) were stirred at rt for 0.5 h, then NaBH(OAc)$_3$ (416 mg, 1.96 mmol) was added. The reaction was stirred at rt overnight. The reaction was quenched with aqu. sat. NaHCO$_3$ (2 mL), extracted with DCM (10 mL×3), washed with brine (10 mL), dried and concentrated. The residue was purified by prep-TLC (DCM:MeOH=10:1) to the title compound (350 mg, Yield 43%).
$^1$H NMR (500 MHz, MeOD): δ 8.28 (s, 1H), 8.21 (s, 1H), 7.83-7.76 (m, 4H), 6.14 (d, J=3.5 Hz, 1H), 5.46-5.44 (m, 1H), 5.01-4.99 (m, 1H), 4.32 (br s, 1H), 3.65-3.62 (m, 2H), 2.85-2.83 (m, 2H), 2.57-2.53 (m, 2H), 1.79-1.76 (m, 2H), 1.58 (s, 3H), 1.37 (s, 3H) ppm; ESI-MS (m/z): 494.2[M+1]$^+$.

Step 2. 2-(3-((((3aR,4R,6R,6aR)-6-(6-amino-9H-purin-9-yl)-2,2-dimethyltetrahydrofuro[3,4-d][1,3]dioxol-4-yl)methyl)(cyclobutyl)amino)propyl)isoindoline-1,3-dione

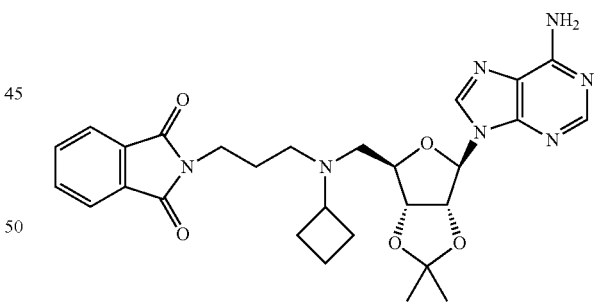

A solution of 1-(3-((((2R,3S,4R,5R)-5-(6-amino-9H-purin-9-yl)-3,4-dihydroxytetrahydrofuran-2-yl)methyl)(cyclobutyl)amino)propyl)-3-(4-(tert-butyl)phenyl)urea (325 mg, 0.659 mmol), cyclobutanone (93 mg, 1.32 mmol) and Ti(Oi-Pr)$_4$ (188 mg, 0.659 mmol) in MeOH (10 mL) were stirred at rt for 0.5 h, then NaBH$_3$CN (63 mg, 0.99 mmol) was added. The reaction was stirred at rt overnight. The reaction was filtered and concentrated. The residue was purified by Prep-TLC (DCM:MeOH=10:1) to obtain the title compound (270 mg, Yield 70%). $^1$H NMR (500 MHz, MeOD): δ 8.22 (s, 1H), 8.17 (s, 1H), 7.76-7.71 (m, 4H), 6.11 (m, 1H), 5.40-5.39 (m, 1H), 4.98-4.97 (m, 1H), 4.27-4.26 (m, 1H), 3.56-3.51 (m, 2H), 3.31-3.30 (m, 2H), 3.05 (br s, 1H), 2.75-2.60 (m, 2H), 2.47-2.45 (br s, 2H), 1.86 (br s, 2H), 1.74-1.69 (m, 4H), 1.56-1.52 (m, 5H), 1.32 (s, 3H) ppm; ESI-MS (m/z): 548.3 [M+1]⁺.

Step 3. N1-(((3aR,4R,6R,6aR)-6-(6-amino-9H-purin-9-yl)-2,2-dimethyltetrahydrofuro[3,4-d][1,3]dioxol-4-yl)methyl)-N1-cyclobutylpropane-1,3-diamine

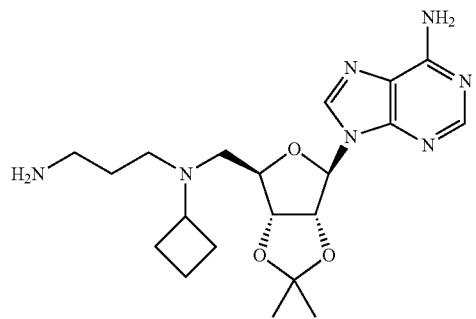 [SMILES: CC1(C)O[C@@H]2[C@H](O1)[C@@H](CN(CCCN)C1CCC1)O[C@H]2n1cnc2c(N)ncnc21]

A solution of 2-(3-((((3aR,4R,6R,6aR)-6-(6-amino-9H-purin-9-yl)-2,2-dimethyltetrahydrofuro[3,4-d][1,3]dioxol-4-yl)methyl)(cyclobutyl)amino)propyl)isoindoline-1,3-dione (230 mg, 0.42 mmol) and hydrazine hydrate (63 mg, 1.26 mmol) in EtOH (20 mL) was refluxed for 2 h. The reaction was filtered and concentrated to obtain the title compound (195 mg, crude, Yield 95%). ¹H NMR (500 MHz, MeOD): δ 8.15 (s, 1H), 8.09 (s, 1H), 7.27-7.14 (m, 9H), 6.14 (d, J=2.5 Hz, 1H), 5.40-5.38 (m, 1H), 4.95-4.93 (m, 1H), 4.38-4.32 (m, 1H), 3.61-3.46 (m, 2H), 3.16-3.13 (m, 2H), 2.70-2.69 (m, 2H), 2.62-2.50 (m, 2H), 1.76-1.58 (m, 2H), 1.54 (s, 3H), 1.28 (s, 9H) ppm; ESI-MS (m/z): 418.2[M+1]⁺.

Step 4. 1-(3-((((3aR,4R,6R,6aR)-6-(6-amino-9H-purin-9-yl)-2,2-dimethyltetrahydrofuro[3,4-d][1,3]dioxol-4-yl)methyl)(cyclobutyl)amino)propyl)-3-(4-(tert-butyl)phenyl)urea

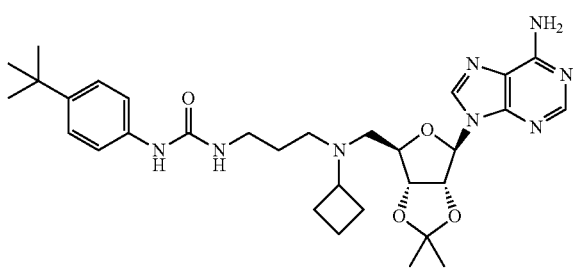 [SMILES: CC1(C)O[C@@H]2[C@H](O1)[C@@H](CN(CCCNC(=O)Nc1ccc(C(C)(C)C)cc1)C1CCC1)O[C@H]2n1cnc2c(N)ncnc21]

To a stirred solution of N1-(((3aR,4R,6R,6aR)-6-(6-amino-9H-purin-9-yl)-2,2-dimethyltetrahydrofuro[3,4-d][1,3]dioxol-4-yl)methyl)-N1-cyclobutylpropane-1,3-diamine (195 mg, 0.468 mmol) in DCM (10 mL) was added dropwise 4-tert-butylphenyl isocyanate (86 mg, 0.49 mmol) at 0° C. The reaction was stirred at rt overnight. The reaction was evaporated to obtain the residue. The residue was purified by Prep-TLC to obtain the title compound (250 mg, Yield 91%) as pale white solid. ¹H NMR (500 MHz, MeOD): δ 8.26 (s, 1H), 8.21 (s, 1H), 7.28-7.22 (m, 4H), 6.18 (d, J=2.0 Hz, 1H), 5.51-5.49 (m, 1H), 5.01-4.99 (m, 1H), 4.34 (br s, 1H), 310-3.08 (m, 3H), 2.69-2.68 (m, 2H), 2.49-2.46 (m, 2H), 1.89-1.87 (br s, 2H), 1.76-1.73 (m, 2H), 1.58-1.53 (m, 7H), 1.36 (s, 3H), 1.28 (s, 9H) ppm; ESI-MS (m/z): 593.4 [M+1]⁺.

Step 5. 1-(3-((((2R,3S,4R,5R)-5-(6-amino-9H-purin-9-yl)-3,4-dihydroxytetrahydrofuran-2-yl)methyl)(cyclobutyl)amino)propyl)-3-(4-(tert-butyl)phenyl)urea

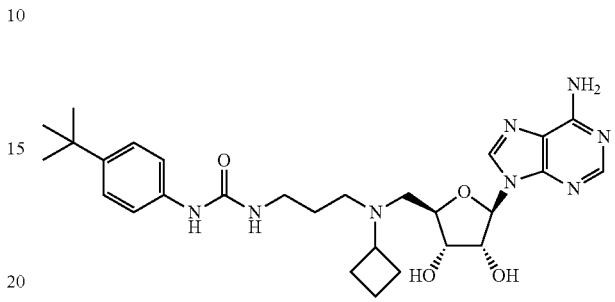

A solution of 1-(3-((((3aR,4R,6R,6aR)-6-(6-amino-9H-purin-9-yl)-2,2-dimethyltetrahydrofuro[3,4-d][1,3]dioxol-4-yl)methyl)(cyclobutyl)amino)propyl)-3-(4-(tert-butyl)phenyl)urea (100 mg, 0.17 mmol) in HCl in MeOH (5 mL) was stirred for 2 hour at room temperature. The reaction was concentrated to dryness, dissolved in MeOH (5 mL) and added dropwise K₂CO₃ (60 mg) in 0.5 mL of water. The reaction was stirred at rt for 0.5 h. Then the reaction was concentrated to obtain the residue. The residue was purified by Prep-TLC to obtain the title compound (95 mg, Yield 85%) as pale white solid. ¹H NMR (500 MHz, MeOD): δ 8.25 (s, 1H), 8.19 (s, 1H), 7.26-7.18 (m, 4H), 5.96 (d, J=5.0 Hz, 1H), 4.69-4.67 (m, 1H), 4.23-4.20 (m, 2H), 3.17-3.12 (m, 3H), 2.89 (m, 2H), 2.60 (br s, 2H), 2.03 (br s, 2H), 1.89-1.88 (m, 2H), 1.69-1.61 (m, 4H), 1.28 (s, 9H) ppm; ESI-MS (m/z): 553.3 [M+1]⁺.

Compound 307

1-(3-((((2R,3S,4R,5R)-5-(6-amino-9H-purin-9-yl)-3,4-dihydroxytetrahydrofuran-2-yl)methyl)(oxetan-3-yl-amino)propyl)-3-(4-(tert-butyl)phenyl)urea

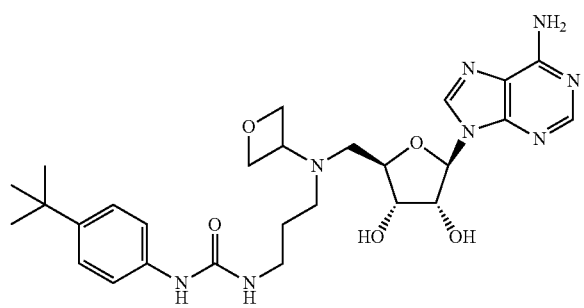 [SMILES: CC(C)(C)c1ccc(NC(=O)NCCCN(C[C@H]2O[C@@H](n3cnc4c(N)ncnc43)[C@H](O)[C@@H]2O)C2COC2)cc1]

Step 1. 1-(3-((((3aR,4R,6R,6aR)-6-(6-amino-9H-purin-9-yl)-2,2-dimethyltetrahydrofuro[3,4-d][1,3]dioxol-4-yl)methyl)(oxetan-3-yl)amino)propyl)-3-(4-(tert-butyl)phenyl)urea

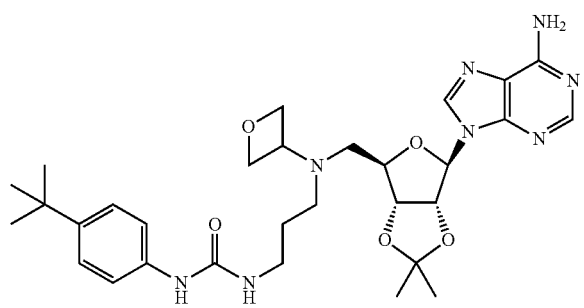 [SMILES: CC1(C)O[C@@H]2[C@H](O1)[C@@H](CN(CCCNC(=O)Nc1ccc(C(C)(C)C)cc1)C1COC1)O[C@H]2n1cnc2c(N)ncnc21]

To a solution of 1-(3-((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl)urea (120 mg, 0.223 mmol) and oxetan-3-one (80 mg, crude, 1.11 mmol) in MeOH (3 mL) was added NaBH(OAc)$_3$ (112 mg, 1.78 mmol) and Ti(Oi-Pr)$_4$ (63 mg, 0.223 mmol) then stirred at rt overnight. After completion of the reaction, the mixture was filtered and the filtrate was concentrated and quenched with aqueous sat. NaHCO$_3$ (2 mL), extracted with DCM (10 mL×3), the combined extracts were washed with brine (10 mL), dried, filtered and concentrated. The residue was purified by Prep-TLC (DCM:MeOH=10:1) to obtain the title compound (80 mg, Yield: 60%). $^1$H NMR (500 MHz, MeOD): δ 8.273 (s, 1H), 8.242 (s, 1H), 7.31-7.29 (m, 2H), 7.264-7.242 (m, 2H), 6.198-6.194 (m, 1H), 5.520-5.504 (m, 1H), 5.04 (dd, J=3.5, 6.0 Hz, 1H), 4.84-4.78 (m, 1H), 4.56-4.44 (m, 3H), 4.33-4.30 (m, 1H), 3.91-3.89 (m, 1H), 3.18-3.16 (m, 2H), 2.88-2.52 (m, 4H), 1.61-1.54 (m, 5H), 1.38 (s, 3H), 1.30 (s, 9H) ppm; ESI-MS (m/z): 363.2[M+1]$^+$.

Step 2. 1-(3-((((2R,3S,4R,5R)-5-(6-amino-9H-purin-9-yl)-3,4-dihydroxytetrahydrofuran-2-yl)methyl)(oxetan-3-yl)amino)propyl)-3-(4-(tert-butyl)phenyl)urea

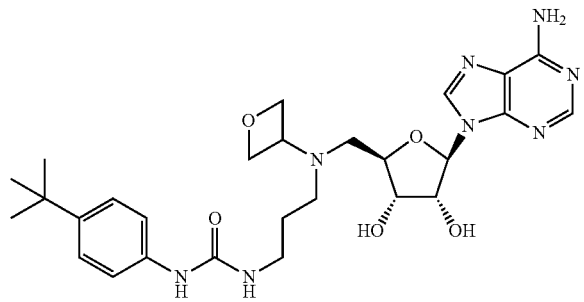 [SMILES: CC(C)(C)c1ccc(NC(=O)NCCCN(C[C@H]2O[C@@H](n3cnc4c(N)ncnc43)[C@H](O)[C@@H]2O)C2COC2)cc1]

A solution of 1-(3-((((3aR,4R,6R,6aR)-6-(6-amino-9H-purin-9-yl)-2,2-dimethyltetrahydrofuro[3,4-d][1,3]dioxol-4-yl)methyl)(oxetan-3-yl)amino)propyl)-3-(4-(tert-butyl)phenyl)urea (80 mg, 0.14 mmol) in HCl in MeOH (5 mL) was stirred for 2 hours at room temperature. The reaction was concentrated to dryness, dissolved in MeOH (5 mL) and added dropwise aqueous sat. K$_2$CO$_3$ till pH=8.0. The reaction was stirred at rt for 0.5 h. Then the reaction was concentrated and the resultant residue was purified by Prep-HPLC to obtain the title compound (15 mg, Yield 20%) as pale white solid. $^1$H NMR (500 MHz, MeOD): δ 8.29 (brs, 1H), 8.203-8.197 (m, 1H), 7.273-7.208 (m, 4H), 6.001 (brs, 1H), 4.730 (brs, 1H), 4.308-4.241 (m, 2H), 3.245 (brs, 2H), 3.115-2.915 (m, 4H), 2.782-2.683 (m, 3H), 2.51-2.43 (m, 2H), 1.726 (br s, 2H), 1.29 (s, 9H) ppm; ESI-MS (m/z): 555.4 [M+1]$^+$.

Compound 308

1-(3-((((2S,3S,4R,5R)-5-(6-amino-9H-purin-9-yl)-3,4-dihydroxytetrahydrofuran-2-yl)methyl)thio)propyl)-3-(4-(tert-butyl)phenyl)urea

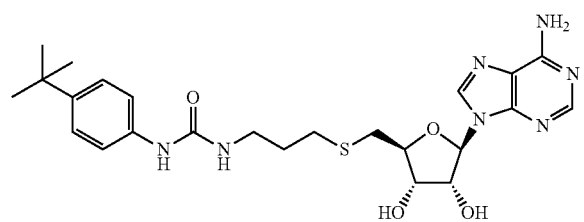 [SMILES: CC(C)(C)c1ccc(NC(=O)NCCCSC[C@H]2O[C@@H](n3cnc4c(N)ncnc43)[C@H](O)[C@@H]2O)cc1]

Step 1. (2R,3R,4S,5S)-2-(6-amino-9H-purin-9-yl)-5-(chloromethyl)tetrahydrofuran-3,4-diol

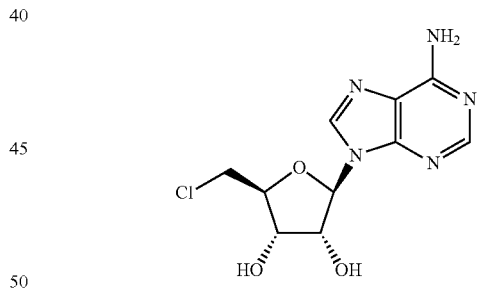

To a solution of (2R,3R,4S,5R)-2-(6-amino-9H-purin-9-yl)-5-(hydroxymethyl)tetrahydrofuran-3,4-diol (1 g, 3.47 mmol) in pyridine (593 mg, 0.6 ml, 7.49 mmol) in acetonitrile (10 ml) cooled in an ice bath was added SOCl$_2$ (2.22 g, 1.36 ml, 18.65 mmol). Stirring was continued at 0-5° C. for 3-4 h, and warming to ambient temperature for overnight. The resulting suspension was concentrated in vacuo. To the reaction mixture was added methanol (20 ml), water (2 ml), and NH$_4$OH (4 ml), followed by stirring for 0.5 h at room temperature. The reaction mixture was concentrated to dryness. The compound was dissolved in MeOH, silica gel (3 g) was added and then solvent was removed. The residue was purified by SGC to elute with EA:MeOH (0%-10%) to obtain the title compound (0.915 g, yield 86%) as yellowish solid. $^1$H NMR (500 MHz, MeOD): δ 8.24 (s, 1H), 8.02 (s, 1H), 7.27-

7.20 (m, 5H), 6.19 (d, J=2.0 Hz, 1H), 5.48-5.46 (m, 1H), 5.08-5.06 (m, 1H), 4.43 (t, J=4.0, Hz, 1H), 3.83-3.81 (m, 2H).

Step 2. 9-((3aR,4R,6S,6aS)-6-(chloromethyl)-2,2-dimethyltetrahydrofuro[3,4-d][1,3]dioxol-4-yl)-9H-purin-6-amine

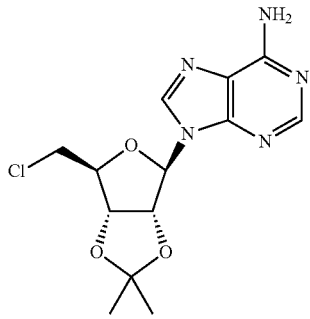 [SMILES: CC1(C)O[C@@H]2[C@H](O1)[C@@H](CCl)O[C@H]2n1cnc2c(N)ncnc21]

(2R,3R,4S,5S)-2-(6-amino-9H-purin-9-yl)-5-(chloromethyl)tetrahydrofuran-3,4-diol (20 g, 70.18 mmol) was suspended in dried acetone (400 mL) containing p-toluenesulfonic acid monohydrate (37.43 g, 197 mmol). Triethyl orthoformate (40 mL, 225 mmol) was then added over a period of 1 h at ambient temperature with vigorous stirring. The mixture was stirred overnight. The mixture was adjusted to pH=8 with saturated aqueous potassium carbonate, the precipitate was filtered off, the filtration was evaporated, extracted with EA (200 ml×4). The combined organic phase was washed with water (1×200 ml), dried, filtered and concentrated. The crude was recrystallized (PE:EA=10:1) to the title compound (18 g, yield: 82%) as a white solid.

$^1$H NMR (500 MHz, CDCl$_3$): δ 8.36 (s, 1H), 7.93 (s, 1H), 6.12 (d, J=1.5 Hz, 1H), 5.68 (s, 2H), 5.47-5.46 (m, 1H), 5.17-5.15 (m, 1H), 4.50-4.47 (m, 1H), 3.84-3.80 (m, 1H), 3.65-3.62 (m, 1H), 1.63 (s, 3H), 1.41 (s, 3H) ppm. LCMS (m/z): 326.1 [M+H]$^+$.

Step 3. S-(3-(1,3-dioxoisoindolin-2-yl)propyl) ethanethioate

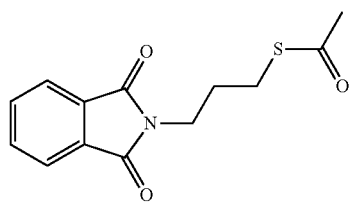 [SMILES: CC(=O)SCCCN1C(=O)c2ccccc2C1=O]

A solution of 2-(3-bromopropyl)isoindoline-1,3-dione (10 g, 37.31 mmol) and potassium ethanethioate (8.5 g, 74.62 mmol) in DMF (20 mL) was stirred at rt overnight. The reaction was poured into water (200 mL), extracted with EtOAc (100 mL×3), the combined extracts were washed with water (100 mL×2) and brine (100 mL), dried, filtered and concentrated to afford the title compound (8 g, Yield 80%). The residue was directly used for next step without further purification. $^1$H NMR (500 MHz, DMSO): δ 7.88-7.83 (m, 4H), 3.64-3.60 (m, 2H), 2.87-2.83 (m, 2H), 2.32 (s, 3H), 1.86-1.82 (m, 2H) ppm; ESI-MS (m/z): 264.0 [M+1]$^+$.

Step 4. 2-(3-mercaptopropyl)isoindoline-1,3-dione

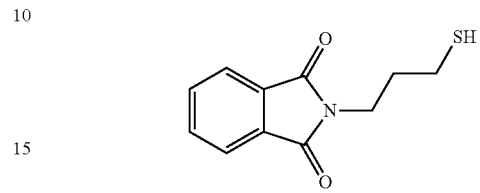

A solution of S-(3-(1,3-dioxoisoindolin-2-yl)propyl) ethanethioate (1.58 g, 6 mmol) in MeOH (15 mL) was added K$_2$CO$_3$ (829 mg, 6 mmol). The reaction was stirred for 20 min at room temperature. The reaction was adjusted to pH=8 with AcOH, diluted with EtOAc (100 mL), washed with water (50 mL) and brine (30 mL), dried, filtered and concentrated to give the residue which was purified by prep-TLC (DCM:MeOH:NH$_4$OH=300:30:8) (V/V) to afford the title compound (900 mg, Yield 70%). The residue was directly used for next step without further purification. $^1$H NMR (500 MHz, CDCl$_3$): δ 7.85-7.70 (m, 4H), 3.83-3.77 (m, 2H), 2.57-2.53 (m, 2H), 2.04-1.97 (m, 2H) ppm; ESI-MS (m/z): 222.0 [M+1]$^+$.

Step 5. 2-(3-((((3aS,4S,6R,6aR)-6-(6-amino-9H-purin-9-yl)-2,2-dimethyltetrahydrofuro[3,4-d][1,3]dioxol-4-yl)methyl)thio)propyl) isoindoline-1,3-dione

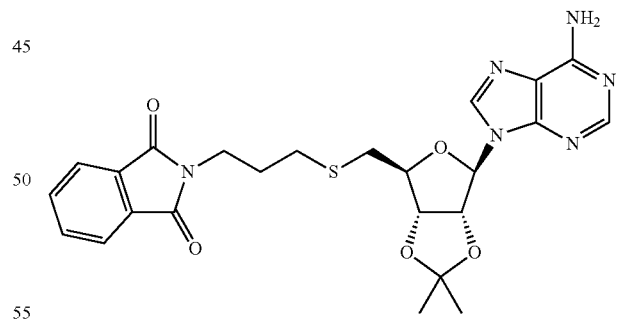

A suspension of Ep-0-A-1 (680 mg, 2.1 mmol), 2-(3-mercaptopropyl)isoindoline-1,3-dione (900 mg, crude) and K$_2$CO$_3$ (1.69 g, 12.2 mmol) in DMF (10 mL) were stirred at 100° C. for 0.5 h. The reaction was diluted with EA (100 mL), washed with water (30 mL) and brine (30 mL), dried and evaporated to obtain the crude. The crude was purified by SGC to afford the title compound 1 (1.3 g, Yield 83%). $^1$H NMR (500 MHz, MeOD): δ 8.26 (s, 1H), 8.22 (s, 1H), 7.82-7.75 (m, 4H), 6.14 (d, J=2.5 Hz, 1H), 5.49-5.47 (m, 1H), 5.04 (d, J=3.0 Hz, 1H), 4.40 (m, 1H), 3.70-3.67 (m, 2H), 2.80-2.79

(m, 2H), 2.56-2.52 (m, 2H), 1.85-1.82 (m, 2H), 1.56 (s, 3H), 1.49 (s, 3H) ppm; ESI-MS (m/z): 511.2[M+1]⁺.

Step 6. 9-((3aR,4R,6S,6aS)-6-(((3-aminopropyl)thio)methyl)-2,2-dimethyltetrahydrofuro[3,4-d][1,3]dioxol-4-yl)-9H-purin-6-amine

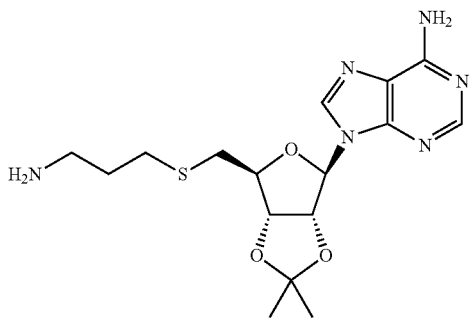 [SMILES: CC1(C)O[C@@H]2[C@H](O1)[C@@H](CSCCCN)O[C@H]2n1cnc2c(N)ncnc21]

A solution of 2-(3-(((((3aS,4S,6R,6aR)-6-(6-amino-9H-purin-9-yl)-2,2-dimethyltetrahydrofuro[3,4-d][1,3]dioxol-4-yl)methyl)thio)propyl)isoindoline-1,3-dione (500 mg, 0.98 mmol) in ethanol (10 mL) added NH₂NH₂.H₂O (150 mg, 2.94 mmol). The reaction was refluxed for 1 h. The reaction was filtered. The filtrate was evaporated to obtain the title compound (380 mg, crude). The residue was directly used for next step without further purification. ESI-MS (m/z): 381.2 [M+1]⁺.

Step 7. 1-(3-(((((3aS,4S,6R,6aR)-6-(6-amino-9H-purin-9-yl)-2,2-dimethyltetrahydrofuro[3,4-d][1,3]dioxol-4-yl)methyl)thio)propyl)-3-(4-(tert-butyl)phenyl)urea

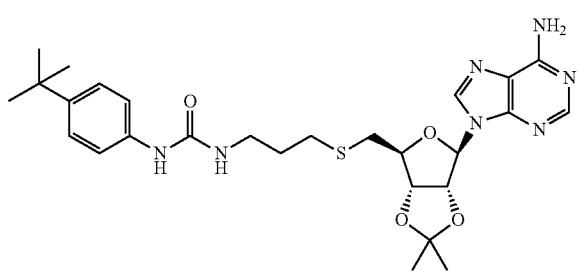 [SMILES: CC1(C)O[C@@H]2[C@H](O1)[C@@H](CSCCCNC(=O)Nc1ccc(C(C)(C)C)cc1)O[C@H]2n1cnc2c(N)ncnc21]

A solution of 9-((3aR,4R,6S,6aS)-6-(((3-aminopropyl)thio)methyl)-2,2-dimethyltetrahydrofuro[3,4-d][1,3]dioxol-4-yl)-9H-purin-6-amine (380 mg, 1.0 mmol) and 4-tertbutyl-benzyl-isocyanate (193 mg, 1.1 mmol) in DCM (10 mL) was stirred at ice-bath for 1 h. The reaction was evaporated to give a residue which was purified by SGC to afford the title compound3 (440 mg, Yield 65%). ¹H NMR (500 MHz, MeOD): δ 8.27 (s, 1H), 8.22 (s, 1H), 7.27-7.21 (m, 4H), 6.17 (d, J=2.0 Hz, 1H), 5.52-5.50 (m, 1H), 5.550-4.87 (m, 1H), 4.41-4.30 (m, 1H), 3.21-3.19 (m, 2H), 2.81-2.78 (m, 2H), 2.56-2.52 (m, 2H), 1.70-1.67 (m, 2H), 1.57 (s, 3H), 1.37 (s, 3H), 1.28 (s, 9H). ppm; ESI-MS (m/z): 556.3[M+1]⁺.

Step 8. 1-(3-(((((2S,3S,4R,5R)-5-(6-amino-9H-purin-9-yl)-3,4-dihydroxytetrahydrofuran-2-yl)methyl)thio)propyl)-3-(4-(tert-butyl)phenyl)urea

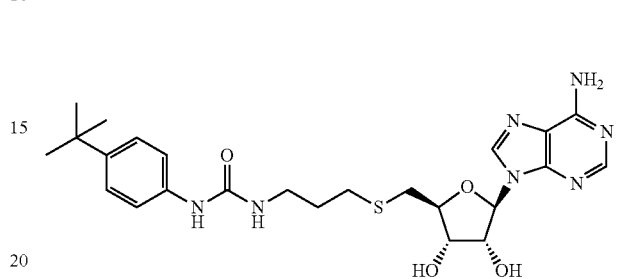

A solution of 1-(3-(((((3aS,4S,6R,6aR)-6-(6-amino-9H-purin-9-yl)-2,2-dimethyltetrahydrofuro[3,4-d][1,3]dioxol-4-yl)methyl)thio)propyl)-3-(4-(tert-butyl)phenyl)urea (190 mg, 0.34 mmol) in TFA (1.80 mL) and 0.20 mL of water was stirred for 1 h at room temperature. The reaction was concentrated to dryness, dissolved in MeOH (2 mL) and EA (100 mL), washed with aq. sat. NaHCO₃ (10×2 mL), dried, filtered and evaporated to give a residue which was purified by prep-HPLC to afford the title compound (97 mg, Yield 55%). ¹H NMR (500 MHz, MeOD): δ 8.31 (s, 1H), 8.20 (s, 1H), 7.27-7.21 (m, 4H), 6.00 (d, J=5.0 Hz, 1H), 4.78-4.76 (m, 1H), 4.34-4.32 (m, 1H), 4.22 (d, J=4.5 Hz, 1H), 3.24-3.21 (m, 2H), 2.98-2.92 (m, 2H), 2.63-2.60 (m, 2H), 1.78-1.75 (m, 2H), 1.27 (s, 9H) ppm; ESI-MS (m/z): 516.3 [M+1]⁺.

Compound 309

N-(((2R,3S,4R,5R)-5-(6-amino-9H-purin-9-yl)-3,4-dihydroxytetrahydrofuran-2-yl)methyl)-N-(3-(3-(4-(tert-butyl)phenyl)ureido)propyl)methanesulfonamide

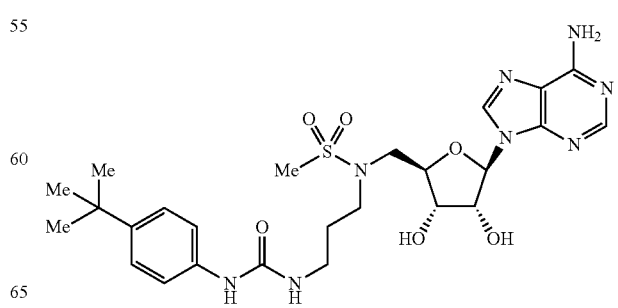

Step 1. N-(((3aR,4R,6R,6aR)-6-(6-amino-9H-purin-9-yl)-2,2-dimethyltetrahydrofuro[3,4-d][1,3]dioxol-4-yl)methyl)-N-(3-(3-(4-(tert-butyl)phenyl)ureido)propyl)methanesulfonamide

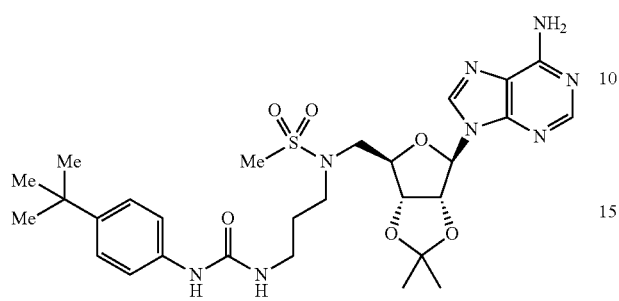

To a solution of 1-(3-(((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl)urea (500 mg, 0.93 mmol) in DCM (20 mL) was added K$_2$CO$_3$ (513 mg, 3.72 mmol) and MsCl (432 mg, 3.72 mmol). The mixture was stirred at rt overnight upon which water (20 mL) was added. The mixture was extracted with DCM (20 mL×3), the combined organic layers were dried over Na$_2$SO$_4$, filtered, concentrated and purified via SGC (DCM:MeOH=100:1 to 10:1) to give the title compound (260 mg, yield: 45%) as a white solid. $^1$H NMR (500 MHz, MeOD): δ 8.23 (s, 1H), 8.21 (s, 1H), 7.25-7.19 (m, 4H), 6.20 (d, J=2.0 Hz, 1H), 5.48 (dd, J=2.0, 6.0 Hz, 1H), 5.10 (dd, J=3.5, 6.0 Hz, 1H), 4.45 (brs, 1H), 3.56-3.48 (m, 2H), 3.18-3.04 (m, 4H), 2.77 (s, 3H), 1.1.61-1.55 (m, 5H), 1.34 (s, 3H), 1.27 (s, 9H) ppm; ESI-MS (m/z): 617.3 [M+1]$^+$.

Step 2. N-(((2R,3S,4R,5R)-5-(6-amino-9H-purin-9-yl)-3,4-dihydroxytetrahydrofuran-2-yl)methyl)-N-(3-(3-(4-(tert-butyl)phenyl)ureido)propyl)methanesulfonamide

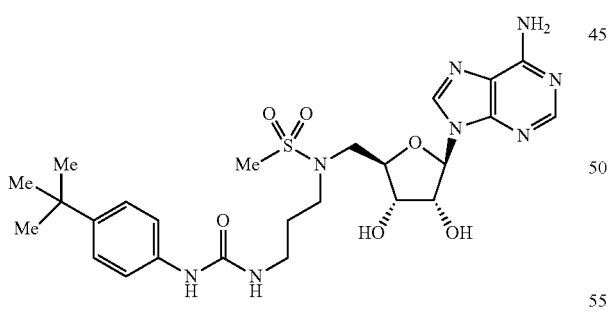

A solution of N-(((3aR,4R,6R,6aR)-6-(6-amino-9H-purin-9-yl)-2,2-dimethyltetrahydrofuro[3,4-d][1,3]dioxol-4-yl)methyl)-N-(3-(3-(4-(tert-butyl)phenyl)ureido)propyl)methanesulfonamide (255 mg, 0.41 mmol) in HCl/MeOH (2.5 mol/L) (12 mL) was stirred at rt for 2 h and concentrated to dryness. K$_2$CO$_3$ (228 mg) in water (0.5 mL) and MeOH (10 mL) were added. The resulting mixture was stirred for another 10 min at rt and filtered. The filtrate was concentrated and the resultant residue was purified by prep-HPLC to give the title compound (80 mg, yield: 33%) as a white solid. $^1$H NMR (500 MHz, MeOD): δ 8.30 (s, 1H), 8.23 (s, 1H), 7.29-7.22 (m, 4H), 6.02 (d, J=4.5 Hz, 1H), 4.81-4.79 (m, 1H), 4.33 (dd, J=2.0, 5.0 Hz, 2H), 3.72-3.63 (m, 2H), 3.42-3.16 (m, 4H), 2.92 (s, 3H), 1.83-1.80 (m, 2H), 1.31 (s, 9H) ppm; ESI-MS (m/z): 577.3 [M+1]$^+$.

Step 1. benzyl (3-((((3aR,4R,6R,6aR)-6-(6-amino-9H-purin-9-yl)-2,2-dimethyltetrahydrofuro[3,4-d][1,3]dioxol-4-ylmethyl)(methyl)amino)propyl)carbamate

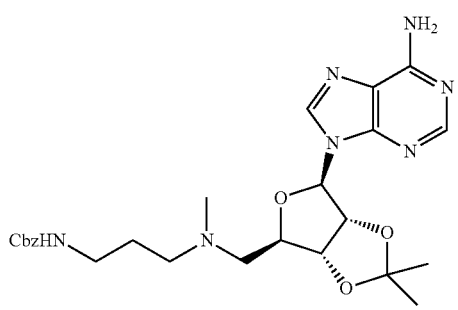 [SMILES: CN(CCCNC(=O)OCc1ccccc1)C[C@H]1O[C@@H](n2cnc3c(N)ncnc32)[C@@H]2OC(C)(C)O[C@@H]21]

To a stirred solution of 9-((3aR,4R,6R,6aR)-2,2-dimethyl-6-((methylamino)methyl)tetrahydrofuro[3,4-d][1,3]dioxol-4-yl)-9H-purin-6-amine (3.2 g, 10 mmol) in DCM (300 mL) was added a solution of benzyl 3-oxopropylcarbamate (2.28 g, 11 mmol) at room temperature. Acetic acid (0.6 g, 10 mmol) was added. The reaction mixture was stirred for 30 min, and then was cooled to 0° C. NaBH(OAc)$_3$ (4.24 g, 20 mmol) was added one portion. The reaction mixture was warmed to room temperature and stirred overnight. The reaction was quenched with water and concentrated under reduced pressure. The residue was extracted with DCM (100 mL×3). The organic layers were combined and washed with brine and dried over Na$_2$SO$_4$, then filtered and concentrated. The crude product was purified by flash chromatography on silica gel eluting with DCM/MeOH (100/1 to 60/1, v/v) to give 3.3 g of the desired product as a white solid (yield: 65%).

Step 2. N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine

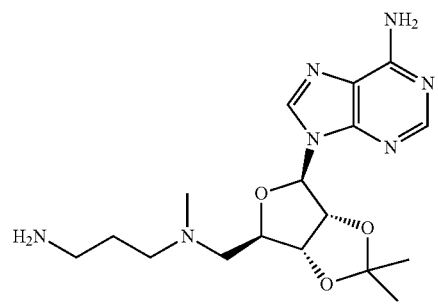 [SMILES: CN(CCCN)C[C@H]1O[C@@H](n2cnc3c(N)ncnc32)[C@@H]2OC(C)(C)O[C@@H]21]

Benzyl (3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl) carbamate (10.3 g, 20 mmol) was dissolved in methanol (200 mL) at room temperature. To the mixture was added Pd/C (1.8 g). The reaction was degassed three times and put under an atmosphere of hydrogen. The reaction was stirred overnight. The suspension was filtered and washed with methanol (40 mL×3). The filtrate was concentrated under reduced pressure to give 5.28 g of desired product as a white solid. $^1$H NMR (500 MHz, DMSO-d6) δ 8.34 (s, 1H), 8.17 (s, 1H), 7.34 (s, 2H), 6.13 (m, 1H), 5.48 (m, 1H), 4.94 (m, 1H), 4.22 (m, 1H), 3.47 (m, 2H), 3.41 (m, 2H), 2.53 (m, 2H), 2.31 (s, 2H), 2.12 (s, 3H), 1.53 (s, 3H), 1.42 (m, 2H), 1.33 (s, 3H).

Step 3. Representative Procedure for Isocyanate Formation

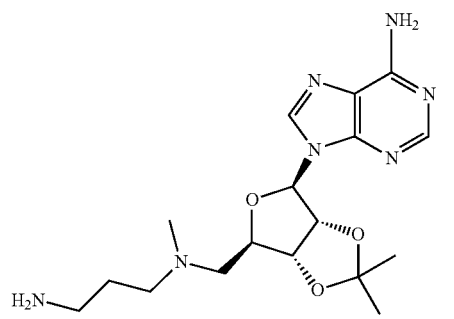

+

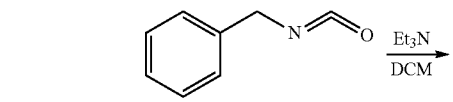

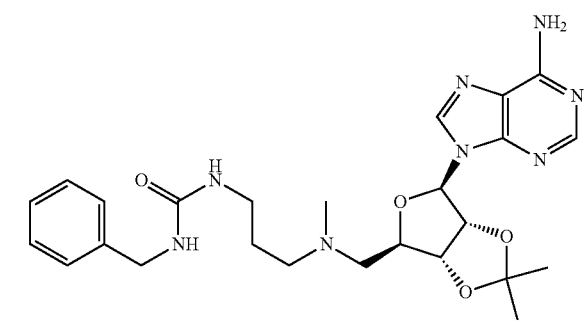

To a stirred solution of N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (70 mg, 0.186 mmol) and triethylamine (19 mg, 0.186 mmol) in DCM (2 mL) was added dropwise a solution of benzyl isocyanate (30 mg, 0.186 mmol) in DCM (1 mL) at −20° C. The reaction mixture was stirred for 30 min and quenched with methanol (0.1 mL). The reaction mixture was concentrated under reduced pressure. The residue was purified by prep-TLC eluting with CH$_2$Cl$_2$/MeOH (20/1, v/v) to give desired product (37 mg, 39%).

Representative Deprotection Reaction

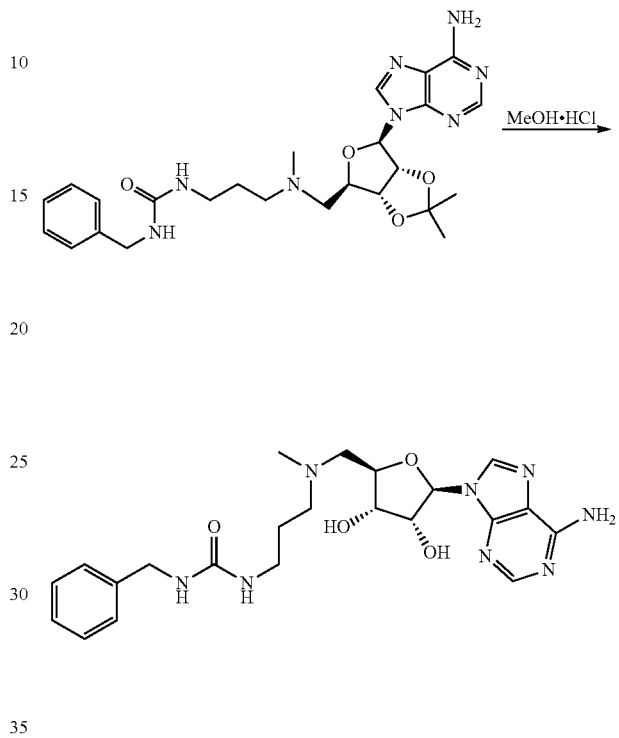

1-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-benzylurea (37 mg, 0.0725 mmol) was dissolved in MeOH.HCl (6 mL, 2M). The reaction mixture was stirred at room temperature for 3 h. The solvent was evaporated under reduced pressure. The residue was purified by reversed phase chromatography using water (0.1% NH$_4$HCO$_3$)/methanol as eluent to give desired product (23.4 mg, 69%) as a white solid. $^1$H NMR (500 MHz, CD$_3$OD) δ 8.26 (s, 1H), 8.22 (s, 1H), 7.21-7.31 (m, 5H), 5.98 (d, J=4.5 Hz, 1H), 4.70 (d, J=4.5 Hz, 1H), 4.21-4.26 (m, 4H), 3.15 (t, J=6.5 Hz, 2H), 2.79 (t, J=3.5 Hz, 2H), 2.50 (t, J=7.5 Hz, 2H), 2.30 (s, 3H), 1.66-1.68 (m, 2H).

Compound 310

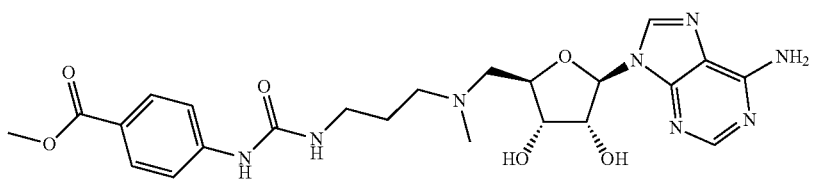 [SMILES: COC(=O)c1ccc(NC(=O)NCCCN(C)C[C@H]2O[C@@H](n3cnc4c(N)ncnc43)[C@H](O)[C@@H]2O)cc1]

methyl 4-(3-(3-(((((2R,3S,4R,5R)-5-(6-amino-9H-purin-9-yl)-3,4-dihydroxytetrahydrofuran-2-yl)methyl)(methyl)amino)propyl)ureido)benzoate was synthesized using the above procedures using methyl 4-isocyanatobenzoate instead of benzyl isocyanate. MS 514.5 (M$^+$+1).

Compound 311

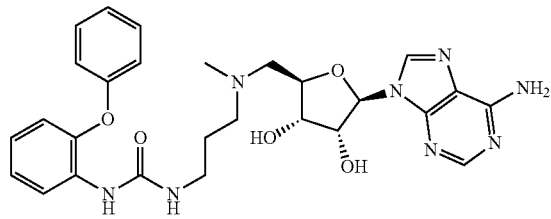 [SMILES: CN(CCCNC(=O)Nc1ccccc1Oc1ccccc1)C[C@H]1O[C@@H](n2cnc3c(N)ncnc32)[C@H](O)[C@@H]1O]

1-(3-((((2R,3S,4R,5R)-5-(6-amino-9H-purin-9-yl)-3,4-dihydroxytetrahydrofuran-2-yl)methyl)(methyl)amino)propyl)-3-(2-phenoxyphenyl)urea was synthesized using the above procedures using 1-isocyanato-2-phenoxybenzene instead of benzyl isocyanate. MS 549.3 (M$^+$+1).

Compound 312

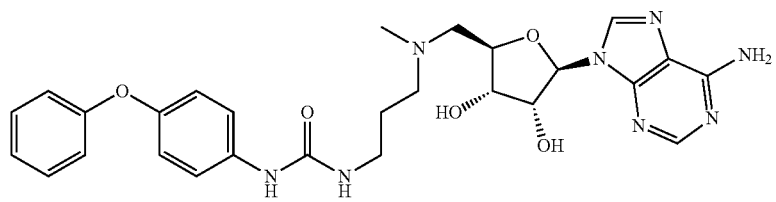 [SMILES: CN(CCCNC(=O)Nc1ccc(Oc2ccccc2)cc1)C[C@H]1O[C@@H](n2cnc3c(N)ncnc32)[C@H](O)[C@@H]1O]

1-(3-((((2R,3S,4R,5R)-5-(6-amino-9H-purin-9-yl)-3,4-dihydroxytetrahydrofuran-2-yl)methyl)(methyl)amino)propyl)-3-(4-phenoxyphenyl)urea was synthesized using the above procedures using 1-isocyanato-4-phenoxybenzene instead of benzyl isocyanate. MS 549.3 (M$^+$+1).

Compound 313

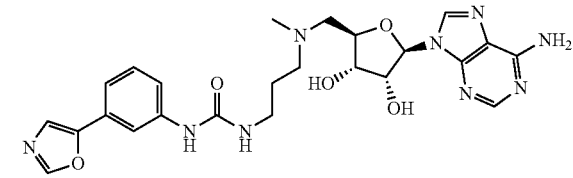 [SMILES: CN(CCCNC(=O)Nc1cccc(-c2cnco2)c1)C[C@H]1O[C@@H](n2cnc3c(N)ncnc32)[C@H](O)[C@@H]1O]

1-(3-((((2R,3S,4R,5R)-5-(6-amino-9H-purin-9-yl)-3,4-dihydroxytetrahydrofuran-2-yl)methyl)(methyl)amino)propyl)-3-(3-(oxazol-5-yl)phenyl)urea was synthesized using the above procedures using 5-(3-isocyanatophenyl)oxazole instead of benzyl isocyanate. MS 524.3 (M$^+$+1).

Compound 314

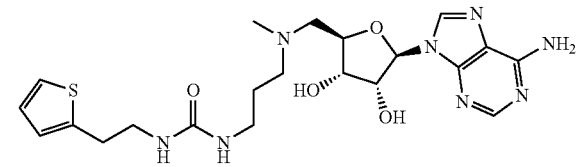 [SMILES: CN(CCCNC(=O)NCCc1cccs1)C[C@H]1O[C@@H](n2cnc3c(N)ncnc32)[C@H](O)[C@@H]1O]

1-(3-((((2R,3S,4R,5R)-5-(6-amino-9H-purin-9-yl)-3,4-dihydroxytetrahydrofuran-2-yl)methyl)(methyl)amino)propyl)-3-(2-(thiophen-2-yl)ethyl)urea was synthesized using the above procedures using 2-(2-isocyanatoethyl)thiophene instead of benzyl isocyanate. MS 491.2 (M$^+$+1).

Compound 315

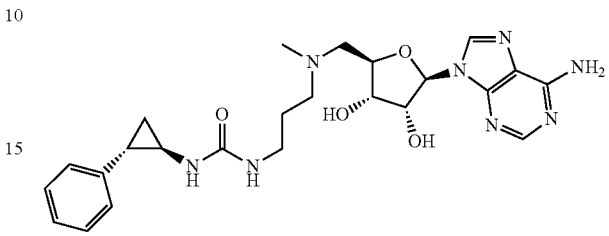

1-(3-((((2R,3S,4R,5R)-5-(6-amino-9H-purin-9-yl)-3,4-dihydroxytetrahydrofuran-2-yl)methyl)(methyl)amino)propyl)-3-((1R,2S)-2-phenylcyclopropyl)urea was synthesized using the above procedures using ((1S,2R)-2-isocyanatocyclopropyl)benzene instead of benzyl isocyanate. MS 497.2 (M$^+$+1).

Compound 316

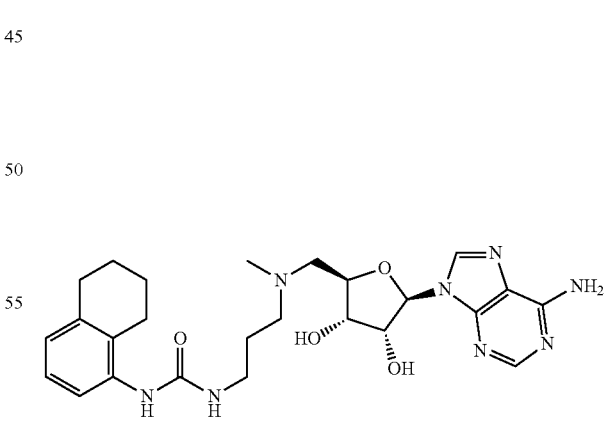

1-(3-((((2R,3S,4R,5R)-5-(6-amino-9H-purin-9-yl)-3,4-dihydroxytetrahydrofuran-2-yl)methyl)(methyl)amino)propyl)-3-(5,6,7,8-tetrahydronaphthalen-1-yl)urea was synthesized using the above procedures using 5-isocyanato-1,2,3,4-tetrahydronaphthalene instead of benzyl isocyanate. MS 511.3 (M$^+$+1).

Compound 317

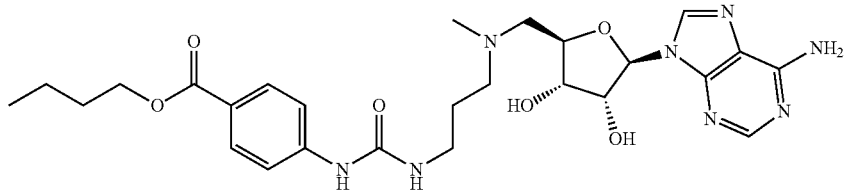 [SMILES: CCCCOC(=O)c1ccc(NC(=O)NCCCN(C)C[C@H]2O[C@@H](n3cnc4c(N)ncnc43)[C@H](O)[C@@H]2O)cc1]

butyl 4-(3-(3-((((2R,3S,4R,5R)-5-(6-amino-9H-purin-9-yl)-3,4-dihydroxytetrahydrofuran-2-yl)methyl)(methyl) amino)propyl)ureido)benzoate was synthesized using the above procedures using butyl 4-isocyanatobenzoate instead of benzyl isocyanate. MS 557.4 (M⁺+1).

Compound 318

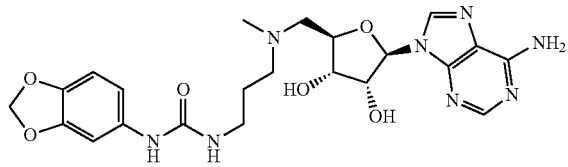 [SMILES: CN(CCCNC(=O)Nc1ccc2c(c1)OCO2)C[C@H]1O[C@@H](n2cnc3c(N)ncnc32)[C@H](O)[C@@H]1O]

1-(3-((((2R,3S,4R,5R)-5-(6-amino-9H-purin-9-yl)-3,4-dihydroxytetrahydrofuran-2-yl)methyl)(methyl)amino)propyl)-3-(benzo[d][1,3]dioxol-5-yl)urea was synthesized using the above procedures using butyl 5-isocyanatobenzo[d][1,3] dioxole instead of benzyl isocyanate. MS 501.2 (M⁺+1).

((3aS,4S,6R,6aR)-6-(6-amino-9H-purin-9-yl)-2,2 dimethyltetrahydro furo[3,4-d][1,3]dioxol-4-yl) methanethiol

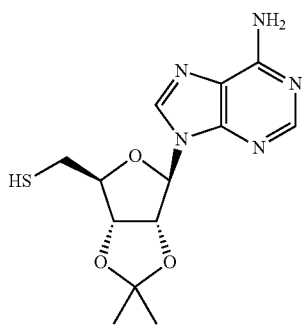 [SMILES: CC1(C)O[C@@H]2[C@H](O1)[C@@H](CS)O[C@H]2n1cnc2c(N)ncnc21]

Step 1. Preparation of (2R,3R,4S,5S)-2-(6-amino-9H-purin-9-yl)-5-(chloromethyl)tetrahydrofuran-3,4-diol

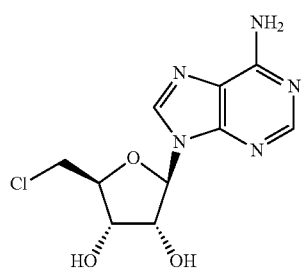 [SMILES: Nc1ncnc2c1ncn2[C@@H]1O[C@H](CCl)[C@@H](O)[C@H]1O]

To a solution of (2R,3R,4S,5R)-2-(6-amino-9H-purin-9-yl)-5-(hydroxymethyl)tetrahydrofuran-3,4-diol (1 g, 3.47 mmol) in pyridine (593 mg, 0.6 ml, 7.49 mmol) in acetonitrile (10 ml) cooled in an ice bath was added $SOCl_2$ (2.22 g, 1.36 ml, 18.65 mmol). Stirring was continued at 0-5° C. for 3-4 h, and warning to ambient temperature for overnight. The resulting suspension was concentrated in vacuo. To this reaction mixture was added methanol (20 ml), water (2 ml), and $NH_4OH$ (4 ml), followed by stirring for 0.5 h at room temperature. The reaction mixture was concentrated to dryness. The compound was dissolved in MeOH, silica gel (3 g) was added and then solvent was removed. The residue was purified by SGC to elute with EA:MeOH (0%-10%) to obtain the target compound (0.915 g, yield 86%) as yellowish solid. $^1$H NMR (500 MHz, MeOD): δ 8.24 (s, 1H), 8.02 (s, 1H), 7.27-7.20 (m, 5H), 6.19 (d, J=2.0 Hz, 1H), 5.48-5.46 (m, 1H), 5.08-5.06 (m, 1H), 4.43 (t, J=4.0, Hz, 1H), 3.83-3.81 (m, 2H), 3.01-2.99 (br s, 2H), 1.60 (s, 3H), 1.38 (s, 3H) ppm, LCMS (m/z): 395.8 [M+H]⁺.

Step 2. Preparation of 9-((3aR,4R,6S,6aS)-6-(chloromethyl)-2,2-dimethyltetrahydrofuro[3,4-d][1,3] dioxol-4-yl)-9H-purin-6-amine

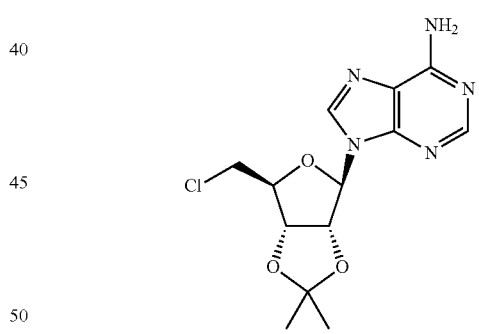

(2R,3R,4S,5S)-2-(6-amino-9H-purin-9-yl)-5-(chloromethyl)tetrahydrofuran-3,4-diol (20 g, 70.18 mmol) was suspended in dried acetone (400 mL) containing p-toluenesulfonic acid monohydrate (37.43 g, 197 mmol). Triethyl orthoformate (40 mL, 225 mmol) was then added over a period of 1 h at ambient temperature with vigorous stirring. The mixture was stirred overnight. The mixture was adjusted to pH=8 with saturated aqueous potassium carbonate, the precipitate was filtered off, the filtration was evaporated, extracted with EA (200 ml×4). The combined organic phase was washed with water (1*200 ml), dried and concentrated. The crude was recrystallized (PE:EA=10:1) to afford the product (18 g, yield: 82%) as a white solid. $^1$H NMR (500 MHz, $CDCl_3$): δ 8.36 (s, 1H), 7.93 (s, 1H), 6.12 (d, J=1.5 Hz, 1H), 5.68 (s, 2H), 5.47-5.46 (m, 1H), 5.17-5.15 (m, 1H), 4.50-4.47 (m, 1H), 3.84-3.80 (m, 1H), 3.65-3.62 (m, 1H), 1.63 (s, 3H), 1.41 (s, 3H) ppm. LCMS (m/z): 326.1 [M+H]+.

Step 3. Preparation of S-(((3aS,4S,6R,6aR)-6-(6-amino-9H-purin-9-yl)-2,2-dimethyltetrahydrofuro[3,4-d][1,3]dioxol-4-yl)methyl)ethanethioate

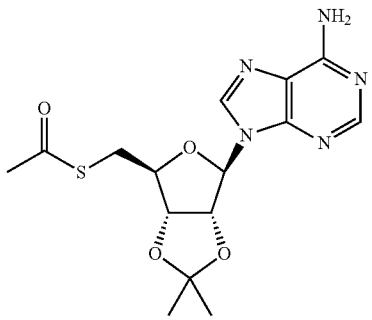 [SMILES: CC(=O)SC[C@H]1O[C@@H](n2cnc3c(N)ncnc32)[C@@H]2OC(C)(C)O[C@@H]21]

9-((3aR,4R,6S,6aS)-6-(chloromethyl)-2,2-dimethyltetrahydrofuro[3,4-d][1,3]dioxol-4-yl)-9H-purin-6-amine (5 g, 15.39 mmol) and AcSK (4.39 g, 38.48 mmol) in DMF (50 mL) was heated to 85° C. overnight. The mixture was added to EA (500 mL), washed with water (100 mL×3), dried and evaporated to afford the product (5.3 g, yield: 95%). The crude was directly used for next step without further purification. $^1$H NMR (500 MHz, CDCl$_3$): δ 8.34 (s, 1H), 7.90 (s, 1H), 6.06 (m, 3H), 5.51-5.450 (m, 1H), 4.98-4.96 (m, 1H), 4.33 (m, 1H), 3.30-3.15 (m, 2H), 2.37 (s, 3H), 1.58 (s, 3H), 1.37 (s, 3H) ppm. LCMS (m/z): 366.0 [M+H]+.

Step 4. Preparation of ((3aS,4S,6R,6aR)-6-(6-amino-9H-purin-9-yl)-2,2 dimethyltetrahydro furo[3,4-d][1,3]dioxol-4-yl)methanethiol

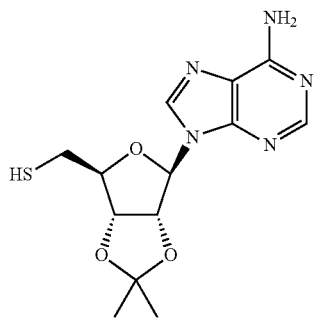 [SMILES: CC1(C)O[C@@H]2[C@H](O1)[C@@H](CS)O[C@H]2n1cnc2c(N)ncnc21]

S-(((3aS,4S,6R,6aR)-6-(6-amino-9H-purin-9-yl)-2,2-dimethyltetrahydrofuro[3,4-d][1,3]dioxol-4-yl)methyl)ethanethioate (1 g, 2.74 mmol) in NH$_3$/MeOH (15 mL) was stirred at rt for 10 min. The reaction was evaporated to dryness to obtain the product (850 mg, 95%). The crude was used directly used for next step without further purification. LCMS (m/z): 324.1 [M+H]+.

((3aR,4R,6R,6aR)-6-(6-chloro-9H-purin-9-yl)-2,2-dimethyltetrahydrofuro[3,4-d][1,3]dioxol-4-yl)methanol

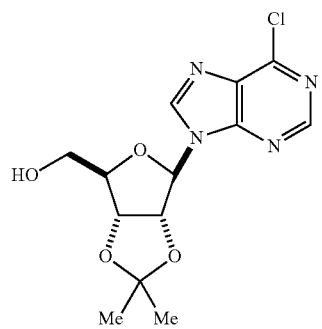

p-Toluenesulfonic acid monohydrate (19.8 g, 104 mmol) was added to a stirred suspension of (2R,3R,4S,5R)-2-(6-chloro-9H-purin-9-yl)-5-(hydroxymethyl)tetrahydrofuran-3,4-diol (3.0 g, 10.5 mmol) in dried acetone (300 mL). The solid dissolved 15 min later. 2 h later, the solution was poured into stirred aqueous NaHCO$_3$ (0.5 N, 300 mL) slowly. After removed acetone in vacuo, the mixture was extracted with DCM (100 mL×5). The combined organic layers were washed with water (100 mL) and brine (100 mL), then dried over Na$_2$SO$_4$, filtered and concentrated to afford the target (3.0 g, yield: 87%, purity >96%) as a pale solid. $^1$H NMR (500 MHz, CD$_3$OD) δ 8.71 (d, J=1.0 Hz, 1H), 8.65 (d, J=1.5 Hz, 1H), 6.23 (d, J=2.0 Hz, 1H), 5.29 (dd, J=2.0, 6.0 Hz, 1H), 4.96 (dd, J=2.0, 6.0 Hz, 1H), 4.31 (d, J=2.0 Hz, 1H), 3.68-3.59 (m, 2H), 1.51 (s, 3H), 1.29 (s, 3H) ppm; LCMS (m/z): 327.1 [M+1]+.

9-((3aR,4R,6R,6aR)-6-(aminomethyl)-2,2-dimethyltetrahydrofuro[3,4-d][1,3]dioxol-4-yl)-9H-purin-6-amine

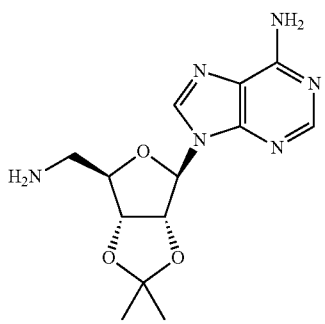 [SMILES: CC1(C)O[C@@H]2[C@H](O1)[C@@H](CN)O[C@H]2n1cnc2c(N)ncnc21]

Step 1. Preparation of ((3aR,4R,6R,6aR)-6-(6-amino-9H-purin-9-yl)-2,2-dimethyltetrahydrofuro[3,4-d][1,3]dioxol-4-yl)methanol

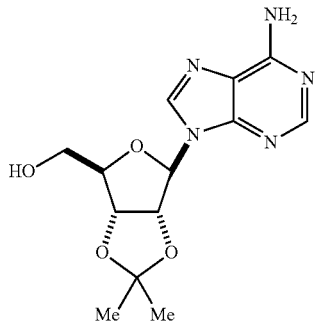

(2R,3R,4S,5R)-2-(6-amino-9H-purin-9-yl)-5-(hydroxymethyl)tetrahydrofuran-3,4-diol (200 g, 748 mmol) was suspended in dried acetone (5 L) containing p-toluenesulfonic acid monohydrate (400 g, 2 mol). Triethyl orthoformate (400 ml, 2.4 mol) was then added over a period of 1 h at ambient temperature with vigorous stirring to give a clear solution and then a white solid formed after a while. The mixture was stirred overnight. The mixture was adjusted pH=8 with saturated aqueous potassium carbonate. The precipitate was filtered off, the filtrate was evaporated and the residue was extracted with EA (1000 ml×12). The combined organic phase was washed with saturated aqueous potassium carbonate (100 ml×2) and water (200 ml), dried and concentrated. The crude was triturated (PE:EA=10:1) to afford the target (190 g, yield: 85%) as a white solid.

Step 2. Preparation of 2-(((3aR,4R,6R,6aR)-6-(6-amino-9H-purin-9-yl)-2,2-dimethyltetrahydrofuro[3,4-d][1,3]dioxol-4-yl)methyl)isoindoline-1,3-dione

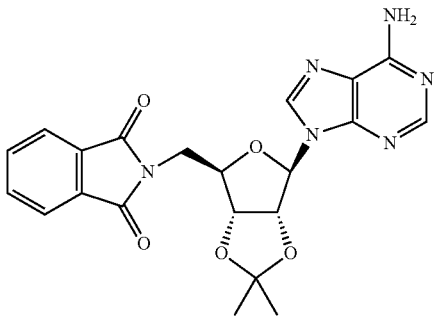 [SMILES: CC1(C)O[C@@H]2[C@H](O1)[C@@H](CN1C(=O)c3ccccc3C1=O)O[C@H]2n1cnc2c(N)ncnc21]

To a suspension of ((3 aR,4R,6R,6aR)-6-(6-amino-9H-purin-9-yl)-2,2-dimethyltetrahydro furo[3,4-d][1,3]dioxol-4-yl)methanol (40 g, 130 mmol), phthalimide (20 g, 134 mmol) and triphenylphosphine (34 g, 130 mmol) in anhydrous THF (600 ml) was added diethylazodicarboxylate (23 g, 130 mmol) at room temperature. The suspension became an orange solution with generation of heat. After 10 min, a precipitate appeared. After stifling for 2 h, the suspension was filtered. The solid was rinsed with ether (100 ml×2) and dried to afford the target (40 g, yield: 71%) as a pale solid.

Step 3. Preparation of 9-((3aR,4R,6R,6aR)-6-(aminomethyl)-2,2-dimethyltetrahydrofuro[3,4-d][1,3]dioxol-4-yl)-9H-purin-6-amine

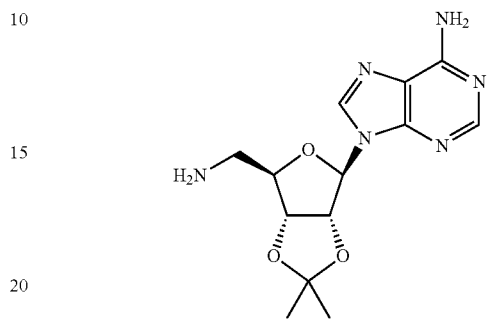

To a suspension of 2-(((3aR,4R,6R,6aR)-6-(6-amino-9H-purin-9-yl)-2,2-dimethyltetrahydrofuro[3,4-d][1,3]dioxol-4-yl)methyl)isoindoline-1,3-dione (53 g, 121 mmol) in ethanol (1.6 L) was added 85% hydrazine hydrate (120 ml, 2.18 mol). The reaction mixture was refluxed for 3 h and cooled to room temperature. The suspension was filtered and washed with ethanol (100 ml). The filtrate was evaporated to dryness to give the crude. The crude was dissolved in CHCl$_3$ (500 ml) and filtered. The filtrate was evaporated to dryness to give the crude. The crude was washed with ethyl acetate (100 ml×2) and petroleum ether (150 ml) to afford the target compound (35 g, yield: 76%) as a white solid.

9-((3aR,4R,6R,6aR)-6-((benzylamino)methyl)-2,2-dimethyltetrahydrofuro[3,4-d][1,3]dioxol-4-yl)-9H-purin-6-amine

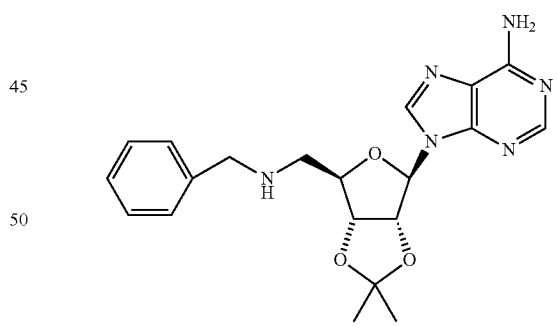

A solution of 9-((3aR,4R,6R,6aR)-6-(aminomethyl)-2,2-dimethyltetrahydrofuro[3,4-d][1,3]dioxol-4-yl)-9H-purin-6-amine (10.58 g, 34.56 mmol) and benzaldehyde (4.63 g, 43.72 mmol) in methanol (200 mL) was stirred for 0.5 h at room temperature. After 0.5 h NaBH(OAc)$_3$ (11.73 g, 55.3 mmol) was added. The reaction mixture was stirred for 2 h. The reaction mixture was adjusted to pH=8 with saturated aqueous potassium carbonate (120 ml). The precipitate was filtered off. The filtrate was evaporated to afford the crude. The crude was purified by SGC to elute with EA:MeOH (0%-10%) to obtain the product (7.6 g, yield 56%) as pale yellowish solid. $^1$H NMR (500 MHz, MeOD): δ 8.24 (s, 1H), 8.02 (s, 1H), 7.27-7.20 (m, 5H), 6.19 (d, J=2.0 Hz, 1H), 5.48-5.46 (m, 1H), 5.08-5.06 (m, 1H), 4.43 (t, J=4.0, Hz, 1H), 3.83-3.81 (m, 2H), 3.01-2.99 (br s, 2H), 1.60 (s, 3H), 1.38 (s, 3H) ppm. LCMS (m/z): 395.8 [M+H]$^+$.

Compound 319

(2R,3R,4S,5R)-2-(6-aminopurin-9-yl)-5-[[4-(5-tert-butyl-1H-benzimidazol-2-yl)butyl-isopropyl-amino]methyl]tetrahydrofuran-3,4-diol

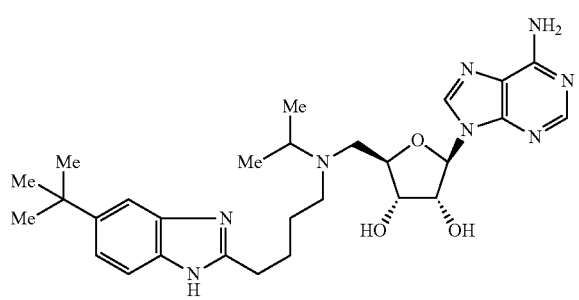 [SMILES: CC(C)N(CCCCc1nc2cc(C(C)(C)C)ccc2[nH]1)C[C@H]1O[C@@H](n2cnc3c(N)ncnc32)[C@H](O)[C@@H]1O]

Step 1. Preparation of 4-(5-tert-butyl-1H-benzimidazol-2-yl)butan-1-ol

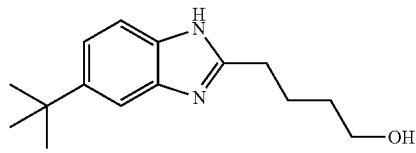 [SMILES: CC(C)(C)c1ccc2[nH]c(CCCCO)nc2c1]

A mixture of 4-tert-butylbenzene-1,2-diamine (646 mg, 3.93 mmol) and tetrahydropyran-2-one (1.18 g, 11.80 mmol) in 50 mL of 4 M HCl was refluxed for 8 h. Then the mixture was neutralized with $K_2CO_3$ (aq) to pH=8. The mixture was extracted with DCM (30 mL x4). The organic layers were concentrated and the residue was purified by SGC (DCM:MeOH=20:1) to afford the product (650 mg, yield: 67%) as a pale solid. MS (ESI): m/z 247.7 [M+1]$^+$.

Step 2. Preparation of 7-tert-butyl-1,2,3,4-tetrahydropyrido[1,2-a]benzimidazol-1-ol

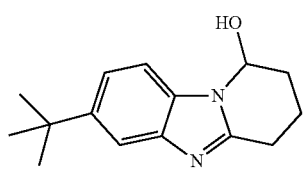 [SMILES: CC(C)(C)c1ccc2c(c1)nc1n2C(O)CCC1]

A mixture of 4-(5-tert-butyl-1H-benzimidazol-2-yl)butan-1-ol (50 mg, 0.203 mmol) and IBX (170 mg, 0.609 mmol) in 8 mL of EA was refluxed for 1.5 h. The mixture was cooled to rt and filtered, then concentrated to afford the product (50 mg, yield: 100%) as a pale oil. $^1$H NMR (500 MHz, MeOD): δ 7.52-7.60 (m, 1H), 7.43-7.45 (m, 1H), 7.27-7.29 (m, 1H), 5.88-5.94 (m, 1H), 2.69-2.72 (m, 2H), 2.04-2.16 (m, 4H), 1.37 (s, 9H) ppm. MS (ESI): m/z 245.7 [M+1]$^+$ Step 3. Preparation of 9-((3aR,4R,6R,6aR)-6-(((4-(5-(tert-butyl)-1H-benzo[d]imidazol-2-yl)butyl)(isopropyl)amino)methyl)-2,2-dimethyltetrahydrofuro[3,4-d][1,3]dioxol-4-yl)-9H-purin-6-amine

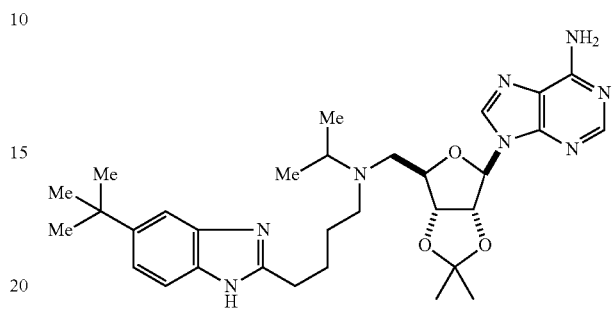

To a stirred solution of] 9-((3aR,4R,6R,6aR)-6-((isopropylamino)methyl)-2,2-dimethyltetrahydrofuro[3,4-d][1,3]dioxol-4-yl)-9H-purin-6-amine (70 mg, 0.201 mmol) and 7-tert-butyl-1,2,3,4-tetrahydropyrido[1,2-a]benzimidazol-1-ol (50 mg, 0.205 mmol) in 8 mL of DCE was added NaBH(OAc)$_3$ (128 mg, 0.615 mmol). Then the mixture was stirred at rt overnight. NaHCO$_3$ (aq) was added to quench the reaction and the mixture was extracted with DCM (15 mL×4). The organic phase was concentrated and the residue was purified by Prep-TLC(CH$_3$OH:DCM=1:18) to afford the product (18 mg, yield: 15%) as a white solid. $^1$H NMR (500 MHz, MeOD): δ 8.22 (s, 2H), 7.49 (d, J=1.0 Hz, 1H), 7.41 (d, J=8.5 Hz, 1H), 728-7.30 (m, 1H), 6.15 (d, J=2.0 Hz, 1H), 4.99-5.02 (m, 1H), 4.20-4.30 (m, 1), 2.50-3.00 (m, 7H), 1.70-1.80 (m, 2H), 1.52 (s, 3H), 1.38-1.52 (m, 2H), 1.37 (s, 9H), 1.35 (s, 3H), 1.03 (d, J=7.0 Hz, 3H), 0.85 (d, J=6.5 Hz, 3H) ppm. MS (ESI): m/z 577.7 [M+1]$^+$.

Step 4. Preparation of (2R,3R,4S,5R)-2-(6-aminopurin-9-yl)-5-[[4-(5-tert-butyl-1H-benzimidazol-2-yl)butyl-isopropyl-amino]methyl]tetrahydrofuran-3,4-diol

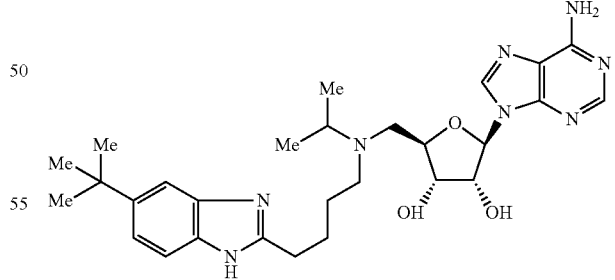

To a mixture of gas HCl (dissolved in MeOH solution, 2.5 M, 8 mL) was added 9-((3aR,4R,6R,6aR)-6-(((4-(5-(tert-butyl)-1H-benzo[d]imidazol-2-yl)butyl)(isopropyl)amino)methyl)-2,2-dimethyltetrahydrofuro[3,4-d][1,3]dioxol-4-yl)-9H-purin-6-amine (18 mg, 0.0312 mmol). The solution was allowed to stand at room temperature for 2 h and evaporated to dryness. Then the residue was dissolved in MeOH (5 mL). The solution was neutralized by K$_2$CO$_3$ (44 mg, dissolved in 0.5 mL of H₂O) with stirring at rt for 30 min. The solvent was removed in vacuo then the crude was purified by Prep-TLC(CH₃OH:DCM:NH₄OH=12.5:100:3) to afford the product 10 mg, yield: 60%) as a white solid. ¹H NMR (500 MHz, MeOD): δ 8.25 (s, 1H), 8.20 (s, 1H), 7.50 (d, J=1.5 Hz, 1H), 7.40 (d, J=8.5 Hz, 1H), 7.28-7.30 (m, 1H), 5.96 (d, J=4.5 Hz, 1H), 4.76-4.77 (m, 1H), 4.34 (d, J=5.5 Hz, 1H), 4.15-4.17 (m, 1H), 2.70-3.20 (m, 7H), 1.84 (t, J=7.5 Hz, 2H), 1.59 (br s, 2H), 1.36 (s, 9H), 1.10 (d, J=6.5 Hz, 3H), 1.04 (d, J=6.5 Hz, 3H) ppm; ESI-MS (m/z): 537.7 [M+1]⁺.

Compound 320

(2R,4S,5R)-2-(6-aminopurin-9-yl)-5-[[4-[(5-tert-butyl-1H-benzimidazol-2-yl)amino]butyl-isopropyl-amino]methyl]tetrahydrofuran-3,4-diol

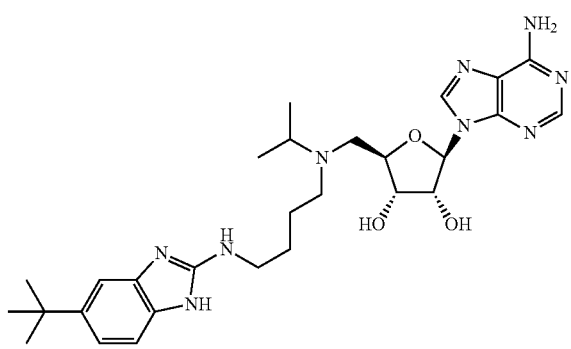 [SMILES: CC(C)N(CCCCNc1nc2cc(C(C)(C)C)ccc2[nH]1)C[C@H]1O[C@@H](n2cnc3c(N)ncnc32)[C@H](O)[C@@H]1O]

Step 1. Preparation of 2-(4-hydroxybutyl)isoindoline-1,3-dione

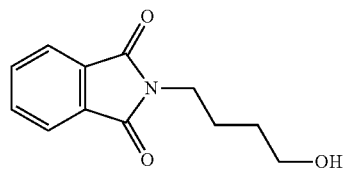 [SMILES: O=C1c2ccccc2C(=O)N1CCCCO]

To a solution of isobenzofuran-1,3-dione (3.4 g, 22.47 mmol) in toluene (50 mL) was added 4-aminobutan-1-ol (2.0 g, 22.47 mmol). The mixture was heated to reflux for 4 h. The mixture was concentrated. Saturated aqueous NaHCO₃ (30 mL) and EA (30 mL×3) were added. The combined organic layers were dried over Na₂SO₄ and concentrated to afford crude product (4.2 g, yield: 85%) as a white solid. ¹H NMR (500 Hz, CDCl₃): δ7.84 (dd, J=3.0, 5.5 Hz, 2H), 7.71 (dd, J=2.5, 5.0 Hz, 2H), 3.76-3.68 (m, 4H), 1.82-1.75 (m, 2H), 1.65-1.59 (m, 2H) ppm; ESI-MS (m/z): 220.0 [M+1]⁺.

Step 2. Preparation of 2-(4-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)butyl)isoindoline-1,3-dione

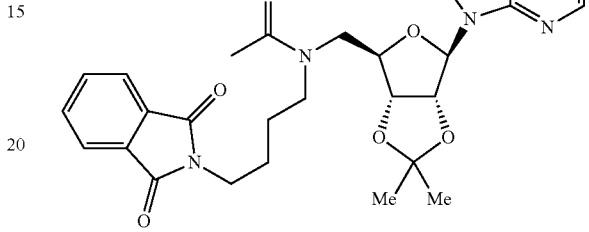

To a solution of 2-(4-hydroxybutyl)isoindoline-1,3-dione (1.7 g, 7.76 mmol) in EA (50 mL) was added IBX (5.4 g, 19.40 mmol). The mixture was heated to reflux for 2 h. After cooling, the mixture was filtered and the filtrate was concentrated to give crude product (1.6 g) which was used directly for next step. To a solution of 9-((3aR,4R,6R,6aR)-6-((isopropylamino)methyl)-2,2-dimethyltetrahydrofuro[3,4-d][1,3]dioxol-4-yl)-9H-purin-6-amine (1.3 g, 3.73 mmol) and 4-(1,3-dioxoisoindolin-2-yl)butanal (from last step) in DCE (50 mL) was added NaBH(OAc)₃ (1.6 g, 7.47 mmol). The reaction mixture was stirred at rt overnight, then saturated aqueous NaHCO₃ (50 mL) was added. The resulting mixture was extracted with DCM (50 mL×3). The combined organic layers were dried over Na₂SO₄ and concentrated. The residue was purified by SGC (DCM:MeOH=100:1 to 30:1) to afford the product (1.5 g, yield: 75%) as a white solid. ¹H NMR (500 MHz, MeOD): δ8.27 (s, 1H), 8.22 (s, 1H), 7.86-7.79 (m, 4H), 6.16 (brs, 1H), 5.50 (t, J=4.5 Hz, 1H), 5.05 (brs, 1H), 4.31 (brs, 1H), 3.66-3.63 (m, 2H), 3.18-2.49 (m, 5H), 1.69-1.64 (m, 2H), 1.57 (s, 3H), 1.51-1.35 (m, 5H), 1.04-0.99 (s, 3H), 0.92-0.87 (s, 3H) ppm; ESI-MS (m/z): 550.3 [M+1]⁺.

Step 3. Preparation of N1-(((3aR,4R,6R,6aR)-6-(6-amino-9H-purin-9-yl)-2,2-dimethyltetrahydrofuro[3,4-d][1,3]dioxol-4-yl)methyl)-N1-isopropylbutane-1,4-diamine

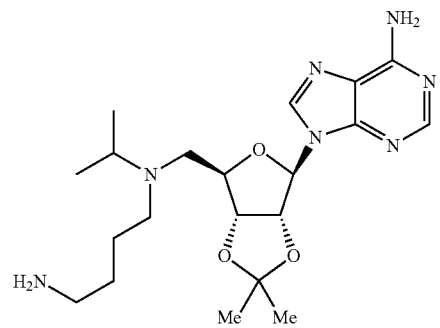 [SMILES: CC(C)N(CCCCN)C[C@H]1O[C@@H](n2cnc3c(N)ncnc32)[C@@H]2OC(C)(C)O[C@@H]21]

To a solution of 2-[4-[[(3aR,4R,6R)-6-(6-aminopurin-9-yl)-2,2-dimethyl-3a,4,6,6a-tetrahydrofuro[3,4-d][1,3]dioxol-4-yl]methyl-isopropyl-amino]butyl]isoindoline-1,3-dione (1.0 g, 1.87 mmol) in EtOH (35 mL) was added NH$_2$—NH$_2$.H$_2$O (85%) (0.44 g, 7.48 mmol) and the mixture was heated to reflux for 2 h. After cooling, the reaction mixture was filtered and the filtrate was concentrated. DCM (60 mL) was added and filtered, the filtrate was concentrated to afford the product (700 mg, yield: 92%) as a white solid. $^1$H NMR (500 MHz, MeOD): δ8.29 (d, J=4.5 Hz, 1H), 8.25 (d, J=4.5 Hz, 1H), 6.19 (t, J=3.5 Hz, 1H), 5.58 (dd, J=3.0, 5.0 Hz, 1H), 5.05 (brs, 1H), 4.29 (brs, 1H), 2.95-2.94 (m, 1H), 2.73-2.49 (m, 6H), 1.61 (d, J=4.0 Hz, 3H), 1.48-1.41 (m, 5H), 1.01-0.99 (m, 3H), 0.85-0.83 (m, 3H) ppm; ESI-MS (m/z): 420.2 [M+1]$^+$.

Step 4. Preparation of N1-(((3aR,4R,6R,6aR)-6-(6-amino-9H-purin-9-yl)-2,2-dimethyltetrahydrofuro[3,4-d][1,3]dioxol-4-yl)methyl)-N$^4$-(5-(tert-butyl)-1H-benzo[d]imidazol-2-yl)-N1-isopropylbutane-1,4-diamine

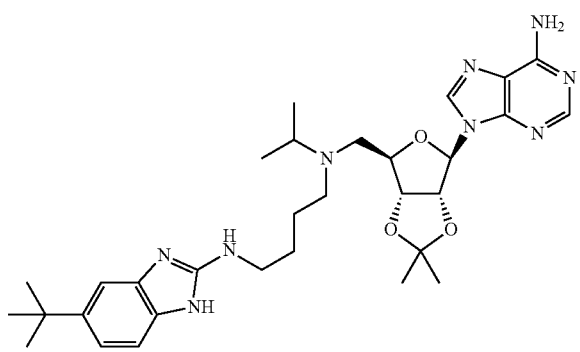 [SMILES: CC(C)N(CCCCNc1nc2cc(C(C)(C)C)ccc2[nH]1)C[C@H]1O[C@@H](n2cnc3c(N)ncnc32)[C@@H]2OC(C)(C)O[C@@H]21]

2-chloro-5-isopropyl-1H-benzimidazole (240 mg, 1.20 mmol), N-[[(3aR,4R,6R)-6-(6-aminopurin-9-yl)-2,2-dimethyl-3a,4,6,6a-tetrahydrofuro[3,4-d][1,3]dioxol-4-yl]methyl]-N-isopropyl-butane-1,4-diamine (250 mg, 0.60 mmol) and DIPEA (125 mg, 1.80 mmol) were dissolved in t-BuOH (3 mL) and treated with KI (10 mg, cat.). The mixture was irradiated by microwave at 160° C. for 4 h. Solvent was removed in vacuo and the crude was purified by SGC (DCM: MeOH=100:1 to 10:1) to afford the product (200 mg, yield: 57%) as a yellow solid. $^1$H NMR (500 MHz, MeOD): δ 8.23-8.22 (m, 2H), 7.28-7.13 (m, 3H), 6.17 (d, J=2.5 Hz, 1H), 5.52 (brs, 1H), 5.03 (dd, J=3.0, 6.5 Hz, 1H), 4.35 (brs, 1H), 3.33-3.20 (m, 2H), 3.08-2.56 (m, 5H), 1.63-1.54 (m, 7H), 1.36-1.31 (m, 12H), 1.04 (d, J=6.5 Hz, 3H), 0.88 (d, J=6.5 Hz, 3H) ppm; ESI-MS (m/z): 592.5 [M+1]$^+$.

Step 5. Preparation of (2R,3R,4S,5R)-2-(6-amino-9H-purin-9-yl)-5-(((4-((5-(tert-butyl)-1H-benzo[d]imidazol-2-yl)amino)butyl)(isopropyl)amino)methyl)tetrahydrofuran-3,4-diol

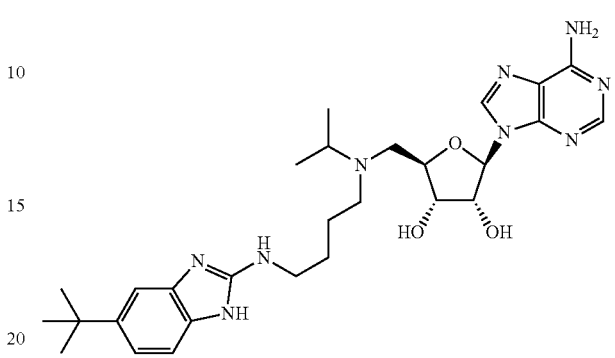

A solution of N-[[(4R,6R,6aR)-4-(6-aminopurin-9-yl)-2,2-dimethyl-3a,4,6,6a-tetrahydrofuro[3,4-d][1,3]dioxol-6-yl]methyl]-N'-(5-tert-butyl-1H-benzimidazol-2-yl)-N-isopropyl-butane-1,4-diamine (200 mg, 0.34 mmol) in HCl/MeOH (2.5 mol/L) (10 mL) was stirred at rt for 2 h and concentrated to dryness. K$_2$CO$_3$ (186 mg) in water (0.5 mL) and MeOH (10 mL) were added. The resulting mixture was stirred for another 10 min at rt and filtrated. The filtrate was concentrated. The residue was purified by Prep-HPLC to afford the product (90 mg, yield: 49%) as a white solid. $^1$H NMR (500 MHz, MeOD): δ8.27 (s, 1H), 8.20 (s, 1H), 7.24-7.03 (m, 3H), 5.96 (d, J=4.5 Hz, 1H), 4.74 (t, J=10.0 Hz, 1H), 4.30 (t, J=10.5 Hz, 1H), 4.13 (brs, 1H), 3.33-3.32 (m, 2H), 3.08-2.58 (m, 5H), 1.66-1.58 (m, 4H), 1.36 (s, 9H), 1.06 (d, J=6.5 Hz, 3H), 1.00 (d, J=6.0 Hz, 3H) ppm; ESI-MS (m/z): 552.4 [M+1]$^+$.

Compound 321

(2R,3R,4S,5S)-2-(6-amino-9H-purin-9-yl)-5-(((4-(5-(tert-butyl)-1H-benzo[d]imidazol-2-yl)butyl)sulfonyl)methyl)tetrahydrofuran-3,4-diol

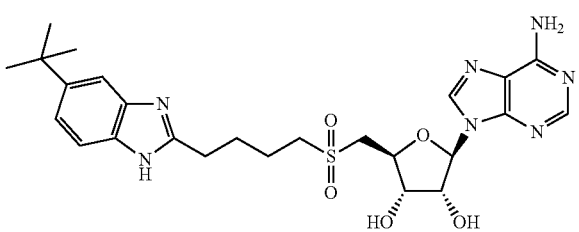 [SMILES: CC(C)(C)c1ccc2[nH]c(CCCCS(=O)(=O)C[C@H]3O[C@@H](n4cnc5c(N)ncnc54)[C@H](O)[C@@H]3O)nc2c1]

Step 1. Preparation of methyl 5-(((((3aS,4S,6R,6aR)-6-(6-amino-9H-purin-9-yl)-2,2-dimethyltetrahydrofuro[3,4-d][1,3]dioxol-4-yl)methyl)thio)pentanoate

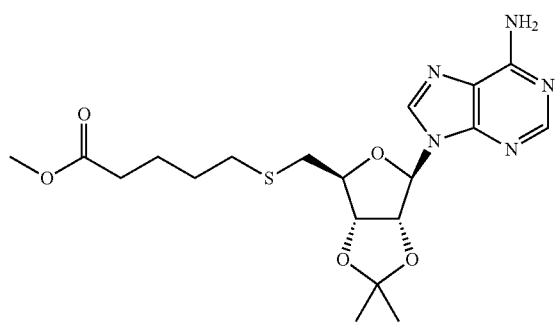 [SMILES: COC(=O)CCCCSC[C@H]1O[C@@H](n2cnc3c(N)ncnc32)[C@@H]2OC(C)(C)O[C@@H]21]

A solution of methyl 5-bromopentanoate (1 g, 5.26 mmol), ((3aS,4S,6R,6aR)-6-(6-amino-9H-purin-9-yl)-2,2-dimethyltetrahydrofuro[3,4-d][1,3]dioxol-4-yl)methanethiol (980 mg, 2.29 mmol) and $K_2CO_3$ (632 mg, 4.58 mmol) in DMF (6 mL) was heated to 100° C. for 30 min. The reaction was added water (20 mL), extracted with EA (3×50 mL), washed with water (20 mL) and brine (20 mL), dried and concentrated. The residue was purified by Prep-HPLC to obtain the product (600 mg, Yield 38%). $^1$H NMR (500 MHz, MeOD): δ 8.27 (s, 1H), 8.22 (s, 1H), 6.17 (d, J=2.5 Hz, 1H), 5.5-5.53 (m, 1H), 5.06-5.04 (m, 1H), 4.33 (d, J=2.5 Hz, 1H), 3.63 (s, 3H), 2.78 (d, J=7.0 Hz, 2H), 2.46 (t, J=7.0 Hz, 2H), 2.25 (t, J=7.0 Hz, 2H), 1.60-1.56 (m, 5H), 1.47 (t, J=7.0 Hz, 2H), 1.38 (s, 3H) ppm; ESI-MS (m/z): 438.3[M+1]+.

Step 2. Preparation of 5-(((((3aS,4S,6R,6aR)-6-(6-amino-9H-purin-9-yl)-2,2-dimethyltetrahydrofuro[3,4-d][1,3]dioxol-4-yl)methyl)thio)pentanoic acid

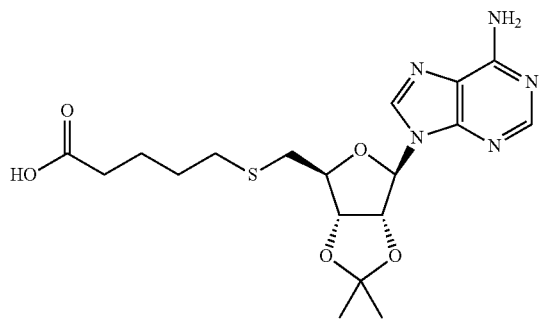 [SMILES: CC1(C)O[C@@H]2[C@H](O1)[C@@H](CSCCCCC(=O)O)O[C@H]2n1cnc2c(N)ncnc21]

A solution of methyl 5-(((((3aS,4S,6R,6aR)-6-(6-amino-9H-purin-9-yl)-2,2-dimethyltetrahydrofuro[3,4-d][1,3]dioxol-4-yl)methyl)thio)pentanoate (1200 mg, 2.88 mmol) and LiOH (606 mg, 14.42 mmol) in MeOH (20 mL) was stirred at rt overnight. The reaction was adjusted pH=6 with aqu. 1 N HCl, evaporated and extracted with EA (3×20 mL), washed with brine (20 mL), dried and concentrated to obtain the product (1100 mg, crude). The crude was directly used for next step without further purification. ESI-MS (m/z): 424.2 [M+1]+.

Step 3. Preparation of N-(2-amino-4-(tert-butyl)phenyl)-5-(((((3aS,4S,6R,6aR)-6-(6-amino-9H-purin-9-yl)-2,2-dimethyltetrahydrofuro[3,4-d][1,3]dioxol-4-yl)methyl)thio)pentanamide

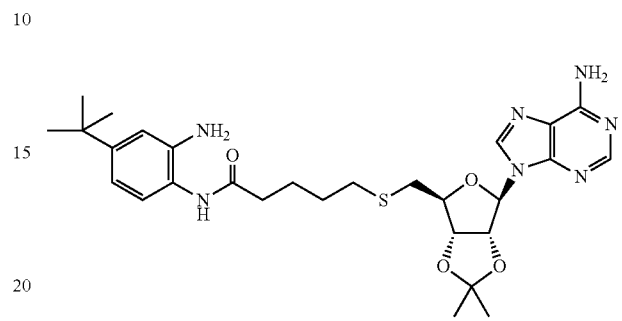

A solution of 5-(((((3aS,4S,6R,6aR)-6-(6-amino-9H-purin-9-yl)-2,2-dimethyltetrahydrofuro[3,4-d][1,3]dioxol-4-yl)methyl)thio)pentanoic acid (1100 mg, 2.88 mmol), HOBT (778 mg, 5.76 mmol) and EDCI (1100 mg, 5.76 mmol) in DCM (25 mL) were added 4-tert-butylbenzene-1,2-diamine (614 mg, 3.74 mmol) in DCM (5 mL) and TEA (1160 mg, 11.52 mmol). The reaction was stirred at rt overnight. The reaction was diluted with DCM (30 mL), washed with water (20 mL) and brine (20 mL), dried and concentrated. The residue was purified by SGC to obtain the product (1200 mg, Yield 75%). $^1$H NMR (500 MHz, MeOD): δ 8.27 (s, 1H), 8.23 (s, 1H), 6.99-6.74 (m, 3H), 6.17 (s, 1H), 5.54 (d, J=5.5 Hz, 1H), 5.05 (d, J=5.5 Hz, 1H), 4.356-4.343 (m, 1H), 2.70-2.65 (m, 2H), 2.53-2.50 (m, 2H), 2.36-2.33 (m, 2H), 1.72-1.68 (m, 2H), 1.58 (s, 3H), 1.38 (s, 3H), 1.34-1.32 (m, 2H), 1.26 (s, 9H) ppm; ESI-MS (m/z): 570.3[M+1]+.

Step 4. Preparation of 9-((3aR,4R,6S,6aS)-6-(((4-(5-(tert-butyl)-1H-benzo[d]imidazol-2-yl)butyl)thio)methyl)-2,2-dimethyltetrahydrofuro[3,4-d][1,3]dioxol-4-yl)-9H-purin-6-amine

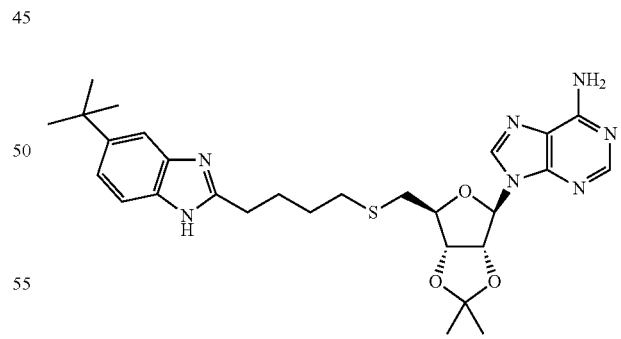

A solution of N-(2-amino-4-(tert-butyl)phenyl)-5-(((((3aS,4S,6R,6aR)-6-(6-amino-9H-purin-9-yl)-2,2-dimethyltetrahydrofuro[3,4-d][1,3]dioxol-4-yl)methyl)thio)pentanamide (1180 mg, 2.05 mmol) in AcOH (15 mL) was heated to 60° C. overnight. The reaction was concentrated to dryness, dissolved in MeOH (2 mL) and EA (100 mL), washed with aq. sat. $NaHCO_3$ (10×2 mL), dried and evaporated to give the crude. The residue was purified by Prep-HPLC to obtain the product (700 mg, Yield 60%). $^1$H NMR (500 MHz, MeOD):

δ 8.27 (s, 1H), 8.22 (s, 1H), 7.49-7.87 (m, 3H), 6.17 (d, J=2.5 Hz, 1H), 5.52-5.51 (m, 1H), 5.05-5.03 (m, 1H), 4.35-4.32 (m, 1H), 2.28-2.76 (m, 4H), 2.53 (t, J=7.0 Hz, 2H), 1.87-1.83 (m, 2H), 1.57-1.38 (m, 5H), 1.37 (s, 12H) ppm; ESI-MS (m/z): 552.3 [M+1]$^+$.

Step 5. Preparation of 9-((3aR,4R,6S,6aS)-6-(((4-(5-(tert-butyl)-1H-benzo[d]imidazol-2-yl)butyl)sulfonyl)methyl)-2,2-dimethyltetrahydrofuro[3,4-d][1,3]dioxol-4-yl)-9H-purin-6-amine

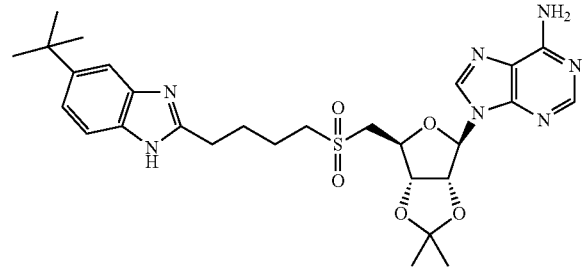 [SMILES: CC1(C)O[C@@H]2[C@H](O1)[C@@H](CS(=O)(=O)CCCCc1nc3cc(C(C)(C)C)ccc3[nH]1)O[C@H]2n1cnc2c(N)ncnc21]

A solution of 9-((3aR,4R,6S,6aS)-6-(((4-(5-(tert-butyl)-1H-benzo[d]imidazol-2-yl)butyl)thio)methyl)-2,2-dimethyltetrahydrofuro[3,4-d][1,3]dioxol-4-yl)-9H-purin-6-amine (700 mg, 1.27 mmol) in DCM (10 mL) was added dropwise m-CPBA (768 mg, 4.46 mmol) in DCM (5 mL) at 0° C. for 25 min. The reaction was quenched with aqueous $Na_2SO_3$ (3 mL), extracted with DCM (3×20 mL), washed with brine (20 mL), dried and concentrated. The residue was purified by Prep-HPLC to obtain the product (260 mg, Yield 35%). NMR (500 MHz, MeOD): δ 8.25 (s, 1H), 8.24 (s, 1H), 7.48-7.26 (m, 3H), 6.24 (d, J=2.0 Hz, 1H), 5.51-5.49 (m, 1H), 5.22-5.21 (m, 1H), 4.70-4.67 (m, 1H), 3.82-3.78 (m, 1H), 3.47-3.43 (m, 1H), 2.93 (t, J=7.0 Hz 2H), 2.69-2.64 (m, 2H), 1.69-1.59 (m, 7H), 1.37 (s, 3H), 1.35 (s, 9H) ppm; ESI-MS (m/z): 584.3 [M+1]$^+$.

Step 6. Preparation of (2R,3R,4S,5S)-2-(6-amino-9H-purin-9-yl)-5-(((4-(5-(tert-butyl)-1H-benzo[d]imidazol-2-yl)butyl)sulfonyl)methyl)tetrahydrofuran-3,4-diol

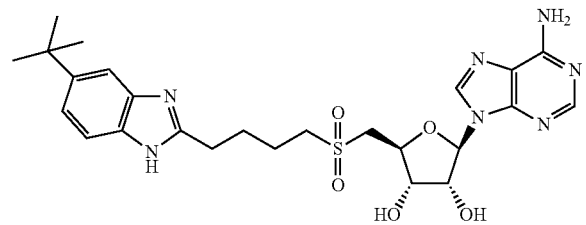 [SMILES: CC(C)(C)c1ccc2[nH]c(CCCCS(=O)(=O)C[C@H]3O[C@@H](n4cnc5c(N)ncnc54)[C@H](O)[C@@H]3O)nc2c1]

A solution of 9-((3aR,4R,6S,6aS)-6-(((4-(5-(tert-butyl)-1H-benzo[d]imidazol-2-yl)butyl)sulfonyl)methyl)-2,2-dimethyltetrahydrofuro[3,4-d][1,3]dioxol-4-yl)-9H-purin-6-amine (240 mg, 0.41 mmol) in TFA (1.80 mL) and 0.20 mL of water were stirred for 1 hour at room temperature. The reaction was concentrated to dryness, dissolved in MeOH (2 mL) and EA (100 mL), washed with aq. sat. $NaHCO_3$ (10×2 mL), dried and evaporated to give the crude. The residue was purified by Prep-HPLC to obtain the product (210 mg, Yield 86%). $^1$H NMR (400 MHz, MeOO): δ 8.23 (s, 1H), 8.22 (s, 1H), 7.47-7.26 (m, 3H), 6.00, (d, J=6.0 Hz, 1H), 4.92-4.89 (m, 1H), 4.50-4.48 (m, 1H), 4.45-4.43 (m, 1H), 3.98-3.92 (m, 1H), 3.41 (m, 1H), 3.09-3.06 (m, 2H), 2.71-2.69 (m, 2H), 1.75-1.70 (m, 4H), 1.35 (s, 9H) ppm; ESI-MS (m/z): 544.3 [M+1]$^+$.

Compound 322

(2R,3R,4S,5S)-2-(6-amino-9H-purin-9-yl)-5-(((3-(5-(tert-butyl)-1H-benzo[d]imidazol-2-yl)propyl)sulfonyl)methyl)tetrahydrofuran-3,4-diol

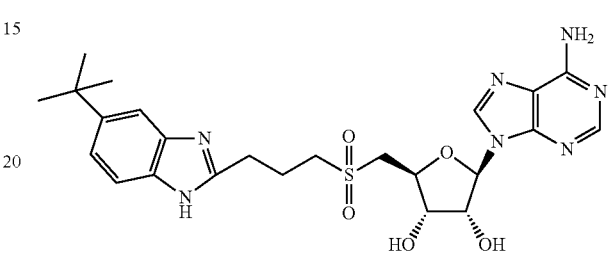

This compound was prepared according to the procedure outlined for compound 321 using ethyl 4-bromobutanoate as the appropriate reagent (90 mg, Yield 58%). $^1$H NMR (400 MHz, DMSO): δ 12.01 (s, 1H), 8.38 (s, 1H), 8.18 (s, 1H), 7.48-7.16 (m, 3H), 5.94 (d, J=4.2 Hz, 1H), 5.63-5.56 (m, 2H), 4.74 (d, J=4.4 Hz, 1H), 4.35-4.32 (m, 1H), 4.26-4.23 (m, 1H), 3.94-3.88 (m, 1H), 3.55-3.51 (m, 2H), 3.16-3.11 (m, 2H), 2.80-2.75 (m, 2H), 2.14-2.11 (m, 2H), 1.31 (s, 9H) ppm; ESI-MS (m/z): 530.3 [M+1]$^+$.

Compound 323

(2R,3R,4S,5S)-2-(6-amino-9H-purin-9-yl)-5-(((4-(5-(tert-butyl)-1H-benzo[d]imidazol-2-yl)butyl)thio)methyl)tetrahydrofuran-3,4-diol

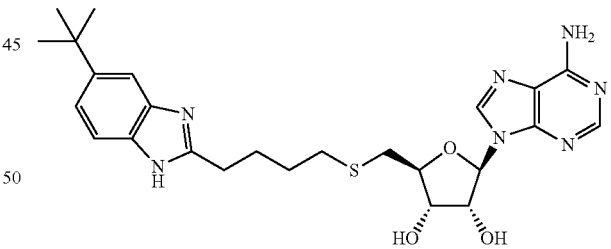

Step 1. Preparation of 4-(5-tert-butyl-1H-benzimidazol-2-yl)butan-1-ol

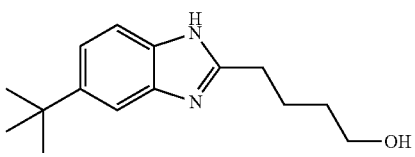 [SMILES: CC(C)(C)c1ccc2[nH]c(CCCCO)nc2c1]

A solution of 4-tert-butylbenzene-1,2-diamine (6 g, 36.59 mmol) and tetrahydropyran-2-one (6.09 g, 60.98 mmol) in 4 M HCl (100 mL) was heated to 100° C. overnight. The reaction was evaporated, added water (50 mL), adjusted to pH=8 with aq. NaHCO$_3$, extracted with EA (3×100 mL), washed with water (20 mL) and brine (20 mL), dried and concentrated. The residue was purified by SGC to obtain the product (4.4 g, Yield 49%). $^1$H NMR (500 MHz, MeOD): δ7.50-7.28 (m, 3H), 3.60 (t, J=6.5 Hz, 2H), 2.91 (t, J=7.5 Hz, 2H), 1.90 (t, J=7.0 Hz, 2H), 1.60 (t, J=7.0 Hz, 2H), 1.37 (s, 9H) ppm; ESI-MS (m/z): 247.2[M+1]$^+$.

Step 2. Preparation of 5-tert-butyl-2-(4-chlorobutyl)-1H-benzimidazole

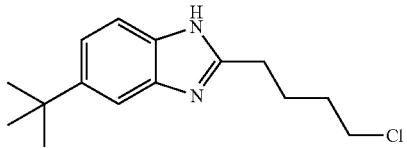 [SMILES: CC(C)(C)c1ccc2[nH]c(CCCCCl)nc2c1]

A solution of 4-(5-tert-butyl-1H-benzimidazol-2-yl)butan-1-ol (2 g, 8.13 mmol) in SOCl$_2$ (15 mL) was stirred at 80° C. 1 h. The reaction was evaporated to dryness, added water (10 mL), adjusted pH=8 with aqu.NaHCO$_3$, extracted with EA (3×50 mL), washed with brine (20 mL), dried and concentrated to obtain the product (2 g, crude). The crude was directly used for next step without further purification. $^1$H NMR (500 MHz, CDCl$_3$): δ8.14 (brs, 1H), 7.56-7.30 (m, 3H), 3.46 (t, J=7.0 Hz, 2H), 2.98 (t, J=7.5 Hz, 2H), 2.03-1.97 (m, 2H), 1.84-1.79 (m, 2H), 1.40 (s, 9H) ppm; ESI-MS (m/z): 265.2[M+1]$^+$.

Step 3. Preparation of 2-[[5-tert-butyl-2-(4-chlorobutyl)benzimidazol-1-yl]methoxy]ethyl-trimethyl-silane

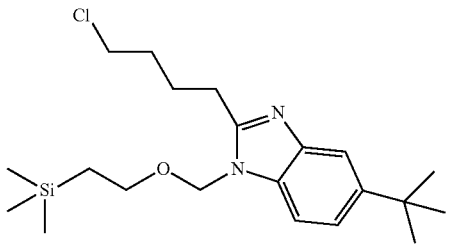 [SMILES: CC(C)(C)c1ccc2c(c1)nc(CCCCCl)n2COCC[Si](C)(C)C]

A solution of NaH (545 mg, 22.7 mmol) in DMF (15 mL) was dropwise added 5-tert-butyl-2-(4-chlorobutyl)-1H-benzimidazole (2 g, 7.57 mmol) in DMF (5 mL) at ice-bath for 10 min, then SEMCl (1.89 g, 15.15 mmol) was added dropwise at ice-bath for 30 min. The reaction was quenched with water (10 mL) at ice-bath, extracted with EA (80×3 mL), washed with water (50 mL) and brine (50 mL), dried and concentrated. The residue was purified by Prep-TLC to obtain the product (800 mg, yield 25%). $^1$H NMR (500 MHz, CDCl$_3$): δ7.72-7.29 (m, 3H), 3.57-3.49 (m, 4H), 2.93-2.90 (m, 2H), 2.03 (t, J=7.5 Hz, 2H), 1.92-1.89 (m, 2H), 1.34 (s, 9H), 0.89-0.85 (m, 2H), −0.027-0.042 (m, 2H), −0.057 (s, 9H) ppm; ESI-MS (m/z): 395.3[M+1]$^+$.

Step 4. Preparation of 9-((3aR,4R,6S,6aS)-6-(((4-(5-(tert-butyl)-1-((2-(trimethylsilyl)ethoxy)methyl)-1H-benzo[d]imidazol-2-yl)butyl)thio)methyl)-2,2-dimethyltetrahydrofuro[3,4-d][1,3]dioxol-4-yl)-9H-purin-6-amine

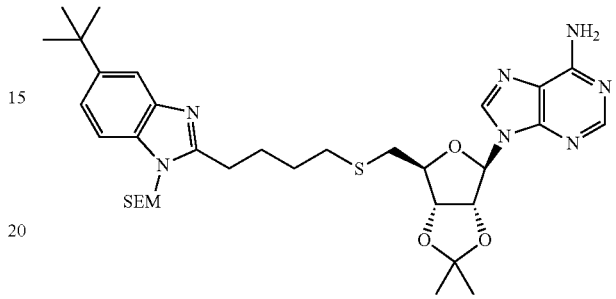

A solution of 2-[[5-tert-butyl-2-(4-chlorobutyl)benzimidazol-1-yl]methoxy]ethyl-trimethyl-silane (800 mg, 2.02 mmol), (980 mg, 3.04 mmol) and K$_2$CO$_3$ (560 mg, 4.07 mmol) in DMF (15 mL) was heated to 100° C. for 30 min. The reaction was concentrated to dryness. The residue was purified by Prep-HPLC to obtain the product (340 mg, Yield 25%). $^1$H NMR (500 MHz, MeOD): δ 8.25 (s, 1H), 8.21 (s, 1H), 7.60-7.33 (m, 3H), 6.15 (s, 1H), 5.56 (s, 1H), 5.52-5.50 (m, 2H), 5.04-5.02 (m, 1H), 4.33-4.32 (m, 1H), 3.57-3.52 (m, 2H), 2.89 (t, J=7.5 Hz, 2H), 2.76 (t, J=6.0 Hz, 2H), 2.53 (t, J=7.5 Hz, 2H), 1.87-1.85 (brs, 2H), 1.60-1.55 (m, 5H), 1.37-1.35 (s, 12H), 0.87-0.83 (m, 2H), −0.113 (s, 9H) ppm; ESI-MS (m/z): 682.4 [M+1]$^+$.

Step 5. Preparation of (2R,3R,4S,5S)-2-(6-amino-9H-purin-9-yl)-5-(((4-(5-(tert-butyl)-1H-benzo[d]imidazol-2-yl)butyl)thio)methyl)tetrahydrofuran-3,4-diol

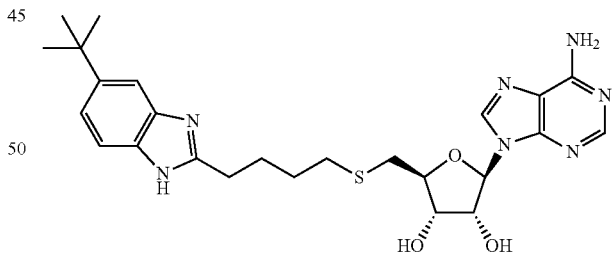

A solution of 9-((3aR,4R,6S,6aS)-6-(((4-(5-(tert-butyl)-1-(2-(trimethylsilyl)ethoxy)methyl)-1H-benzo[d]imidazol-2-yl)butyl)thio)methyl)-2,2-dimethyltetrahydrofuro[3,4-d][1,3]dioxol-4-yl)-9H-purin-6-amine (100 mg, 0.19 mmol) in TFA (0.90 mL) and 0.10 mL of water was stirred for 1.5 hour at 45° C. The reaction was concentrated to dryness, dissolved in MeOH (2 mL) and EA (100 mL), washed with aq. sat. NaHCO$_3$ (10×2 mL), dried and evaporated to the crude. The residue was purified by prep-HPLC to obtain the product (7 mg, Yield 5%). $^1$H NMR (500 MHz, MeOD): δ 8.29 (s, 1H), 8.19 (s, 1H), 7.48-7.26 (m, 3H), 5.99 (d, J=5.0 Hz, 1H), 4.785-4.765 (m, 1H), 4.331-4.311 (m, 1H), 4.19-4.18 (m, 1H), 2.94-2.93 (m, 2H), 2.85-2.82 (m, 2H), 2.61-2.58 (m, 2H), 1.88-1.85 (m, 2H), 1.63-1.60 (m, 2H), 1.35 (s, 9H) ppm; ESI-MS (m/z): 512.3 [M+1]⁺.

Compound 324

(2R,3R,4S,5R)-2-(6-amino-9H-purin-9-yl)-5-(((4-(5-isopropoxy-1H-benzo[d]imidazol-2-yl)butyl)(isopropyl)amino)methyl)tetrahydrofuran-3,4-diol

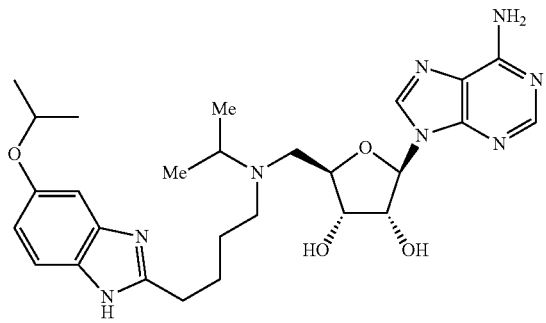 [SMILES: CC(C)Oc1ccc2[nH]c(CCCCN(C[C@H]3O[C@@H](n4cnc5c(N)ncnc54)[C@H](O)[C@@H]3O)C(C)C)nc2c1]

Step 1. Preparation of 4-isopropoxy-1,2-dinitro-benzene

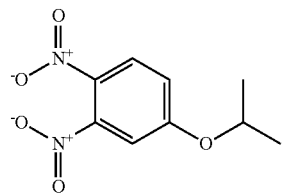

To a solution of 4-fluoro-1,2-dinitro-benzene (9.5 g, 52 mmol) and isopropanol (4.3 mL, 56.2 mmol) in THF (100 mL) was added 60% NaH (3.3 g, 81.7 mmol) at rt in a period of 20 min. After addition, the mixture was stirred at 55° C. o/n. The mixture was concentrated. The residue was dissolved in EA (300 mL), washed with water (200 mL×2) and brine (300 mL). The organic phase was dried over Na₂SO₄, filtered and concentrated. The residue was purified by Combiflash (80 g silica gel, start PE:EA=from 10:0 to 20:1 by gradient, 80 mL/min, 40 min, 3.2 L total solvent volume) to afford the product as a yellow oil (3.5 g, 30%). ¹H NMR (500 MHz, CDCl₃): δ 8.04 (d, J=7.0 Hz, 1H), 7.17 (d, J=2.5 Hz, 1H), 7.09 (dd, J=9.5 2.5 Hz, 1H), 4.67-4.72 (m, 1H), 1.43 (s, 3H), 1.42 (s, 3H) ppm; LC-MS (m/z): 227.1 [M+1]⁺.

Step 2. Preparation of 4-isopropoxybenzene-1,2-diamine

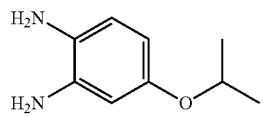

To a solution of 4-isopropoxy-1,2-dinitro-benzene (3.5 g, 15.49 mmol) in EtOH (100 mL) was added SnCl₂.2H₂O (35 g, 154.88 mmol). The mixture was stirred at reflux for 4 h. The mixture was concentrated. The residue was dissolved in EA (200 mL), washed with 10% NaOH solution (100 mL×2), water (100 mL) and brine (100 mL). The organic phase was dried over Na₂SO₄, filtered and concentrated to afford the product as a black solid (2.3 g, 89%). ¹H NMR (500 MHz, DMSO-d6): δ 6.40 (d, J=8.0 Hz, 1H), 6.16 (d, J=2.5 Hz, 1H), 5.98 (dd, J=2.5, 8.5 Hz, 1H), 4.23-4.29 (m, 5H), 1.18 (s, 3H), 1.17 (s, 3H) ppm; LC-MS (m/z): 167.3 [M+1]⁺.

Step 3. Preparation of N-(2-amino-4-isopropoxyphenyl)-5-((((3aR,4R,6R,6aR)-6-(6-amino-9H-purin-9-yl)-2,2-dimethyltetrahydrofuro[3,4-d][1,3]dioxol-4-ylmethyl)(isopropyl)amino)pentanamide

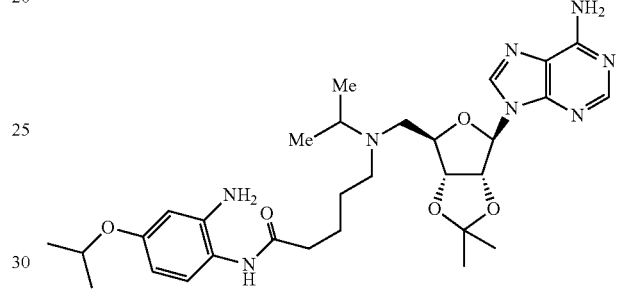

To a solution of 5-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)pentanoic acid (400 mg, 0.89 mmol), HATU (508 mg, 1.34 mmol) and HOAT (182 mg, 1.34 mmol) in DMF (4 mL) was added 4-isopropoxybenzene-1,2-diamine (296 mg, 1.78 mmol) and TEA (0.62 mL, 4.46 mmol). The mixture was stirred at rt overnight. The mixture was concentrated. The residue was dissolved in EA (40 mL), washed with water (20 mL×2) and brine (20 mL). The organic phase was dried over Na₂SO₄, filtered and concentrated. The residue was purified by Prep-TLC (EA:DCM:MeOH=5:5:1) to afford the product as a deep brown solid (300 mg, 56%). LC-MS (m/z): 597.4 [M+1]⁺.

Step 4. Preparation of 9-((3aR,4R,6R,6aR)-6-(((4-(5-isopropoxy-1H-benzo[d]imidazol-2-yl)butyl)(isopropyl)amino)methyl)-2,2-dimethyltetrahydrofuro[3,4-d][1,3]dioxol-4-yl)-9H-purin-6-amine

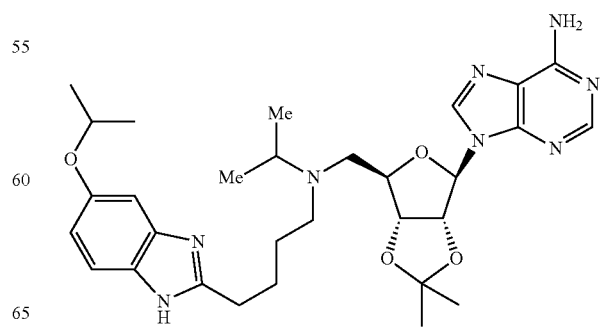

A solution of N-(2-amino-4-isopropoxyphenyl)-5-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)pentanamide (300 mg, 0.5 mmol) in AcOH (10 mL) was stirred at 65° C. overnight. The solvent was removed under reduced pressure to afford the product as a black oil (280 mg, 97%), which was used in next step without further purification. LC-MS (m/z): 579.4 [M+1]$^+$.

Step 5. Preparation of (2R,3R,4S,5R)-2-(6-amino-9H-purin-9-yl)-5-(((4-(5-isopropoxy-1H-benzo[d]imidazol-2-yl)butyl)(isopropyl)amino)methyl)tetrahydrofuran-3,4-diol

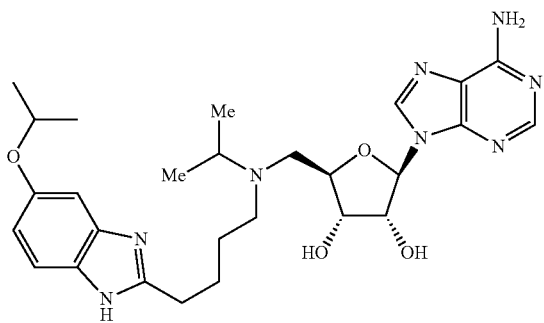 [SMILES: CC(C)Oc1ccc2[nH]c(CCCCN(C[C@H]3O[C@@H](n4cnc5c(N)ncnc54)[C@H](O)[C@@H]3O)C(C)C)nc2c1]

A solution of 9-((3aR,4R,6R,6aR)-6-(((4-(5-isopropoxy-1H-benzo[d]imidazol-2-yl)butyl)(isopropyl)amino)methyl)-2,2-dimethyltetrahydrofuro[3,4-d][1,3]dioxol-4-yl)-9H-purin-6-amine (280 mg, 0.48 mmol) in 2.5 M HCl/MeOH (15 mL) was stirred at rt for 2 h. The volatiles were removed under reduced pressure. The residue was dissolved in MeOH (10 mL), a solution of K$_2$CO$_3$ (410 mg, 3 mmol) in water (1 mL) was added and the mixture was stirred at rt for 20 min, filtered and the filtrate was concentrated. The residue was purified by Prep-HPLC to afford the product as a yellow solid (81 mg, 31%). $^1$H NMR (500 MHz, methanol-d$_4$): δ 8.27 (s, 1H), 8.19 (s, 1H), 7.34 (d, J=8.5 Hz, 1H), 6.99 (s, 1H), 6.80 (dd, J=2.5, 9.0 Hz, 1H), 5.96 (d, J=5.0 Hz, 1H), 4.762-4.742 (m, 1H), 4.52-4.57 (m, 1H), 4.28 (t, J=5.5 Hz, 1H), 4.09-4.12 (m, 1H), 2.97-3.02 (m, 1H), 2.88-2.92 (m, 1H), 2.83 (t, J=8.0 Hz, 2H), 2.69-2.73 (m, 1H), 2.54 (t, J=7.0 Hz, 2H), 1.78-1.84 (m, 2H), 1.50-1.56 (m, 2H), 1.32 (s, 3H), 1.31 (s, 3H), 1.036 (d, J=7.0 Hz, 3H), 0.975 (d, J=6.5 Hz, 3H) ppm; LC-MS (m/z): 539.4 [M+1]$^+$.

Compound 325

(2R,3S,4R,5R)-2-(((4-(5-(tert-butyl)-1H-benzo[d]imidazol-2-yl)butyl)(isopropyl)amino)methyl)-5-(9H-purin-9-yl)tetrahydrofuran-3,4-diol

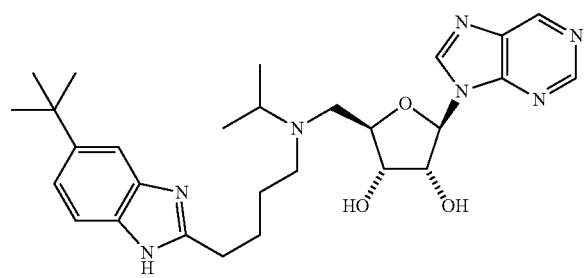 [SMILES: CC(C)N(CCCCc1nc2cc(C(C)(C)C)ccc2[nH]1)C[C@H]1O[C@@H](n2cnc3cncnc32)[C@H](O)[C@@H]1O]

Step 1. Preparation of ((3aR,4R,6R,6aR)-2,2-dimethyl-6-(9H-purin-9-yl)tetrahydrofuro[3,4-d][1,3]dioxol-4-yl)methanol

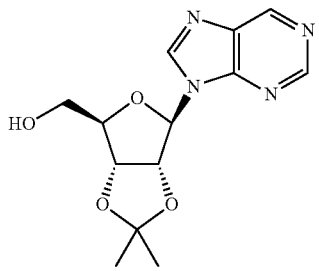 [SMILES: CC1(C)O[C@@H]2[C@H](O1)[C@@H](CO)O[C@H]2n1cnc2cncnc21]

To a solution of ((3aR,4R,6R,6aR)-6-(6-chloro-9H-purin-9-yl)-2,2-dimethyltetrahydrofuro[3,4-d][1,3]dioxol-4-yl)methanol (7 g, 21.5 mmol) in THF (80 mL) was added K$_2$CO$_3$ (5.9 g, 42.9 mmol) and 10% Pd/C (1.5 g). The mixture was stirred under H$_2$ atmosphere at rt for 15 h, then filtered and the filtrate was concentrated to obtain the target product (6 g, yield: 95%) as a light yellow oil. NMR (500 MHz, CDCl$_3$): δ 9.14 (s, 1H), 8.91 (s, 1H), 8.12 (s, 1H), 5.92 (d, J=4.5 Hz, 1H), 5.39-5.36 (m, 1H), 5.19-5.16 (m, 1H), 5.08-5.05 (m, 1H), 4.49 (s, 1H), 3.93-3.90 (m, 1H), 3.78-3.73 (m, 1H), 1.59 (s, 3H), 1.32 (s, 3H) ppm; ESI-MS (m/z): 293.2 [M+1]$^+$.

Step 2. Preparation of ((3aR,4R,6R,6aR)-2,2-dimethyl-6-(9H-purin-9-yl)tetrahydrofuro[3,4-d][1,3]dioxol-4-yl)methyl methanesulfonate

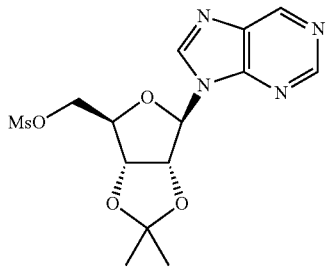 [SMILES: CC1(C)O[C@@H]2[C@H](O1)[C@@H](COS(C)(=O)=O)O[C@H]2n1cnc2cncnc21]

To a solution of ((3aR,4R,6R,6aR)-2,2-dimethyl-6-(9H-purin-9-yl)tetrahydrofuro[3,4-d][1,3]dioxol-4-yl)methanol (6 g, 20.5 mmol) and TEA (6.2 g, 61.5 mmol) in DCM (50 mL) was added MsCl (14 g, 123.3 mmol) and the mixture was stirred at 0° C. for 10 min. Saturated NaHCO$_3$ (15 mL) was added and the mixture was extracted with DCM (40 mL×3). The combined organic phase was concentrated to obtain the target product (11 g, yield: >95%) as a light yellow oil. The crude was used to next step without further purification. ESI-MS (m/z): 371.2 [M+1]$^+$.

Step 3. Preparation of 9-((3aR,4R,6R,6aR)-6-(azidomethyl)-2,2-dimethyltetrahydrofuro[3,4-d][1,3]dioxol-4-yl)-9H-purine

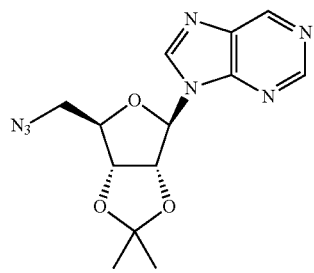 [SMILES: CC1(C)O[C@@H]2[C@H](O1)[C@@H](CN=[N+]=[N-])O[C@H]2n1cnc2cncnc21]

To a solution of ((3aR,4R,6R,6aR)-2,2-dimethyl-6-(9H-purin-9-yl)tetrahydrofuro[3,4-d][1,3]dioxol-4-yl)methyl methanesulfonate (11 g, crude, 29.7 mmol) in DMF (100 mL) was added NaN₃ (9.8 g, 148.5 mmol) and the mixture was stirred at 80° C. for 15 h. The mixture was washed with H₂O (20 mL×2), brine (40 mL×2). The combined organic phase was concentrated to obtain the target product (3.4 g, yield: 39%) as a light yellow oil. ¹H NMR (500 MHz, CDCl₃): δ 9.18 (s, 1H), 9.02 (s, 1H), 8.26 (d, J=6.5 Hz, 1H), 6.24-6.21 (m, 1H), 5.47-5.45 (m, 1H), 5.16-5.06 (m, 1H), 4.42-4.39 (m, 1H), 2.96 (s, 1H), 2.88 (s, 1H), 1.66-1.64 (m, 3H), 1.42-1.37 (m, 3H) ppm; ESI-MS (m/z): 318.2 [M+1]⁺.

Step 4. Preparation of ((3aR,4R,6R,6aR)-2,2-dimethyl-6-(9H-purin-9-yl)tetrahydrofuro[3,4-d][1,3]dioxol-4-yl)methanamine

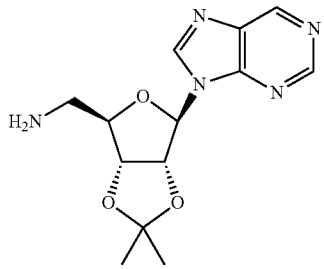 [SMILES: CC1(C)O[C@@H]2[C@H](O1)[C@@H](CN)O[C@H]2n1cnc2cncnc21]

To a solution of 9-((3aR,4R,6R,6aR)-6-(azidomethyl)-2,2-dimethyltetrahydrofuro[3,4-d][1,3]dioxol-4-yl)-9H-purine (3.4 g, 10.7 mmol) in MeOH (30 mL) was added 10% Pd/C (800 mg). The mixture was stirred under H₂ at rt for 15 h, then filtered and the filtrate was concentrated. The crude was purified by Prep-TLC (DCM:MeOH=10:1) to obtain the target product (1.6 g, yield: 52%) as a light yellow oil. ¹H NMR (500 MHz, MeOD): δ 9.12 (s, 1H), 8.96 (s, 1H), 8.69 (s, 1H), 6.29 (d, J=2.5 Hz, 1H), 5.55-5.52 (m, 1H), 5.07-5.05 (m, 1H), 4.30-4.26 (m, 1H), 2.94-2.92 (m, 2H), 1.61 (s, 3H), 1.39 (s, 3H) ppm; ESI-MS (m/z): 292.3 [M+1]⁺.

Step 5. Preparation of N-(((3aR,4R,6R,6aR)-2,2-dimethyl-6-(9H-purin-9-yl)tetrahydrofuro[3,4-d][1,3]dioxol-4-yl)methyl)propan-2-amine

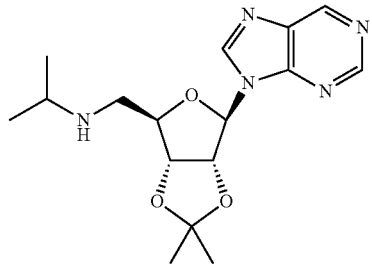 [SMILES: CC(C)NC[C@H]1O[C@@H](n2cnc3cncnc32)[C@@H]2OC(C)(C)O[C@@H]21]

To a solution of ((3aR,4R,6R,6aR)-2,2-dimethyl-6-(9H-purin-9-yl)tetrahydrofuro[3,4-d][1,3]dioxol-4-yl)methanamine (1.6 g, 5.49 mmol) and K₂CO₃ (759 mg, 5.49 mmol) in MeCN (25 mL) was added 2-iodopropane (1.4 g, 8.24 mmol) and the mixture was stirred at 80° C. for 15 h. The mixture was concentrated and the crude was purified by SGC (DCM:MeOH=50:1 to 20:1) to obtain the target product (870 mg, yield: 54%) as a light yellow oil. ¹H NMR (500 MHz, MeOD): δ 9.13 (s, 1H), 8.97 (s, 1H), 8.71 (s, 1H), 6.31 (d, J=2.5 Hz, 1H), 5.60-5.57 (m, 1H), 5.07-5.05 (m, 1H), 4.39-4.36 (m, 1H), 2.89-2.86 (m, 2H), 2.73-2.70 (m, 1H), 1.61 (s, 3H), 1.39 (s, 3H), 0.99 (d, J=6.5 Hz, 3H), 0.95 (d, J=6.5 Hz, 3H) ppm; ESI-MS (m/z): 334.3 [M+1]⁺.

Step 6. Preparation of ethyl 5-((((3aR,4R,6R,6aR)-2,2-dimethyl-6-(9H-purin-9-yl)tetrahydrofuro[3,4-d][1,3]dioxol-4-ylmethyl)(isopropyl)amino)pentanoate

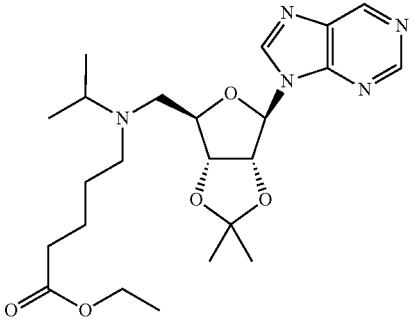 [SMILES: CCOC(=O)CCCCN(C[C@H]1O[C@@H](n2cnc3cncnc32)[C@@H]2OC(C)(C)O[C@@H]21)C(C)C]

A solution of N-(((3aR,4R,6R,6aR)-2,2-dimethyl-6-(9H-purin-9-yl)tetrahydrofuro[3,4-d][1,3]dioxol-4-yl)methyl)propan-2-amine (850 mg, 2.55 mmol) and ethyl 5-oxopentanoate (551 mg, 3.83 mmol) in DCE (20 mL) was stirred at rt for 20 min and NaBH(OAc)₃ (812 mg, 3.83 mmol) was added. The mixture was stirred at rt for 15 h. The mixture was concentrated and water (5 mL) was added. The solution was extracted with DCM (30 mL×3). The combined organic phase was concentrated and the crude was purified by Prep-TLC (DCM:MeOH=10:1) to obtain the target product (1.6 g, yield: 52%) as a light yellow oil. NMR (500 MHz, MeOD): δ 9.13 (s, 1H), 8.98 (s, 1H), 8.69 (s, 1H), 8.29 (d, J=2.0 Hz, 1H), 5.62-5.60 (m, 1H), 5.08-5.05 (m, 1H), 4.30-4.29 (m, 1H), 4.13-4.07 (m, 3H), 3.55 (t, J=7.0 Hz, 1H), 2.93-2.89 (m, 1H), 2.70-2.68 (m, 1H), 2.57-2.54 (m, 1H), 2.39 (t, J=7.5 Hz, 2H), 2.33 (t, J=7.5 Hz, 1H), 2.24 (t, J=7.5 Hz, 2H), 1.69-1.65 (m, 1H), 1.60 (s, 3H), 1.57-1.52 (m, 2H), 1.39 (s, 3H), 1.37-1.33 (m, 2H), 1.25-1.21 (m, 5H), 0.98 (d, J=6.5 Hz, 3H), 0.82 (d, J=6.5 Hz, 3H) ppm; ESI-MS (m/z): 462.4 [M+1]⁺.

Step 7. Preparation of (2R,3S,4R,5R)-2-(((4-(5-(tert-butyl)-1H-benzo[d]imidazol-2-yl)butyl)(isopropyl)aminomethyl)-5-(9H-purin-9-yl)tetrahydrofuran-3,4-diol

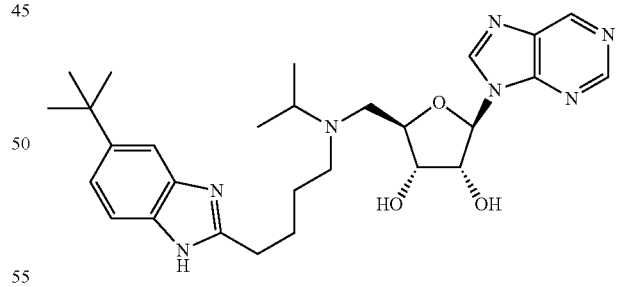

Trimethylaluminum ((1.22 mL, 2.43 mmol, 2.0 M toluene solution) was added to a 12 mL of toluene containing of 4-tert-butylbenzene-1,2-diamine (267 mg, 1.62 mmol) at rt. After stifling for 1.5 h ethyl 5-((((3aR,4R,6R,6aR)-2,2-dimethyl-6-(9H-purin-9-yl)tetrahydrofuro[3,4-d][1,3]dioxol-4-yl)methyl)(isopropyl)amino)pentanoate (300 mg, 0.65 mmol) was added and the mixture was heated to 85° C. for 15 h. Then, the solution was poured into 100 mL of chloroform containing 50 g of silica gel and filtered off. The residue was washed with 30 mL of methanol and the filtrate was concentrated to obtain the crude (220 mg). The mixture of CH₃COOH (4 mL) and the crude product was heated at 80° C. for 15 h and then the solution was concentrated. The residue was diluted with 15 mL of DCM and saturated NaHCO₃ was added to adjust to pH=7. The solution was extracted with DCM (20 mL×3). The combined organic phase was dried over Na₂SO₄ and concentrated to obtain the product (190 mg, 52%) as a light yellow solid. ESI-MS (m/z): 562.3 [M+1]⁺.

((2R,3R,4S,5R)-2-(6-amino-9H-purin-9-yl)-5-(((3-(((6-(tert-butyl)-1H-benzo[d]imidazol-2-yl)amino)propyl)(methyl)amino)methyl)tetrahydrofuran-3,4-diol

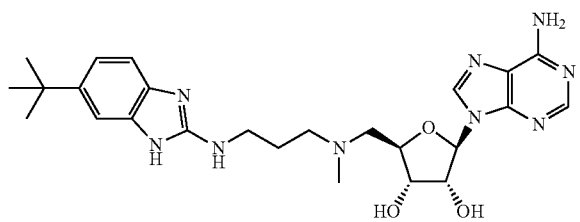 [SMILES: CN(CCCNc1nc2ccc(C(C)(C)C)cc2[nH]1)C[C@H]1O[C@@H](n2cnc3c(N)ncnc32)[C@H](O)[C@@H]1O]

Step 1. Preparation of N-[[(3aR,4R,6R,6aR)-4-(6-aminopurin-9-yl)-2,2-dimethyl-3a,4,6,6a-tetrahydrofuro[3,4-d][1,3]dioxol-6-yl]methyl]-N'-(6-tert-butyl-1H-benzimidazol-2-yl)-N-methyl-propane-1,3-diamine

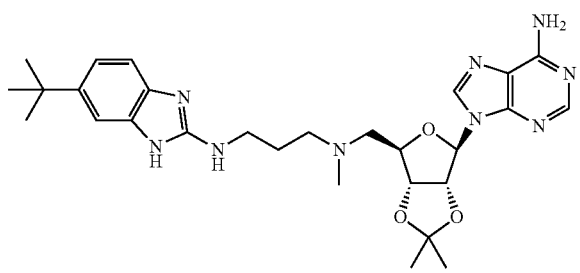 [SMILES: CN(CCCNc1nc2ccc(C(C)(C)C)cc2[nH]1)C[C@H]1O[C@@H](n2cnc3c(N)ncnc32)[C@@H]2OC(C)(C)O[C@@H]21]

5-tert-butyl-2-chloro-1H-benzimidazole (50 mg, 0.24 mmol), N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (90 mg, 0.24 mmol) and TEA (40 mg, 0.37 mmol) were dissolved in n-BuOH (2 mL) and treated with KI (20 mg, cal.). The mixture was irradiated by microwave at 160° C. for 2 h. Solvent was removed in vacuo and the crude was purified by Prep-TLC (DCM:MeOD=10:1) to afford the product (40 mg, yield: 30%) as a yellow solid. ESI-MS (m/z): 550.4 [M+1]⁺.

Step 2. Preparation of ((2R,3R,4S,5R)-2-(6-amino-9H-purin-9-yl)-5-(((3-(((6-(tert-butyl)-1H-benzo[d]imidazol-2-yl)amino)propyl)(methyl)amino)methyltetrahydrofuran-3,4-diol

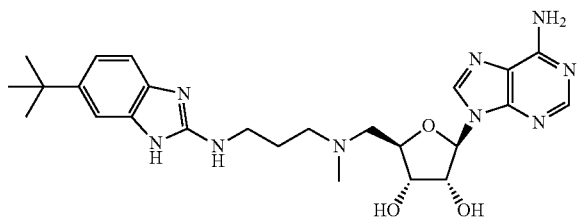 [SMILES: CN(CCCNc1nc2ccc(C(C)(C)C)cc2[nH]1)C[C@H]1O[C@@H](n2cnc3c(N)ncnc32)[C@H](O)[C@@H]1O]

To a mixture of TFA (0.9 mL) and water (0.1 mL) was added N-[[(3aR,4R,6R,6aR)-4-(6-aminopurin-9-yl)-2,2-dimethyl-3a,4,6,6a-tetrahydrofuro[3,4-d][1,3]dioxol-6-yl]methyl]-N'-(6-tert-butyl-1H-benzimidazol-2-yl)-N-methyl-propane-1,3-diamine (40 mg, 0.07 mmol). The solution was allowed to stand at room temperature for 2 h and evaporated to dryness. The residue was co-evaporated with methanol (5 mL) twice. Then the residue was dissolved in MeOH (5 mL). The solution was neutralized by K₂CO₃ (100 mg, dissolved in 1 mL of H₂O) with stirring at rt for 1 h. Solvent was removed in vacuo, then the crude was purified by Prep-HPLC to afford the product (19 mg, yield: 51%) as a white solid. ¹H NMR (500 MHz, MeOD): δ 8.23 (s, 1H), 8.26 (s, 1H), 7.21 (d, J=1.5 Hz, 1H), 7.07-7.03 (m, 2H), 5.60 (d, J=4.5 Hz, 1H), 4.748-4.730 (m, 1H), 4.276-4.261 (m, 2H), 3.38-3.33 (m, 2H), 2.91-2.87 (m, 2H), 2.63 (t, J=7.0 Hz, 2H), 2.35 (s, 3H), 1.87-1.82 (m, 2H) 1.29 (s, 9H) ppm; ESI-MS (m/z): 510.4 [M+1]⁺.

Compound 327

N-(((2R,3S,4R,5R)-5-(6-amino-9H-purin-9-yl)-3,4-dihydroxytetrahydrofuran-2-yl)methyl)-N-(4-(5-(tert-butyl)-1H-benzo[d]imidazol-2-yl)butyl)methanesulfonamide

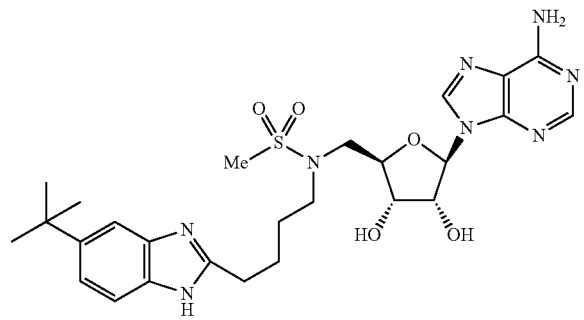 [SMILES: CC(C)(C)c1ccc2[nH]c(CCCCN(C[C@H]3O[C@@H](n4cnc5c(N)ncnc54)[C@H](O)[C@@H]3O)S(C)(=O)=O)nc2c1]

Step 1. Preparation of methyl 5-(((((3aR,4R,6R,6aR)-6-(6-amino-9H-purin-9-yl)-2,2-dimethyltetrahydrofuro[3,4-d][1,3]dioxol-4-yl)methyl)(benzyl)amino)pentanoate

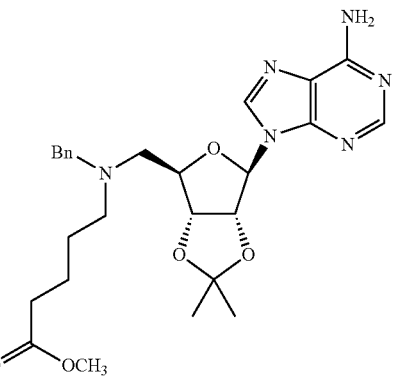

To a solution of 9-((3aR,4R,6R,6aR)-6-((benzylamino)methyl)-2,2-dimethyltetrahydrofuro[3,4-d][1,3]dioxol-4-yl)-9H-purin-6-amine (6.9 g, 0.83 mmol) and methyl 5-oxopentanoate (3.3 g, 25.38 mmol) in DCE (300 mL) was added NaBH(OAc)₃ (5.38 g, 25.38 mmol). The reaction was stirred at rt overnight. The reaction was quenched with aq. sat. NaHCO₃ (80 mL), extracted with DCM (100 mL×3), dried and evaporated. The crude was purified by SGC to obtain the product (7.9 g, 91%). ¹H NMR (500 MHz, MeOD): δ 8.18 (s, 1H), 8.10 (s, 1H), 7.24-7.17 (m, 5H), 6.13 (d, J=2.0 Hz, 1H), 5.44-5.42 (m, 1H), 4.95-4.93 (m, 1H), 4.34-4.33 (m, 1H), 3.62-3.60 (m, 4H), 3.47-3.45 (m, 1H), 2.69-2.59 (m, 2H), 2.45-2.40 (m, 2H), 2.22-2.19 (m, 2H), 1.57-1.50 (m, 5H), 1.43-1.36 (m, 5H) ppm; LC-MS (m/z): 511.4 [M+1]+.

Step 2. Preparation of methyl 5-(((((3aR,4R,6R,6aR)-6-(6-amino-9H-purin-9-yl)-2,2-dimethyltetrahydrofuro[3,4-(1][1,3]dioxol-4-yl)methyl)amino)pentanoate

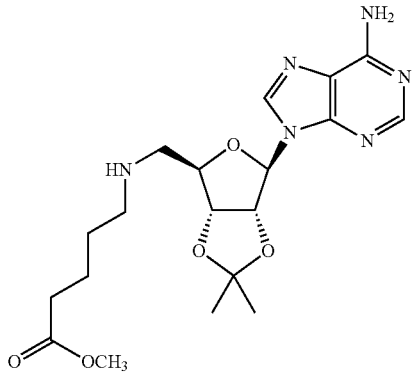 [SMILES: COC(=O)CCCCNC[C@H]1O[C@@H](n2cnc3c(N)ncnc32)[C@@H]2OC(C)(C)O[C@@H]21]

A solution of methyl 5-(((((3aR,4R,6R,6aR)-6-(6-amino-9H-purin-9-yl)-2,2-dimethyltetrahydrofuro[3,4-d][1,3]dioxol-4-yl)methyl)(benzyl)amino)pentanoate (2 g, 3.92 mmol) and Pd/C (300 mg) in MeOH (80 mL) and AcOH (20 mL) was treated with H₂ for 2 h. The reaction was filtered, the filtrate was evaporated to dryness. The crude was dissolved EA (200 mL) and washed with sat. NaHCO₃ (50 mL×3), water (50 mL) and brine (50 mL), dried and evaporated to the crude product (1 g, crude). The crude was directly used for next step without further purification. LC-MS (m/z): 421.2 [M+1]+.

Step 3. Preparation of methyl 5-(N-(((3aR,4R,6R,6aR)-6-(6-amino-9H-purin-9-yl)-2,2-dimethyltetrahydrofuro[3,4-d][1,3]dioxol-4-yl)methyl)methylsulfonamido)pentanoate

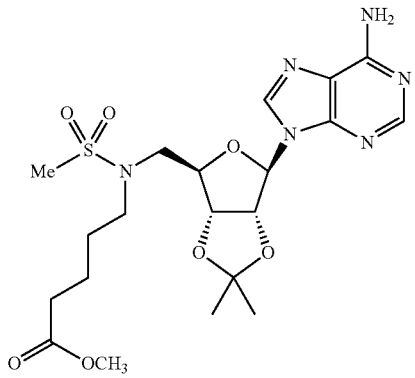 [SMILES: COC(=O)CCCCN(C[C@H]1O[C@@H](n2cnc3c(N)ncnc32)[C@@H]2OC(C)(C)O[C@@H]21)S(C)(=O)=O]

A solution of methyl 5-(((((3aR,4R,6R,6aR)-6-(6-amino-9H-purin-9-yl)-2,2-dimethyltetrahydrofuro[3,4-d][1,3]dioxol-4-yl)methyl)amino)pentanoate (1 g, 2.38 mmol) and K₂CO₃ (985 mg, 7.14 mmol) in DCM (80 mL) was added MsCl (330 mg, 2.86 mmol). The reaction was heated to 55° C. for 2 h. After K₂CO₃ (985 mg, 7.14 mmoL) was added. The reaction was heated to 55° C. overnight. The reaction was filtered and the filtrate was evaporated and purified by SGC to afford the product (260 mg, 26%). ¹H NMR (500 MHz, MeOD): δ 8.27 (s, 1H), 8.24 (s, 1H), 6.23 (s, 1H), 5.54-5.53 (brs, 1H), 5.12 (brs, 1H), 4.47-4.37 (brs, 1H), 3.62 (s, 3H), 3.58-3.57 (m, 1H), 3.47-3.46 (m, 1H), 3.04 (brs, 2H), 2.29 (s, 3H), 2.17 (brs, 2H), 1.59 (S, 3H), 1.38 (BRS, 7H) ppm; LC-MS (m/z): 499.2 [M+1]+.

Step 4. Preparation of 5-(N-(((3aR,4R,6R,6aR)-6-(6-amino-9H-purin-9-yl)-2,2-dimethyltetrahydrofuro[3,4-d][1,3]dioxol-4-yl)methyl)methylsulfonamido)pentanoic acid

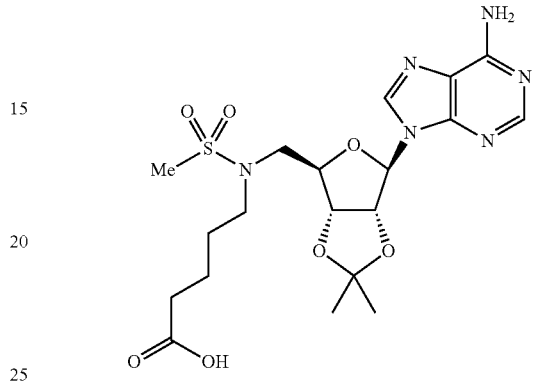

A mixture of methyl 5-(N-(((3aR,4R,6R,6aR)-6-(6-amino-9H-purin-9-yl)-2,2-dimethyltetrahydrofuro[3,4-d][1,3]dioxol-4-yl)methyl)methylsulfonamido)pentanoate (100 mg, 0.2 mmol) and LiOH (50 mg, 1.2 mmol) in 8 mL of solvent (MeOH/THF/H₂O=1/1/1) was stirred at rt for 1.5 h. The system was neutralized with HCl to pH=6-7. The solvent was removed to give the product (300 mg, 100%) as a white solid directly used for next step. MS (ESI): m/z 485.7 [M+1]+.

Step 5. Preparation of 5 N-(2-amino-5-(tert-butyl)phenyl)-5-(N-(43aR,4R,6R,6aR)-6-(6-amino-9H-purin-9-yl)-2,2-dimethyltetrahydrofuro[3,4-d][1,3]dioxol-4-yl)methyl)methylsulfonamido)pentanamide

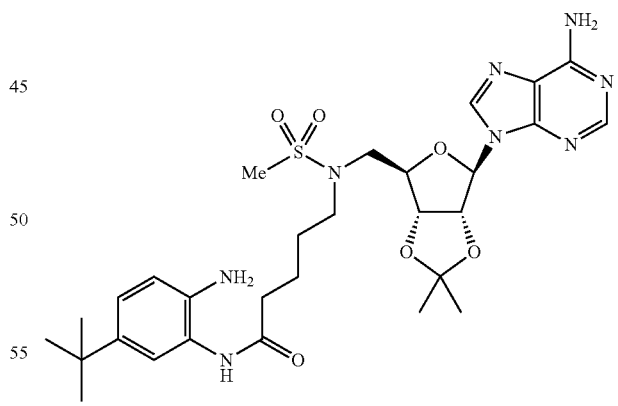

A mixture of 5-(N-(((3aR,4R,6R,6aR)-6-(6-amino-9H-purin-9-yl)-2,2-dimethyltetrahydrofuro[3,4-d][1,3]dioxol-4-yl)methyl)methylsulfonamido)pentanoic acid (300 mg, 0.62 mmol), diamine (204 mg, 1.24 mmol), HOAT (169 mg, 1.24 mmol), HATU (472 mg, 1.24 mmol), Et₃N (0.52 mL, 3.72 mmol) and DMF (10 mL) was stirred at rt overnight. The reaction was then quenched with water (10 mL), and extracted with EtOAc (20 mL×3). The combined organic layers were washed with brine, dried over Na₂SO₄ and concentrated under reduced pressure. The obtained residue was purified by Prep-TLC to give the desired compound (175 mg, 45%) as a pale solid. LC-MS (m/z): 631.2 [M+1]$^+$.

Step 6. Preparation of N-(((3aR,4R,6R,6aR)-6-(6-amino-9H-purin-9-yl)-2,2-dimethyltetrahydrofuro[3,4-d][1,3]dioxol-4-yl)methyl)-N-(4-(5-(tert-butyl)-1H-benzo[d]imidazol-2-yl)butyl) methanesulfonamide

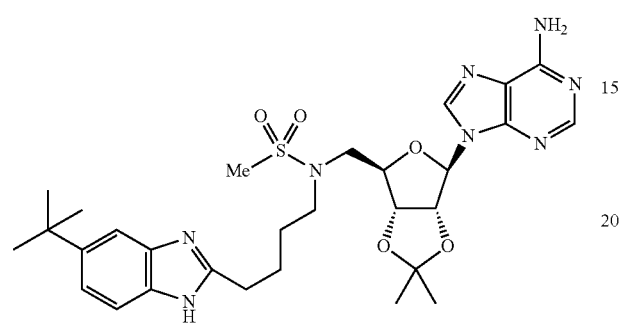

A reaction solution of N-(2-amino-5-(tert-butyl)phenyl)-5-(N-(((3aR,4R,6R,6aR)-6-(6-amino-9H-purin-9-yl)-2,2-dimethyltetrahydrofuro[3,4-d][1,3]dioxol-4-yl)methyl)methylsulfonamido)pentanamide in AcOH (5 mL) was stirred at 65° C. overnight. After concentration under reduced pressure, the residue was neutralized with NaHCO$_3$ to pH=8. The mixture was extracted with DCM (20 mL×3). The organic phase was dried and concentrated to give the desired compound (150 mg, 89%) as a pale solid. $^1$H NMR (500 MHz, MeOD): δ 8.22 (s, 1H), 8.20 (s, 1H), 7.49 (s, 1H), 7.40 (d, J=8.5 Hz, 1H), 7.28 (dd, J=2.0, 8.5 Hz, 1H), 6.17 (d, J=2.0 Hz, 1H), 5.47-5.49 (m, 1H), 5.08 (dd, J=3.0, 6.5 Hz, 1H), 4.43 (brs, 1H), 3.40-3.59 (m, 2H), 3.08-3.12 (m, 2H), 2.76-2.80 (m, 5H), 1.52-1.69 (m, 2H), 1.46-1.52 (m, 5H), 1.28-1.36 (m, 12H) ppm; LC-MS (m/z): 613.2 [M+1]$^+$.

Step 7 Preparation of N-(((2R,3S,4R,5R)-5-(6-amino-9H-purin-9-yl)-3,4-dihydroxytetrahydrofuran-2-yl)methyl)-N-(4-(5-(tert-butyl)-1H-benzo[d]imidazol-2-yl)butyl)methanesulfonamide

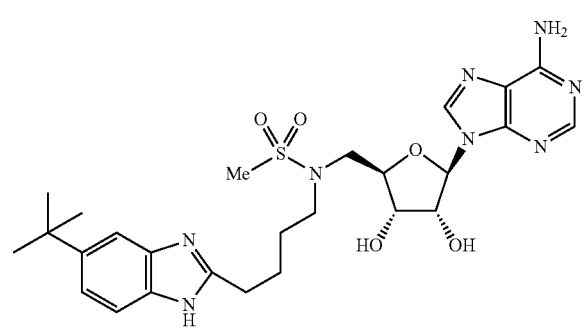 [SMILES: CC(C)(C)c1ccc2[nH]c(CCCCN(C[C@H]3O[C@@H](n4cnc5c(N)ncnc54)[C@H](O)[C@@H]3O)S(C)(=O)=O)nc2c1]

A reaction solution of N-(((3aR,4R,6R,6aR)-6-(6-amino-9H-purin-9-yl)-2,2-dimethyltetrahydrofuro[3,4-d][1,3]dioxol-4-yl)methyl)-N-(4-(5-(tert-butyl)-1H-benzo[d]imidazol-2-yl)butyl)methanesulfonamide in HCl/CH$_3$OH (2.5 M, 10 mL) was stirred at rt for 1.5 h. The mixture was concentrated under vacuum. The residue was purified by Prep-HPLC to give the desired compound (47 mg, 34%) as a white solid. $^1$H NMR (500 MHz, MeOD): δ 8.24 (s, 1H), 8.19 (s, 1H), 7.48 (s, 1H), 7.39 (d, J=8.5 Hz, 1H), 7.27 (dd, J=2.0, 8.5 Hz, 1H), 5.97 (d, J=4.5 Hz, 1H), 4.80 (t, J=5.0 Hz, 1H), 4.26-4.31 (m, 1H), 3.53-3.69 (m, 2H), 3.19-3.34 (m, 1H), 2.86 (s, 3H), 2.80 (t, J=7.5 Hz, 2H), 1.65-1.76 (m, 4H), 1.36 (s, 9H) ppm; LC-MS (m/z): 573.2 [M+1]$^+$.

Compound 328

(2R,3R,4S,5R)-2-(6-amino-9H-purin-9-yl)-5-(((3-((5-(tert-butyl)-1H-benzo[d]imidazol-2-yl)-amino) propyl)(ethyl)amino)methyl)tetrahydrofuran-3,4-diol Step 1. Preparation of 2-(3-(((((3aR,4R,6R,6aR)-6-(6-amino-9H-purin-9-yl)-2,2-dimethyltetrahydrofuro[3,4-d][1,3]dioxol-4-yl)methyl)(ethyl)amino)propyl) isoindoline-1,3-dione To a solution of 2-(3-(((((3aR,4R,6R,6aR)-6-(6-amino-9H-purin-9-yl)-2,2-dimethyltetrahydrofuro[3,4-d][1,3]dioxol-4-yl)methyl)amino)propyl)isoindoline-1,3-dione (crude, 500 mg, 1.5 mmol), acetaldehyde (249 mg in DCE (dry, 6 mL) was added NaBH(OAc)$_3$ (200 mg, 3 mmol) in one portion. Then the resulting reaction mixture was stirred at rt overnight. Saturated aqueous NaHCO$_3$ (10 mL) was added to quench the reaction, then was extracted with DCM (20 mL×4), dried over anhydrous Na$_2$SO$_4$ and concentrated. The crude was purified by Prep-TLC (DCM:MeOH=20:1) then re-purified by Prep-HPLC to afford the product (120 mg, yield: 25%) as a colorless slurry. $^1$H NMR (500 MHz, MeOD): δ 8.145 (s, 1H), 8.098 (s, 1H), 7.728-7.663 (m, 4H), 6.02 (d, J=2.0 Hz, 1H), 5.352 (dd, J=2.5, 8.5 Hz, 1H), 4.920 (dd, J=3.5, 6.5 Hz, 1H), 4.210-4.177 (m, 1H), 3.585-3.498 (m, 2H), 2.668-2.375 (m, 6H), 1.662-1.619 (m, 2H), 1.459 (s, 3H), 1.265 (s, 3H), 0.838 (t, J=14.0 Hz, 3H) ppm; ESI-MS (m/z): 522.3 [M+1]+.

Step 2. Preparation of N1-(((3aR,4R,6R,6aR)-6-(6-amino-9H-purin-9-yl)-2,2-dimethyltetrahydrofuro[3,4-d][1,3]dioxol-4-yl)methyl)-N1-ethylpropane-1,3-diamine

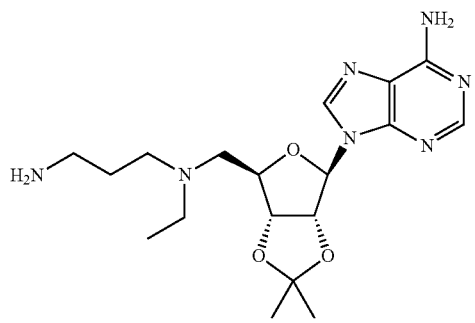 [SMILES: CCN(CCCN)C[C@H]1O[C@@H](n2cnc3c(N)ncnc32)[C@@H]2OC(C)(C)O[C@@H]21]

To a solution of 2-(3-(((((3aR,4R,6R,6aR)-6-(6-amino-9H-purin-9-yl)-2,2-dimethyltetrahydrofuro[3,4-d][1,3]dioxol-4-yl)methyl)(ethyl)amino)propyl)isoindoline-1,3-dione (1.0 g, 1.87 mmol) in EtOH (35 mL) was added NH₂—NH₂.H₂O (85%) (0.44 g, 7.48 mmol), and the mixture was heated to reflux for 2 h. After cooling, the reaction mixture was filtered and the filtrate was concentrated. DCM (60 mL) was added and filtered, the filtrate was concentrated to afford the product (700 mg, yield: 92%) as a white solid. ¹H NMR (500 MHz, MeOD): δ 8.22 (s, 1H), 8.16 (s, 1H), 6.12 (d, J=2.0 Hz, 1H), 5.461 (dd, J=2.0, 6.0 Hz, 1H), 4.952-4.920 (m, 1H), 4.301-4.268 (m, 1H), 2.664-2.612 (m, 4H), 2.491-2.408 (m, 4H), 1.528-1.436 (m, 5H), 1.323 (s, 3H), 0.845 (t, J=14.0 Hz, 3H) ppm. ESI-MS (m/z): 392.3 [M+1]+:

Step 3. Preparation of N1-(((3aR,4R,6R,6aR)-6-(6-amino-9H-purin-9-yl)-2,2-dimethyltetrahydrofuro[3,4-d][1,3]dioxol-4-ylmethyl)-N-3-(5-(tert-butyl)-1H-benzo[d]imidazol-2-yl)-N1-ethylpropane-1,3-diamine

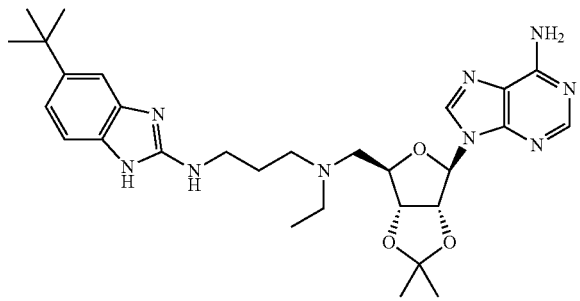 [SMILES: CCN(CCCNc1nc2cc(C(C)(C)C)ccc2[nH]1)C[C@H]1O[C@@H](n2cnc3c(N)ncnc32)[C@@H]2OC(C)(C)O[C@@H]21]

5-tert-butyl-2-chloro-1H-benzimidazole (50 mg, 0.24 mmol), N1-(((3aR,4R,6R,6aR)-6-(6-amino-9H-purin-9-yl)-2,2-dimethyltetrahydrofuro[3,4-d][1,3]dioxol-4-yl)methyl)-N1-ethylpropane-1,3-diamine (90 mg, 0.24 mmol) and TEA (40 mg, 0.37 mmol) were dissolved in n-BuOH (2 mL) and treated with KI (20 mg, cal.). The mixture was irradiated by microwave at 160° C. for 2 h. Solvent was removed in vacuo and the crude was purified by Prep-TLC (DCM:MeOH=10:1) to afford the product (40 mg, yield: 30%) as a yellow solid. ESI-MS (m/z): 564.3 [M+1]+.

Step 4. Preparation of (2R,3R,4S,5R)-2-(6-amino-9H-purin-9-yl)-5-(((3-((5-(tert-butyl)-1H-benzo[d]imidazol-2-yl)amino)propyl)(ethyl)amino)methyl)tetrahydrofuran-3,4-diol

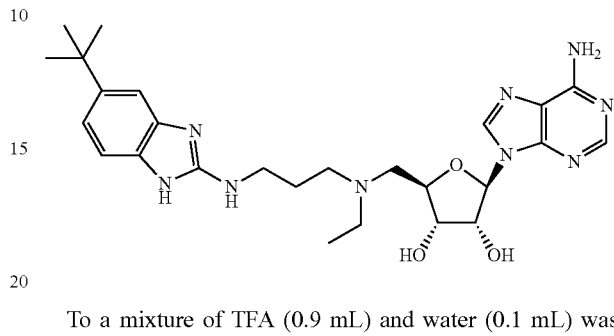

To a mixture of TFA (0.9 mL) and water (0.1 mL) was added N1-(((3aR,4R,6R,6aR)-6-(6-amino-9H-purin-9-yl)-2,2-dimethyltetrahydrofuro[3,4-d][1,3]dioxol-4-yl)methyl)-N3-(5-(tert-butyl)-1H-benzo[d]imidazol-2-yl)-N1-ethylpropane-1,3-diamine (40 mg, 0.07 mmol). The solution was allowed to stand at room temperature for 2 h and evaporated to dryness. The residue was co-evaporated with methanol (5 mL) twice. Then the residue was dissolved in MeOH (5 mL). The solution was neutralized by K₂CO₃ (100 mg, dissolved in 1 mL of H₂O) with stirring at rt for 1 h. Solvent was removed in vacuo, then the crude was purified by Prep-HPLC to afford the product (19 mg, yield: 51%) as a white solid. ¹H NMR (500 MHz, MeOD): δ 8.23 (s, 1H), 8.19 (s, 1H), 7.22 (s, 1H), 7.07-7.05 (m, 1H), 5.982 (d, J=4.5 Hz, 1H), 4.750-4.730 (m, 1H), 4.291-4.246 (m, 2H), 2.939-2.927 (m, 2H), 2.744-2.675 (m, 4H), 1.864-1.824 (m, 2H) 1.074 (t, J=17 Hz, 3H) ppm; ESI-MS (m/z): 524.3 [M+1]+.

Compound 329

(2R,3R,4S,5S)-2-(6-amino-9H-purin-9-yl)-5-(((4-(5-(tert-butyl)-1H-benzo[d]imidazol-2-yl)butyl)sulfinyl)methyl)tetrahydrofuran-3,4-diol

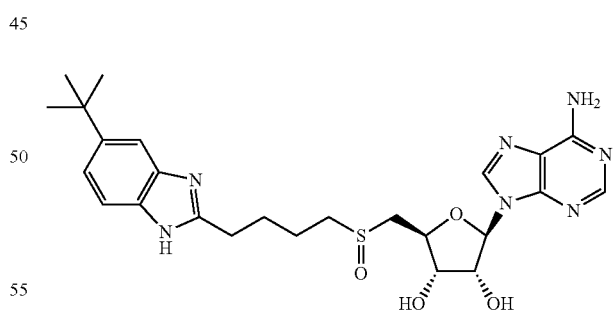

A solution 9-((3aR,4R,6S,6aS)-6-(((4-(5-(tert-butyl)-1-((2-(trimethylsilyl)ethoxy)methyl)-1H-benzo[d]imidazol-2-yl)butyl)thio)methyl)-2,2-dimethyltetrahydrofuro[3,4-d][1,3]dioxol-4-yl)-9H-purin-6-amine (200 mg, 0.29 mmol) in TFA (1.80 mL) and 0.20 mL of water were stirred at 45° C. for 1 hour. The reaction was concentrated to dryness, dissolved in MeOH (2 mL) and EA (100 mL), washed with aq. sat. NaHCO₃ (10×2 mL), dried over Na₂SO₄ and evaporated to give the crude. The residue was purified by Prep-HPLC to obtain the product (18 mg, Yield 16%). ¹H NMR (500 MHz, MeOO): δ 8.26 (d, J=6.0 Hz, 1H), 8.22 (d, J=8.5 Hz, 1H), 7.49-7.268 (m, 3H), 6.01 (m, 1H), 4.94-4.86 (m, 1H), 4.51-4.42 (m, 2H), 2.95-2.85 (m, 4H), 1.97-1.76 (m, 4H), 1.37 (s, 9H), 1.31-1.29 (m, 2H) ppm; ESI-MS (m/z): 528.3 [M+1]⁺.

Compound 330

(2R,3R,4S,5R)-2-(6-amino-9H-purin-9-yl)-5-(((3-((5-(tert-butyl)-1H-benzo[d]imidazol-2-yl)amino)propyl)amino)methyl)tetrahydrofuran-3,4-diol

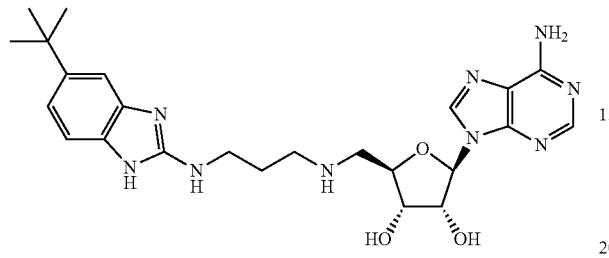

Step 1. Preparation of 3-(1,3-dioxoisoindolin-2-yl)propanal

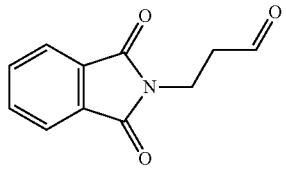 [SMILES: O=CCCN1C(=O)c2ccccc2C1=O]

2-(3-hydroxypropyl)isoindoline-1,3-dione (414 mg, 2.0 mmol) and IBX (1.68 g, 6 mmol) were dissolved in EA (25 mL) and the reaction mixture was heated to reflux with stirring for 3 h. And then the mixture was filtrated and rinsed with EA (15 mL×3), the filtrate was concentrated to afford the product (crude, 412 mg, yield: 100%) as a yellow solid which was directly used for next step without further purification.

Step 2. Preparation of 2-(3-(((((3aR,4R,6R,6aR)-6-(6-amino-9H-purin-9-yl)-2,2-dimethyltetrahydrofuro[3,4-d][1,3]dioxol-4-yl)methyl)amino)propyl)isoindoline-1,3-dione

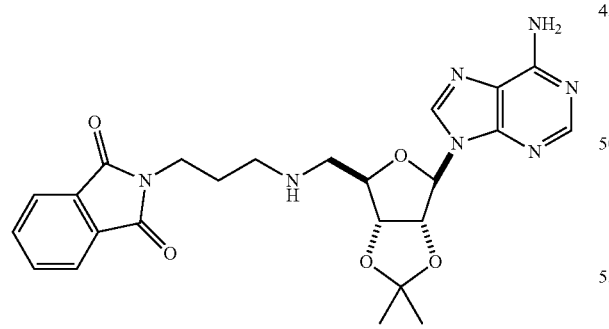

a solution of 3-(1,3-dioxoisoindolin-2-yl)propanal (crude, 412 mg, 2.0 mmol), Ep-5 (612 mg, 2.0 mmol) and Molecular sieve (4A, 0.5 g) in MeOH (dry, 6 mL) was added NaCNBH₃ (200 mg, 3 mmol) in one portion. Then the resulting reaction mixture was stirred at rt overnight. Saturated aqueous NaHCO₃ (10 mL) was added to quench the reaction, then was extracted with DCM (20 mL×4), dried over anhydrous Na₂SO₄ and concentrated. The crude was purified by Prep-TLC (DCM:MeOH=20:1) to afford the product (500 mg, yield: 50%) as a colorless slurry. ¹H NMR (500 MHz, MeOD): δ 8.29 (s, 1H), 8.23 (s, 1H), 7.86-7.795 (m, 4H), 6.21 (d, J=2.5 Hz, 2H), 5.470 (dd, J=2.5, 6.5 Hz, 1H), 5.084 (dd, J=3.5, 6.5 Hz, 1H), 4.429-4.398 (m, 1H), 3.683 (t, J=13.5 Hz, 1H), 3.182-3.139 (m, 1H), 3.069-3.036 (m, 1H), 2.769-2.703 (m, 1H), 1.885-1.823 (m, 1H), 1.613 (s, 3H), 1.351 (s, 1H) ppm; ESI-MS (m/z): 494.3 [M+1]⁺.

Step 3. Preparation of tert-butyl (((3aR,4R,6R,6aR)-6-(6-amino-9H-purin-9-yl)-2,2-dimethyltetrahydrofuro[3,4-d][1,3]dioxol-4-yl)methyl)(3-(1,3-dioxoisoindolin-2-yl)propyl)carbamate

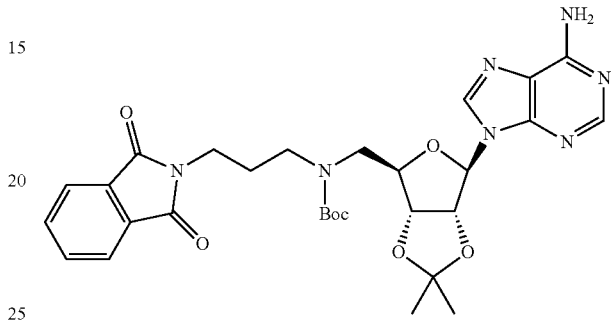

To a stirred solution of 2-(3-(((((3aR,4R,6R,6aR)-6-(6-amino-9H-purin-9-yl)-2,2-dimethyltetrahydrofuro[3,4-d][1,3]dioxol-4-yl)methyl)amino)propyl)isoindoline-1,3-dione (1.08 g, 10 mmol) and TEA (2.02 g, 20 mmol) in DCM (20 mL) was added Boc₂O (2.18 g, 10 mmol) dropwise at 0° C. The mixture was stirred at rt overnight. The reaction mixture was poured into water (10 mL), and extracted with DCM (30 mL×2). The organic phase was dried over anhydrous Na₂SO₄ and concentrated. The crude was purified by prep-TLC (DCM:MeOH=50:1) to afford the product (1.7 g, yield: 88%). ¹H NMR (500 MHz, MeOD): δ 8.16 (s, 1H), 8.13 (s, 1H), 7.690-7.670 (m, 4H), 6.06 (brs, 1H), 5.35 (brs, 1H), 4.83 (brs, 1H), 4.26 (brs, 1H), 3.58-3.21 (m, 4H), 2.96-2.95 (m, 2H), 1.61-1.57 (m, 2H), 1.47 (s, 3H), 1.31-1.18 (m, 12H) ppm; ESI-MS (m/z): 594.3[M+1]⁺.

Step 4. Preparation of tert-butyl (((3aR,4R,6R,6aR)-6-(6-amino-9H-purin-9-yl)-2,2-dimethyltetrahydrofuro[3,4-d][1,3]dioxol-4-yl)methyl)(3-aminopropyl)carbamate

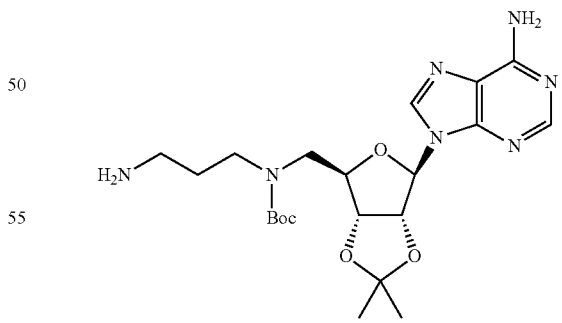

To a solution of tert-butyl (((3aR,4R,6R,6aR)-6-(6-amino-9H-purin-9-yl)-2,2-dimethyltetrahydrofuro[3,4-d][1,3]dioxol-4-yl)methyl)(3-(1,3-dioxoisoindolin-2-yl)propyl) carbamate (1.0 g, 1.87 mmol) in EtOH (35 mL) was added NH₂—NH₂.H₂O (85%) (0.44 g, 7.48 mmol), and the mixture was heated to reflux for 2 h. After cooling, the reaction mixture was filtered and the filtrate was concentrated. DCM (60 mL) was added and filtered, the filtrate was concentrated to afford the product (700 mg, yield: 92%) as a white solid. ¹H NMR (500 MHz, MeOD): δ 8.22 (s, 1H), 8.15 (s, 1H), 6.12-6.08 (m, 1H), 5.41 (brs, 1H), 4.98 (brs, 1H), 4.34 (brs, 1H), 3.57-3.50 (m, 2H), 3.13-2.80 (m, 2H), 2.43-2.37 (m, 2H), 1.50 (s, 3H), 1.46-0.99 (m, 14H), ppm; ESI-MS (m/z): 464.4. [M+1]⁺.

Step 5. Preparation of tert-butyl (((3aR,4R,6R,6aR)-6-(6-amino-9H-purin-9-yl)-2,2-dimethyltetrahydrofuro[3,4-d][1,3]dioxol-4-yl)methyl)(3-((5-(tert-butyl)-1H-benzo[d]imidazol-2-yl)amino)propyl)carbamate

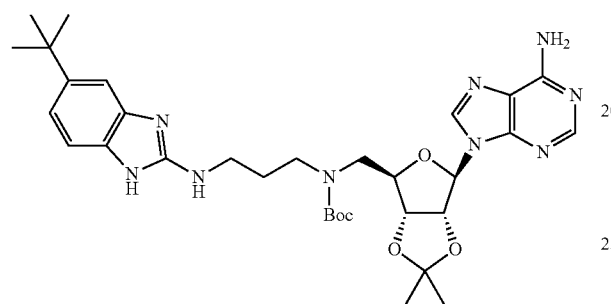

5-tert-butyl-2-chloro-1H-benzimidazole (50 mg, 0.24 mmol), tert-butyl (((3aR,4R,6R,6aR)-6-(6-amino-9H-purin-9-yl)-2,2-dimethyltetrahydrofuro[3,4-d][1,3]dioxol-4-yl)methyl)(3-aminopropyl)carbamate (90 mg, 0.24 mmol) and TEA (40 mg, 0.37 mmol) were dissolved in n-BuOH (2 mL) and treated with KI (20 mg, cal.). The mixture was irradiated by microwave at 160° C. for 2 h. Solvent was removed in vacuo and the crude was purified by Prep-TLC (DCM:MeOH=10:1) to afford the product (40 mg, yield: 30%) as a yellow solid. ESI-MS (m/z): 636.5 [M+1]⁺.

Step 6. Preparation of (2R,3R,4S,5R)-2-(6-amino-9H-purin-9-yl)-5-(((3-((5-(tert-butyl)-1H-benzo[d]imidazol-2-yl)amino)propyl)amino)methyl)tetrahydrofuran-3,4-diol

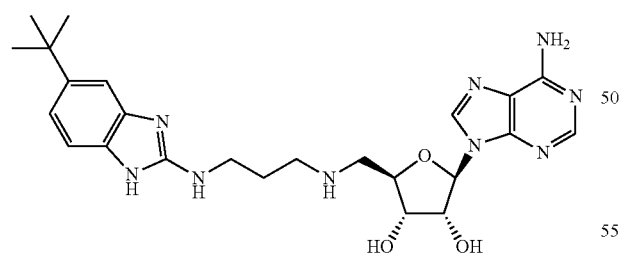

To a mixture of TFA (0.9 mL) and water (0.1 mL) was added tert-butyl (((3aR,4R,6R,6aR)-6-(6-amino-9H-purin-9-yl)-2,2-dimethyltetrahydrofuro[3,4-d][1,3]dioxol-4-yl)methyl)(3-((5-(tert-butyl)-1H-benzo[d]imidazol-2-yl)amino)propyl)carbamate (40 mg, 0.07 mmol). The solution was allowed to stand at room temperature for 2 h and evaporated to dryness. The residue was co-evaporated with methanol (5 mL) twice. Then the residue was dissolved in MeOH (5 mL). The solution was neutralized by K₂CO₃ (100 mg, dissolved in 1 mL of H₂O) with stirring at rt for 1 h. Solvent was removed in vacuo, then the crude was purified by prep-HPLC to afford the product (19 mg, yield: 51%) as a white solid. ¹H NMR (500 MHz, MeOD): δ 8.26 (s, 1H), 8.21 (s, 1H), 7.23-7.01 (m, 3H), 5.98 (d, J=5.5 Hz, 1H), 4.52-4.831 (m, 1H), 4.333-4.313 (m, 1H), 4.266-4.235 (m, 1H), 3.43-3.40 (m, 2H), 3.08-2.99 (m, 2H), 2.83-2.81 (m, 2H), 1.91-1.85 (m, 2H) 1.35 (s, 9H) ppm; ESI-MS (m/z): 496.2 [M+1]⁺.

Compound 331

N-(((2R,3S,4R,5R)-5-(6-amino-9H-purin-9-yl)-3,4-dihydroxytetrahydrofuran-2-yl)methyl)-4-(5-(tert-butyl)-1H-benzo[d]imidazol-2-yl)-N-isopropylbutanamide

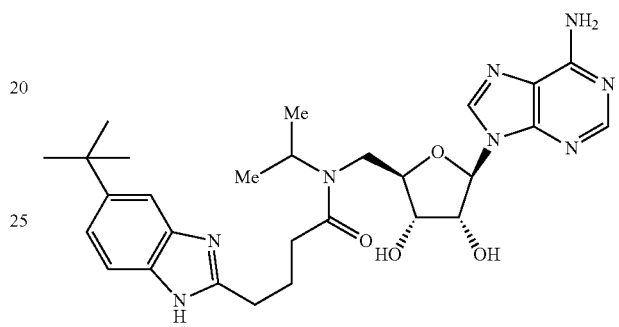

Step 1. Preparation of methyl 5-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)-5-oxopentanoate

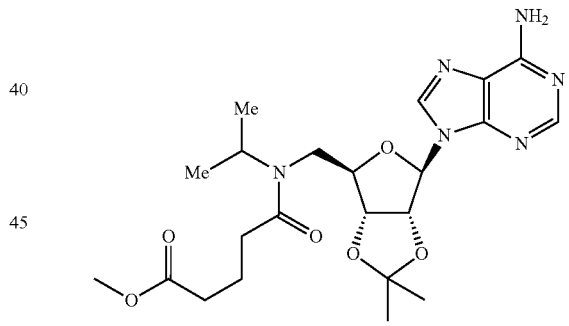

To a solution of monomethyl glutarate (7.6 g, 51.72 mmol), EDCI (13.2 g, 68.97 mmol) and HOBt (9.3 g, 68.97 mmol) in DCM (150 mL) was added 9-((3aR,4R,6R,6aR)-6-((isopropylamino)methyl)-2,2-dimethyltetrahydrofuro[3,4-d][1,3]dioxol-4-yl)-9H-purin-6-amine (12 g, 34.48 mmol) and TEA (24 mL, 172.41 mmol). The mixture was stirred at rt overnight. The mixture was washed with water (100 mL×2) and brine (100 mL). The organic phase was dried over Na₂SO₄, filtered and concentrated. The residue was purified by column chromatography (PE:EA=1:2) to afford the product as a yellow oil (13 g, 79%). ¹H NMR (500 MHz, CDCl₃): δ 8.34-8.37 (m, 1H), 7.87-8.00 (m, 1H), 6.04-6.09 (m, 1H), 5.89-5.94 (m, 2H), 5.43-5.46 (m, 1H), 5.15-5.17 (m, 0.8H), 5.08-5.11 (m, 0.2H), 4.48-4.51 (m, 0.8H), 4.28-4.35 (m, 0.5H), 3.97-4.03 (m, 0.8H), 3.80-3.85 (m, 0.9H), 3.55-3.69 (m, 4H), 2.96-3.13 (m, 1H), 2.34-2.51 (m, 2H), 2.09-2.12 (m, 2H), 1.72-2.00 (m, 2H), 1.58-1.62 (m, 3H), 1.37-1.40 (m, 3H), 0.98-1.18 (m, 6H) ppm; LC-MS (m/z): 477.3 [M+1]+.

Step 2. Preparation of 5-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)-5-oxopentanoic acid

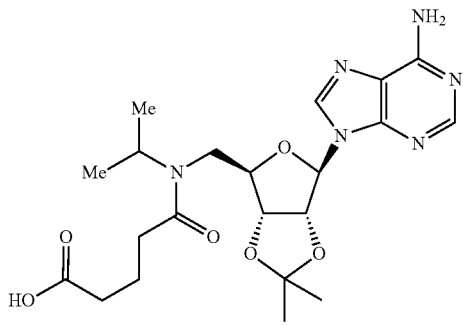 [SMILES: CC(C)N(C[C@H]1O[C@@H](n2cnc3c(N)ncnc32)[C@@H]2OC(C)(C)O[C@@H]21)C(=O)CCCC(=O)O]

To a solution of methyl 5-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)-5-oxopentanoate (13 g, 27.28 mmol) in THF/MeOH (150 mL/100 mL) was added a solution of LiOH·H₂O (5.73 g, 136.4 mmol) in water (50 mL). The mixture was stirred at rt for 5 h. The volatiles were removed under reduced pressure and the residue was extracted with DCM (100 mL×2). The basic water phase was adjusted to pH=5-6 with 4 M HCl solution and extracted with DCM (150 mL×3). The combined organic layers were washed with brine (100 mL×2). The organic phase was dried over Na₂SO₄, filtered and concentrated to afford the product as a light yellow solid (11 g, 87%). ¹H NMR (500 MHz, CDCl₃): δ 8.26-8.31 (m, 1H), 7.93-8.15 (m, 1H), 6.98-7.06 (m, 2H), 6.05-6.13 (m, 1H), 5.42 (m, 1H), 5.07-5.14 (m, 1H), 4.35-4.50 (m, 1.4H), 4.03-4.05 (m, 0.6H), 3.64-3.78 (m, 1.4H), 3.18-3.22 (m, 0.6H), 2.45-2.50 (m, 2.5H), 1.73-2.23 (m, 5H), 1.59-1.62 (m, 3H), 1.38-1.39 (m, 3H), 1.04-1.24 (m, 6H) ppm; LC-MS (m/z): 463.3 [M+23]+.

Step 3. Preparation of N1-(2-amino-4-(tert-butyl)phenyl)-N5-(((3aR,4R,6R,6aR)-6-(6-amino-9H-purin-9-yl)-2,2-dimethyltetrahydrofuro[3,4-d][1,3]dioxol-4-yl)methyl)-N5-isopropylglutaramide

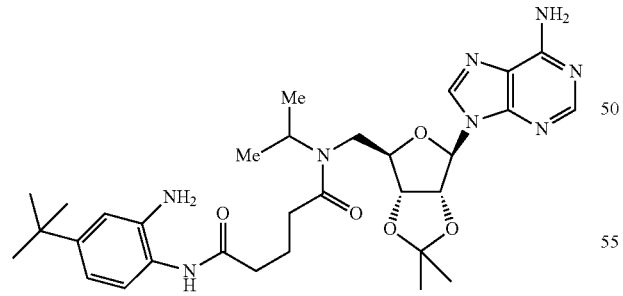

To a solution of 5-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)-5-oxopentanoic acid (400 mg, 0.86 mmol), EDCI (332 mg, 1.73 mmol) and HOBt (234 mg, 1.73 mmol) in DCM (15 mL) was added 4-tert-butylbenzene-1,2-diamine (2.0 eq., 1.73 mmol) and TEA (0.6 mL, 4.32 mmol). The mixture was stirred at rt overnight. The mixture was washed with water (15 mL×2) and brine (15 mL). The organic phase was dried over Na₂SO₄, filtered and concentrated. The residue was purified by Combi-flash (12 g silica gel, start 10:0-EA:MeOH to 10:1 by gradient, 40 mL/min, 30 min, 1.2 total solvent volume) to afford the product (310 mg, 59%). LC-MS (m/z): 609.5 [M+1]+.

Step 4. Preparation of N-(((3aR,4R,6R,6aR)-6-(6-amino-9H-purin-9-yl)-2,2-dimethyltetrahydrofuro[3,4-d][1,3]dioxol-4-yl)methyl)-4-(5-(tert-butyl)-1H-benzo[d]imidazol-2-yl)-N-isopropylbutanamide

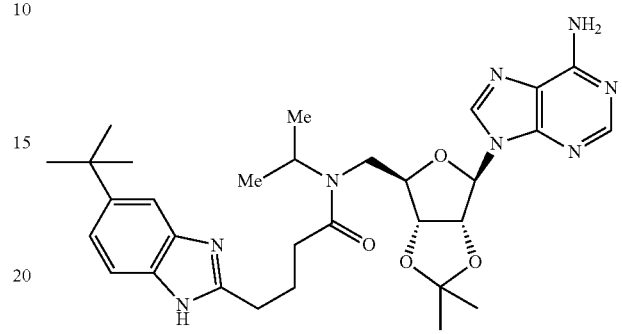

A solution of N1-(2-amino-4-(tert-butyl)phenyl)-N5-(((3aR,4R,6R,6aR)-6-(6-amino-9H-purin-9-yl)-2,2-dimethyltetrahydrofuro[3,4-d][1,3]dioxol-4-yl)methyl)-N5-isopropylglutaramide in AcOH (8-10 mL) was stirred at 65° C. overnight. The solvent was removed under reduced pressure. The residue was dissolved in DCM (20 mL) and washed with sat. NaHCO₃ solution (20 mL), water (20 mL) and brine (20 mL). The organic phase was dried over Na₂SO₄, filtered and concentrated to afford the product (270 mg, 90%). ¹H NMR (500 MHz, CDCl₃): δ 8.30-8.36 (m, 1H), 7.84-8.00 (m, 1H), 7.55-7.58 (m, 1H), 7.46-7.50 (m, 1H), 7.27-7.32 (m, 1H), 6.22-6.30 (m, 2H), 6.03-6.11 (m, 1H), 5.37-5.47 (m, 1H), 5.08-5.32 (m, 1H), 4.54-4.58 (m, 0.7H), 4.29-4.36 (m, 0.3H), 3.95-4.00 (m, 0.7H), 3.79-3.84 (m, 0.7H), 3.53-3.74 (m, 0.3H), 3.27-3.31 (m, 0.6H), 3.05-3.10 (m, 0.4H), 2.99-3.02 (m, 1.3H), 2.57-2.82 (m, 0.6H), 2.39-2.48 (m, 1.4H), 2.03-2.34 (m, 3H), 1.79-1.81 (m, 0.4H), 1.57-1.61 (m, 3H), 1.35-1.36 (m, 12H), 1.07-1.22 (m, 6H) ppm; LC-MS (m/z): 591.4 [M+1]+.

Step 5. Preparation of N-(((2R,3S,4R,5R)-5-(6-amino-9H-purin-9-yl)-3,4-dihydroxytetrahydrofuran-2-yl)methyl)-4-(5-(tert-butyl)-1H-benzo[d]imidazol-2-yl)-N-isopropylbutanamide

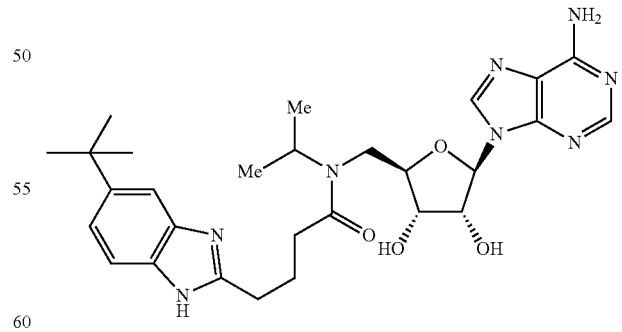

A solution of N-(((3aR,4R,6R,6aR)-6-(6-amino-9H-purin-9-yl)-2,2-dimethyltetrahydrofuro[3,4-d][1,3]dioxol-4-yl)methyl)-4-(5-(tert-butyl)-1H-benzo[d]imidazol-2-yl)-N-isopropylbutanamide in TFA (8-10 mL) was stirred at rt for 2-3 h. The solvent was removed under reduced pressure. The residue was dissolved in EA:MeOH (v:v=10:1, 20 mL) and washed with sat. NaHCO₃ solution (10 mL), water (10 mL) and brine (10 mL). The organic phase was dried over Na₂SO₄, filtered and concentrated to afford the product (142 mg, 56%). ¹H NMR (400 MHz, methanol-d4): δ 8.13-8.34 (m, 2H), 7.47-7.49 (m, 1H), 7.24-7.42 (m, 2H), 5.90-5.97 (m, 1H), 4.63-4.65 (m, 0.6H), 4.40-4.44 (m, 0.4H), 4.27-4.34 (m, 1.6H), 4.05-4.15 (m, 1.1H), 3.67-3.87 (m, 1.5H), 3.45-3.51 (m, 0.6H), 2.92-2.96 (m, 1.3H), 2.66-2.70 (m, 0.8H), 2.41-2.56 (m, 2.1H), 2.09-2.17 (m, 1.2H), 1.94-1.98 (m, 0.8H), 1.35-1.36 (m, 9H), 1.07-1.22 (m, 6H) ppm; LC-MS (m/z): 551.4 [M+1]⁺.

Compound 332

(2R,3R,4S,5R)-2-(6-amino-9H-purin-9-yl)-5-(((4-(5-fluoro-6-isopropyl-1H-benzo[d]imidazol-2-yl)butyl)(isopropyl)aminomethyl)tetrahydrofuran-3,4-diol

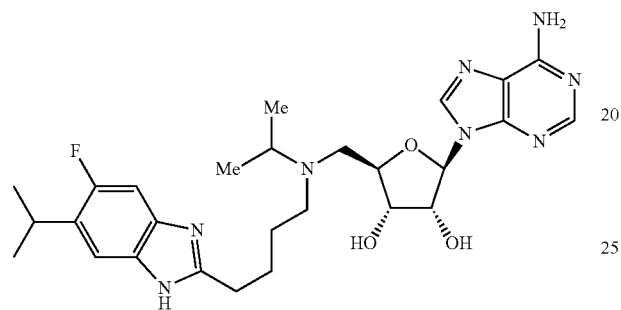

Step 1. Preparation of ethyl 5-oxopentanoate

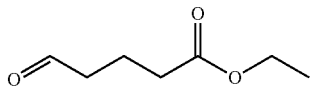

The mixture of ethyl 5-bromopentanoate (84 g, 0.402 mol), sodium bicarbonate (68 g, 0.804 mol) and pyridine N-oxide (76 g, 0.804 mil) in toluene (600 ml) was refluxed in an atmosphere of nitrogen under vigorous stirring for overnight. After cooling, the product was partitioned with water (400 ml). The toluene layer was separated and the aqueous layer was extracted with a further amount of toluene (500 ml). The combined toluene extracts were dried over magnesium sulphate and the toluene was removed in vacuo. The product (7.4 g, 13%) as colorless oil was obtained by fractional distillation. ¹H NMR (500 MHz, CDCl₃): δ 9.8 (s, 1H), 4.14 (q, J=7.0 Hz, 1H), 2.52-2.56 (m, 2H), 2.34-2.39 (m, 2H), 1.94-1.98 (m, 2H), 1.25 (t, J=7.0 Hz, 3H) ppm.

Step 2. Preparation of ethyl 5-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)pentanoate

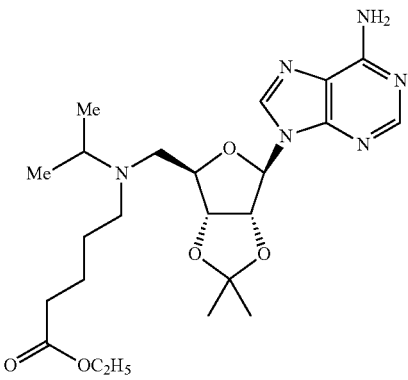 [SMILES: CCOC(=O)CCCCN(C[C@H]1O[C@@H](n2cnc3c(N)ncnc32)[C@@H]2OC(C)(C)O[C@@H]21)C(C)C]

To a stirred solution of 9-((3aR,4R,6R,6aR)-6-((isopropylamino)methyl)-2,2-dimethyltetrahydrofuro[3,4-d][1,3]dioxol-4-yl)-9H-purin-6-amine (5.1 g, 14.66 mmol) and ethyl 5-oxopentanoate (3.5 g, 24.31 mmol) in 80 mL of DCE was added NaBH(OAc)₃ (6.2 g, 29.32 mmol). Then the mixture was stirred at rt overnight. NaHCO₃ (aq) was added to quench the reaction and the mixture was extracted with DCM (50 mL×3). The organic phase was concentrated and the residue was purified by SGC(CH₃OH:DCM=1:50) to afford the product (6.0 g, yield: 86%) as a syrup. ¹H NMR (500 MHz, MeOD): δ 8.28 (s, 1H), 8.24 (s, 1H), 6.18 (d, J=2.5 Hz, 1H), 5.70 (dd, J=2.0, 6.5 Hz, 2H), 5.05 (dd, J=3.0, 6.5 Hz, 1H), 4.24-4.28 (m, 1H), 4.12 (q, J=7.0 Hz, 2H), 2.25-2.93 (m, 7H), 1.54-1.60 (m, 5H), 1.34-1.40 (m, 5H), 1.25 (t, J=7.0 Hz, 3H), 1.00 (d, J=6.5 Hz, 3H), 0.85 (d, J=6.5 Hz, 3H) ppm. MS (ESI): m/z 477.7 [M+1]⁺.

Step 3. Preparation of 5-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)pentanoic acid

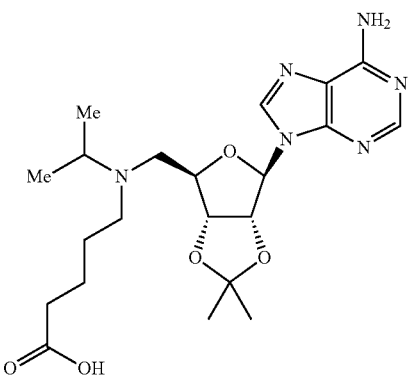 [SMILES: CC(C)N(CCCCC(=O)O)C[C@H]1O[C@@H](n2cnc3c(N)ncnc32)[C@@H]2OC(C)(C)O[C@@H]21]

A mixture of ethyl 5-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)pentanoate (5.5 g, 1.56 mmol) and LiOH (2.5 g, 59.5 mmol) in 50 mL of solvent (MeOH/THF/H₂O=1/1/1) was stirred at rt for 1 h. The system was neutralized with HCl to pH=6-7. The solvent was removed and the residue was purified by Prep-HPLC to give the product (4.6 g, 82%) as a white solid. ¹H NMR (500 MHz, MeOD): δ 8.29 (s, 1H), 8.26 (s, 1H), 6.25 (d, J=2.5 Hz, 1H), 5.54 (dd, J=2.0, 6.5 Hz, 2H), 5.11 (dd, J=3.0, 6.5 Hz, 1H), 4.43 (d, J=3.0 Hz, 1H), 3.15-3.30 (m, 1H), 3.04 (d, J=7.0 Hz, 2H), 2.68-2.72 (m, 2H), 2.17 (t, J=7.0 Hz, 2H), 1.49-1.81 (m, 7H), 1.41 (s, 3H), 1.11 (d, J=6.5 Hz, 3H), 0.91 (d, J=6.5 Hz, 3H) ppm. MS (ESI): m/z 449.7 [M+1]⁺.

Step 4. Preparation of N-(2-amino-4-fluoro-5-isopropylphenyl)-5-((((3aR,4R,6R,6aR)-6-(6-amino-9H-purin-9-yl)-2,2-dimethyltetrahydrofuro[3,4-d][1,3]dioxol-4-ylmethyl)(isopropyl)amino)pentanamide

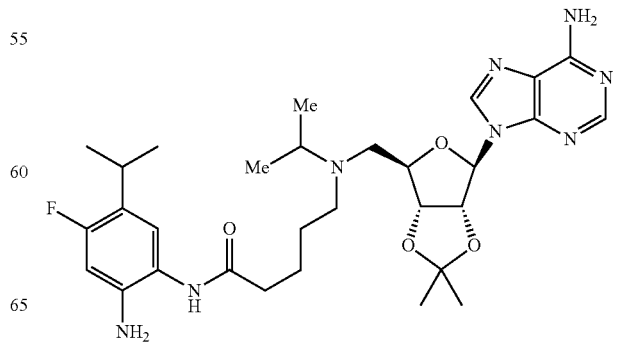

A mixture of 5-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)pentanoic acid (400 mg, 0.89 mmol), 4-fluoro-5-isopropyl-benzene-1,2-diamine (1.78 mmol), EDCI (341 mg, 1.78 mmol), HOBt (241 mg, 1.78 mmol), Et₃N (541 mg, 5.35 mmol) and CH₂Cl₂ (10 mL) was stirred at rt overnight. The reaction was then quenched with water (10 mL), and extracted with EtOAc (20 mL×3). The combined organic layers was washed with brine, dried over Na₂SO₄ and concentrated under reduced pressure. The obtained residue was purified by silica-gel column chromatography to give the desired compound as a solid (50 mg, 37%). ¹H NMR (500 MHz, MeOD): δ 8.25 (s, 1H), 8.17 (s, 1H), 7.32 (d, J=6.5 Hz, 1H), 7.10 (d, J=10.5 Hz, 1H), 5.94 (d, J=5.0 Hz, 1H), 4.73 (t, J=5.0 Hz, 1H), 4.25-4.27 (m, 1H), 4.07-4.09 (m, 1H), 3.23-3.25 (m, 1H), 2.49-2.97 (m, 7H), 1.77-1.80 (m, 2H), 1.50-1.52 (m, 2H), 1.27 (dd, J=2.0, 7.0 Hz, 6H), 1.00 (d, J=6.5 Hz, 3H), 0.95 (d, J=6.5 Hz, 3H). LC-MS (m/z): 541 [M+H]⁺.

Step 5. Preparation of (2R,3R,4S,5R)-2-(6-amino-9H-purin-9-yl)-5-(((4-(5-fluoro-6-isopropyl-1H-benzo[d]imidazol-2-yl)butyl)(isopropyl)amino)methyl)tetrahydrofuran-3,4-diol

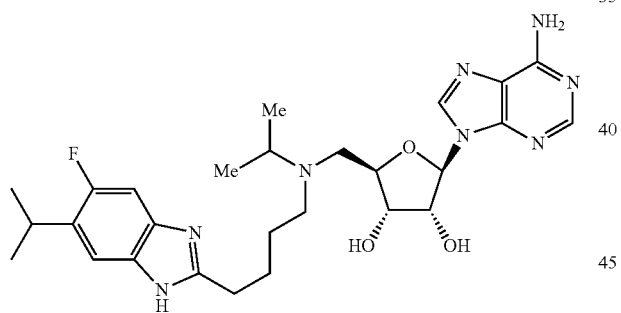

A reaction solution of N-(2-amino-4-fluoro-5-isopropylphenyl)-5-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)pentanamide in AcOH (10 mL) was stirred at 65° C. overnight. After concentration under reduced pressure, the residue was directly used for next reaction. A reaction solution of the crude protected diol was placed in HCl/CH₃OH (2.5 M, 10 mL) and stirred at rt for 2-3 h. After disappearance of the starting material, the mixture was concentrated in vacuum. The obtained residue was dissolved in MeOH (5 mL), saturated K₂CO₃ was then added to adjust the pH to 8-9. The mixture was concentrated again to give a solid substance. MeOH (5 mL) was added, filtered, concentrated. The residue was purified by Prep-HPLC to give the desired product (50 mg, 37%). ¹H NMR (500 MHz, MeOD): δ 8.25 (s, 1H), 8.17 (s, 1H), 7.32 (d, J=6.5 Hz, 1H), 7.10 (d, J=10.5 Hz, 1H), 5.94 (d, J=5.0 Hz, 1H), 4.73 (t, J=5.0 Hz, 1H), 4.25-4.27 (m, 1H), 4.07-4.09 (m, 1H), 3.23-3.25 (m, 1H), 2.49-2.97 (m, 7H), 1.77-1.80 (m, 2H), 1.50-1.52 (m, 2H), 1.27 (dd, J=2.0, 7.0 Hz, 6H), 1.00 (d, J=6.5 Hz, 3H), 0.95 (d, J=6.5 Hz, 3H). LC-MS (m/z): 541 [M+H]⁺.

Compound 500

(2R,3R,4S,5R)-2-(6-amino-9H-purin-9-yl)-5-(((4-(6-chloro-1H-benzo[d]imidazol-2-yl)butyl)(isopropyl)amino)methyl)tetrahydrofuran-3,4-diol

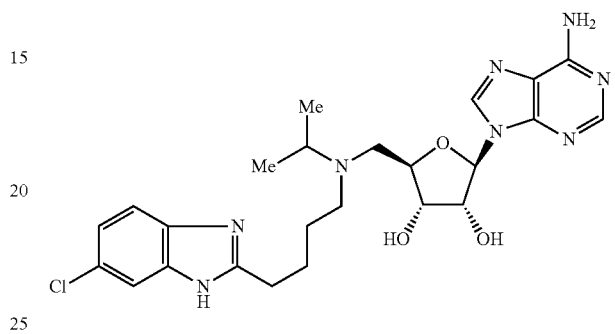

This compound was prepared using the same procedure as described for compound 332 substituting 4-chlorobenzene-1,2-diamine as the diamine (130 mg, 56%). ¹H NMR (500 MHz, MeOD): δ 8.15-8.27 (m, 2H), 7.40-7.50 (m, 2H), 7.12-7.16 (m, 1H), 5.95-6.10 (m, 1H), 4.73-4.75 (m, 1H), 4.28 (t, J=5.0 Hz, 1H), 4.10-4.13 (m, 1H), 2.55-3.04 (m, 7H), 1.79-1.86 (m, 2H), 1.51-1.58 (m, 2H), 0.92-1.05 (m, 6H). LC-MS (m/z): 515 [M+H]⁺.

Compound 333

(2R,3R,4S,5R)-2-(6-amino-9H-purin-9-yl)-5-(((isopropyl(4-(7-methyl-1H-benzo[d]imidazol-2-yl)butyl)amino)methyl)tetrahydrofuran-3,4-diol

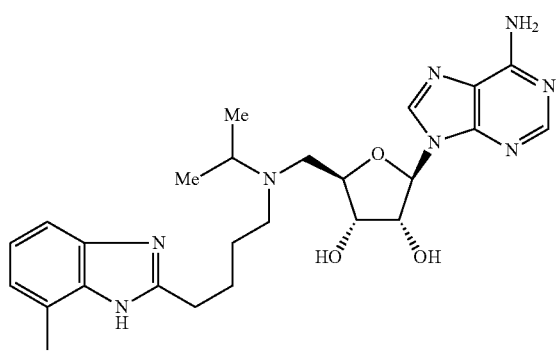 [SMILES: Cc1cccc2nc(CCCCN(C[C@H]3O[C@@H](n4cnc5c(N)ncnc54)[C@H](O)[C@@H]3O)C(C)C)[nH]c12]

This compound was prepared using the same procedure as described for compound 332 substituting 3-methylbenzene-1,2-diamine as the diamine (120 mg, 52%). ¹H NMR (500 MHz, MeOD): δ 8.26 (s, 1H), 8.20 (s, 1H), 7.30 (d, J=9.0 Hz, 1H), 7.05 (t, J=7.5 Hz, 1H), 6.95 (d, J=7.0 Hz, 1H), 5.95 (d, J=4.5 Hz, 1H), 4.73-4.75 (m, 1H), 4.26-4.28 (m, 1H), 4.10-4.11 (m, 1H), 2.54-3.00 (m, 7H), 2.53 (s, 3H), 1.82-1.85 (m, 2H), 1.53-1.56 (m, 2H), 1.03 (d, J=7.0 Hz, 3H), 0.96 (d, J=6.0 Hz, 3H). LC-MS (m/z): 495 [M+H]⁺.

Compound 334

(2R,3R,4S,5R)-2-(6-amino-9H-purin-9-yl)-5-(((4-(5,6-dichloro-1H-benzo[d]imidazol-2-yl)butyl)(isopropyl)amino)methyl)tetrahydrofuran-3,4-diol

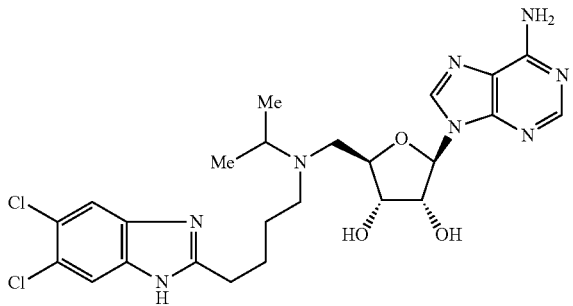 [SMILES: CC(C)N(CCCCc1nc2cc(Cl)c(Cl)cc2[nH]1)C[C@H]1O[C@@H](n2cnc3c(N)ncnc32)[C@H](O)[C@@H]1O]

This compound was prepared using the same procedure as described for substituting 3,4-dichlorobenzene-1,2-diamine as the diamine (135 mg, 48%). ¹H NMR (500 MHz, MeOD): δ 8.27 (s, 1H), 8.19 (s, 1H), 7.62 (s, 2H), 5.95 (d, J=4.5 Hz, 1H), 4.74 (t, J=5.0 Hz, 1H), 4.27 (t, J=5.0 Hz, 1H), 4.12-4.09 (m, 1H), 3.02-2.99 (m, 1H), 2.92-2.85 (m, 3H), 2.74 (dd, J=6.5, 14.0 Hz, 1H), 2.55 (t, J=8.0 Hz, 1H), 1.84-1.81 (m, 2H), 1.56-1.52 (m, 2H), 1.05 (d, J=6.5 Hz, 3H), 0.99 (d, J=7.0 Hz, 3H). LCMS (m/z): 549.2 (M+H)⁺.

Compound 335

(2R,3R,4S,5R)-2-(6-amino-9H-purin-9-yl)-5-((isopropyl(4-(5-(trifluoromethyl)-1H-benzo[d]imidazol-2-yl)butyl)amino)methyl)tetrahydrofuran-3,4-diol

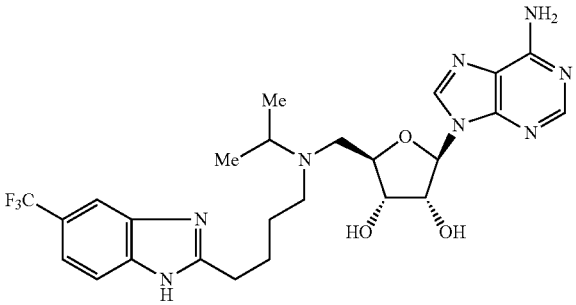 [SMILES: CC(C)N(CCCCc1nc2cc(C(F)(F)F)ccc2[nH]1)C[C@H]1O[C@@H](n2cnc3c(N)ncnc32)[C@H](O)[C@@H]1O]

This compound was prepared using the same procedure as described for compound 332 substituting 4-trifluoromethyl-benzene-1,2-diamine as the diamine (113 mg, 40%). ¹H NMR (500 MHz, MeOD): δ 8.28 (s, 1H), 8.19 (s, 1H), 7.80 (s, 1H), 7.64 (d, J=8.5 Hz, 1H), 7.48 (d, J=8.5 Hz, 1H), 5.96 (d, J=5.0 Hz, 1H), 4.76 (t, J=5.0 Hz, 1H), 4.29 (t, J=5.5 Hz, 1H), 4.13-4.10 (m, 1H), 3.02-2.99 (m, 1H), 2.93-2.89 (m, 1H), 2.72 (dd, J=7.0, 14 Hz, 1H), 2.56 (t, J=7.5 Hz, 2H), 1.87-1.82 (m, 2H), 1.57-1.53 (m, 2H), 1.05 (d, J=7.0 Hz, 3H), 0.99 (d, J=6.5 Hz, 3H). LCMS (m/z): 549.3 (M+H)⁺.

Compound 336

(2R,3R,4S,5R)-2-(6-amino-9H-purin-9-yl)-5-(((4-(5-fluoro-1H-benzo[d]imidazol-2-yl)butyl)(isopropyl)amino)methyl)tetrahydrofuran-3,4-diol

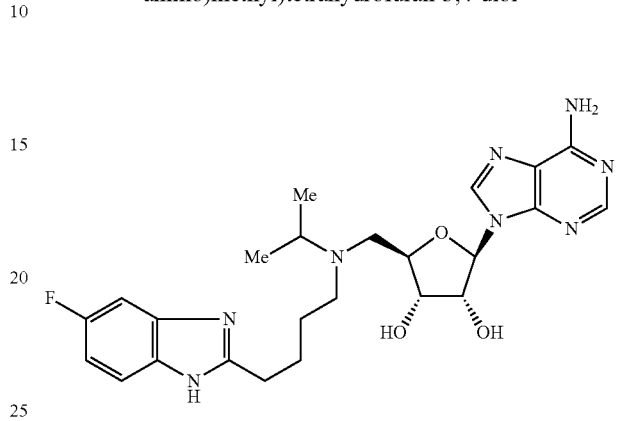

This compound was prepared using the same procedure as described for compound 332 substituting 4-fluorobenzene-1,2-diamine as the diamine (113 mg, 40%). ¹H NMR (500 MHz, MeOD): δ 8.27 (s, 1H), 8.19 (s, 1H), 7.43-7.41 (m, 1H), 7.17 (dd, J=9.5, 2.5 Hz, 1H), 6.95-9.91 (m, 1H), 5.97 (d, J=4.5 Hz, 1H), 4.75 (t, J=4.5 Hz, 1H), 4.29 (t, J=5.0 Hz, 1H), 4.12-4.11 (m, 1H), 3.01-2.72 (m, 5H), 2.54 (t, J=7.5 Hz, 2H), 1.82-1.77 (m, 2H), 1.54-1.50 (m, 2H), 1.03 (d, J=7.0 Hz, 3H), 0.99 (d, J=7.0 Hz, 3H). LCMS (m/z): 499.3 (M+H)⁺.

Compound 337

(2R,3R,4S,5R)-2-(6-amino-9H-purin-9-yl)-5-(((4-(7-chloro-5-(trifluoromethyl)-1H-benzo[d]imidazol-2-yl)butyl)(isopropyl)amino)methyl)tetrahydrofuran-3,4-diol

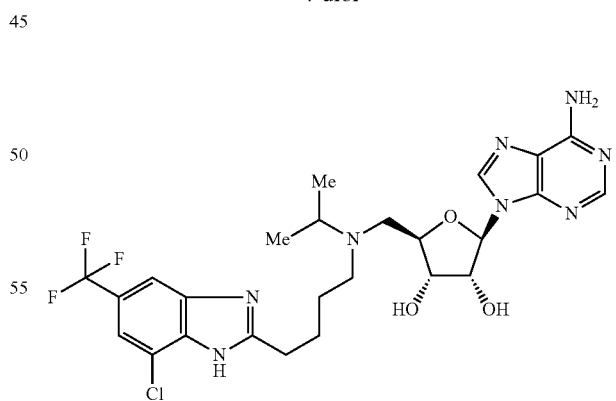

This compound was prepared using the same procedure as described for compound 332 substituting 3-chloro-5-(trifluoromethyl)benzene-1,2-diamine as the diamine (10 mg, 60%). ¹H NMR (500 MHz, MeOD): δ 8.27 (d, J=6.0 Hz, 1H), 8.20 (d, J=6.5 Hz, 1H), 7.76 (d, J=5.0 Hz, 1H), 7.51 (t, d=4.5 Hz, 1H), 5.96-5.98 (m, 1H), 4.76 (t, J=5.0 Hz, 1H), 4.29-4.31 (m, 1H), 4.12-4.13 (m, 1H), 2.61-3.07 (m, 7H), 1.83-1.88 (m, 2H), 1.57-1.59 (m, 2H), 0.92-1.07 (m, 6H). LC-MS (m/z): 584 [M+H]$^+$.

Compound 338

(2R,3R,4S,5R)-2-(6-amino-9H-purin-9-yl)-5-((iso-propyl(4-(4,5,6-trifluoro-1H-benzo[d]imidazol-2-yl)butyl)amino)methyl)tetrahydrofuran-3,4-diol

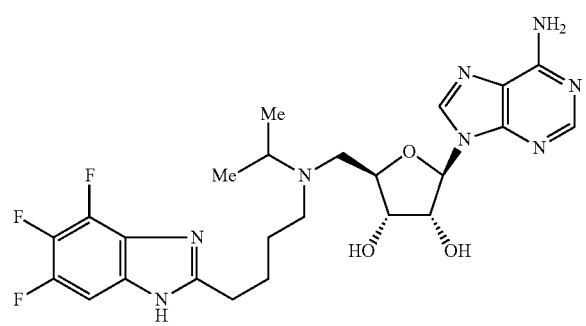 [SMILES: CC(C)N(CCCCc1nc2c(F)c(F)c(F)cc2[nH]1)C[C@H]1O[C@@H](n2cnc3c(N)ncnc32)[C@H](O)[C@@H]1O]

This compound was prepared using the same procedure as described for compound 332 substituting 3,4,5-trifluorobenzene-1,2-diamine as the diamine (10 mg, 60%). $^1$H NMR (500 MHz, MeOD): δ 8.28 (s, 1H), 8.18 (s, 1H), 7.17-7.13 (m, 1H), 5.97 (d, J=4.0 Hz, 1H), 4.74 (t, J=5.0 Hz, 1H), 4.28 (d, J=5.0 Hz, 1H), 4.12-4.08 (m, 1H), 3.00-2.95 (m, 1H), 2.92-2.83 (m, 3H), 2.72 (dd, J=6.5, 14 Hz, 1H), 2.53 (t, J=7.5 Hz, 2H), 1.82-1.78 (m, 2H), 1.54-1.50 (m, 2H), 1.03 (d, J=6.5 Hz, 3H), 0.97 (d, J=6.5 Hz, 3H). LCMS (m/z): 535.3 (M+H)$^+$.

Compound 339

(2R,3R,4S,5R)-2-(6-amino-9H-purin-9-yl)-5-(((4-(5,7-bis(trifluoromethyl)-1H-benzo[d]imidazol-2-yl)butyl)(isopropyl)amino)methyl)tetrahydrofuran-3,4-diol

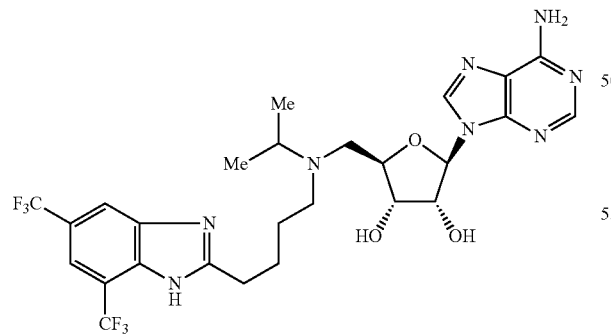

This compound was prepared using the same procedure as described for compound 332 substituting 3,5-bis(trifluoromethyl)benzene-1,2-diamine as the diamine (63 mg, 21%). $^1$H NMR (500 MHz, MeOD): δ 8.28 (s, 1H), 8.19 (s, 1H), 8.07 (s, 1H), 7.75 (s, 1H), 5.97 (d, J=5.0 Hz, 1H), 4.76-4.78 (m, 1H), 4.31-4.33 (m, 1H), 4.14-4.15 (m, 1H), 2.64-3.01 (m, 7H), 1.86-1.89 (m, 2H), 1.59-1.62 (m, 2H), 1.08 (d, J=6.0 Hz, 3H), 1.01 (d, J=6.0 Hz, 3H). LC-MS (m/z): 617 [M+H]$^+$.

Compound 340

(2R,3R,4S,5R)-2-(6-amino-9H-purin-9-yl)-5-(((4-(5,7-difluoro-1H-benzo[d]imidazol-2-yl)butyl)(isopropyl)amino)methyl)tetrahydrofuran-3,4-diol

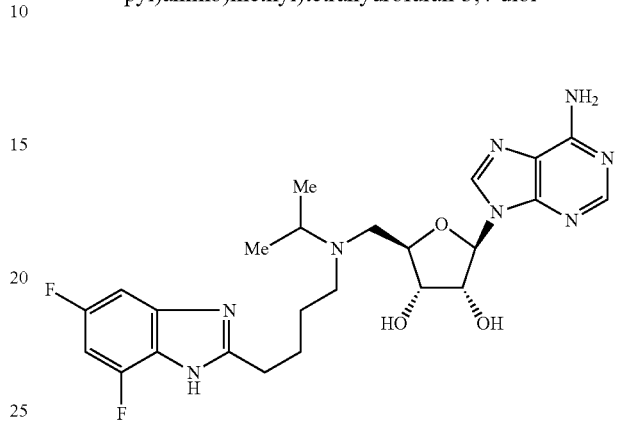

This compound was prepared using the same procedure as described for compound 332 substituting 3,5-difluorobenzene-1,2-diamine as the diamine (63 mg, 21%). $^1$H NMR (500 MHz, MeOD): δ 8.28 (s, 1H), 8.19 (s, 1H), 7.00-7.02 (m, 1H), 6.73-6.78 (m, 1H), 5.95 (d, J=4.5 Hz, 1H), 4.73-4.75 (m, 1H), 4.27-4.29 (m, 1H), 4.10-4.12 (m, 1H), 2.53-3.01 (m, 7H), 1.81-1.84 (m, 2H), 1.52-1.55 (m, 2H), 1.03 (d, J=6.5 Hz, 3H), 0.98 (d, J=7.0 Hz, 3H). LC-MS (m/z): 517 [M+H]$^+$.

Compound 341

(2R,3R,4S,5R)-2-(6-amino-9H-purin-9-yl)-5-(((4-(5,6-dimethyl-1H-benzo[d]imidazol-2-yl)butyl)(isopropyl)amino)methyl)tetrahydrofuran-3,4-diol

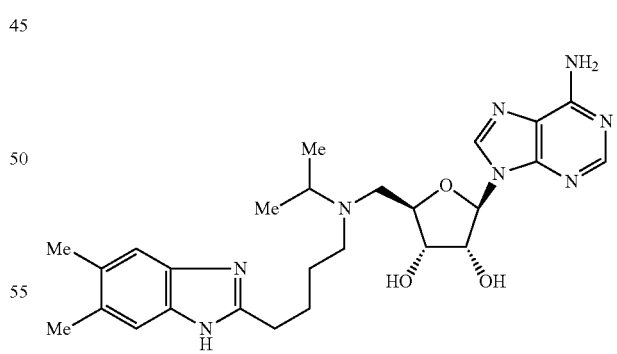

This compound was prepared using the same procedure as described for compound 332 substituting 4,5-dimethylbenzene-1,2-diamine as the diamine (90 mg, 57%). $^1$H NMR (500 MHz, MeOD): δ 8.26 (s, 1H), 8.19 (s, 1H), 7.22 (s, 2H), 5.94 (d, J=5.0 Hz, 1H), 4.73 (t, J=5.0 Hz, 1H), 4.26 (t, J=5.5 Hz, 1H), 4.12-4.08 (m, 1H), 3.00-2.97 (m, 1H), 2.92 (dd, J=5.0, 14.0 Hz, 1H), 2.82 (t, J=8.0 Hz, 2H), 2.70 (dd, J=7.0, 14.0 Hz, 1H), 2.54 (t, J=7.0 Hz, 2H), 2.32 (s, 6H), 1.84-1.77

(m, 2H), 1.56-1.49 (m, 2H), 1.04 (d, J=6.5 Hz, 3H), 0.98 (d, J=6.5 Hz, 3H). LCMS (m/z): 509.3 (M+H)⁺.

Compound 342

(2R,3R,4S,5R)-2-(6-amino-9H-purin-9-yl)-5-((iso-propyl(4-(6-methyl-1H-benzo[d]imidazol-2-yl)butyl)amino)methyl)tetrahydrofuran-3,4-diol

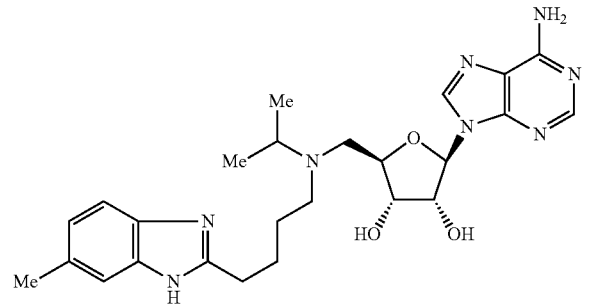 [SMILES: Cc1ccc2nc(CCCCN(C[C@H]3O[C@@H](n4cnc5c(N)ncnc54)[C@H](O)[C@@H]3O)C(C)C)[nH]c2c1]

This compound was prepared using the same procedure as described for compound 332 substituting 4-methylbenzene-1,2-diamine as the diamine (115 mg, 42%). ¹H NMR (500 MHz, MeOD): δ 8.26 (s, 1H), 8.19 (s, 1H), 7.22 (s, 2H), 5.94 (d, J=5.0 Hz, 1H), 4.73 (t, J=5.0 Hz, 1H), 4.26 (t, J=5.5 Hz, 1H), 4.12-4.08 (m, 1H), 3.00-2.97 (m, 1H), 2.92 (dd, J=5.0, 14.0 Hz, 1H), 2.82 (t, J=8.0 Hz, 2H), 2.70 (dd, J=7.0, 14.0 Hz, 1H), 2.54 (t, J=7.0 Hz, 2H), 2.32 (s, 6H), 1.84-1.77 (m, 2H), 1.56-1.49 (m, 2H), 1.04 (d, J=6.5 Hz, 3H), 0.98 (d, J=6.5 Hz, 3H). LCMS (m/z): 509.3 (M+H)⁺.

Compound 343

(2R,3R,4S,5R)-2-(6-amino-9H-purin-9-yl)-5-((iso-propyl(4-(5-(trifluoromethoxy)-1H-benzo[d]imidazol-2-yl)butyl)amino)methyl)tetrahydrofuran-3,4-diol

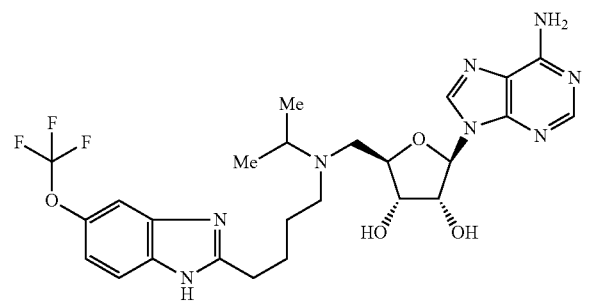 [SMILES: CC(C)N(CCCCc1nc2cc(OC(F)(F)F)ccc2[nH]1)C[C@H]1O[C@@H](n2cnc3c(N)ncnc32)[C@H](O)[C@@H]1O]

This compound was prepared using the same procedure as described for compound 332 substituting 5-trifluoromethoxybenzene-1,2-diamine as the diamine (115 mg, 46%). ¹H NMR (500 MHz, MeOD): δ 8.28 (s, 1H), 8.19 (s, 1H), 7.51 (d, J=9.0 Hz, 1H), 7.39 (d, J=1.0 Hz, 1H), 7.10 (dd, J=1.5, 8.5 Hz, 1H), 5.96 (d, J=4.5 Hz, 1H), 4.74 (t, J=5.0 Hz, 1H), 4.27-4.29 (m, 1H), 4.09-4.11 (m, 1H), 2.53-3.01 (m, 7H), 1.82-1.86 (m, 2H), 1.51-1.54 (m, 2H), 1.04 (d, J=7.0 Hz, 3H), 0.98 (d, J=6.0 Hz, 3H). LC-MS (m/z): 565 [M+H]⁺.

Compound 344

(2R,3R,4S,5R)-2-(6-amino-9H-purin-9-yl)-5-(((4-(6-chloro-5-fluoro-1H-benzo[d]imidazol-2-yl)butyl)(isopropyl)amino)methyl)tetrahydrofuran-3,4-diol

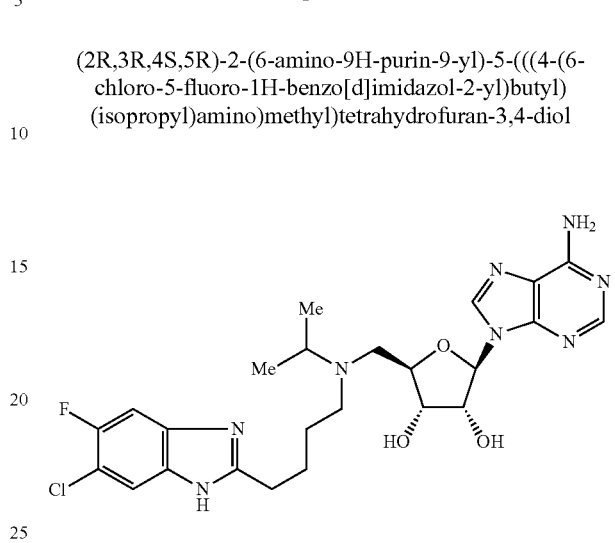

This compound was prepared using the same procedure as described for compound 332 substituting 4-chloro-5-fluorobenzene-1,2-diamine as the diamine (103 mg, 34%). ¹H NMR (500 MHz, MeOD): δ 8.27 (s, 1H), 8.19 (s, 1H), 7.55 (d, J=7.5 Hz, 1H), 7.33 (d, J=9 Hz, 1H), 5.95 (d, J=4.0 Hz, 1H), 4.74 (t, J=5.0 Hz, 1H), 4.27 (t, J=5.0 Hz, 1H), 4.12-4.09 (m, 1H), 3.01-2.98 (m, 1H), 2.93-2.84 (m, 3H), 2.73 (dd, J=6.5, 14.0 Hz, 1H), 2.55 (t, J=7.5 Hz, 2H), 1.84-1.80 (m, 2H), 1.55-1.52 (m, 2H), 1.05 (d, J=6.5 Hz, 3H), 0.98 (d, J=6.5 Hz, 3H). LCMS (m/z): 533.3 (M+H)⁺.

Compound 345

(2R,3R,4S,5R)-2-(6-amino-9H-purin-9-yl)-5-(((4-(4,6-dichloro-1H-benzo[d]imidazol-2-yl)butyl)(isopropyl)amino)methyl)tetrahydrofuran-3,4-diol

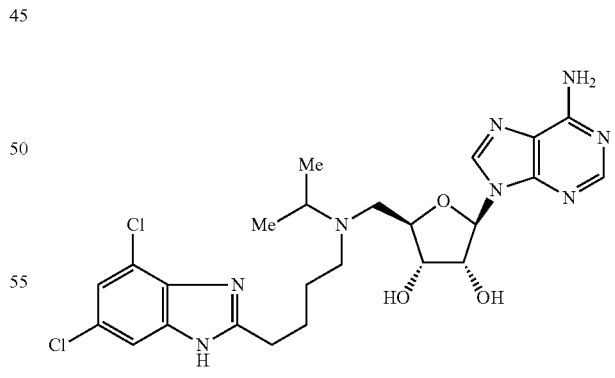

This compound was prepared using the same procedure as described for compound 332 substituting 3,4-dichlorobenzene-1,2-diamine as the diamine (115 mg, 56%). ¹H NMR (500 MHz, MeOD): δ 8.28 (s, 1H), 8.19 (s, 1H), 7.40 (d, J=2.0 Hz, 1H), 7.20 (t, d=1.5 Hz, 1H), 5.95 (d, J=4.5 Hz, 1H), 5.75 (d, J=4.5 Hz, 1H), 4.73-4.75 (m, 1H), 4.26-4.28 (m, 1H), 4.10-4.11 (m, 1H), 2.53-3.01 (m, 7H), 1.81-1.84 (m, 2H), 1.52-1.55 (m, 2H), 1.03 (d, J=6.5 Hz, 3H), 0.97 (d, J=6.5 Hz, 3H). LC-MS (m/z): 550 [M+H]⁺.

Compound 346

(2R,3R,4S,5R)-2-(6-amino-9H-purin-9-yl)-5-(((4-(6-ethoxy-1H-benzo[d]imidazol-2-yl)butyl)(isopropyl)amino)methyl)tetrahydrofuran-3,4-diol

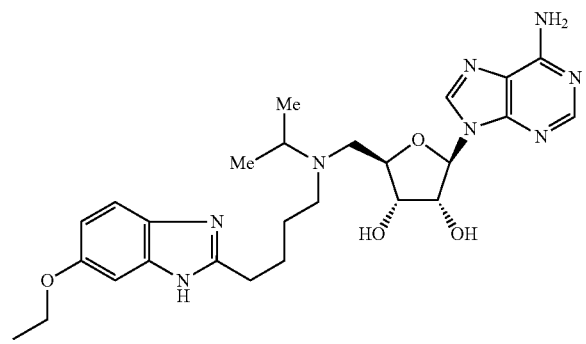 [SMILES: CCOc1ccc2nc(CCCCN(C[C@H]3O[C@@H](n4cnc5c(N)ncnc54)[C@H](O)[C@@H]3O)C(C)C)[nH]c2c1]

This compound was prepared using the same procedure as described for compound 332 substituting 4-ethoxybenzene-1,2-diamine as the diamine (120 mg, 46%). ¹H NMR (500 MHz, MeOD): δ 8.27 (d, J=6.5 Hz, 1H), 8.20 (d, J=6.5 Hz, 1H), 6.97-6.98 (m, 1H), 6.80-6.82 (m, 1H), 5.94-5.97 (m, 1H), 4.74 (d, J=5.0 Hz, 1H), 4.26-4.28 (m, 1H), 4.02-4.12 (m, 3H), 2.52-3.00 (m, 7H), 1.79-1.82 (m, 2H), 1.39-1.43 (m, 3H), 0.96-1.05 (m, 6H). LC-MS (m/z): 525 [M+H]⁺.

Compound 347

(2R,3R,4S,5R)-2-(6-amino-9H-purin-9-yl)-5-(((4-(7-chloro-1H-benzo[d]imidazol-2-yl)butyl)(isopropyl)amino)methyl)tetrahydrofuran-3,4-diol

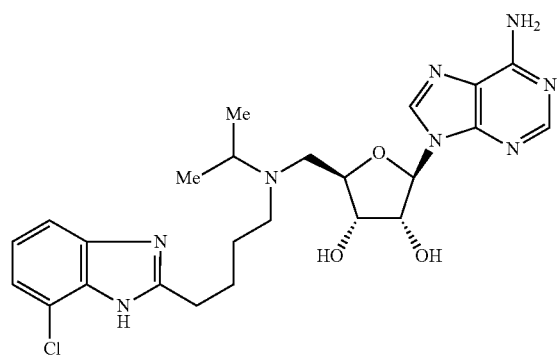 [SMILES: CC(C)N(CCCCc1nc2cccc(Cl)c2[nH]1)C[C@H]1O[C@@H](n2cnc3c(N)ncnc32)[C@H](O)[C@@H]1O]

This compound was prepared using the same procedure as described for compound 332 substituting 3-chlorobenzene-1,2-diamine as the diamine (110 mg, 46%). ¹H NMR (500 MHz, MeOD): δ 8.28 (s, 1H), 8.19 (s, 1H), 7.41 (dd, J=0.5, 7.5 Hz, 1H), 7.11-7.19 (m, 2H), 5.96 (d, J=4.5 Hz, 1H), 4.74 (t, J=5.0 Hz, 1H), 4.27-4.29 (m, 1H), 4.10-4.11 (m, 1H), 2.53-3.01 (m, 7H), 1.82-1.85 (m, 2H), 1.53-1.56 (m, 2H), 1.03 (d, J=6.5 Hz, 3H), 0.98 (d, J=7.0 Hz, 3H). LC-MS (m/z): 516 [M+H]⁺.

Compound 348

(2R,3R,4S,5R)-2-(6-amino-9H-purin-9-yl)-5-((iso-propyl(4-(4-(trifluoromethyl)-1H-benzo[d]imidazol-2-yl)butyl)amino)methyl)tetrahydrofuran-3,4-diol

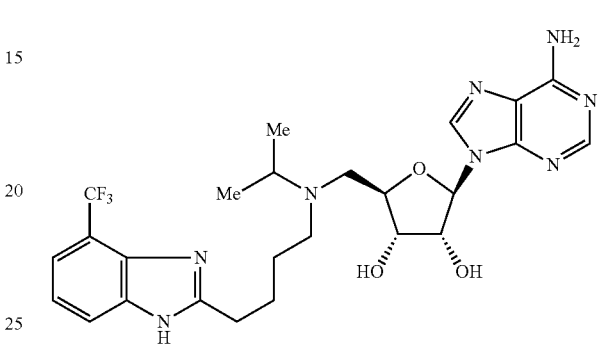

This compound was prepared using the same procedure as described for compound 332 substituting 3-trifluoromethyl-benzene-1,2-diamine as the diamine (175 mg, 67%). ¹H NMR (500 MHz, MeOD): δ 8.29 (s, 1H), 8.20 (s, 1H), 7.75 (d, J=8.0 Hz, 1H), 7.49 (d, J=7.5 Hz, 1H), 7.32 (t, J=7.5 Hz, 1H), 5.97 (d, J=4.5 Hz, 1H), 4.75 (t, J=5.0 Hz, 1H), 4.28 (t, J=5.0 Hz, 1H), 4.13-4.10 (m, 1H), 3.01-2.98 (m, 1H), 2.95-2.89 (m, 3H), 2.72 (dd, J=6.5, 14.0 Hz, 1H), 2.55 (t, J=7.0 Hz, 2H), 1.86-1.82 (m, 2H), 1.57-1.54 (m, 2H), 1.04 (d, J=6.5 Hz, 3H), 0.98 (d, J=7.0 Hz, 3H). LCMS (m/z): 549.3 (M-1-H)⁺.

Compound 349

(2R,3R,4S,5R)-2-(6-amino-9H-purin-9-yl)-5-((iso-propyl(4-(6-(((trifluoromethyl)sulfonyl)-1H-benzo[d]imidazol-2-yl)butyl)amino)methyl)tetrahydrofuran-3,4-diol

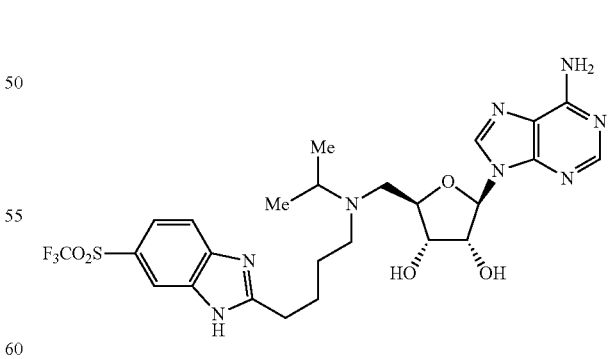

This compound was prepared using the same procedure as described for compound 332 substituting 4-(((trifluoromethyl)sulfonyl)benzene-1,2-diamine as the diamine (63 mg, 31%). ¹H NMR (500 MHz, MeOD): δ 8.28 (s, 1H), 8.19 (d, J=2.0 Hz, 1H), 7.74-7.79 (m, 4H), 5.96 (d, J. 5.0 Hz, 1H), 4.75-4.77 (m, 1H), 4.10-4.13 (m, 1H), 2.54-3.01 (m, 7H), 1.88-1.89 (m, 2H), 1.55-1.59 (m, 2H), 1.03 (d, J=6.5 Hz, 3H), 0.97 (d, J. 6.0 Hz, 3H). LC-MS (m/z): 613 [M+H]+.

Compound 350

(2R,3R,4S,5R)-2-(6-amino-9H-purin-9-yl)-5-(((4-(5-chloro-6-(trifluoromethyl)-1H-benzo[d]imidazol-2yl)butyl)(isopropyl)amino)methyl)tetrahydrofuran-3,4-diol

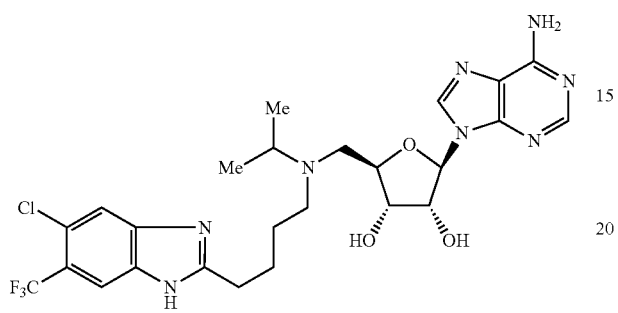

This compound was prepared using the same procedure as described for compound 332 substituting 4-chloro-5-(trifluoromethyl)benzene-1,2-diamine as the diamine (135 mg, 42%). ¹H NMR (500 MHz, MeOD): δ 8.28 (s, 1H), 8.18 (s, 1H), 7.89 (s, 1H), 7.68 (s, 1H), 5.96 (d, J. 5.0 Hz, 1H), 4.76 (t, J=5.0 Hz, 1H), 4.28 (t, J. 5.0 Hz, 1H), 4.13-4.10 (m, 1H), 3.02-2.99 (m, 1H), 2.94-2.89 (m, 3H), 2.72 (dd, J. 6.5, 14.0 Hz, 1H), 2.56 (t, J. 7.0 Hz, 2H), 1.86-1.83 (m, 2H), 1.56-1.53 (m, 2H), 1.05 (d, J. 6.5 Hz, 3H), 0.99 (d, J. 6.5 Hz, 3H). LCMS (m/z): 583.3 (M+H)+.

9-((3aR,4R,6R,6aR)-2,2-dimethyl-6-((methylamino)methyl)tetrahydrofuro[3,4-d][1,3]dioxol-4-yl)-9H-purin-6-amine

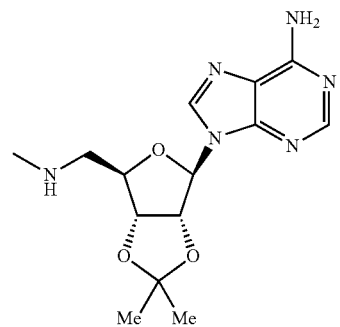 [SMILES: CNC[C@H]1O[C@@H](n2cnc3c(N)ncnc32)[C@@H]2OC(C)(C)O[C@@H]21]

To a solution of 9-[(3aR,4R,6R)-4-(aminomethyl)-2,2-dimethyl-3a,4,6,6a-tetrahydrofuro[3,4-d][1,3]dioxol-6-yl]purin-6-amine (20.0 g, 65.36 mmol) in MeCN:DMF=80:1 (600 mL) was added 2-iodopropane (22.2 g, 130.72 mmol) and K₂CO₃ (18.0 g). The mixture was heated to 80° C. overnight. After cooling, the mixture was filtered. The filtrate was concentrated and purified with SGC (DCM:MeOH=80:1 to 10:1) to afford the title compound (17.0 g, yield: 75%) as a white solid. ¹H NMR (500 MHz, MeOD): δ 8.30 (s, 1H), 8.24 (s, 1H), 6.21 (d, J=2.0 Hz, 1H), 5.54 (dd, J=2.0, 6.0 Hz, 1H), 5.07 (dd, J=3.5, 6.5 Hz, 1H), 4.39 (brs, 1H), 3.05-2.85 (m, 3H), 1.62 (s, 3H), 1.42 (s, 3H), 1.05 (d, J=3.5 Hz, 3H), 1.01 (d, J=3.5 Hz, 3H) ppm; ESI-MS (m/z): 349.2 [M+1]+.

(3-((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl) urea

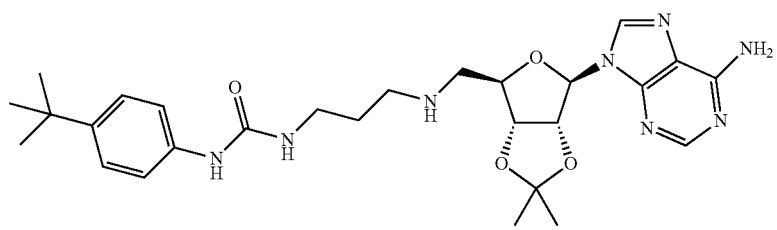 [SMILES: CC1(C)O[C@@H]2[C@H](O1)[C@@H](CNCCCNC(=O)Nc1ccc(C(C)(C)C)cc1)O[C@H]2n1cnc2c(N)ncnc21]

Step 1. Preparation of 1-(4-tert-butylphenyl)-3-(3-oxopropyl)urea

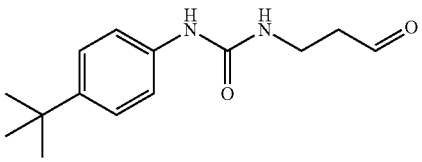 [SMILES: CC(C)(C)c1ccc(NC(=O)NCCC=O)cc1]

A mixture of 1-(4-tert-butylphenyl)-3-(3-hydroxypropyl)urea (500 mg, 0.20 mmol) and IBX (1.68 g, 0.60 mmol) in 20 mL of EA was refluxed for 1.5 h. The mixture was filtered and the filtrate was concentrated to give 1-(4-tert-butylphenyl)-3-(3-oxopropyl)urea (500 mg, 100%) as brown syrup.

Step 2. 1-(3-((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl)urea

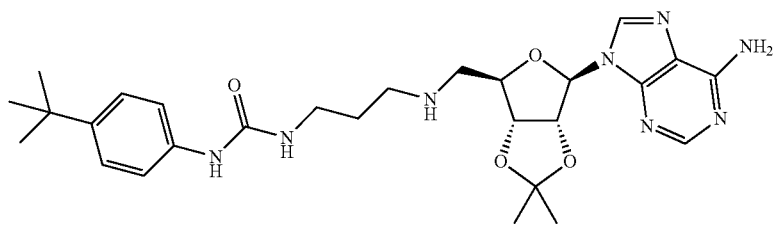 [SMILES: CC1(C)O[C@@H]2[C@H](O1)[C@@H](CNCCCNC(=O)Nc1ccc(C(C)(C)C)cc1)O[C@H]2n1cnc2c(N)ncnc21]

To a stirred solution of 1-(4-tert-butylphenyl)-3-(3-oxopropyl)urea (1.0 g, 4.02 mmol) and 9-((3aR,4R,6R,6aR)-2,2-dimethyl-6-((methylamino)methyl)tetrahydrofuro[3,4-d][1,3]dioxol-4-yl)-9H-purin-6-amine (1.1 g, 3.58 mmol) in 150 mL of DCE was added NaBH(OAc)₃ (1.9 g, 8.96 mmol). Then the mixture was stirred at rt overnight. NaHCO₃ (aq) was added to quench the reaction and the mixture was extracted with DCM (40 mL×4). The organic phase was concentrated and the residue was purified by SGC(CH₃OH: DCM=1:10) to the title compound (1.16 g. yield: 61%) as a white solid. ¹H NMR (500 MHz, MeOD): δ8.204 (s, 1H), 8.164 (s, 1H), 7.228-7.162 (m, 4H), 6.143 (d, J=2.5 Hz, 1H), 5.402 (dd, J=2.5, 6.0 Hz, 1H), 5.047 (dd, J=3.5, 6.0 Hz, 1H), 4.366 (dd, J=4.0, 8.0 Hz, 1H), 3.137-3.010 (m, 3H), 2.722-2.694 (m, 3H), 1.849 (s, 1H), 1.647-1.545 (m, 5H), 1.321 (s, 3H), 1.225 (s, 9H) ppm. MS (ESI): m/z 539.7 [M+1]⁺.

2-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)isoindoline-1,3-dione

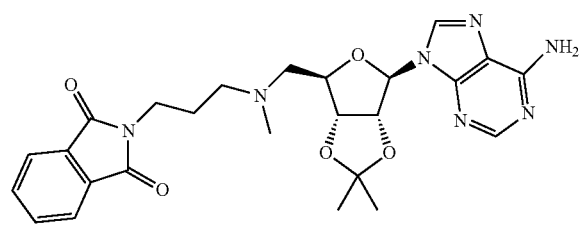 [SMILES: CN(CCCN1C(=O)c2ccccc2C1=O)C[C@H]1O[C@@H](n2cnc3c(N)ncnc32)[C@@H]2OC(C)(C)O[C@@H]21]

Step 1. Preparation of 2-(3-hydroxypropyl)isoindoline-1,3-dione

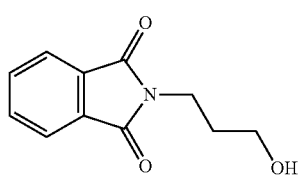 [SMILES: O=C1c2ccccc2C(=O)N1CCCO]

To a solution of isobenzofuran-1,3-dione (10.0 g, 135.1 mmol) in toluene (250 mL) was added 3-amino-1-propanol (10.0 g, 67.6 mmol) and the mixture was heated to reflux for 4 h under N₂. The mixture was concentrated and water was added. The mixture was extracted with EA (100 mL x4). The organic phase was dried with Na₂SO₄ and concentrated to afford 2-(3-hydroxypropyl)isoindoline-1,3-dione (11.0 g, 79%) as white solid. ¹H NMR (500 MHz, CDCl₃): 157.84-7.87 (m, 2H), 7.72-7.75 (m, 2H), 3.85-3.88 (m, 2H), 3.61-3.63 (m, 2H), 2.42 (brs, 1H), 1.86-1.9 (m, 2H) ppm. MS (ESI): m/z 206.7 [M+1]⁺.

Step 2. Preparation of 3-(1,3-dioxoisoindolin-2-yl)propanal

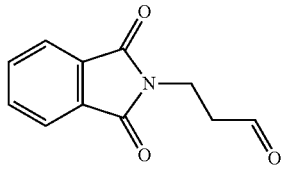 [SMILES: O=CCCN1C(=O)c2ccccc2C1=O]

A mixture of 2-(3-hydroxypropyl)isoindoline-1,3-dione (2.0 g, 8.76 mmol) and IBX (8.2 g, 29.27 mmol) in 60 mL EA was refluxed for 2 h. The mixture was filtered and filtrate was concentrated to afford 3-(1,3-dioxoisoindolin-2-yl)propanal (2.0 g, yield: 100%) as white solid. ¹H NMR (500 MHz, CDCl₃): δ 9.82 (s, 2H), 7.84-7.86 (m, 2H), 7.72-7.74 (m, 2H), 4.04 (t, J=7.0 Hz, 2H), 2.87-2.89 (m, 2H) ppm. MS (ESI): m/z 553.7 [M+1]⁺.

Step 3. 2-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)isoindoline-1,3-dione

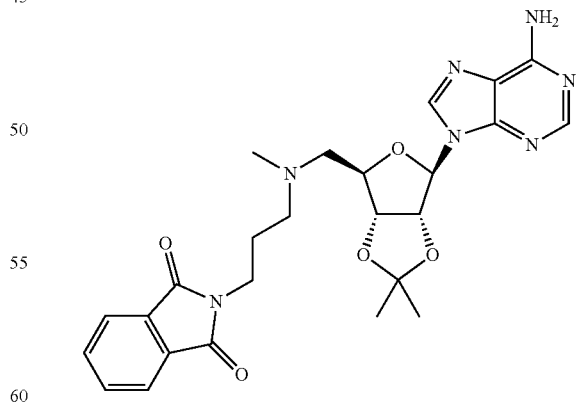

To a stirred solution of 9-((3aR,4R,6R,6aR)-2,2-dimethyl-6-((methylamino)methyl)tetrahydrofuro[3,4-d][1,3]dioxol-4-yl)-9H-purin-6-amine (1.6 g, 5.0 mmol) and 3-(1,3-dioxoisoindolin-2-yl)propanal (2.0 g, 9.8 mmol) in 50 mL DCE was added NaBH(OAc)₃ (3.18 g, 15.0 mmol). Then the mixture was stirred at rt overnight. Saturated NaHCO₃ aqueous solution was added to quench the reaction and the mixture was extracted with DCM (20 mL×4). The organic phase was concentrated and the residue was purified by SGC(CH₃OH: DCM=1:100) to afford the title compound (2.47 g, yield: 94%) as white solid. ¹H NMR (500 MHz, MeOD): δ 8.26 (s, 1H), 8.21 (s, 1H), 7.77-7.84 (m, 4H), 6.15 (d, J=2.5 Hz, 1H), 5.45-5.47 (m, 1H), 5.01-5.03 (m, 1H), 4.34-4.35 (m, 2H), 363-3.69 (m, 2H), 2.70-2.72 (m, 2H), 2.46-2.50 (m, 2H), 2.27 (s, 3H), 1.74-1.78 (m, 2H), 1.37 (s, 3H), 1.24 (s, 3H) ppm. MS (ESI): m/z 508.7 [M+1]⁺.

Step 4. Preparation of 2-(3-(((((2R,3S,4R,5R)-5-(6-amino-9H-purin-9-yl)-3,4-dihydroxytetrahydrofuran-2-yl)methyl)(methyl)amino)propyl)isoindoline-1,3-dione

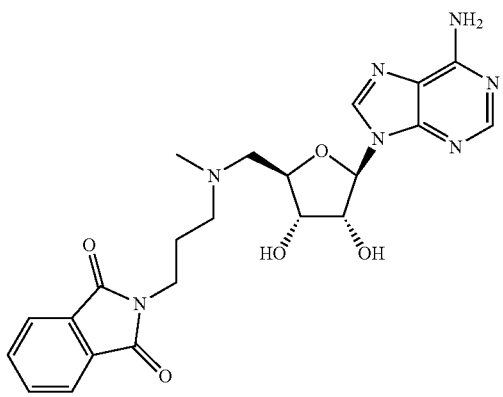 [SMILES: CN(CCCN1C(=O)c2ccccc2C1=O)C[C@H]1O[C@@H](n2cnc3c(N)ncnc32)[C@H](O)[C@@H]1O]

To a mixture of TFA (0.9 mL) and water (0.1 mL) was added 2-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)isoindoline-1,3-dione (100 mg, 0.197 mmol). The solution was stirred at rt for 1 h and evaporated to dryness. The residue was co-evaporated with methanol twice then dissolved in MeOH (3 mL). The solution was neutralized by anion exchange resin (600 mg) with stirring for 1 h. After filtered, the filtrate was concentrated and the residue was purified by Prep-TLC (MeOH:DCM:NH₄OH=1:5:0.5) to afford the title compound (45 mg, yield 49%) as white solid. ¹H NMR (500 MHz, MeOD): δ 8.23 (s, 1H), 8.20 (s, 1H), 7.75-7.81 (m, 4H), 5.91 (d, J=4.5 Hz, 1H), 4.67 (t, J=4.5 Hz, 1H), 4.21-4.25 (m, 2H), 3.69 (t, J=7.0 Hz, 2H), 2.95-3.02 (m, 2H), 2.70 (t, J=7.5 Hz, 2H), 2.43 (s, 3H), 1.89-1.92 (m, 2H) ppm. MS (ESI): m/z 468.7 [M+1]⁺.

Example 351

5-(((((2R,3S,4R,5R)-5-(6-amino-9H-purin-9-yl)-3,4-dihydroxytetrahydrofuran-2-yl)methyl)(isopropyl)amino)-N-(4-(tert-butyl)phenyl)pentanamide

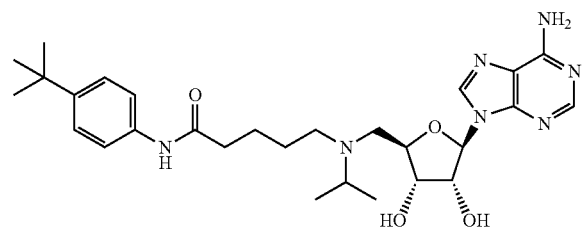 [SMILES: CC(C)N(CCCCC(=O)Nc1ccc(C(C)(C)C)cc1)C[C@H]1O[C@@H](n2cnc3c(N)ncnc32)[C@H](O)[C@@H]1O]

Step 1. Preparation of benzyl 5-(((((3aR,4R,6R,6aR)-6-(6-amino-9H-purin-9-yl)-2,2-dimethyltetrahydrofuro[3,4-(1][1,3]dioxol-4-yl)methyl)(isopropyl)amino)pentanoate

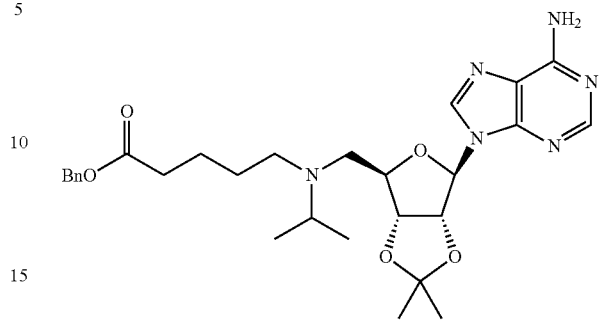

9-((3aR,4R,6R,6aR)-6-((isopropylamino)methyl)-2,2-dimethyltetrahydrofuro[3,4-d][1,3]dioxol-4-yl)-9H-purin-6-amine (200 mg, 0.57 mmol) and benzyl 5-oxopentanoate (237 mg, 1.14 mmol) was dissolved in DCE/MeOH (1/1, 6 mL). The solution was stirred for 20 min at rt. Then NaBH(OAc)₃ (427 mg, 1.15 mmol) was added the above solution in one portion. The reaction mixture was stirred overnight. The solution was concentrated. The residue was extracted with EA (20 mL×2) and with saturated NaHCO₃ (50 mL). The organic phase was concentrated in vacuo and purified by Prep-TLC (DCM:MeOH=7:1) to afford the title compound (198 mg, yield: 64%). ¹H NMR (500 MHz, MeOD): δ 8.15 (s, 1H), 8.11 (s, 1H), 7.24-7.18 (m, 5H), 6.05 (d, J=2.0 Hz, 1H), 5.44 (dd, J=2.0 and 6.5 Hz, 1H), 5.00 (s, 2H), 4.93 (dd, J=3.5, 6.5 Hz, 1H), 4.15-4.12 (m, 1H), 2.80-2.74 (m, 1H), 2.60-2.56 (m, 1H), 2.43-2.39 (m, 1H), 2.27-2.21 (m, 4H), 1.50-1.43 (m, 5H), 1.30-1.18 (m, 5H), 0.88 (d, J=6.5 Hz, 3H), 0.71 (d, J=6.5 Hz, 3H); ESI-MS (m/z): 583 [M+1]⁺.

Step 2. Preparation of 5-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)pentanoic acid

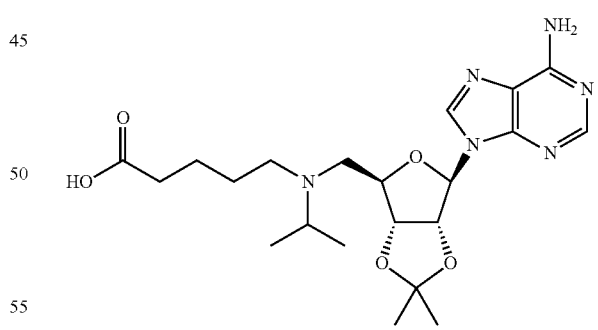

To a solution of benzyl 5-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)pentanoate (198 mg, 0.368 mmol) in MeOH (5 mL) was added Pd/C (10%, 50 mg). The reaction was degassed and purged with H₂. The mixture was stirred at rt overnight under H₂ atmosphere. Then the reaction was filtered and filtrate was concentrated to afford the title compound without further purification. ¹H NMR (500 MHz, MeOD): δ 8.18 (s, 1H), 8.14 (s, 1H), 6.12 (d, J=1.5 Hz, 1H), 5.44 (dd, J=1.5, 6.0 Hz, 1H), 4.98 (dd, J=3.5, 6.5 Hz, 1H), 4.28 (br s, 1H), 3.07-3.04 (m, 1H), 2.85 (br s, 1H), 2.52 (br s, 1H), 2.06-2.04 (m, 2H), 1.49 (s, 3H), 1.47-1.36 (m, 4H), 1.29 (s, 3H), 0.96 (d, J=6.5 Hz, 3H), 0.77 (d, J=6.5 Hz, 3H); ESI-MS (m/z): 449 [M+1]+.

Step 3. Preparation of 5-(((((3aR,4R,6R,6aR)-6-(6-amino-9H-purin-9-yl)-2,2-dimethyltetrahydrofuro[3,4-d][1,3]dioxol-4-ylmethyl)(isopropyl)amino)-N-(4-(tert-butyl)phenyl)pentanamide

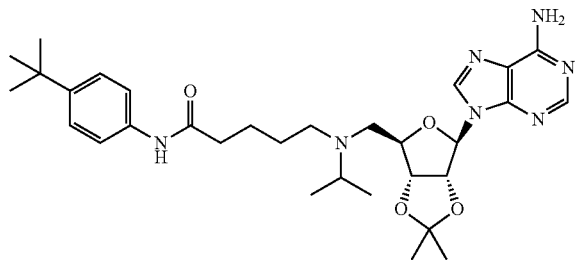 [SMILES: CC(C)N(CCCCC(=O)Nc1ccc(C(C)(C)C)cc1)C[C@H]1O[C@@H](n2cnc3c(N)ncnc32)[C@@H]2OC(C)(C)O[C@@H]21]

To a stirred solution of 5-(((((3aR,4R,6R,6aR)-6-(6-amino-9H-purin-9-yl)-2,2-dimethyltetrahydrofuro[3,4-d][1,3]dioxol-4-yl)methyl)(isopropylamino)pentanoic acid (145 mg, 0.269 mmol), BOP (218 mg, 0.40 mmol) and TEA (65 mg, 0.53 mmol) in DMF (1 mL) was added 4-tert-butylbenzeneamine. The reaction mixture was stirred at rt for 3 h and then diluted with EA (50 mL). The resulting mixture was washed with water and brine. The organic layer was dried over Na$_2$SO$_4$, filtered and concentrated in vacuo to the title compound (89 mg, yield: 57%), which was used for next reaction without further purification. $^1$H NMR (500 MHz, MeOD): δ 8.16 (s, 1H), 8.12 (s, 1H), 7.35 (d, J=7.0 Hz, 2H), 7.22 (d, J=7.0 Hz, 2H), 6.04 (d, J=2.0 Hz, 1H), 5.42 (dd, J=2.0 and 6.0 Hz, 1H), 4.92 (dd, J=3.0 and 6.5 Hz, 1H), 4.16-4.16 (m, 1H), 2.83-2.80 (m, 1H), 2.60-2.59 (m, 1H), 2.46-2.42 (m, 1H), 2.35-2.20 (m, 4H), 1.57-1.48 (m, 5H), 1.36-1.26 (m, 5H), 1.19 (s, 9H), 0.89 (d, J=7.0 Hz, 3H), 0.73 (d, J=7.0 Hz, 3H); ESI-MS (m/z): 580 [M+1]+.

Step 4. Preparation of 5-(((((2R,3S,4R,5R)-5-(6-amino-9H-purin-9-yl)-3,4-dihydroxytetrahydrofuran-2-yl)methyl)(isopropyl)amino)-N-(4-(tert-butyl)phenyl)pentanamide

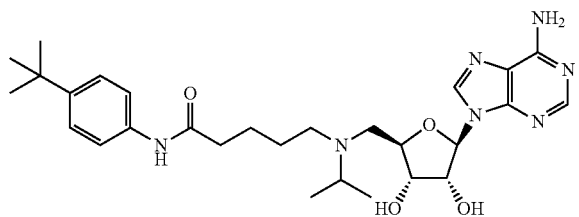 [SMILES: CC(C)N(CCCCC(=O)Nc1ccc(C(C)(C)C)cc1)C[C@H]1O[C@@H](n2cnc3c(N)ncnc32)[C@H](O)[C@@H]1O]

A solution of 5-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)-N-(4-(tert-butyl)phenyl)pentanamide (89 mg, 0.154 mmol) in 90% TFA (1 mL) was stirred at rt for 1 h and evaporated to dryness. The residue was co-evaporated with methanol twice. The residue was dissolved in MeOH (10 mL) and K$_2$CO$_3$ (127 mg, 1.07 mmol) was added then water was added dropwise until all K$_2$CO$_3$ was dissolved. The reaction mixture was stirred at rt for 30 min then concentrated. Then residue was purified by Prep-TLC (DCM:MeOH=10:1, with 0.5% NH$_3$—H$_2$O) to afford the title compound (45 mg, yield: 33%). $^1$H NMR (500 MHz, MeOD): δ 8.29 (s, 1H), 8.20 (s, 1H), 7.42 (d, J=8.5 Hz, 2H), 7.32 (d, J=8.0 Hz, 2H), 5.96 (d, J=5.0 Hz, 1H), 4.75-4.73 (m, 1H), 4.30-4.27 (m, 1H), 4.11-4.10 (m, 1H), 2.93-2.81 (m, 1H), 2.65-2.61 (m, 1H), 2.55-2.53 (m, 1H), 2.34-2.31 (m, 2H), 1.68-1.65 (m, 2H), 1.54-1.36 (m, 2H), 1.19 (s, 9H), 0.95 (d, J=6.0 Hz, 3H), 0.88 (d, J=6.0 Hz, 3H); ESI-MS (m/z): 580 [M+1]+.

Compound 352

1-(3-(((((2R,3S,4R,5R)-5-(6-amino-9H-purin-9-yl)-3,4-dihydroxytetrahydrofuran-2-yl)methyl)(isopropyl)amino)propyl)-3-(3-ethylphenyl)urea

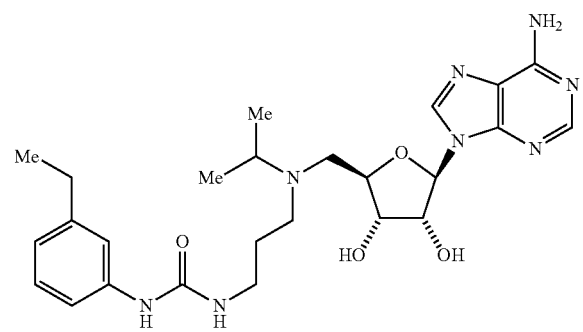 [SMILES: CCc1cccc(NC(=O)NCCCN(C[C@H]2O[C@@H](n3cnc4c(N)ncnc43)[C@H](O)[C@@H]2O)C(C)C)c1]

Step 1. Preparation of 1-(3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)propyl)-3-(3-ethylphenyl)urea

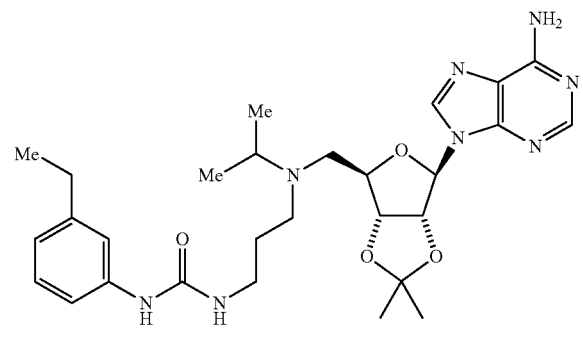

To a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-isopropylpropane-1,3-diamine (30 mg, 0.074 mmol) and TEA (15 mg, 0.14 mmol) in DCM (1.5 mL) was added 1-ethyl-3-isocyanato-benzene (12 mg, 0.081 mmol). The mixture was stirred at rt for 1 h. The volatiles were removed under reduced pressure. The residue was directly purified by prep-TLC (DCM:MeOH=10:1 with 0.4% NH$_3$—H$_2$O) to afford the title compound (33 mg, yield: 81%) as white solid. $^1$H NMR (500 MHz, MeOD): δ 8.15 (s, 1H), 8.11 (s, 1H), 7.10 (s, 1H), 7.04 (d, J=5.0 Hz, 2H), 6.72-6.71 (m, 1H), 6.07 (d, J=2.5 Hz, 1H), 5.45-5.44 (m, 1H), 4.94 (dd, J=3.5, 6.5 Hz, 1H), 4.20-4.19 (m, 1H), 3.10-3.06 (m, 2H), 2.84-2.83 (m, 1H), 2.61-2.59 (m, 1H), 2.51-2.47 (m, 3H), 2.40-2.37 (m, 2H), 1.52-1.44 (m, 5H), 1.27 (s, 3H), 1.11 (t, J=9.0 Hz, 3H), 0.89 (d, J=6.0 Hz, 3H), 0.72 (d, J=6.5 Hz, 3H); ESI-MS (m/z): 553 [M+1]$^+$.

Step 2. Preparation of 1-(3-(((((2R,3S,4R,5R)-5-(6-amino-9H-purin-9-yl)-3,4-dihydroxytetrahydrofuran-2-yl)methyl)(isopropyl)amino)propyl)-3-(3-ethylphenyl)urea

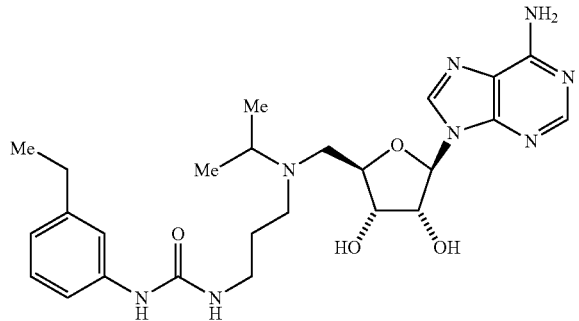 [SMILES: CCc1cccc(NC(=O)NCCCN(C[C@H]2O[C@@H](n3cnc4c(N)ncnc43)[C@H](O)[C@@H]2O)C(C)C)c1]

A solution 1-(3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)propyl)-3-(3-ethylphenyl)urea (29 mg, 0.053 mmol) in 90% TFA (1 mL) was stirred at rt for 1 h and then evaporated to dryness. The residue was co-evaporated with methanol twice. The residue was dissolved in MeOH (10 mL) and K$_2$CO$_3$ (51 mg, 0.36 mmol) was added then water was added dropwise until all K$_2$CO$_3$ was dissolved. The reaction mixture was stirred at rt for 30 min then concentrated. The residue was purified by Prep-TLC (DCM:MeOH=10:1 with 0.7% NH$_3$H$_2$O) to afford the title compound (25 mg, yield: 93%). $^1$H NMR (500 MHz, MeOD): δ 8.12 (s, 1H), 8.09 (s, 1H), 7.06 (s, 1H), 7.03-7.00 (m, 2H), 6.71-6.70 (m, 1H), 5.87 (d, J=4.5 Hz, 1H), 4.65-4.63 (m, 1H), 4.26 (br s, 1H), 4.13 (br s, 1H), 3.20-3.07 (m, 4H), 2.75-2.65 (m, 2H), 2.48 (q, J=7.5 Hz, 2H), 1.65 (br s, 2H), 1.12-0.95 (m, 9H); ESI-MS (m/z): 513 [M+1]$^+$.

Compound 353

1-(3-(((((2R,3S,4R,5R)-5-(6-amino-9H-purin-9-yl)-3,4-dihydroxytetrahydrofuran-2-yl)methyl)(isopropyl)amino)propyl)-3-(4-chloro-3-(trifluoromethyl)phenyl)urea

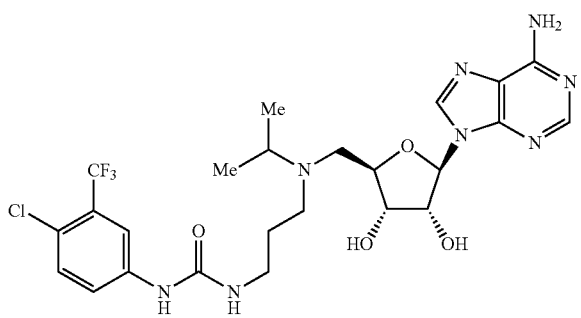 [SMILES: CC(C)N(CCCNC(=O)Nc1ccc(Cl)c(C(F)(F)F)c1)C[C@H]1O[C@@H](n2cnc3c(N)ncnc32)[C@H](O)[C@@H]1O]

Step 1. Preparation of 1-(3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)propyl)-3-(4-chloro-3-(trifluoromethyl)phenyl)urea

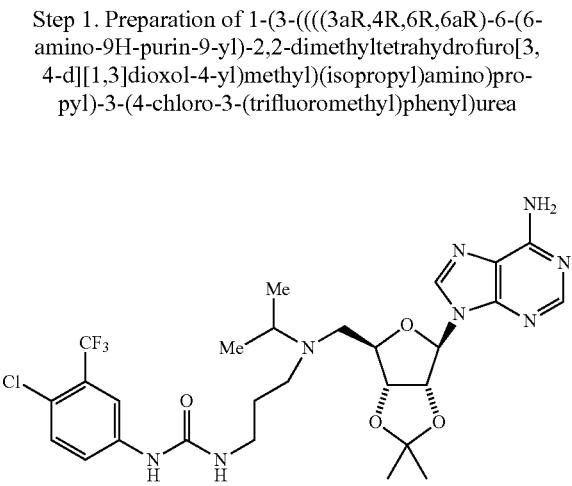

To a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-isopropylpropane-1,3-diamine (30 mg, 0.074 mmol) and TEA (15 mg, 0.14 mmol) in DCM (1.5 mL) was added 1-chloro-4-isocyanato-2-(trifluoromethyl)benzene (18 mg, 0.081 mmol). The mixture was stirred at rt for 1 h. The volatiles were removed under reduced pressure. The residue was directly purified from prep-TLC (DCM:MeOH=10:1 with 0.4% NH$_3$—H$_2$O) to afford the title compound (35 mg, yield: 75%) as white solid. $^1$H NMR (500 MHz, MeOD): δ 8.16 (s, 1H), 8.12 (s, 1H), 7.82 (d, J=2.5 Hz, 1H), 7.44-7.33 (m, 4H), 6.11 (d, J=1.5 Hz, 1H), 5.42 (dd, J=2.0, 6.5 Hz, 1H), 4.97 (br s, 1H), 4.28 (br s, 1H), 3.08-3.07 (m, 3H), 3.03-2.77 (m, 2H), 2.60-2.45 (m, 1H), 1.56-1.46 (m, 5H), 1.27 (S, 3H), 0.96 (d, J=5.5 Hz, 3H), 0.77 (d, J=5.5 Hz, 3H); ESI-MS (m/z): 627 [M+1]$^+$.

Step 2. Preparation of 1-(3-(((((2R,3S,4R,5R)-5-(6-amino-9H-purin-9-yl)-3,4-dihydroxytetrahydrofuran-2-yl)methyl)(isopropyl)amino)propyl)-3-(4-chloro-3-(trifluoromethyl)phenyl)urea

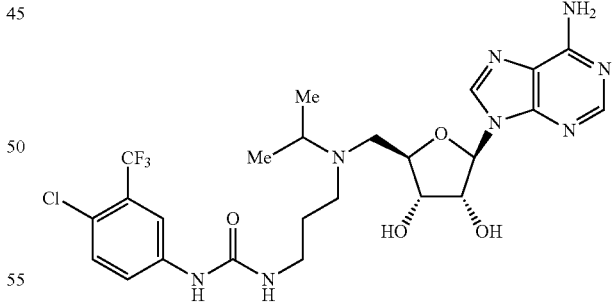

A solution of 1-(3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)propyl)-3-(4-chloro-3-(trifluoromethyl)phenyl)urea (30 mg, 0.053 mmol) in 90% TFA (1 mL) was stirred at rt for 1 h and then evaporated to dryness. The residue was co-evaporated with methanol twice. The residue was dissolved in MeOH (10 mL) and K$_2$CO$_3$ (51 mg, 0.36 mmol) was added then water was added dropwise until all K$_2$CO$_3$ was dissolved. The reaction mixture was stirred at rt for 30 min then concentrated. The residue was purified by Prep-TLC (DCM:MeOH=10:1 with 0.7% NH₃—H₂O) to afford the title compound (25 mg, yield: 93%). ¹H NMR (500 MHz, Acetone-d6): δ 8.16 (s, 1H), 8.05 (s, 1H), 7.76 (d, J=2.5 Hz, 1H), 7.37 (dd, J=2.5 and 8.5 Hz, 1H), 7.28 (d, J=8.0 Hz, 1H), 5.87 (d, J=4.5 Hz, 1H), 4.61-4.59 (m, 1H), 4.18-4.16 (m, 1H), 4.07-4.05 (m, 1H), 3.17-3.07 (m, 2H), 2.97-2.95 (m, 1H), 2.82-2.78 (m, 1H), 2.66-2.60 (m, 1H), 2.50-2.45 (m, 2H), 1.60-1.57 (m, 2H), 0.95 (d, J=7.0 Hz, 3H), 0.91 (d, J=6.5 Hz, 3H); ESI-MS (m/z): 588 [M+1]⁺.

Compound 354

1-(3-((((2R,3S,4R,5R)-5-(6-amino-9H-purin-9-yl)-3,4-dihydroxytetrahydrofuran-2-yl)methyl)(methyl)amino)propyl)-3-(3-ethylphenyl)urea

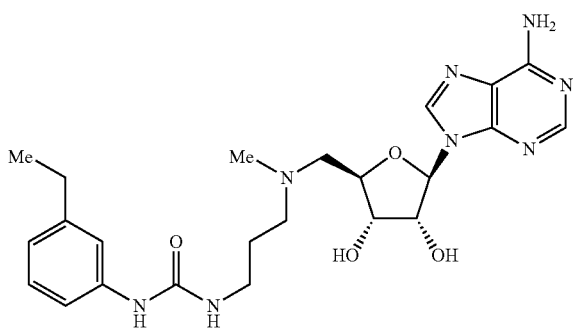 [SMILES: CCc1cccc(NC(=O)NCCCN(C)C[C@H]2O[C@@H](n3cnc4c(N)ncnc43)[C@H](O)[C@@H]2O)c1]

Step 1. Preparation of 1-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(3-ethylphenyl)urea

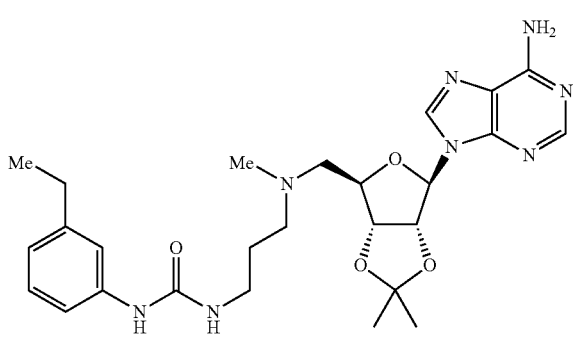 [SMILES: CCc1cccc(NC(=O)NCCCN(C)C[C@H]2O[C@@H](n3cnc4c(N)ncnc43)[C@@H]3OC(C)(C)O[C@@H]32)c1]

To a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (120 mg, 0.31 mmol) and TEA (64 mg, 0.63 mmol) in DCM (1.5 mL) was added 1-ethyl-3-isocyanato-benzene (56 mg, 0.38 mmol). The mixture was stirred at rt for 1 h. The volatiles were removed under reduced pressure. The residue was directly purified from Prep-TLC (DCM:MeOH=6:1) to afford the title compound (115 mg, 69%) as white solid. ¹H NMR (500 MHz, MeOD): δ 8.16 (s, 1H), 8.12 (s, 1H), 7.18 (s, 1H), 7.11-7.03 (m, 3H), 6.73-6.71 (m, 1H), 6.08 (d, J=2.0 Hz, 1H), 5.39-5.38 (m, 1H), 4.91 (dd, J=3.5, 6.5 Hz, 1H), 4.30-4.29 (m, 1H), 3.04-3.01 (m, 2H), 2.60-2.47 (m, 4H), 2.37 (t, J=7.0 Hz, 2H), 2.17 (s, 3H), 1.52-1.46 (m, 5H), 1.27 (s, 3H), 1.15-1.09 (m, 3H) ESI-MS (m/z): 525 [M+1]⁺.

Step 2. Preparation of 1-(3-((((2R,3S,4R,5R)-5-(6-amino-9H-purin-9-yl)-3,4-dihydroxytetrahydrofuran-2-yl)methyl)(methyl)amino)propyl)-3-(3-ethylphenyl)urea

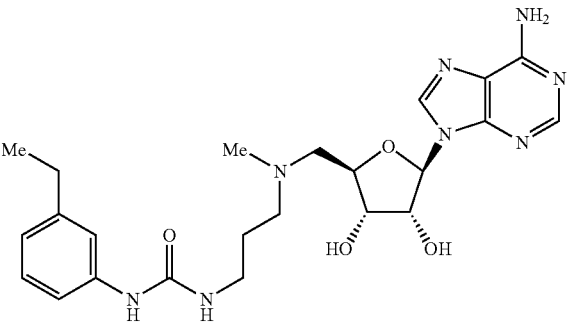 [SMILES: CCc1cccc(NC(=O)NCCCN(C)C[C@H]2O[C@@H](n3cnc4c(N)ncnc43)[C@H](O)[C@@H]2O)c1]

A solution of -(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(3-ethylphenyl)urea (115 mg, 0.21 mmol) in 90% TFA (1 mL) was stirred at rt for 1 h and then evaporated to dryness. The residue was co-evaporated with methanol. The residue was dissolved in MeOH (10 mL), and K₂CO₃ (212 mg, 1.53 mmol) was added, then water was added dropwise until all K₂CO₃ was dissolved. The reaction mixture was stirred at rt for 30 min then concentrated. The residue was purified by Prep-TLC give the title compound (85 mg, yield: 80%). NMR (500 MHz, MeOD): δ 8.13 (s, 1H), 8.12 (s, 1H), 7.08 (s, 1H), 7.05-7.01 (m, 2H), 6.74-6.71 (m, 1H), 5.91 (d, J=4.5 Hz, 1H), 4.73 (t, J=5.0 Hz, 1H), 4.34-4.31 (m, 1H), 4.27 (t, J=5.0 Hz, 1H), 3.50-3.48 (m, 1H), 3.17-3.10 (m, 2H), 3.05-2.98 (m, 2H), 2.68 (s, 3H), 2.48 (q, J=7.5 Hz, 2H), 1.81-1.75 (m, 2H), 1.10 (t, J=7.5 Hz, 3H) ppm; ESI-MS (m/z): 485 [M+1]⁺.

Example 355

1-(3-((((2R,3S,4R,5R)-5-(6-amino-9H-purin-9-yl)-3,4-dihydroxytetrahydrofuran-2-yl)methyl)(methyl)amino)propyl)-3-(4-chloro-3-(trifluoromethyl)phenyl)urea

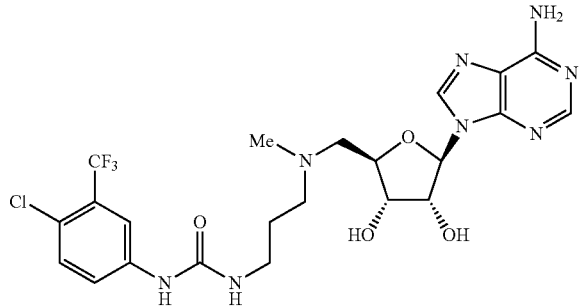 [SMILES: CN(CCCNC(=O)Nc1ccc(Cl)c(C(F)(F)F)c1)C[C@H]1O[C@@H](n2cnc3c(N)ncnc32)[C@H](O)[C@@H]1O]

Step 1. Preparation of 1-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(4-chloro-3-(trifluoromethyl)phenyl)urea

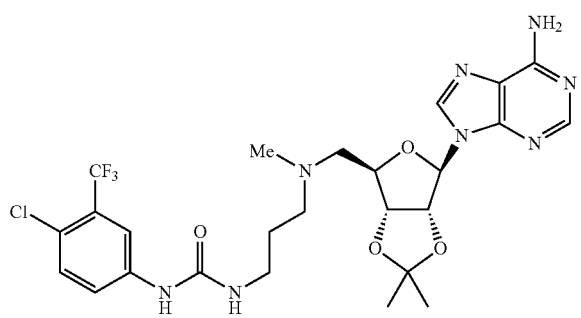 [SMILES: CN(CCCNC(=O)Nc1ccc(Cl)c(C(F)(F)F)c1)C[C@H]1O[C@@H](n2cnc3c(N)ncnc32)[C@@H]2OC(C)(C)O[C@@H]21]

To a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (120 mg, 0.31 mmol) and TEA (64 mg, 0.63 mmol) in DCM (1.5 mL) was added 1-chloro-4-isocyanato-2-(trifluoromethyl)benzene (64 mg, 0.38 mmol). The mixture was stirred at rt for 1 h. The volatiles were removed under reduced pressure. The residue was directly purified from Prep TLC (DCM:MeOH=6:1) to afford the title compound (110 mg, yield: 58%) as white solid. $^1$H NMR (500 MHz, MeOD): δ 8.17 (s, 1H), 8.11 (s, 1H), 7.80 (d, J=2.5 Hz, 1H), 7.41 (dd, J=2.5 and 8.5 Hz, 1H), 7.32 (d, J=9.0 Hz, 1H), 6.08 (d, J=2.5 Hz, 1H), 5.38 (dd, J=2.0 and 6.5 Hz, 1H), 4.90 (dd, J=3.5, 6.5 Hz, 1H), 4.31-4.29 (m, 1H), 3.04-3.03 (m, 2H), 2.63-2.57 (m, 2H), 2.38-2.35 (m, 2H), 2.16 (s, 3H), 1.52-1.46 (m, 5H), 1.27 (s, 3H); ESI-MS (m/z): 599 [M+1]$^+$.

Step 2. Preparation of 1-(3-(((((2R,3S,4R,5R)-5-(6-amino-9H-purin-9-yl)-3,4-dihydroxytetrahydrofuran-2-ylmethyl)(methyl)amino)propyl)-3-(4-chloro-3-(trifluoromethyl)phenyl)urea

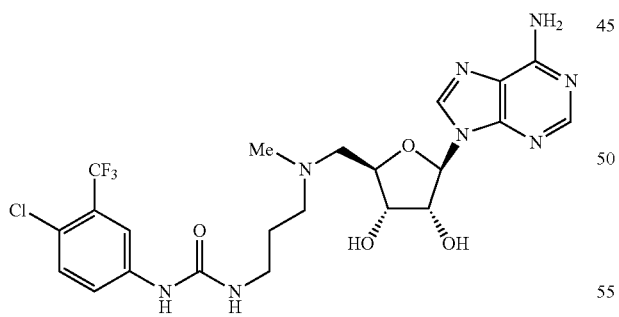

A solution of 1-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(4-chloro-3-(trifluoromethyl)phenyl)urea (110 mg, 0.18 mmol) in 90% TFA (1 mL) was stirred at rt for 1 h and then evaporated to dryness. The residue was co-evaporated with methanol twice. The residue was dissolved in MeOH (10 mL) and K$_2$CO$_3$ (178 mg, 1.28 mmol) was added then water was added dropwise until all K$_2$CO$_3$ was dissolved. The reaction mixture was stirred at rt for 30 min then concentrated. The residue was purified by Prep-TLC (DCM:MeOH=10:1 with 0.8% NH$_3$—H$_2$O) to afford 1-[3-[[[(2R,3S,5R)-5-(6-aminopurin-9-yl)-3,4-dihydroxy-tetrahydrofuran-2-yl]methyl-methyl-amino]propyl]-3-[4-chloro-3-(trifluoromethyl)phenyl]urea (89 mg, yield: 86%) as white solid. $^1$H NMR (500 MHz, MeOD): δ 8.12 (s, 1H), 8.11 (s, 1H), 7.79 (d, J=2.5 Hz, 1H), 7.40 (dd, J=2.5 and 9.0 Hz, 1H), 7.32 (d, J=8.5 Hz, 1H), 5.91 (d, J=5.0 Hz, 1H), 4.70-4.68 (m, 1H), 4.28-4.22 (m, 2H), 3.20-3.25 (m, 1H), 3.17-3.12 (m, 3H), 2.89 (br s, 2H), 2.59 (s, 3H), 1.77-1.74 (m, 2H); ESI-MS (m/z): 559 [M+1]$^+$.

Compound 356

1-(4-(tert-butyl)phenyl)-3-(3-(((((2R,3S,4R,5R)-5-(6-(dimethylamino)-9H-purin-9-yl)-3,4-dihydroxytetrahydrofuran-2-yl)methyl)(isopropyl)amino)propyl)urea

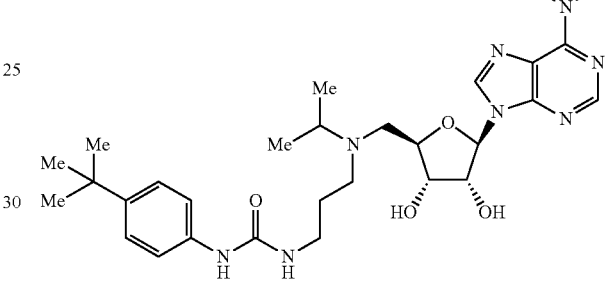

Step 1. Preparation of ((3aR,4R,6R,6aR)-6-(6-chloro-9H-purin-9-yl)-2,2-dimethyltetrahydrofuro[3,4-d][1,3]dioxol-4-yl)methanol

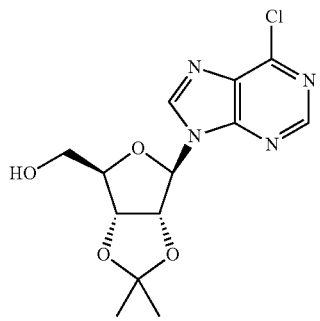 [SMILES: CC1(C)O[C@@H]2[C@H](O1)[C@@H](CO)O[C@H]2n1cnc2c(Cl)ncnc21]

p-Toluenesulfonic acid monohydrate (134 g, 700 mmol) was added to a stirred suspension of (2R,3R,4S,5R)-2-(6-chloro-9H-purin-9-yl)-5-(hydroxymethyl)tetrahydrofuran-3,4-diol (20 g, 70 mmol) in acetone (100 mL). After stirred at 25° C. for 6 h, the reaction mixture was poured into stirred aqueous NaHCO$_3$ (0.5 N, 2000 mL) slowly. After removed acetone in vacuo, the mixture was extracted with DCM (800 mL×3). The combined organic layers were washed with water (500 mL) and brine (500 mL), then dried over Na$_2$SO$_4$ and concentrated to afford the title compound (19.5 g, yield: 86%) as a white solid. $^1$H NMR (500 MHz, CDCl$_3$): δ 8.75 (s, 1H), 8.30 (s, 1H), 6.01 (d, J=4.5 Hz, 1H), 5.19-5.17 (m, 1H), 5.10-5.09 (m, 1H), 4.54 (s, 1H), 3.96 (dd, J=1.0, 12.5 Hz, 1H), 3.82 (dd, J=2.0, 12.5 Hz, 1H), 1.64 (s, 3H), 1.37 (s, 3H) ppm; ESI (m/z): 327.1 [M+1]+.

Step 2. Preparation of 43aR,4R,6R,6aR)-6-(6-(dimethylamino)-9H-purin-9-yl)-2,2-dimethyltetrahydrofuro[3,4-d][1,3]dioxol-4-yl)methanol

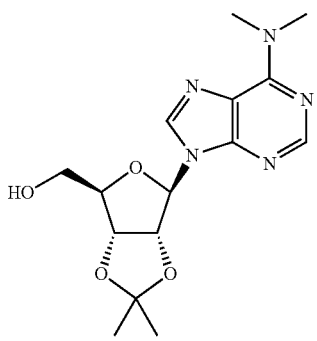 [SMILES: CN(C)c1ncnc2c1ncn2[C@@H]1O[C@H](CO)[C@H]2OC(C)(C)O[C@H]21]

((3aR,4R,6R,6aR)-6-(6-chloro-9H-purin-9-yl)-2,2-dimethyltetrahydrofuro[3,4-d][1,3]dioxol-4-yl)methanol (2 g, 6.13 mmol) was dissolved in 30% methylamine ethanol solution (120 mL) and the mixture was stirred at 60° C. overnight. The mixture was concentrated to dryness, the residue was dissolved in DCM (150 mL), then washed with sat. K₂CO₃ solution (50 mL), brine (50 mL). The organic phase was dried over Na₂SO₄, filtered and concentrated to afford the title compound (1.9 g, yield: 92%) as a white solid. ¹H NMR (500 MHz, CDCl₃): δ 8.26 (s, 1H), 7.73 (s, 1H), 6.90 (d, J=11.5 Hz, 1H), 5.82 (d, J=5.0 Hz, 1H), 5.25-5.23 (m, 1H), 5.13-5.11 (m, 1H), 4.53 (s, 1H), 3.98 (d, J=12.5 Hz, 1H), 3.78 (t, J=12.0 Hz, 1H), 3.48 (br s, 6H), 1.65 (s, 3H), 1.38 (s, 3H) ppm; ESI (m/z): 336.3 [M+1]

Step 3. Preparation of ((3aR,4R,6R,6aR)-6-(6-(dimethylamino)-9H-purin-9-yl)-2,2-dimethyltetrahydrofuro[3,4-d][1,3]dioxol-4-yl)methyl 4-methylbenzenesulfonate

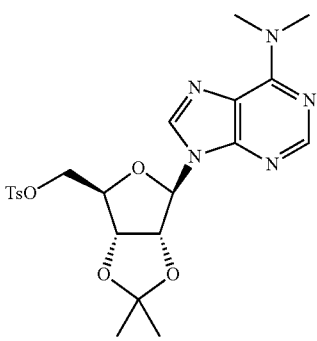 [SMILES: Cc1ccc(S(=O)(=O)OC[C@H]2O[C@@H](n3cnc4c(N(C)C)ncnc43)[C@@H]3OC(C)(C)O[C@@H]32)cc1]

To a suspension of ((3aR,4R,6R,6aR)-6-(6-(dimethylamino)-9H-purin-9-yl)-2,2-dimethyltetrahydrofuro[3,4-d][1,3]dioxol-4-yl)methanol (800 mg, 2.39 mmol) in anhydrous THF (20 mL) was added NaH (540 mg, 60% in oil, 13.4 mmol). The mixture was stirred at 25° C. for 30 min. p-Toluenesulfonyl chloride (1.02 g, 5.38 mmol) was added in one portion. The resulting reaction mixture was stirred at 25° C. for 6 h. 10 mL of water was added to quench the reaction, and then extracted with EA (20 mL×3). The combined organic layers were washed with brine (20 mL), dried over Na₂SO₄, filtered and concentrated to afford the title compound (1 g, yield: 88%) as a yellowish solid. ¹H NMR (500 MHz, CDCl₃) δ 8.19 (s, 1H), 7.71 (s, 1H), 7.63 (d, J=8.5 Hz, 2H), 7.16 (d, J=8.0 Hz, 2H), 6.02 (d, J=1.5 Hz, 1H), 5.32 (dd, J=2.0, 6.5 Hz, 1H), 5.05 (dd, J=3.0, 6.0 Hz, 1H), 4.46-4.45 (m, 1H), 4.30-4.25 (m, 2H), 3.54 (br s, 6H), 2.38 (s, 3H), 1.58 (s, 3H), 1.36 (s, 3H) ppm; ESI (m/z): 490.2 [M+1]+.

Step 4. Preparation of 9-((3aR,4R,6R,6aR)-6-((isopropylamino)methyl)-2,2-dimethyltetrahydrofuro[3,4-d][1,3]dioxol-4-yl)-N,N-dimethyl-9H-purin-6-amine

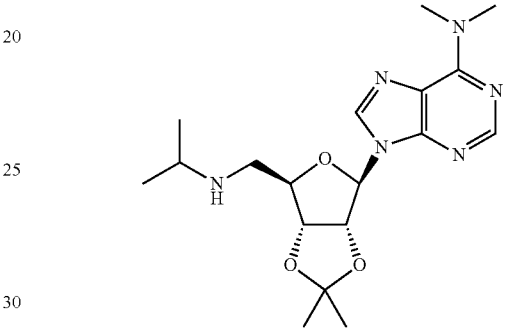

((3aR,4R,6R,6aR)-6-(6-(dimethylamino)-9H-purin-9-yl)-2,2-dimethyltetrahydrofuro[3,4-d][1,3]dioxol-4-yl)methyl 4-methylbenzenesulfonate (990 mg, 2.0 mmol) was dissolved in isopropylamine (5 mL) in a sealed tube, then stirred at 60° C. for 4 h. Solvent was removed in vacuo, the residue was dissolved in DCM (30 mL), then washed with water (5 mL×3), dried and concentrated. The crude was purified by SGC (DCM:MeOH=50:1 to 30:1) to the title compound (250 mg, 34%) as a white solid. ¹H NMR (500 MHz, MeOD): δ 8.11 (s, 1H), 8.06 (s, 1H), 6.04 (d, J=2.0 Hz, 1H), 5.41-5.39 (m, 1H), 4.90 (dd, J=3.5, 6.5 Hz, 1H), 4.23-4.20 (m, 1H), 3.38 (br s, 6H), 2.76-2.74 (m, 2H), 2.62-2.57 (m, 1H), 1.49 (s, 3H), 1.28 (s, 3H), 0.89 (d, J=6.5 Hz, 3H), 0.86 (d, J=6.5 Hz, 3H) ppm; ESI (m/z): 377.3 [M+1]

Step 5. Preparation of 1-(4-(tert-butyl)phenyl)-3-(3-((((3aR,4R,6R,6aR)-6-(6-(dimethylamino)-9H-purin-9-yl)-2,2-dimethyltetrahydrofuro[3,4-d][1,3]dioxol-4-yl)methyl)(isopropyl)amino)propyl)urea

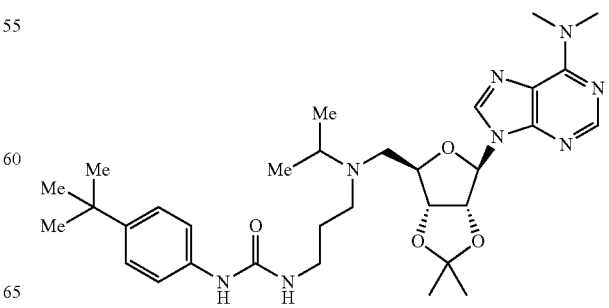

1-(4-tert-butylphenyl)-3-(3-hydroxypropyl)urea (400 mg, 1.6 mmol) and IBX (1.34 g, 4.8 mmol) were dissolved in EA (25 mL), and the reaction mixture was heated to reflux with stirring for 2 h. And then the mixture was filtrated and rinsed with EA (10 mL×3), the filtrate was concentrated to afford 1-(4-tert-butylphenyl)-3-(3-oxopropyl)urea (crude, 415 mg) as a yellowish solid, which was used for next step directly without further purification.

To a solution of 9-((3aR,4R,6R,6aR)-6-((isopropylamino)methyl)-2,2-dimethyltetrahydrofuro[3,4-d][1,3]dioxol-4-yl)-N,N-dimethyl-9H-purin-6-amine (415 mg, crude, 0.84 mmol) in DCE (15 mL) was added NaBH(OAc)$_3$ (543 mg, 2.56 mmol) in one portion. Then the resulting reaction mixture was stirred at 25° C. overnight. Saturated aqueous NaHCO$_3$ (15 mL) was added to quench the reaction, then was extracted with DCM (15 mL×3), dried over anhydrous Na$_2$SO$_4$ and concentrated. The crude was purified by Prep-TLC (EA) to afford the title compound (242 mg, yield: 62%) as a white solid. $^1$H NMR (400 MHz, MeOD): δ 8.22 (s, 1H), 8.16 (s, 1H), 7.29-7.22 (m, 4H), 6.17 (d, J=2.4 Hz, 1H), 5.52-5.51 (m, 1H), 5.03 (dd, J=3.6, 6.8 Hz, 1H), 4.29-4.28 (m, 1H), 3.49 (br s, 6H), 3.19-2.47 (m, 7H), 1.60-1.55 (m, 5H), 1.38 (s, 3H), 1.28 (s, 9H), 1.00 (d, J=6.4 Hz, 3H), 0.84 (d, J=6.4 Hz, 3H); ESI (m/z): 609.5 [M+1]$^+$.

Step 6. Preparation of 1-(4-(tert-butyl)phenyl)-3-(3-(((((2R,3S,4R,5R)-5-(6-(dimethylamino)-9H-purin-9-yl)-3,4-dihydroxytetrahydrofuran-2-yl)methyl)(isopropyl)amino)propyl)urea

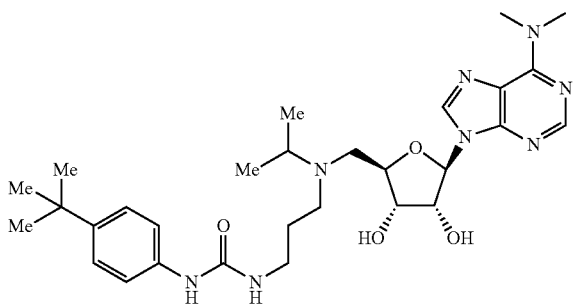 [SMILES: CC(C)N(CCCNC(=O)Nc1ccc(C(C)(C)C)cc1)C[C@H]1O[C@@H](n2cnc3c(N(C)C)ncnc32)[C@H](O)[C@@H]1O]

1-(4-(tert-butyl)phenyl)-3-(3-(((((3aR,4R,6R,6aR)-6-(6-(dimethylamino)-9H-purin-9-yl)-2,2-dimethyltetrahydrofuro[3,4-d][1,3]dioxol-4-yl)methyl)(isopropyl)amino)propyl)urea (50 mg, 0.082 mmol) was dissolved in 6 mL of 2.5 M (HCl gas in MeOH), the solution was allowed to stand at 25° C. for 3 h and evaporated to dryness as a white solid. Then the white solid was dissolved in MeOH (3 mL), the solution was neutralized by K$_2$CO$_3$ (70 mg, 0.51 mmol, dissolved in 0.3 mL of H$_2$O) with stirring at 25° C. for 1 h. Solvent was removed in vacuo and the crude was purified by reversed phase chromatography (MeOH/H2O/0.1% NH$_4$HCO$_3$) to afford the title compound (35 mg, yield: 75%) as a white solid. $^1$H NMR (500 MHz, MeOD): δ 8.19 (s, 1H), 8.17 (s, 1H), 7.25-7.17 (m, 4H), 5.99 (d, J=4.0 Hz, 1H), 4.68 (t, J=5.0 Hz, 1H), 4.26 (t, J=5.0 Hz, 1H), 4.15-4.14 (m, 1H), 3.48 (br s, 6H), 3.24-2.73 (m, 5H), 2.58 (t, J=7.0 Hz, 1H), 1.69-1.66 (m, 2H), 1.28 (s, 9H), 1.05 (d, J=6.5 Hz, 3H), 1.00 (d, J=6.5 Hz, 3H) ppm; ESI (m/z): 569.4 [M+1]$^+$.

Compound 357

1-((S)-4-(((((2R,3S,4R,5R)-5-(6-amino-9H-purin-9-yl)-3,4-dihydroxytetrahydrofuran-2-yl)methyl)(methyl)amino)butan-2-yl)-3-(4-(tert-butyl)phenyl)urea

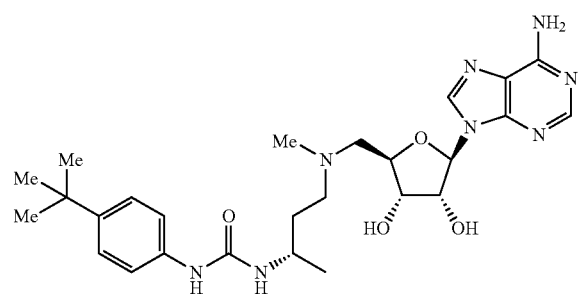

Step 1. Preparation of tert-butyl (3S)-3-[(4-tert-butylphenyl)carbamoylamino]butanoate

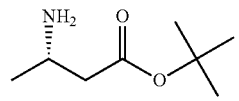

To a stirred solution of tert-butyl (3S)-3-aminobutanoate (250 mg, 1.57 mmol) and DIPEA (405 mg, 3.14 mmol) in dry DCM (5 mL) was added 4-tert-butylbenzenamine (302 mg, 1.73 mmol) dropwise at 0° C. The reaction mixture was stirred at rt overnight, then extracted with DCM (10 mL×2), dried over Na$_2$SO$_4$ and concentrated to give crude product. The crude was purified by Prep TLC (PE:EA=3.5:1) to afford the title compound (430 mg, yield: 82%) as a white solid. $^1$H NMR (500 MHz, CDCl$_3$): δ7.32-7.30 (m, 2H), 7.21-7.19 (m, 2H), 4.26-4.22 (m, 2H), 2.49-2.39 (m, 2H), 1.41 (s, 9H), 1.29 (s, 9H), 1.23 (d, J=6.5 Hz, 3H) ppm; ESI-MS (m/z): 335.7 [M+1]$^+$.

Step 2. Preparation of (S)-tert-butyl 3-(3-(4-(tert-butyl)phenyl)ureido)butanoate

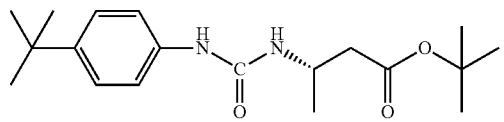 [SMILES: C[C@@H](CC(=O)OC(C)(C)C)NC(=O)Nc1ccc(C(C)(C)C)cc1]

A mixture of tert-butyl (3S)-3-[(4-tert-butylphenyl)carbamoylamino]butanoate (430 mg, 1.29 mmol) and LiBH$_4$ (124 mg, 5.15 mmol) in dry THF (5 mL) was stirred at rt overnight then extracted with EA (20 mL×2), washed with brine, dried with Na$_2$SO$_4$ and concentrated to afford the title compound (306 mg, yield 90%) without further purification. $^1$H NMR (500 MHz, CDCl$_3$): δ7.35 (t, J=8.5 Hz, 2H), 7.17 (t, J=8.5 Hz, 2H), 4.66-4.62 (m, 1H), 4.15-4.11 (m, 1H), 3.68-

3.64 (m, 2H), 1.96-1.81 (m, 1H), 1.30 (s, 9H), 1.21-1.17 (m, 3H) ppm; ESI-MS (m/z): 265.7 [M+1]+.

Step 3. Preparation of 1-[(1S)-3-[[(3aR,4R,6R,6aR)-4-(6-aminopurin-9-yl)-2,2-dimethyl-3a,4,6,6a-tetrahydrofuro[3,4-d][1,3]dioxol-6-yl]methyl-methyl-amino]-1-methyl-propyl]-3-(4-tert-butylphenyl)urea

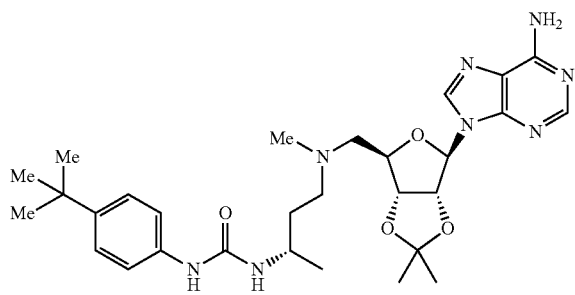 [SMILES: C[C@@H](CCN(C)C[C@H]1O[C@@H](n2cnc3c(N)ncnc32)[C@@H]2OC(C)(C)O[C@@H]21)NC(=O)Nc1ccc(C(C)(C)C)cc1]

A mixture of 1-(4-tert-butylphenyl)-3-[(1S)-3-hydroxy-1-methyl-propyl]urea (180 mg, 0.68 mmol) and IBX (572 mg, 2.04 mmol) in EA (10 mL) was refluxed for 2 h. After the solid was filtered and washed with EA (10 mL×2), the combined organic layers were concentrated to (S)-1-(4-(tert-butyl)phenyl)-3-(4-oxobutan-2-yl)urea (180 mg, crude) without further purification.

A solution 9-((3aR,4R,6R,6aR)-2,2-dimethyl-6-((methylamino)methyl)tetrahydrofuro[3,4-d][1,3]dioxol-4-yl)-9H-purin-6-amine (140 mg, 0.44 mmol) and (S)-1-(4-(tert-butyl)phenyl)-3-(4-oxobutan-2-yl)urea (180 mg, crude) in DCE (5 mL) was added NaB(OAc)$_3$H (139 mg, 0.66 mmol). The mixture was stirred at rt overnight. Then saturated aqueous NaHCO$_3$ (10 mL) was added to the solution. The mixture was extracted with DCM (20 mL×2). The combined organic layers were washed with brine and dried over Na$_2$SO$_4$ and concentrated. The crude was purified by Prep TLC (DCM: MeOH=10:1) to afford title compound (25 mg, yield: 15%) as white solid. $^1$H NMR (500 MHz, MeOD): δ8.25-8.22 (m, 2H), 7.29-7.21 (m, 4H), 6.17 (d, J=2.0 Hz, 1H), 5.49-5.48 (m, 1H), 5.04-5.02 (m, 1H), 4.43-4.39 (m, 1H), 3.68-3.62 (m, 2H), 2.69-2.68 (m, 1H), 2.53-2.49 (m, 2H), 2.28 (s, 3H), 1.71 (s, 3H), 1.64-1.49 (m, 2H), 1.36 (s, 3H), 1.29 (s, 12H), 1.09 (d, J=7.0 Hz, 3H) ppm; ESI-MS (m/z): 567.7 [M+1]+.

Step 5. Preparation of 1-((S)-4-((((2R,3S,4R,5R)-5-(6-amino-9H-purin-9-yl)-3,4-dihydroxytetrahydrofuran-2-yl)methyl)(methyl)amino)butan-2-yl)-3-(4-(tert-butyl)phenyl)urea

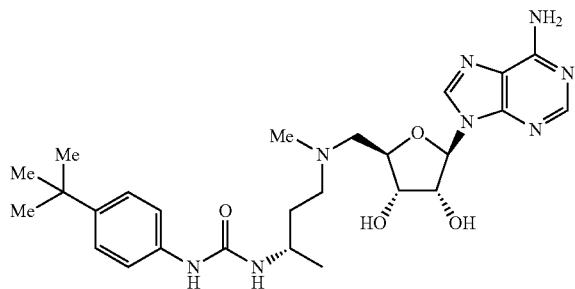 [SMILES: C[C@@H](CCN(C)C[C@H]1O[C@@H](n2cnc3c(N)ncnc32)[C@H](O)[C@@H]1O)NC(=O)Nc1ccc(C(C)(C)C)cc1]

A solution of 1-[(1S)-3-[[(3aR,4R,6R,6aR)-4-(6-aminopurin-9-yl)-2,2-dimethyl-3a,4,6,6a-tetrahydrofuro[3,4-d][1,3]dioxol-6-yl]methyl-methyl-amino]-1-methyl-propyl]-3-(4-tert-butylphenyl)urea (25 mg, 0.044 mmol) in 90% TFA (1.5 mL) was stirred at rt for 2 h, then concentrated as a solid to remove TFA, dissolved in MeOH (5 mL) and H$_2$O (1 mL), K$_2$CO$_3$ (24 mg, 0.176 mmol) was added and stirred at rt for 0.5 h then filtered and the filtrate was concentrated to give crude product. The crude was purified by Prep TLC (DCM: MeOH=5:1) to afford title compound (15 mg, yield: 65%) as a white solid. $^1$H NMR (500 MHz, MeOD): δ 8.23 (s, 1H), 8.20 (s, 1H), 7.28-7.21 (m, 4H), 6.02 (d, J=4.5 Hz, 1H), 4.85 (m, 1H), 4.48-4.46 (m, 1H), 4.40-4.38 (m, 1H), 3.78-3.73 (m, 2H), 3.50-3.43 (m, 1H), 3.23-3.17 (m, 2H), 2.90 (s, 3H), 2.88 (s, 3H), 1.96-1.90 (m, 1H), 1.78-1.74 (m, 1H), 1.28 (s, 9H), 1.15 (d, J=6.5 Hz, 3H) ppm; ESI-MS (m/z): 527.7 [M+1]+.

Compound 358

1-(4-(((((2R,3S,4R,5R)-5-(6-amino-9H-purin-9-yl)-3,4-dihydroxytetrahydrofuran-2-ylmethyl)(isopropyl)amino)butyl)-3-(4-(tert-butyl)phenyl)urea

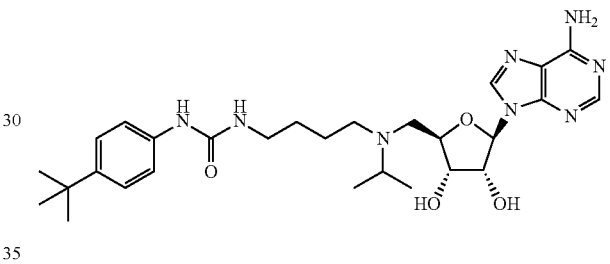

Step 1. Preparation benzyl (4-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)butyl)carbamate

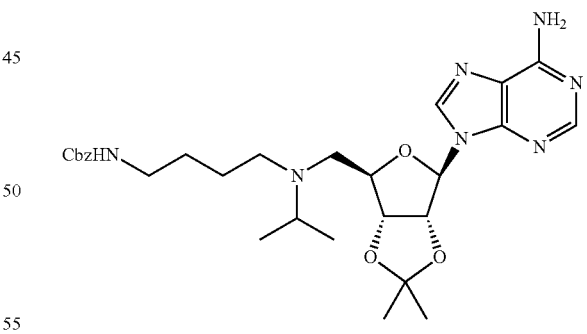

Benzyl N-(4-hydroxybutyl)carbamate (800 mg, 3.59 mmol) and IBX (3.01 g, 10.76 mmol) were dissolved in EA (25 mL) and the reaction mixture was heated to reflux with stirring for 3 h. Then the mixture was filtrated and rinsed with EA (10 mL×3). The filtrate was concentrated to afford benzyl N-(4-oxobutyl)carbamate (crude, 825 mg) as a yellowish solid which was directly used for next step without further purification.

To a solution 9-((3aR,4R,6R,6aR)-6-((isopropylamino)methyl)-2,2-dimethyltetrahydrofuro[3,4-d][1,3]dioxol-4-yl)-9H-purin-6-amine (250 mg, 0.72 mmol) and benzyl N-(4- oxobutyl)carbamate (825 mg, crude, 1.02 mmol) in DCE (15 mL) was added NaB(OAc)$_3$H (530 mg, 2.5 mmol) in one portion. Then the resulting mixture was stirred at 25° C. overnight. Saturated aqueous NaHCO$_3$ (15 mL) was added to quench the reaction. Then the reaction was extracted with DCM (15 mL×3). The organic phase was dried over Na$_2$SO$_4$ and concentrated. The crude was purified by Prep-TLC (DCM:MeOH=10:1) to afford the title compound (100 mg, yield: 25%) as a white solid. $^1$H NMR (500 MHz, MeOD): δ 8.27 (s, 1H), 8.24 (s, 1H), 7.35-7.33 (m, 5H), 6.18 (d, J=2.0 Hz, 1H), 5.56 (dd, J=2.0, 6.5 Hz, 1H), 5.07-5.05 (m, 3H), 4.30-4.29 (m, 1H), 3.09 (t, J=6.5 Hz, 3H), 2.93-2.45 (m, 5H), 1.59 (s, 3H), 1.46-1.42 (m, 4H), 1.39 (s, 3H), 1.01 (d, J=7.0 Hz, 3H), 0.85 (d, J=6.5 Hz, 3H) ppm; LC-MS (m/z): 554.3 [M+1]$^+$.

Step 2. Preparation of N1-(((3aR,4R,6R,6aR)-6-(6-amino-9H-purin-9-yl)-2,2-dimethyltetrahydrofuro[3,4-d][1,3]dioxol-4-yl)methyl)-N1-isopropylbutane-1,4-diamine

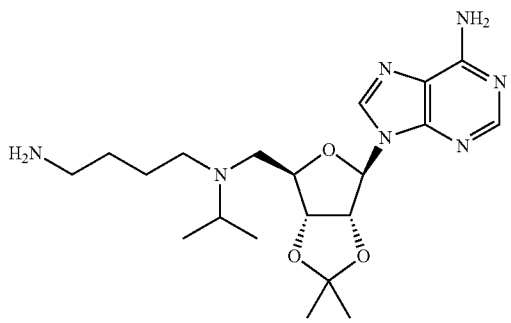 [SMILES: CC(C)N(CCCCN)C[C@H]1O[C@@H](n2cnc3c(N)ncnc32)[C@@H]2OC(C)(C)O[C@@H]21]

Benzyl (4-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)butyl)carbamate (100 mg, 0.18 mmol) was dissolved in MeOH (10 mL). Pd(OH)$_2$ (20% on carbon, 30 mg) was added and the resultant mixture was stirred under 1 atm H$_2$ overnight. The mixture was then filtered and rinsed with MeOH (5 mL×3). The filtrate was evaporated in vacuo to afford the title compound (50 mg, yield: 66%) as a white solid which was used for next step without further purification. $^1$H NMR (500 MHz, MeOD): δ 8.29 (s, 1H), 8.25 (s, 1H), 6.21 (s, 1H), 5.58-5.57 (m, 1H), 5.04 (dd, J=3.5, 6.5 Hz, 1H), 4.30-4.29 (m, 1H), 2.94-2.43 (m, 7H), 1.61 (s, 3H), 1.47-1.41 (m, 4H), 1.39 (s, 3H), 0.99 (d, J=6.5 Hz, 3H), 0.83-0.81 (m, 3H) ppm; LC-MS (m/z): 420.2 [M+1]$^+$.

Step 3. Preparation of 1-(4-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)butyl)-3-(4-(tert-butyl)phenyl)urea

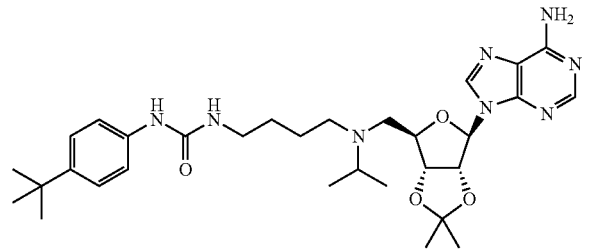 [SMILES: CC(C)N(CCCCNC(=O)Nc1ccc(C(C)(C)C)cc1)C[C@H]1O[C@@H](n2cnc3c(N)ncnc32)[C@@H]2OC(C)(C)O[C@@H]21]

To a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-isopropylbutane-1,4-diamine (45 mg, 0.11 mmol) in DCM (2 mL) at 0° C. was added a solution of 1-tert-butyl-4-isocyanatobenzene (25 mg, 0.14 mmol) in anhydrous DCM (0.5 mL) dropwise. And then the resulting mixture was stirred at 25° C. for 2 h. Solvent was removed in vacuo. The residue was purified by Prep-TLC (DCM:MeOH=10:1) to afford the title compound (32 mg, yield: 51%) as a white solid. $^1$H NMR (500 MHz, MeOD): δ 8.25 (s, 1H), 8.23 (s, 1H), 7.30-7.23 (m, 4H), 6.17 (d, J=1.5 Hz, 1H), 5.54-5.53 (m, 1H), 5.04-5.02 (m, 1H), 4.29-4.28 (m, 1H), 3.16-3.13 (m, 2H), 2.97-2.45 (m, 5H), 1.57 (s, 3H), 1.54-1.40 (m, 4H), 1.37 (s, 3H), 1.29 (s, 9H), 1.01 (d, J=5.5 Hz, 3H), 0.84 (d, J=6.0 Hz, 3H) ppm; LC-MS (m/z): 595.4 [M+1]$^+$.

Step 4. Preparation of 1-(4-(((((2R,3S,4R,5R)-5-(6-amino-9H-purin-9-yl)-3,4-dihydroxytetrahydrofuran-2-yl)methyl)(isopropyl)amino)butyl)-3-(4-(tert-butyl)phenyl)urea

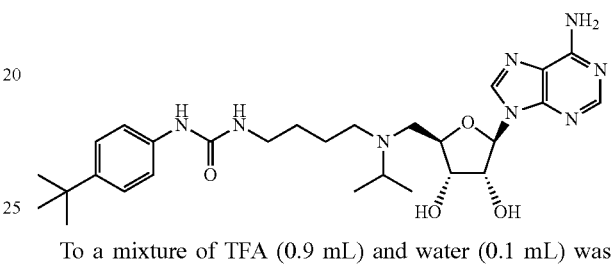

To a mixture of TFA (0.9 mL) and water (0.1 mL) was added 1-(4-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)butyl)-3-(4-(tert-butyl)phenyl)urea (32 mg, 0.054 mmol). The solution was allowed to stand at 25° C. for 2 h and evaporated to dryness. The residue was co-evaporated with methanol twice. Then the residue was dissolved in MeOH (5 mL). The solution was neutralized by K$_2$CO$_3$ (35 mg) dissolved in 0.5 mL of H$_2$O with stirring at 25° C. for 1 h. Solvent was removed in vacuo then the crude was purified by Prep-TLC (DCM:MeOH:27% NH$_3$.H$_2$O=150:20:2) to afford the title compound (20 mg, yield: 90%) as a white solid. $^1$H NMR (500 MHz, MeOD): δ 8.24 (s, 1H), 8.22 (s, 1H), 7.28-7.22 (dd, J=9.0, 21.5 Hz, 4H), 6.01 (d, J=4.0 Hz, 1H), 4.75 (d, J=5.0 Hz, 1H), 4.42-4.41 (m, 1H), 4.29-4.28 (m, 1H), 3.45-3.44 (m, 1H), 3.19-3.16 (m, 3H), 2.93 (br s, 2H), 1.66-1.51 (m, 4H), 1.29 (s, 9H), 1.22 (d, J=6.0 Hz, 3H), 1.16 (d, J=4.5 Hz, 3H) ppm; LC-MS (m/z): 555.4 [M+1]$^+$.

Compound 359

1-(3-(((((2R,3S,4R,5R)-5-(6-amino-9H-purin-9-yl)-3,4-dihydroxytetrahydrofuran-2-ylmethyl)(isopropyl)amino)propyl)-3-(3-chlorophenyl)urea

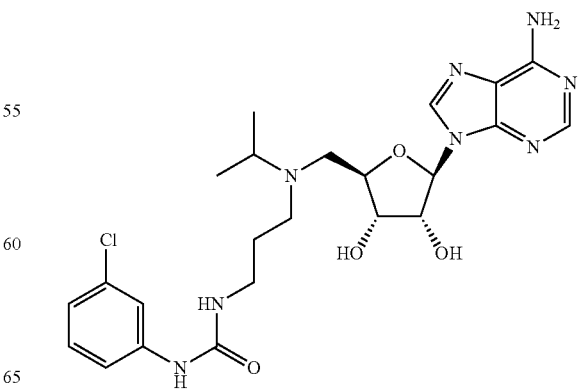

Step 1. Preparation of 2-(3-(((((3aR,4R,6R,6aR)-6-(6-amino-9H-purin-9-yl)-2,2-dimethyltetrahydrofuro[3,4-d][1,3]dioxol-4-yl)methyl)amino)propyl)isoindoline-1,3-dione

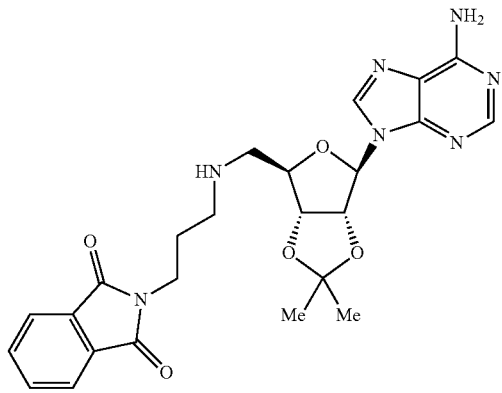 [SMILES: CC1(C)O[C@@H]2[C@H](O1)[C@@H](CNCCCN1C(=O)c3ccccc3C1=O)O[C@H]2n1cnc2c(N)ncnc21]

To a solution of 2-(3-hydroxypropyl)isoindoline-1,3-dione (1.0 g, 4.88 mmol) in EA (50 mL) was added IBX (3.4 g, 12.19 mmol). The mixture was heated to reflux for 2 h. After cooling, the mixture was filtered and the filtrate was concentrated to give 3-(1,3-dioxoisoindolin-2-yl)propanal crude (not weight), which was directly used for next step.

To a solution of 9-((3aR,4R,6R,6aR)-6-(aminomethyl)-2,2-dimethyltetrahydrofuro[3,4-d][1,3]dioxol-4-yl)-9H-purin-6-amine (1.5 g, 4.90 mmol) and 3-(1,3-dioxoisoindolin-2-yl)propanal (from last step) in DCE (50 mL) was added NaBH(OAc)$_3$ (1.56 g, 7.30 mmol). The reaction mixture was stirred at rt overnight then saturated NaHCO$_3$ aqueous solution (50 mL) was added. The resulting mixture was extracted with DCM (50 mL×2). The combined organic layers were dried over Na$_2$SO$_4$ and concentrated. The residue was purified by SGC (DCM:MeOH=100:1 to 10:1) to afford the title compound (1.38 g, yield: 57%) as a white solid. $^1$H NMR (500 MHz, MeOD): δ8.30 (s, 1H), 8.23 (s, 1H), 7.85-7.79 (m, 4H), 6.17 (d, J=2.5 Hz, 1H), 5.48 (dd, J=2.5, 6.0 Hz, 1H), 5.03 (dd, J=3.0, 6.5 Hz, 1H), 4.36 (t, J=3.5 Hz, 1H), 3.67-3.65 (m, 2H), 2.94-2.89 (m, 2H), 2.62-2.60 (m, 2H), 1.82-1.79 (m, 2H), 1.60 (s, 9H), 1.39 (s, 3H) ppm; ESI-MS (m/z): 494.2 [M+1]$^+$.

Step 2. Preparation of 2-(3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)propyl)isoindoline-1,3-dione

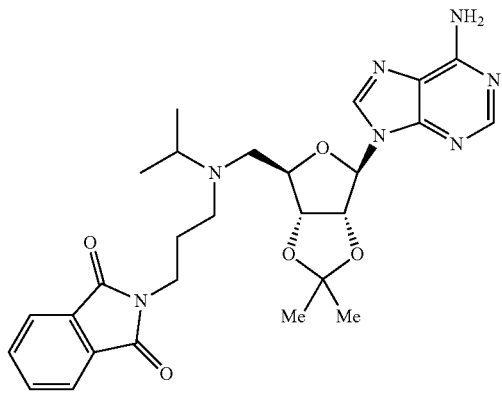 [SMILES: CC(C)N(CCCN1C(=O)c2ccccc2C1=O)C[C@H]1O[C@@H](n2cnc3c(N)ncnc32)[C@@H]2OC(C)(C)O[C@@H]21]

To a solution of 2-(3-(((((3aR,4R,6R,6aR)-6-(6-amino-9H-purin-9-yl)-2,2-dimethyltetrahydrofuro[3,4-d][1,3]dioxol-4-yl)methyl)amino)propyl)isoindoline-1,3-dione (300 mg, 0.61 mmol) and 2-iodopropane (620 mg, 3.65 mmol) in MeCN (15 mL) was added K$_2$CO$_3$ (168 mg, 1.22 mmol). The reaction mixture was heated to 80° C. for 3 days. The mixture was concentrated and water (25 mL) was added. The resulting mixture was extracted with DCM (50 mL×2). The combined organic layers were dried over Na$_2$SO$_4$ and concentrated. The residue was purified by Prep-TLC (DCM:MeOH=15:1) to afford the title compound (110 mg, yield: 34%) as a white solid. $^1$H NMR (500 MHz, MeOD): δ8.14 (s, 1H), 8.10 (s, 1H), 7.73-7.67 (m, 4H), 6.02 (d, J=2.0 Hz, 1H), 5.40-5.38 (m, 1H), 4.96 (dd, J=1.5, 3.5 Hz, 1H), 4.14 (d, J=3.0 Hz, 1H), 3.60-3.53 (m, 2H), 2.84-2.37 (m, 5H), 1.67-1.62 (m, 2H), 1.46 (s, 3H), 1.27 (s, 3H), 0.90 (d, J=6.5 Hz, 3H), 0.74 (d, J=6.0 Hz, 3H) ppm; ESI-MS (m/z): 536.3 [M+1]$^+$.

Step 3. Preparation of N1-(((3aR,4R,6R,6aR)-6-(6-amino-9H-purin-9-yl)-2,2-dimethyltetrahydrofuro[3,4-d][1,3]dioxol-4-yl)methyl)-N1-isopropylpropane-1,3-diamine

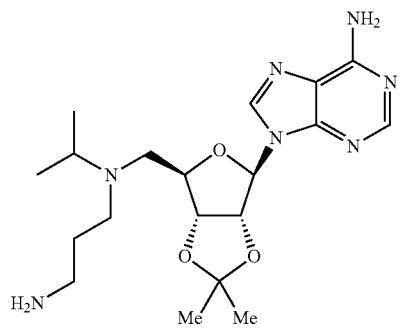 [SMILES: CC(C)N(CCCN)C[C@H]1O[C@@H](n2cnc3c(N)ncnc32)[C@@H]2OC(C)(C)O[C@@H]21]

To a solution of 2-(3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)propyl)isoindoline-1,3-dione (130 mg, 0.24 mmol) in EtOH (5 mL) was added NH$_2$—NH$_2$.H$_2$O (85%) (61 mg, 0.97 mmol), and the mixture was heated to reflux for 2 h. The reaction mixture was filtered and the filtrate was concentrated. DCM (5 mL) was added and filtered, the filtrate was concentrated to afford the title compound (110 mg, yield: 100%) as a white solid. $^1$H NMR (500 MHz, MeOD): δ8.17 (s, 1H), 8.13 (s, 1H), 6.09 (d, J=2.0 Hz, 1H), 5.46 (dd, J=2.0, 6.5 Hz, 1H), 4.92 (dd, J=3.0, 6.0 Hz, 1H), 4.20-4.18 (m, 1H), 2.84-2.55 (m, 4H), 2.46-2.41 (m, 3H), 1.49-1.44 (m, 5H), 1.29 (s, 3H), 0.88 (d, J=6.5 Hz, 3H), 0.65 (d, J=6.5 Hz, 3H) ppm; ESI-MS (m/z): 406.2 [M+1]$^+$.

Step 4. Preparation of 1-(3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)propyl)-3-(3-chlorophenyl)urea

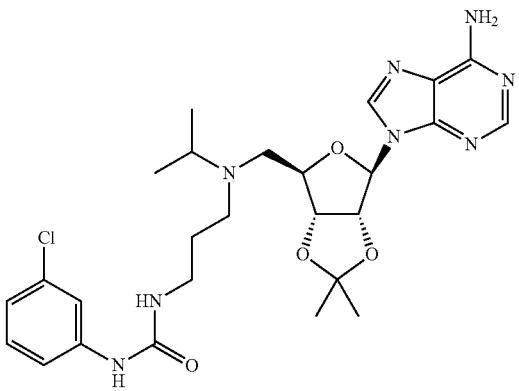 [SMILES: CC(C)N(CCCNC(=O)Nc1cccc(Cl)c1)C[C@H]1O[C@@H](n2cnc3c(N)ncnc32)[C@@H]2OC(C)(C)O[C@@H]21]

To a solution of N1-(((3aR,4R,6R,6aR)-6-(6-amino-9H-purin-9-yl)-2,2-dimethyltetrahydrofuro[3,4-d][1,3]dioxol- 4-yl)methyl)-N1-isopropylpropane-1,3-diamine (50 mg, 0.12 mmol) in DCM (5 mL) was added TEA (25 mg, 0.25 mmol) and 1-chloro-3-isocyanato-benzene (23 mg, 0.15 mmol). The mixture was stirred at rt for 2 h. Water (8 mL) was added to quench the reaction. The mixture was extracted with DCM (10 mL×3). The organic phase was dried over anhydrous Na$_2$SO$_4$ and concentrated. The crude was purified by prep-TLC (DCM:MeOH:NH$_3$.H$_2$O=10:1:0.01) to afford the title compound (50 mg, yield: 72%) as a white solid. $^1$H NMR (500 MHz, MeOD): δ 8.16 (s, 1H), 8.11 (s, 1H), 7.45 (d, J=1.5 Hz, 1H), 7.11-7.07 (m, 2H), 6.85-6.82 (m, 1H), 6.08 (d, J=2.0 Hz, 1H), 5.44 (dd, J=1.5, 6.0 Hz, 1H), 4.94 (dd, J=3.0, 6.5 Hz, 1H), 4.20 (d, J=2.5 Hz, 1H), 3.10-3.06 (m, 2H), 2.84-2.28 (m, 5H), 1.51-1.45 (m, 5H), 1.27 (s, 3H), 0.90 (d, J=7.0 Hz, 3H), 0.73 (d, J. 7.0 Hz, 3H) ppm; ESI-MS (m/z): 559.3 [M+1]$^+$.

Step 5. Preparation of 1-(3-(((((2R,3S,4R,5R)-5-(6-amino-9H-purin-9-yl)-3,4-dihydroxytetrahydrofuran-2-yl)methyl)(isopropyl)amino)propyl)-3-(3-chlorophenyl)urea

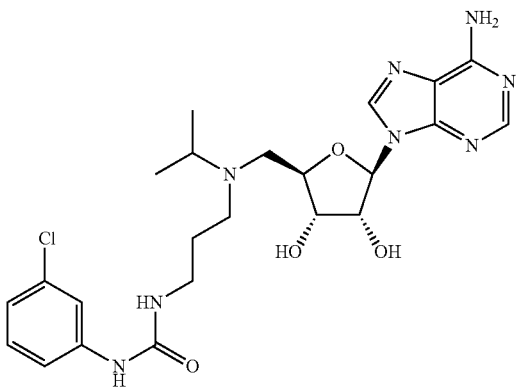 [SMILES: CC(C)N(CCCNC(=O)Nc1cccc(Cl)c1)C[C@H]1O[C@@H](n2cnc3c(N)ncnc32)[C@H](O)[C@@H]1O]

A solution of 1-(3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)propyl)-3-(3-chlorophenyl)urea (50 mg, 0.09 mmol) in 90% TFA (1 mL) was stirred at rt for 2 h and concentrated to dryness. K$_2$CO$_3$ (50 mg) in water (0.5 mL) and MeOH (5 mL) were added. The resulting mixture was stirred for another 5 min at rt and concentrated. The residue was purified by prep-TLC (DCM:MeOH: NH$_3$.H$_2$O=5:1:0.01) to the title compound (30 mg, yield: 64%) as a white solid. $^1$H NMR (500 MHz, (CD$_3$)$_2$CO): δ8.22 (s, 1H), 8.19 (s, 1H), 7.82 (t, J=4.0 Hz, 1H), 7.39 (dd, J=1.0, 8.0 Hz, 1H), 7.19-7.16 (m, 1H), 6.88-6.86 (m, 1H), 6.05 (d, J. 4.0 Hz, 1H), 4.82 (d, J=4.0 Hz, 1H), 4.63 (d, J. 5.5 Hz, 1H), 4.47 (brs, 1H), 3.76-2.88 (m, 7H), 1.93-1.92 (m, 2H), 1.32-1.23 (m, 6H) ppm; ESI-MS (m/z): 519.2 [M+1]$^+$.

Compound 360

N-(((2R,3S,4R,5R)-5-(6-amino-9H-purin-9-yl)-3,4-dihydroxytetrahydrofuran-2-yl)methyl)-3-(3-(4-(tert-butyl)phenyl)ureido)-N-ethylpropanamide

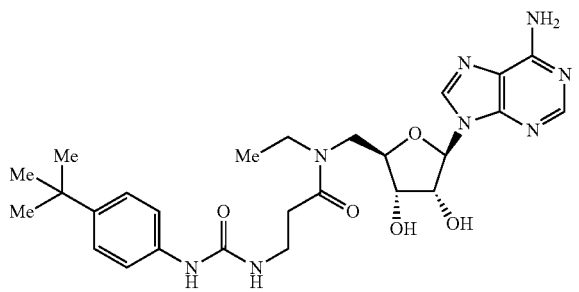 [SMILES: CCN(C[C@H]1O[C@@H](n2cnc3c(N)ncnc32)[C@H](O)[C@@H]1O)C(=O)CCNC(=O)Nc1ccc(C(C)(C)C)cc1]

Step 1. Preparation ethyl 3-(3-(4-(tert-butyl)phenyl)ureido)propanoate

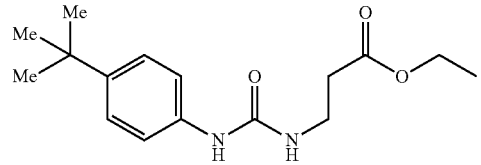 [SMILES: CCOC(=O)CCNC(=O)Nc1ccc(C(C)(C)C)cc1]

To a solution of TEA (742 mg, 7.35 mmol) and ethyl 3-aminopropanoate (750 mg, 4.90 mmol) in DCM (15 mL) was added dropwise 1-tert-butyl-4-isocyanatobenzene (943 mg, 5.39 mmol). The mixture was stirred at rt for 2 h. The mixture was extracted with DCM (50 mL×3). The combined organic phase was dried over Na$_2$SO$_4$ and concentrated. The crude was purified by SGC (PE:EA=4:1) to afford the title compound (1.0 g, yield: 71%) as a white solid. $^1$H NMR (500 MHz, CDCl$_3$): δ 7.34-7.32 (m, 2H), 7.20-7.18 (m, 2H), 6.50 (s, 1H), 5.50 (s, 1H), 4.15-4.11 (m, 2H), 3.54-3.51 (m, 2H), 2.59-2.56 (m, 2H), 1.30 (s, 9H), 1.26 (t, J=12.0 Hz, 3H) ppm; ESI-MS (m/z): 293.2 [M+1]

Step 2. Preparation of 3-(3-(4-(tert-butyl)phenyl)ureido)propanoic acid

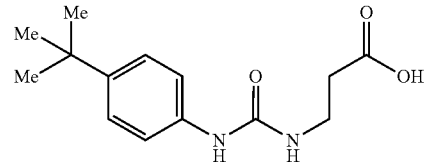 [SMILES: CC(C)(C)c1ccc(NC(=O)NCCC(=O)O)cc1]

To a solution ethyl 3-(3-(4-(tert-butyl)phenyl)ureido)propanoate (1.0 g, 3.42 mmol) in THF (40 mL) was added dropwise NaOH (410 mg, 10.27 mmol) in water (2 mL). The mixture was stirred at rt for 3 h. 1 N HCl (12 mL) was added. The mixture was extracted with EA (30 mL×2). The combined organic phase was dried over Na$_2$SO$_4$ and concentrated to afford the tile compound (900 mg, yield: 99%) as a white solid. $^1$H NMR (500 MHz, DMSO): δ 12.26 (s, 1H), 8.45 (s, 1H), 7.28-7.21 (m, 4H), 6.15 (brs, 1H), 3.29-3.25 (m, 2H), 2.42-2.39 (m, 2H), 1.23 (s, 9H) ppm; ESI-MS (m/z): 265.3 [M+1]+.

Step 3. Preparation of 9-((3aR,4R,6R,6aR)-6-((ethylamino)methyl)-2,2-dimethyltetrahydrofuro[3,4-d][1,3]dioxol-4-yl)-9H-purin-6-amine

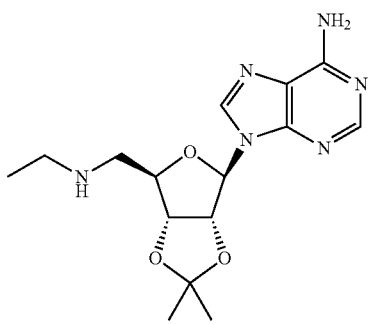 [SMILES: CCNC[C@H]1O[C@@H](n2cnc3c(N)ncnc32)[C@@H]2OC(C)(C)O[C@@H]21]

To a solution of 9-((3aR,4R,6R,6aR)-6-(aminomethyl)-2,2-dimethyltetrahydrofuro[3,4-d][1,3]dioxol-4-yl)-9H-purin-6-amine (500 mg, 1.63 mmol) and acetaldehyde solution (40%) (162 mg, 1.47 mmol) in DCE (20 mL) was added NaBH(OAc)$_3$ (415 mg, 1.96 mmol). The reaction mixture was stirred at rt for 2 h then saturated aqueous NaHCO$_3$ (20 mL) was added. The resulting mixture was extracted with DCM (20 mL×3). The combined organic layers were dried over Na$_2$SO$_4$ and concentrated. The residue was purified by Pre-TLC (DCM:MeOH=10:1) to afford the title compound (100 mg, yield: 37%) as a white solid. $^1$H NMR (500 MHz, MeOD): δ 8.28 (s, 1H), 8.22 (s, 1H), 6.17 (d, J=2.5 Hz, 1H), 5.50 (dd, J=2.5, 5.5 Hz, 1H), 5.02 (dd, J=3.5, 6.5 Hz, 1H), 4.36 (brs, 1H), 2.94-2.91 (m, 2H), 2.63-2.60 (m, 2H), 1.61 (s, 3H), 1.39 (s, 3H), 1.05 (m, 3H) ppm; ESI-MS (m/z): 335.3 [M+1]$^+$.

Step 4. Preparation of N-(((3aR,4R,6R,6aR)-6-(6-amino-9H-purin-9-yl)-2,2-dimethyltetrahydrofuro[3,4-d][1,3]dioxol-4-yl)methyl)-3-(3-(4-(tert-butyl)phenyl)ureido)-N-ethylpropanamide

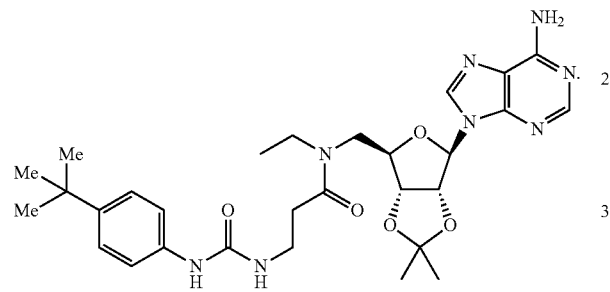

To a solution of TEA (45 mg, 0.45 mmol), BOP (159 mg, 0.36 mmol) and 3-(3-(4-(tert-butyl)phenyl)ureido)propanoic acid d in DMF (2.5 mL) was added 9-((3aR,4R,6R,6aR)-6-((ethylamino)methyl)-2,2-dimethyltetrahydrofuro[3,4-d][1,3]dioxol-4-yl)-9H-purin-6-amine (100 mg, 0.30 mmol). The mixture was heated to 45° C. overnight. The mixture was extracted with EA (15 mL×3) and washed with brine (10 mL). The combined organic phase was dried over Na$_2$SO$_4$ and concentrated. The crude was purified by Prep-TLC (DCM:MeOH=10:1) to afford the title compound (130 mg) as a white solid. $^1$H NMR (500 MHz, MeOD): δ 8.16-8.13 (m, 2H), 7.18-7.12 (m, 4H), 6.10-6.07 (m, 1H), 5.45-5.44 (m, 1H), 4.98-4.96 (m, 1H), 4.42-4.38 (m, 1H), 3.49-2.48 (m, 8H), 1.47 (d, J=3.0 Hz, 3H), 1.26 (d, J=3.0 Hz, 3H), 1.21 (s, 9H), 0.91-0.81 (m, 3H) ppm; ESI-MS (m/z): 581.4 [M+1]$^+$.

Step 5. Preparation of N-(((2R,3S,4R,5R)-5-(6-amino-9H-purin-9-yl)-3,4-dihydroxytetrahydrofuran-2-ylmethyl)-3-(3-(4-(tert-butyl)phenyl)ureido)-N-ethylpropanamide

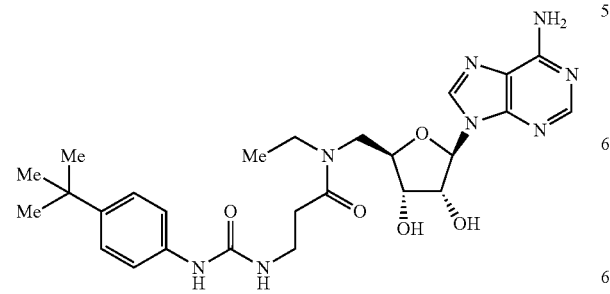

A solution of N-(((3aR,4R,6R,6aR)-6-(6-amino-9H-purin-9-yl)-2,2-dimethyltetrahydrofuro[3,4-d][1,3]dioxol-4-yl)methyl)-3-(3-(4-(tert-butyl)phenyl)ureido)-N-ethylpropanamide (130 mg, 0.22 mmol) in HCl/MeOH (2.5 mol/L) (8 mL) was stirred at rt for 2 h and concentrated to dryness. K$_2$CO$_3$ (123 mg) in water (0.5 mL) and MeOH (8 mL) were added. The resulting mixture was stirred for another 10 min at rt and filtrated. The filtrate was concentrated. The residue was purified by Prep-HPLC to afford the title compound (45 mg, yield: 37%) as a white solid. $^1$H NMR (500 MHz, MeOD): δ 8.31-8.22 (m, 2H), 7.30-7.22 (m, 4H), 5.97-5.96 (m, 1H), 4.74-4.71 (m, 0.36H), 4.43-4.20 (m, 0.41H), 4.30-4.18 (m, 1.67H), 3.96-3.94 (m, 0.63H), 3.85-3.81 (m, 0.86H), 3.68-3.64 (m, 0.66H) 3.51-3.32 (m, 6H), 2.66-2.63 (m, 2H) 1.30 (s, 9H), 1.15-1.09 (m, 3H) ppm; ESI-MS (m/z): 541.4 [M+1]$^+$.

Compound 118

1-(3-((((2R,3S,4R,5R)-5-(6-amino-9H-purin-9-yl)-3,4-dihydroxytetrahydrofuran-2-yl)methyl)(methyl)amino)propyl)-3-(4-(tert-butyl)phenyl)urea

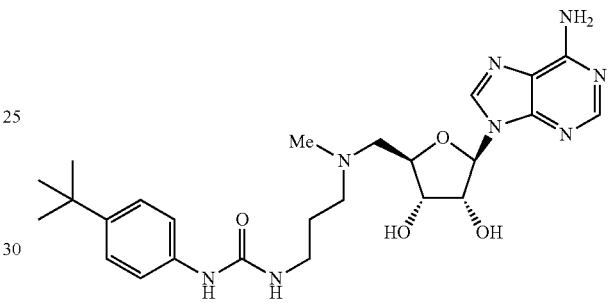

Step 1. Preparation of 1-(4-(tert-butyl)phenyl)-3-(3-oxopropyl)urea

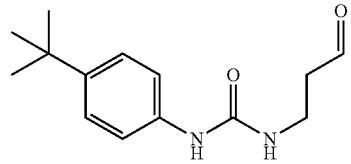 [SMILES: CC(C)(C)c1ccc(NC(=O)NCCC=O)cc1]

A mixture of 1-(4-(tert-butyl)phenyl)-3-(3-hydroxypropyl)urea (1.2 g, 4.79 mmol) and IBX (4.03 g, 14.4 mmol) in 60 mL of EA was refluxed for 2 h. The mixture was filtered and filtrate was concentrated to give the title compound as an oil (1.15 g, yield: 99%).

Step 2. Preparation of 1-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(4-(tert-butyl)phenyl)urea

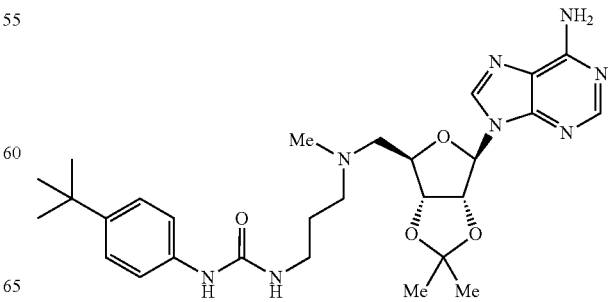

307

To a stirred solution of 1-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(4-(tert-butyl)phenyl)urea (2.4 g, 7.5 mmol) and 1-(4-tert-butylphenyl)-3-(3-oxopropyl)urea (3.4 g, 13.7 mmol) in 150 mL of DCE was added NaBH(OAc)₃ (4.77 g, 22.5 mmol). Then the mixture was stirred at rt overnight. Saturated NaHCO₃ aqueous solution was added to quench the reaction and the mixture was extracted with DCM (60 mL×3). The organic phase was concentrated and the residue was purified by SGC(CH₃OH: DCM=1:40) to afford the title compound (2.2 g, yield: 50%) as pale solid. ¹H NMR (500 MHz, MeOD): δ 8.23 (s, 1H), 8.20 (s, 1H), 7.25 (d, J=9.0 Hz, 2H), 7.20 (d, J=9.0 Hz, 2H), 6.15 (d, J=2.0 Hz, 1H), 5.46 (dd, J=2.5, 6.5 Hz, 1), 4.98 (dd, J=3.5, 6.5 Hz, 1H), 4.36-4.37 (m, 1H), 3.09-3.12 (m, 2H), 2.67-2.70 (m, 2H), 2.30-2.35 (m, 2H), 1.99 (s, 3H), 1.53-1.59 (m, 5H), 1.34 (s, 3H), 1.23 (s, 9H) ppm. MS (ESI): m/z 553.7 [M+1]⁺.

Step 3. Preparation of 1-(3-((((2R,3S,4R,5R)-5-(6-amino-9H-purin-9-yl)-3,4-dihydroxytetrahydrofuran-2-yl)methyl)(methyl)amino)propyl)-3-(4-(tert-butyl)phenyl)urea

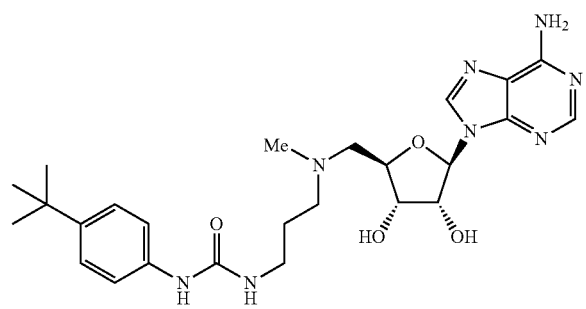 [SMILES: CN(CCCNC(=O)Nc1ccc(C(C)(C)C)cc1)C[C@H]1O[C@@H](n2cnc3c(N)ncnc32)[C@H](O)[C@@H]1O]

To a mixture of TFA (3.6 mL) and water (0.4 mL) was added 1-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(4-(tert-butyl)phenyl)urea (1.15 g, 2.08 mmol). The solution was stirred at rt for 3 h and evaporated to dryness. The residue was co-evaporated with methanol twice then dissolved in MeOH (25 mL). The solution was neutralized by anion exchange resin (5.0 g) with stirring for 1 h. After filtered, the filtrate was concentrated and the residue was purified by Prep-HPLC to afford the title compound (510 mg, yield 68%) as white solid. ¹H NMR (500 MHz, MeOD): δ 8.27 (s, 1H), 8.21 (s, 1H), 7.27 (d, J=8.0 Hz, 2H), 7.22 (d, J=9.5 Hz, 2H), 6.00 (d, J=4.0 Hz, 1H), 4.71-4.73 (m, 1H), 4.23-4.28 (m, 2H), 3.21-3.23 (m, 2H), 2.81-2.84 (m, 2H), 2.55-2.58 (m, 2H), 2.33 (s, 3H), 1.72 (t, J=7.0 Hz, 2H), 1.29 (s, 9H) ppm. MS (ESI): m/z 513.7 [M+1]⁺.

308

Compound 361

1-(3-(((((2R,3S,4R,5R)-5-(6-amino-9H-purin-9-yl)-3,4-dihydroxytetrahydrofuran-2-yl)methyl)(ethyl)amino)propyl)-3-(4-(tert-butyl)phenyl)urea

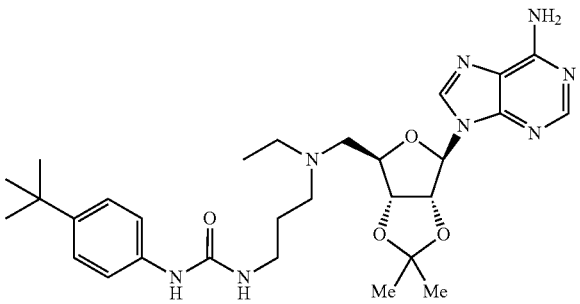 [SMILES: CCN(CCCNC(=O)Nc1ccc(C(C)(C)C)cc1)C[C@H]1O[C@@H](n2cnc3c(N)ncnc32)[C@@H]2OC(C)(C)O[C@@H]21]

Step 1. Preparation 1-(3-((((3aR,4R,6R,6aR)-6-(6-amino-9H-purin-9-yl)-2,2-dimethyltetrahydrofuro[3,4-d][1,3]dioxol-4-yl)methyl)(ethyl)amino)propyl)-3-(4-(tert-butyl)phenyl)urea

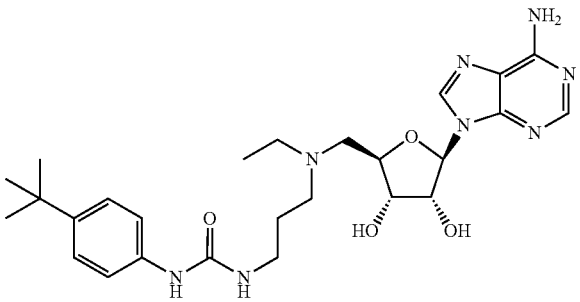 [SMILES: CCN(CCCNC(=O)Nc1ccc(C(C)(C)C)cc1)C[C@H]1O[C@@H](n2cnc3c(N)ncnc32)[C@H](O)[C@@H]1O]

A solution of 1-(3-((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl)urea (150 mg, 0.279 mmol) and acetaldehyde (2 mL) in DCE/THF (1:1, 6 mL) was stirred at rt for 0.5 h. Then NaBH(OAc)₃ (120 mg, 0.558 mmol) was added. The reaction was stirred overnight. The reaction was quenched with saturated aqueous NaHCO₃ solution (1 mL), extracted with DCM (10 mL×3), washed with brine (10 mL), dried and concentrated to give the crude. The crude was purified by SGC (DCM:MeOH=40:1) to afford the title compound (95 mg, Yield 68%). ¹H NMR (500 MHz, MeOD): δ 8.26 (s, 2H), 8.24 (s, 2H), 7.27 (dd, J=8.5, 9.0 Hz, 4H), 6.26-6.27 (d, J=2.0 Hz, 1H), 5.49-5.46 (m, 1H), 5.18-5.16 (m, 1H), 4.62-4.59 (m, 1H), 3.65-3.59 (m, 1H), 3.08-3.01 (m, 6H), 1.74-1.65 (m, 2H), 1.59 (s, 3H), 1.39 (s, 3H), 1.28 (s, 9H), 1.12-1.09 (t, J=14.0 Hz, 3H) ppm; LC-MS (m/z): 567.3[M+1]⁺.

Step 2. Preparation 1-(3-((((2R,3S,4R,5R)-5-(6-amino-9H-purin-9-yl)-3,4-dihydroxytetrahydrofuran-2-yl)methyl)(ethyl)amino)propyl)-3-(4-(tert-butyl)phenyl)urea A solution of 1-(3-((((3aR,4R,6R,6aR)-6-(6-amino-9H-purin-9-yl)-2,2-dimethyltetrahydrofuro[3,4-d][1,3]dioxol-4-yl)methyl)(ethyl)amino)propyl)-3-(4-(tert-butyl)phenyl)urea (90 mg, 0.168 mmol) in TFA (0.90 mL) and 0.10 mL water was stirred for 1.5 h at room temperature. The reaction was concentrated to dryness, dissolved in MeOH (5 mL). The solution was neutralized by anion exchange resin (600 mg) with stirring for 1 h. After filtered and washed with MeOH (2 mL×3), the filtrate was concentrated and the residue was purified by Prep-TLC to afford the title compound (75 mg, yield 85%) as a white solid. $^1$H NMR (500 MHz, MeOD): δ 8.25 (s, 2H), 8.21 (s, 2H), 7.25 (dd, J=9.0, 9.0 Hz, 4H), 6.01 (d, J=4.0 Hz, 1H), 4.75 (t, J=9.5 Hz, 1H), 4.37-4.31 (m, 2H), 3.24-3.17 (m, 4H), 2.91-2.86 (m, 4H), 1.80-1.77 (m, 2H), 1.29 (s, 9H), 1.16-1.13 (t, J=14.5 Hz, 3H). ppm; LC-MS (m/z): 527.3 [M+1]$^+$.

Compound 365

1-(4-((((2R,3S,4R,5R)-5-(6-amino-9H-purin-9-yl)-3,4-dihydroxytetrahydrofuran-2-yl)methyl)(methyl)amino)-2-methylbutan-2-yl)-3-(4-(tert-butyl)phenyl)urea

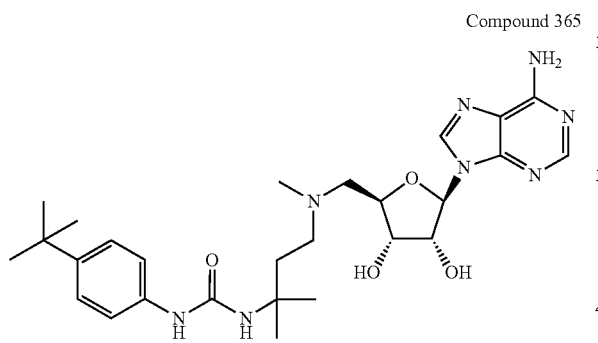

Compound 365

Step 1. Preparation of 4-methoxy-2,2-dimethyl-4-oxo-butanoic acid

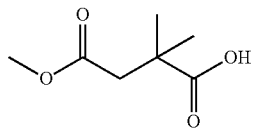

To a stirred solution of 2,2-dimethylbutanedioic acid (4.5 g, 31 mmol) in MeOH (45 mL) was added 98% H$_2$SO$_4$ (0.45 mL) dropwise at 0° C. Then the reaction mixture was stirred at rt for 16 h. The solution was concentrated. Then saturated aqueous NaHCO$_3$ (20 mL) was added to the residue and washed with hexane (50 mL×3). Then 6N HCl was added to the aqueous phase until pH=2, extracted with EA (200 mL×4), dried with Na$_2$SO$_4$ and concentrated to afford the title compound (2.5 g, yield 51%) as a colorless oil without purification. $^1$H NMR (500 MHz, CDCl$_3$): δ 3.65 (s, 3H), 2.61 (s, 2H), 1.27 (s, 6H) ppm.

Step 2. Preparation of methyl 3-(((benzyloxy)carbonyl)amino)-3-methylbutanoate

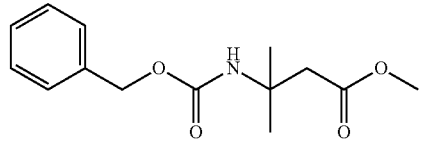 [SMILES: COC(=O)CC(C)(C)NC(=O)OCc1ccccc1]

To a stirred solution of 4-methoxy-2,2-dimethyl-4-oxo-butanoic acid (2.5 g, 15.6 mmol) in toluene (25 mL) was added TEA (1.6 g, 15.8 mmol) and DPPA (4.7 g, 17.2 mmol). The stirred reaction mixture was heated to reflux for 45 min then benzyl alcohol (3.38 g, 31.2 mmol) was added and refluxed overnight. After cooling to rt, the solution was concentrated and extracted with EA (100 mL×2), washed with NaHCO$_3$, dried over Na$_2$SO$_4$ and concentrated. The residue was purified by SGC (PE:EA=20:1) to afford the title compound (2.9 g, yield 70%). $^1$H NMR (500 MHz, CDCl$_3$): δ 7.36 (s, 5H), 5.06 (s, 2H), 3.65 (s, 3H), 2.70 (s, 2H), 1.41 (s, 6H) ppm; ESI-MS (m/z): 266.7 [M+1]$^+$.

Step 3. Preparation of benzyl (4-hydroxy-2-methylbutan-2-yl)carbamate

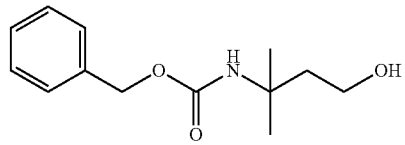 [SMILES: CC(C)(CCO)NC(=O)OCc1ccccc1]

A mixture of methyl 3-(((benzyloxy)carbonyl)amino)-3-methylbutanoate (795 mg, 3.0 mmol) and LiBH$_4$ (144 mg, 6.0 mmol) in anhydrous THF (10 mL) was stirred at rt overnight. Then the solvent was removed and extracted with EA (30 mL×2), washed with brine, dried over Na$_2$SO$_4$ and concentrated to afford the title compound (600 mg, yield 88%) as a colorless oil without purification. $^1$H NMR (500 MHz, CDCl$_3$): δ 7.39-7.27 (m, 5H), 5.05 (s, 2H), 3.81-3.78 (m, 2H), 1.91-1.88 (m, 2H), 1.38 (s, 6H).

Step 4. Preparation of benzyl (2-methyl-4-oxobutan-2-yl)carbamate

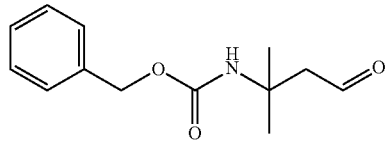 [SMILES: CC(C)(CC=O)NC(=O)OCc1ccccc1]

A mixture of benzyl (4-hydroxy-2-methylbutan-2-yl)carbamate (300 mg, 1.3 mmol) and IBX (1.06 g, 3.8 mmol) in EA (20 mL) was refluxed for 2 h. After the solid was filtered and washed with EA (10 mL×2), the combined organic layers were concentrated to afford the title compound (253 mg, yield: 85%) as a red solid without purification. $^1$H NMR (500 MHz, CDCl$_3$): δ 9.78 (t, J=2.0 Hz, 1H), 7.38-7.32 (m, 5H), 5.06 (s, 2H), 4.92 (s, 1H), 2.88 (s, 2H), 1.40 (s, 6H).

Step 5. Preparation of benzyl (4-(((((3aR,4R,6R,6aR)-6-(6-amino-9H-purin-9-yl)-2,2-dimethyltetrahydrofuro[3,4-d][1,3]dioxol-4-yl)methyl)(methyl)amino)-2-methylbutan-2-yl)carbamate

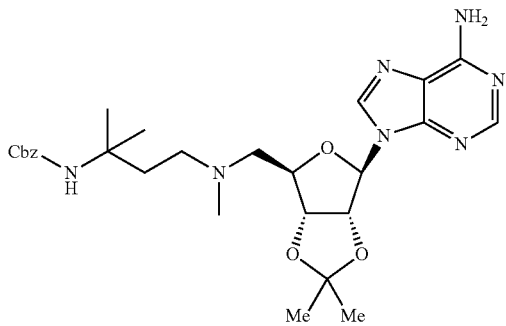 [SMILES: CN(CCC(C)(C)NC(=O)OCc1ccccc1)C[C@H]1O[C@@H](n2cnc3c(N)ncnc32)[C@@H]2OC(C)(C)O[C@@H]21]

A solution 9-((3aR,4R,6R,6aR)-2,2-dimethyl-6-((methylamino)methyl)tetrahydrofuro[3,4-d][1,3]dioxol-4-yl)-9H-purin-6-amine (320 mg, 1.0 mmol) and benzyl N-(1,1-dimethyl-3-oxo-propyl)carbamate (253 mg, 1.1 mmol) in DCE (15 mL) was added NaBH(OAc)$_3$ (320 mg, 1.5 mmol). The mixture was stirred at rt overnight. Then saturated aqueous NaHCO$_3$ (20 mL) was added to quench the reaction. The mixture was extracted with DCM (30 mL×2). The combined organic layers were washed with brine, dried over Na$_2$SO$_4$ and concentrated. The crude was purified by Prep TLC (DCM:MeOH=10:1) to the title compound (323 mg, yield: 60%) as white solid. $^1$H NMR (500 MHz, MeOD): δ 8.24 (s, 1H), 8.21 (s, 1H), 7.34-7.25 (m, 5H), 6.16 (d, J=1.5 Hz, 1H), 5.48 (dd, J=2.0, 6.5 Hz, 1H), 5.00-4.98 (m, 3H), 4.40-4.36 (m, 1H), 2.77-2.73 (m, 1H), 2.64-2.61 (m, 1H), 2.42 (t, J=2.5 Hz, 2H), 2.22 (s, 3H), 1.69-1.61 (m, 2H), 1.59 (s, 3H), 1.37 (s, 3H), 1.21 (s, 3H), 1.16 (s, 3H); ESI-MS (m/z): 540.7 [M+1]$^+$.

Step 6. Preparation of N1-(((3aR,4R,6R,6aR)-6-(6-amino-9H-purin-9-yl)-2,2-dimethyltetrahydrofuro[3,4-d][1,3]dioxol-4-yl)methyl)-N1,3-dimethylbutane-1,3-diamine

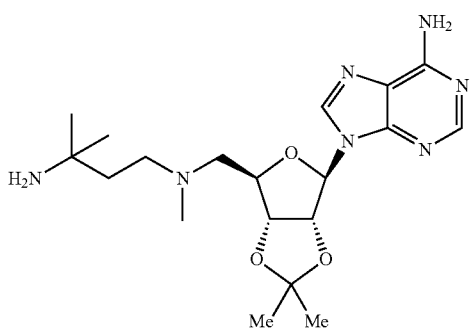 [SMILES: CN(CCC(C)(C)N)C[C@H]1O[C@@H](n2cnc3c(N)ncnc32)[C@@H]2OC(C)(C)O[C@@H]21]

A mixture of benzyl (4-(((((3aR,4R,6R,6aR)-6-(6-amino-9H-purin-9-yl)-2,2-dimethyltetrahydrofuro[3,4-d][1,3]dioxol-4-yl)methyl)(methyl)amino)-2-methylbutan-2-yl)carbamate (200 mg, 0.37 mmol) and Pd(OH)$_2$ (26 mg) in EtOH (10 mL) was stirred at rt under H$_2$ pressure overnight. The mixture was filtered and the filtrate was concentrated to afford the title compound (140 mg, yield 93%) as a white powder. $^1$H NMR (500 MHz, MeOD): δ 8.29 (s, 1H), 8.24 (s, 1H), 6.20 (d, J=2.5 Hz, 1H), 5.53 (dd, J=2.5, 6.5 Hz, 1H), 5.01-4.99 (m, 1H), 4.40-4.37 (m, 1H), 2.77-2.73 (m, 1H), 2.64-2.62 (m, 1H), 2.49-2.41 (m, 2H), 2.23 (s, 3H), 1.60 (s, 3H), 1.45-1.41 (m, 2H), 1.39 (s, 3H), 1.06 (s, 3H), 1.00 (s, 3H); ESI-MS (m/z): 406.7 [M+1]$^+$.

Step 7. Preparation of 1-(4-(((((3aR,4R,6R,6aR)-6-(6-amino-9H-purin-9-yl)-2,2-dimethyltetrahydrofuro[3,4-d][1,3]dioxol-4-yl)methyl)(methyl)amino)-2-methylbutan-2-yl)-3-(4-(tert-butyl)phenyl)urea

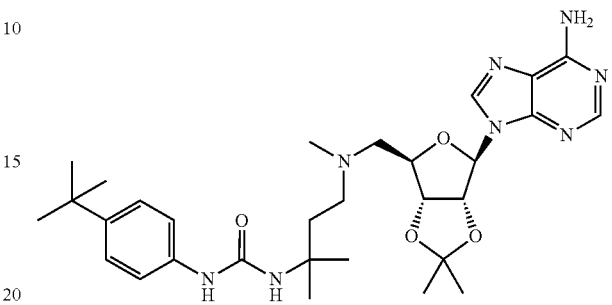

To a stirred solution of N1-(((3aR,4R,6R,6aR)-6-(6-amino-9H-purin-9-yl)-2,2-dimethyltetrahydrofuro[3,4-d][1,3]dioxol-4-yl)methyl)-N1,3-dimethylbutane-1,3-diamine (130 mg, 0.32 mmol) and DIPEA (124 mg, 0.96 mmol) in anhydrous DCM (10 mL), was added 4-tert-butylbenzenamine (67 mg, 0.39 mmol) dropwise at 0° C. The reaction mixture was stirred at rt overnight. Then the solution was extracted with DCM (10 mL×3) and washed with brine (10 mL×2). The organic phase was dried over Na$_2$SO$_4$ and concentrated to give crude product. The crude was purified by Prep TLC (DCM:MeOH=10:1) to afford the title compound (140 mg, yield: 70%) as white solid. $^1$H NMR (500 MHz, MeOD): δ 8.14 (s, 1H), 8.12 (s, 1H), 7.19 (d, J=9.0 Hz, 2H), 7.12 (d, J=8.5 Hz, 2H), 6.10 (d, J=2.5 Hz, 1H), 5.39 (dd, J=2.5, 6.5 Hz, 1H), 4.92-4.90 (m, 1H), 4.35-4.31 (m, 1H), 2.75-2.70 (m, 1H), 2.57-2.54 (m, 1H), 2.41 (t, J=7.0 Hz, 2H), 2.18 (s, 3H), 1.66-1.58 (m, 2H), 1.50 (s, 3H), 1.28 (s, 3H), 1.21 (s, 9H), 1.19 (s, 3H), 1.12 (s, 3H); ESI-MS (m/z): 581.7 [M+1]$^+$.

Step 8. Preparation of 1-(4-(((((2R,3S,4R,5R)-5-(6-amino-9H-purin-9-yl)-3,4-dihydroxytetrahydrofuran-2-yl)methyl)(methyl)amino)-2-methylbutan-2-yl)-3-(4-(tert-butyl)phenyl)urea

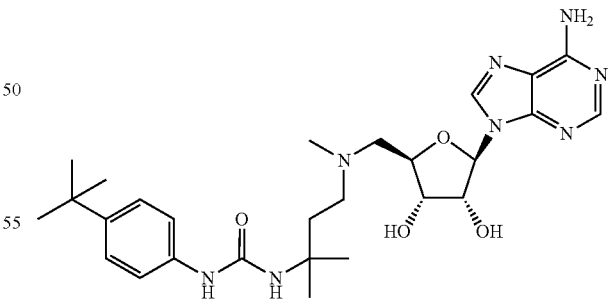

A solution of 1-(4-(((((3aR,4R,6R,6aR)-6-(6-amino-9H-purin-9-yl)-2,2-dimethyltetrahydrofuro[3,4-d][1,3]dioxol-4-yl)methyl)(methyl)amino)-2-methylbutan-2-yl)-3-(4-(tert-butyl)phenyl)urea (80 mg, 0.14 mmol) in 90% TFA (2 mL) was stirred at rt for 3 h. The solution was concentrated to dryness. The residue was co-evaporated with methanol twice. The residue was dissolved in MeOH (10 mL) and K$_2$CO$_3$ (76 mg, 0.56 mmol) in H$_2$O (1 mL) was added and stirred at rt for 0.5 h. The mixture was filtered and the filtrate was concentrated to give crude product. The crude was purified by Prep TLC (DCM:MeOH=5:1) to afford the title compound (57 mg, yield: 77%) as a white solid. $^1$H NMR (500 MHz, MeOD): δ 8.22 (s, 1H), 8.19 (s, 1H), 7.26 (d, J=8.5 Hz, 2H), 7.18 (d, J=8.5 Hz, 2H), 6.00 (d, J=5.0 Hz, 1H), 4.83-4.81 (m, 1H), 4.38-4.36 (m, 1H), 4.31-4.29 (m, 1H), 3.45-3.41 (m, 1H), 3.17-3.15 (m, 1H), 2.96 (s, 2H), 2.65 (s, 3H), 2.10-2.03 (m, 2H), 1.31 (s, 3H), 1.28 (s, 12H); ESI-MS (m/z): 541.7 [M+1]$^+$.

Compound 363

1-(3-(((((2S,4R,5R)-5-(6-amino-9H-purin-9-yl)-4-hydroxytetrahydrofuran-2-yl)methyl)(isopropyl)amino)propyl)-3-(4-(tert-butyl)phenyl)urea

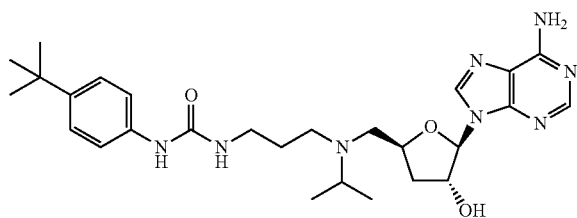 [SMILES: CC(C)N(CCCNC(=O)Nc1ccc(C(C)(C)C)cc1)C[C@@H]1C[C@@H](O)[C@H](n2cnc3c(N)ncnc32)O1]

Step 1. Preparation (2R,3R,5S)-2-(6-amino-9H-purin-9-yl)-5-(((tert-butyldimethylsilyl)oxy)methyl)tetrahydrofuran-3-ol

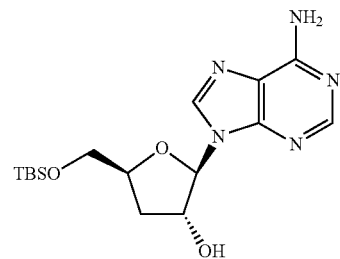 [SMILES: CC(C)(C)[Si](C)(C)OC[C@@H]1C[C@@H](O)[C@H](n2cnc3c(N)ncnc32)O1]

To a solution (2R,3R,5S)-2-(6-amino-9H-purin-9-yl)-5-(hydroxymethyl)tetrahydrofuran-3-ol (1.5 g, 6 mmol) and imidazole (680 mg, 10 mmol) in dried DMF (8 mL) was added TBSCl (1.5 g, 10 mmol) and the solution was stirred at 25° C. for 9 h. The reaction mixture was diluted with EA (100 mL) and washed with water (3×40 mL). The organic phase was dried over Na$_2$SO$_4$ and concentrated to afford the title compound (1.48 g, yield: 74%) as a white solid, which was used directly in the next step without further purification. $^1$H NMR (500 MHz, CDCl$_3$) δ 8.31 (s, 1H), 8.28 (s, 1H), 5.96 (d, J=2.5 Hz, 1H), 5.88 (br s, 2H), 4.65-4.60 (m, 2H), 4.05-4.02 (m, 1H), 3.73 (dd, J=2.5 Hz, 11.5 Hz, 1H), 2.34-2.30 (m, 1H), 2.11-2.08 (m, 1H), 0.89 (s, 9H), 0.11 (s, 6H); LC-MS (m/z): 366.2 [M+1]$^+$.

Step 2. Preparation of (2R,3R,5S)-2-(6-amino-9H-purin-9-yl)-5-(((tert-butyldimethylsilyl)oxy)methyl)tetrahydrofuran-3-yl acetate

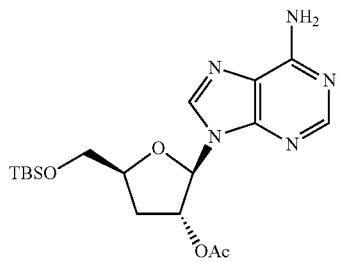

To a solution of (2R,3R,5S)-2-(6-amino-9H-purin-9-yl)-5-(((tert-butyldimethylsilyl)oxy)methyl)tetrahydrofuran-3-ol (1.48 g, 4.05 mmol) and DMAP (75 mg, 0.61 mmol) in dried pyridine (18 mL) was added Ac$_2$O (820 mg, 8.1 mmol) in drops. The reaction solution was stirred at rt for 2 h. The solvent was removed in vacuum, and the residue was diluted with EA (50 mL) and washed with water (2×30 mL). The organic phase was dried over Na$_2$SO$_4$ and concentrated to afford the title compound (1.4 g, yield: 85%) as a white solid, which was directly used for next step without further purification. $^1$H NMR (500 MHz, CDCl$_3$) δ 8.33 (s, 1H), 8.25 (s, 1H), 6.19 (d, J=1.5 Hz 1H), 5.80 (br s, 2H), 5.56 (d, J=5.5 Hz, 1H), 4.50-4.47 (m, 1H), 4.07-4.04 (m, 1H), 3.79-3.76 (m, 1H), 2.63-2.57 (m, 1H), 2.16 (s, 3H), 2.10-2.08 (m, 1H), 0.92 (s, 9H), 0.12 (s, 6H); LC-MS (m/z): 408.2 [M+1]$^+$.

Step 3. Preparation of (2R,3R,5S)-2-(6-amino-9H-purin-9-yl)-5-(hydroxymethyl)tetrahydrofuran-3-yl acetate

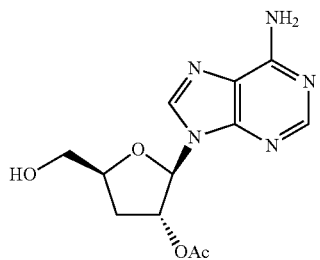

To a solution of (2R,3R,5S)-2-(6-amino-9H-purin-9-yl)-5-(((tert-butyldimethylsilyl)oxy)methyl)tetrahydrofuran-3-yl acetate (1.38 g, 3.4 mmol) in 1:2 Py/THF (15 mL) was added 40% HF aqueous solution (5.0 mL) in drops. The reaction solution was stirred at rt for 9 h. The solvent was removed and the reaction was neutralized with saturated aqueous NaHCO$_3$, and then extracted with CHCl$_3$ (10×60 mL). The combined organic phase was washed with brine (40 mL), dried over Na$_2$SO$_4$ and concentrated to afford the title compound (900 mg, yield: 90%) as a white solid. $^1$H NMR (500 MHz, DMSO-d$_6$) δ 8.34 (s, 1H), 8.14 (s, 1H), 7.32 (br s, 2H), 6.08 (d, J=2.5 Hz, 1H), 5.61-5.59 (m, 1H), 5.13 (t, J=5.5 Hz, 1H), 4.34-4.33 (m, 1H), 3.68-3.64 (m, 1H), 3.54-3.50 (m, 1H), 2.56-2.54 (m, 1H), 2.14-2.10 (m, 1H), 2.08 (s, 3H); LC-MS (m/z): 294.2 [M+1]$^+$.

Step 4. Preparation of (2R,3R,5S)-2-(6-amino-9H-purin-9-yl)-5-((tosyloxy)methyl)tetrahydrofuran-3-yl acetate

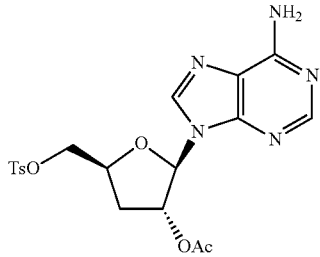

To a suspension of (2R,3R,5S)-2-(6-amino-9H-purin-9-yl)-5-(hydroxymethyl)tetrahydrofuran-3-yl acetate (500 mg, 1.71 mmol) in anhydrous THF (10 mL) was added NaH (206 mg, 60% in oil, 5.13 mmol). The mixture was stirred at rt for 0.5 h. p-Toluenesulfonyl chloride (1.31 g, 6.84 mmol) was added in one lot. The mixture was stirred for additional 6 h. The reaction was diluted with EA (100 mL) and washed with water (3×20 mL). The organic phase was dried over $Na_2SO_4$ and concentrated to afford the title compound (1.2 g, yield: 65%) as a straw-yellow solid, which was used in the next step without further purification. $^1$H NMR (500 MHz, CDCl$_3$) δ 7.94 (s, 1H), 7.92 (s, 1H), 7.68 (d, J=8.5 Hz, 2H), 7.41 (d, J=8.5 Hz, 2H), 5.84 (br s, 2H), 5.65 (s, 1H), 4.65-4.62 (m, 1H), 4.32-4.28 (m, 2H), 2.50 (s, 3H), 2.41-2.37 (m, 2H), 2.04 (s, 3H); LC-MS (m/z): 448.1 [M+1]$^+$.

Step 5. Preparation of (2R,3R,5S)-2-(6-amino-9H-purin-9-yl)-5-((isopropylamino)methyl)tetrahydrofuran-3-ol

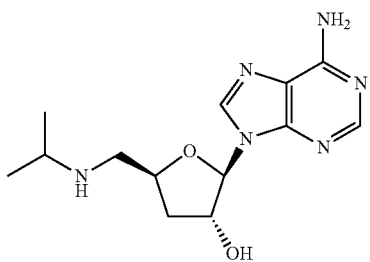 [SMILES: CC(C)NC[C@@H]1C[C@@H](O)[C@H](n2cnc3c(N)ncnc32)O1]

(2R,3R,5S)-2-(6-amino-9H-purin-9-yl)-5-((tosyloxy)methyl)tetrahydrofuran-3-yl acetate (1.2 g, crude, 1.13 mmol) was dissolved in isopropylamine (10 mL) and the reaction solution was irradiated by microwave at 150° C. for 50 min. Solvent was removed in vacuum, the crude was purified by SGC eluting with DCM:MeOH (30:1→10:1) to the title compound (155 mg, yield: 48%) as a white solid. $^1$H NMR (500 MHz, CD$_3$OD) δ 8.25 (s, 1H), 8.23 (s, 1H), 6.01 (d, J=2.5 Hz, 1H), 4.85 (t, J=3.0 Hz, 1H), 4.71-4.69 (m, 1H), 3.44-3.34 (m, 4H), 2.49-2.37 (m, 1H), 2.29-2.27 (m, 1H), 1.30-1.28 (m, 6H); LC-MS (m/z): 293.2 [M+1]$^+$.

Step 6. Preparation of 1-(3-((((2S,4R,5R)-5-(6-amino-9H-purin-9-yl)-4-hydroxytetrahydrofuran-2-yl)methyl)(isopropyl)amino)propyl)-3-(4-(tert-butyl)phenyl)urea

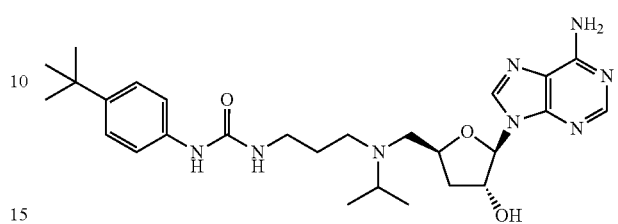

To a stirred solution of (COCl)$_2$ (262 mg, 2.08 mmol) in anhydrous CH$_2$Cl$_2$ (5 mL) at −78° C. was added DMSO (324 mg, 4.18 mmol) dropwise and the mixture was stirred for 10 min. 1-(4-tert-butylphenyl)-3-(3-hydroxypropyl)urea (430 mg, 1.73 mmol) in CH$_2$Cl$_2$ (3 mL) was added slowly to the reaction and the mixture was stirred for 30 min. TEA (524 mg, 5.2 mmol) was added slowly and the mixture was stirred at −78° C. for another 10 min, followed by warming up to 0° C. in 40 min. Water (6 mL) was added to quench the reaction and the mixture was extracted with CH$_2$Cl$_2$ (8 mL×3). The combined organic layers were washed with brine, dried over Na$_2$SO$_4$ and concentrated to afford 1-(4-tert-butylphenyl)-3-(3-oxopropyl)urea (465 mg, crude) as a white solid, which was used for next step directly without further purification.

To a solution of (2R,3R,5S)-2-(6-amino-9H-purin-9-yl)-5-((isopropylamino)methyl)tetrahydrofuran-3-ol (70 mg, 0.24 mmol) and 1-(4-tert-butylphenyl)-3-(3-oxopropyl)urea (465 mg, crude, 0.72 mmol) in MeOH (6 mL) was added NaB(OAc)$_3$H (203 mg, 0.96 mmol). The mixture was stirred at rt overnight. Saturated aqueous NaHCO$_3$ (10 mL) was added to quench the reaction, and then the solvent was removed in vacuo. The crude residue was purified by prep-TLC eluting with DCM:MeOH:27% NH$_3$.H$_2$O (150:30:1) to afford the title compound (28 mg, 23%) as a white solid. $^1$H NMR (500 MHz, CD$_3$OD) δ 8.22 (s, 1H), 8.19 (s, 1H), 7.25-7.19 (m, 4H), 5.98 (d, J=1.0 Hz, 1H), 4.72-4.65 (m, 2H), 3.28-3.17 (m, 3H), 2.96-2.77 (m, 4H), 2.30-2.28 (m, 1H), 2.19 (t, J=2.5 Hz, 1H), 1.74-1.72 (m, 2H), 1.27 (s, 9H), 1.45-1.06 (m, 6H); LC-MS (m/z): 525.4 [M+1]$^+$.

Compound 364

N-(((2R,3S,4R,5R)-5-(6-amino-9H-purin-9-yl)-3,4-dihydroxytetrahydrofuran-2-yl)methyl)-3-(3-(4-(tert-butyl)phenyl)ureido)-N-methylpropanamide

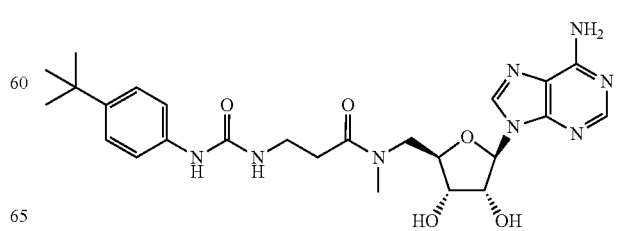

Step 1. Preparation of ethyl 3-[(4-tert-butylphenyl)carbamoylamino]propanoate

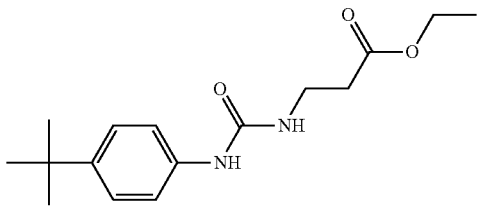 [SMILES: CCOC(=O)CCNC(=O)Nc1ccc(C(C)(C)C)cc1]

To a solution of TEA (517 mg, 5.12 mmol) and ethyl 3-aminopropanoate (300 mg, 2.56 mmol) in DCM (10 mL) was added dropwise 1-tert-butyl-4-isocyanatobenzene (449 mg, 2.56 mmol). The mixture was stirred at 0° C. for 30 min. The mixture was extracted with DCM (30 mL×3) and washed with brine (10 mL). The combined organic phase was dried over Na$_2$SO$_4$ and concentrated. The crude was purified by SGC (PE: EA=3:1) to afford the title compound (400 mg) as a white solid. $^1$H NMR (500 MHz, CDCl$_3$): δ 7.33 (d, J=8.0 Hz, 2H), 7.20 (d, J=8.5 Hz, 2H), 4.13 (q, J=7.0 Hz, 2H), 3.54-3.51 (m, 2H), 2.58 (t, J=6.0 Hz, 2H), 1.30 (s, 9H), 1.24 (t, J=7.5 Hz, 3H); ESI-MS (m/z): 293.7 [M+1]$^+$.

Step 2. Preparation of 3[(4-tert-butylphenyl)carbamoylamino]propanoic acid

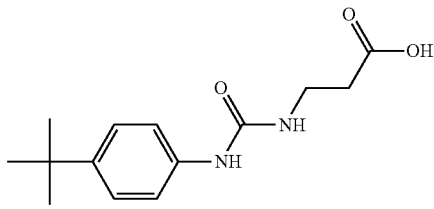 [SMILES: CC(C)(C)c1ccc(NC(=O)NCCC(=O)O)cc1]

To a solution of ethyl 3-[(4-tert-butylphenyl)carbamoylamino]propanoate (440 mg, 1.5 mmol) in THF (30 mL) was added dropwise NaOH (180 mg, 4.5 mmol) in water (10 mL). The mixture was stirred at rt for 3 h. 1N HCl (12 mL) was added. The mixture was extracted with EA (30 mL×3). The combined organic phase was washed with brine (15 mL), dried over Na$_2$SO$_4$ and concentrated to give the title compound. $^1$H NMR (500 MHz, CDCl$_3$): δ 7.34 (d, J=8.5 Hz, 2H), 7.16 (d, J=8.5 Hz, 2H), 3.53 (t, J=6.0 Hz, 2H), 2.65 (t, J=5.5 Hz, 2H), 1.30 (s, 9H); ESI-MS (m/z): 265.7 [M+1]$^+$.

Step 3. Preparation of N-(((3aR,4R,6R,6aR)-6-(6-amino-9H-purin-9-yl)-2,2-dimethyltetrahydrofuro[3,4-d][1,3]dioxol-4-yl)methyl)-3-(3-(4-(tert-butyl)phenyl)ureido)-N-methylpropanamide

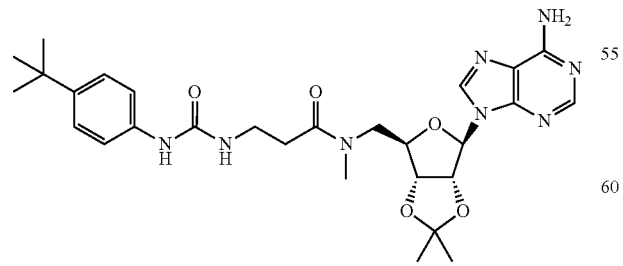

To a solution of TEA (142 mg, 1.4 mmol), HOBt (95 mg, 0.7 mmol), 3-[(4-tert-butylphenyl)carbamoylamino]propanoic acid (124 mg, 0.7 mmol) and EDCI (135 mg, 0.7 mmol) in DCM (3 mL) was added 9-((3aR,4R,6R,6aR)-2,2-dimethyl-6-((methylamino)methyl)tetrahydrofuro[3,4-d][1,3]dioxol-4-yl)-9H-purin-6-amine (150 mg, 0.47 mmol). The mixture was stirred at rt overnight. The mixture was extracted with DCM (15 mL×3) and washed with brine (10 mL) was added. The combined organic phase was dried over Na$_2$SO$_4$ and concentrated. The crude was purified by Prep-TLC (DCM:MeOH=10:1) to afford the title compound (130 mg) as a white solid. $^1$H NMR (500 MHz, MeOD): δ 8.24-8.22 (m, 2H), 7.27-7.21 (m, 4H), 6.18-6.14 (m, 1H), 5.49-5.42 (m, 1H), 5.08-5.03 (m, 1H), 4.43-4.36 (m, 1H), 3.88-3.77 (m, 1H), 3.50-3.39 (m, 2H), 3.29-3.23 (m, 1H), 2.85-2.82 (m, 3H), 2.57-2.24 (m, 2H), 1.56-1.55 (m, 3H), 1.35-1.34 (m, 3H), 1.26 (s, 9H) ppm; ESI-MS (m/z): 567.7 [M+1]$^+$.

Step 4. Preparation of N-(((2R,3S,4R,5R)-5-(6-amino-9H-purin-9-yl)-3,4-dihydroxytetrahydrofuran-2-yl)methyl)-3-(3-(4-(tert-butyl)phenyl)ureido)-N-methylpropanamide A solution of N-(((3aR,4R,6R,6aR)-6-(6-amino-9H-purin-9-yl)-2,2-dimethyltetrahydrofuro[3,4-d][1,3]dioxol-4-yl)methyl)-3-(3-(4-(tert-butyl)phenyl)ureido)-N-methylpropanamide (100 mg, 0.18 mmol) in 90% TFA (1 mL) was stirred at rt for 1 h and evaporated to dryness. The residue was co-evaporated with methanol twice. The mixture was dissolved in 10 mL MeOH and K$_2$CO$_3$ (100 mg, 0.72 mmol) was added. Then water was added dropwise until all K$_2$CO$_3$ was dissolved. The reaction mixture was stirred at rt for 1.5 h, then concentrated to remove MeOH and water. The residue was purified by Prep-TLC (DCM:MeOH=5:1) afford the title compound (37 mg, yield: 40%). $^1$H NMR (500 MHz, MeOD): δ 8.31-8.21 (m, 2H), 7.28-7.21 (m, 4H), 5.96-5.95 (m, 1H), 4.81-4.70 (m, 1H), 4.45-4.20 (m, 2H), 3.91-3.68 (m, 2H), 3.48-3.35 (m, 2H), 3.03-2.92 (m, 3H), 2.65-2.03 (m, 2H), 1.28 (s, 9H) ppm; ESI-MS (m/z): 527.7 [M+1]$^+$.

Compound 365

1-(4-((((2R,3S,4R,5R)-5-(6-amino-9H-purin-9-yl)-3,4-dihydroxytetrahydrofuran-2-yl)methyl)(methyl)amino)butan-2-yl)-3-(4-(tert-butyl)phenyl)urea

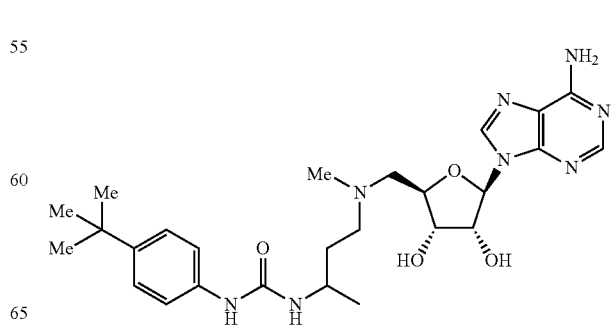

Step 1. Preparation of ethyl 3-(3-(4-(tert-butyl)phenyl)ureido)butanoate

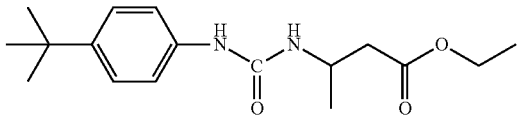

To a stirred solution of ethyl 3-aminobutanoate (362 mg, 2.0 mmol) and DIPEA (774 mg, 6.0 mmol) in dry DCM (10 mL) was added dropwise 4-tert-butylbenzenamine (385 mg, 2.2 mmol) under 0° C. The reaction mixture was stirred at rt overnight, and extracted with DCM (10 mL×2). The organic phase was dried over Na$_2$SO$_4$ and concentrated to give crude product. The crude was purified by Prep TLC (PE:EA=2:1) to afford the title compound (400 mg, yield: 66%) as a colorless oil. $^1$H NMR (500 MHz, CDCl$_3$): δ7.33 (d, J=1.5 HZ, 2H), 7.21 (d, J=8.0 Hz, 1H), 4.29 (dd, J=6.0, 12.5 Hz, 1H), 4.15-4.11 (m, 2H), 2.59-2.49 (m, 2H), 1.30 (s, 9H), 1.28-1.22 (m, 6H); ESI-MS (m/z): 307.7 [M+1]$^+$.

Step 2. Preparation of 1-(4-(tert-butyl)phenyl)-3-(4-hydroxybutan-2-yl)urea

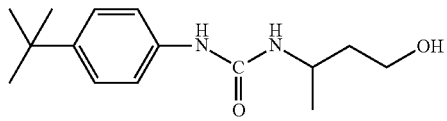 [SMILES: CC(CCO)NC(=O)Nc1ccc(C(C)(C)C)cc1]

A mixture of ethyl 3-(3-(4-(tert-butyl)phenyl)ureido)butanoate (400 mg, 1.31 mmol) and LiBH$_4$ (63 mg, 2.62 mmol) in anhydrous THF (5 mL) was stirred at rt overnight. Then the reaction was extracted with EA (15 mL×2), washed with brine, dried with Na$_2$SO$_4$ and concentrated to afford the title compound (300 mg, yield 87%) without purification. $^1$H NMR (500 MHz, CDCl$_3$): δ7.34 (d, J=8.5 HZ, 2H), 7.18 (d, J=8.5 HZ, 2H), 4.15-4.11 (m, 1H), 3.38-3.63 (m, 2H), 1.86-1.81 (m, 2H), 1.30 (s, 9H), 1.25-1.18 (m, 3H); ESI-MS (m/z): 265.7 [M+1]$^+$.

Step 3. Preparation of 1-(4-(((((3aR,4R,6R,6aR)-6-(6-amino-9H-purin-9-yl)-2,2-dimethyltetrahydrofuro[3,4-d][1,3]dioxol-4-yl)methyl)(methyl)amino)butan-2-yl)-3-(4-(tert-butyl)phenyl)urea

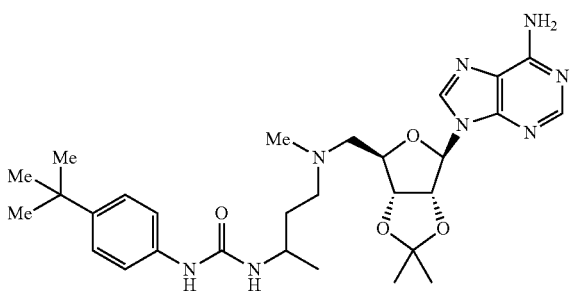

A mixture of 1-(4-(tert-butyl)phenyl)-3-(4-hydroxybutan-2-yl)urea (100 mg, 0.38 mmol) and IBX (318 mg, 1.34 mmol) in EA (10 mL) was refluxed for 2 h. After the solid was filtered and washed with EA (10 mL×2), the combined filtrates were concentrated to afford 1-(4-tert-butylphenyl)-3-(1-methyl-3-oxo-propyl)urea (100 mg, crude) without purification. A solution of 9-((3aR,4R,6R,6aR)-2,2-dimethyl-6-((methylamino)methyl)tetrahydrofuro[3,4-d][1,3]dioxol-4-yl)-9H-purin-6-amine (120 mg, 0.38 mmol) and 1-(4-tert-butylphenyl)-3-(1-methyl-3-oxo-propyl)urea (100 mg, crude) in DCE (5 mL) was added NaBH(OAc)$_3$ (120 mg, 0.57 mmol). The mixture was stirred at rt overnight, then saturated aqueous NaHCO$_3$ (10 mL) was added to the solution. The mixture was extracted with DCM (20 mL×2). The combined organic layers were washed with brine and dried over Na$_2$SO$_4$ and concentrated. The crude was purified by Prep TLC (DCM: MeOH=10:1) to afford the title compound (60 mg, yield: 63%) as white solid. $^1$H NMR (500 MHz, MeOD): δ8.23 (t, J=7.0 Hz, 2H), 7.29-7.21 (m, 4H), 6.17 (t, J=3.0 Hz, 1H), 5.49-5.47 (m, 1H), 5.04-4.98 (m, 1H), 4.40-4.30 (m, 1H), 3.78-3.70 (m, 1H), 2.73-2.67 (m, 2H), 2.49-2.46 (m, 2H), 2.27-2.24 (m, 3H), 1.59 (s, 3H), 1.57-1.40 (m, 2H), 1.37 (s, 3H), 1.30 (s, 9H), 1.11-1.07 (m, 3H); ESI-MS (m/z): 567.7 [M+1]$^+$.

Step 4. Preparation of 1-(4-(((((2R,3S,4R,5R)-5-(6-amino-9H-purin-9-yl)-3,4-dihydroxytetrahydrofuran-2-yl)methyl)(methyl)amino)butan-2-yl)-3-(4-(tert-butyl)phenyl)urea

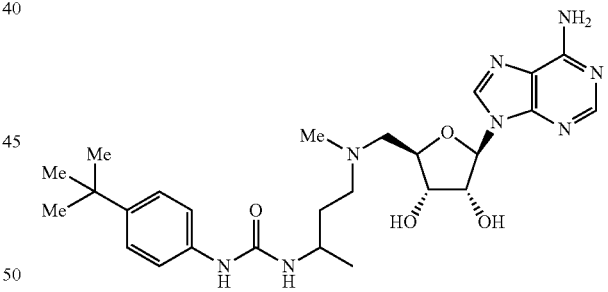

A solution of 1-(4-(((((3aR,4R,6R,6aR)-6-(6-amino-9H-purin-9-yl)-2,2-dimethyltetrahydrofuro[3,4-d][1,3]dioxol-4-yl)methyl)(methyl)amino)butan-2-yl)-3-(4-(tert-butyl)phenyl)urea (55 mg, 0.097 mmol) in 90% TFA (2 mL) was stirred at rt for 2 h. Then the solution was concentrated as a solid to remove TFA and dissolved in MeOH (5 mL). K$_2$CO$_3$ (53 mg, 0.39 mmol) in H$_2$O (1 mL) was added and stirred at rt for 0.5 h, filtrated and the filtrate was concentrated to give crude product. The crude was purified by Prep TLC (DCM: MeOH=10:1) to afford the title compound (40 mg, yield: 77%) as a white solid. $^1$H NMR (500 MHz, MeOD): δ8.27 (s, 1H), 8.25 (s, 1H), 8.22 (s, 1H), 8.20 (s, 1H), 7.31-7.29 (m, 2H), 7.25 (t, J=8.5 Hz, 2H), 6.04-6.02 (m, 2H), 4.85 (t, J=5.0 Hz, 1H), 4.51-4.49 (m, 3H), 4.40 (t, J=5.5 Hz, 2H), 3.85-3.76 (m, 4H), 3.52-3.46 (m, 2H), 3.33-3.26 (m, 4H), 2.91 (t, J=1.5

Hz, 6H), 1.98-1.94 (m, 2H), 1.80-1.76 (m, 2H), 1.23 (d, J=7.0 Hz, 2H), 1.17 (d, J=6.5 Hz, 2H); ESI-MS (m/z): 527.7 [M+1]$^+$.

Compound 366

1-(3-(((((2R,3S,4R,5R)-5-(6-amino-9H-purin-9-yl)-3,4-dihydroxytetrahydrofuran-2-ylmethyl)(3-aminopropyl)amino)propyl)-3-(4-(tert-butyl)phenyl)urea

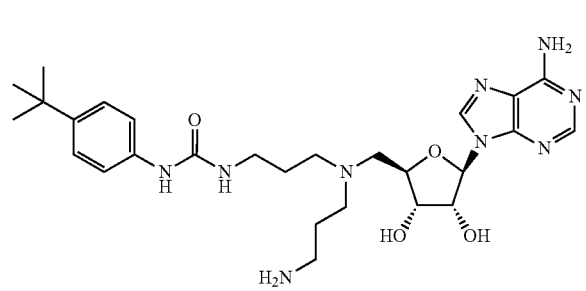 [SMILES: CC(C)(C)c1ccc(NC(=O)NCCCN(CCCN)C[C@H]2O[C@@H](n3cnc4c(N)ncnc43)[C@H](O)[C@@H]2O)cc1]

Step 1. Preparation of tert-butyl (3-(((((3aR,4R,6R,6aR)-6-(6-amino-9H-purin-9-yl)-2,2-dimethyltetrahydrofuro[3,4-d][1,3]dioxol-4-yl)methyl)(3-(4-(tert-butyl)phenyl)ureido)propyl)amino)propyl)carbamate

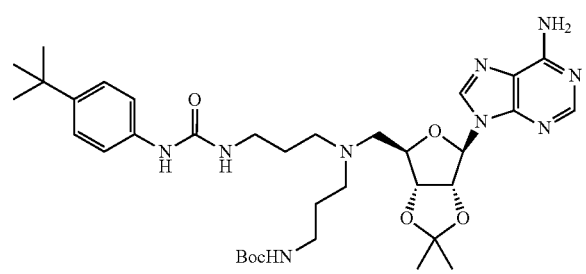 [SMILES: CC(C)(C)OC(=O)NCCCN(CCCNC(=O)Nc1ccc(C(C)(C)C)cc1)C[C@H]1O[C@@H](n2cnc3c(N)ncnc32)[C@@H]2OC(C)(C)O[C@@H]21]

To a solution of tert-butyl N-(3-hydroxypropyl)carbamate (200 mg, 1.14 mmol) in EA (30 mL) IBX (800 mg, 2.85 mmol) was added. The mixture was heated to reflux for 2 h. After cooling to room temperature, the mixture was filtered and the filtrate was concentrated to give crude tert-butyl N-(3-oxopropyl)carbamate (not weight), which was used directly for next step.

To a solution of 1-(3-(((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl)urea e in DCE (20 mL) was added NaBH(OAc)$_3$ (71 mg, 0.33 mmol). The reaction mixture was stirred at rt overnight then saturated aqueous NaHCO$_3$ (20 mL) was added. The resulting mixture was extracted with DCM (30 mL×2). The combined organic layers were dried over Na$_2$SO$_4$ and concentrated. The residue was purified by Prep-TLC (DCM:MeOH=10:1) to afford the title compound (100 mg, yield: 64%) as a white solid. $^1$H NMR (500 MHz, MeOD): δ 8.26 (s, 1H), 8.24 (s, 1H), 7.31-7.25 (m, 4H), 6.20 (d, J=2.0 Hz, 1H), 5.53 (br s, 1H), 5.06 (t, J=3.5 Hz, 1H), 4.38 (br s, 1H), 3.20-3.01 (m, 6H), 2.50-2.47 (m, 4H), 1.70-1.56 (m, 7H), 1.53 (s, 9H), 1.40 (s, 3H), 1.33 (s, 9H) ppm; ESI-MS (m/z): 696.4 [M+1]$^+$.

Step 2. Preparation of 1-(3-(((((2R,3S,4R,5R)-5-(6-amino-9H-purin-9-yl)-3,4-dihydroxytetrahydrofuran-2-yl)methyl)(3-aminopropyl)amino)propyl)-3-(4-(tert-butyl)phenyl)urea

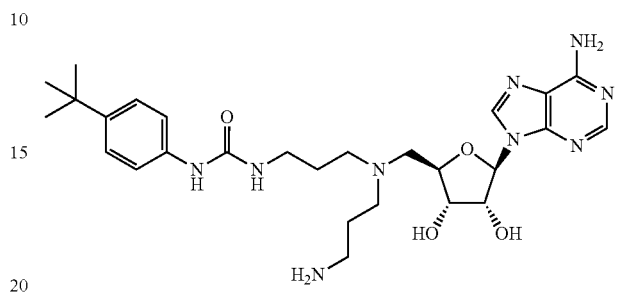

A solution of tert-butyl (3-(((((3aR,4R,6R,6aR)-6-(6-amino-9H-purin-9-yl)-2,2-dimethyltetrahydrofuro[3,4-d][1,3]dioxol-4-yl)methyl)(3-(3-(4-(tert-butyl)phenyl)ureido)propyl)amino)propyl)carbamate (100 mg, 0.14 mmol) in 90% TFA (1 mL) was stirred at rt for 3 h and concentrated to dryness. K$_2$CO$_3$ (100 mg) in water (0.5 mL) and MeOH (10 mL) were added. The resulting mixture was stirred for another 5 min at rt and concentrated. The residue was purified by Prep-TLC (DCM:MeOH:NH$_3$.H$_2$O=3:1:0.1) to afford the title compound (35 mg, yield: 43%) as a white solid. $^1$H NMR (500 MHz, MeOD): δ 8.14 (s, 1H), 8.11 (s, 1H), 7.20-7.12 (m, 4H), 5.91 (d, J=4.5 Hz, 1H), 4.65 (t, J=4.5 Hz, 1H), 4.35 (m, 2H), 3.60-2.88 (m, 10H), 1.95-1.81 (m, 4H), 1.19 (s, 9H) ppm; ESI-MS (m/z): 556.3 [M+1]$^+$.

Compound 367

1-(3-(((((2R,3S,4R,5R)-5-(6-amino-9H-purin-9-yl)-3,4-dihydroxytetrahydrofuran-2-yl)methyl)(2-aminoethyl)amino)propyl)-3-(4-(tert-butyl)phenyl)urea

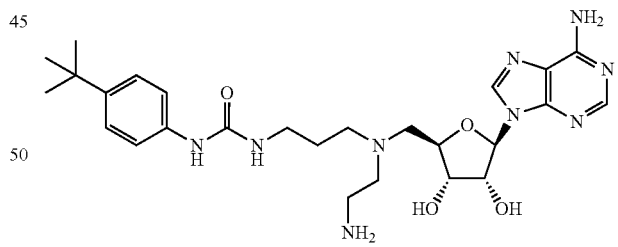

Step 1. Preparation of tert-butyl N-(2-oxoethyl)carbamate

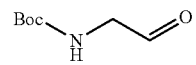

Under nitrogen atmosphere, a mixture of tert-butyl N-(2-hydroxyethyl)carbamate (300 mg, 1.86 mmol) and IBX (1.56 g, 5.58 mmol) in EA (15 mL) was refluxed for 2 h. The reaction mixture was cooled to rt and filtered. The filter cake was washed with EA (5 mL×2) and the filtrate was concentrated to afford tert-butyl N-(2-oxoethyl)carbamate (290 mg, crude) as colorless oil which was used for next reaction directly.

Step 2. Preparation of tert-butyl (2-(((((3aR,4R,6R,6aR)-6-(6-amino-9H-purin-9-yl)-2,2-dimethyltetrahydrofuro[3,4-d][1,3]dioxol-4-yl)methyl)(3-(3-(4-(tert-butyl)phenyl)ureido)propyl)amino)ethyl)carbamate

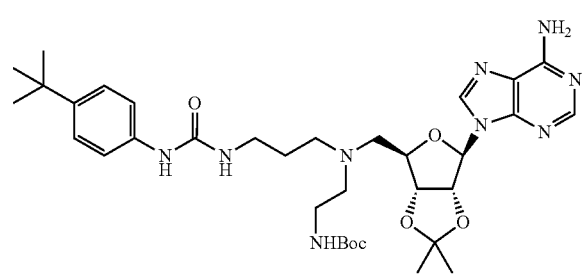 [SMILES: CC(C)(C)OC(=O)NCCN(CCCNC(=O)Nc1ccc(C(C)(C)C)cc1)C[C@H]1O[C@@H](n2cnc3c(N)ncnc32)[C@@H]2OC(C)(C)O[C@@H]21]

A solution of 1-(3-(((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl)urea (150 mg, 0.278 mmol) and tert-butyl N-(2-oxoethyl)carbamate (290 mg, crude from last step) in DCE (4 mL) was stirred at rt for 30 min and NaBH(OAc)$_3$ (118 mg, 0.557 mmol) was added. The reaction was stirred at rt overnight. The mixture was concentrated and the residue was purified by Prep-TLC (DCM:MeOH=10:1) to afford the title compound (80 mg, yield: 42%) as white solid. $^1$H NMR (500 MHz, CDCl$_3$): δ 8.32 (s, 1H), 7.90 (brs, 1H), 7.27-7.34 (m, 4H), 6.20 (br s, 2H), 5.97 (d, J=2.0 Hz, 1H), 5.75 (br s, 1H), 5.50 (br s, 1H), 5.16 (br s, 1H), 4.31-4.30 (m, 1H), 3.12-3.29 (m, 4H), 2.47-2.71 (m, 6H), 1.54-1.62 (m, 5H), 1.42 (s, 9H), 1.40 (s, 3H), 1.30 (s, 9H); ESI-MS (m/z): 682.4 [M+1]$^+$.

Step 3. Preparation of 1-(3-(((((2R,3S,4R,5R)-5-(6-amino-9H-purin-9-yl)-3,4-dihydroxytetrahydrofuran-2-yl)methyl)(2-aminoethyl)amino)propyl)-3-(4-(tert-butyl)phenyl) urea

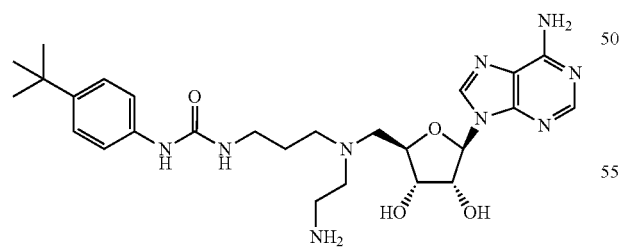

A solution of tert-butyl (2-(((((3aR,4R,6R,6aR)-6-(6-amino-9H-purin-9-yl)-2,2-dimethyltetrahydrofuro[3,4-d][1,3]dioxol-4-yl)methyl)(3-(3-(4-(tert-butyl)phenyl)ureido)propyl)amino)ethyl)carbamate (80 mg, 0.11 mmol) in TFA/H$_2$O (1.8 mL/0.2 mL) was stirred at 25° C. for 1.5 h. The volatiles were removed and the residue was dissolved in MeOH (3 mL) with stirring at rt. A solution of K$_2$CO$_3$ (130 mg,) in water (0.5 mL) was added and stirred at rt for 1 h. The volatiles were removed under reduced pressure and purified by Prep-TLC (MeOH:DCM=1:4) to afford the title compound (47 mg, yield: 74%) as a yellow solid. $^1$H NMR (500 MHz, MeOD): δ 8.24 (s, 1H), 8.22 (s, 1H), 7.26-7.30 (m, 4H), 5.96 (d, J=4.5 Hz, 1H), 4.71 (q, J=5.5 Hz, 1H), 4.32 (t, J=5.5 Hz, 1H), 4.18-4.17 (m, 1H), 3.26 (t, J=6.5 Hz, 2H), 2.92-2.97 (m, 4H), 2.76-2.79 (m, 2H), 2.65-2.68 (m, 2H), 1.70-1.73 (m, 2H), 1.65 (s, 9H). HPLC purity: 99% (254 nm); ESI-MS (m/z): No molecular ion peak found.

Compound 368

1-(3-(((((2R,3S,4R,5R)-5-(6-amino-9H-purin-9-yl)-3,4-dihydroxytetrahydrofuran-2-yl)methyl)(2-hydroxyethyl)amino)propyl)-3-(4-(tert-butyl)phenyl)urea

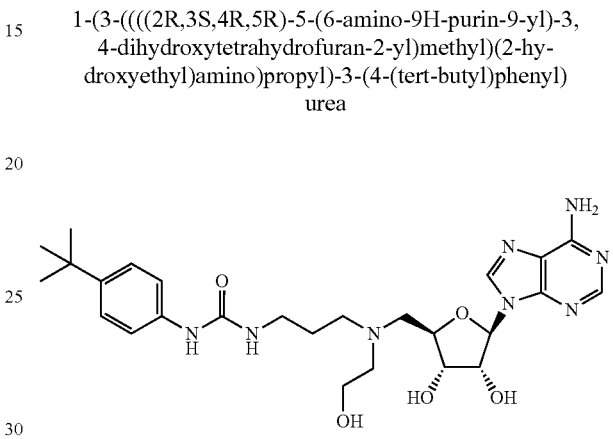

Step 1. Preparation of 1-(3-(((((3aR,4R,6R,6aR)-6-(6-amino-9H-purin-9-yl)-2,2-dimethyltetrahydrofuro[3,4-d][1,3]dioxol-4-yl)methyl)(2-hydroxyethyl)amino)propyl)-3-(4-(tert-butyl)phenyl)urea

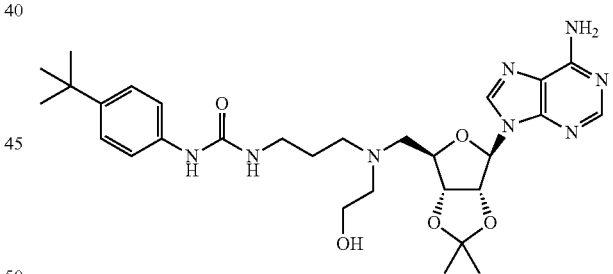

To a solution of 1-(3-(((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl)urea (100 mg, 0.19 mmol) in MeCN (4 mL) was added 2-iodoethanol (96 mg, 0.29 mmol) and K$_2$CO$_3$ (51 mg, 0.37 mmol). The mixture was stirred at 80° C. overnight. The volatiles were removed under reduced pressure. The residue was extracted with DCM (10 mL×3) and the organic phase was washed with water (10 mL) and brine (10 mL), dried over Na$_2$SO$_4$ and concentrated in vacuo to give a crude. The crude was purified by Prep-TLC (DCM:MeOH=6:1) to afford the title compound (50 mg, 46%) as white solid. $^1$H NMR (500 MHz, MeOD): δ 8.14 (s, 1H), 8.12 (s, 1H), 7.18-7.16 (m, 2H), 7.14-7.12 (m, 2H), 6.07 (d, J=2.0 Hz, 1H), 5.39-5.37 (m, 1H), 4.98-4.80 (m, 1H), 4.26-4.25 (m, 1H), 3.49 (s, 2H), 3.47-3.44

(m, 2H), 3.10-3.07 (m, 2H), 2.72-2.47 (m, 6H), 1.53-1.51 (m, 2H), 1.47 (s, 3H), 1.25 (s, 3H), 1.19 (s, 9H); ESI-MS (m/z): 583 [M+1]⁺.

Step 2. Preparation of 1-(3-(((((2R,3S,4R,5R)-5-(6-amino-9H-purin-9-yl)-3,4-dihydroxytetrahydrofuran-2-yl)methyl)(2-hydroxyethyl)amino)propyl)-3-(4-(tert-butyl)phenyl)urea

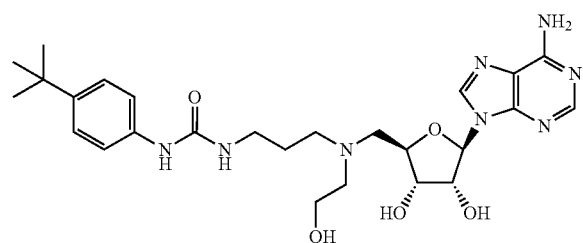 [SMILES: CC(C)(C)c1ccc(NC(=O)NCCCN(CCO)C[C@H]2O[C@@H](n3cnc4c(N)ncnc43)[C@H](O)[C@@H]2O)cc1]

A solution of 1-(3-(((((3aR,4R,6R,6aR)-6-(6-amino-9H-purin-9-yl)-2,2-dimethyltetrahydrofuro[3,4-d][1,3]dioxol-4-yl)methyl)(2-hydroxyethyl)amino)propyl)-3-(4-(tert-butyl)phenyl)urea (40 mg, 0.18 mmol) in 90% TFA (1 mL) was stirred at rt for 1 h and then evaporated to dryness. The residue was co-evaporated with methanol. The residue was dissolved in MeOH (10 mL), and K₂CO₃ (57 mg, 1.11 mmol) was added, then water was added dropwise until all K₂CO₃ was dissolved. The reaction mixture was stirred at rt for 30 min then concentrated. The residue was purified by Prep-TLC give the title compound (35 mg, yield: 74%). ¹H NMR (500 MHz, Acetone-d6): δ 8.09 (s, 1H), 8.08 (s, 1H), 7.30-7.28 (m, 2H), 7.10-7.09 (m, 2H), 5.91 (d, J=4.5 Hz, 1H), 4.65 (t, J=5.0 Hz, 1H), 4.46 (t, J=5.5 Hz 1H), 4.28 (br s, 1H), 3.64 (br s, 2H), 3.17-3.15 (m, 4H), 2.96-2.75 (m, 2H), 1.71 (br s, 2H), 1.14 (s, 9H); ESI-MS (m/z): 545 [M+1]⁺.

Compound 369

1-(3-(((((2R,3S,4R,5R)-5-(6-amino-9H-purin-9-yl)-3,4-dihydroxytetrahydrofuran-2-ylmethyl)(methyl)amino)propyl)-3-(4-isopropylphenyl)urea

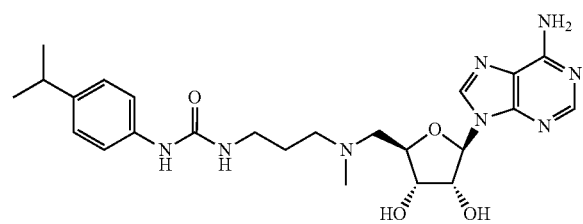 [SMILES: CC(C)c1ccc(NC(=O)NCCCN(C)C[C@H]2O[C@@H](n3cnc4c(N)ncnc43)[C@H](O)[C@@H]2O)cc1]

Step 1. Preparation of 1-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(4-isopropylphenyl)urea

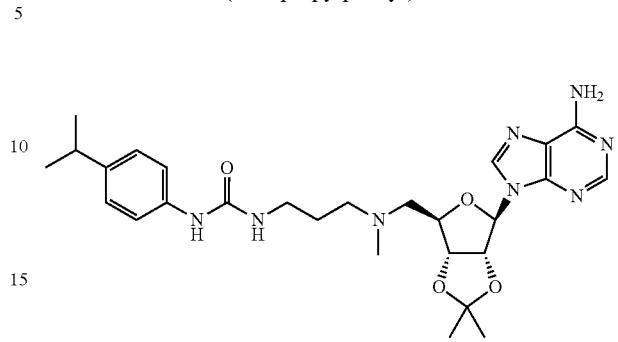

To a solution of TEA (54 mg, 0.54 mmol) and N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (100 mg, 2.9 mmol) in DCM (10 mL) was added 1-isocyanato-4-isopropylbenzene (52 mg, 0.32 mmol) dropwise. The mixture was stirred at 0° C. for 30 min. The mixture was extracted with DCM (10 mL×3) and washed with brine (5 mL). The combined organic phase was dried over Na₂SO₄ and concentrated. The crude was purified by Prep-TLC (DCM:MeOH=10:1) to afford the title compound (110 mg, 77%) as a white solid. ¹H NMR (500 MHz, MeOD): δ 8.26 (s, 1H), 8.22 (s, 1H), 7.23 (d, J=7.5 Hz, 2H), 7.11 (d, J=8.0 Hz, 2H), 6.18 (s, 1H), 5.49 (s, 1H), 5.02-5.00 (m, 1H), 4.40-4.38 (m, 1H), 3.13 (t, J=6.5 Hz, 2H), 2.85-2.82 (m, 1H), 2.74-2.70 (m, 2H), 2.48 (t, J=7.0 Hz, 2H), 2.27 (s, 3H), 1.63-1.55 (m, 5H), 1.37 (s, 3H), 1.22 (s, 3H), 1.20 (s, 3H); ESI-MS (m/z): 539.7 [M+1]⁺.

Step 2. Preparation of 1-(3-(((((2R,3S,4R,5R)-5-(6-amino-9H-purin-9-yl)-3,4-dihydroxytetrahydrofuran-2-yl)methyl)(methyl)amino)propyl)-3-(4-isopropylphenyl)urea

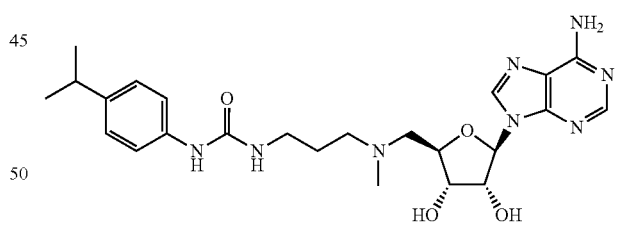

A solution of 1-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(4-isopropylphenyl)urea (105 mg, 0.2 mmol) in 90% TFA (1 mL) was stirred at rt for 1 h and then evaporated to dryness. The residue was co-evaporated with methanol. The residue was dissolved in MeOH (10 mL) and K₂CO₃ (110 mg, 0.8 mmol) was added. Then water was added dropwise until all K₂CO₃ was dissolved. The reaction mixture was stirred at rt for 1.5 h and concentrated. The residue was purified by Prep-TLC (DCM:MeOH=5:1) to the title compound (70 mg, yield: 72%). ¹H NMR (500 MHz, MeOD): δ 8.27 (s, 1H), 8.24 (s, 1H), 7.25 (d, J=9.0 Hz, 2H), 7.12 (d, J=8.5 Hz, 2H), 6.05 (d, J=5.0 Hz, 1H), 4.53-4.50 (m, 1H), 4.43 (t, J=4.5 Hz, 1H), 3.89-3.47 (m, 2H), 3.26-3.20 (m, 2H), 2.95 (brs, 3H), 2.88-2.82 (m, 1H), 1.96-1.94 (m, 2H), 1.25 (s, 3H), 1.22 (s, 3H); ESI-MS (m/z): 499.7 [M+1]⁺.

Compound 370

1-(3-(((((2R,3S,4R,5R)-5-(6-amino-9H-purin-9-yl)-3,4-dihydroxytetrahydrofuran-2-yl)methyl)(methyl)amino)propyl)-3-(3-chlorophenyl)urea

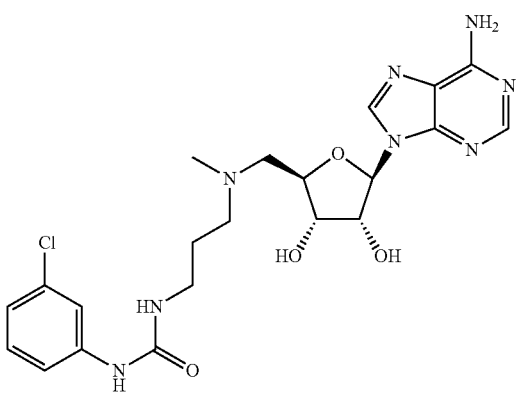 [SMILES: CN(CCCNC(=O)Nc1cccc(Cl)c1)C[C@H]1O[C@@H](n2cnc3c(N)ncnc32)[C@H](O)[C@@H]1O]

Step 1. Preparation of 1-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(3-chlorophenyl)urea

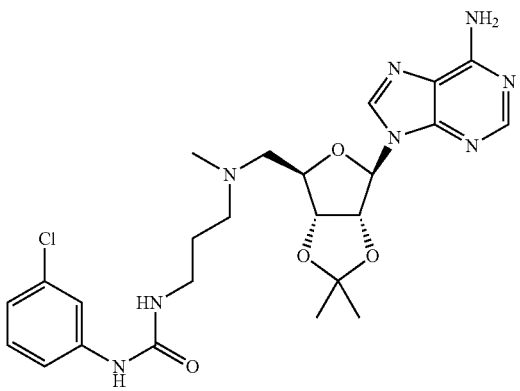 [SMILES: CN(CCCNC(=O)Nc1cccc(Cl)c1)C[C@H]1O[C@@H](n2cnc3c(N)ncnc32)[C@@H]2OC(C)(C)O[C@@H]21]

To a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (80 mg, 0.21 mmol) in DCM (5 mL) was added TEA (32 mg, 0.32 mmol) and 1-chloro-3-isocyanato-benzene (36 mg, 0.23 mmol). The mixture was stirred at rt for 2 h. Water (8 mL) was added to quench the reaction. The mixture was extracted with DCM (10 mL×3). The organic phase was dried over anhydrous Na₂SO₄ and concentrated. The crude was purified by Prep-TLC (DCM:MeOH:NH₃.H₂O=10:1:0.01) to the title compound (75 mg, yield: 67%) as a white solid. ¹H NMR (500 MHz, MeOD): δ 8.26 (s, 1H), 8.21 (s, 1H), 7.53 (t, J=3.5 Hz, 1H), 7.20-7.15 (m, 2H), 6.94-6.91 (m, 1H), 6.17 (d, J=2.5 Hz, 1H), 5.48 (dd, J=3.0, 4.0 Hz, 1H), 5.00 (dd, J=3.5, 6.5 Hz, 1H), 4.39-4.37 (m, 1H), 3.14-3.11 (m, 2H), 2.67-2.43 (m, 4H), 2.24 (s, 3H), 1.60-1.55 (m, 5H), 1.36 (s, 3H) ppm; ESI-MS (m/z): 531.2 [M+1]⁺.

Step 2. Preparation of 1-(3-(((((2R,3S,4R,5R)-5-(6-amino-9H-purin-9-yl)-3,4-dihydroxytetrahydrofuran-2-yl)methyl)(methyl)amino)propyl)-3-(3-chlorophenyl)urea

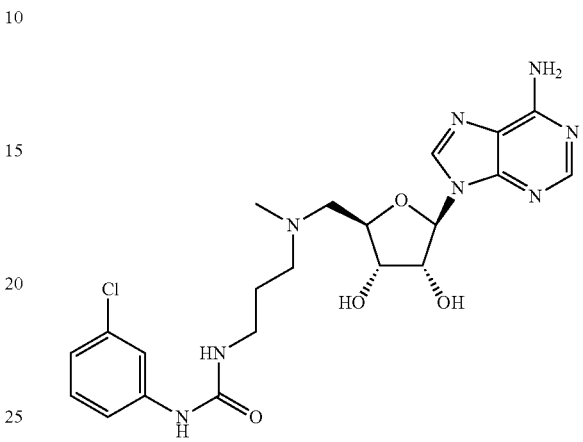

A solution of 1-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(3-chlorophenyl)urea (70 mg, 0.13 mmol) in 90% TFA (1 mL) was stirred at rt for 2 h and then evaporated to dryness. The residue was dissolved in MeOH (5 mL) and K₂CO₃ (73 mg, 0.53 mmol) in water (0.5 mL) was added dropwise. The reaction mixture was stirred at rt for 10 min and concentrated. The residue was purified by Prep-TLC (DCM:MeOH:NH₃.H₂O=4:1:0.01) to afford the title compound (50 mg, yield: 77%). ¹H NMR (500 MHz, MeOD): δ 8.14 (s, 1H), 8.08 (s, 1H), 7.40 (t, J=2.0 Hz, 1H), 7.07-7.01 (m, 2H), 6.82-6.79 (m, 1H), 5.88 (d, J=4.0 Hz, 1H), 4.58 (t, J=4.5 Hz, 1H), 4.14-4.11 (m, 2H), 3.12-3.09 (m, 2H), 2.73-2.43 (m, 4H), 2.22 (s, 3H), 1.63-1.60 (m, 2H) ppm; ESI-MS (m/z): 491.2 [M+1]⁺.

Compound 371

1-(3-(((((2R,3S,4R,5R)-5-(6-amino-9H-purin-9-yl)-3,4-dihydroxytetrahydrofuran-2-yl)methyl)(methyl)amino)propyl)-3-(4-chlorophenyl)urea

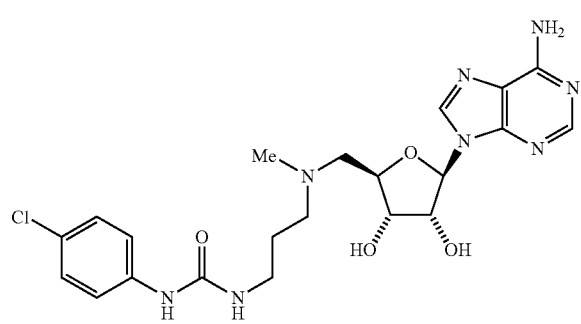 [SMILES: CN(CCCNC(=O)Nc1ccc(Cl)cc1)C[C@H]1O[C@@H](n2cnc3c(N)ncnc32)[C@H](O)[C@@H]1O]

329

Step 1. Preparation of 1-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(4-chlorophenyl)urea

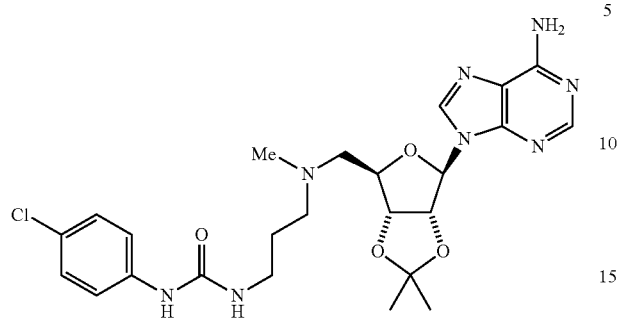

To a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (120 mg, 0.32 mmol) in DCM (5 mL) were added 1-chloro-4-isocyanato-benzene (54 mg, 0.35 mmol) and Et$_3$N (2 drops). The mixture was stirred at rt for 2 h. Then the reaction mixture was concentrated and purified by Prep TLC (DCM:MeOH=9:1) to afford the title compound (120 mg, yield: 71%) as a white solid. $^1$H NMR (500 MHz, MeOD): δ 8.26 (s, 1H), 8.22 (s, 1H), 7.32 (d, J=9.0 Hz, 2H), 7.20 (d, J=8.5 Hz, 2H), 6.18 (d, J=2.0 Hz, 1H), 5.48-5.47 (m, 1H), 5.01-4.88 (m, 1H), 4.41-4.39 (m, 1H), 3.12 (t, J=6.5 Hz, 2H), 2.74-2.69. (m, 2H), 2.47 (t, J=7.0 Hz, 2H), 2.27 (s, 3H), 1.62-1.56 (m, 2H), 1.58 (s, 3H), 1.37 (s, 3H) ppm; ESI-MS (m/z): 531.2 [M+1]$^+$.

Step 2. Preparation of 1-(3-(((((2R,3S,4R,5R)-5-(6-amino-9H-purin-9-yl)-3,4-dihydroxytetrahydrofuran-2-yl)methyl)(methyl)amino)propyl)-3-(4-chlorophenyl)urea

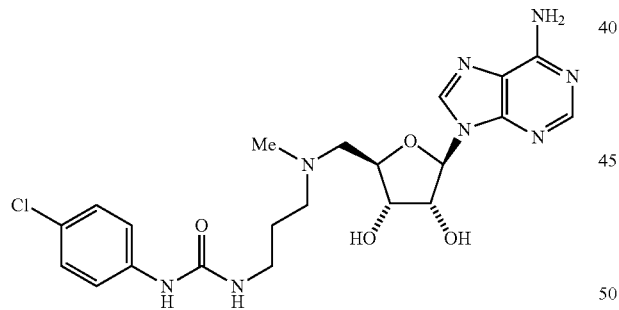

To a mixture of TFA (0.9 mL) and water (0.1 mL) was added 1-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(4-chlorophenyl)urea (100 mg, 0.19 mmol). The solution was stirred at 27° C. for 2 h and evaporated to dryness. The residue was co-evaporated with methanol twice. Then the residue was dissolved in MeOH (5 mL). Saturated K$_2$CO$_3$ solution was added to adjust the solution to pH 8. Then the mixture was stirred for 5 min and concentrated in vacuo. At last, the residue was purified by Prep TLC (DCM:MeOH=1:1, 100 mL with 0.5 mL NH$_4$OH) to afford the title compound (55 mg, yield: 60%) as a white solid. $^1$H NMR (500 MHz, MeOD): δ 8.20 (s, 1H), 8.14 (s, 1H), 7.25 (d, J=7.0 Hz, 2H), 7.13 (d, J=7.0 Hz, 2H), 5.94 (d, J=4.5 Hz, 1H), 4.64 (t, J=5.0 Hz, 1H), 4.21-4.17 (m, 2H), 3.18-3.14 (m, 2H), 2.80-2.74 (m, 2H), 2.50 (t, J=7.0 Hz, 2H), 2.28 (s, 3H), 1.70-1.65 (m, 2H) ppm; ESI-MS (m/z): 491.2 [M+1]$^+$.

Compound 372

1-(3-(((((2R,3S,4R,5R)-5-(6-amino-9H-purin-9-yl)-3,4-dihydroxytetrahydrofuran-2-yl)methyl)(methyl)amino)propyl)-3-(3,4-dichlorophenyl)urea

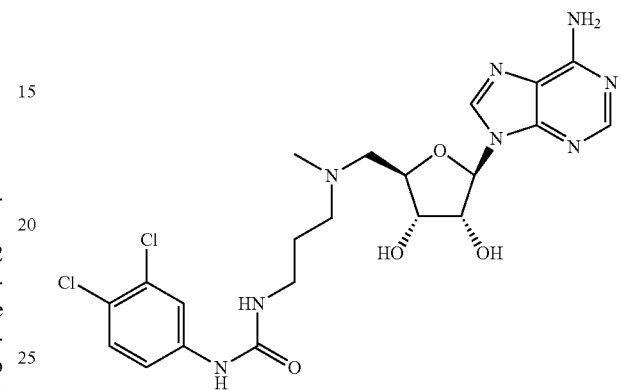

Step 1. Preparation of 1-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(3,4-dichlorophenyl)urea

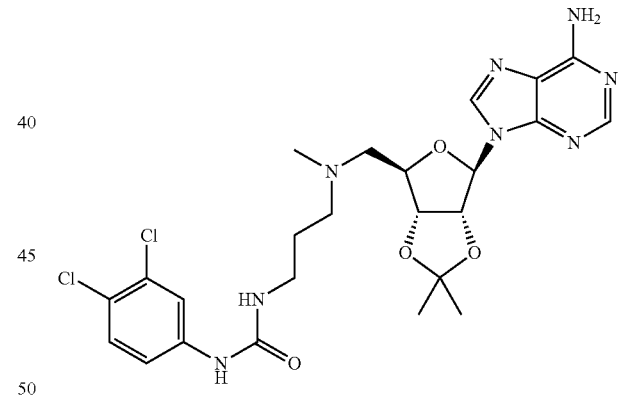

To a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (120 mg, 0.32 mmol) in DCM (20 mL) was added TEA (64 mg, 0.64 mmol) and 1,2-dichloro-4-isocyanato-benzene (66 mg, 0.35 mmol). The mixture was stirred at rt overnight. Water (8 mL) was added to quench the reaction. The mixture was extracted with DCM (10 mL×3). The organic phase was dried over anhydrous Na$_2$SO$_4$ and concentrated. The crude was purified by prep-TLC (DCM:MeOH:NH$_3$.H$_2$O=10:1:0.01) to afford the title compound (70 mg, yield: 39%) as a white solid. $^1$H NMR (500 MHz, MeOD): δ 8.16 (s, 1H), 8.11 (s, 1H), 7.59 (d, J=2.0 Hz, 1H), 7.23 (d, J=9.0 Hz, 1H), 7.08 (dd, J=2.5, 8.5 Hz, 1H), 6.08 (d, J=2.0 Hz, 1H), 5.37 (dd, J=2.5, 6.5 Hz, 1H), 4.88 (dd, J=3.5, 7.0 Hz, 1H), 4.28 (dd, J=3.0, 6.0 Hz, 1H), 3.05-3.02

(m, 2H), 2.59-2.55 (m, 2H), 2.36-2.33 (m, 2H), 2.14 (s, 3H), 1.51-1.46 (m, 5H), 1.27 (s, 3H) ppm; ESI-MS (m/z): 565.2 [M+1]⁺.

Step 2. Preparation of 1-(3-((((2R,3S,4R,5R)-5-(6-amino-9H-purin-9-yl)-3,4-dihydroxytetrahydrofuran-2-yl)methyl)(methyl)amino)propyl)-3-(3,4-dichlorophenyl)urea

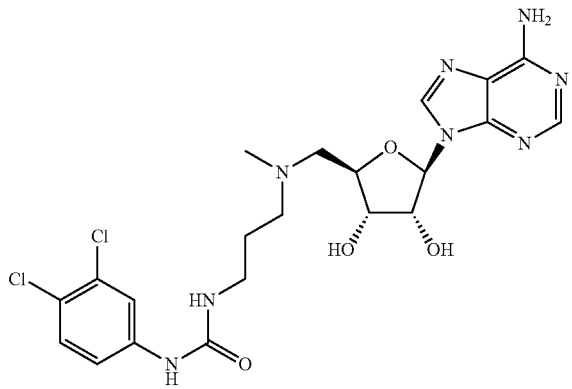 [SMILES: CN(CCCNC(=O)Nc1ccc(Cl)c(Cl)c1)C[C@H]1O[C@@H](n2cnc3c(N)ncnc32)[C@H](O)[C@@H]1O]

A solution of 1-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(3,4-dichlorophenyl)urea (70 mg, 0.12 mmol) in 90% TFA (1 mL) was stirred at rt for 2 h and then evaporated to dryness. The residue was dissolved in MeOH (5 mL) and K₂CO₃ (68 mg, 0.50 mmol) in water (0.5 mL) was added. The reaction mixture was stirred at rt for 10 min and concentrated. The residue was purified by Prep-TLC (DCM:MeOH:NH₃.H₂O=3:1:0.01) to give the title compound (50 mg, yield: 77%). ¹H NMR (500 MHz, MeOD): δ 8.24 (s, 1H), 8.18 (s, 1H), 7.65 (d, J=2.5 Hz, 1H), 7.29 (d, J=9.0 Hz, 1H), 7.15 (dd, J=2.5, 9.0 Hz, 1H), 5.98 (d, J=4.0 Hz, 1H), 4.67 (t, J=9.0 Hz, 1H), 4.24-4.23 (m, 2H), 3.24-3.19 (m, 2H), 2.88-2.78 (m, 2H), 2.57-2.55 (m, 2H), 2.33 (s, 3H), 1.73-1.70 (m, 2H) ppm. ESI-MS (m/z): 525.2 [M+1]⁺.

Compound 373

1-(3-(((((2R,3S,4R,5R)-5-(6-amino-9H-purin-9-yl)-3,4-dihydroxytetrahydrofuran-2-yl)methyl)(methyl)amino)propyl)-3-(3-chloro-4-fluorophenyl)urea

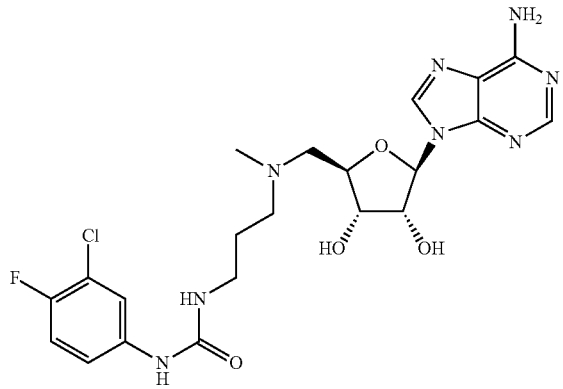 [SMILES: CN(CCCNC(=O)Nc1ccc(F)c(Cl)c1)C[C@H]1O[C@@H](n2cnc3c(N)ncnc32)[C@H](O)[C@@H]1O]

Step 1. Preparation of 1-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(3-chloro-4-fluorophenyl)urea

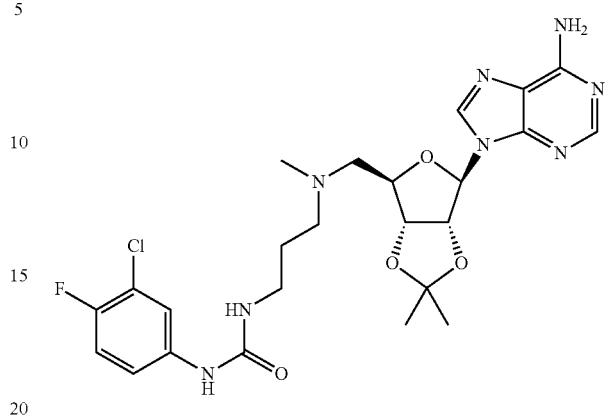

To a solution of N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (120 mg, 0.32 mmol) in DCM (5 mL) was added TEA (64 mg, 0.64 mmol) and 2-chloro-1-fluoro-4-isocyanato-benzene (60 mg, 0.35 mmol). The mixture was stirred at rt for 2 h. Water (8 mL) was added to quench the reaction. The mixture was extracted with DCM (10 mL×3). The organic phase was dried over anhydrous Na₂SO₄ and concentrated. The crude was purified by Prep-TLC (DCM:MeOH:NH₃.H₂O=10:1:0.01) to afford the title compound (100 mg, yield: 57%) as a white solid. ¹H NMR (400 MHz, MeOD): δ 8.28 (s, 1H), 8.22 (s, 1H), 7.60 (dd, J=2.4, 6.8 Hz, 1H), 7.19-7.08 (m, 2H), 6.19 (d, J=2.0 Hz, 1H), 5.50-5.48-(m, 1H), 5.00 (dd, J=3.2, 6.4 Hz, 1H), 4.41-4.37 (m, 1H), 3.15-3.12 (m, 2H), 2.69-2.43 (m, 4H), 2.25 (s, 3H), 1.63-1.55 (m, 5H), 1.38 (s, 3H) ppm; ESI-MS (m/z): 549.2 [M+1]⁺.

Step 2. Preparation of 1-(3-(((((2R,3S,4R,5R)-5-(6-amino-9H-purin-9-yl)-3,4-dihydroxytetrahydrofuran-2-ylmethyl)(methyl)amino)propyl)-3-(3-chloro-4-fluorophenyl)urea

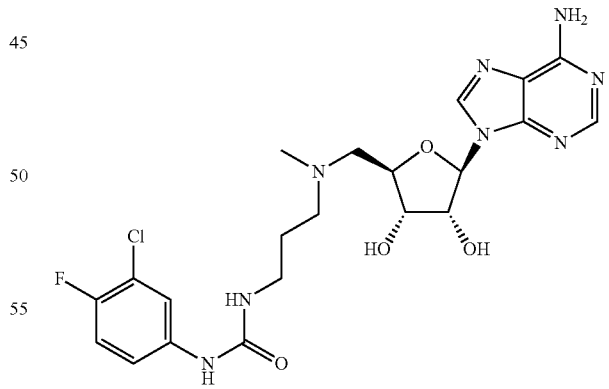

A solution of 1-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)propyl)-3-(3-chloro-4-fluorophenyl)urea (100 mg, 0.18 mmol) in 90% TFA (1 mL) was stirred at rt for 2 h then evaporated to dryness. The residue was dissolved in MeOH (5 mL) and K₂CO₃ (105 mg, 0.76 mmol) in water (0.5 mL) was added. The reaction mixture was stirred at rt for 10 min and concentrated. The residue was purified by Prep-TLC (DCM:MeOH:NH$_3$.H$_2$O=3:1:0.01) to afford the title compound (75 mg, yield: 77%). $^1$H NMR (500 MHz, MeOD): δ 8.14 (s, 1H), 8.08 (s, 1H), 7.46 (dd, J=3.0, 7.0 Hz, 1H), 7.03-6.94 (m, 2H), 5.88 (d, J=4.5 Hz, 1H), 4.58 (t, J=9.0 Hz, 1H), 4.12 (dd, J=2.5, 5.0 Hz, 1H), 3.13-3.08 (m, 2H), 2.79-2.69 (m, 2H), 2.47-2.44 (m, 2H), 2.23 (s, 3H), 1.63-1.60 (m, 2H) ppm; ESI-MS (m/z): 509.2 [M+1]$^+$.

Compound 374

1-(3-(((((2R,3S,4R,5R)-5-(6-amino-9H-purin-9-yl)-3,4-dihydroxytetrahydrofuran-2-yl)methyl)amino)propyl)-3-(4-(tert-butyl)phenyl)urea

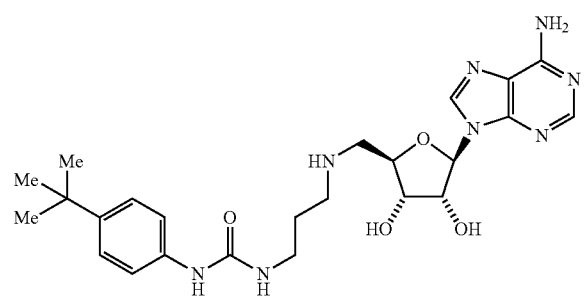 [SMILES: CC(C)(C)c1ccc(NC(=O)NCCCNC[C@H]2O[C@@H](n3cnc4c(N)ncnc43)[C@H](O)[C@@H]2O)cc1]

Step 1. Preparation of 1-(4-tert-butylphenyl)-3-(3-oxopropyl)urea

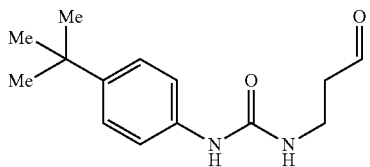 [SMILES: CC(C)(C)c1ccc(NC(=O)NCCC=O)cc1]

To a solution 1-(4-tert-butylphenyl)-3-(3-hydroxypropyl)urea (150.0 mg, 0.6 mmol) in 15 mL EA at RT was added IBX (495.9 mg, 1.77 mmol). Then the mixture was heated to reflux for 1 h. After cooling to rt, the mixture was filtered and the filtrate was evaporated to give the title compound which was directly used for next step. (150 mg, Yield: 100%). ESI-MS (m/z): 249.1[M+1]$^+$.

Step 2. Preparation of 1-(3-(((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl)urea

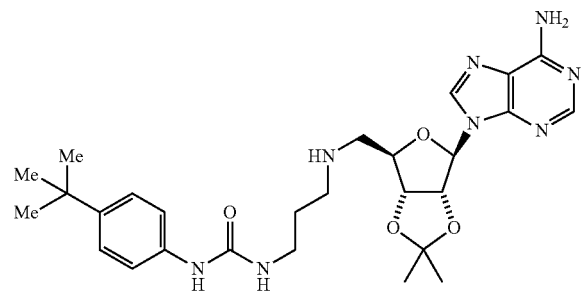

To a solution of 9-((3aR,4R,6R,6aR)-6-(aminomethyl)-2,2-dimethyltetrahydrofuro[3,4-d][1,3]dioxol-4-yl)-9H-purin-6-amine (198.9 mg, 0.65 mmol) in DCE (5 mL) was added NaB(OAc)$_3$H (375.2 mg, 1.77 mmol). The mixture was stirred at 25° C. for 2 h. Sat. NaHCO$_3$ (10 mL) was added to quench the reaction. The mixture was extracted with DCM (50 mL×6). The combined organic phases were washed with brine (20 mL), dried over Na$_2$SO$_4$ and concentrated. The crude was purified by Prep-TLC (DCM:MeOH=10:1) to afford the title compound (100 mg, yield: 31.1%) as a white solid. $^1$H NMR (500 MHz, MeOD): δ 8.17 (s, 1H), 8.16 (s, 1H), 7.22-7.15 (m, 4H), 6.19 (s, 1H), 5.36 (d, J=6.0 Hz, 1H), 5.16-5.14 (m, 1H), 4.55 (s, 1H), 4.46 (t, J=4.5 Hz, 1H), 3.48 (s, 1H), 3.16-3.10 (m, 2H), 2.90 (t, J=7.0 Hz, 2H), 2.12 (s, 1H), 1.96 (d, J=4.0 Hz, 1H), 1.70 (t, J=6.5 Hz, 2H), 1.55 (s, 3H), 1.32 (s, 3H), 1.22 (s, 9H) ppm; ESI-MS (m/z): 499.3 [M+1]$^+$.

Step 3. Preparation of 1-(3-(((((2R,3S,4R,5R)-5-(6-amino-9H-purin-9-yl)-3,4-dihydroxytetrahydrofuran-2-yl)methyl)amino)propyl)-3-(4-(tert-butyl)phenyl)urea

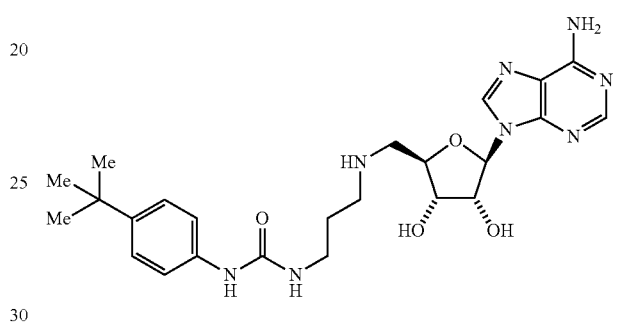

To a mixture of TFA (1.8 mL) and water (0.2 mL) was added 1-(3-(((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl)urea (100 mg, 0.19 mmol). The solution was kept at 25° C. for 1 h and the volatiles were evaporated to dryness. The residue was co-evaporated with methanol (5 mL) twice and dissolved in MeOH (10 mL). The solution was neutralized by K$_2$CO$_3$ (55.2 mg, 0.4 mmol) solution in water (1 mL) with stirring for 1 h. After filtration, the filtrate was concentrated and purified by Prep-TLC (DCM:MeOH=5:1) to afford the title compound (25 mg, yield: 27%). $^1$H NMR (500 MHz, MeOD): δ 8.19 (s, 1H), 8.17 (s, 1H), 7.17 (d, J. 1.5 Hz, 4H), 5.97 (d, J. 5.5 Hz, 1H), 4.39 (t, J=5.0 Hz, 2H), 3.56 (d, J=9.0 Hz, 1H), 3.39 (d, J=3.0 Hz, 1H), 3.08 (t, J=6.5 Hz, 2H), 1.83 (t, J=7.0 Hz, 2H), 1.21 (s, 9H), 1.94-1.88 (m, 2H) ppm; ESI-MS (m/z): 499.3 [M+1]$^+$.

Compound 375

1-(3-(((((2R,3S,4R,5R)-5-(6-amino-9H-purin-9-yl)-3,4-dihydroxytetrahydrofuran-2-yl)methyl)(benzyl)amino)propyl)-3-(4-(tert-butyl)phenyl)urea

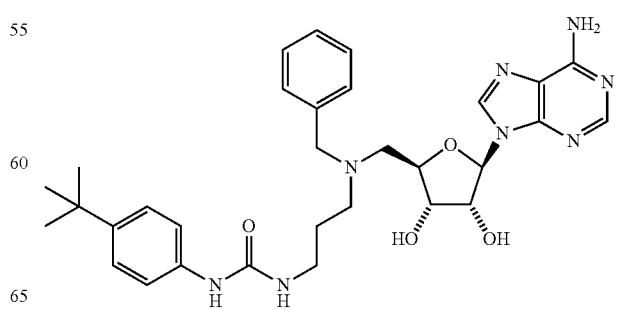

Step 1. Preparation of 1-(3-((((3aR,4R,6R,6aR)-6-(6-amino-9H-purin-9-yl)-2,2-dimethyltetrahydrofuro[3,4-d][1,3]dioxol-4-yl)methyl)(benzyl)amino)propyl)-3-(4-(tert-butyl)phenyl)urea

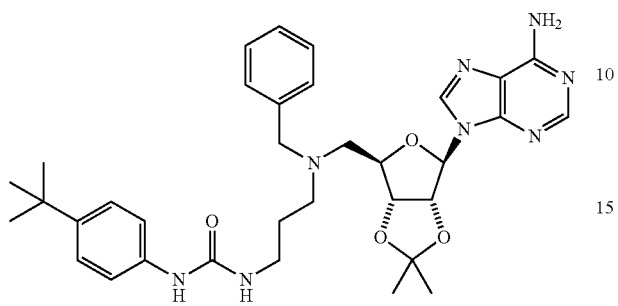

A solution 9-((3aR,4R,6R,6aR)-6-((benzylamino)methyl)-2,2-dimethyltetrahydrofuro[3,4-d][1,3]dioxol-4-yl)-9H-purin-6-amine (150 mg, 0.38 mmol) and 1-(4-tert-butylphenyl)-3-(3-oxopropyl)urea (540 mg, crude) in DCE (8 mL) was stirred at rt for 0.5 h. Then NaBH(OAc)$_3$ (184 mg, 0.87 mmol) was added. The reaction was stirred at rt overnight. The reaction was quenched with saturated NaHCO$_3$ (2 mL) and extracted with DCM (10 mL×3), washed with brine (10 mL), dried over Na$_2$SO$_4$ and concentrated. The residue was purified by prep-TLC (DCM:MeOH=10:1) to afford the title compound (80 mg, Yield 34%). $^1$H NMR (500 MHz, MeOD): δ 8.15 (s, 1H), 8.09 (s, 1H), 7.27-7.14 (m, 9H), 6.14 (d, J=2.5 Hz, 1H), 5.40-5.38 (m, 1H), 4.95-4.93 (m, 1H), 4.38-4.32 (m, 1H), 3.61-3.46 (m, 2H), 3.16-3.13 (m, 2H), 2.70-2.50 (m, 4H), 1.76-1.58 (m, 2H), 1.54 (s, 3H), 1.34 (s, 3H), 1.28 (s, 9H); ESI-MS (m/z): 629.3[M+1]$^+$.

Step 2. Preparation of 1-(3-((((2R,3S,4R,5R)-5-(6-amino-9H-purin-9-yl)-3,4-dihydroxytetrahydrofuran-2-yl)methyl)(benzyl)amino)propyl)-3-(4-(tert-butyl)phenyl)urea

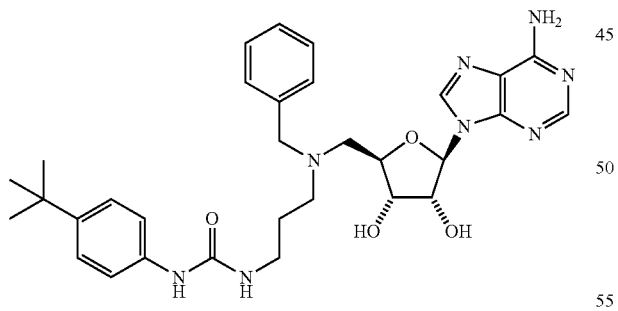

A solution of -(3-((((3aR,4R,6R,6aR)-6-(6-amino-9H-purin-9-yl)-2,2-dimethyltetrahydrofuro[3,4-d][1,3]dioxol-4-yl)methyl)(benzyl)amino)propyl)-3-(4-(tert-butyl)phenyl)urea (75 mg, 0.12 mmol) in TFA (0.90 mL) and 0.10 mL of water were stirred for 1 h at room temperature. The reaction was concentrated to dryness, dissolved in MeOH (5 mL) and added dropwise K$_2$CO$_3$ (60 mg) in water (0.5 mL). The reaction was stirred at rt for 0.5 h. Then the reaction was concentrated. The residue was purified by prep-TLC (DCM:MeOH: NH$_4$OH=150:15:4) (V/V) to afford the title compound (30 mg, yield 52%) as a pale white solid. $^1$H NMR (500 MHz, MeOD): δ 8.12 (s, 1H), 8.11 (s, 1H), 7.34-7.20 (m, 9H), 5.99 (d, J=4.0 Hz, 1H), 4.67 (t, J=4.5 Hz, 1H), 4.332 (s, 1H), 4.328 (s, 1H), 3.85 (br s, 2H), 3.25-3.15 (m, 2H), 3.05 (br s, 2H), 2.77 (br s, 2H), 1.79 (t, J=6.5 Hz, 2H), 1.27 (s, 9H); ESI-MS (m/z): 589.3 [M+1]$^+$.

Compound 376

1-(3-((((2R,3S,4R,5R)-5-(6-amino-9H-purin-9-yl)-3,4-dihydroxytetrahydrofuran-2-yl)methyl)(cyclopropylmethyl)amino)propyl)-3-(4-(tert-butyl)phenyl)urea

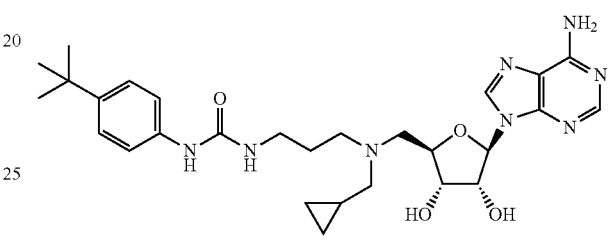

Step 1. Preparation of 1-[3-[[(3aR,4R,6R,6aR)-4-(6-aminopurin-9-yl)-2,2-dimethyl-3a,4,6,6a-tetrahydrofuro[3,4-d][1,3]dioxol-6-yl]methyl-(cyclopropylmethyl)amino]propyl]-3-(4-tert-butylphenyl)urea

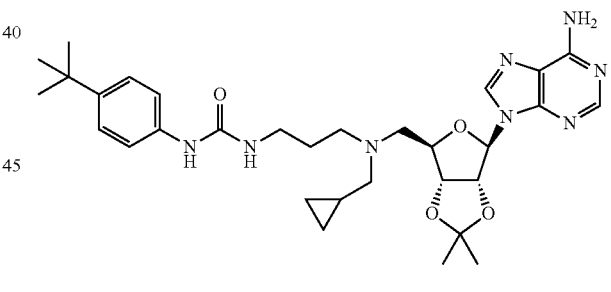

To a solution of 1-(3-((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl)urea (90 mg, 0.17 mmol) and cyclopropanecarbaldehyde (18 mg, 0.25 mmol) in DCE (8 mL) was added NaBH(OAc)$_3$ (53 mg, 0.25 mmol). The resulting mixture was stirred at rt overnight. Saturated NaHCO$_3$ solution (8 mL) was added to quench the reaction. The mixture was extracted with DCM (10 mL×3). The combined organic phase was dried over anhydrous Na$_2$SO$_4$ and concentrated. The crude was purified by Prep-TLC (DCM:MeOH=10:1) to afford the title compound (70 mg, yield: 70%) as a white solid. $^1$H NMR (500 MHz, MeOD): δ 8.27 (s, 1H), 8.22 (s, 1H), 7.29-7.23 (m, 4H), 6.20 (d, J=2.0 Hz, 1H), 5.52 (dd, J=2.5, 6.5 Hz, 1H), 5.05 (dd, J=3.5, 6.5 Hz 1H), 4.41 (br s, 1H), 3.15 (t, J=6.0 Hz, 2H), 2.85 (br s, 2H), 2.65 (br s, 2H), 2.38 (br s, 2H), 1.63-1.54 (m, 5H), 1.38 (s, 3H), 1.29 (s, 9H), 0.79-0.75 (m, 1H), 0.43 (d, J=7.5 Hz, 2H), 0.09-0.06 (m, 2H) ppm; ESI-MS (m/z): 593.7 [M+1]⁺.

Step 2. Preparation of 1-(3-(((((2R,3S,4R,5R)-5-(6-amino-9H-purin-9-yl)-3,4-dihydroxytetrahydrofuran-2-yl)methyl)(cyclopropylmethyl)amino)propyl)-3-(4-(tert-butyl)phenyl)urea

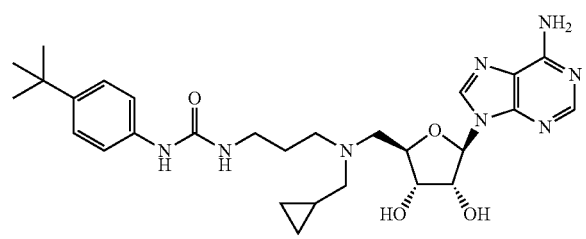 [SMILES: CC(C)(C)c1ccc(NC(=O)NCCCN(CC2CC2)C[C@H]2O[C@@H](n3cnc4c(N)ncnc43)[C@H](O)[C@@H]2O)cc1]

A solution 1-[3-[[(3aR,4R,6R,6aR)-4-(6-aminopurin-9-yl)-2,2-dimethyl-3a,4,6,6a-tetrahydrofuro[3,4-d][1,3]dioxol-6-yl]methyl-(cyclopropylmethyl)amino]propyl]-3-(4-tert-butylphenyl)urea (65 mg, 0.11 mmol) in 90% TFA (1 mL) was stirred at rt for 1 h and evaporated to dryness. The residue was co-evaporated with methanol. The mixture was dissolved in MeOH (10 mL) and K₂CO₃ (61 mg, 0.44 mmol) was added. Then water was added dropwise until all K₂CO₃ was dissolved. The reaction mixture was stirred at rt for 1.5 h, then concentrated to remove MeOH and water. The residue was purified by Prep-TLC (DCM:MeOH=5:1) to afford the title compound (52 mg, yield: 70%). ¹H NMR (500 MHz, MeOD): δ 8.26 (s, 1H), 8.19 (s, 1H), 7.26-7.19 (m, 4H), 5.98 (d, J=4.5 Hz, 1H), 4.72 (t, J=4.5 Hz, 1H), 4.32 (t, J=5.0 Hz, 1H), 4.26-4.25 (m, 1H), 3.23-3.19 (m, 2H), 3.07 (br s, 2H), 2.79 (br s, 2H), 2.52 (br s, 2H), 1.75-1.71 (m, 2H), 1.28 (s, 9H), 0.92-0.90 (m, 1H), 0.51 (d, J=8.0 Hz, 2H), 0.16 (br s, 2H) ppm; ESI-MS (m/z): 553.7 [M+1]⁺.

Compound 377

1-(3-(((((2R,3S,4R,5R)-5-(6-amino-9H-purin-9-yl)-3,4-dihydroxytetrahydrofuran-2-yl)methyl)(methyl)amino)propyl)-3-(3-chloro-4-methylphenyl)urea

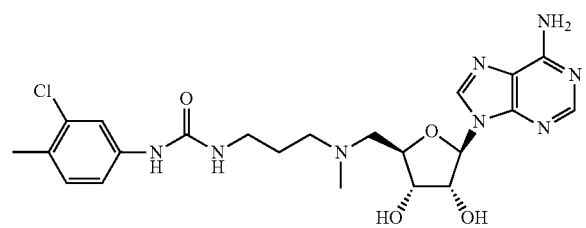 [SMILES: Cc1ccc(NC(=O)NCCCN(C)C[C@H]2O[C@@H](n3cnc4c(N)ncnc43)[C@H](O)[C@@H]2O)cc1Cl]

Step 1. Preparation of 1-[3-[[(4R,6R,6aR)-4-(6-aminopurin-9-yl)-2,2-dimethyl-3a,4,6,6a-tetrahydrofuro[3,4-d][1,3]dioxol-6-yl]methyl-methyl-amino]propyl]-3-(3-chloro-4-methyl-phenyl)urea

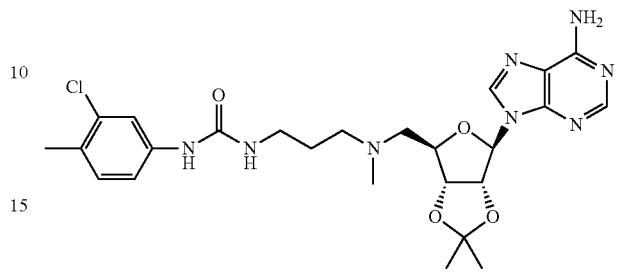

To a mixture of N1-(((3aR,4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (120 mg, 0.32 mmol) in DCM (5 mL) was added 2-chloro-4-isocyanato-1-methyl-benzene (53 mg, 0.32 mmol) and stirred for 1 h. Then concentrated to remove the solvent and the residue was purified by Pre-TLC (DCM:MeOH=10:1) to afford the title compound as a white powder (120 mg, 69%). ¹H NMR (500 MHz, MeOD): δ 8.25 (s, 1H), 8.20 (s, 1H), 7.47 (s, 1H), 7.11-7.06 (m, 2H), 6.16 (s, 1H), 5.45 (s, 1H), 4.99-4.960m 1H), 4.290-4.369 (m, 1H), 3.11 (t, J=8.5 Hz, 2H), 2.67-2.63 (m, 2H), 2.42 (t, J=8.5 Hz, 2H), 2.25 (s, 3H), 2.23 (s, 3H), 1.56 (s, 3H), 1.35 (s, 3H) ppm. ESI-MS (m/z): 545.3 [M+1]⁺.

Step 2. Preparation of 1-(3-(((((2R,3S,4R,5R)-5-(6-amino-9H-purin-9-yl)-3,4-dihydroxytetrahydrofuran-2-yl)methyl)(methyl)amino)propyl)-3-(3-chloro-4-methylphenyl)urea

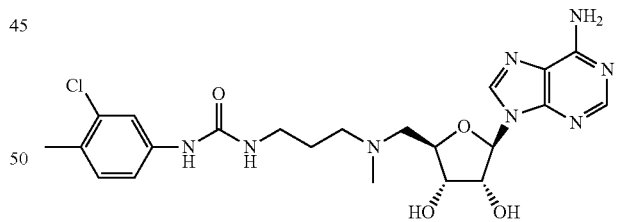

A mixture of 1-[3-[[(4R,6R,6aR)-4-(6-aminopurin-9-yl)-2,2-dimethyl-3a,4,6,6a-tetrahydrofuro[3,4-d][1,3]dioxol-6-yl]methyl-methyl-amino]propyl]-3-(3-chloro-4-methyl-phenyl)urea (110 mg, 0.22 mmol) and 90% TFA (2 mL) was stirred at rt for 2 h, then concentrated in high vacuo to remove the solvent. The residue was dissolved in MeOH and K₂CO₃ (40 mg in 0.5 mL H₂O) was added dropwise until pH=7-8, then concentrated to remove the solvent. The residue was purified by Pre-TLC (DCM:MeOH=5:1) to afford the title compound (58 mg, 63%). ¹H NMR (500 MHz, MeOD): 6.22 (s, 1H), 8.21 (s, 1H), 7.48 (d, J=2.0 Hz, 1H), 7.12-7.05 (m, 2H), 6.01 (d, J=4.5 Hz 1H), 4.81-4.79 (m, 1H), 4.42-4.40 (m, 1H), 4.36-4.34 (m, 1H), 3.28-3.20 (m, 2H), 3.08-3.06 (m, 1H), 2.76 (br s, 3H), 2.27 (s, 3H), 1.90-1.84 (m, 2H) ppm. ESI-MS (m/z): 505.7 [M+1]⁺.

Compound 378

1-((S)-1-((((2R,3S,4R,5R)-5-(6-amino-9H-purin-9-yl)-3,4-dihydroxytetrahydrofuran-2-yl)methyl)(methyl)amino)-4-methylpentan-3-yl)-3-(4-(tert-butyl)phenyl)urea

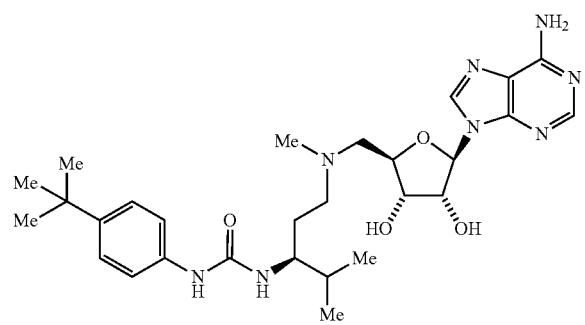 [SMILES: CC(C)[C@H](CCN(C)C[C@H]1O[C@@H](n2cnc3c(N)ncnc32)[C@H](O)[C@@H]1O)NC(=O)Nc1ccc(C(C)(C)C)cc1]

Step 1. Preparation of methyl (3S)-3-amino-4-methyl-pentanoate.HCl

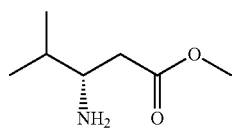

Sulfurous dichloride (1 mL, 7.63 mmol) was added to MeOH (10 mL) at −10° C. The reaction was stirred for 1 h. Then (3S)-3-amino-4-methyl-pentanoic acid (500 mg, 3.82 mmol) was added in one portion. The reaction was stirred at 25° C. overnight. The reaction was concentrated to afford methyl the title compound (625 mg, yield 83%). ¹H NMR (500 MHz, DMSO): δ 8.25 (s, 3H), 3.64 (s, 3H), 3.30-73.29 (m, 1H), 2.71-2.63 (m, 2H), 1.96-1.95 (m, 1H), 0.91 (s, 6H) ppm.

Step 2. Preparation of (S)-methyl 3-(3-(4-(tert-butyl)phenyl)ureido)-4-methylpentanoate

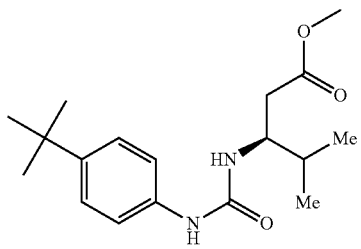 [SMILES: COC(=O)C[C@H](NC(=O)Nc1ccc(C(C)(C)C)cc1)C(C)C]

A solution of methyl (3S)-3-amino-4-methyl-pentanoate (100 mg, 0.69 mmol) and DIPEA (170 mg, 1.31 mmol) in DCM (5 mL) was stirred for 0.5 h. Then tert-butylbenzene isocyanate (115 mg, 0.66 mmol) was added. The reaction was stirred at rt overnight. The reaction was concentrated to dryness. The residue was purified by Prep-TLC (PE:EA:NH₄OH=210:370:5) (V/V) to obtain the title compound (150 mg, yield 68%). ¹H NMR (500 MHz, CDCl₃): δ 7.31-7.21 (m, 4H), 6.89 (br s, 1H), 5.38-5.37 (br s, 1H), 3.98-3.95 (m, 1H), 3.65 (s, 3H), 2.59-2.48 (m, 2H), 1.84-1.80 (m, 1H), 1.28 (s, 9H), 0.95-0.83 (m, 6H) ppm; ESI-MS (m/z): 321.1 [M+1]⁺.

Step 3. Preparation of (S)-1-(4-(tert-butyl)phenyl)-3-(1-hydroxy-4-methylpentan-3-yl)urea

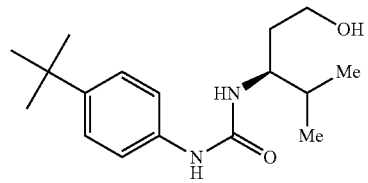 [SMILES: CC(C)[C@H](CCO)NC(=O)Nc1ccc(C(C)(C)C)cc1]

To a solution of (S)-methyl 3-(3-(4-(tert-butyl)phenyl)ureido)-4-methylpentanoate (130 mg, 0.41 mmol) in THF (3 mL) was added LiBH₄ (36 mg, 1.63 mmol) at rt. The reaction was stirred at rt overnight. The reaction was quenched with water (1 mL), extracted with DCM (2 mL×3), dried and concentrated to afford the title compound (100 mg, yield 85%). ¹H NMR (500 MHz, MeOD): δ 7.29-7.23 (m, 4H), 3.72-3.69 (m, 1H), 3.63-3.61 (m, 2H), 1.80-1.75 (m, 2H), 1.53-1.48 (m, 1H), 1.30 (S, 9H), 0.96-0.93 (m, 6H) ppm; ESI-MS (m/z): 293.2 [M+1]⁺.

Step 4. Preparation of (S)-1-(4-(tert-butyl)phenyl)-3-(4-methyl-1-oxopentan-3-yl)urea

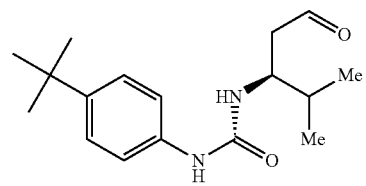

A suspension of (S)-1-(4-(tert-butyl)phenyl)-3-(1-hydroxy-4-methylpentan-3-yl)urea (100 mg, 0.34 mmol) and IBX (290 mg, 1.03 mmol) in EA (10 mL) were refluxed for 1.5 h. The reaction was filtered. The filtrate was concentrated to afford the title compound (110 mg, crude). The residue was directly used for next step without further purification.

Step 5. Preparation of 1-((S)-1-((((3aR,4R,6R,6aR)-6-(6-amino-9H-purin-9-yl)-2,2-dimethyltetrahydrofuro[3,4-d][1,3]dioxol-4-ylmethyl)(methyl)amino)-4-methylpentan-3-yl)-3-(4-(tert-butyl)phenyl)urea

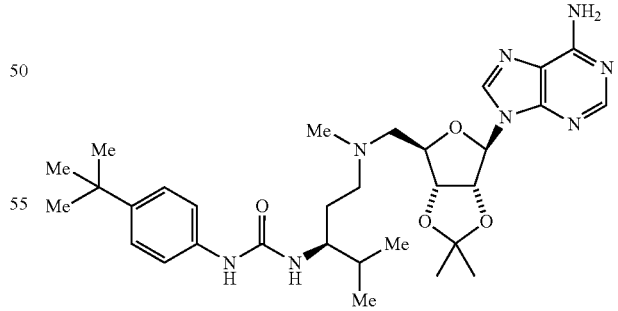

A solution of (S)-1-(4-(tert-butyl)phenyl)-3-(4-methyl-1-oxopentan-3-yl)urea (0.34 mmol) 9-((3aR,4R,6R,6aR)-2,2-dimethyl-6-((methylamino)methyl)tetrahydrofuro[3,4-d][1,3]dioxol-4-yl)-9H-purin-6-amine (120 mg, 0.38 mmol) in DCE (10 mL) were stirred at rt for 0.5 h, then NaBH(OAc)₃ (109 mg, 0.51 mmol) was added. The reaction was stirred at rt overnight. The reaction was quenched with sat. NaHCO₃

(1.5 mL), extracted with DCM (10 mL×3), washed with brine (10 mL), dried and concentrated. The residue was purified by Prep-TLC (DCM:MeOH:NH$_4$OH=200:10:4) (V/V) to afford the title compound (55 mg, yield 27%). $^1$H NMR (400 MHz, MeOD): δ 8.20 (br s, 2H), 7.28-7.21 (m, 4H), 6.16 (br s, 1H), 5.46-5.43 (m, 1H), 5.04-5.02 (m, 1H), 4.42-4.40 (m, 1H), 3.47 (br s, 1H), 2.90-2.88 (m, 2H), 2.56 (br s, 2H), 2.33 (s, 3H), 1.54 (br s, 5H), 1.43-1.35 (br s, 4H), 1.28 (s, 9H), 0.83-0.82 (m, 6H) ppm; ESI-MS (m/z): 595.4 [M+1]$^+$.

Step 6. Preparation of 1-((S)-1-((((2R,3S,4R,5R)-5-(6-amino-9H-purin-9-yl)-3,4-dihydroxytetrahydrofuran-2-yl)methyl)(methyl)amino)-4-methylpentan-3-yl)-3-(4-(tert-butyl)phenyl)urea

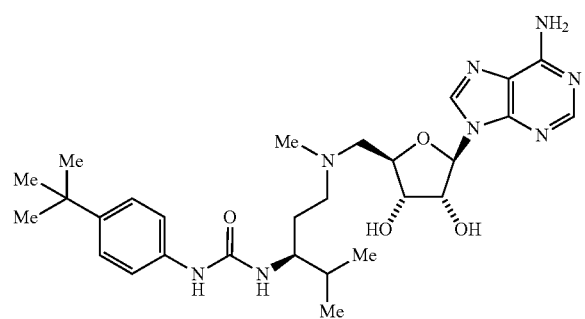 [SMILES: CC(C)[C@H](CCN(C)C[C@H]1O[C@@H](n2cnc3c(N)ncnc32)[C@H](O)[C@@H]1O)NC(=O)Nc1ccc(C(C)(C)C)cc1]

A solution of 1-((S)-1-((((3aR,4R,6R,6aR)-6-(6-amino-9H-purin-9-yl)-2,2-dimethyltetrahydrofuro[3,4-d][1,3]dioxol-4-yl)methyl)(methyl)amino)-4-methylpentan-3-yl)-3-(4-(tert-butyl)phenyl)urea (55 mg, 0.12 mmol) in HCl in MeOH (5 mL) was stirred at 25° C. for 3 h. The reaction was concentrated to dryness, dissolved in MeOH (5 mL) and adjusted pH=8 with sat. K$_2$CO$_3$. The reaction was stirred at rt for 0.5 h. Then the reaction was concentrated to obtain the residue. The residue was purified by Prep-TLC (DCM:MeOH:NH$_4$OH=300:30:8) (V/V) to afford the title compound (26 mg, yield 51%). $^1$H NMR (500 MHz, MeOD): δ 8.20-8.19 (m, 2H), 7.24-7.23 (m, 4H), 5.97 (br s, 1H), 4.75-4.73 (m, 1H), 4.35-4.32 (m, 2H), 3.51 (br s, 1H), 3.30 (br s, 1H), 3.25 (br s, 1H), 2.86 (br s, 2H), 2.56 (s, 3H), 1.82-1.80 (m, 1H), 1.64-1.58 (m, 2H), 1.25 (s, 9H), 0.85 (s, 6H) ppm; ESI-MS (m/z): 555.3 [M+1]$^+$.

Compound 379

1-(3-((((2R,3S,4R,5R)-5-(6-amino-9H-purin-9-yl)-3,4-dihydroxytetrahydrofuran-2-yl)methyl)(methyl)amino)propyl)-3-(4-(tert-butyl)-3-fluorophenyl)urea

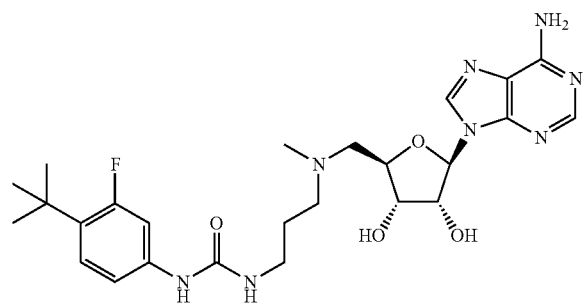 [SMILES: CN(CCCNC(=O)Nc1ccc(C(C)(C)C)c(F)c1)C[C@H]1O[C@@H](n2cnc3c(N)ncnc32)[C@H](O)[C@@H]1O]

Step 1. Preparation of 2-tert-butyl-5-nitro-aniline

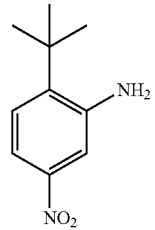

To H$_2$SO$_4$ (98%, 40 mL) was added 2-tert-butyl aniline (4 g, 26.8 mmol). The reaction was cooled to −10° C. and KNO$_3$ (2.95 g, 29.5 mmol) was added slowly by maintaining the temperature at −5° C. to −10° C. After final addition of KNO$_3$, the reaction was stirred for 5 min then it was poured into ice (5 g). The black mix was diluted with H$_2$O (10 mL) and extracted with EA (30 mL). The aqueous layer was basified with solid NaOH (5 g) slowly then extracted with EA (20 mL). The combined organic layers were washed with 6N NaOH (20 mL) and then with a mix of 6N NaOH (20 mL) and brine (20 mL), dried over Na$_2$SO$_4$, filtered and concentrated in vacuo to afford title compound (2.85 g, yield: 55%). $^1$H NMR (500 MHz, CDCl$_3$): δ 7.50 (dd, J$_1$=2.5, J$_2$=8.5 Hz, 1H), 7.45 (d, J=2.5 Hz, 1H), 7.32 (d, J=8.5 Hz, 1H), 1.42 (s, 9H) ppm; ESI-MS (m/z): 195.7 [M+1]$^+$.

Step 2. Preparation of 1-tert-butyl-2-fluoro-4-nitro-benzene

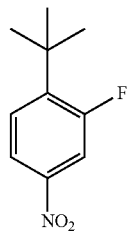

To 2-tert-butyl-5-nitro-aniline (2 g, 10 mmol) solid at 0° C. was added ice cooled Con HCl (30 mL) slowly and the mixture was stirred for 5 min. Sodium nitrite (816 mg, 12 mmol) was added and the mixture was stirred for 1 h then sodium tetrafluoroborate (5.4 g, 50 mmol) was added. After 1 h the precipitate was filtered off (caution—potentially explosive), washed with water and diethyl ether to afford a solid. This was diluted with solid sand and heated at 130° C. for 1 h (gas evolution observed). After cooling to rt, dichloromethane (30 mL) was added and the solids filtered off. The filtrate was collected and the solvent removed in vacuo to afford the crude product. The crude was purified by SGC (EA:PE=1:30) to afford the title compound (800 mg, yield: 39%). $^1$H NMR (500 MHz, CDCl₃): δ 6.82-6.80 (m, 2H), 6.72 (d, J=8.5 Hz, 1H), 1.56 (s, 2H), 1.26 (s, 9H) ppm; ESI-MS (m/z): 198.7 [M+1]+.

Step 3. Preparation of 4-tert-butyl-3-fluoro-aniline

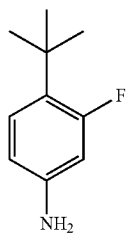

A mixture of 1-tert-butyl-2-fluoro-4-nitro-benzene (800 mg, 4.06 mmol) and Pd/C (10%, 400 mg) in EA (30 mL) was stirred under H₂ at rt overnight. The mixture was filtered and the filtrate was concentrated to afford the title compound (480 mg, yield: 98%). ¹H NMR (500 MHz, CDCl₃): δ 7.96 (d, J=8.5 Hz, 1H), 7.87 (d, J=12.0 Hz, 1H), 7.48 (t, J=8.5 Hz, 1H), 1.42 (s, 9H) ppm; ESI-MS (m/z): 208.7 [M+1]⁺.

Step 4. Preparation of 1-[3-[[(4R,6R,6aR)-4-(6-aminopurin-9-yl)-2,2-dimethyl-3a,4,6,6a-tetrahydrofuro[3,4-d][1,3]dioxol-6-yl]methyl-methyl-amino]propyl]-3-(4-tert-butyl-3-fluoro-phenyl)urea

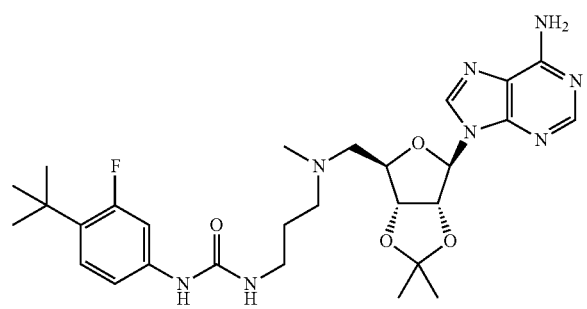 [SMILES: CN(CCCNC(=O)Nc1ccc(C(C)(C)C)c(F)c1)C[C@H]1O[C@@H](n2cnc3c(N)ncnc32)[C@@H]2OC(C)(C)O[C@@H]21]

To a mixture of Triphosgene (19 mg, 0.06 mmol) in DCM (3 mL) was added dropwise to 4-tert-butyl-3-fluoro-aniline (30 mg, 0.18 mmol) and TEA (36 mg, 0.36 mmol) in DCM (2 mL). The solvents were stirred at 0° C. for 10 min. N1-(43aR, 4R,6R,6aR)-6-(6-amino-9H-purin-9-yl)-2,2-dimethyltetrahydrofuro[3,4-d][1,3]dioxol-4-yl)methyl)-N1-methylpropane-1,3-diamine (68 mg, 0.18 mmol) was added. The mixture was stirred at 0° C. for 30 min. Water (20 mL) was added into the mixture. The mixture was extracted with DCM (20 mL×3). The combined organic layers were washed with brine (20 mL×2), dried over Na₂SO₄ and concentrated. The crude was purified by SGC (DCM:MeOH=10:1) to afford the title compound (70 mg, yield: 68%) as a white solid. ¹H NMR (500 MHz, MeOD): δ 8.26 (s, 1H), 8.2 (s, 1H), 7.24-7.14 (m, 2H), 6.91-6.90 (m, 1H), 6.18 (d, J=1.5 Hz, 1H), 5.48 (d, J=2.0 Hz, 1H), 4.99 (dd, J=3.5, J₂=6.0 Hz, 1H), 4.38 (br s, 1H), 3.13 (t, J=6.5 Hz, 2H), 2.70-2.67 (m, 2H), 2.46-2.44 (m, 2H), 2.25 (s, 3H), 1.61-1.54 (m, 5H), 1.36-1.33 (m, 12H) ppm; ESI-MS (m/z): 571.3 [M+1]⁺.

Step 5. Preparation of 1-(3-(((((2R,3S,4R,5R)-5-(6-amino-9H-purin-9-yl)-3,4-dihydroxytetrahydrofuran-2-yl)methyl)(methyl)amino)propyl)-3-(4-(tert-butyl)-3-fluorophenyl)urea

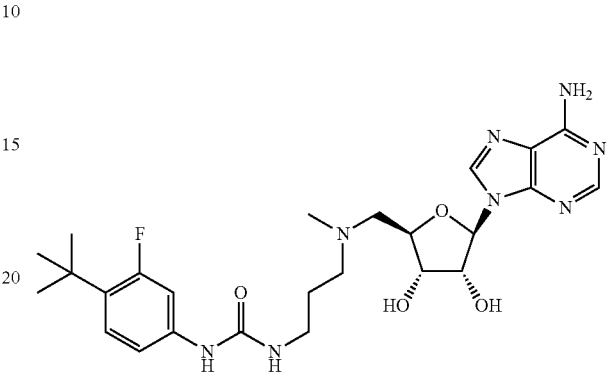

A solution of 1-[3-[[(4R,6R,6aR)-4-(6-aminopurin-9-yl)-2,2-dimethyl-3a,4,6,6a-tetrahydrofuro[3,4-d][1,3]dioxol-6-yl]methyl-methyl-amino]propyl]-3-(4-tert-butyl-3-fluoro-phenyl)urea (70 mg, 0.12 mmol) in 90% TFA (1 mL) was stirred at rt for 1 h and then evaporated to dryness. The residue was co-evaporated with methanol. The residue was dissolved in MeOH (10 mL) and K₂CO₃ (66 mg, 0.48 mmol) was added. Water was added dropwise until all K₂CO₃ was dissolved. The reaction mixture was stirred at rt for 1.5 h and concentrated. The residue was purified by Prep-TLC (DCM:MeOH=5:1) to afford the title compound (45 mg, yield: 69%). ¹H NMR (500 MHz, MeOD): δ 8.25 (s, 1H), 8.22 (s, 1H), 7.26-7.16 (m, 2H), 6.94-6.92 (m, 1H), 6.03 (t, J=6.0 Hz, 1H), 4.88 (1H, overlapping H₂O), 4.49-4.46 (m, 1H), 4.41 (t, J=6.0 Hz, 1H), 3.77 (brs, 1H), 3.49-3.45 (m, 1H), 3.26-3.23 (m, 4H), 2.89 (s, 3H), 1.96-1.89 (m, 2H), 1.34 (s, 9H) ppm; ESI-MS (m/z): 531.7 [M+1]⁺.

Compound 380

1-(3-(((((2R,3S,4R,5R)-5-(6-amino-9H-purin-9-yl)-3,4-dihydroxytetrahydrofuran-2-ylmethyl)(sec-butyl)amino)propyl)-3-(4-(tert-butyl)phenyl)urea

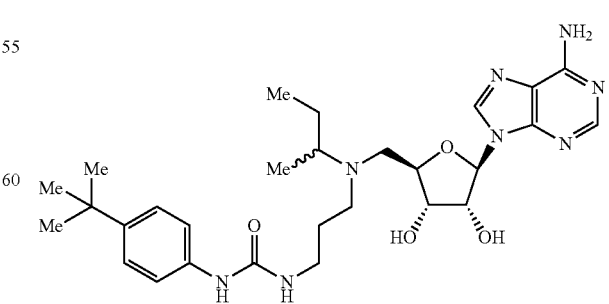

Step 1. Preparation of 1-(3-((((3aR,4R,6R,6aR)-6-(6-amino-9H-purin-9-yl)-2,2-dimethyltetrahydrofuro[3,4-d][1,3]dioxol-4-yl)methyl)(sec-butyl)amino)propyl)-3-(4-(tert-butyl)phenyl)urea

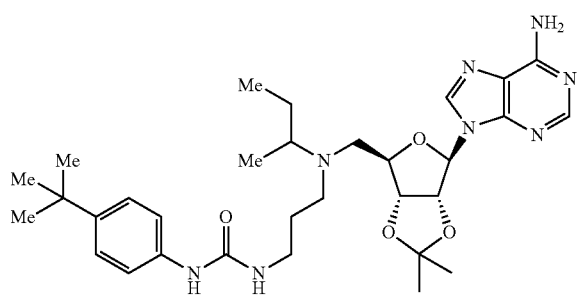 [SMILES: CCC(C)N(CCCNC(=O)Nc1ccc(C(C)(C)C)cc1)C[C@H]1O[C@@H](n2cnc3c(N)ncnc32)[C@@H]2OC(C)(C)O[C@@H]21]

A solution of 1-(3-((((3aR,4R,6R,6aR)-6-(6-amino-9H-purin-9-yl)-2,2-dimethyltetrahydrofuro[3,4-d][1,3]dioxol-4-yl)methyl)amino)propyl)-3-(4-(tert-butyl)phenyl)urea (150 mg, 0.28 mmol), 2-Butanone (440 mg, 6.13 mmol) and Ti(O-iPr)$_4$ (482 mg, 1.7 mmol) in MeOH (10 mL) was stirred at 25° C. for 1 h, then NaBH(OAc)$_3$ (385 mg, 6.13 mmol) was added and stirred at 25° C. for 5 days. The volatiles were concentrated and the residue was added DCM (30 mL). The organic phase was washed with water (15 mL×3) and brine (20 mL), dried over Na$_2$SO$_4$, filtered and concentrated. The residue was purified by Combi-flash (4 g silica gel, start 10:0 DCM:MeOH to 10:3 by gradient, 20 mL/min, 30 min, 0.6 total solvent volume) to afford the title compound as a yellow oil (120 mg, impure, 72%).

Step 2. Preparation of 1-(3-((((2R,3S,4R,5R)-5-(6-amino-9H-purin-9-yl)-3,4-dihydroxytetrahydrofuran-2-yl)methyl)(sec-butyl)amino)propyl)-3-(4-(tert-butyl)phenyl)urea

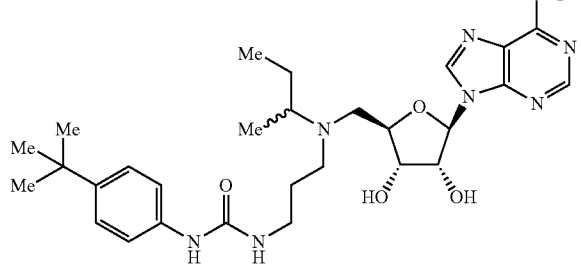

A solution of 1-(3-((((3aR,4R,6R,6aR)-6-(6-amino-9H-purin-9-yl)-2,2-dimethyltetrahydrofuro[3,4-d][1,3]dioxol-4-yl)methyl)(sec-butyl)amino)propyl)-3-(4-(tert-butyl)phenyl)urea (120 mg, impure, 0.017 mmol) in HCl/MeOH (5 mL) was stirred at rt for 3 h. The volatiles were removed under reduced pressure. The residue was dissolved in MeOH (1.5 mL) and added a solution of K$_2$CO$_3$ (214 mg, 1.55 mmol) in water (0.5 mL). The mixture was stirred at rt for 35 min, concentrated and the residue was purified by Prep-HPLC to the title compounds. Isomer A (5 mg, 5%): $^1$H NMR (500 MHz, MeOD): 8.26 (s, 1H), 8.19 (s, 1H), 7.20-7.27 (m, 4H), 6.00 (d, J=5 Hz, 1H), 4.79 (t, J=5.0 Hz, 1H), 4.31 (t, J=4.5 Hz, 1H), 4.19 (m, 1H), 3.20-3.25 (m, 2H), 2.59-2.87 (m, 5H), 1.67-1.69 (m, 2H), 1.54-1.56 (m, 1H), 1.23-1.35 (m, 10H), 0.95-1.03 (m, 3H), 0.83-0.86 (m, 3H) ppm; LC-MS (m/z): 555.4 [M+1]$^+$. Isomer B (7 mg, 6%): $^1$H NMR (500 MHz, MeOD): δ 8.27 (s, 1H), 8.20 (s, 1H), 7.22-7.28 (m, 4H), 5.98 (d, J=5 Hz, 1H), 4.82 (t, J=5.0 Hz, 1H), 4.31 (t, J=4.5 Hz, 1H), 4.15 (q, J=4.5 Hz, 1H), 3.23-3.27 (m, 2H), 2.93-2.97 (m, 1H), 2.56-2.71 (m, 4H), 1.65-1.70 (m, 2H), 1.56-1.62 (m, 1H), 1.28-1.34 (m, 10H), 0.93-0.97 (m, 6H) ppm; LC-MS (m/z): 555.4 [M+1]$^+$.

Compound 381

1-(3-(((((2S,3S,4R,5R)-5-(6-amino-9H-purin-9-yl)-3,4-dihydroxytetrahydrofuran-2-yl)methyl)sulfinyl)propyl)-3-(4-(tert-butyl)phenyl)urea

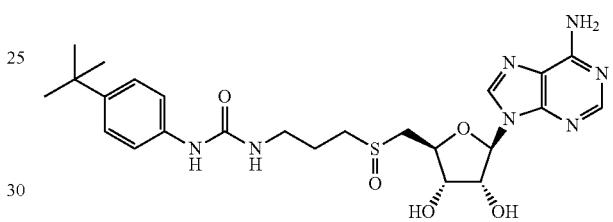

Step 1. Preparation of 1-[3-[[(4R,6S,6aS)-4-(6-aminopurin-9-yl)-2,2-dimethyl-3a,4,6,6a-tetrahydrofuro[3,4-d][1,3]dioxol-6-yl]methylsulfinyl]propyl]-3-(4-tert-butylphenyl)urea

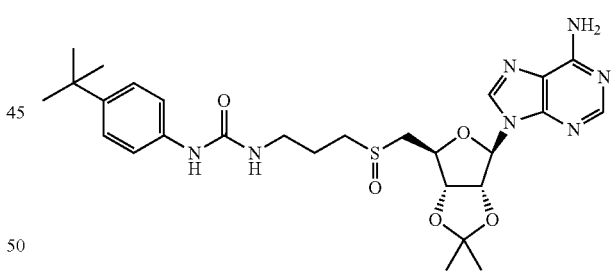

A solution of 1-(3-((((3aS,4S,6R,6aR)-6-(6-amino-9H-purin-9-yl)-2,2-dimethyltetrahydrofuro[3,4-d][1,3]dioxol-4-yl)methyl)thio)propyl)-3-(4-(tert-butyl)phenyl)urea (200 mg, 0.36 mmol), water (2 mL, 1.8 mmol) and NaHCO$_3$ (61 mg, 0.72 mmol) in DCM (10 mL) was stirred at ice-bath, then added dropwise the solution of m-CPAB (63 mg, 0.36 mmol) in DCM (3 mL) within 25 min. The reaction was quenched with aqueous. Sat. Na$_2$SO$_3$ (2 mL), extracted with DCM (10 mL×3), washed with brine (10 mL), dried and concentrated. The residue was purified by Prep-HPLC to the title compound (120 mg, yield 64%). $^1$H NMR (500 MHz, MeOD): δ 8.26 (s, 1H), 8.24 (s, 1H), 7.28-7.23 (m, 4H), 6.24-6.22 (m, 1H), 5.53-5.49 (m, 1H), 5.25-5.20 (m, 1H), 4.71-4.62 (m, 1H), 3.40-3.35 (m, 1H), 3.28-3.21 (m, 3H), 2.90-2.68 (m, 2H), 1.94-1.76 (m, 2H), 1.60-1.59 (m, 3H), 1.38-1.37 (m, 3H), 1.27 (s, 9H) ppm; ESI-MS (m/z): 572.3[M+1]$^+$.

Step 2. Preparation of 1-(3-(((((2S,3S,4R,5R)-5-(6-amino-9H-purin-9-yl)-3,4-dihydroxytetrahydrofuran-2-yl)methyl)sulfinyl)propyl)-3-(4-(tert-butyl)phenyl)urea

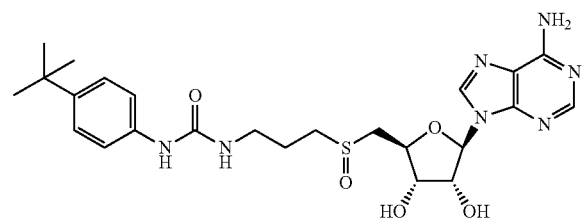 [SMILES: CC(C)(C)c1ccc(NC(=O)NCCCS(=O)C[C@H]2O[C@@H](n3cnc4c(N)ncnc43)[C@H](O)[C@@H]2O)cc1]

A solution of 1-[3-[[(4R,6S,6aS)-4-(6-aminopurin-9-yl)-2,2-dimethyl-3a,4,6,6a-tetrahydrofuro[3,4-d][1,3]dioxol-6-yl]methylsulfinyl]propyl]-3-(4-tert-butylphenyl)urea (120 mg, 0.21 mmol) in TFA (1.80 mL) and 0.20 mL of water were stirred for 1 h at room temperature. The reaction was concentrated to dryness, dissolved in MeOH (2 mL) and EA (100 mL), washed with aq. sat. NaHCO$_3$ (10×2 mL), dried and evaporated to give the crude. The residue was purified by Prep-HPLC to afford the title compound (85 mg, yield 76%). $^1$H NMR (400 MHz, MeOD): δ 8.37-8.36 (m, 1H), 8.34-8.33 (m, 1H), 8.13 (s, 1H), 7.28-7.24 (m, 4H), 7.20-7.18 (m, 2H), 6.21-6.19 (m, 1H), 5.91 (dd, J=3.5, 6.5 Hz, 1H), 5.62-5.43 (br s, 2H), 4.76-4.72 (m, 1H), 4.29-4.23 (m, 2H), 3.20-3.09 (m, 4H), 2.76-2.72 (m, 2H), 1.78-1.73 (m, 2H), 1.21 (s, 9H) ppm; ESI-MS (m/z): 532.3 [M+1]$^+$.

Compound 382

1-(3-(((((2S,3S,4R,5R)-5-(6-amino-9H-purin-9-yl)-3,4-dihydroxytetrahydrofuran-2-yl)methyl)sulfonyl)propyl)-3-(4-(tert-butyl)phenyl)urea

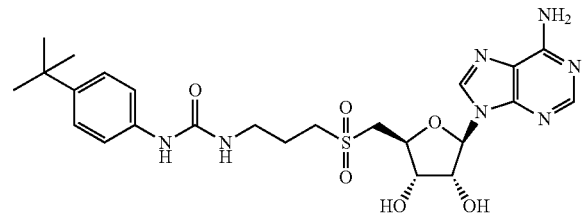 [SMILES: CC(C)(C)c1ccc(NC(=O)NCCCS(=O)(=O)C[C@H]2O[C@@H](n3cnc4c(N)ncnc43)[C@H](O)[C@@H]2O)cc1]

Step 1. Preparation of 1-(3-(((((3aS,4S,6R,6aR)-6-(6-amino-9H-purin-9-yl)-2,2-dimethyltetrahydrofuro[3,4-d][1,3]dioxol-4-yl)methyl)sulfonyl)propyl)-3-(4-(tert-butyl)phenyl)urea

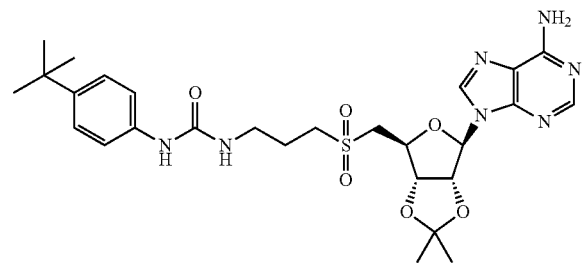 [SMILES: CC1(C)O[C@@H]2[C@H](O1)[C@@H](CS(=O)(=O)CCCNC(=O)Nc1ccc(C(C)(C)C)cc1)O[C@H]2n1cnc2c(N)ncnc21]

A solution of 1-(3-(((((3aS,4S,6R,6aR)-6-(6-amino-9H-purin-9-yl)-2,2-dimethyltetrahydrofuro[3,4-d][1,3]dioxol-4-yl)methyl)thio)propyl)-3-(4-(tert-butyl)phenyl)urea (150 mg, 0.27 mmol) in DCM (10 mL) was stirred at ice-bath, then added dropwise the solution of m-CPBA (93 mg, 0.54 mmol) in DCM (3 mL) for 25 min. The reaction was quenched with aqueous saturated Na$_2$SO$_3$ (2 mL), extracted with DCM (10 mL×3), washed with brine (10 mL), dried and concentrated. The residue was purified by Prep-HPLC to afford the title compound (100 mg, yield 65%). $^1$H NMR (500 MHz, MeOD): δ 8.25 (s, 1H), 8.23 (s, 1H), 7.28-7.21 (m, 4H), 6.24 (d, J=2.0 Hz, 1H), 5.49-5.48 (m, 1H), 5.24-5.22 (m, 1H), 4.71-4.68 (m, 1H), 3.80-3.75 (m, 1H), 3.53-3.50 (m, 1H), 3.06 (m, 2H), 2.89-2.92 (m, 2H), 1.89-1.79 (m, 1H), 1.59-1.57 (m, 4H), 1.37 (s, 3H), 1.28 (s, 9H) ppm; ESI-MS (m/z): 588.3[M+1]$^+$.

Step 2. Preparation of 1-(3-(((((2S,3S,4R,5R)-5-(6-amino-9H-purin-9-yl)-3,4-dihydroxytetrahydrofuran-2-yl)methyl)sulfonyl)propyl)-3-(4-(tert-butyl)phenyl)urea

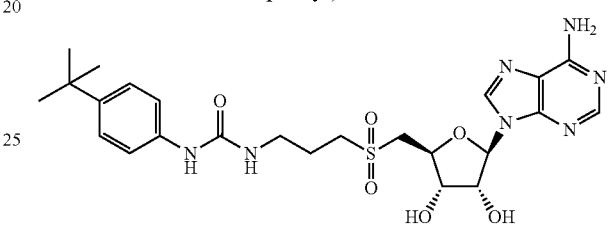

A solution of 1-(3-(((((3aS,4S,6R,6aR)-6-(6-amino-9H-purin-9-yl)-2,2-dimethyltetrahydrofuro[3,4-d][1,3]dioxol-4-yl)methyl)sulfonyl)propyl)-3-(4-(tert-butyl)phenyl)urea (100 mg, 0.17 mmol) in TFA (0.90 mL) and 0.10 mL of water were stirred for 1 hour at room temperature. The reaction was concentrated to dryness, dissolved in MeOH (2 mL) and EA (100 mL), washed with aq. sat. NaHCO$_3$ (10×2 mL), dried and evaporated to give the crude. The residue was purified by Prep-HPLC to afford the title compound (63 mg, yield 68%). $^1$H NMR (500 MHz, MeOD): δ 8.39 (s, 1H), 8.33 (s, 1H), 8.17 (s, 1H), 7.32 (s, 2H), 7.26-7.19 (m, 4H), 6.12-6.11 (m, 2H), 5.94-5.93 (d, J=7.0 Hz, 1H), 5.62 (d, J=7.5 Hz, 1H), 5.55 (d, J=6.5 Hz, 1H), 4.76-4.74 (m, 1H), 4.34-4.32 (m, 1H), 4.24-4.23 (m, 1H), 3.92-3.86 (m, 1H), 3.53-3.49 (m, 1H), 3.03-2.95 (m, 4H), 1.77-1.72 (m, 2H), 1.28 (s, 9H) ppm; ESI-MS (m/z): 548.3 [M+1]$^+$.

Inhibition of DOT1L

118

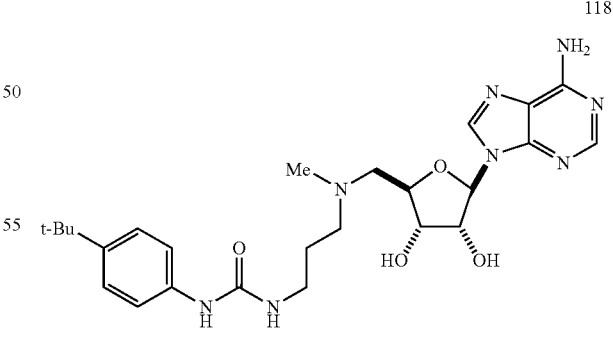

Figure 2:
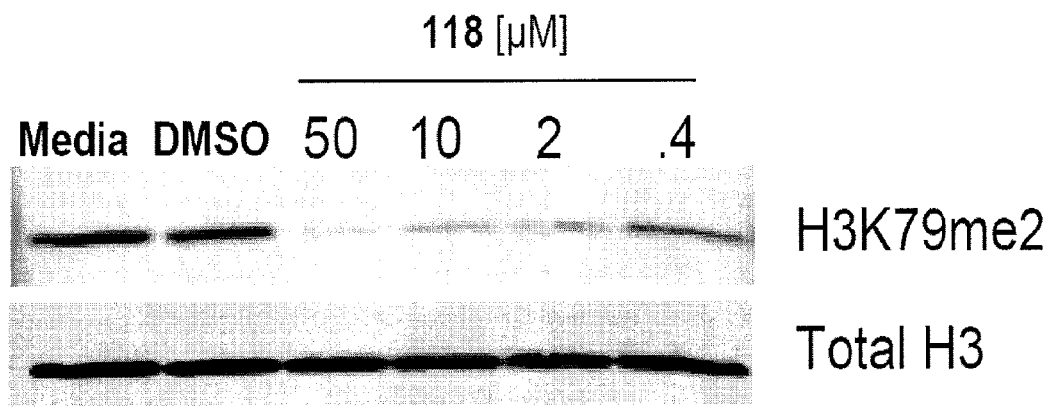
FIG. 2 depicts results demonstrating that inhibition of cellular H3K79 methylation is dose responsive. THP-1 cells were treated and processed as in FIG. 1 except that several concentrations of 118 were tested. Clear reduction in H3K79me2 was observed down to the lowest 118 concentration of 0.4 μM
Figure 3:
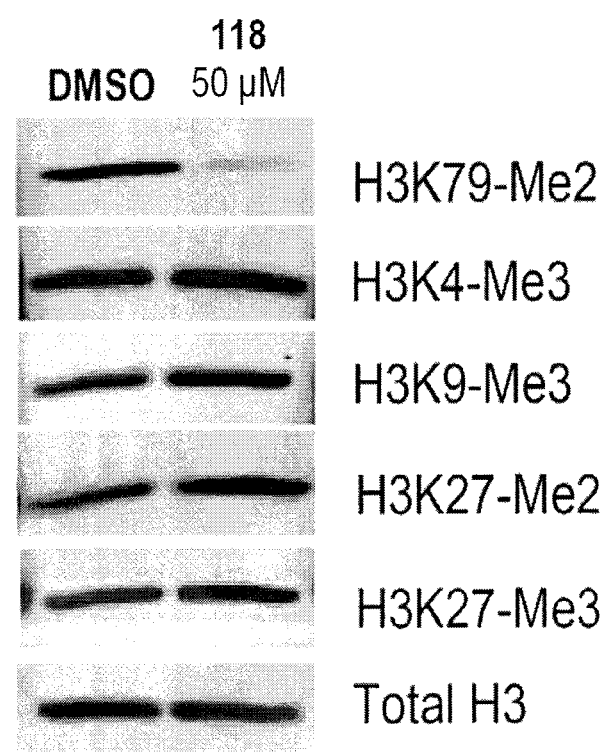
FIG. 3 depicts results demonstrating that 118 selectively inhibits cellular H3K79 methylation: THP-1 cells were treated and processed as in FIG. 1 except that nitrocellulose membranes were probed with site-specific methyl-lysine antibodies to H3K4me3, H3K9me3, H3K27me2 and H3K27me3 in addition to the anti-H3K79me2 and anti-histone H3 antibody.

118 and several related compounds are potent inhibitors of DOT1L in biochemical assays (see Table in FIG. 1). To evaluate the ability of these compounds to inhibit DOT1L in cells, their effect on cellular histone H3 lysine 79 (H3K79) methylation was examined. DOT1L is the only known histone methyltransferase capable of methylating H3K79, and so inhibition of cellular DOT1L should lead to a reduction of cellular H3K79 methylation. This is confirmed by the demonstration that depletion of DOT1L by shRNA knockdown in the MLL-AF9 leukemia cell line THP-1 leads to reduced levels of dimethylated H3K79 (compare shDOT1L and shNTC in FIG. 1). Treatment of THP-1 cells with 50 µM 118 leads to dramatically reduced cellular histone H3 lysine 79 dimethylation (FIG. 1). This indicates that 118 can enter cells and inhibit DOT1L in a cellular context. Several related compounds also exhibited clear decreases in H3K79me2 levels (FIG. 1), although none were as potent as 118, as might be expected from their lower biochemical $IC_{50}$s. In a separate experiment, varying the concentration of 118 led to a dose dependent reduction in H3K79me2 levels. A small, but clear reduction was still observable at 0.4 µM, the lowest concentration tested (FIG. 2). The specificity of 118 on cellular histone methylation was investigated by examining its effect on other methylation sites not targeted by DOT1L. As shown in FIG. 3, 118 treatment of THP-1 cells led to a reduction in H3K79 methylation, but did not affect sites targeted by other histone methyltransferases such as H3K4, H3K9 and H3K27. Therefore 118 is selective in its effects and does not act as a general inhibitor of histone methyltransferases.

Figure 4:
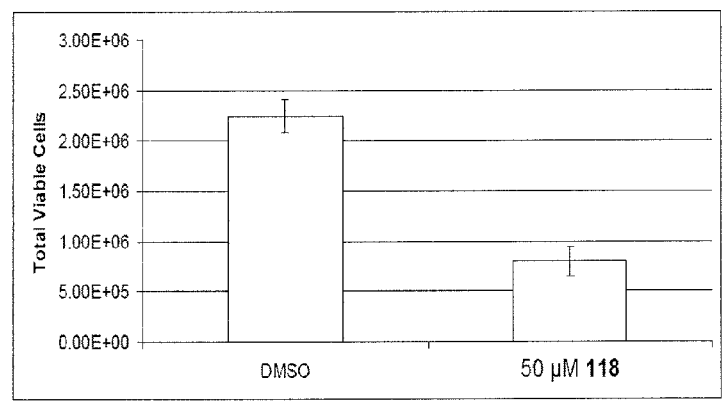
FIG. 4 depicts results demonstrating that 118 impairs cell growth in MLL-rearranged leukemia cell lines. THP-1 (MLL-AF9), MOLM-13 (MLL-AF9) and RS4; 11 (MLL-AF4) cells were incubated in the presence of 50 μM 118 for fourteen days. Part [a] depicts the results of a THP-1 Proliferation/Viability Assay; [b] depicts the results of a MOLM-13 Proliferation/Viability Assay; and [c] depicts the results of a RS4; 11 Proliferation/Viability Assay. Vehicle (DMSO)-treated cells were included as controls. Cell number and viability was determined using the Guava Viacount assay in a Guava EasyCyte Plus instrument.
Figure 4:
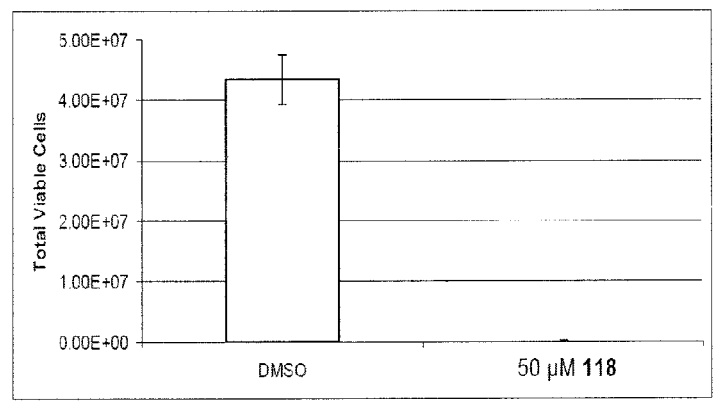
Figure 4:
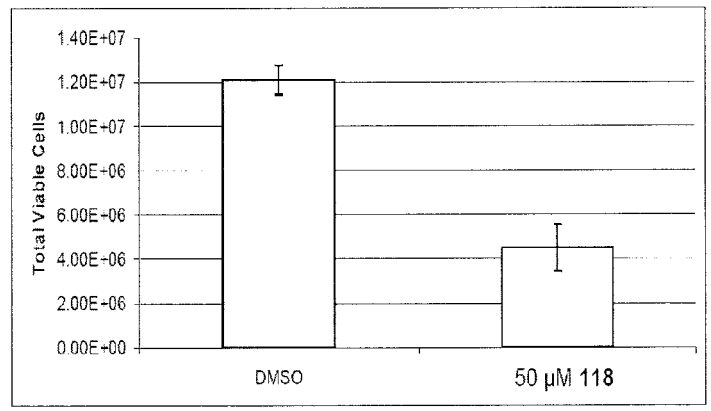
Figure 5:
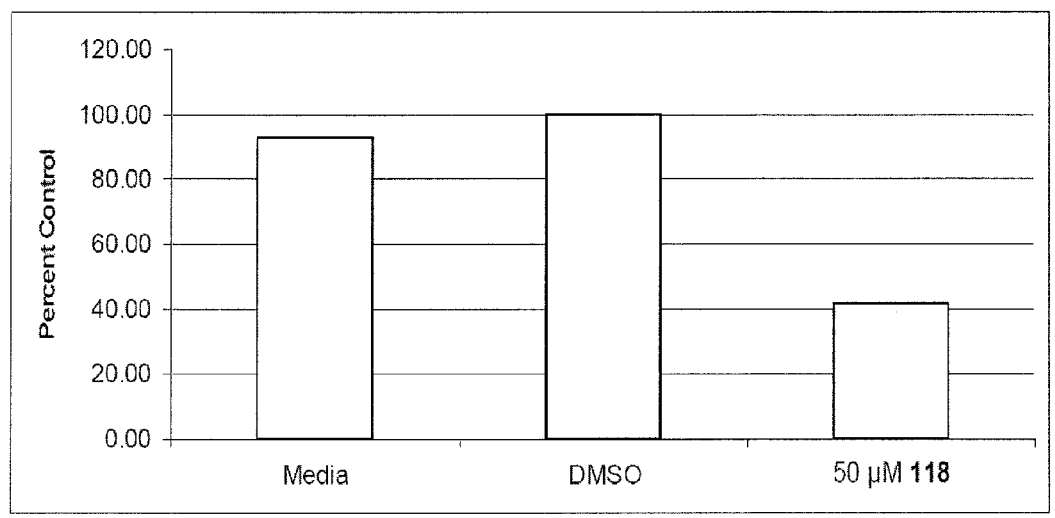
FIG. 5 depicts results demonstrating that 118 treatment reduces HOXA9 mRNA levels in THP-1 cells. THP-1 cells were incubated in the presence of 50 μM 118 for seven days. Untreated (media) and vehicle (DMSO)-treated cells were included as controls. Following treatment, cells were harvested, and total RNA was isolated and HOXA9 RNA levels were quantitated by RT-qPCR and normalized to the B2 microglobulin RNA levels.

MLL fusion proteins such as MLL-AF9 and MLL-AF4 are thought to drive leukemia cell growth by a mechanism that involves aberrant DOT1L recruitment leading to inappropriate H3K79 methylation and activation of genes important in leukemogenesis such as HOXA9. Treatment of MLL-rearranged cell lines with a DOT1L inhibitor would therefore be expected to impair cell growth and reduce HOXA9 gene expression. The effect of 118 on the growth of three MLL-rearranged leukemia cell lines was examined by treating THP-1 (MLL-AF9), MOLM-13 (MLL-AF9) and RS4; 11 (MLL-AF4) cells with 50 µM 118 for several days and monitoring effects on viable cell number. FIG. 4 shows that extended incubation of all three MLL-rearranged leukemia lines with 118 led to a dramatic decrease in viable cell number when compared to vehicle-treated controls. The effect of 118 on HOXA9 mRNA expression was evaluated in THP-1 cells following seven-day incubation with compound. As shown in FIG. 5, 118 treatment of THP-1 cells reduced HOXA9 mRNA levels by approximately 60% relative to untreated and vehicle-treated control cells.

In summary, inhibition of DOT1L activity with 118 leads to depletion of H3K79 methylation, reduced HOXA9 mRNA expression and a dramatic decrease in growth and viability of MLL-rearranged leukemia cell lines.

INCORPORATION BY REFERENCE

All of the U.S. patents and U.S. published patent applications and all references cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:

1. A compound of formula I:

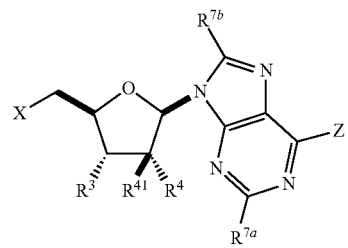

or a pharmaceutically acceptable salt, hydrate, enantiomer or stereoisomer thereof, wherein independently for each occurrence, X is

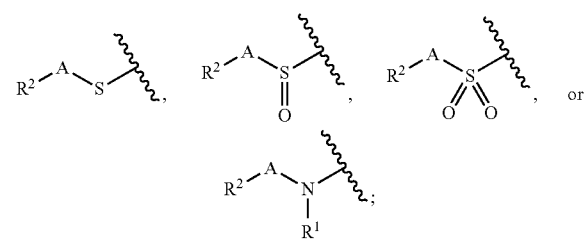

$R^1$ is hydrogen, alkyl, cycloalkyl, alkylcycloalkyl, alkylaryl, haloalkyl, formyl, heterocyclyl, heterocyclylalkyl,

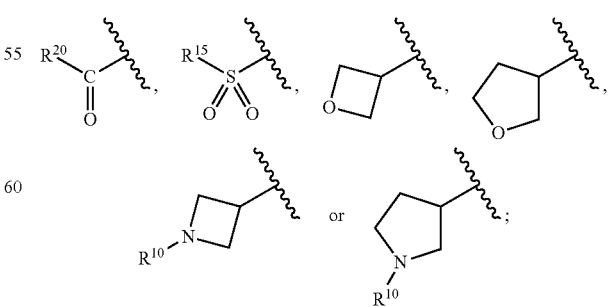

or $(C_2-C_4)$alkyl substituted with

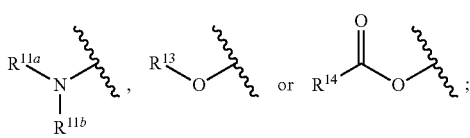

- $R^{10}$ is hydrogen or alkyl;
- $R^{11a}$ is hydrogen, alkyl, or alkyl-cycloalkyl;
- $R^{11b}$ is hydrogen or alkyl; or taken together with $R^{11a}$ and the nitrogen to which it is attached forms a 4- to 8-membered heterocyclyl comprising 0 or 1 additional heteroatoms;
- $R^{13}$ is hydrogen, alkyl, aryl, heteroaryl, aralkyl, heteroaralkyl or silyl;
- $R^{14}$ is hydrogen, alkyl, aryl, heteroaryl, aralkyl or heteroaralkyl;
- $R^{15}$ is alkyl, cycloalkyl or cycloalkylalkyl;
- $R^{20}$ is hydrogen, alkyl, cycloalkyl or cycloalkylalkyl;
- A is

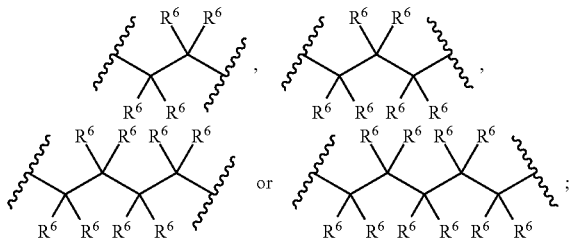

$R^2$ is

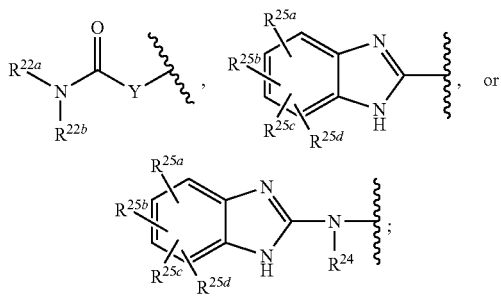

- Y is —NH—, —N(alkyl)-, —O—, or —$CR^6{}_2$—;
- $R^{22a}$ is aryl, heteroaryl, aralkyl, heteroaralkyl, fused bicyclyl, biaryl, aryloxyaryl, heteroaryloxyaryl, aryloxyheteroaryl or heteroaryloxyheteroaryl, each of which is unsubstituted or substituted;
- $R^{22b}$ is hydrogen or alkyl;
- $R^{24}$ is hydrogen or alkyl;
- $R^{25a}$, $R^{25b}$, $R^{25c}$, $R^{25d}$ are each independently -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
- $R^3$ is hydrogen, halogen, hydroxy, alkyloxy, aralkyloxy, alkylcarbonyloxy or silyloxy;
- $R^4$ is hydrogen, halogen, hydroxy, alkyloxy, aralkyloxy, alkylcarbonyloxy or silyloxy;
- $R^{41}$ is hydrogen, alkyl or alkynyl;
- Z is hydrogen or

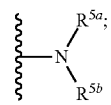

- $R^{5a}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl;
- $R^{5b}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl; or taken together with $R^{5a}$ and the nitrogen to which it is attached forms a 4- to 8-membered heterocyclyl comprising 0 or 1 additional heteroatoms;
- each $R^6$ independently is hydrogen, alkyl or halo; or two geminal $R^6$ taken together are ethylene, propylene or butylene;
- $R^{7a}$ is hydrogen, lower alkyl, lower haloalkyl, cyano, halo, lower alkoxy, or C3-C5 cycloalkyl, optionally substituted with 1, 2 or 3 substituents independently selected from the group consisting of cyano, lower alkoxy and halo; and
- $R^{7b}$ is hydrogen, lower alkyl, lower haloalkyl, cyano, halo, lower alkoxy, or C3-C5 cycloalkyl, optionally substituted with 1, 2 or 3 substituents independently selected from the group consisting of cyano, lower alkoxy and halo.

2. The compound of claim 1, wherein X is

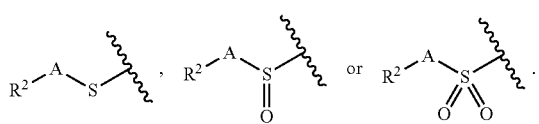

3. The compound of claim 1, wherein X is

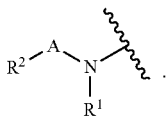

4. A compound of formula I:

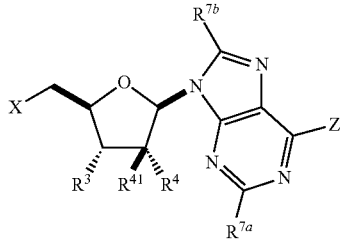

or a pharmaceutically acceptable salt, hydrate, enantiomer or stereoisomer thereof, wherein independently for each occurrence, X is

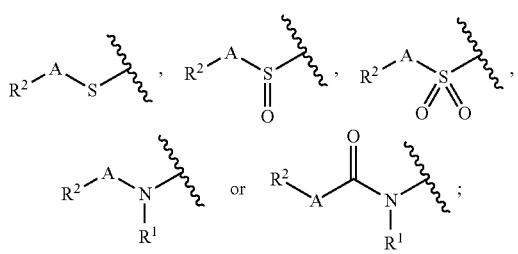

$R^1$ is hydrogen, alkyl, cycloalkyl, alkylcycloalkyl, alkylaryl, haloalkyl, formyl, heterocyclyl, heterocyclylalkyl,

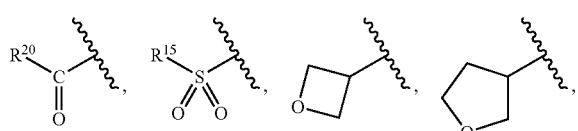

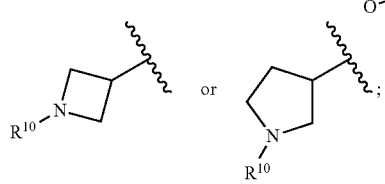

or $(C_1-C_4)$alkyl substituted with

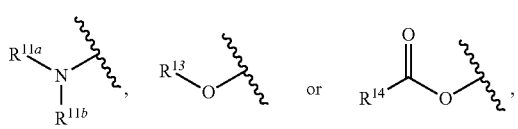

except that when X is

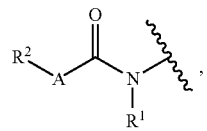

$R^1$ is not

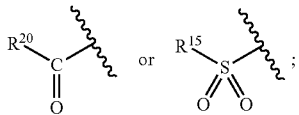

$R^{10}$ is hydrogen or alkyl;
$R^{11a}$ is hydrogen, alkyl, or alkyl-cycloalkyl;
$R^{11b}$ is hydrogen or alkyl; or taken together with $R^{11a}$ and the nitrogen to which it is attached forms a 4- to 8-membered heterocyclyl comprising 0 or 1 additional heteroatoms;
$R^{13}$ is hydrogen, alkyl, aryl, heteroaryl, aralkyl, heteroaralkyl or silyl;
$R^{14}$ is hydrogen, alkyl, aryl, heteroaryl, aralkyl or heteroaralkyl;
$R^{15}$ is alkyl, cycloalkyl or cycloalkylalkyl;
$R^{20}$ is hydrogen, alkyl, cycloalkyl or cycloalkylalkyl;

A is

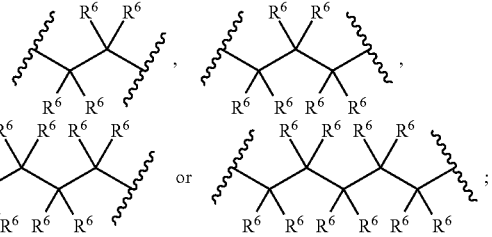

$R^2$ is

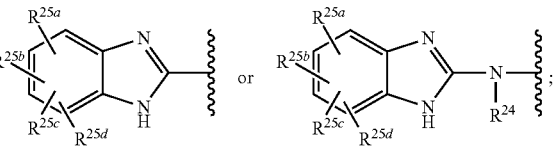

Y is —NH—, —N(alkyl)-, —O—, or —$CR^6_2$—;
$R^{24}$ is hydrogen or alkyl;
$R^{25a}$, $R^{25b}$, $R^{25c}$, $R^{25d}$ are each independently -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

R³ is hydrogen, halogen, hydroxy, alkyloxy, aralkyloxy, alkylcarbonyloxy or silyloxy;

R⁴ is hydrogen, halogen, hydroxy, alkyloxy, aralkyloxy, alkylcarbonyloxy or silyloxy;

R⁴¹ is hydrogen, alkyl or alkynyl;

Z is hydrogen or

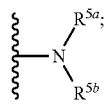

R$^{5a}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl;

R$^{5b}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl; or taken together with R$^{5a}$ and the nitrogen to which it is attached forms a 4- to 8-membered heterocyclyl comprising 0 or 1 additional heteroatoms;

each R⁶ independently is hydrogen, alkyl or halo; or two geminal R⁶ taken together are ethylene, propylene or butylene;

R$^{7a}$ is hydrogen, lower alkyl, lower haloalkyl, cyano, halo, lower alkoxy, or C3-C5 cycloalkyl, optionally substituted with 1, 2 or 3 substituents independently selected from the group consisting of cyano, lower alkoxy and halo; and R$^{7b}$ is hydrogen, lower alkyl, lower haloalkyl, cyano, halo, lower alkoxy, or C3-C5 cycloalkyl, optionally substituted with 1, 2 or 3 substituents independently selected from the group consisting of cyano, lower alkoxy and halo.

5. The compound of claim 4, wherein R²⁴ is hydrogen or alkyl.

6. The compound of claim 4, wherein R$^{25a}$ is hydrogen, alkyl, —O-alkyl, halogen, trifluoroalkyl, —O-trifluoromethyl, or —SO₂-trifluoromethyl.

7. The compound of claim 6, wherein R$^{25b}$ is hydrogen, alkyl, halogen, or trifluoroalkyl.

8. The compound of claim 7, wherein R$^{25c}$ is hydrogen, alkyl, or halogen; and R$^{25d}$ is hydrogen.

9. The compound of claim 1, wherein R² is

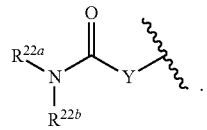

10. The compound of claim 9, wherein Y is —NH—, —N(alkyl)-, —O—, or —CH₂—.

11. A compound of formula I:

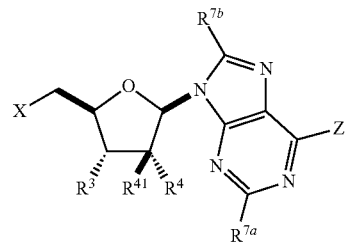

or a pharmaceutically acceptable salt, hydrate, enantiomer or stereoisomer thereof, wherein independently for each occurrence, X is

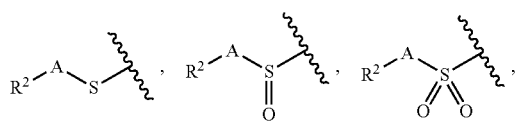

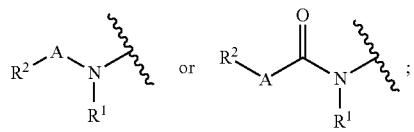

R¹ is hydrogen, alkyl, cycloalkyl, alkylcycloalkyl, alkylaryl, haloalkyl, formyl, heterocyclyl, heterocyclylalkyl,

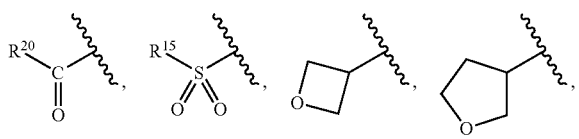

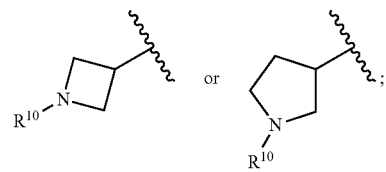

or (C₁-C₄)alkyl substituted with

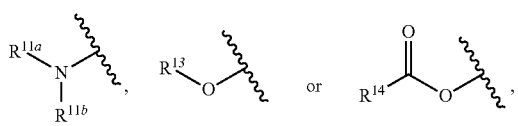, except that when X is

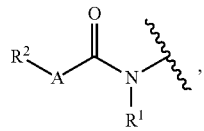,

R¹ is not

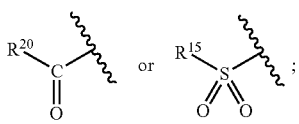;

R¹⁰ is hydrogen or alkyl;
R¹¹ᵃ is hydrogen, alkyl, or alkyl-cycloalkyl;
R¹¹ᵇ is hydrogen or alkyl; or taken together with R¹¹ᵃ and the nitrogen to which it is attached forms a 4- to 8-membered heterocyclyl comprising 0 or 1 additional heteroatoms;
R¹³ is hydrogen, alkyl, aryl, heteroaryl, aralkyl, heteroaralkyl or silyl;
R¹⁴ is hydrogen, alkyl, aryl, heteroaryl, aralkyl or heteroaralkyl;
R¹⁵ is alkyl, cycloalkyl or cycloalkylalkyl;
R²⁰ is hydrogen, alkyl, cycloalkyl or cycloalkylalkyl;
A is

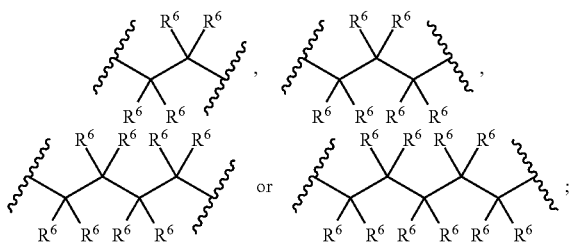;

R² is

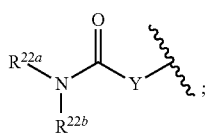;

R²²ᵃ is aryl or aralkyl, each of which is unsubstituted or substituted;
R²²ᵇ is hydrogen or alkyl;
Y is —NH—, —N(alkyl)-, —O—, or —CR⁶₂—;
R³ is hydrogen, halogen, hydroxy, alkyloxy, aralkyloxy, alkylcarbonyloxy or silyloxy;
R⁴ is hydrogen, halogen, hydroxy, alkyloxy, aralkyloxy, alkylcarbonyloxy or silyloxy;

R⁴¹ is hydrogen, alkyl or alkynyl;
Z is hydrogen or $$\begin{array}{c}\xi\\\xi\end{array}\!\!\!\!\!\!\!\!\!\!\!\!\text{N}\!\!\!\!\!<\!\!\!\!\!\begin{array}{c}R^{5a}\\R^{5b}\end{array};$$

R⁵ᵃ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl;

R⁵ᵇ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl; or taken together with R⁵ᵃ and the nitrogen to which it is attached forms a 4- to 8-membered heterocyclyl comprising 0 or 1 additional heteroatoms;

each R⁶ independently is hydrogen, alkyl or halo; or two geminal R⁶ taken together are ethylene, propylene or butylene;

R⁷ᵃ is hydrogen, lower alkyl, lower haloalkyl, cyano, halo, lower alkoxy, or C3-C5 cycloalkyl, optionally substituted with 1, 2 or 3 substituents independently selected from the group consisting of cyano, lower alkoxy and halo; and R⁷ᵇ is hydrogen, lower alkyl, lower haloalkyl, cyano, halo, lower alkoxy, or C3-C5 cycloalkyl, optionally substituted with 1, 2 or 3 substituents independently selected from the group consisting of cyano, lower alkoxy and halo.

12. The compound of claim 9, wherein R²²ᵇ is hydrogen or methyl.

13. The compound of claim 1, wherein A is

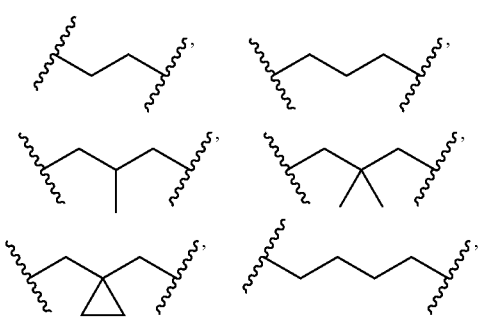

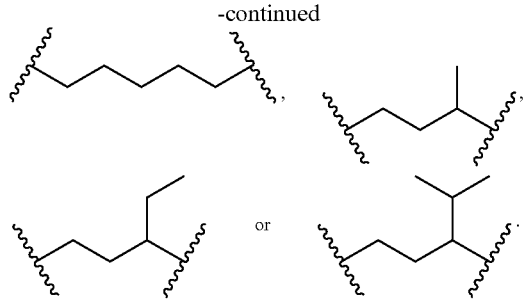

14. The compound of claim 1, wherein $R^3$ is hydroxyl or hydrogen.

15. The compound of claim 1, wherein $R^4$ is hydroxyl or hydrogen.

16. The compound of claim 1, wherein $R^{41}$ is hydrogen or methyl.

17. A pharmaceutical composition comprising a compound of claim 1 and a pharmaceutically acceptable diluent or carrier.

18. A kit or packaged pharmaceutical comprising a compound of claim 1 and instructions for use thereof.

19. A method of treating cancer, comprising administering to a subject in need thereof a therapeutically effective amount of a compound of claim 1.

20. The compound of claim 9, wherein $R^{22a}$ is substituted phenyl or substituted benzyl.

21. The compound of claim 9, wherein $R^{22a}$ is

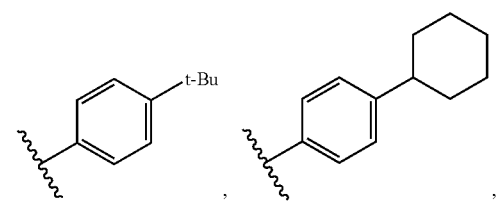

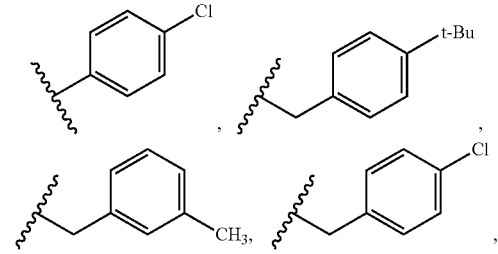

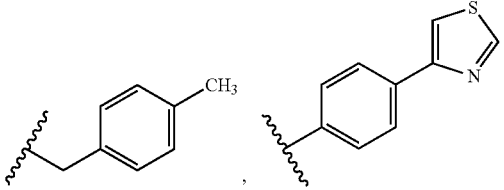

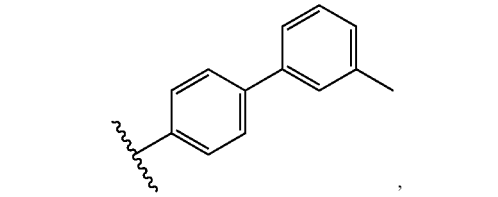

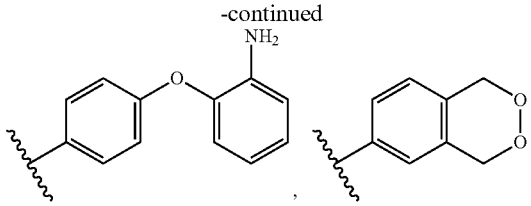

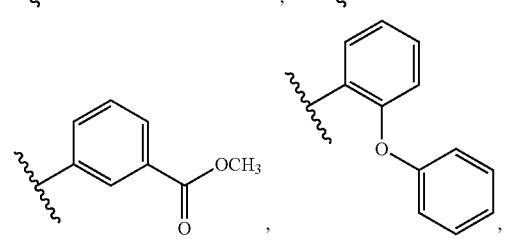

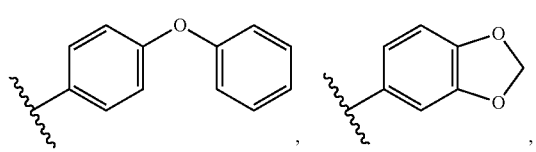

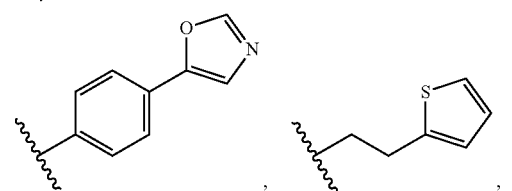

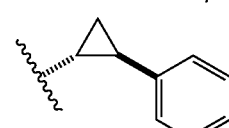

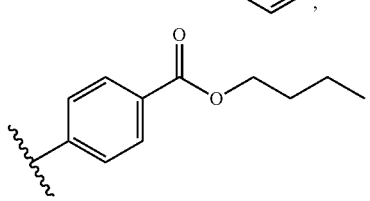

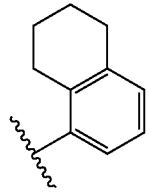

22. The compound of claim 11, wherein $R^{22a}$ is substituted phenyl or substituted benzyl.

23. The compound of claim 11, wherein $R^{22a}$ is

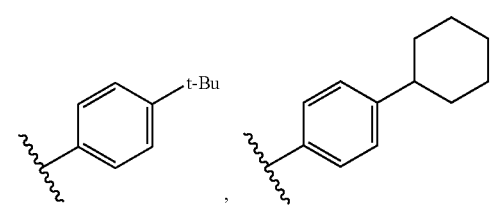

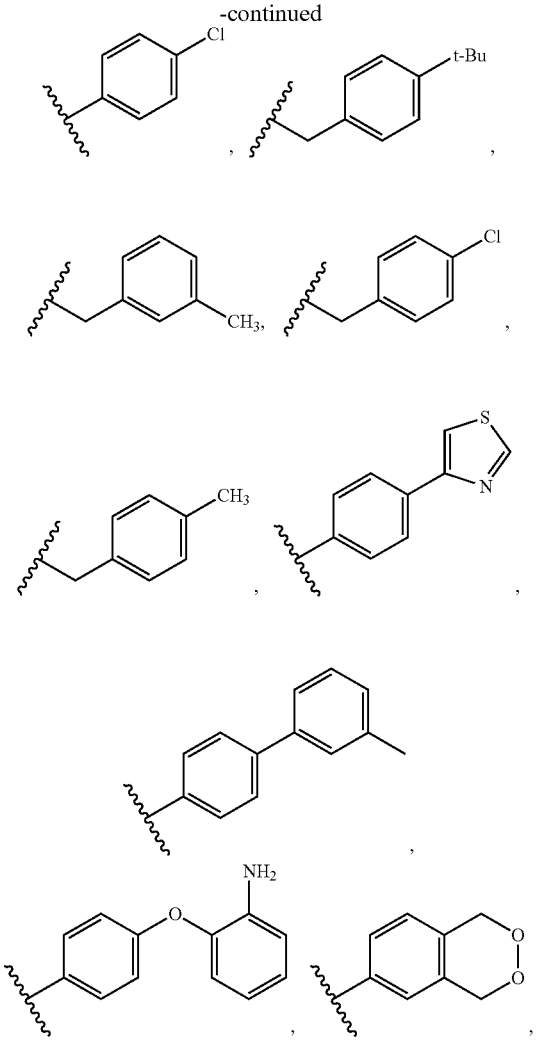
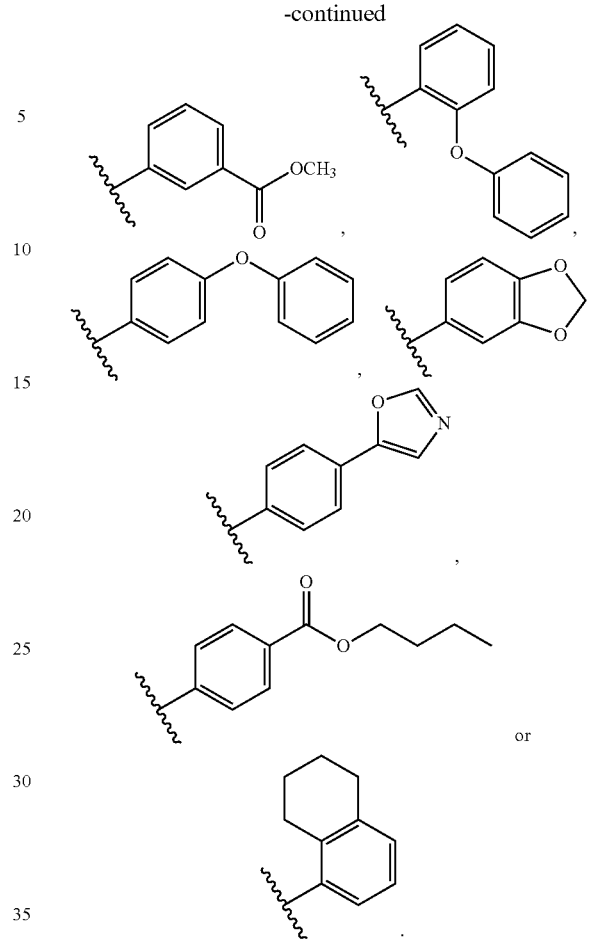
24. The compound of claim 11, wherein $R^{22b}$ is hydrogen or methyl.
* * * * *